United States Patent
Zheng et al.

(10) Patent No.: US 12,122,778 B2
(45) Date of Patent: *Oct. 22, 2024

(54) ACTIVATING PYRUVATE KINASE R

(71) Applicant: Novo Nordisk Health Care AG, Zurich (CH)

(72) Inventors: Xiaozhang Zheng, Lexington, MA (US); Anna Ericsson, Shrewsbury, MA (US); Neal Green, Newton, MA (US); Gary Gustafson, Ridgefield, CT (US); David R. Lancia, Jr., Westwood, MA (US); Jian Lin, Watertown, MA (US); Lorna Mitchell, West Beach (AU); David Richard, Littleton, MA (US); Tatiana Shelekhin, Ridgefield, CT (US)

(73) Assignee: Novo Nordisk Health Care AG, Zurich (CH)

( * ) Notice: Subject to any disclaimer, the term of this patent is extended or adjusted under 35 U.S.C. 154(b) by 804 days.

This patent is subject to a terminal disclaimer.

(21) Appl. No.: 17/277,425

(22) PCT Filed: Sep. 19, 2019

(86) PCT No.: PCT/US2019/051831
§ 371 (c)(1),
(2) Date: Mar. 18, 2021

(87) PCT Pub. No.: WO2020/061255
PCT Pub. Date: Mar. 26, 2020

(65) Prior Publication Data
US 2023/0055923 A1 Feb. 23, 2023

Related U.S. Application Data

(60) Provisional application No. 62/733,546, filed on Sep. 19, 2018.

(51) Int. Cl.
*C07D 487/04* (2006.01)
*A61K 9/00* (2006.01)

(52) U.S. Cl.
CPC .......... *C07D 487/04* (2013.01); *A61K 9/0053* (2013.01)

(58) Field of Classification Search
CPC ..................... C07D 487/04; A61K 9/0053
See application file for complete search history.

(56) References Cited

U.S. PATENT DOCUMENTS

| | | | |
|---|---|---|---|
| 4,602,093 A | 7/1986 | Baldwin et al. | |
| 4,918,073 A | 4/1990 | Ruger et al. | |
| 5,030,631 A | 7/1991 | Bauer | |
| 5,037,467 A | 8/1991 | Cho et al. | |
| 5,059,605 A | 10/1991 | Clough et al. | |
| 5,089,621 A | 2/1992 | Kim et al. | |
| 5,091,384 A | 2/1992 | Kim et al. | |
| 5,180,719 A | 1/1993 | White et al. | |
| 5,250,544 A | 10/1993 | Lavielle et al. | |
| 5,336,772 A | 8/1994 | Saiki et al. | |
| 5,480,899 A | 1/1996 | Yano et al. | |
| 5,672,601 A | 9/1997 | Cignarella | |
| 5,714,625 A | 2/1998 | Hada et al. | |
| 5,747,502 A | 5/1998 | Hanaoka et al. | |
| 5,962,703 A | 10/1999 | Moszner et al. | |
| 6,214,879 B1 | 4/2001 | Abraham et al. | |
| 6,534,501 B2 | 3/2003 | Abraham et al. | |
| 6,710,052 B2 | 3/2004 | Pease et al. | |
| 6,878,715 B1 | 4/2005 | Klein et al. | |
| 7,138,401 B2 | 11/2006 | Kasibhatla et al. | |
| 7,160,885 B2 | 1/2007 | Currie et al. | |
| 7,875,603 B2 | 1/2011 | Rathinavelu et al. | |
| 8,501,953 B2 | 8/2013 | Salituro et al. | |
| 8,552,050 B2 | 10/2013 | Cantley et al. | |
| 8,692,001 B2 | 4/2014 | Becker et al. | |
| 8,742,119 B2 | 6/2014 | Salituro et al. | |
| 8,785,450 B2 | 7/2014 | Salituro et al. | |
| 8,841,305 B2 | 9/2014 | Thomas et al. | |
| 8,877,791 B2 | 11/2014 | Cantley et al. | |
| 8,889,667 B2 | 11/2014 | Salituro et al. | |
| 8,952,171 B2 | 2/2015 | Xu et al. | |
| 9,012,450 B2 | 4/2015 | Metcalf et al. | |
| 9,018,210 B2 | 4/2015 | Metcalf et al. | |
| 9,108,921 B2 | 8/2015 | Cianchetta et al. | |
| 9,181,231 B2 | 11/2015 | Su | |

(Continued)

FOREIGN PATENT DOCUMENTS

| | | |
|---|---|---|
| CN | 101812063 A | 8/2010 |
| CN | 102206217 A | 10/2011 |
| CN | 102952139 A | 3/2013 |
| CN | 103570722 A | 2/2014 |
| CN | 104736534 A | 6/2015 |
| CN | 105037367 A | 11/2015 |
| CN | 105085528 A | 11/2015 |
| CN | 105153119 A | 12/2015 |
| CN | 105254628 A | 1/2016 |
| CN | 105294694 A | 2/2016 |
| CN | 105348286 A | 2/2016 |
| CN | 106928222 A | 7/2017 |
| CN | 109912610 A | 6/2019 |
| DE | 102008010661 A1 | 9/2009 |

(Continued)

OTHER PUBLICATIONS

Abbady M.A., et al., Synthesis and biological activity of some new 4-(2-pyrazolin-3-yl)-, 4-(2-isoxazolin-e-yl)- and 4-(1,2,5,6-tetrahydro-2-thioxopyrimidin-4-yl)phenyl aminophenyl sulfides and sulfones., *Egyptian Journal of Pharmaceutical Sciences*, vol. 27, No. 1-4, (1986), Abstract Only.

(Continued)

*Primary Examiner* — Timothy R Rozof
(74) *Attorney, Agent, or Firm* — Jianjie Hu

(57) ABSTRACT

The disclosure provides novel chemical compounds useful as activators of PKR. PKR activating compounds are useful in the treatment of disease and disorders associated with modulation of PKR and/or PKM2, such as pyruvate kinase deficiency (PKD).

19 Claims, 1 Drawing Sheet

(56) References Cited

U.S. PATENT DOCUMENTS

| | | | |
|---|---|---|---|
| 9,221,792 B2 | 12/2015 | Salituro et al. |
| 9,248,199 B2 | 2/2016 | Metcalf |
| 9,328,077 B2 | 5/2016 | Salituro et al. |
| 9,394,257 B2 | 7/2016 | Ho et al. |
| 9,422,279 B2 | 8/2016 | Metcalf et al. |
| 9,458,132 B2 | 10/2016 | Cianchetta et al. |
| 9,458,139 B2 | 10/2016 | Xu et al. |
| 9,604,999 B2 | 3/2017 | Harris et al. |
| 9,708,267 B2 | 7/2017 | Boxer et al. |
| 9,744,145 B1 | 8/2017 | Liu et al. |
| 9,776,960 B2 | 10/2017 | Xu et al. |
| 9,802,900 B2 | 10/2017 | Li et al. |
| 9,957,250 B2 | 5/2018 | Metcalf et al. |
| 9,981,939 B2 | 5/2018 | Metcalf et al. |
| 10,004,725 B2 | 6/2018 | Dufu et al. |
| 10,017,491 B2 | 7/2018 | Metcalf et al. |
| 10,034,879 B2 | 7/2018 | Metcalf et al. |
| 10,077,249 B2 | 9/2018 | Li et al. |
| 10,100,040 B2 | 10/2018 | Li et al. |
| 10,100,043 B2 | 10/2018 | Metcalf et al. |
| 10,208,052 B1 | 2/2019 | Zheng et al. |
| 10,266,551 B2 | 4/2019 | Li et al. |
| 10,315,991 B2 | 6/2019 | Xu et al. |
| 10,377,741 B2 | 8/2019 | Metcalf et al. |
| 10,435,393 B2 | 10/2019 | Xu et al. |
| 10,450,269 B1 | 10/2019 | Xu et al. |
| 10,472,371 B2 | 11/2019 | Zheng et al. |
| 10,493,035 B2 | 12/2019 | Dalziel et al. |
| 10,577,345 B2 | 3/2020 | Li et al. |
| 10,675,274 B2 | 6/2020 | Ericsson et al. |
| 10,683,285 B2 | 6/2020 | Li |
| 10,695,330 B2 | 6/2020 | Li et al. |
| 11,001,588 B2 | 5/2021 | Lancia, Jr. et al. |
| 2004/0077648 A1 | 4/2004 | Timmer et al. |
| 2004/0102458 A1 | 5/2004 | Chiosis et al. |
| 2005/0002861 A1 | 1/2005 | Krause et al. |
| 2005/0049263 A1 | 3/2005 | Kasibhatla et al. |
| 2005/0059663 A1 | 3/2005 | Martin et al. |
| 2005/0181305 A1 | 8/2005 | Shibuya |
| 2005/0256103 A1 | 11/2005 | Suzuki et al. |
| 2006/0074121 A1 | 4/2006 | Chen et al. |
| 2006/0211737 A1 | 9/2006 | Huang et al. |
| 2007/0015752 A1 | 1/2007 | Hangauer, Jr. |
| 2007/0270433 A1 | 11/2007 | Brinkman et al. |
| 2008/0058315 A1 | 3/2008 | Cai et al. |
| 2008/0184495 A1 | 8/2008 | Brun et al. |
| 2008/0253965 A1 | 10/2008 | Chiosis et al. |
| 2008/0269234 A1 | 10/2008 | Gandhi et al. |
| 2009/0042966 A1 | 2/2009 | Coleman et al. |
| 2009/0163545 A1 | 6/2009 | Goldfarb |
| 2009/0291921 A1 | 11/2009 | Jabri et al. |
| 2010/0029575 A1 | 2/2010 | Junien et al. |
| 2010/0120863 A1 | 5/2010 | Biftu et al. |
| 2010/0144594 A1 | 6/2010 | Zoller et al. |
| 2010/0144722 A1 | 6/2010 | Alexander et al. |
| 2010/0152157 A1 | 6/2010 | Puech et al. |
| 2010/0179154 A1 | 7/2010 | Almario Garcia et al. |
| 2010/0216774 A1 | 8/2010 | Bender et al. |
| 2010/0324030 A1 | 12/2010 | Dale et al. |
| 2011/0059089 A1 | 3/2011 | Swagemakers et al. |
| 2011/0085969 A1 | 4/2011 | Rollo et al. |
| 2011/0104054 A1 | 5/2011 | Chiosis et al. |
| 2012/0252818 A1 | 10/2012 | Chiosis et al. |
| 2013/0109684 A1 | 5/2013 | Blagg et al. |
| 2013/0116430 A1 | 5/2013 | Fujiwara et al. |
| 2013/0155489 A1 | 6/2013 | Kato et al. |
| 2013/0190315 A1 | 7/2013 | Metcalf et al. |
| 2013/0190316 A1 | 7/2013 | Metcalf et al. |
| 2014/0228360 A1 | 8/2014 | Duncan et al. |
| 2014/0242602 A1 | 8/2014 | Chiosis et al. |
| 2015/0246025 A1* | 9/2015 | Desai .................. A61K 45/06 548/410 |
| 2016/0106728 A1 | 4/2016 | Shen et al. |
| 2016/0200681 A1 | 7/2016 | Yu et al. |
| 2017/0121338 A1 | 5/2017 | Zhang et al. |
| 2017/0216434 A1 | 8/2017 | Hines et al. |
| 2017/0217964 A1 | 8/2017 | Li |
| 2018/0215765 A1 | 8/2018 | Di Giorgio et al. |
| 2019/0218221 A1 | 7/2019 | Zheng et al. |
| 2020/0031839 A1 | 1/2020 | Zheng et al. |
| 2020/0069643 A1 | 3/2020 | Ericsson |
| 2020/0085798 A1 | 3/2020 | Ericsson |
| 2020/0087309 A1 | 3/2020 | Lancia, Jr. |
| 2020/0129485 A1 | 4/2020 | Ericsson et al. |
| 2020/0253939 A1 | 8/2020 | Ericsson et al. |

FOREIGN PATENT DOCUMENTS

| | | |
|---|---|---|
| EP | 0007529 A1 | 2/1980 |
| EP | 0036711 A2 | 9/1981 |
| EP | 0264883 A2 | 4/1988 |
| EP | 0273534 A2 | 7/1988 |
| EP | 0338372 A2 | 10/1988 |
| EP | 0363212 A2 | 4/1990 |
| EP | 0378255 A2 | 7/1990 |
| EP | 0424850 A1 | 5/1991 |
| EP | 0424851 A1 | 5/1991 |
| EP | 0424852 A1 | 5/1991 |
| EP | 0486022 A2 | 5/1992 |
| EP | 0520277 A2 | 12/1992 |
| EP | 0590415 A2 | 4/1994 |
| EP | 0737670 A1 | 10/1996 |
| EP | 1096310 A2 | 5/2001 |
| EP | 1099692 A1 | 5/2001 |
| EP | 1249233 A1 | 10/2002 |
| EP | 1952800 A2 | 8/2008 |
| EP | 3141542 A1 | 3/2017 |
| EP | 2797416 B1 | 8/2017 |
| IN | 1809/MUM/2013 | 5/2013 |
| IN | 2013/MU01809 | 3/2015 |
| JP | S 61 200544 | 9/1986 |
| JP | 3 13040 B2 | 2/1991 |
| JP | 3 275666 | 12/1991 |
| JP | 04 054181 A | 2/1992 |
| JP | 05125050 A | 5/1993 |
| JP | 05 196976 | 8/1993 |
| JP | 7 164400 | 6/1995 |
| JP | 1 110376 | 1/1999 |
| JP | 2001261653 A | 9/2001 |
| JP | 2003514673 | 4/2003 |
| JP | 2004175674 A | 6/2004 |
| JP | 2007246885 A | 9/2007 |
| JP | 2007328090 A | 12/2007 |
| JP | 2008031064 A | 2/2008 |
| JP | 2008063256 A | 3/2008 |
| JP | 2009149707 A | 7/2009 |
| JP | 2009212473 A | 9/2009 |
| JP | 2010192782 A | 9/2010 |
| JP | 2011246649 A | 12/2011 |
| JP | 2012188474 A | 10/2012 |
| JP | 2012188475 A | 10/2012 |
| JP | 2013171968 A | 9/2013 |
| KR | 20110096442 A | 8/2011 |
| LB | 11379 | 7/2018 |
| RU | 2517693 C2 | 4/2011 |
| RU | 2472794 C1 | 11/2012 |
| WO | WO 1993/011106 | 6/1993 |
| WO | WO 1993/022298 A1 | 11/1993 |
| WO | WO 1995/019353 A1 | 7/1995 |
| WO | WO 1998/038239 | 9/1998 |
| WO | WO 1998/050364 A1 | 11/1998 |
| WO | WO 1999/001442 A1 | 1/1999 |
| WO | WO 1999/002493 A1 | 1/1999 |
| WO | WO 1999/047489 A1 | 9/1999 |
| WO | WO 1999/047516 A1 | 9/1999 |
| WO | WO 1999/048461 A2 | 9/1999 |
| WO | WO 1999/048490 A1 | 9/1999 |
| WO | WO 1999/065895 A1 | 12/1999 |
| WO | WO 1999/065901 | 12/1999 |
| WO | WO 2000/004023 A1 | 1/2000 |
| WO | WO 2000/021951 A1 | 4/2000 |
| WO | WO 2000/053591 A1 | 9/2000 |
| WO | WO 2001/010842 A2 | 2/2001 |
| WO | WO 2001/032764 | 5/2001 |

(56) References Cited

FOREIGN PATENT DOCUMENTS

| | | |
|---|---|---|
| WO | WO 2001/043744 A1 | 6/2001 |
| WO | WO 2001/053288 A2 | 7/2001 |
| WO | WO 2001/057037 A2 | 8/2001 |
| WO | WO 2001/085728 A2 | 11/2001 |
| WO | WO 2002/030358 | 4/2002 |
| WO | WO 2002/034754 A2 | 5/2002 |
| WO | WO 2002/060902 A1 | 8/2002 |
| WO | WO 2002/076989 A1 | 10/2002 |
| WO | WO 2002/095063 A1 | 11/2002 |
| WO | WO 2003/015769 A1 | 2/2003 |
| WO | WO 2003/037860 A2 | 5/2003 |
| WO | WO 2003/063794 | 8/2003 |
| WO | WO 2003/067332 A2 | 8/2003 |
| WO | WO 2003/084948 A1 | 10/2003 |
| WO | WO 2004/002490 A2 | 1/2004 |
| WO | WO 2004/007770 A2 | 1/2004 |
| WO | WO 2004/009600 A1 | 1/2004 |
| WO | WO 2004/013144 A1 | 2/2004 |
| WO | WO 2004/014374 A1 | 2/2004 |
| WO | WO 2004/014382 | 2/2004 |
| WO | WO 2004/024676 A1 | 3/2004 |
| WO | WO 2004/080457 A1 | 9/2004 |
| WO | WO 2004/089470 A2 | 10/2004 |
| WO | WO 2004/089947 A2 | 10/2004 |
| WO | WO 2004/104000 A1 | 12/2004 |
| WO | WO 2005/000098 A2 | 1/2005 |
| WO | WO 2005/002577 A1 | 1/2005 |
| WO | WO 2005/009965 A1 | 2/2005 |
| WO | WO 2005/011653 A2 | 2/2005 |
| WO | WO 2005/011656 A2 | 2/2005 |
| WO | WO 2005/016915 A1 | 2/2005 |
| WO | WO 2005/023761 A2 | 3/2005 |
| WO | WO 2005/049570 | 6/2005 |
| WO | WO 2005/058869 | 6/2005 |
| WO | WO 2005/058870 | 6/2005 |
| WO | WO 2005/058871 | 6/2005 |
| WO | WO 2005/058873 | 6/2005 |
| WO | WO 2005/058874 | 6/2005 |
| WO | WO 2005/084667 A1 | 9/2005 |
| WO | WO 2005/094251 A2 | 10/2005 |
| WO | WO 2005/094834 A1 | 10/2005 |
| WO | WO 2005/103015 A1 | 11/2005 |
| WO | WO 2006/002100 A2 | 1/2006 |
| WO | WO 2006/009886 A1 | 1/2006 |
| WO | WO 2006/018279 A2 | 2/2006 |
| WO | WO 2006/018280 A2 | 2/2006 |
| WO | WO 2006/021448 A1 | 3/2006 |
| WO | WO 2006/023608 A2 | 3/2006 |
| WO | WO 2006/034315 A2 | 3/2006 |
| WO | WO 2006/038172 A1 | 4/2006 |
| WO | WO 2006/060122 A2 | 6/2006 |
| WO | WO 2006/084030 A2 | 8/2006 |
| WO | WO 2006/086445 A2 | 8/2006 |
| WO | WO 2006/099884 A1 | 9/2006 |
| WO | WO 2006/101521 A2 | 9/2006 |
| WO | WO 2006/110390 A1 | 10/2006 |
| WO | WO 2006/123121 A1 | 11/2006 |
| WO | WO 2006/130469 A1 | 12/2006 |
| WO | WO 2006/137485 A1 | 12/2006 |
| WO | WO 2007/006926 A2 | 1/2007 |
| WO | WO 2007/007069 A1 | 1/2007 |
| WO | WO 2007/019344 A1 | 2/2007 |
| WO | WO 2007/027734 A2 | 3/2007 |
| WO | WO 2007/042325 A1 | 4/2007 |
| WO | WO 2007/083119 A2 | 7/2007 |
| WO | WO 2007/087231 A2 | 8/2007 |
| WO | WO 2007/088123 A2 | 8/2007 |
| WO | WO 2007/097931 A2 | 8/2007 |
| WO | WO 2007/098418 A1 | 8/2007 |
| WO | WO 2007/126745 A2 | 11/2007 |
| WO | WO 2007/136603 A2 | 11/2007 |
| WO | WO 2007/138351 A2 | 12/2007 |
| WO | WO 2008/005937 A2 | 1/2008 |
| WO | WO 2008/019139 A2 | 2/2008 |
| WO | WO 2008/032905 A1 | 3/2008 |
| WO | WO 2008/057608 A2 | 5/2008 |
| WO | WO 2008/083027 A1 | 7/2008 |
| WO | WO 2008/094203 A2 | 8/2008 |
| WO | WO 2008/115719 A1 | 9/2008 |
| WO | WO 2008/120003 A1 | 10/2008 |
| WO | WO 2008/135141 A1 | 11/2008 |
| WO | WO 2008/139585 A1 | 11/2008 |
| WO | WO 2009/001126 A1 | 12/2008 |
| WO | WO 2009/004356 A1 | 1/2009 |
| WO | WO 2009/025781 A1 | 2/2009 |
| WO | WO 2009/025784 A1 | 2/2009 |
| WO | WO 2009/063244 A1 | 5/2009 |
| WO | WO 2009/077527 A1 | 6/2009 |
| WO | WO 2009/093032 A1 | 7/2009 |
| WO | WO 2009/112677 | 9/2009 |
| WO | WO 2009/121623 A2 | 10/2009 |
| WO | WO 2009/136889 A1 | 11/2009 |
| WO | WO 2009/153554 A1 | 12/2009 |
| WO | WO 2010/002802 A1 | 1/2010 |
| WO | WO 2010/021717 A2 | 2/2010 |
| WO | WO 2010/028761 A1 | 3/2010 |
| WO | WO 2010/042867 A2 | 4/2010 |
| WO | WO 2010/058318 A1 | 5/2010 |
| WO | WO 2010/092181 A1 | 8/2010 |
| WO | WO 2010/105243 A1 | 9/2010 |
| WO | WO 2010/108268 A1 | 9/2010 |
| WO | WO 2010/115688 A1 | 10/2010 |
| WO | WO 2010/118063 | 10/2010 |
| WO | WO 2010/129596 | 11/2010 |
| WO | WO 2010/132599 A1 | 11/2010 |
| WO | WO 2010/135524 A1 | 11/2010 |
| WO | WO 2010/151797 | 12/2010 |
| WO | WO 2011/002816 | 1/2011 |
| WO | WO 2011/002817 | 1/2011 |
| WO | WO 2011/025690 A1 | 3/2011 |
| WO | WO 2011/037793 A1 | 3/2011 |
| WO | WO 2011/050210 | 4/2011 |
| WO | WO 2011/050211 | 4/2011 |
| WO | WO 2011/060321 A1 | 5/2011 |
| WO | WO 2011/063055 A2 | 5/2011 |
| WO | WO 2011/103256 A1 | 8/2011 |
| WO | WO 2011/116282 A2 | 9/2011 |
| WO | WO 2011/137089 A1 | 11/2011 |
| WO | WO 2011/146358 A1 | 11/2011 |
| WO | WO 2012/002577 A1 | 1/2012 |
| WO | WO 2012/007861 A1 | 1/2012 |
| WO | WO 2012/007868 A2 | 1/2012 |
| WO | WO 2012/007877 A2 | 1/2012 |
| WO | WO 2012/019426 A1 | 2/2012 |
| WO | WO 2012/019427 A1 | 2/2012 |
| WO | WO 2012/056319 A1 | 5/2012 |
| WO | WO 2012/068096 A2 | 5/2012 |
| WO | WO 2012/071519 A1 | 5/2012 |
| WO | WO 2012/071684 A1 | 6/2012 |
| WO | WO 2012/080729 A2 | 6/2012 |
| WO | WO 2012/083246 | 6/2012 |
| WO | WO 2012/088314 | 6/2012 |
| WO | WO 2012/092426 A1 | 7/2012 |
| WO | WO 2012/092442 | 7/2012 |
| WO | WO 2012/092485 A1 | 7/2012 |
| WO | WO 2012/151440 A1 | 11/2012 |
| WO | WO 2012/151448 A1 | 11/2012 |
| WO | WO 2012/151450 A1 | 11/2012 |
| WO | WO 2012/151451 A1 | 11/2012 |
| WO | WO 2012/151452 A1 | 11/2012 |
| WO | WO 2012/160392 | 11/2012 |
| WO | WO 2012/160447 A1 | 11/2012 |
| WO | WO 2012/174126 | 12/2012 |
| WO | WO 2013/003249 A1 | 1/2013 |
| WO | WO 2013/003250 A1 | 1/2013 |
| WO | WO 2013/021054 A1 | 2/2013 |
| WO | WO 2013/038390 A1 | 3/2013 |
| WO | WO 2013/056153 | 4/2013 |
| WO | WO 2013/102142 A1 | 7/2013 |
| WO | WO 2013/102826 A1 | 7/2013 |
| WO | WO 2013/118805 A1 | 8/2013 |
| WO | WO 2013/126856 A1 | 8/2013 |
| WO | WO 2013/127266 A1 | 9/2013 |
| WO | WO 2013/155223 A1 | 10/2013 |

(56) References Cited

FOREIGN PATENT DOCUMENTS

| | | |
|---|---|---|
| WO | WO 2013/177224 A1 | 11/2013 |
| WO | WO 2013/184794 A2 | 12/2013 |
| WO | WO 2014/008458 A2 | 1/2014 |
| WO | WO 2014/014050 A1 | 1/2014 |
| WO | WO 2014/018355 A1 | 1/2014 |
| WO | WO 2014/023814 A1 | 2/2014 |
| WO | WO 2014/044356 A1 | 3/2014 |
| WO | WO 2014/048865 A1 | 4/2014 |
| WO | WO 2014/061031 A1 | 4/2014 |
| WO | WO 2014/062838 A2 | 4/2014 |
| WO | WO 2014/074848 | 5/2014 |
| WO | WO 2014/102817 A1 | 7/2014 |
| WO | WO 2014/118634 A1 | 8/2014 |
| WO | WO 2014/130890 A1 | 8/2014 |
| WO | WO 2014/139144 A1 | 9/2014 |
| WO | WO 2014/139325 A1 | 9/2014 |
| WO | WO 2014/139978 A1 | 9/2014 |
| WO | WO 2014/144715 A1 | 9/2014 |
| WO | WO 2014/150276 A1 | 9/2014 |
| WO | WO 2014/152588 A1 | 9/2014 |
| WO | WO 2014/172638 A2 | 10/2014 |
| WO | WO 2015/030514 A1 | 3/2015 |
| WO | WO 2015/036078 | 3/2015 |
| WO | WO 2015/042397 A1 | 3/2015 |
| WO | WO 2015/048336 A2 | 4/2015 |
| WO | WO 2015/051230 A1 | 4/2015 |
| WO | WO 2015/054555 A1 | 4/2015 |
| WO | WO 2015/078374 A1 | 6/2015 |
| WO | WO 2015/093948 A2 | 6/2015 |
| WO | WO 2015/116061 A1 | 8/2015 |
| WO | WO 2015/130915 A1 | 9/2015 |
| WO | WO 2015/144605 A1 | 10/2015 |
| WO | WO 2015/172732 A1 | 11/2015 |
| WO | WO 2015/183173 A1 | 12/2015 |
| WO | WO 2015/192701 A1 | 12/2015 |
| WO | WO 2016/005576 A1 | 1/2016 |
| WO | WO 2016/005577 A1 | 1/2016 |
| WO | WO 2016/014324 A1 | 1/2016 |
| WO | WO 2016/014522 A1 | 1/2016 |
| WO | WO 2016/021815 | 2/2016 |
| WO | WO 2016/044604 A1 | 3/2016 |
| WO | WO 2016/044629 A1 | 3/2016 |
| WO | WO 2016/044650 A1 | 3/2016 |
| WO | WO 2016/046837 A1 | 3/2016 |
| WO | WO 2016/047592 A1 | 3/2016 |
| WO | WO 2016/168647 A1 | 10/2016 |
| WO | WO 2016/181408 A2 | 11/2016 |
| WO | WO 2016/196816 | 12/2016 |
| WO | WO 2016/201227 A1 | 12/2016 |
| WO | WO 2017/006270 | 1/2017 |
| WO | WO 2017/050791 A1 | 3/2017 |
| WO | WO 2017/050792 A1 | 3/2017 |
| WO | WO 2017/191274 A2 | 11/2017 |
| WO | WO 2017/214002 A1 | 12/2017 |
| WO | WO 2018/049263 A1 | 3/2018 |
| WO | WO 2018/109277 A1 | 6/2018 |
| WO | WO 2018/175474 A1 | 9/2018 |
| WO | WO 2019/035863 A1 | 2/2019 |
| WO | WO 2019/035864 A1 | 2/2019 |
| WO | WO 2019/035865 A1 | 2/2019 |
| WO | WO 2019/099651 A1 | 5/2019 |
| WO | WO 2019/104134 | 5/2019 |
| WO | WO 2019/113359 | 6/2019 |
| WO | WO 2020/061252 | 3/2020 |
| WO | WO 2020/061255 | 3/2020 |
| WO | WO 2020/061261 | 3/2020 |
| WO | WO 2020/061378 | 3/2020 |
| WO | WO 2020/191022 | 9/2020 |

OTHER PUBLICATIONS

Abraham DJ, Mehanna AS, Wireko FC, et al. "Vanillin, a potential agent for the treatment of sickle cell anemia." *Blood*. 1991;77(6):1334-41.

Adakveo [package insert]. East Hanover, New Jersey, Novartis Pharmaceuticals Corporation (Nov. 2019), 10 pgs.

Agios First Quarter 2020 Financial Results (Apr. 30, 2020), pp. 1-22.

Agrawal RK, Patel RK, Shah V, Nainiwal L, Trivedi B. "Hydroxyurea in sickle cell disease: drug review." *Indian J Hematol Blood Transfus*. Jun. 2014, 30(2):91-96.

Agrawal, R. K. et al., "Hydroxyurea in Sickle Cell Disease: Drug Review", *Indian J. Hematol Blood Transfus*, 30(2), pp. 91-96, (Apr.-Jun. 2014).

Aiuti, A. et al, Progress and prospects: gene therapy clinical trials (part 2), *Gene Ther*, 14(22): 1555-1563 (2007).

Al-Hakim, A.K. et al., 14-3-3 cooperates with LKB1 to regulate the activity and localization of QSK and SIK, *Journal of Cell Science* 118 (23), pp. 5661-5673 (Aug. 2005).

Al-Hakim, A.K. et al., "Control of AMPK-related kinases by USP9X and atypical Lys29/Lys33-linked polyubiquitin chains", *Biochemical Journal*, 411 (2), pp. 249-260, (Feb. 2008).

Alves-Filho, J.C. & Palsson-Mcdermott, E.M., Pyruvate Kinase M2: A Potential Target for Regulating Inflammation, *Frontiers in Immunology*, 7(145): Article 145 (2016).

Ambrus, J. et al.,Studies on the vasoocclusive crisis of sickle cell disease. III. In vitro and in vivo effect of the pyrimido-pyrimidine derivative, RA-233: studies on its mechanism of action, *J Med*, 18(3-4):165-198 (1987).

Amer, J. et al., Red blood cells, platelets and polymorphonuclear neutrophils of patients with sickle cell disease exhibit oxidative stress that can be ameliorated by antioxidants, *British Journal of Haematology*, 132(1):108-113 (2006).

Andresen, C.A. et al., "Protein Interaction Screening for the Ankyrin Repeats and Suppressor of Cytokine Signaling (SOCS) Box (ASB) Family Identify Asb11 as a Novel Endoplasmic Reticulum Resident Ubiquitin Ligase", *The Journal of Biological Chemistry*, vol 289, No. 4, pp. 2043-2054, (Jan. 24, 2014).

Ataga KI, Kutlar A, Kanter J, Liles D, Cancado R, Friedrisch J, Guthrie TH, Knight-Madden J, Alvarez OA, Gordeuk VR, Gualandro S, Colella MP, Smith WR, Rollins SA, Stocker JW, Rother RP. "Crizanlizumab for the prevention of pain crises in sickle cell disease." *N Engl J Med*. Feb. 2, 2017 376(5):429-439.

Atkinson, Peter J., et al., 3,4-Dihydro-2H-benzoxazinones are 5-HT1A receptor antagonists with potent 5-HT reuptake inhibitory activity, *BioOrganic & Medicinal Chemistry Letters*, 15(3), pp. 737-741 (2005).

Austin, Nigel E., et al., "Novel 2,3,4,5-tetrahydro-1H-3-benzazepines with high affinity and selectivity for the dopamine D3 receptor", *BioOrganic & Medicinal Chemistry Letters*, 10(22), pp. 2553-2555, (2000).

Bailey, S.D. et al., "Variation at the NFATC2 Locus Increases the Risk of Thiazolidinedione-Induced Edema in the Diabetes Reduction Assessment with Ramipril and rosiglitazone Medication (DREAM) Study", *Diabetes Care*, vol. 33, No. 10, pp. 2250-2254, (Oct. 2010).

Bakshi N, Sinha CB, Ross D, Khemani K, Loewenstein G, Krishnamurti L. "Proponent or collaborative: Physician perspectives and approaches to disease modifying therapies in sickle cell disease." *PLoS One*. Jul. 20, 2017, 12(7):e0178413.

Balakin, Konstantin V. et al., Comprehensive Computational Assessment of ADME Properties using Mapping Techniques, *Current Drug Discovery Technologies*, 2(2), pp. 99-113 (2005).

Banerjee, S. et al., "Interplay between Polo kinase, LKB1-activated NUAK1 kinase, PP1β phosphatase complex and the SCFβ$^{TrCP}$ E3 ubiquitin ligase", *Biochem. J.* 461, pp. 233-245, (2014).

Banerjee, T. and Kuypers F.A., Reactive oxygen species and phosphatidylserine externalization in murine sickle red cells, *British Journal of Haematology*, 124:391-402 (2004).

Barbier AJ, Bodie S, Connor G, et al. "Safety, tolerability, pharmacokinetics and pharmacodynamics of multiple doses of AG-519, an allosteric activator of pyruvate kinase-R, in healthy subjects." *Blood*. 2016, 128:1264.

Barua, A.K., et al., Chemistry and Industry Communications to the Editor 1376 24 (Oct. 1970).

Bennett, Eric J., et al., "Dynamics of Cullin-RING Ubiquitin Ligase Network Revealed by Systematic Quantitative Proteomics", *Cell* 143, pp. 951-965, (Dec. 10, 2010).

(56) References Cited

OTHER PUBLICATIONS

Betz T, Lenz M, Joanny JF, Sykes C. "ATP-dependent mechanics of red blood cells." *Proc Natl Acad Sci USA.* 2009;106(36):15320-5.
Beutler, E. and Gelbart, T., "Estimating the prevalence of pyruvate kinase deficiency from the gene frequency in the general white population", *Blood*, 95(11): 3585-3588 (2000).
Bianchi, P. and Zanella, A., "Hematologically important mutations: red cell pyruvate kinase", (Third update), *Blood Cells Mol Dis.*, 26(1): 47-53 (2000).
Biftu, T. et al., "Omarigliptin (MK-3102): A Novel Long-Acting DPP-4 Inhibitor for Once-Weekly Treatment of Type 2 Diabetes", *Journal of Medicinal Chemistry*, 57, pp. 3205-3212, (2014).
Bouwmeester, T. et al., "A physical and functional map of the human TNF-α/NF-κB signal transduction pathway", *Nature Cell Biology*, vol. 6, No. 2, pp. 97-105, (Feb. 2004).
Boxer, M.B. et al., "Evaluation of Substituted N,N$^1$-Diarylsulfonamides as Activators of the Tumor Cell Specific M2 Isoform of Pyruvate Kinase", *J. Med. Chem.*, 53: pp. 1048-1055 (2010).
Brajenovic, M. et al., "Comprehensive Proteomic Analysis of Human Par Protein Complexes Reveals an Interconnected Protein Network", *The Journal of Biological Chemistry*, vol. 275, No. 13, pp. 12804-12811 (Mar. 2004).
Brehme, M. et al., "Charting the molecular network of the drug target Bcr-Abl", *PNAS*, vol. 106, No. 18, pp. 7414-7419, (May 2009).
Bridges, C.R., et al., "USP9X deubiquitylating enzyme maintains RAPTOR protein levels, mTORC1 signalling and proliferation in neural progenitors", *Scientific Reports* 7:391, pp. 1-15, (Mar. 2017).
Brown, R. Clark, et al., "FT-4202, an Allosteric Activator of Pyruvate Kinase-R, Demonstrates Proof of Mechanism and Proof of Concept after a Single Dose and after Multiple Daily Doses in a Phase 1 Study of Patients with Sickle Cell Disease," *Blood* (2020) 136 (Supplement 1):19-20, Nov. 4, 2020.
Brown, R. Clark, et al., "FT-4202, an Allosteric Activator of Pyruvate Kinase-R, Demonstrates Proof of Mechanism and Proof of Concept after a Single Dose and after Multiple Daily Doses in a Phase 1 Study of Patients with Sickle Cell Disease," *ASH* 2020, Dec. 7, 2020.
Budzikiewicz, Herbert et al., "Vincetene, a benzopyrroloisoquinoline alkaloid, from *Cynanchum vincetoxicum* (L.) Pers. (Asclepiadaceae)", Liebigs Annalen Der Chemie, (8), pp. 1212-1231 (1979).
Buontempo P, Jubin RG, Buontempo C, Real R, Kazo F, O'Brien S, Adeel F, Abuchowski A. "Pegylated carboxyhemoglobin bovine (SANGUINATE) restores RBCs roundness and reduces pain during a sickle cell vaso-occlusive crisis." *Blood.* 2017, 130:969.
Cabrales, P. et al., "A look inside the mechanistic black box: Are red blood cells the critical effectors of RRx-001 cytotoxicity?", *Med Oncol.*, 33(7):63 (2016).
CAS Registry No. 1208929-16-1, Tert-Butyl 1H,2H,3H,4H,5H,6H-Pyrrolo[3,4-C]Pyrrole-2-Carboxylate Hydrochloride (Mar. 11, 2010).
Castilhos, L. et al., "Altered E-NTPDase/E-ADA activities and CD39 expression in platelets of sickle cell anemia patients", *Biomed Pharmacother.*, 79:241-246 (2016).
Castilhos, L. et al., "Increased oxidative stress alters nucleosides metabolite levels in sickle cell anemia", *Redox Rep.*, 22(6):451-459 (2017).
Castilhos, L. et al., "Sickle cell anemia induces changes in peripheral lymphocytes E-NTPDase/E-ADA activities and cytokines secretion in patients under treatment", *Biomedicine & Pharmacotherapy* 73 (2015), pp. 102-108.
Castro, O., Viability and function of stored sickle erythrocytes, *Transfusion*, 20(6):695-703 (1980).
Cazzola, M., Pyruvate kinase deficiency, Haematologica, 90(1): 1-2 (2005).
Charache, S. et al., Effect of 2,3-Diphosphateglycerate on oxygen affinity of blood in sickle, Cell Anemia, Journal of Clinical Investigation, 49(4):806-812 (1970).

Chaudhary, Neelam & Maddika, Subbareddy, "WWP2-WWP1 Ubiquitin Ligase Complex Coordinated by PPM1G Maintains the Balance Between Cellular p73 and ΔNp73 Levels", Mol. Cell. Biol. (Oct. 2014).
Chen, Yue et al.—Preclinical Pharmacokinetic/Pharmacodynamic Relationships for AG-348, an Investigational Small-Molecule Activator of Pyruvate Kinase, European Hematology Association, Jun. 13, 2015.
Cheung, Yiu-Yin et al., Solution-Phase Parallel Synthesis and SAR of Homopiperazinyl Analogs as Positive Allosteric Modulators of MGlu$_4$, ACS Comb Sci. 13(2), pp. 159-165, (Mar. 2011).
Chiosis et al., Development of a Purine-Scaffold Novel Class of Hsp90 Binders that Inhibit the Proliferation of Cancer Cells and Induce the Degradation of Her2 Tyrosine Kinase, BioOrganic & Medicinal Chemistry, vol. 10, Iss 11, (Nov. 2002), pp. 3555-3564.
Chiou WL, Barve A. "Linear correlation of the fraction of oral dose absorbed of 64 drugs between humans and rats." *Pharm Res.* Nov. 1998, 15(11):1792-5.
Chonat, S. et al.,—Improvement in Red Blood Cell Physiology in Children With Sickle Cell Anemia Receiving Voxelotor—Childrens Healthcare of Atlanta (Dec. 2019).
Choudhury, N.R., et al., "RNA-binding activity of TRIM25 is mediated by its PRY/SPRY domain and is required for ubiquitination", BMC Biology 15:105, pp. 1-20, (2017).
Christensen, R.D. et al., Siblings with Severe Pyruvate Kinase Deficiency and a Complex Genotype, American Journal of Medical Genetics, Part A, (2016), pp. 2449-2452.
Chubukov V, Johnson K, Kosinski PA, et al. "Characterization of metabolic response to AG-348, an allosteric activator of red cell pyruvate kinase, in healthy volunteers and pyruvate kinase deficiency patients." Poster presented at: 58th American Society of Hematology Annual Meeting and Exposition; Dec. 4, 2016; San Diego, California. http://investor.agios.com/staticfiles/e1e9fd70-c84b-4472-bff3-bef0ecf05482 Accessed Jul. 28, 2017.
Chung, J.Y.L. et al., "Evolution of a Manufacturing Route to Omarigliptin, a Long-Acting DPP-4 Inhibitor for the Treatment of Type 2 Diabetes", Organic Process Research & Development, 19, pp. 1760-1768, (2015).
Clinical Trial Study—NCT02604433—U.S. National Library of Medicine, an Efficacy and Safety Study of Luspatercept (ACE-536) Versus Placebo in Adults Who Require Regular Red Blood Cell Transfusions Due to Beta (β) Thalassemia (BELIEVE), Submitted Date: Nov. 13, 2015, 24 pgs.
ClinicalTrials.gov, NCT03815695, (v1)—U.S. National Library of Medicine, "A SAD/MAD to Assess the Safety, Pharmacokinetics and Pharmacodynamics of FT-4202 in Healthy Volunteers and Sickle Cell Disease Patients" (Jan. 22, 2019).
Clinical Trials Study, NCT03815695, (v2)—U.S. National Library of Medicine, "A SAD/MAD to Assess the Safety, Pharmacokinetics and Pharmacodynamics of FT-4202 in Healthy Volunteers and Sickle Cell Disease Patients," (Mar. 13, 2019) pp. 1-5.
ClinicalTrials.gov, NCT03815695, (v3)—U.S. National Library of Medicine, "A SAD/MAD to Assess the Safety, Pharmacokinetics and Pharmacodynamics of FT-4202 in Healthy Volunteers and Sickle Cell Disease Patients" (Sep. 16, 2019).
Clinical Trial Study—NCT03815695, (v4)—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Sep. 19, 2019 (v4), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Sep. 23, 2019 (v5), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Oct. 9, 2019 (v6), 5 pgs.
Clinical Trial Study NCT03815695—U.S. National Library of Medicine, "A SAD/MAD to Assess the Safety, Pharmacokinetics

(56) References Cited

OTHER PUBLICATIONS and Pharmacodynamics of FT-4202 in Healthy Volunteers and Sickle Cell Disease Patients," Submitted Date: Oct. 10, 2019 (v7), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Nov. 27, 2019 (v8), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Jan. 15, 2020 (v9), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Jan. 16, 2020 (v10), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Feb. 21, 2020 (v11), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Apr. 1, 2020, (v12), 12 pgs.
ClinicalTrials.gov, NCT03815695 (v13), "A SAD/MAD to Assess the Safety, Pharmacokinetics and Pharmacodynamics of FT-4202 in Healthy Volunteers and Sickle Cell Patients," Jun. 15, 2020.
ClinicalTrials.gov, NCT03815695 (v14), "A SAD/MAD to Assess the Safety, Pharmacokinetics and Pharmacodynamics of FT-4202 in Healthy Volunteers and Sickle Cell Patients," Jul. 17, 2020.
ClinicalTrials.gov, NCT03815695 (v15), "A SAD/MAD to Assess the Safety, Pharmacokinetics and Pharmacodynamics of FT-4202 in Healthy Volunteers and Sickle Cell Patients," Aug. 19, 2020.
ClinicalTrials.gov, NCT03815695 (v16), "A SAD/MAD to Assess the Safety, Pharmacokinetics and Pharmacodynamics of FT-4202 in Healthy Volunteers and Sickle Cell Patients," Sep. 1, 2020.
ClinicalTrials.gov, NCT03815695 (v17), "A SAD/MAD to Assess the Safety, Pharmacokinetics and Pharmacodynamics of FT-4202 in Healthy Volunteers and Sickle Cell Patients," Sep. 18, 2020.
ClinicalTrials.gov, NCT03815695 (v18), "A SAD/MAD to Assess the Safety, Pharmacokinetics and Pharmacodynamics of FT-4202 in Healthy Volunteers and Sickle Cell Patients," Oct. 15, 2020.
ClinicalTrials.gov, NCT03815695 (v19), "A SAD/MAD to Assess the Safety, Pharmacokinetics and Pharmacodynamices of FT-4202 in Healthy Volunteers and Sickle Cell Patients," Study Record Versions 19—Dec. 24, 2020.
ClinicalTrials.gov, NCT03815695 (v20), "A SAD/MAD to Assess the Safety, Pharmacokinetics and Pharmacodynamices of FT-4202 in Healthy Volunteers and Sickle Cell Patients," Study Record Versions 20, Jan. 8, 2021.
ClinicalTrials.gov, NCT04624659 (v1), "A Study of FT-4202 in Adults and Adolescents With Sickle Cell Disease," Study Record Version 1—Nov. 5, 2020.
ClinicalTrials.gov, NCT04624659 (v2), "A Study of FT-4202 in Adults and Adolescents With Sickle Cell Disease," Study Record Version 2—Nov. 10, 2020.
ClinicalTrials.gov, NCT04624659 (v3), "A Study of FT-4202 in Adults and Adolescents With Sickle Cell Disease," Study Record Versions 3—Dec. 10, 2020.
ClinicalTrials.gov, NCT04624659 (v4), "A Study of FT-4202 in Adults and Adolescents With Sickle Cell Disease," Study Record Versions 4, Dec. 28, 2020.
ClinicalTrials.gov, NCT04624659 (v5), "A Study of FT-4202 in Adults and Adolescents With Sickle Cell Disease," Study Record Versions 5, Jan. 7, 2021.
ClinicalTrials.gov, NCT04624659 (v6), "A Study of FT-4202 in Adults and Adolescents With Sickle Cell Disease," Study Record Versions 6, Jan. 14, 2021.
ClinicalTrials.gov, NCT04624659 (v7), "A Study of FT-4202 in Adults and Adolescents With Sickle Cell Disease," Study Record Versions 7, Feb. 8, 2021.
Cloutier, P. et al., "R2TP/Prefoldin-like component RUVBL1/RUVBL2 directly interacts with ZNHIT2 to regulate assembly of U5 small nuclear ribonucleoprotein", Nature Communications, pp. 1-14 (May 2017).
Cole, D.C. et al., Conformationally Constrained N1-arylsulfonyltryptamine derivatives as 5-HT6 receptor antagonists, BioOrganic & Medicinal Chemistry Letters, vol. 15, No. 21, (Nov. 1, 2005), pp. 4780-4785.
Cox, J.L., et al., "The SOX2-Interactome in Brain Cancer Cell Identifies the Requirement of MSI2 and USP9X for the Growth of Brain Tumor Cell", PLoS One, vol. 8, Issue 5, pp. 1-13, (May 2013).
Croasdell, G., European Hematology Association—20th Annual Congress (Jun. 11-14, 2015—Vienna, Austria) Meeting Report, Drugs of Today (2015), 51(7),I pp. 441-445.
Das, A. et al., "USP9X counteracts differential ubiquitination of NPHP5 by MARCH7 and BBS11 to regulate ciliogenesis", PLoS Genetics, pp. 1-24, (May 12, 2017).
Davis, Z.H., et al., "Global Mapping of Herpesvirus-Host Protein Complexes Reveals a Transcription Strategy for Late Genes", Molecular Cell 57, pp. 349-360; (Jan. 22, 2015).
De Furia, F. et al., The effects of cyanate in vitro on red blood cell metabolism and function in sickle cell anemia, J Clin Invest., 51(3):566-574 (1972).
De Jong, K. and Kuypers, F., Sulphydryl modifications alter scramblase activity in murine sickle cell disease, British Journal of Haematology, 133(4):427-432 (2006).
De Rosa MC, Carelli Alinovi C, Galtieri A, Russo A, Giardina B. "Allosteric properties of hemoglobin and the plasma membrane of the erythrocyte: New insights in gas transport and metabolic modulation." IUBMB Life. 2008, 60(2):87-93.
Diez, A. et al., Life-threatening nonspherocytic hemolytic anemia in a patient with a null mutation in the PKLR gene and no compensatory PKM gene expression, Blood, 106:1851 (2005).
Diez-Silva M, Dao M, Han J, Lim CT, Suresh S. "Shape and biomechanical characteristics of human red blood cells in health and disease." MRS Bull. May 2010, 35(5):382-8.
Drissi, R. et al., "Quantitative Proteomics Reveals Dynamic Interactions of the Mini chromosome Maintenance Complex (MCM) in the Cellular Response to Etoposide Induced DNA Damage", Molecular & Cellular Proteomics, pp. 2002-2013, (2015).
Droxia [package insert]. Princeton, New Jersey, Bristol-Myers Squibb Company, (Dec. 2017), 28 pgs.
Droxia [package insert]. Princeton, New Jersey, Bristol-Myers Squibb Company (Dec. 2019), 25 pgs.
Dupont, S. et al., "FAM/USP9x, a Deubiquitinating Enzyme Essential for TGFβ Signaling, Controls Smad4 Monoubiquitination", Cell, 136, pp. 123-135, (Jan. 9, 2009).
Dzandu JK, Johnson RM. "Membrane protein phosphorylation in intact normal and sickle cell erythrocytes." J Biol Chem. Jul. 10, 1980 255(13):6382-6.
El-Sharief, A.M., et al., Some halogenated sulfonamides with biological interest, Journal of the Indian Chemical Society, vol. 61, No. 6, (1984), pp. 537-543.
Emam, H.A., et al., Heterocyclization of sulfamido chalcones to pyrazoline, cyanopyridone, nicotinonitrile and hydrobenzo [1,2-c] pyrazole derivatives, Journal of the Serbian Chemical Society, vol. 62, No. 7, (1997), Abstract only.
Endari [package insert]. Torrance, California: Emmaus Medical, Inc., (Jul. 2017), 8 pgs.
Endari [package insert]. Torrance, California, Emmaus Medical, Inc., (Nov. 2019), 10 pgs.
Ernst, A. et al., "A Strategy for Modulation of Enzymes in the Ubiquitin System", Science, 339, pp. 1-15, (Feb. 2013).
Estepp, et al., Phase 1 Single (SAD) and Multiple Ascending Dose (MAD) Study of the Safety, Pharmacokinetics (PK) and Pharmacodynamics (PD) of FT-4202, A PKR-Activator, in Healthy

(56) References Cited

OTHER PUBLICATIONS and Sickle Cell Disease Subjects, Abstract, e-Poster, European Hematology Association Open Access Library, Presentation EHA25, (May 14, 2020), 2 pgs.
Estepp, et al., Phase 1 Single (SAD) and Multiple Ascending Dose (MAD) Study of the Safety, Phyarmacokinetics (PK) and Pharmacodynamics (PD) of FT-4202, a PKR Activator, in Healthy and Sickle Cell Disease Subjects, Poster, EP1531, (Jun. 12, 2020), 1 pg.
Estepp, J.H. et al., A clinically meaningful fetal hemoglobin threshold for children with sickle cell anemia during hydroxyurea therapy, Am J Hematol., 92:1333-1339 (2017).
Estepp, Jeremie H., et al., "Phase 1 Single (SAD) and Multiple Ascending Dose (MAD) Study of the Safety, Pharmacokinetics (PK) and Pharmacodynamics (PD) of FT-4202, a PKR Activator, in Healthy Volunteers and Patients with Sickle Cell Disease," Virtual meeting [poster EP1531] presented at the $25^{th}$ Congress of the European Hematology Association; Jul. 11-21, 2020.
European Hematology Association HemaSphere Abstract Book, $15^{th}$ Annual Sickle Cell & Thalassaemia & $1^{st}$ EHA European Sickle Cell Conference, Oct. 26-31, 2020.
Fioravanti, R., et al., Synthesis and Biological Evaluation of N-substituted -3, 5-diphenyl—2-pyrazoline derivatives as cyclooxygenase (COX-2) inhibitors, European Journal of Medicinal Chemistry, vol. 45, No. 12, (Dec. 1, 2010), pp. 6135-6138, XP027526583.
Fitch, R. W. et al., Phantasmidine: An Epibatidine Congener from the Ecuadorian Poison Frog Epipedobates anthonyi', Journal of Natural Products (2010), vol. 73, No. 3, pp. 331-337.
Fleischhacker, W., et al., "Heterocyclic fused naphthalene systems from thebaine. 1", Liebigs Annalen Der Chemie, (5), pp. 844-851, (1983).
Fogeron, M.L. et al., "LGALS3BP regulates centriole biogenesis and centrosome hypertrophy in cancer cells", Nature Communications, 4:1531, pp. 1-14; (2013).
Forma Therapeutics, Press Release, "Forma Therapeutics Presents Clinical Proof-of-Concept Data at the $62^{nd}$ Annual ASH Meeting Supporting the Potential of its Novel Investigational PKR Activator, FT-4202, to Treat Sickle Cell Disease (SCD)" (Dec. 7, 2020).
Forma Therapeutics, Inc., Press Release—"Forma Therapeutics Announces Positive FT-4202 600 mg Multiple Ascending Dose Cohort Data Supporting the Doses Being Evaluated in Phase 2/3 Registrational Trial, Called the Hibiscus Study", Mar. 30, 2021—2 pgs.
Frost, David A., et al., "Naturally occurring compounds related to phenalenone. V. Synthetic approaches to structures based on 8,9-dihydro-8,8,9-trimethylphenaleno [1,2-b] furan-7-one", Journal of the Chemical Society, Perkin Transactions 1: Organic and Bio-Organic Chemistry (1972-1999), pp. 2159-2169.
Gaudet, P. et al., "Phylogenetic-based propagation of functional annotations within the Gene Ontology consortium", vol. 12, No. 5, pp. 449-462; (Aug. 2011).
Giannone, R.J., et al., "The Protein Network Surrounding the Human Telomere Repeat Binding Factors TRF1, TRF2, and POT1", PLoS One, vol. 5, Issue 8, pp. 1-10, (Aug. 2010).
Gizi, A. et al., Assessment of oxidative stress in patients with sickle cell disease: The glutathione system and the oxidant-antioxidant status, Blood Cells Mol Dis., 46(3):220-225 (2011).
Gladwin, M., Adenosine recepter crossroads in sickle cell disease, Nature Medicine, 17(1):38-40, (2011).
Glombitza, S. et al., Adenosine causes cAMP-dependent activation of chick embryo red cell carbonic anhydrase and 2,3-DPG synthesis, American Journal of Physiology, 271(4):973-81 (1996).
Gomez-Bougie, P. et al., "Noxa controls Mule-dependent Mcl-1 ubiquitination through the regulation of the Mcl-1/USP9X interaction", Biochemical and Biophysical Research Communications 413, pp. 460-464, (2011).
Goncharov, T. et al., "OTUB1 modulates c-IAP1 stability to regulate signaling pathways", The EMBO Journal 32, No. 8, pp. 1103-1114, (2013).

Grace RF, Rose C, Layton DM, Yaish HM, Barcellini W, Galactéros F, Morton DH, Ravindranath Y, Kuo KHM, van Beers EJ, Kwiatkowski JL, Silver BA, Merica E, Kung C, Cohen M, Yang H, Hixon J, Kosinski PA, Silver L, Dang L, Yuan Z, Barbier AJ, Glader B. "Effects of AG_348, a pyruvate kinase activator, on anemia and hemolysis in patients with pyruvate kinase deficiency: Data from the DRIVE PK study". Blood. 2016, 128:402.
Grace, et al., Safety and Efficacy of Mitapivat in Pyruvate Kinase Deficiency, N. Engl. J. Med. 381, 10, (Sep. 5, 2019), p. 933-944.
Grasso, D. et al., "Zymophagy, a Novel Selective Autophagy Pathway Mediated by VMP1-USP9x-p62, Prevents Pancreatic Cell Death", The Journal of Biological Chemistry, vol. 286, No. 10, pp. 8308-8324, (Mar. 2011).
Greco, T.M. et al., "Nuclear Import of Histone Deacetylase 5 by Requisite Nuclear Localization Signal Phosphorylation", Molecular & Cellular Proteomics 10: , pp. 1-15, (2011).
Grou, C.P., et al., "Identification of ubiquitin-specific protease 9X (USP9X) as a deubiquitinase acting on the ubiquitin-peroxin 5 (PEX5) thioester conjugate", J. Biol. Chem., pp. 1-24; (Feb. 27, 2012).
Habata, S. et al., "BAG3-mediated Mcl-1 stabilization contributes to drug resistance via interaction with USP9X in ovarian cancer", International Journal of Oncology 49: pp. 402-410, (2016).
Han, K.J. et al., "Ubiquitin-specific Protease 9x Deubiquitinates and Stabilizes the Spinal Muscular Atrophy Protein—Survival Motor Neuron", J. Biol. Chem., pp. 1-22, (Oct. 2012).
Hanson, D. et al., "Identifying biological pathways that underlie primordial short stature using network analysis", Journal of Molecular Endocrinology, pp. 333-344, (2014).
Harada, R. et al., "Structure of pristimerine, a quinonoid triterpene", Tetrahedron Letters, pp. 603-607, (1962).
Harayama, Takashi et al., "Novel synthesis of naphthobenzazepines from N-bromobenzylnaphthylamines by regioselective C—H activation utilizing the intramolecular coordination of an amine to Pd", Synlett, (8), pp. 1141-1144, (2003).
Hauri, S. et al., "Interaction proteome of human Hippo signaling: modular control of the co-activator YAP1", Molecular Systems Biology, 9: 713, pp. 1-16 (Nov. 2013).
Havugimana, P. et al., "A Census of Human Soluble Protein Complexes", Cell 150, pp. 1068-1081, (Aug. 2012).
Hebbel RP, Eaton JW, Balasingam M, Steinberg MH. "Spontaneous oxygen radical generation by sickle erythrocytes." J Clin Invest. 1982, 70(6):1253-9.
Hein, M.Y., et al., "A Human Interactome in Three Quantitative Dimensions Organized by Stoichiometries and Abundances", Cell 163, pp. 712-723, (Oct. 2015).
Hierso, R. et al., Effects of oxidative stress on red blood cell rheology in sickle cell patients, British Journal of Haematology, 166(4):601-606 (2014).
Homan, C.C. et al., "Mutations in USP9X Are Associated with X-linked Intellectual Disability and Disrupt Neuronal Cell Migration and Growth", The American Journal of Human Genetics 94, pp. 470-478, (Mar. 2014).
Hoppe CC, Inati AC, Brown C, et al. "Initial results from a cohort in a phase 2a study (GBT440-007) evaluating adolescents with sickle cell disease treated with multiple doses of GBT440, a HbS polymerization inhibitor." Blood. 2017:130(Suppl 1): 689.
Husain, M.I., et al., Synthesis of some new N-[4-(acetyl/phenyl-5-arylpyrazolin-3-yl)phenyl]arylsulfonamides as oral hypoglycemic agents, Indian Drugs, vol. 24, No. 4, (1987), Abstract only.
Huttlin, E. L., et al., "The BioPlex Network: A Systematic Exploration of the Human Interactome", Cell 162, pp. 425-440, (Jul. 2015).
Huttlin, E.L., et al., "Architecture of the human interactome defines protein communities and disease networks", Nature, pp. 1-35, (May 2017).
Hydrea [package insert]. Princeton, New Jersey, Bristol-Myers Squibb Company (Jul. 2019), 29 pgs.
Imamura K, Tanaka T. "Multimolecular forms of pyruvate kinase from rat and other mammalian tissues. I Electrophoretic studies." J Biochem. 1972, 71:1043-51.
Imamura K, Tanaka T. "Pyruvate kinase isozymes from rat." Methods Enzymol. 1982, 90:150-65.

(56) References Cited

OTHER PUBLICATIONS

International Search Report and Written Opinion for PCT/US2019/051831, dated Dec. 6, 2019 (Dec. 6, 2019).
Iwasaki, Tameo et al., "Novel Selective PDE IV Inhibitors as Antiasthmatic Agents. Synthesis and Biological Activities of a Series of 1-Aryl-2,3-bis (hydroxymethyl) naphthalene Lignans", Journal of Medicinal Chemistry (1996), pp. 2696-2704.
Jendralla, H. et al., Synthesis of 1,2,3,4,5,6-Hexahydropyrrolo[3,4-c]pyrrole dihydrobromide and 1,2,3,5-Tetrahydro-2-[(4-Methyl-Phenyl)Sulfonyl]Pyrrolo[3,4-c]Pyrrole, Heterocycles, 41(6): 1291-1298 (1995).
Jin, Y. et al., Effects of gamma irradiation on red cells from donors with sickle cell trait, Transfusion, 37(8):804-808 (1997).
Johansen, L.D., et al., "IKAP localizes to membrane ruffles with filamin A and regulates actin cytoskeleton organization and cell migration", Journal of Cell Science 121, pp. 854-864, (Dec. 2007).
Jones, M.H., et al., "The *Drosophila* developmental gene fat facets has a human homologue in Xp11.4 which escapes X-inactivation and has related sequences on Yq11.2", Human Molecular Genetics, vol. 5, No. 11, pp. 1695-1701, (Aug. 1996).
Jorgensen, Eugene C., et al., "Thyroxine analogs. 20. Substituted 1- and 2-naphthyl ethers of 3,5-diiodotyrosine", Journal of Medicinal Chemistry 14(11), pp. 1023-1026, (1971).
Joshi, B., et al., Indian J. Chem., Sect. B (1983), 22B(2), Abstract only. Chemical Abstract No. 99:105146
Joshi, P., et al., "The functional interactome landscape of the human histone deacetylase family", Molecular Systems Biology 9, 672, (2013).
Kalai, T. et al., Synthesis of Pyrroline Nitroxide Annulated Carbocycles and Heterocycles, Synthesis No. 6, pp. 831-837 (2000).
Kalfa, et al., FORMA Therapeutics, Inc., Watertown, MA, Power Pointe Presentation, Dated Nov. 6, 2019 , Phase 1 Single and Multiple Ascending Dose Study of the Safety, Tolerability, Pharmacokinetics and Pharmacodynamics of FT-4202, an Allosteric activator of Pyruvate Kinase-R, in Healthy and Sickle Cell Disease Subjects, 15 pgs.
Kalfa, T. A. et al., "Phase 1 Single (SAD) and Multiple Ascending Dose (MAD) Study of the Safety, Pharmacokinetics (PK) and Pharmacodynamics (PD) of FT-4202, a PKR Activator, in Healthy and Sickle Cell Diseases Subjects", JSCDH-D-20-0053, vol. VII, Pub. Date: Jun. 12, 2020; pp. 83-84.
Kalfa, T. et al., "Phase 1 Single (SAD) and Multiple Ascending Dose (MAD) Study of the Safety, Pharmacokinetics (PK) and Pharmacodynamics (PD) of FT-4202, a PKR Activator, in Healthy and Sickle Cell Diseases Subjects", $14^{th}$ Annual Sickle Cell Disease Research and Educational Symposium/$43^{rd}$ National Sickle Cell Disease Scientific Meeting (Sep. 23-25, 2020).
Kalfa, T.A. et al., "616 Phase 1 Single (SAD) and Julotiple Ascending Dose (MAD) Studies of the Safety, Tolerability, Pharmacokinetics (PK) and Pharmacodynamics (PD) of FT-4202, an Allosteric Activator of Pyruvate Kinase-R, in Healthy and Sickle Cell Disease Subjects", (Nov. 2019).
Kaltenbach, L.S., et al., "Huntingtin Interacting Proteins Are Genetic Modifiers of Neurodegeneration", PLoS Genetics, vol. 3, Issue 5, pp. 689-708, (May 2007).
Kasturi, Tirumalai R., et al., "Reactions of tetrahalo-1,2-benzoquinones. III. Reaction of tetrachloro-1,2-benzoquinone withtetralones and naphthols: pathway to the condensates", Journal of the Chemical Society C: Organic, (9), pp. 1257-1259, (1970).
Katzenellenbogen, R.A., et al., "NFX1-123 and Poly(A) Binding Proteins Synergistically Augment Activation of Telomerase in Human Papillomavirus Type 16 E6-Expressing Cells", Journal of Virology, vol. 81, pp. 3786-3796, (Apr. 2007).
Khafagy, M.M., Synthesis of some pyrimidine and pyrazoline derivatives, Al-Azhar Bulletin of Science, vol. 3, No. 1, (1992), Abstract only.
Kharalkar, S.S. et al., Identification of Novel Allosteric Regulators of Human-Erythrocyte Pyruvate Kinase, Chemistry & Biodiversity, vol. 4, pp. 2603-2617 (Feb. 2007).

Kim H, Kosinski P, Kung C, Dang L, Chen Y, Yang H, Chen YS, Kramer J, Liu G. "A fit-for-purpose LC-MS/MS method for the simultaneous quantitation of ATP and 2,3-DPG in human K2EDTA whole blood." J Chromatogr B Analyt Technol Biomed Life Sci. Sep 1, 2017 1061-1062:89-96.
Kim J, Lee H, Shin S. "Advances in the measurement of red blood cell deformability: A brief review." J Cell Biotech. 2015;1:63-79.
Kim, M., et al., "Role of Angiomotin-like 2 mono-ubiquitination on YAP inhibition", EMBO reports, vol. 17, No. 1., pp. 64-78, (Nov. 23, 2015).
Kimura, K., et al., "Diversification of transcriptional modulation: Large-scale identification and characterization of putative alternative promoters of human genes", Genome Research 16, pp. 55-65, (2006).
Kirli, K., et al., "A deep proteomics perspective on CRM1-mediated nuclear export and nucleocytoplasmic partitioning", eLife, pp. 1-28; (2015).
Knauff, E.A.H., et al., "Genome-wide association study in premature ovarian failure patients suggests ADAMTS19 as a possible candidate gene", Human Reproduction, vol. 24, No. 9, pp. 2372-2379, (2009).
Kodama, K. et al., Solvent-induced dual chirality switching in the optical resolution of tropic acid via diastereomeric salt formation with (1R,2S)-2-amino-1,2-diphenylethanol, Tetrahedron 70:7923-7928 (2014).
Konstantinidis, Diamantis G., et al., "Ex-Vivo FT-4202 Treatment Improves Hemoglobin Oxygen Affinity and Membrane Health in Red Blood Cells of Patients with Hemoglobin SS and Hemoglobin SC Disease Irrespective of Prior Hydroxyurea Use," Blood (2020) 136 (Supplement1):23-24, Nov. 4, 2020.
Konstantinidis, Diamantis G., et al., "Ex-Vivo FT-4202 Treatment Improves Hemoglobin Oxygen Affinity and Membrane Health in Red Blood Cells of Patients with Hemoglobin SS and Hemoglobin SC Disease Irrespective of Prior Hydroxyurea Use," Presented at the $62^{nd}$ American Society of Hematology (ASH) Annual Meeting, Dec. 5, 2020.
Kristensen, A.R., Gsponer, J. and Foster, L.J., "A high-throughput approach for measuring temporal changes in the interactome", Nat Methods, 9(9), pp. 1-12, (2012).
Kuehl, G. et al., In vitro interactions of 51Cr in human red blood cells and hemolysates, Vox Sang., 40(4):260-272 (1981).
Kung C, Hixon J, Kosinski PA, et al. "AG-348 enhances pyruvate kinase activity in red blood cells from patients with pyruvate kinase deficiency." Blood. 2017;130(11):1347-1356.
Kurita, R. et al., Establishment of Immortalized Human Erythroid Progenitor Cell Lines Able to Produce Enucleated Red Blood Cells, PLoS One, vol. 8, Iss.3, pp. 1-15 (Mar. 2013).
Kushwaha, D., et al., "USP9X inhibition promotes radiation-induced apoptosis in non-small cell lung cancer cells expressing mid-to-high MCL1", Cancer Biology & Therapy 16:3, pp. 392-401, (Mar. 2015).
Kwasna, D., et al., "Discovery and Characterization of ZUFSP/ZUP1, a Distinct Deubiquitinase Class Important for Genome Stability", Molecular Cell 70, pp. 150-164, (2018).
Le Quesne, P.W. et al., One-Step Preparation of Tetrakis(bromomethyl)ethylene from Pinacolyl Alcohol, J. Org. Chem., 40(1): 142-143 (1975).
Le, Kha et al., Population pharmacokinetics and pharmacodynamics of AG-519, a pyruvate kinase activator for the treatment of pyruvate kinase deficiency, in human healthy volunteers, Agios Pharma—1263 Poster,—58th American Society of Hematology Annual Meeting and Exposition, Dec. 3-6, 2016—San Diego, CA.
Le, Kha et al., Population pharmacokinetics and pharmacodynamics of AG-348 in healthy human volunteers guide dose selection for the treatment of pyruvate kinase deficiency, Agios Pharma—3336 Poster,—57th American Society of Hematology Annual Meeting and Exposition, Dec. 5-8, 2015—Orlando, FL.
Lehrer-Graiwer J, Howard J, Hemmaway CJ, et al. "Long-term dosing in sickle cell disease subjects with GBT440, a novel HbS polymerization inhibitor." Blood, 2016:128(22): 2488.

(56) References Cited

OTHER PUBLICATIONS

Lehrer-Graiwer, Josh et al., Long-Term Dosinig in Sickle Cell Disease Subjects with GBT440, a Novel HbS Polymerization Inhibitor, blood, 114, Hemoglobinopathies, Excluding Thalassemia—Clinical Poster II, Dec. 2, 2016.
Lenihan, J.A., Saha, Orthis, and Young P.W., "Proteomic analysis reveals novel ligands and substrates for LNX1 E3 ubiquitin ligase", PLoS One, pp. 1-18; (Nov. 2017).
Li, X., et al., "Defining the protein-protein interaction network of the human protein tyrosine phosphatase family", The American Society for Biochemistry and Molecular Biology, Inc., pp. 1-54, (2016).
Litinov RI, Weisel JW. "Role of red blood cells in haemostasis and thrombosis." ISBT Sci Ser. Feb. 2017, 12(1):176-183.
Liu, X.H., et al., European Journal of Cancer, vol. 31A, No. 6, pp. 953-963, (1995).
Llauger et al., "Evaluation of 8-Arylsulfanyl, 8-Arylsulfoxyl, and 8-Arylsulfonyl Adenine Derivatives as Inhibitors of the Heat Shock Protein 90", J. Med. Chem., 48 (8), pp. 2892-2905, (Mar. 25, 2005).
Llauger et al., "Synthesis of 8-arylsulfoxyl/sulfonyl adenines", Tetrahedron Letters, vol. 45, Issue 52, (Dec. 20, 2004), pp. 9549-9552.
Lochmatter, C. et al., Integrative phosphoproteomics links IL-23R signalling with metabolic adaption in lymphocytes, Scientific Reports, 6:24491 (2016).
Lockwood, S. et al., Endothelium-derived nitric oxide production is increased by ATP released from red blood cells incubated with hydroxyurea, Nitric Oxide, 38:1-7 (2014).
Loriga G. et al., Synthesis of 3,6-diazabicyclo [3.1.1]heptanes as novel ligands for the opioid receptors, Bioorganic & Medicinal Chemistry, Pergamon, GB, vol. 14, No. 3, pp. 676-691, (Feb. 1, 2006).
Lu, L., et al., "The HECT Type Ubiquitin Ligase NEDL2 Is Degraded by Anaphase-promoting Complex/Cyclosome (APC/C)-Cdh1, and Its Tight Regulation Maintains the Metaphase to Anaphase Transition", The Journal of Biological Chemistry, vol. 288, No. 50, pp. 35637-35650; (Dec. 2013).
Lucas, et al., "Facile Synthesis of a Library of 9-Alkyl-8-benzyl-9H-purin-6-ylamine Derivatives", J. Comb. Chem., 3 (6), pp. 518-520, (Sep. 21, 2001).
MacDonald, Gregor J., et al, "Design and Synthesis of trans-3-(2-(4-((3-(3-(5-Methyl-1,2,4-oxadiazolyl))-phenyl(carboxamido)cyclohexyl)ethyl)-7-methylsulfonyl-2,3,4,5-tetrahydro-1H-3-benzazepine (SB-414796): A Potent and Selective Dopamine D3 Receptor Antagonist", Journal of Medicinal Chemistry, 46(23), pp. 4952-4964 (2003).
Macdonald, Rosemary, Red cell 2,3-diphosphoglycerate and oxygen affinity, Anaesthesia, vol. 32, pp. 544-553, (1977).
Martinez-Mayorga Karina et al, Ligand/kappa-opioid receptor interactions: Insights from the X-ray crystal structure, European Journal of Medicinal Chemistry, vol. 66, pp. 114-121 (May 30, 2013).
Mathe-Allainmat, Monique et al., "Synthesis of 2-Amido-2, 3-dihydro-1H-phanalene Derivatives as New Conformationally Restricted Ligands for Melatonin Receptors", Journal of Medicinal Chemistry, 39(16), pp. 3089-3095, (1996).
McCluskey A., et al., BioOrganic & Medicinal Chemistry Letters 10 (2000), pp. 1687-1690.
McCluskey A., et al., Bioorganic & Medicinal Chemistry Letters 11 (2001), pp. 2941-2946.
McGarry, E., et al., "The deubiquitinase USP9X maintains DNA replication fork stability and DNA damage checkpoint responses by regulating CLASPIN during S-phase", Cancerres.aacrjournals.org, pp. 1-39; (2016).
Metcalf B, Chuang C, Dufu K, et al. "Discovery of GBT440, an orally bioavailable R-state stabilizer of sickle cell hemoglobin." ACS Med Chem Lett. 2017; 8(3):321-326.
Meza, N.W. et al, In vitro and in vivo expression of human erythrocyte pyruvate kinase in erythroid cells: a gene therapy approach, Hum Gene Ther, 18(6):502-514 (2007).

Middelkoop, E. et al., Studies on sickled erythrocytes provide evidence that the asymmetric distribution of phosphatidylserine in the red cell membrane is maintained by both ATP-dependent translocation and interaction with membrane skeletal proteins, Biochimica et Biophysica Acta, 937:281-288 (1988).
Misra H. Bainbridge J, Berryman J, Abuchowski A, Galvez KM, Uribe LF, Hernandez AL, Sosa NR. "A phase 1b open label, randomized, safety study of SANGUINATE™ in patients with sickle cell anemia." Rev Bras Hematol Hemoter. Jan.-Mar. 2017, 39(1):20-7.
Miwa, S. and Fujii, H., Molecular basis of erythroenzymopathies associated with hereditary hemolytic anemia: tabulation of mutant enzymes, Am J Hematol., 51(2): 122-132 (1996).
Moehrle, H., et al., "1,2,3,4-Tetrahydroquinolines as substrates for Mannich compounds", Chemical Sciences, 53(7), pp. 742-752; (1998).
Moriyama R, Lombardo CR, Workman RF, Low PS. "Regulation of linkages between the erythrocyte membrane and its skeleton by 2,3-diphosphoglycerate." J Biol Chem. May 25, 1993 268(15):10990-6.
Mouchantaf, R., et al., "The Ubiquitin Ligase Itch Is Auto-ubiquitylated in Vivo and in Vitro but Is Protected from Degradation by Interacting with the Deubiquitylating Enzyme FAM/USP9X", The Journal of Biological Chemistry, vol. 281, No. 50, pp. 38738-38747, (Dec. 2006).
Murn, J. et al., "Control of a neuronal morphology program by an RNA-binding zinc finger protein, Unkempt", Genes & Development 29, pp. 501-512, (2015).
Murray, R.Z., Jolly, L.A., Wood, S.A., "The FAM Deubiquitylating Enzyme Localizes to Multiple Points of Protein Trafficking in Epithelia, where It Associates with E-cadherin and β-catenin", Molecular Biology of the Cell, vol, 15, pp. 1591-1599; (Apr. 2004).
Muzyamba, M. and Gibson, J., Effect of 1-chloro-2,4-dinitrobenzene on K+ transport in normal and sickle human red blood cells, Journal of Physiology, 547(3):903-911 (2003).
Nagai, H., et al., "Ubiquitine-like Sequence in ASK1 Plays Critical Roles in the Recognition and Stabilization by USP9X and Oxidative Stress-Induced Cell Death", Molecular Cell 36, pp. 805-818, (Dec. 2009).
Nagy, Peter I., et al., "Theoretical and Experimental Study on Ion-Pair Formation and Partitioning of Organic Salts in Octanol/Water and Dichloromethane/Water Sytems", Journal of the American Chemical Society, 122 (28), pp. 6583-6593 (2000).
Nam, Keun-Soo et al., "Synthesis of quinolone antimicrobial agents and their antibacterial activities," 5 Korean J. Med. Chem. (1995), pp. 2-5.
Narayanan, N., Wang, Z., Li, L., and Yang, Y., "Arginine methylation of USP9X promotes its interaction with TDRD3 and its anti-apoptotic activities in breast cancer cells", Cell Discovery 3, pp. 1-17, (2017).
Nathan, J.A., et al., "The Ubiquitin E3 Ligase MARCH7 is Differentially Regulated by the Deubiquitylating Enzymes USP7 and USP9X", Traffic, 9, pp. 1130-1145, (2008).
Neto, E.D. et al., "Shotgun sequencing of the human transcriptome with ORF expressed sequence tags", PNAS, vol. 97, No. 7, pp. 3491-3496, (Mar. 2000).
Noma, T., et al., "Stage- and sex-dependent expressions of Usp9x, an X-linked mouse ortholog of *Drosophila* Fat facets, during gonadal development and oogenesis in mice", Gene Expression Patters 2, pp. 87-91, (2002).
O'Connor, H.F., et al., "Ubiquitin-Activated Interaction Traps (UBAITs) identify E3 ligase binding partners", EMBO reports, vol. 16, No. 12., (2015).
Obach RS. "Prediction of human clearance of twenty-nine drugs from hepatic microsomal intrinsic clearance data: An examination of in vitro half-life approach and nonspecific binding to microsomes." Drug Metab Dispos. Nov. 1999, 27(11):1350-9.
Oksenberg D, Dufu K, Patel MP, Chuang C, Li Z, Xu Q, Silva-Garcia A, Zhou C, Hutchaleelaha A, Patskovska L, Patskovsky Y, Almo SC, Sinha U, Metcalf BW, Archer DR. "GBT440 increases haemoglobin oxygen affinity, reduces sickling and prolongs RBC half-life in a murine model of sickle cell disease." Br J Haematol. Oct. 2016, 175(1):141-53.

(56) References Cited

OTHER PUBLICATIONS

Oliviero, G., et al., "The variant Polycomb Repressor Complex 1 component PCGF1 interacts with a pluripotency sub-network that includes DPPA4, a regulator of embryogenesis", pp. 1-11, (2015).
Olsen, J.V., et al., "Global, In Vivo, and Site-Specific Phosphorylation Dynamics in Signaling Networks", Cell 127, pp. 635-648, (Nov. 2006).
Oski, M.D., Frank A., "The Role of Organic Phosphates in Erythrocytes on the Oxygen Dissociation of Hemoglobin," Annals of Clinical Laboratory Science, vol. 1, No. 2 (Nov. 1970), pp. 162-176.
Ould Amar, A.K. et al., Assessment of qualitative functional parameters of stored red blood cells from donors with sickle cell trait (AS) or with heterozygote (AC) status, Transfus Clin Biol., 3(4):225-233 (1996).
Ouyang, W., et al., "β-catenin is regulated by USP9x and mediates resistance to TRAIL-induced apoptosis in breast cancer", Oncology Reports 35, pp. 717-724, (2016).
Oxbryta [package insert]. San Francisco, California, Global Blood Therapeutics, Inc. (Nov. 2019), 15 pgs.
Oxbryta Slide Show—Jan. 2020.
Paemka, L., et al., "Seizures Are Regulated by Ubiquitin-specific Peptidase 9 X-linked (USP9X), a De-Ubiquitinase", PLoS Genetics, 11(3): pp. 1-16, (Mar. 2015).
Palsson-Mcdermott, EM et al., Pyruvate kinase M2 regulates Hif-1a activity and IL-1β induction and is a critical determinant of the Warburg Effect in LPS-activated macrophages, Cell Metabolism, 21:65-80 (2015).
Papp, S.J., et al., "DNA damage shifts circadian clock time via Hausp-dependent Cry1 stabilization", eLIFE, pp. 1-19, (2015).
Park, Yoon, Jin, Hyung-seung, and Liu, Yun-Cai, "Regulation of T cell function by the ubiquitin-specific protease USP9X via modulating the Carma 1-Bcl10-Malt1 complex", PNAS, vol. 110, No. 23, pp. 9433-9438, (Jun. 2013).
Pászty C. "Transgenic and gene knock-out mouse models of sickle cell anemia and the thalassemias." Curr Opin Hematol. 1997, 4(2):88-93.
Patel, P., et al., Synthesis of some novel pyrazoline and cyanopyridine derivatives as antimicrobial agents, II Farmaco, vol. 51, No. 1, (1996), Abstract only.
Pavagadhi, T.H., et al., 3-(3'-phenoxyphenylmethyl)-5-aryl-1-acetylpyrazolines, Journal of the Institution of Chemists (India), vol. 73, No. 3, (2001), Abstract only.
Peddaboina, C. et al., "The downregulation of Mcl-1 via USP9X inhibition sensitizes solid tumors to Bcl-xl inhibition", BMC Cancer, 12:541, pp. 1-12, (2012).
Perez-Mancera, P.A., et al., "The deubiquitinase USP9X suppresses pancreatic ductal adenocarcinoma", Nature, 486(7402): pp. 266-270; (Dec. 2012).
Platt OS. "Hydroxyurea for the treatment of sickle cell anemia." N Engl J Med. 2008;358(13):1362-9.
Poillon W., & Kim, B., 2,3-Diphosphoglycerate and intracellular pH as interdependent determinants of the physiologic solubility of deoxyhemoglobin S, Blood, 76:1028-1036 (1990).
Poillon, W. et al., Antisickling effects of 2,3-Diphosphoglycerate Depletion, Blood, 85(11):3289-3296 (1995).
Poillon, W. et al., Intracellular hemoglobin S polymerization and the clinical severity of sickle cell anemia, Blood, 91:1777-1783 (1998).
Poillon, W. et al., The Effect of 2,3-Diphosphoglycerate on the Solubility of Deoxyhemoglobin S1, Archives of Biochemistry and Biophysics, vol. 249, No. 2, pp. 301-305, (Sep. 1986).
Press Release—"Agios Announces New Data from AG-348 and AG-519 Demonstrating Potential for First Disease-modifying Treatment for Patients with PK Deficiency" Dec. 4 2016—Globe Newswire.
Press Release—"Agios Presents Updated Data from DRIVE PK Study Demonstrating AG-348 is Well-Tolerated and Results in Clinically Relevant, Rapid and Sustained Hemoglobin Increases in Patients with Pyruvate Kinase Deficiency" Dec. 10, 2017—Globe Newswire.
PubChem SID: 440235168, modify date Feb. 25, 2021 (Feb. 25, 2021), Version 2, p. 1-7, Structure.
PubChem SID: 440235168, date Feb. 18, 2021 (Feb. 18, 2021), Version 1 of 2, p. 1-7, Structure.
PubChem CID: 135338361, create date: Dec. 15, 2018 (Dec. 15, 2018), p. 1, formula.
PubChem CID: 135338378, create date: Dec. 15, 2018 (Dec. 15, 2018), p. 1, formula.
PubChem CID: 69203074, create date: Nov. 30, 2012 (Nov. 30, 2012), pp. 1-20, compound summary.
PubChem CID: 69203505, create date: Nov. 30, 2012 (Nov. 30, 2012), pp. 1-20, compound summary.
Rab, et al., AG-348 (Mitapivat), an allosteric activator of red blood cell pyruvate kinase, increases enzymatic activity, protein stability, and ATP levels over a broad range of PKLR genotypes, Haematologica, 105:xxx, (Jan. 23, 2020).
Rab, M.A.E. et al., Rapid and reproducible characterization of sickling during automated deoxygenation in sickle cell disease patients, Am. J. Hematol. (2019; 94; pp. 575-584.
Rabai M, Detterich JA, Wenby RB, et al. "Deformability analysis of sickle blood using ektacytometry." Biorheology. 2014;51(2-3):159-70.
Ramdani, G. and Langsley, G., ATP, an Extracellular Signaling Molecule in Red Blood Cells: A Messenger for Malaria?, Biomed Journal, 37(5):284-292 (2014).
Raththagala, M. et al., Hydroxyurea stimulates the release of ATP from rabbit erythrocytes through an increase in calcium and nitric oxide production, European Journal of Pharmacology, 645(1-3):32-38 (2010).
Reblozyl [package insert]. Cambridge, Massachusetts, Acceleron Pharma, Inc. (2020), 27 pgs.
Reblozyl [package insert]. Summit, New Jersey, Celgene Corporation (Nov. 2019), 16 pgs.
Rice-Evans C, Omorphos SC, Baysal E. "Cell membranes and oxidative damage." Biochem J. Jul. 1, 1986 237(1):265-9.
Rosa, M. et al., Allosteric properties of hemoglobin and the plasma membrane of the erythrocyte: New insights in gas transport and metabolic modulation, Life, 60(2):87-93 (2008).
Ross, M.T., et al., "The DNA sequence of the human X chromosome", Nature, 434, pp. 325-337; (Mar. 2005).
Rott, Ruth, et al., "α-Synuclein fate is determined by USP9X-regulated monoubiquitination", PNAS, (2011).
Roy, R., et al., "hnRNPA1 couples nuclear export and translation of specific mRNAs downstream of FGF-2/S6K2 signalling", Nucleic Acids Research, vol. 42, No. 20, pp. 12483-12497, (Oct. 2014).
Rush, J., et al., "Immunoaffinity profiling of tyrosine phosphorylation in cancer cells", Nature Biotechnology, vol. 23, No. 1, pp. 94-101, (2005).
Sampson M, Archibong AE, Powell A, et al. "Perturbation of the developmental potential of preimplantation mouse embryos by hydroxyurea." Int J Environ Res Public Health. 2010;7(5):2033-44.
Sato, Y., et al., "Ubiquitin-specific protease 9X in host cells interacts with herpes simplex virus 1 ICP0", J. Vet. Med. Sci. 78(3), pp. 405-410; (2016).
Savio et al., "USP9X Controls EGFR Fate by Deubiquitinating the Endocytic Adaptor Eps15", Current Biology 26, pp. 173-183, (Jan. 2016).
Schwartz, R. et al., Two distinct pathways mediate the formation of intermediate density cells and hyperdense cells from normal density sickle red blood cells, Blood, 92(12):4844-4855 (1998).
Schwickart, M., et al., "Deubiquitinase USP9X stabilizes MCL1 and promotes tumour cell survival", Nature vol. 463, pp. 103-108; (Jan. 2010).
Sega, M. et al., Fluorescence assay of the interaction between hemoglobin and the cytoplasmic domain of erythrocyte membrane band 3, Blood Cells Mol Dis., 55(3):266-271 (2015).
Shen, G., et al., "MicroRNA-26b inhibits epithelial-mesenchymal transition in hepatocellular carcinoma by targeting USP9X," BMC Cancer 14:393, pp. 1-11, (2014).
Shrestha, Archana, et al., "Oral Administration of FT-4202, an Allosteric Activator of Pyruvate Kinase-R, Has Potent Anti-Sickling Effects in a Sickle Cell Anemia (SCA) Mouse Model, Resulting in Improved RBC Survival and Hemoglobin Levels," Blood (2020) 136 (Supplement 1):21-22, Nov. 4, 2020.

(56) References Cited

OTHER PUBLICATIONS

Shrestha, Archana, et al., "Oral Administration of FT-4202, an Allosteric Activator of Pyruvate Kinase-R, Has Potent Anti-Sickling Effects in a Sickle Cell Anemia (SCA) Mouse Model, Resulting in Improved RBC Survival and Hemoglobin Levels," Presented at the $62^{nd}$ American Society of Hematology (ASH) Annual Meeting, Dec. 5, 2020.

Siklos [package insert]. Lannoy, France, Delpharm Lille, (May 2019), 24 pgs.

Siklos [package insert]. Paris, France, Addmedica, (Dec. 2017), 25 pgs.

Siklos [package insert]. Paris, France, Addmedica, (May 2018), 23 pgs.

Smidrkal, Jan., "Synthesis of fagaronine", Collection of Czechoslovak Chemical Communications, 53(12), pp. 3184-3192, (1988).

Sorathiya, S.D., et al., Preparation and antimicrobial activity of 3-(p-(2',5'-dibromobenzenesulfonamido)phenyl)-5-aryl-1H/acetyl/phenyl-2-pyrazolines, Indian Journal of Chemistry, Section B: Organic, Incl. Medicinal Chemistry, vol. 36B, No. 7, (1997), Abstract only.

Soupene, E. and Kuypers, F., Identification of an erythroid ATP-dependent aminophospholipid transporter, British Journal of Haematology, 133(4): 436-438 (2006).

Space SL, Lane PA, Pickett CK, Weil JV. "Nitric oxide attenuates normal and sickle red blood cell adherence to pulmonary endothelium." Am J Hematol. Apr. 2000, 63(4):200-4.

Spinella, J.F., et al., "Genomic characterization of pediatric T-cell acute lymphoblastic leukemia reveals novel recurrent driver mutations", Oncotarget, vol. 7, No. 40, pp. 65485-65503, (Sep. 2016).

Stasiuk, M. et al., Transformations of erythrocytes shape and its regulation, Postepy Biochem., 55(4):425-33 (2009). English Abstract.

St-Denis, N., et al., "Phenotypic and Interaction Profiling of the Human Phosphatases Identifies Diverse Mitotic Regulators", Cell Reports 17, pp. 2488-2501, (Nov. 2016).

Stebbins et al., Crystal Structure of an Hsp90-Geldanamycin Complex: Targeting of a Protein Chaperone by an Antitumor Agent, Cell, (Apr. 1997), 89, p. 241.

Steinberg, Martin H., Pathophysiologically based drug treatment of sickle cell disease, Trends in Pharmacological Sciences, vol. 27, No. 4, (Apr. 2006).

Strausberg, R.L., et al., "Generation and initial analysis of more than 15,000 full-length human and mouse cDNA sequences", PNAS vol. 99, No. 26, pp. 16899-16903, (Dec. 2002).

Sun, H., et al., "Bcr-Abl ubiquitination and Usp9x inhibition block kinase signaling and promote CML cell apoptosis", Blood, (Jan. 2011).

Sundd, Prithu et al., Pathophysiology of Sickle Cell Disease, Annual Review of Pathology: Mechanisms of Disease, (Oct. 9, 2018), pp. 261-290.

Swanson, Devin M. et al., "Identification and biological evaluation of 4-(3-trifluoromethylpyridine-2-yl) piperazine-1-c arboxylic acid (5-trifluoromethylpyridin-2-yl) amide, a high affinity TRPV1 (VR1) vanilloid receptor antagonist", Journal of Medicinal Chemistry, 48(6), pp. 1857-1872 (2005).

Taipale, M., et al., "A Quantitative Chaperone Interaction Network Reveals the Architecture of Cellular Protein Homeostasis Pathways", Cell 158, pp. 434-448, (Jul. 2014).

Takenaka, M. et al, Isolation and characterization of the human pyruvate kinase M gene, Eur J Biochem, 198(1):101-106 (1991).

Talmud, P.J., et al., "Gene-centric Association Signals for Lipids and Apolipoproteins Identified via the Human CVD Bead Chip", The American Journal of Human Genetics 85, pp. 628-642, (Nov. 2009).

Tanphaichitr, V.S. et al, Successful bone marrow transplantation in a child with red blood cell pyruvate kinase deficiency, Bone Marrow Transplant, 26(6):689-690 (2000).

Taya, S., et al., "The deubiquitinating enzyme Fam interacts with and stabilizes β-catenin", Genes to Cells 4, pp. 757-767, (1999).

Taya, S., et al., "The Ras Target AF-6 is a Substrate of the Fam Deubiquitinating Enzyme", The Journal of Cell Biology, vol. 142, No. 4, pp. 1053-1062, (Aug. 1998).

Telen, Marilyn, Malik, Punam, and Vercellotti, Gregory M., Therapeutic strategies for sickle cell disease: towards a multi-agent approach, Nature Reviews/Drug Discovery; (Dec. 4, 2018).

Terao, Y., et al., "Trifluoroacetic Acid-Catalyzed 1,3-Cycloaddition of the Simplest Iminium Ylide Leading to 3- or 3,4-Substituted Pyrrolidines and 2,5-Dihydropyrroles", Chem. Pharm. Bull., 33(7), pp. 2762-2766, (1985).

Théard, D., et al., "USP9x-mediated deubiquitination of EFA6 regulates de novo tight junction assembly", The EMBO Journal, vol. 29, No. 9, pp. 1499-1509, (2010).

Thein, Swee Lay, The Molecular Basis of β-Thalassemia, Cold Spring Harb Perspect Med. (2013).

Thompson, Alexis, M.D., M.P.H., "A Targeted Agent for Sickle Cell Disease—Changing the Protein but Not the Gene," The New England Journal of Medicine, (Jun. 14, 2019).

Tian, S., et al., Yaoxue Xueba (1993), 28(11), pp. 870-875. Chemical Abstract No. 120:299229.

Toloczko, A., et al., "Deubiquitinating Enzyme USP9X Suppresses Tumor Growth via LATS kinase and Core Components of the Hippo pathway", Cancer Research, pp. 1-37, (Jul. 2017).

Tripathi, Ashutoshi and Safo, Martin K., In Silico-Screening Approaches for Lead Generation: Identification of Novel Allosteric Modulators of Human-Erythrocyte Pyruvate Kinase, Allostery: Methods and Protocols, Methods in Molecular Biology, Chpt. 19, vol. 796, pp. 351-367 (2012).

Trivigno, D., et al., "Deubiquitinase USP9x Confers Radioresistance through Stabilization of Mcl-1 1,2", NEO Plasia, vol. 14, No. 10, pp. 893-904, (Oct. 2012).

Tsai, Y.C., et al., "Functional Proteomics Establishes the Interaction of SIRT7 with Chromatin Remodeling Complexes and Expands Its Role in Regulation of RNA Polymerase I Transcription", Molecular & Cellular Proteomics 11.5, pp. 60-76, (2012).

Tsutsumi H, Tani K, Fujii H, Miwa S. "Expression of L- and M-type pyruvate kinase in human tissues. Genomics." 1988, 2(1):86-9.

United States Securities and Exchange Commission, Form S-1 Registration Statement, Forma Therapeutics Holdings, Inc., dated Dec. 8, 2020, 374 pages.

United States Securities and Exchange Commission, Form S-1, Registration Statement—Forma Therapeutics Holdings, Inc., May 29, 2020.

Upadhyay J., et al., Studies on pyrazolines. Part III. Preparation and antimicrobial activity of 3-(4-phenylsulfonamidophenyl)-5-aryl-1-ace tyl/phenyl-4,5-dihydropyrazoles, Journal of the Indian Chemical Society, vol. 68, No. 7, (1991), pp. 413-414.

Van Zweiten, R. et al., Inborn defects in the antioxidant systems of human red blood cells, Free Radio Biol Med., 67:377-386 (2014).

Vanderah et al, Novel d-amino acid tetrapeptides produce potent antinociception by selectively acting at peripheral kappa-opioid receptors, European Journal of Pharmacology, Elsevier Science, vol. 583, No. 1, pp. 62-72 (Jan. 24, 2008).

Varjosalo, M., et al., The Protein Interaction Landscape of the Human CMGC Kinase Group, Cell Reports 3, pp. 1306-1320, (Apr. 2013).

Verma, S.K. et al., Imidazole-Catalyzed Monoacylation of Symmetrical Diamines, Organic Letters, 12(19): 4232-4235 (201).

Vichinsky, E. et al., "A Phase 3 Randomized Trial of Voxelotor in Sickle Cell Disease," N Engl J Med. DOI: 10.1056/NEJMoa1903212 (Jun. 2019).

Vichinsky, E. et al., Protocol to a Phase 3 Randomized Trial of Voxelotor in Sickle Cell Disease, (Jun. 14, 2019).

Vichinsky, E. et al., Supplementary Appendix to a Phase 3 Randomized Trial of Voxelotor in Sickle Cell Disease, (Jun. 14, 2019).

Vong, Q. P., et al., "Chromosome Alignment and Segregation Regulated by Ubiquitination of Survivin", Science, vol. 310, pp. 1499-1504, (Dec. 2, 2005).

Voskou S, Aslan M, Fanis P, Phylactides M, Kleanthous M. "Oxidative stress in β-thalassaemia and sickle cell disease." Redox Biol. Dec. 2015, 6:226-39.

Wagner, G. et al., Red cell vesiculation—a common membrane physiologic event, J Lab Clin., 108(4):315-324 (1986).

Wan, C., et al., "Panorama of ancient metazoan macromolecular complexes", Nature 525(7569), pp. 339-344, (Sep. 2015).

(56) References Cited

OTHER PUBLICATIONS

Wang, G.S., et al., Journal of Ethnopharmacology, 26 (1989), pp. 147-162.
Wang, H. et al., JMJD5 regulates PKM2 nuclear translocation and reprograms HIF-1a-mediated glucose metabolism, PNAS, 111(1):279-284 (2014).
Wang, J., et al, "TopBP1 Controls BLM Protein Level to Maintain Genome Stability", Molecular Cell 52, pp. 667-678, (Dec. 2013).
Wang, Q., et al., "The X-linked Deubiquitinase USP9X Is an Integral Component of Centrosome", The American Society for Biochemistry and Molecular Biology, Inc., pp. 1-33, (2017).
Wang, S. et al., "Ablation of the oncogenic transcription factor ERG by deubiquitinase inhibition in prostate cancer", PNAS, vol. 111, No. 11, pp. 4251-4256, (Mar. 2014).
Wang, S., et al., "The ubiquitin ligase TRIM25 targets ERG for degradation in prostate cancer", Oncotarget, vol. 7, No. 40, pp. 64921-64931, (2016).
Wang, X, et al., "Hsp90 Cochaperone Aha1 Downregulation Rescues Misfolding of CFTR in Cystic Fibrosis", Cell 127, pp. 803-815, (Nov. 2006).
Waza et al., Nature, 11, No. 10, (Oct. 2005), pp. 1088-1095.
Weatherall, D., The inherited diseases of hemoglobin are an emerging global health burden, Blood, 115(22): 4331-43336 (2010).
Wei, Wan-Guo et al., "A practical procedure for multisubstituted .beta.-naphthols and their derivatives", Tetrahedron, 59(34), pp. 6621-6625, (2003).
Willcocks, J. et al., Simultaneous determination of low free Mg2+ and pH in human sickle cells using P NMR spectroscopy, The Journal of Biological Chemistry, 277(51):49911-49920 (2002).
Wood BL, Gibson DF, Tait JF. "Increased erythrocyte phosphatidylserine exposure in sickle cell disease: flow-cytometric measurement and clinical associations." Blood., 88(5):1873-80 (Sep. 1, 1996).
Wood, Kenneth W., et al., "An Adaptive, Randomized, Placebo-Controlled, Double-Blind, Multi-Center Study of Oral FT-4202, a Pyruvate Kinase Activator in Patients with Sickle Cell Disease (PRAISE)," Blood (2020) 136 (Supplement 1):19-20, Nov. 4, 2020.
Wood, Kenneth W., et al., "An Adaptive, Randomized, Placebo-Controlled, Double-Blind, Multi-Center Study of Oral FT-4202, a Pyruvate Kinase Activator in Patients with Sickle Cell Disease," Presented at the 62$^{nd}$ American Society of Hematology (ASH) Annual Meeting, Dec. 7, 2020.
Woods, N.T., et al., "Charting the Landscape of Tandem BRCT Domain-Mediated Protein Interactions", Sci Signal, 5(242), pp. 1-35, (2014).
Wright, S.W. et al., A Convenient Preparation of Heteroaryl Sulfonamides and Sulfonyl Fluorides from Heteroaryl Thiols, J. Org. Chem., 71: 1080-1084 (2006).
Wu, Y., et al., "Aberrant phosphorylation of SMAD4 Thr277-mediated USP9x-SMAD4 interaction by free fatty acids promotes breast cancer matastasis", Cancer Research, pp. 1-34, (2017).
Wu, Z., et al., "Targeted Ubiquitination and Degradation of G-Protein-Coupled Receptor Kinase 5 by the DDB1-CUL4 Ubiquitin Ligase Complex", PLoS One, vol. 7, Issue 8, pp. 1-11, (Aug. 2012).
Xie, Y., et al., "Deubiquitinase FAM/USP9X Interacts with the E3 Ubiquitin Ligase SMURF1 Protein and Protects It from Ligase Activity-dependent Self-degradation", The Journal of Biological Chemistry., vol. 288, No. 5, pp. 2976-2985, (Feb. 2013).
Xu, Z., et al., "Identification of a Deubiquitinating Enzyme as a Novel AGS3-Interacting Protein", PLoS One, vol. 5, Issue 3, pp. 1-12, (Mar. 2010).
Yan, J., et al., "Usp9x- and Noxa-mediated Mcl-1 downregulation contributes to pemetrexed-induced apoptosis in human non-small-cell lung cancer cells", Cell Death and Disease 5, pp. 1-7, (2014).
Yang H, Merica E, Chen Y, Cohen M, Goldwater R, Hill C, et al. "Phase I single (SAD) and multiple ascending dose (MAD) studies of the safety, tolerability, pharmacokinetics (PK) and pharmacodynamics (PD) of AG-348, a first-in-class allosteric activator of pyruvate kinase-R, in healthy subjects." Blood. 2014, 124:4007.
Yang H, Merica E, Chen Y, et al. "Phase 1 Single- and Multiple-Ascending-Dose Randomized Studies of the Safety, Pharmacokinetics, and Pharmacodynamics of AG-348, a First-in-Class Allosteric Activator of Pyruvate Kinase R, in Healthy Volunteers." Clin Pharmacol Drug Dev. Aug. 9, 2018.
Yang, H. et al., Phase 1 Single- and Multiple-Ascending-Dose Randomized Studies of the Safety, Pharmacokinetics, and Pharmacodynamics of AG-348, a First-in-Class Allosteric Activator of Pyruvate Kinase R, in Healthy Volunteers, 8 Clin. Pharmacol. Drug Dev. 246-259 (2019).
Yi, S., et al., Leukemia Research, vol. 15(10), (1991), pp. 883-886.
You, J. and Pickart, C.M., "A HECT Domain E3 Enzyme Assembles Novel Polyubiquitin Chains", vol. 276, No. 23, pp. 19871-19878, (2001).
Yu, W., et al., "Large-Scale Concatenation cDNA Sequencing", Genome Research 7, pp. 353-358, (1997).
Zanella A, Fermo E, Bianchi P, Chiarelli LR, Valentini G. "Pyruvate kinase deficiency: The genotype-phenotype association." Blood Rev. 2007, 23:217-31.
Zanella A, Fermo E, Bianchi P, Valentini G. "Red cell pyruvate kinase deficiency: molecular and clinical aspects." Br J Haematol. 2005;130(1):11-25.
Zhang, C., et al., "Synergistic anti-tumor activity of gemcitabine and ABT-737 in vitro and in vivo through disrupting the interaction of USP9X and Mcl-1", Molecular Cancer Therapeutics, (May 12, 2011).
Zhang, C., et al., "USP9X destabilizes pVHL and promotes cell proliferation", Oncotarget, vol. 7, No. 37, pp. 60519-60534, (2016).
Zhang, Y & Xia, Y., Adenosine signaling in normal and sickle erythrocytes and beyond, Microbes Infect., 14(10) (2012).
Zhang, Y. et al., Detrimental effects of adenosine signaling in sickle cell disease, Nature Medicine, 17(1):79-87 (2011).
Zhang, Yongmin et al., "Organic reactions in chiral micelles. 7. The structural effects on the asymmetric oxidation of prochiral sulfides in chiral micelles", Chinese Journal of Chemistry, (1990), pp. 89-96.
Zhao, Y., et al.,"Noncanonical regulation of alkylation damage resistance by the OTUD4 deubiquitinase", EMBO Journal, vol. 34, No. 12, pp. 1687-1703, (2015).
Zhi et al., Hybrid Antibacterals. DNA Polymerase—Topoisomerase Inhibitors. J. Med. Chem., published on Web Jan. 25, 2006., vol. 49, pp. 1455-1465, especially p. 1456. Scheme 3, compound 4; p. 1457, Scheme 4, compound 13, p. 1462.
Zhou, L., et al., "The Scaffold Protein KSR1, A Novel Therapeutic Target for the Treatment of Merlin-Deficient Tumors", Oncogene 35(26), pp. 3443-3453, (Jun. 2016).
Zhou, ZH et al., Phosphorus, Sulfur and Silicon and the Related Elements (1999), 152, pp. 45-52. Chemical Abstract No. 132: 180853.
Zhu, Tong et al., Polymer-Supported Synthesis of Pyridone-Focused Libraries as Inhibitors of Anaplastic Lymphoma Kinase, Journal of Combinatorial Chemistry, 8(3), pp. 401-409.

\* cited by examiner

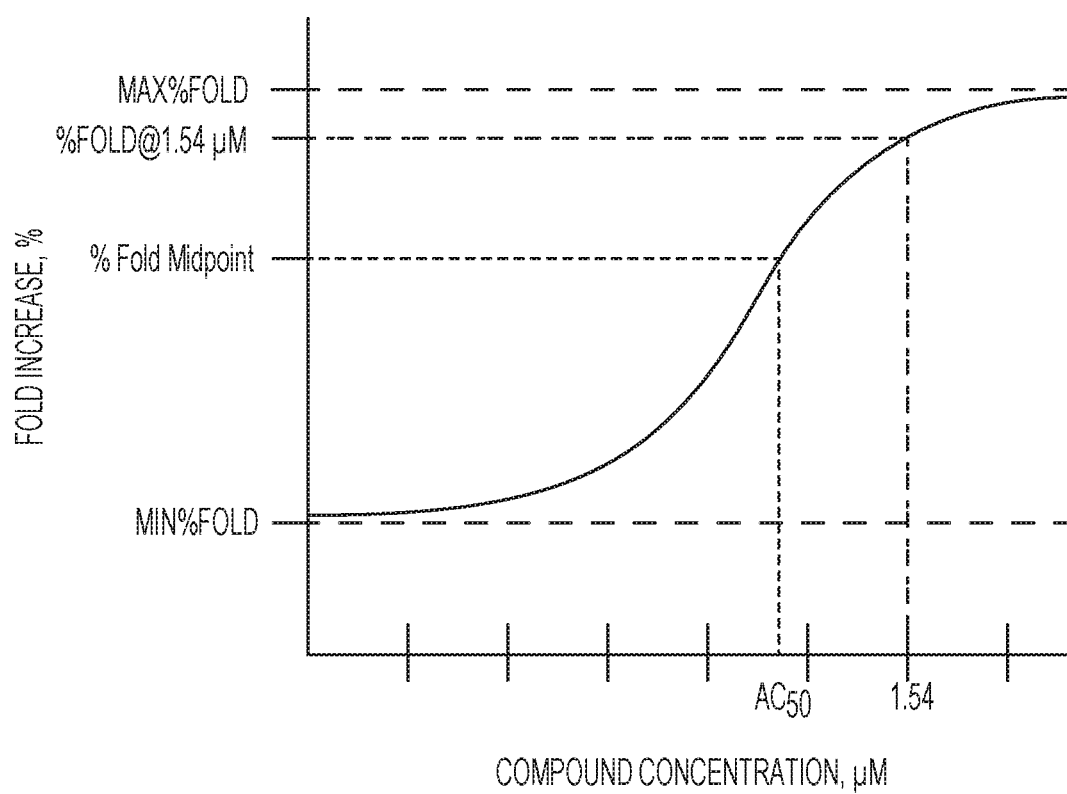

ACTIVATING PYRUVATE KINASE R

CROSS-REFERENCE TO RELATED APPLICATION

This application is a National Stage application of International Application No. PCT/US2019/051831, filed Sep. 19, 2019, which claims priority to and the benefit of U.S. Provisional Application No. 62/733,546, filed Sep. 19, 2018, the entire contents of each of which are incorporated herein by reference.

TECHNICAL FIELD

This disclosure relates to novel chemical compositions for activating pyruvate kinase (PKR).

BACKGROUND

Pyruvate Kinase (PK) converts phosphoenolpyruvate (PEP) and adenosine diphosphate (ADP) to pyruvate and adenosine triphosphate (ATP), respectively, which is the final step in glycolysis. In humans, four PK isoforms are expressed by two structural genes. The PKLR gene encodes PKR and PKL, tissue specific isoforms expressed in erythroid cells and liver cells, respectively. The PKM gene codes for isoforms PKM1, expressed in brain and skeletal muscle, and PKM2 (M2-type pyruvate kinase), expressed in fetal and most adult tissues except erythroid cells.

Mutations in the PKLR gene can lead to pyruvate kinase deficiency (PKD), an autosomal recessive disorder, which is the most frequent enzymatic defect of the glycolytic pathway in erythrocytes. Over 200 different mutations have been identified on the structural PKLR gene. Generally, most PKD patients are heterozygous with two different mutant alleles, but homozygous mutations have also been described. Clinical symptoms of PKD vary considerably from mild to severe anemia. Mutations can reduce PK enzymatic activity or decrease PK protein stability. Pathological manifestations are usually observed when enzyme activity falls below 25% normal PK activity, and severe disease has been associated with a high degree of reticulocytosis. Although the global incidence of PKD is unknown, it has been estimated at 51 cases per million in North America.

Currently, there is no definitive treatment for severe PKD. Although splenectomy can be clinically useful in patients with severe disease, in some cases, allogeneic hematopoietic transplantation is required. In these patients, hematopoietic stem cell (HSC) gene therapy might be a good and more effective treatment. Gene therapy strategies for PKD have been addressed in animal models demonstrating that introduction of the correct version of the human PKLR gene into hematopoietic stem cells using retroviral vectors alleviates the disease. Although bone marrow transplant (BMT) or gene therapy strategies would be definitive treatments of the disease, they have yet to be realized clinically, and important adverse effects are associated with both approaches.

There remains a need for strategies to improve the treatment of diseases related to PKR, such as PKD, including the discovery and development of PKR activating small molecules. PKR exists in both a dimeric and tetrameric state, but functions most efficiently as a tetramer. Small molecules have been shown to be capable of shifting the equilibrium of PKR to the tetrameric (most active) form, providing a mechanistic rationale for their use as therapy for PKD-associated hemolytic anemia. Thus, there is a need for PKR activating compounds, useful for treating diseases and disorders associated with modulation of PKR and/or PKM2.

SUMMARY

The disclosure relates in part to compounds and compositions useful for activating PKR, including the discovery of a novel compound active with wild type (wt) PKR and/or mutant isozyme forms of PKR. For example, compounds and methods provided herein can be used for activating wild type PKR isozyme and/or a mutant PKR isozyme. Examples of mutant PKR isozyme include G332S, G364D, T384M, G37E, R479H, R479K, R486W, R532W, R510Q, I90N, and R490W. The invention is based in part on the discovery of a novel compound demonstrating activation of (wt) PKR and the G332S and R510Q mutant forms of PKR.

A method for treating pyruvate kinase deficiency (PKD) in a subject in need thereof, comprising administering to the subject a therapeutically effective amount of: (a) compound of Formula (I) or a pharmaceutically acceptable salt thereof, (b) a composition comprising a compound of Formula (I) or a salt thereof and a carrier; or (c) a pharmaceutical composition comprising a compound of Formula (I) or a pharmaceutically acceptable salt thereof, and a pharmaceutically acceptable carrier, to thereby treat PKD in the subject. The method can include or result in activating one or more isozymes of pyruvate kinase. One or more isozymes of pyruvate kinase can be selected from PKR, PKM2, and PKL; the method can also include or result in activating a mutant PKR isozyme.

One aspect of this invention relates to compounds of Formula I:

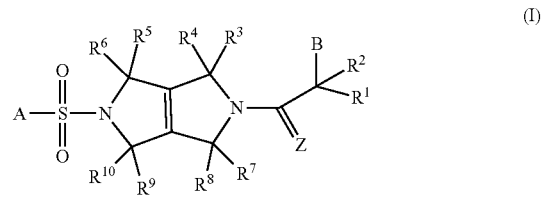

(I)

or a pharmaceutically acceptable salt thereof, wherein:
A is phenyl or monocyclic 5- to 6-membered heteroaryl ring containing 1-4 heteroatoms independently selected from the group consisting of O, N, and S,
wherein each aryl or heteroaryl is optionally substituted with one or more $R^a$;
each $R^a$ is independently selected from the group consisting of halogen, —OR, —OC(O)R', —NR$_2$, —NRC(O)R', —NRS(O)$_2$R', —CN, —NO$_2$, —SR, —C(O)R', —C(O)OR, —C(O)NR$_2$, —S(O)$_2$R', —S(O)$_2$NR$_2$, —C$_1$-C$_6$alkyl, —C$_2$-C$_6$alkenyl, —C$_2$-C$_6$alkynyl, —C$_3$-C$_{12}$cycloalkyl, —C$_4$-C$_{12}$cycloalkenyl, 3- to 14-membered heterocyclyl containing 1-4 heteroatoms independently selected from the group consisting of O, N, and S, C$_6$-C$_{14}$aryl, and 5- to 14-membered heteroaryl containing 1-4 heteroatoms independently selected from the group consisting of O, N, and S,
wherein each alkyl is optionally substituted with one or more halogen;
Z is O, S, or NR;
$R^1$ and $R^2$ are each independently selected from the group consisting of —H, halogen, —C$_1$-C$_6$alkyl, —C$_2$-C$_6$alkenyl, —C$_2$-C$_6$alkynyl, —(CR$^b$R$^c$)$_n$C$_3$-C$_{12}$cycloalkyl, —(CR$^b$R$^c$)$_n$C$_4$-C$_{12}$cycloalkenyl, —(CR$^b$R$^c$)$_n$heterocyclyl, —(CR$^b$R$^c$)$_n$C$_6$-C$_{14}$aryl, —(CR$^b$R$^c$)$_n$heteroaryl, —OR, —OC(O)R', —OS(O)$_2$R', —OS(O)$_2$NR$_2$, —OC(O)NR$_2$, —OC(O)OR, —(CR$^b$R$^c$)$_n$NR$_2$, —(CR$^b$R$^c$)$_n$NRC(O)R', —(CR$^b$R$^c$)$_n$NRS(O)$_2$R', —(CR$^b$R$^c$)$_n$NRC(O)NR$_2$, —(CR$^b$R$^c$)$_n$NRC(O)OR, —(CR$^b$R$^c$)$_n$CN, —(CR$^b$R$^c$)$_n$NO$_2$, —(CR$^b$R$^c$)$_n$SR, —(CR$^b$R$^c$)$_n$C(O)R', —(CR$^b$R$^c$)$_n$C(O)OR, —(CR$^b$R$^c$)$_n$C(O)NR$_2$, —(CR$^b$R$^c$)$_n$SO$_2$R', —(CR$^b$R$^c$)$_n$SO$_2$NR$_2$, and —(CR$^b$R$^c$)$_n$SO$_2$OR,
- wherein each cycloalkyl, cycloalkenyl, heterocyclyl, aryl, or heteroaryl is optionally substituted with one or more substituents selected from the group consisting of halogen, —C$_1$-C$_6$ alkyl, —C$_2$-C$_6$alkenyl, —C$_2$-C$_6$alkynyl, oxo, and —OR, wherein —OR does not result in an O in the γ-position relative to C(=Z),
- wherein each alkyl, alkenyl, or alkynyl is optionally substituted with one or more halogen,
- wherein each heterocyclyl is 3- to 14-membered and contains 1-4 heteroatoms independently selected from the group consisting of O, N, and S and wherein the heterocyclyl does not contain an O in the γ-position relative to C(=Z), and
- wherein each heteroaryl is 5- to 14-membered and contains 1-4 heteroatoms independently selected from the group consisting of O, N, and S;

or R$^1$ and R$^2$ combine with the carbon to which they are attached to form oxo, a C$_3$-C$_{12}$cycloalkyl, or 3- to 8-membered heterocyclyl containing 1-4 heteroatoms independently selected from the group consisting of O, N and S, and
- wherein the heterocyclyl does not contain an O in the γ-position relative to C(=Z), and
- wherein each cycloalkyl or heterocyclyl is optionally substituted with one or more substituents selected from the group consisting of halogen, —C$_1$-C$_6$alkyl, —C$_2$-C$_6$alkenyl, —C$_2$-C$_6$alkynyl, oxo, —OR, and wherein —OR does not result in an O in the γ-position relative to C(=Z);

R$^b$ and R$^c$ are each independently selected from the group consisting of —H, halogen, and —C$_1$-C$_6$alkyl; each n is independently 0, 1, 2, 3, or 4;

B is a monocyclic or bicyclic 3- to 14-membered ring,
- wherein the ring is saturated, fully or partially unsaturated, or aromatic,
- wherein the ring contains 0-4 heteroatoms independently selected from the group consisting of O, N, and S, and
- wherein the ring is optionally substituted with (R$^d$)$_m$, and
- when the ring is saturated or partially unsaturated, then the ring does not contain an O in the γ-position relative to C(=Z);

each R$^d$ is independently selected from the group consisting of halogen, oxo, —OR, —OC(O)R', —NR$_2$, —NRC(O)R', —NRS(O)$_2$R', —CN, —NO$_2$, —SR, —C(O)R', —C(O)OR, —C(O)NR$_2$, —S(O)$_2$R', —S(O)$_2$NR$_2$, —C$_1$-C$_6$alkyl, —C$_2$-C$_6$alkenyl, —C$_2$-C$_6$alkynyl, —C$_3$-C$_{12}$cycloalkyl, —C$_4$-C$_{12}$cycloalkenyl, 3- to 14-membered heterocyclyl containing 1-4 heteroatoms independently selected from the group consisting of O, N, and S, C$_6$-C$_{14}$aryl, and 5- to 14-membered heteroaryl containing 1-4 heteroatoms independently selected from the group consisting of O, N, and S,
- wherein each alkyl, alkenyl, alkynyl, cycloalkyl, cycloalkenyl, heterocyclyl, aryl, or heteroaryl is optionally substituted with one or more halogen, —C$_1$-C$_6$ alkyl, —C$_2$-C$_6$alkenyl, —C$_2$-C$_6$alkynyl, or —OR;

m is 0, 1, 2, 3, 4, 5, 6, 7, 8, 9, or 10;

R$^3$, R$^4$, R$^5$, R$^6$, R$^7$, R$^8$, R$^9$, and R$^{10}$ are each independently —H or —C$_2$-C$_6$ alkyl,
- wherein each alkyl is optionally substituted with one or more halogen;

or R$^3$ and R$^4$, R$^5$ and R$^6$, R$^7$ and R$^8$, R$^9$ and R$^{10}$, or combinations thereof, combine with the carbon to which they are attached to form oxo, a C$_3$-C$_8$cycloalkyl, or a 3- to 8-membered heterocyclyl containing 1-4 heteroatoms independently selected from the group consisting of O, N, and S;

each R is independently selected from the group consisting of —H, —OH, —O(C$_1$-C$_3$alkyl), —NH$_2$, —NH(C$_1$-C$_6$alkyl), —N(C$_1$-C$_6$alkyl)$_2$, —C$_{1-6}$alkyl, —C$_2$-C$_6$alkenyl, —C$_2$-C$_6$alkynyl, —C$_3$-C$_{12}$cycloalkyl, —C$_4$-C$_{12}$cycloalkenyl, 3- to 14-membered heterocyclyl containing 1-4 heteroatoms independently selected from the group consisting of O, N, and S, C$_6$-C$_{14}$aryl, and 5- to 14-membered heteroaryl containing 1-4 heteroatoms independently selected from the group consisting of O, N, and S,
- wherein each alkyl, alkenyl, alkynyl, cycloalkyl, cycloalkenyl, heterocyclyl, aryl, or heteroaryl is optionally substituted with one or more halogen, —C$_1$-C$_6$alkyl, —C$_2$-C$_6$alkenyl, —C$_2$-C$_6$alkynyl, —O(C$_1$-C$_6$alkyl), —NH(C$_1$-C$_6$alkyl), or —N(C$_1$-C$_6$alkyl)$_2$; and each R' is independently selected from the group consisting of —C$_1$-C$_6$alkyl, —C$_2$-C$_6$alkenyl, —C$_2$-C$_6$alkynyl, —C$_3$-C$_{12}$cycloalkyl, —C$_4$-C$_{12}$cycloalkenyl, 3- to 14-membered heterocyclyl containing 1-4 heteroatoms independently selected from the group consisting of O, N, and S, C$_6$-C$_{14}$aryl, and 5- to 14-membered heteroaryl containing 1-4 heteroatoms independently selected from the group consisting of O, N, and S,
- wherein each alkyl, alkenyl, alkynyl, cycloalkyl, cycloalkenyl, heterocyclyl, aryl, or heteroaryl is optionally substituted with one or more halogen, —C$_1$-C$_6$alkyl, —C$_2$-C$_6$alkenyl, —C$_2$-C$_6$alkynyl, —O—C$_1$-C$_6$alkyl, —NH(C$_1$-C$_6$alkyl), or —N(C$_1$-C$_6$alkyl)$_2$.

Another aspect of this invention relates to compounds of Formula II:

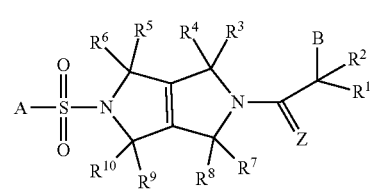

(II)

or a pharmaceutically acceptable salt thereof, wherein:

A is a monocyclic or bicyclic 3- to 14-membered ring,
- wherein the ring is saturated, fully or partially unsaturated, or aromatic, and
- wherein the ring contains 0-4 heteroatoms independently selected from the group consisting of O, N, and S; and
- wherein the ring is optionally substituted with one or more R$^a$;

each R$^a$ is independently selected from the group consisting of halogen, —OR, —OC(O)R', —NR$_2$, —NRC(O)R', —NRS(O)$_2$R', —CN, —NO$_2$, —SR, —C(O)R', —C(O)OR, —C(O)NR$_2$, —S(O)$_2$R', —S(O)$_2$NR$_2$, —C$_1$-C$_6$alkyl, —C$_2$-C$_6$alkenyl, —C$_2$-C$_6$alkynyl, —C$_3$-C$_{12}$cycloalkyl, —C$_4$-C$_{12}$cycloalkenyl, 3- to 14-membered heterocyclyl containing 1-4 heteroatoms independently selected from the group consisting of O, N, and S, $C_6$-$C_{14}$aryl, and 5- to 14-membered heteroaryl containing 1-4 heteroatoms independently selected from the group consisting of O, N, and S,
  wherein each alkyl is optionally substituted with one or more halogen;
Z is O, S, or NR;
$R^1$, $R^2$, and B are each independently —H, halogen, —$C_1$-$C_6$alkyl, —$C_2$-$C_6$alkenyl, —$C_2$-$C_6$alkynyl, —OR, —OC(O)R', —OS(O)$_2$R', —OS(O)$_2$NR$_2$, —OC(O)NR$_2$, —OC(O)OR, —(CR$^b$R$^c$)$_n$NR$_2$, —(CR$^b$R$^c$)$_n$NRC(O)R', —(CR$^b$R$^c$)$_n$NRS(O)$_2$R', —(CR$^b$R$^c$)$_n$NRC(O)NR$_2$, —(CR$^b$R$^c$)$_n$NR$_2$, —(CR$^b$R$^c$)$_n$NRC(O)OR, —(CR$^b$R$^c$)$_n$CN, —(CR$^b$R$^c$)$_n$NO$_2$, —(CR$^b$R$^c$)$_n$SR, —(CR$^b$R$^c$)$_n$C(O)R', —(CR$^b$R$^c$)$_n$C(O)OR, —(CR$^b$R$^c$)$_n$C(O)NR$_2$, —(CR$^b$R$^c$)$_n$SO$_2$R', —(CR$^b$R$^c$)$_n$SO$_2$NR$_2$, or —(CR$^b$R$^c$)$_n$SO$_2$OR,
  wherein each alkyl, alkenyl, or alkynyl is optionally substituted with one or more halogen,
or $R^1$ and $R^2$ combine with the carbon to which they are attached to form oxo, a $C_3$-$C_{12}$cycloalkyl, or a 3- to 14-membered heterocyclyl containing 1-4 heteroatoms independently selected from the group consisting of O, N and S,
  wherein the heterocyclyl does not contain an O in the γ-position relative to C(=Z),
  wherein each cycloalkyl or heterocyclyl is optionally substituted with one or more substituents selected from the group consisting of halogen, —$C_1$-$C_6$alkyl, —$C_2$-$C_6$alkenyl, —$C_2$-$C_6$alkynyl, —OR, oxo, —$C_6$aryl, and —C(O)R', and
  wherein each cycloalkyl or heterocyclyl is optionally fused with a phenyl or 5- to 6-membered heteroaryl containing 1-4 heteroatoms independently selected from the group consisting of O, N, and S;
each $R^b$ and $R^c$ is independently selected from the group consisting of —H, —$C_1$-$C_6$alkyl, and halogen;
each n is independently 0, 1, 2, 3, or 4;
$R^3$, $R^4$, $R^5$, $R^6$, $R^7$, $R^8$, $R^9$, and $R^{10}$ are each independently —H or —$C_1$-$C_3$ alkyl,
  wherein each alkyl is optionally substituted with one or more halogen;
or $R^3$ and $R^4$, $R^5$ and $R^6$, $R^7$ and $R^8$, $R^9$ and $R^{10}$, or combinations thereof, combine with the carbon to which they are attached to form oxo, a $C_3$-$C_8$cycloalkyl, or a 3- to 8-membered heterocyclyl containing 1-4 heteroatoms independently selected from the group consisting of O, N, and S;
each R is independently selected from the group consisting of —H, —OH, —O($C_1$-$C_3$alkyl), —NH$_2$, —NH($C_1$-$C_6$alkyl), —N($C_1$-$C_6$alkyl)$_2$, —$C_1$-$C_6$alkyl, —$C_2$-$C_6$alkenyl, —$C_2$-$C_6$alkynyl, —$C_3$-$C_{12}$cycloalkyl, —$C_4$-$C_{12}$cycloalkenyl, 3- to 14-membered heterocyclyl containing 1-4 heteroatoms independently selected from the group consisting of O, N, and S, —$C_6$-$C_{14}$aryl, and 5- to 14-membered heteroaryl containing 1-4 heteroatoms independently selected from the group consisting of O, N, and S,
  wherein each alkyl, alkenyl, alkynyl, cycloalkyl, cycloalkenyl, heterocyclyl, aryl, or heteroaryl is optionally substituted with one or more halogen, —$C_1$-$C_6$alkyl, —$C_2$-$C_6$alkenyl, —$C_2$-$C_6$alkynyl, —O($C_1$-$C_6$alkyl), —NH($C_1$-$C_6$alkyl), or —N($C_1$-$C_6$alkyl)$_2$; and
each R' is independently selected from the group consisting of —$C_1$-$C_6$alkyl, —$C_2$-$C_6$alkenyl, —$C_2$-$C_6$alkynyl, —$C_3$-$C_{12}$cycloalkyl, —$C_4$-$C_{12}$cycloalkenyl, 3- to 14-membered heterocyclyl containing 1-4 heteroatoms independently selected from the group consisting of O, N, and S, —(CR$^b$R$^c$)$_n$$C_6$-$C_{14}$aryl, —(CR$^b$R$^c$)$_n$O($C_6$-$C_{14}$aryl), and 5- to 14-membered heteroaryl containing 1-4 heteroatoms independently selected from the group consisting of O, N, and S,
  wherein each alkyl, alkenyl, alkynyl, cycloalkyl, cycloalkenyl, heterocyclyl, aryl, or heteroaryl is optionally substituted with one or more halogen, —$C_1$-$C_6$alkyl, —$C_2$-$C_6$alkenyl, —$C_2$-$C_6$alkynyl, —O($C_1$-$C_6$alkyl), —NH($C_1$-$C_6$alkyl), or —N($C_1$-$C_6$alkyl)$_2$:
provided that the compound is other than:

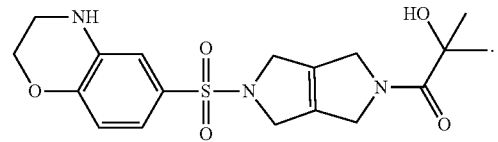 [SMILES: CC(C)(O)C(=O)N1CC2=C(C1)CN(S(=O)(=O)c1ccc3c(c1)NCCO3)C2]

Another aspect of this invention relates to compounds of Formula III:

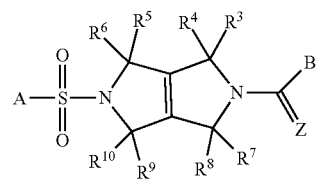

(III)

or a pharmaceutically acceptable salt thereof, wherein:
A is a monocyclic or bicyclic 3- to 14-membered ring,
  wherein the ring is saturated, fully or partially unsaturated, or aromatic, and
  wherein the ring contains 0-4 heteroatoms independently selected from the group consisting of O, N, and S; and
  wherein the ring is optionally substituted with one or more $R^a$;
each $R^a$ is independently selected from the group consisting of halogen, —OR, —OC(O)R', —NR$_2$, —NRC(O)R', —NRS(O)$_2$R', —CN, —NO$_2$, —SR, —C(O)R', —C(O)OR, —C(O)NR$_2$, —S(O)$_2$R', —S(O)$_2$NR$_2$, —$C_1$-$C_6$alkyl, —$C_2$-$C_6$alkenyl, —$C_2$-$C_6$alkynyl, —$C_3$-$C_{12}$cycloalkyl, —$C_4$-$C_{12}$cycloalkenyl, 3- to 14-membered heterocyclyl containing 1-4 heteroatoms independently selected from the group consisting of O, N, and S, $C_6$-$C_{14}$aryl, and 5- to 14-membered heteroaryl containing 1-4 heteroatoms independently selected from the group consisting of O, N, and S,
  wherein each alkyl is optionally substituted with one or more halogen;
Z is O, S, or NR;
B is a ring selected from the group consisting of —$C_6$-$C_{14}$aryl and 5- to 14-membered heteroaryl containing 1-4 heteroatoms independently selected from the group consisting of O, N, and S,
  wherein the ring is optionally substituted with one or more $R^d$;
each $R^d$ is independently selected from the group consisting of halogen, —OR, —OC(O)R', —NR$_2$, —NRC(O)R', —NRS(O)$_2$R', —CN, —NO$_2$, —SR, —C(O)R', —C(O)OR, —C(O)NR$_2$, —S(O)$_2$R', —S(O)$_2$NR$_2$, —$C_1$-$C_6$alkyl, —$C_2$-$C_6$alkenyl, —$C_2$-$C_6$alkynyl, —$C_3$-$C_{12}$cycloalkyl, —$C_4$-$C_{12}$cycloalkenyl, 3- to 14-membered heterocyclyl containing 1-4 heteroatoms independently selected from the group consisting of O, N, and S, $C_6$-$C_{14}$aryl, and 5- to 14-membered heteroaryl containing 1-4 heteroatoms independently selected from the group consisting of O, N, and S,
  wherein each alkyl, alkenyl, alkynyl, cycloalkyl, cycloalkenyl, heterocyclyl, aryl, or heteroaryl is optionally substituted with one or more halogen, —$C_1$-$C_6$ alkyl, —$C_2$-$C_6$alkenyl, —$C_2$-$C_6$alkynyl, or —OR;

$R^3$, $R^4$, $R^5$, $R^6$, $R^7$, $R^8$, $R^9$, and $R^{10}$ are each independently —H or —$C_1$-$C_6$, alkyl,
  wherein each alkyl is optionally substituted with one or more halogen;

or $R^3$ and $R^4$, $R^5$ and $R^6$, $R^7$ and $R^8$, $R^9$ and $R^{10}$, or combinations thereof, combine with the carbon to which they are attached to form oxo, a $C_3$-$C_8$cycloalkyl, or a 3- to 8-membered heterocyclyl containing 1-4 heteroatoms independently selected from the group consisting of O, N, and S;

each R is independently selected from the group consisting of —H, —OH, —O($C_1$-$C_3$alkyl), —$NH_2$, —NH($C_1$-$C_6$alkyl), —N($C_1$-$C_6$alkyl)$_2$, —$C_1$-$C_6$alkyl, —$C_2$-$C_6$alkenyl, —$C_2$-$C_6$alkynyl, —$C_3$-$C_{12}$cycloalkyl, —$C_4$-$C_{12}$cycloalkenyl, 3- to 14-membered heterocyclyl containing 1-4 heteroatoms independently selected from the group consisting of O, N, and S, $C_6$-$C_{14}$aryl, and 5- to 14-membered heteroaryl containing 1-4 heteroatoms independently selected from the group consisting of O, N, and S,
  wherein each alkyl, alkenyl, alkynyl, cycloalkyl, cycloalkenyl, heterocyclyl, aryl, or heteroaryl is optionally substituted with one or more halogen, —$C_1$-$C_6$alkyl, —$C_2$-$C_6$alkenyl, —$C_2$-$C_6$alkynyl, —O—$C_1$-$C_6$alkyl, —NH($C_1$-$C_6$alkyl), or —N($C_1$-$C_3$alkyl)$_2$; and each R' is independently selected from the group consisting of —$C_1$-$C_6$alkyl, —$C_2$-$C_6$alkenyl, —$C_2$-$C_6$alkynyl, —$C_3$-$C_{12}$cycloalkyl, —$C_4$-$C_{12}$cycloalkenyl, 3- to 14-membered heterocyclyl containing 1-4 heteroatoms independently selected from the group consisting of O, N, and S, $C_6$-$C_{14}$aryl, and 5- to 14-membered heteroaryl containing 1-4 heteroatoms independently selected from the group consisting of O, N, and S,
  wherein each alkyl, alkenyl, alkynyl, cycloalkyl, cycloalkenyl, heterocyclyl, aryl, or heteroaryl is optionally substituted with one or more halogen, —$C_1$-$C_6$alkyl, —$C_2$-$C_6$alkenyl, —$C_2$-$C_6$alkynyl, —O—$C_1$-$C_6$alkyl, —NH($C_1$-$C_6$alkyl), or —N($C_1$-$C_6$alkyl)$_2$.

Another aspect of this invention relates to compounds of Formula IV:

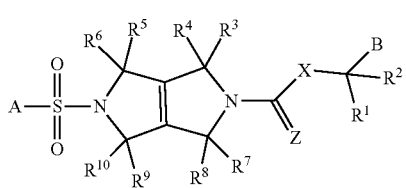

(IV)

or a pharmaceutically acceptable salt thereof, wherein:
A is a monocyclic or bicyclic 3- to 14-membered ring,
  wherein the ring is saturated, fully or partially unsaturated, or aromatic, and
  wherein the ring contains 0-4 heteroatoms independently selected from the group consisting of O, N, and S; and
  wherein the ring is optionally substituted with one or more $R^a$;

each $R^a$ is independently selected from the group consisting of halogen, —OR, —OC(O)R', —$NR_2$, —NRC(O)R', —NRS(O)$_2$R', —CN, —$NO_2$, —SR, —C(O)R', —C(O)OR, —C(O)$NR_2$, —S(O)$_2$R', —S(O)$_2NR_2$, —$C_1$-$C_6$alkyl, —$C_2$-$C_6$alkenyl, —$C_2$-$C_6$alkynyl, —$C_3$-$C_{12}$cycloalkyl, —$C_4$-$C_{12}$cycloalkenyl, 3- to 14-membered heterocyclyl containing 1-4 heteroatoms independently selected from the group consisting of O, N, and S, $C_6$-$C_{14}$aryl, and 5- to 14-membered heteroaryl containing 1-4 heteroatoms independently selected from the group consisting of O, N, and S,
  wherein each alkyl is optionally substituted with one or more halogen;

Z is O, S, or NR;
X is O or $NR^e$;
$R^e$ is —H or —$C_1$-$C_6$alkyl;
B is —H, or a monocyclic or bicyclic 3- to 14-membered ring,
  wherein the ring is saturated, fully or partially unsaturated, or aromatic, and
  wherein the ring contains 0-4 heteroatoms independently selected from the group consisting of O, N, and S; and
  wherein the ring is optionally substituted with one or more $R^d$;

each $R^d$ is independently selected from the group consisting of halogen, —OR, —OC(O)R', —$NR_2$, —NRC(O)R', —NRS(O)$_2$R', —CN, —$NO_2$, —SR, —C(O)R', —C(O)OR, —C(O)$NR_2$, —S(O)$_2$R', —S(O)$_2NR_2$, —$C_1$-$C_6$alkyl, —$C_2$-$C_6$alkenyl, —$C_2$-$C_6$alkynyl, —$C_3$-$C_{12}$cycloalkyl, —$C_4$-$C_{12}$cycloalkenyl, 3- to 14-membered heterocyclyl containing 1-4 heteroatoms independently selected from the group consisting of O, N, and S, $C_6$-$C_{14}$aryl, and 5- to 14-membered heteroaryl containing 1-4 heteroatoms independently selected from the group consisting of O, N, and S,
  wherein each alkyl, alkenyl, alkynyl, cycloalkyl, cycloalkenyl, heterocyclyl, aryl, or heteroaryl is optionally substituted with one or more halogen, —$C_1$-$C_6$alkyl, —$C_2$-$C_6$alkenyl, —$C_2$-$C_6$alkynyl, or —OR;

$R^1$ and $R^2$ are each independently —H, halogen, —$C_1$-$C_6$alkyl, —$C_2$-$C_6$alkenyl, —$C_2$-$C_6$alkynyl, —$(CR^bR^c)_nC_3$-$C_{12}$cycloalkyl, —$(CR^bR^c)_nC_4$-$C_{12}$cycloalkenyl, —$(CR^bR^c)_n$heterocyclyl, —$(CR^bR^c)_nC_6$-$C_{14}$aryl, —$(CR^bR^c)_n$heteroaryl, —$(CR^bR^c)_n$OR, —$(CR^bR^c)_n$OC(O)R', —$(CR^bR^c)_n$OS(O)$_2$R', —$(CR^bR^c)_n$OS(O)$_2NR_2$, —$(CR^bR^c)_n$OC(O)$NR_2$, —$(CR^bR^c)_n$OC(O)OR, —$(CR^bR^c)_nNR_2$, —$(CR^bR^c)_n$NRC(O)R', —$(CR^bR^c)_n$NRS(O)$_2$R', —$(CR^bR^c)_n$NRC(O)$NR_2$, —$(CR^bR^c)_n$NRC(O)OR, —$(CR^bR^c)_n$CN, —$(CR^bR^c)_n$$NO_2$, —$(CR^bR^c)_n$SR, —$(CR^bR^c)_n$C(O)R', —$(CR^bR^c)_n$C(O)OR, —$(CR^bR^c)_n$C(O)$NR_2$, —$(CR^bR^c)_n$SO$_2$R', —$(CR^bR^c)_n$SO$_2NR_2$, or —$(CR^bR^c)_n$SO$_2$OR,
  wherein each alkyl, alkenyl, alkynyl, cycloalkyl, cycloalkenyl, heterocyclyl, aryl, or heteroaryl is optionally substituted with one or more substituents selected from the group consisting of halogen, —$C_1$-$C_6$alkyl, —$C_2$-$C_6$alkenyl, —$C_2$-$C_6$alkynyl, —OR, and oxo,
  wherein each heterocyclyl is 3- to 14-membered and contains 1-4 heteroatoms independently selected from the group consisting of O, N, and S, and
  wherein each heteroaryl is 5- to 14-membered and contains 1-4 heteroatoms independently selected from the group consisting of O, N, and S;

or $R^1$ and $R^2$ combine with the carbon to which they are attached to form oxo, a G-$C_{12}$cycloalkyl, or a 3- to 14-membered heterocyclyl containing 1-4 heteroatoms independently selected from the group consisting of O, N, and S,
  wherein each cycloalkyl or heterocyclyl is optionally substituted with one or more substituents selected from the group consisting of halogen, —$C_1$-$C_6$alkyl, —$C_2$-$C_6$alkenyl, —$C_2$-$C_6$alkynyl, —OR, and oxo;
or $R^e$ and $R^1$ combine with the nitrogen to which they are attached to form a 3- to 14-membered heterocyclyl containing 1-4 heteroatoms independently selected from the group consisting of O, N, and S,
  wherein the heterocyclyl is optionally substituted with one or more halogen, —$C_1$-$C_6$alkyl, —$C_2$-$C_6$alkenyl, —$C_2$-$C_6$alkynyl, oxo, —OR, and —$(CR^bR^c)_n C_6$-$C_{14}$aryl;
or $R^2$ is absent, and $R^1$ and B combine with the carbon to which they are attached to form $C_6$-$C_{14}$aryl or 5- to 14-membered heteroaryl containing 1-4 heteroatoms independently selected from the group consisting of O, N, and S,
  wherein each aryl or heteroaryl is optionally substituted with one or more halogen, —$C_1$-$C_6$alkyl, —$C_2$-$C_6$alkenyl, —$C_2$-$C_6$alkynyl, or —OR;
each $R^b$ and $R^c$ is independently selected from the group consisting of —H, —$C_1$-$C_6$alkyl, and halogen;
each n is independently 0, 1, 2, 3, or 4;
$R^3$, $R^4$, $R^5$, $R^6$, $R^7$, $R^8$, $R^9$, and $R^{10}$ are each independently —H or —$C_1$-$C_6$alkyl, wherein each alkyl is optionally substituted with one or more halogen;
or $R^3$ and $R^4$, $R^5$ and $R^6$, $R^7$ and $R^8$, $R^9$ and $R^{10}$, or combinations thereof, combine with the carbon to which they are attached to form oxo, a $C_3$-$C_8$cycloalkyl, or a 3- to 8-membered heterocyclyl containing 1-4 heteroatoms independently selected from the group consisting of O, N, and S;
each R is independently selected from the group consisting of —H, —OH, —O($C_1$-$C_3$alkyl), —$NH_2$, —NH($C_1$-$C_6$alkyl), —N($C_1$-$C_6$alkyl)$_2$, —$C_1$-$C_6$alkyl, —$C_2$-$C_6$alkenyl, —$C_2$-$C_6$alkynyl, —$C_3$-$C_{12}$cycloalkyl, —$C_4$-$C_{12}$cycloalkenyl, 3- to 14-membered heterocyclyl containing 1-4 heteroatoms independently selected from the group consisting of O, N, and S, $C_6$-$C_{14}$aryl, and 5- to 14-membered heteroaryl containing 1-4 heteroatoms independently selected from the group consisting of O, N, and S,
  wherein each alkyl, alkenyl, alkynyl, cycloalkyl, cycloalkenyl, heterocyclyl, aryl, or heteroaryl is optionally substituted with one or more halogen, —$C_1$-$C_6$alkyl, —$C_2$-$C_6$alkenyl, —$C_2$-$C_6$alkynyl, —O—$C_1$-$C_6$alkyl, —NH($C_1$-$C_0$alkyl), or —N($C_1$-$C_6$alkyl)$_2$; and
each R' is independently selected from the group consisting of —$C_1$-$C_6$alkyl, —$C_2$-$C_6$alkenyl, —$C_2$-$C_6$alkynyl, —$C_3$-$C_{12}$cycloalkyl, —$C_4$-$C_{12}$cycloalkenyl, 3- to 14-membered heterocyclyl containing 1-4 heteroatoms independently selected from the group consisting of O, N, and S, $C_6$-$C_{14}$aryl, and 5- to 14-membered heteroaryl containing 1-4 heteroatoms independently selected from the group consisting of O, N, and S,
  wherein each alkyl, alkenyl, alkynyl, cycloalkyl, cycloalkenyl, heterocyclyl, aryl, or heteroaryl is optionally substituted with one or more halogen, —$C_1$-$C_6$alkyl, —$C_2$-$C_6$alkenyl, —$C_2$-$C_6$alkynyl, —O—$C_1$-$C_6$alkyl, —NH($C_1$-$C_6$alkyl), or —N($C_1$-$C_6$alkyl)$_2$.

Another aspect of this invention relates to compounds of Formula I, II, III, or IV that are PKR Activating Compounds. In some embodiments, a PKR Activating Compound as used herein refers to a compound having one or more of the following characteristics when tested according to the Luminescence Assay Protocol of Example 24 below: (1) an $AC_{50}$ value of less than 40 μM; (2) a maximum % Fold (MAX % Fold) value of greater than 75%; and/or (3) a % Fold value at 1.54 μM compound concentration (% Fold@1.54 μM) of at least 75%. In some embodiments, the PKR Activating Compound has: (1) an $AC_{50}$ value of less than 0.1 μM, 0.1-1.0 μM, or 1.01-40 μM; (2) a MAX % Fold of 75%-250%, 251-500%, or 75%-500%; and/or (3) a % Fold@1.54 μM of 75%-250%, 251-500%, or 75%-500%. In some embodiments, a PKR Activating Compound has (1) an $AC_{50}$ value of less than 1.0 μM; (2) a MAX % Fold of 75%-500%; and/or (3) a % Fold@1.54 μM of 75%-500%. In some embodiments, the Luminescence Assay Protocol of Example 24 is performed with wild type (wt) PKR, G332S mutant form of PKR or R510Q mutant form of PKR. In some embodiments, a PKR Activating Compound is a compound of Formula I, II, III, or IV.

BRIEF DESCRIPTION OF THE DRAWING

FIG. 1 shows an exemplary dose-response curve for compounds disclosed herein. Dose-response curves may be generated using the standard four parameter fit algorithm of ActivityBase XE Runner to determine MAX % Fold, MIN % Fold, slope and $AC_{50}$. MAX % Fold is the highest % fold increase observed at any concentration of compound, and MIN % Fold is the lowest % fold increase observed at any concentration of compound. The $AC_{50}$ value for a compound is the concentration (μM) corresponding to the midway between the maximum and minimum values of the four parameter logistic curve fit (i.e., at which the % fold increase along the four parameter logistic curve fit is halfway between MAX % Fold and MIN % Fold (% Fold Midpoint). Another useful parameter for evaluating compounds of this disclosure is % Fold@1.54 μM, which is the % fold increase at a compound concentration of 1.5 μM (e.g., 1.54 μM). X-axis and y-axis not necessarily to scale.

DETAILED DESCRIPTION

One aspect of this invention relates to compounds of Formula I:

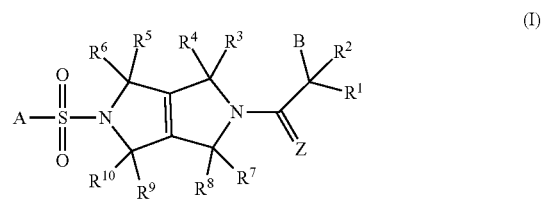

or a pharmaceutically acceptable salt thereof, wherein A, B, $R^1$, $R^2$, $R^3$, $R^4$, $R^5$, $R^6$, $R^7$, $R^8$, $R^9$, $R^{10}$, and Z are as defined above for Formula I and described in classes and subclasses herein, both singly and in combination.

In some embodiments, compounds are provided that are compounds of Formula I-a:

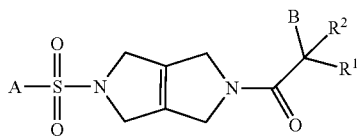
(I-a)

or a pharmaceutically acceptable salt thereof,
wherein A, B, R¹, and R² are as defined above for Formula I and described in classes and subclasses herein, both singly and in combination.

In some embodiments, compounds are provided that are compounds of Formula I-b:

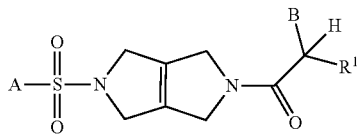
(I-b)

or a pharmaceutically acceptable salt thereof,
wherein A, B, and R¹ are as defined above for Formula I and described in classes and subclasses herein, both singly and in combination.

In some embodiments, compounds are provided that are compounds of Formula I-c:

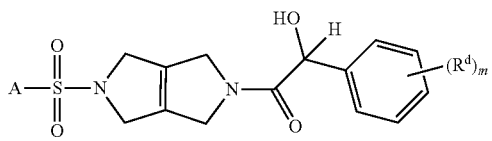
(I-c)

or a pharmaceutically acceptable salt thereof,
wherein A is as defined above for Formula I and described in classes and subclasses herein, both singly and in combination, and
wherein m is 0, 1, 2, 3, 4, or 5.

In some embodiments, compounds are provided that are compounds of Formula I-d-1:

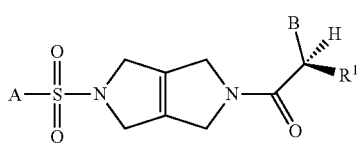
(I-d-1)

or a pharmaceutically acceptable salt thereof,
wherein A, B, and R¹ are as defined above for Formula I and described in classes and subclasses herein, both singly and in combination.

In some embodiments, compounds are provided that are compounds of Formula I-d-2:

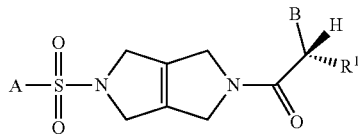
(I-d-2)

or a pharmaceutically acceptable salt thereof,
wherein A, B, and R¹ are as defined above for Formula I and described in classes and subclasses herein, both singly and in combination.

In some embodiments, a compound of Formula I-a is provided wherein:
A is phenyl or a monocyclic 5- to 6-membered heteroaryl ring containing 1-4 heteroatoms independently selected from the group consisting of O, N, and S,
  wherein each aryl or heteroaryl is optionally substituted with one or more $R^a$;
each $R^a$ is independently selected from the group consisting of halogen, —OR, —NRC(O)R', —CN, —S(O)$_2$NR$_2$, and —C$_1$-C$_6$alkyl,
  wherein each alkyl is optionally substituted with one or more halogen;
R¹ and R² are each independently selected from the group consisting of —H, halogen, —C$_1$-C$_6$alkyl, and —OR;
B is a monocyclic or bicyclic 3- to 14-membered ring,
  wherein the ring is partially unsaturated or aromatic, and
  wherein the ring contains 0-4 heteroatoms independently selected from the group consisting of O, N, and S, and
  wherein the ring is optionally substituted with $(R^d)_m$, and when the ring is partially unsaturated, then the ring does not contain an O in the γ-position relative to C(=Z);
each $R^d$ is independently selected from the group consisting of halogen, —C$_1$-C$_6$alkyl, and —OR,
  wherein each alkyl is optionally substituted with one or more halogen;
m is 0, 1, or 2;
each R is independently selected from the group consisting of —H and —C$_1$-C$_6$alkyl, wherein each alkyl is optionally substituted with one or more halogen; and
each R' is —C$_1$-C$_6$alkyl, In some embodiments, a compound of Formula I-a is provided wherein:
A is phenyl, pyridyl, thiophenyl, imidazolyl, isoxazolyl, or pyrazolyl,
  wherein each phenyl, pyridyl, thiophenyl, imidazolyl, isoxazolyl, or pyrazolyl is optionally substituted with one or more $R^a$;
each $R^a$ is independently selected from the group consisting of fluoro, chloro, methyl, —CF$_3$, —OMe, —OiPr, —OCF$_3$, —OCF$_2$H, —NHC(O)Me, —CN, and —SO$_2$NH$_2$;
R¹ and R² are each independently selected from the group consisting of —H, fluoro, methyl, ethyl, isopropyl, and —OH;
B is a monocyclic or bicyclic 3- to 10-membered ring selected from the group consisting of:

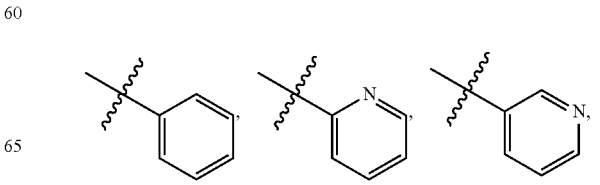

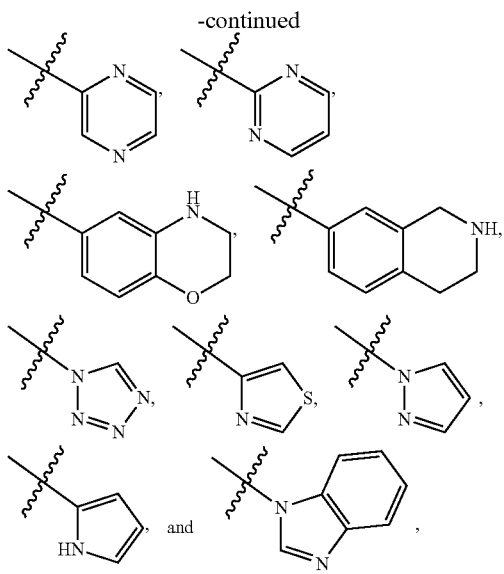

wherein the ring is optionally substituted with $(R^d)_m$; each $R^d$ is independently selected from the group consisting of fluoro, chloro, methyl, —CF$_3$, and —OMe; and m is 0, 1, or 2.

In some embodiments of Formula I, I-a, I-b, I-c, I-d-1, and I-d-2, A is a phenyl or monocyclic 5- to 6-membered heteroaryl ring containing 1-4 heteroatoms independently selected from the group consisting of O, N, and S, optionally substituted with one or more $R^a$. In some embodiments, A is phenyl optionally substituted with one or more $R^a$. In some embodiments, A is monocyclic 5- to 6-membered heteroaryl containing 1-4 heteroatoms independently selected from the group consisting of O, N, and S (e.g., pyridyl, thiophenyl, imidazolyl, isoxazolyl, or pyrazolyl), optionally substituted with one or more $R^a$. In some embodiments, A is phenyl, pyridyl, or thiophenyl, each optionally substituted with one or more $R^a$. In some embodiments, A is phenyl or pyridyl, each optionally substituted with one or more $R^a$. In some embodiments, A is pyridyl. In some embodiments, A is unsubstituted.

In some embodiments of Formula I, I-a, I-b, I-c, I-d-1, and I-d-2, each $R^a$ is independently selected from the group consisting of halogen (e.g., fluoro or chloro), —OR (e.g., —OMe, —OiPr, —OCF$_3$, or —OCF$_2$H), —NRC(O)R' (e.g., —NHC(O)Me), —CN, —S(O)$_2$NR$_2$ (e.g., —SO$_2$NH$_2$), and —C$_1$-C$_6$alkyl (e.g., methyl or —CF$_3$), wherein each alkyl is optionally substituted with one or more halogen. In some embodiments, each $R^a$ is independently selected from the group consisting of halogen (e.g., fluoro or chloro), —OR (e.g., —OMe, —OiPr, or —OCF$_2$H), —CN, —C$_1$-C$_6$alkyl (e.g., methyl or —CF$_3$). In some embodiments, each $R^a$ is independently selected from the group consisting of halogen (e.g., fluoro), —C$_1$-C$_6$alkyl (e.g., methyl), and —OR (e.g., —OMe or —OCF$_2$H).

In some embodiments of Formula I, Z is O or S. In some embodiments, Z is O. In some embodiments, Z is S. In some embodiments, Z is NR (e.g., NH$_2$, NOH, or NNH$_2$).

In some embodiments of Formula I, I-a, I-b, I-d-1, and I-d-2, $R^1$ and $R^2$ are each independently selected from the group consisting of —H, halogen, —C$_1$-C$_6$alkyl, —OR, —OC(O)R', —OS(O)$_2$R', —OS(O)$_2$NR$_2$, —OC(O)NR$_2$, —OC(O)OR, —(CR$^b$R$^c$)$_n$NR$_2$, —(CR$^b$R$^c$)$_n$NRC(O)R', —(CR$^b$R$^c$)$_n$NRS(O)$_2$R', —(CR$^b$R$^c$)$_n$NRC(O)NR$_2$, and —(CR$^b$R$^c$)$_n$NRC(O)OR. In some embodiments, $R^1$ and $R^2$ are each independently selected from the group consisting of —H, halogen (e.g., fluoro), —C$_1$-C$_6$alkyl (e.g., methyl, ethyl, or isopropyl), and —OR (e.g., —OH). In some embodiments, $R^1$ and $R^2$ are each independently selected from the group consisting of —H, halogen (e.g., fluoro), and —OR (e.g., —OH). In some embodiments, one of $R^1$ and $R^2$ is —H. In some embodiments, $R^1$ is —OH and $R^2$ is —H.

In some embodiments of Formula I and I-a, $R^1$ and $R^2$ combine with the carbon to which they are attached to form oxo, a C$_3$-C$_{12}$cycloalkyl, or 3- to 8-membered heterocyclyl containing 1-4 heteroatoms independently selected from the group consisting of O, N, and S, and wherein the heterocyclyl does not contain an O in the γ-position relative to C(=Z), and wherein each cycloalkyl or heterocyclyl is optionally substituted with one or more substituents selected from the group consisting of halogen, —C$_1$-C$_6$alkyl, oxo, and —OR, wherein —OR does not result in an O in the γ-position relative to C(=Z). In some embodiments of Formula I and I-a, $R^1$ and $R^2$ combine with the carbon to which they are attached to form a C$_3$-C$_6$cycloalkyl or 3- to 6-membered heterocyclyl containing 1-4 heteroatoms independently selected from the group consisting of O, N, and S, wherein the heterocyclyl does not contain an O in the γ-position relative to C(=Z), and wherein each cycloalkyl or heterocyclyl is optionally substituted with one or more substituents selected from the group consisting of halogen, —C$_1$-C$_6$alkyl, oxo, and —OR, wherein —OR does not result in an O in the γ-position relative to C(=Z).

In some embodiments of Formula I, I-a, I-b, I-c, I-d-1, and I-d-2, $R^b$ and $R^c$ are each —H. In some embodiments, $R^b$ and $R^c$ are each independently —H or halogen (e.g., fluoro). In some embodiments, $R^b$ and $R^c$ are each independently —H or —C$_1$-C$_6$alkyl (e.g., methyl).

In some embodiments of Formula I, I-a, I-b, I-c, I-d-1, and I-d-2, each n is independently 0, 1, or 2. In some embodiments, each n is 0 or 1. In some embodiments, each n is 0. In some embodiments, each n is 1. In some embodiments, each n is 2.

In some embodiments of Formula I, I-a, I-b, I-d-1, and I-d-2, B is:
(i) a monocyclic 3- to 8-membered ring, comprising a C$_3$-C$_8$cycloalkyl, 3- to 8-membered heterocyclyl, phenyl, or 5- to 8-membered heteroaryl ring,
  wherein the ring contains 0-4 heteroatoms independently selected from the group consisting of O, N, and S,
  wherein the ring is optionally substituted with $(R^d)_m$, and
  wherein the ring comprising a 3- to 8-membered heterocyclyl does not contain an O in the γ-position relative to C(=Z); or
(ii) a bicyclic 6- to 14-membered ring, comprising a C$_3$-C$_{10}$cycloalkyl, 3- to 11-membered heterocyclyl, phenyl, or 5- to 11-membered heteroaryl ring,
  wherein the ring is fused to an aromatic, saturated, or partially saturated 3- to 8-membered carbocyclic or an aromatic, saturated, or partially saturated 3- to 8-membered heterocyclic ring,
  wherein the ring contains 0-4 heteroatoms independently selected from the group consisting of O, N, and S,
  wherein the ring is optionally substituted with $(R^d)_m$, and
  wherein the ring comprising a 3- to 11-membered heterocyclyl does not contain an O in the γ-position relative to C(=Z).

In some embodiments of Formula I, I-a, I-b, I-d-1, and I-d-2, B is an aromatic monocyclic ring or a bicyclic ring wherein at least one of the rings is aromatic, and wherein the monocyclic ring or bicyclic ring contains 0-4 heteroatoms independently selected from the group consisting of O, N, and S, and wherein the monocyclic ring or bicyclic ring is optionally substituted with $(R^d)_m$. In some embodiments, B is phenyl optionally substituted with $(R^d)_m$. In some embodiments, B is unsubstituted phenyl. In some embodiments, B is phenyl fused to a saturated or partially saturated 5- to 8-membered heterocyclic ring. In some embodiments, B is a monocyclic or bicyclic heteroaryl ring, wherein the ring contains 1-4 heteroatoms independently selected from the group consisting of O, N, and S, and wherein the ring is optionally substituted with $(R^d)_m$.

In some embodiments of Formula I, I-a, I-b, I-d-1, and I-d-2, B is a monocyclic or bicyclic 3- to 10-membered ring, wherein the ring is partially unsaturated or aromatic, and wherein the ring contains 0-4 heteroatoms independently selected from the group consisting of O, N, and S; and wherein the ring is optionally substituted with $(R^d)_m$, and when the ring is partially unsaturated, then the ring does not contain an O in the γ-position relative to C(=Z).

In some embodiments of Formula I, I-a, I-b, I-d-1, and I-d-2, B is a monocyclic or bicyclic 3- to 10-membered ring selected from the group consisting of:

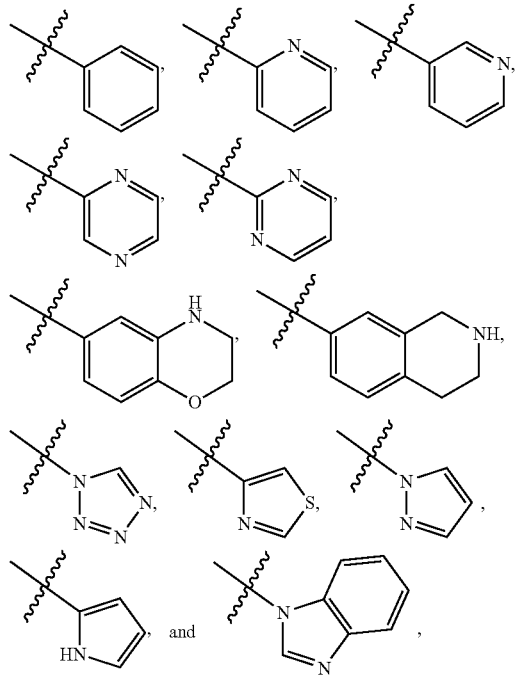

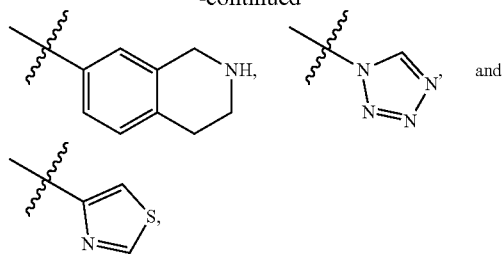

wherein the ring is optionally substituted with $(R^d)_m$.

In some embodiments of Formula I, I-a, I-b, I-d-1, and I-d-2, B is a monocyclic or bicyclic 3- to 10-membered ring selected from the group consisting of:

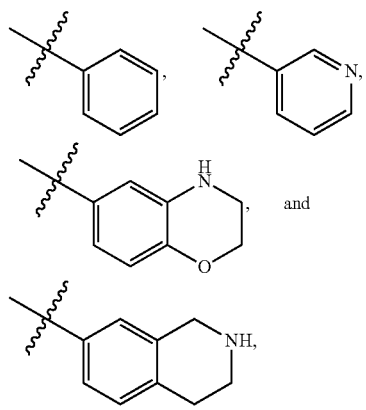

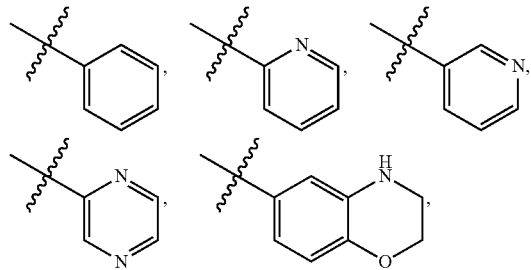

wherein the ring is optionally substituted with $(R^d)_m$.

In some embodiments of Formula I, I-a, I-b, I-c, I-d-1, and I-d-2, each $R^d$ is independently selected from the group consisting of halogen, —$C_1$-$C_6$alkyl, —$C_3$-$C_{12}$cycloalkyl, heterocyclyl, —OR, and —$NR_2$, wherein each alkyl, cycloalkyl, or heterocyclyl are optionally substituted with one or more halogen. In some embodiments, each $R^d$ is independently selected from the group consisting of halogen (e.g., fluoro or chloro), —$C_1$-$C_6$alkyl (e.g., methyl or —$CF_3$), and —OR (e.g., —OMe), wherein each alkyl is optionally substituted with one or more halogen. In some embodiments, each $R^d$ is independently selected from the group consisting of halogen (e.g., fluoro), —$C_1$-$C_6$alkyl (e.g., methyl), and —OR (e.g., —OMe).

In some embodiments of Formula I, I-a, I-b, I-c, I-d-1, and I-d-2, m is 0, 1, 2, 3, 4, or 5. In some embodiments, m is 0, 1, 2, or 3. In some embodiments, m is 0, 1, or 2. In some embodiments, m is 0. In some embodiments, m is 1. In some embodiments, m is 2.

In some embodiments of Formula I, $R^3$, $R^4$, $R^5$, $R^6$, $R^7$, $R^8$, $R^9$, and $R^{10}$ are each —H. In some embodiments, one of $R^3$, $R^4$, $R^5$, $R^6$, $R^7$, $R^8$, $R^9$, and $R^{10}$ is —$C_1$-$C_6$alkyl (e.g., methyl) and the others are —H.

In some embodiments of Formula I, I-a, I-b, I-c, I-d-1, and I-d-2, each R is independently selected from the group consisting of —H, —$C_1$-$C_6$alkyl, —$C_3$-$C_{12}$cycloalkyl, and 3- to 14-membered heterocyclyl containing 1-4 heteroatoms independently selected from the group consisting of O, N, and S, wherein each alkyl, cycloalkyl, or heterocyclyl is optionally substituted with one or more halogen. In some embodiments, each R is independently selected from the group consisting of —H and —$C_1$-$C_6$alkyl (e.g., methyl or isopropyl), wherein each alkyl is optionally substituted with one or more halogen (e.g., fluoro).

In some embodiments of Formula I, I-a, I-b, I-c, I-d-1, and I-d-2, each R' is independently —$C_1$-$C_6$alkyl, —$C_3$-$C_{12}$cycloalkyl, or 3- to 14-membered heterocyclyl containing 1-4 heteroatoms independently selected from the group consisting of O, N, and S, wherein each alkyl, cycloalkyl, or heterocyclyl is optionally substituted with one or more halogen. In some embodiments, each R' is —$C_1$-$C_6$alkyl (e.g., methyl).

In some embodiments of Formula I, I-a, I-b, I-c, I-d-1, and I-d-2, the compound is other than:

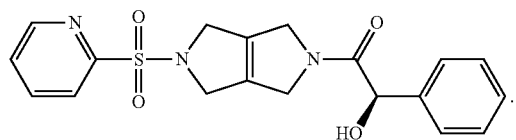 [SMILES: O=C([C@H](O)c1ccccc1)N1CC2=C(C1)CN(S(=O)(=O)c1ccccn1)C2]

For example, some embodiments provide a compound of any one or more of Formula I, I-a, I-b, I-c, I-d-1, and I-d-2, other than the compound of the formula:

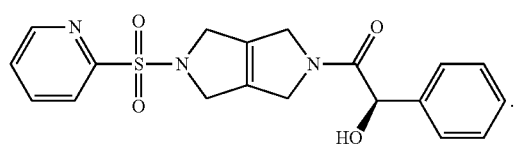 [SMILES: O=C([C@H](O)c1ccccc1)N1CC2=C(C1)CN(S(=O)(=O)c1ccccn1)C2]

Another aspect of this invention relates to compounds of Formula II:

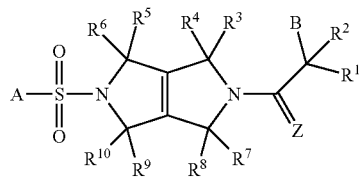

(II)

or a pharmaceutically acceptable salt thereof,
wherein A, B, $R^1$, $R^2$, $R^3$, $R^4$, $R^5$, $R^6$, $R^7$, $R^8$, $R^9$, $R^{10}$, and Z are as defined above for Formula II and described in classes and subclasses herein, both singly and in combination.

In some embodiments, compounds are provided that are compounds of Formula II-a:

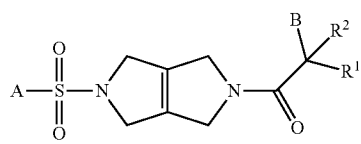

(II-a)

or a pharmaceutically acceptable salt thereof,
wherein A, B, $R^1$, and $R^2$ are as defined above for Formula II and described in classes and subclasses herein, both singly and in combination.

In some embodiments, compounds are provided that are compounds of Formula II-b-1:

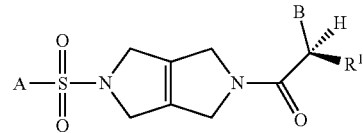

(II-b-1)

or a pharmaceutically acceptable salt thereof,
wherein A is as defined above for Formula II and described in classes and subclasses herein, both singly and in combination,
wherein $R^1$ is —H, halogen, —$C_1$-$C_6$alkyl, —$C_2$-$C_6$alkenyl, or —$C_2$-$C_6$alkynyl,
wherein each alkyl, alkenyl, or alkynyl is optionally substituted with one or more halogen, and
wherein B is —OR, —OC(O)R', —OS(O)$_2$R', —OS(O)$_2$NR$_2$, —OC(O)NR$_2$, —OC(O)OR, —(CR$^b$R$^c$)$_n$NR$_2$, —(CR$^b$R$^c$)$_n$NRC(O)R', —(CR$^b$R$^c$)$_n$NRS(O)$_2$R', —(CR$^b$R$^c$)$_n$NRC(O)NR$_2$, —(CR$^b$R$^c$)$_n$NRC(O)OR, —(CR$^b$R$^c$)$_n$CN, —(CR$^b$R$^c$)$_n$NO$_2$, —(CR$^b$R$^c$)$_n$SR, —(CR$^b$R$^c$)$_n$C(O)R', —(CR$^b$R$^c$)$_n$C(O)OR, —(CR$^b$R$^c$)$_n$C(O)NR$_2$, —(CR$^b$R$^c$)$_n$SO$_2$R', —(CR$^b$R$^c$)$_n$SO$_2$NR$_2$, or —(CR$^b$R$^c$)$_n$SO$_2$OR.

In some embodiments, compounds are provided that are compounds of Formula II-b-2:

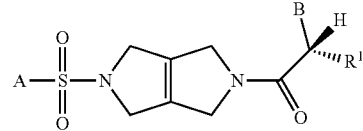

(II-b-2)

or a pharmaceutically acceptable salt thereof,
wherein A is as defined above for Formula II and described in classes and subclasses herein, both singly and in combination,
wherein $R^1$ is —H, halogen, —$C_1$-$C_6$alkyl, —$C_2$-$C_6$alkenyl, or —$C_2$-$C_6$alkynyl,
wherein each alkyl, alkenyl, or alkynyl is optionally substituted with one or more halogen, and
wherein B is —OR, —OC(O)R', —OS(O)$_2$R', —OS(O)$_2$NR$_2$, —OC(O)NR$_2$, —OC(O)OR, —(CR$^b$R$^c$)$_n$NR$_2$, —(CR$^b$R$^c$)$_n$NRC(O)R', —(CR$^b$R$^c$)$_n$NRS(O)$_2$R', —(CR$^b$R$^c$)$_n$NRC(O)NR$_2$, —(CR$^b$R$^c$)$_n$NRC(O)OR, —(CR$^b$R$^c$)$_n$CN, —(CR$^b$R$^c$)$_n$NO$_2$, —(CR$^b$R$^c$)$_n$SR, —(CR$^b$R$^c$)$_n$C(O)R', —(CR$^b$R$^c$)$_n$C(O)OR, —(CR$^b$R$^c$)$_n$C(O)NR$_2$, —(CR$^b$R$^c$)$_n$SO$_2$R', —(CR$^b$R$^c$)$_n$SO$_2$NR$_2$, or —(CR$^b$R$^c$)$_n$SO$_2$OR.

In some embodiments, a compound of Formula II-a is provided wherein:
A is a monocyclic or bicyclic 3- to 14-membered ring,
wherein the ring is partially unsaturated or aromatic, and
wherein the ring contains 0-4 heteroatoms independently selected from the group consisting of O, N, and S; and
wherein the ring is optionally substituted with one or more $R^a$;
each $R^a$ is independently selected from the group consisting of —$C_1$-$C_6$alkyl and —OR;
$R^1$, $R^2$, and B are each independently —H, —$C_1$-$C_6$alkyl, —OR, —(CR$^b$R$^c$)$_n$NR$_2$, —(CR$^b$R$^c$)$_n$NRS(O)$_2$R', or —(CR$^b$R$^c$)$_n$C(O)OR,
wherein each alkyl is optionally substituted with one or more halogen;

or R¹ and R² combine with the carbon to which they are attached to form a $C_3$-$C_{12}$cycloalkyl or 3- to 14-membered heterocyclyl containing 1-4 heteroatoms independently selected from the group consisting of O, N and S, wherein the heterocyclyl does not contain an O in the γ-position relative to C(=O),
wherein each cycloalkyl or heterocyclyl is optionally substituted with one or more substituents selected from the group consisting of —$C_6$aryl, and —C(O)R', and
wherein each cycloalkyl or heterocyclyl is optionally fused with a $C_6$aryl or 5- to 6-membered heteroaryl containing 1-4 heteroatoms independently selected from the group consisting of O, N, and S;
each $R^b$ and $R^c$ is —H;
each n is independently 0 or 1;
each R is independently selected from the group consisting of —H, —$C_1$-$C_6$alkyl, and $C_6$-$C_{14}$aryl,
wherein each aryl is optionally substituted with one or more halogen or —O($C_1$-$C_3$alkyl); and
each R' is independently selected from the group consisting of —$C_1$-$C_6$alkyl, —$(CR^bR^c)_nC_6$-$C_{14}$aryl, and —$(CR^bR^c)_nO(C_6$-$C_{14}$aryl),
wherein each alkyl or aryl is optionally substituted with one or more —O($C_1$-$C_3$alkyl).

In some embodiments, a compound of Formula II-a is provided wherein:
A is a monocyclic or bicyclic 3- to 10-membered ring selected from:

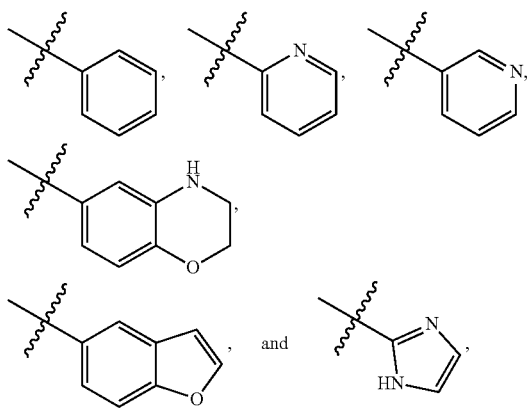

wherein the ring is optionally substituted with one or more $R^a$;
each $R^a$ is independently selected from the group consisting of methyl and —$OCHF_2$;
R¹, R², and B are each independently —H, methyl, ethyl, —$CH_2CHF_2$, propyl, —OR, —$CH_2NH_2$, —$CH_2NMe_2$, —$NHS(O)_2Me$, or —$CH_2C(O)OMe$,
wherein each methyl or ethyl is optionally substituted with one or more halogen;
or R¹ and R² combine with the carbon to which they are attached to form a cyclopropyl, cyclopentyl, cyclohexyl, pyrrolidinyl, tetrahydrofuranyl, or chromanyl,
wherein each cyclopropyl, cyclopentyl, cyclohexyl, or pyrrolidinyl is optionally substituted with one or more substituents selected from the group consisting of —$C_6$aryl, and —C(O)R', and
wherein each tetrahydrofuranyl or chromanyl does not contain an O in the γ-position relative to C(=O);
each R is independently selected from the group consisting of —H, methyl, and phenyl,
wherein each phenyl is optionally substituted with one or more fluoro or —OMe; and
each R' is independently selected from the group consisting of methyl, phenyl, —$CH_2$phenyl, and —$CH_2O$(phenyl),
wherein each methyl or phenyl is optionally substituted with one or more —OMe or —OEt.

In some embodiments of Formula II, II-a, II-b-1, and II-b-2, A is:
(i) a monocyclic 3- to 8-membered ring, comprising a $C_3$-$C_8$cycloalkyl, 3- to 8-membered heterocyclyl, phenyl, or 5- to 8-membered heteroaryl ring,
wherein the ring contains 0-4 heteroatoms independently selected from the group consisting of O, N, and S, and
wherein the ring is optionally substituted with one or more $R^a$; or
(ii) a bicyclic 6- to 14-membered ring, comprising a $C_3$-$C_8$cycloalkyl, 3- to 11-membered heterocyclyl, phenyl, or 5- to 11-membered heteroaryl ring,
wherein the ring is fused to an aromatic, saturated, or partially unsaturated 3- to 8-membered carbocyclic or an aromatic, saturated, or partially unsaturated 3- to 8-membered heterocyclic ring,
wherein the ring contains 0-4 heteroatoms independently selected from the group consisting of O, N, and S, and
wherein the ring is optionally substituted with one or more $R^a$.

In some embodiments of Formula II, II-a, II-b-1, and II-b-2, A is an aromatic monocyclic ring or a bicyclic ring wherein at least one of the rings is aromatic, and wherein the monocyclic ring or bicyclic ring contains 0-4 heteroatoms independently selected from the group consisting of O, N, and S, and wherein the monocyclic ring or bicyclic ring is optionally substituted with one or more $R^a$.

In some embodiments of Formula II, II-a, II-b-1, and II-b-2, A is a monocyclic or bicyclic 3- to 10-membered ring,
wherein the ring is partially unsaturated or aromatic, and
wherein the ring contains 0-4 heteroatoms independently selected from the group consisting of O, N, and S; and
wherein the ring is optionally substituted with one or more $R^a$.

In some embodiments of Formula II, II-a, II-b-1, and II-b-2, A is a monocyclic or bicyclic 3- to 10-membered ring selected from:

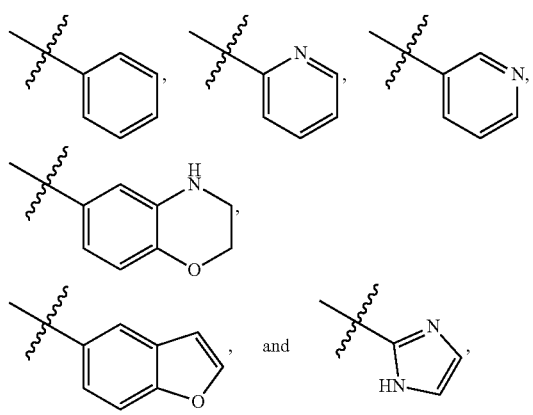

wherein the ring is optionally substituted with one or more $R^a$. In some embodiments, A is a bicyclic ring selected from:

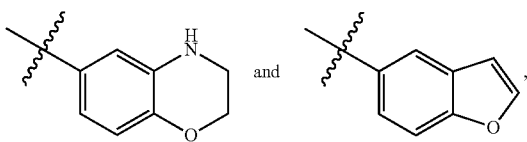 [SMILES: *c1ccc2c(c1)NCCO2 ; *c1ccc2occc2c1]

wherein the ring is optionally substituted with one or more $R^a$. In some embodiments, A is unsubstituted.

In some embodiments of Formula II, II-a, II-b-1, and II-b-2, each $R^a$ is independently selected from the group consisting of halogen, —$C_1$-$C_6$alkyl, —$C_3$-$C_{12}$cycloalkyl, 3- to 14-membered heterocyclyl containing 1-4 heteroatoms independently selected from the group consisting of O, N, and S, —OR, and —$NR_2$, wherein each alkyl, cycloalkyl, or heterocyclyl are optionally substituted with one or more halogen. In some embodiments of Formula II and II-a, each $R^a$ is independently selected from the group consisting of —$C_1$-$C_6$alkyl (e.g., methyl) and —OR (e.g., —$OCHF_2$).

In some embodiments of Formula II, Z is O or S. In some embodiments, Z is O. In some embodiments, Z is S. In some embodiments, Z is NR (e.g., $NH_2$, NOH, or $NNH_2$).

In some embodiments of Formula II, II-a, II-b-1, and II-b-2, $R^1$, $R^2$, and B are each independently —H, halogen, —$C_1$-$C_6$alkyl, —OR, —OC(O)R', —OS(O)$_2$R', —OS(O)$_2$NR$_2$, —OC(O)NR$_2$, —OC(O)OR, —(CR$^b$R$^c$)$_n$NR$_2$, —(CR$^b$R$^c$)$_n$NRC(O)R', —(CR$^b$R$^c$)$_n$NRS(O)$_2$R', —(CR$^b$R$^c$)$_n$NRC(O)NR$_2$, —(CR$^b$R$^c$)$_n$NRC(O)OR, or —(CR$^b$R$^c$)$_n$C(O)OR,
  wherein each alkyl is optionally substituted with one or more halogen;
or $R^1$ and $R^2$ combine with the carbon to which they are attached to form oxo, a $C_3$-$C_{12}$cycloalkyl, or a 3- to 14-membered heterocyclyl containing 1-4 heteroatoms independently selected from the group consisting of O, N, and S,
  wherein the heterocyclyl does not contain an O in the γ-position relative to C(=Z),
  wherein each cycloalkyl or heterocyclyl is optionally substituted with one or more substituents selected from the group consisting of halogen, —$C_1$-$C_6$alkyl, —OR, oxo, —$C_6$aryl, and —C(O)R', and
  wherein each cycloalkyl or heterocyclyl is optionally fused with a $C_6$aryl or 5- to 6-membered heteroaryl containing 1-4 heteroatoms independently selected from the group consisting of O, N, and S.

In some embodiments of Formula II, II-a, II-b-1, and II-b-2, $R^1$, $R^2$, and B are each independently —H, —$C_1$-$C_6$alkyl (e.g., methyl ethyl, propyl, or —$CH_2CHF_2$), —OR, —(CR$^b$R$^c$)$_n$NR$_2$ (e.g., —$CH_2NH_2$ or —$CH_2NMe_2$), —(CR$^b$R$^c$)$_n$NRS(O)$_2$R' (e.g., —NHS(O)$_2$Me), or —(CR$^b$R$^c$)$_n$C(O)OR (e.g, —$CH_2$C(O)OMe);
or $R^1$ and $R^2$ combine with the carbon to which they are attached to form a $C_3$-$C_{12}$cycloalkyl (e.g., cyclopropyl, cyclopentyl, or cyclohexyl) or 3- to 14-membered heterocyclyl containing 1-4 heteroatoms independently selected from the group consisting of O, N, and S (e.g., pyrrolidinyl, tetrahydrofuranyl, or chromanyl),
  wherein the heterocyclyl (e.g., tetrahydrofuranyl or chromanyl) does not contain an O in the γ-position relative to C(=Z), and
  wherein each cycloalkyl or heterocyclyl is optionally substituted with one or more substituents selected from the group consisting of —$C_6$aryl, and —C(O)R'.

In some embodiments of Formula II, II-a, II-b-1, and II-b-2, $R^1$, $R^2$, and B are each independently —H, —$C_1$-$C_6$alkyl (e.g., methyl ethyl, propyl, or —$CH_2CHF_2$), —OR, —(CR$^b$R$^c$)$_n$NR$_2$ (e.g., —$CH_2NH_2$ or —$CH_2NMe_2$), —(CR$^b$R$^c$)$_n$NRS(O)$_2$R' (e.g., —NHS(O)$_2$Me), or —(CR$^b$R$^c$)$_n$C(O)OR (e.g, —$CH_2$C(O)OMe). In some embodiments, $R^1$ and $R^2$ combine with the carbon to which they are attached to form a $C_3$-$C_{12}$cycloalkyl (e.g., cyclopropyl, cyclopentyl, or cyclohexyl) or 3- to 14-membered heterocyclyl containing 1-4 heteroatoms independently selected from the group consisting of N and S (e.g., pyrrolidinyl, tetrahydrofuranyl, or chromanyl), wherein the heterocyclyl does not contain an O in the γ-position relative to C(=Z), and wherein each cycloalkyl or heterocyclyl is optionally substituted with one or more substituents selected from the group consisting of —$C_6$aryl, and —C(O)R'.

In some embodiments of Formula II, II-a, II-b-1, and II-b-2, $R^b$ and $R^c$ are each —H. In some embodiments, $R^b$ and $R^c$ are each independently —H or halogen (e.g., fluoro). In some embodiments, $R^b$ and $R^c$ are each independently —H or —$C_1$-$C_6$alkyl (e.g., methyl).

In some embodiments of Formula II, II-a, II-b-1, and II-b-2, each n is independently 0, 1, or 2. In some embodiments, each n is independently 0 or 1. In some embodiments, each n is 0. In some embodiments, each n is 1. In some embodiments, each n is 2.

In some embodiments of Formula II, $R^3$, $R^4$, $R^5$, $R^6$, $R^7$, $R^8$, $R^9$, and $R^{10}$ are each —H. In some embodiments, one of $R^3$, $R^4$, $R^5$, $R^6$, $R^7$, $R^8$, $R^9$, and $R^{10}$ is —$C_1$-$C_6$alkyl (e.g., methyl) and the others are —H.

In some embodiments of Formula II, II-a, II-b-1, and II-b-2, each R is independently selected from the group consisting of —H, —$C_1$-$C_6$alkyl, —$C_3$-$C_{12}$cycloalkyl, 3- to 14-membered heterocyclyl containing 1-4 heteroatoms independently selected from the group consisting of O, N, and S, and $C_6$-$C_{14}$aryl, wherein each alkyl, cycloalkyl, heterocyclyl or aryl is optionally substituted with one or more halogen or —O($C_1$-$C_3$alkyl). In some embodiments, each R is independently selected from the group consisting of —H, —$C_1$-$C_6$alkyl (e.g., methyl), and $C_6$-$C_{14}$aryl (e.g., phenyl, or naphthyl or anthracenyl), wherein each alkyl or aryl is optionally substituted with one or more halogen (e.g., fluoro) or —O($C_1$-$C_3$alkyl) (e.g., —OMe). In some embodiments, each R is independently —H or methyl. In some embodiments, each R is —H.

In some embodiments of Formula II, II-a, II-b-1, and II-b-2, each R' is independently selected from the group consisting of —$C_1$-$C_6$alkyl, —$C_3$-$C_{12}$cycloalkyl, 3- to 14-membered heterocyclyl containing 1-4 heteroatoms independently selected from the group consisting of O, N, and S, —(CR$^b$R$^c$)$_n$$C_6$-$C_{14}$aryl, or —(CR$^b$R$^c$)$_n$O($C_6$-$C_{14}$aryl), wherein each alkyl, cycloalkyl, heterocyclyl, or aryl is optionally substituted with one or more halogen. In some embodiments, each R' is independently selected from the group consisting of —$C_1$-$C_6$alkyl (e.g., methyl), —(CR$^b$R$^c$)$_n$aryl (e.g., phenyl or —$CH_2$phenyl), or —(CR$^b$R$^c$)$_n$O(aryl) (e.g., —$CH_2$O(phenyl)), wherein each methyl or phenyl is optionally substituted with one or more —OMe or —OEt. In some embodiments, each R' is methyl.

Another aspect of this invention relates to compounds of Formula III:

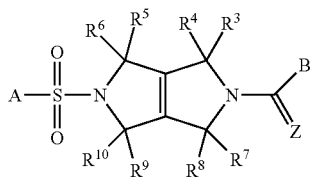

(III)

or a pharmaceutically acceptable salt thereof,
wherein A, B, Z, $R^3$, $R^4$, $R^5$, $R^6$, $R^7$, $R^8$, $R^9$, and $R^{10}$ are as defined above for Formula III and described in classes and subclasses herein, both singly and in combination.

In some embodiments, compounds are provided that are compounds of Formula III-a:

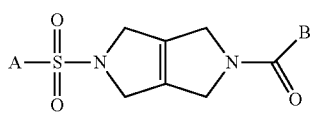

(III-a)

or a pharmaceutically acceptable salt thereof,
wherein A and B are as defined above for Formula III and described in classes and subclasses herein, both singly and in combination.

In some embodiments, a compound of Formula III-a is provided wherein:
A is a bicyclic 3- to 14-membered ring,
  wherein the ring is aromatic, and
  wherein the ring contains 0-4 heteroatoms independently selected from the group consisting of O, N, and S;
B is a ring selected from the group consisting of —$C_6$-$C_{14}$aryl and 5- to 14-membered heteroaryl containing 1-4 heteroatoms independently selected from the group consisting of O, N, and S,
  wherein the ring is optionally substituted with one or more $R^d$;
each $R^d$ is independently selected from the group consisting of —$C_1$-$C_6$alkyl, —OR, and —$NR_2$,
  wherein each alkyl is optionally substituted with one or more halogen; and
each R is independently selected from the group consisting of —H, —$C_1$-$C_6$alkyl, and 5- to 14-membered heteroaryl containing 1-4 heteroatoms independently selected from the group consisting of O, N, and S,
  wherein each alkyl is optionally substituted with one or more halogen.

In some embodiments, a compound of Formula III-a is provided wherein:
A is benzofuranyl;
B is a ring selected from the group consisting of phenyl, pyridyl, pyrazinyl, pyrimidinyl, thiazolyl, furanyl, and pyrazolyl,
  wherein the ring is optionally substituted with one or more $R^d$; and
each $R^d$ is independently selected from the group consisting of methyl, —$CF_3$, —OH, —$OCH_2CF_3$, and —NH (pyridyl).

In some embodiments of Formula III and III-a, A is:
(i) a monocyclic 3- to 8-membered ring, comprising a $C_3$-$C_8$cycloalkyl, 3- to 8-membered heterocyclyl, phenyl, or 5- to 8-membered heteroaryl ring,
  wherein the ring contains 0-4 heteroatoms independently selected from the group consisting of O, N, and S, and
  wherein the ring is optionally substituted with one or more $R^a$; or
(ii) a bicyclic 6- to 14-membered ring, comprising a $C_3$-$C_8$cycloalkyl, 3- to 11-membered heterocyclyl, phenyl, or 5- to 11-membered heteroaryl ring,
  wherein the ring is fused to an aromatic, saturated, or partially unsaturated 3- to 8-membered carbocyclic or an aromatic, saturated, or partially unsaturated 3- to 8-membered heterocyclic ring,
  wherein the ring contains 0-4 heteroatoms independently selected from the group consisting of O, N, and S, and
  wherein the ring is optionally substituted with one or more $R^a$.

In some embodiments of Formula III and III-a, A is an aromatic monocyclic ring or a bicyclic ring wherein at least one of the rings is aromatic, and wherein the monocyclic ring or bicyclic ring contains 0-4 heteroatoms independently selected from the group consisting of O, N, and S, and wherein the monocyclic ring or bicyclic ring is optionally substituted with one or more $R^a$. In some embodiments, A is a bicyclic ring wherein at least one of the rings is aromatic, and wherein the bicyclic ring contains 0-4 heteroatoms independently selected from the group consisting of O, N, and S, and wherein the bicyclic ring is optionally substituted with one or more $R^a$. In some embodiments, A is an aromatic monocyclic ring, wherein the monocyclic ring contains 0-4 heteroatoms independently selected from the group consisting of O, N, and S, and wherein the monocyclic ring is optionally substituted with one or more $R^a$. In some embodiments, A is benzofuranyl. In some embodiments, A is unsubstituted.

In some embodiments of Formula III and III-a, each $R^a$ is independently selected from the group consisting of halogen, —$C_1$-$C_6$alkyl, —$C_3$-$C_{12}$cycloalkyl, 3- to 14-membered heterocyclyl containing 1-4 heteroatoms independently selected from the group consisting of O, N, and S, —OR, and —$NR_2$, wherein each alkyl, cycloalkyl, or heterocyclyl are optionally substituted with one or more halogen.

In some embodiments of Formula III, Z is O or S. In some embodiments, Z is O. In some embodiments, Z is S. In some embodiments, Z is NR (e.g., $NH_2$, NOH, or $NNH_2$).

In some embodiments of Formula III and III-a, B is a ring selected from the group consisting of phenyl and 5- to 6-membered heteroaryl (e.g., pyridyl, pyrazinyl, pyrimidinyl, thiazolyl, furanyl, or pyrazolyl) containing 1-4 heteroatoms independently selected from the group consisting of O, N, and S, wherein the ring is optionally substituted with one or more $R^d$. In some embodiments, B is a 5- to 6-membered heteroaryl ring (e.g., pyridyl, pyrazinyl, pyrimidinyl, thiazolyl, furanyl, or pyrazolyl) containing 1-4 heteroatoms independently selected from the group consisting of O, N, and S, wherein the ring is optionally substituted with one or more $R^d$.

In some embodiments of Formula III and III-a, each $R^d$ is independently selected from the group consisting of halogen, —$C_1$-$C_6$alkyl, —$C_3$-$C_{12}$cycloalkyl, 3- to 14-membered heterocyclyl containing 1-4 heteroatoms independently selected from the group consisting of O, N, and S, —OR, and —$NR_2$, wherein each alkyl, cycloalkyl, or heterocyclyl are optionally substituted with one or more halogen. In some embodiments, each $R^d$ is independently selected from the group consisting of —$C_1$-$C_6$alkyl (e.g., methyl or —$CF_3$), —OR (e.g., —OH, —$OCH_2CF_3$), and —$NR_2$ (e.g., —NH (pyridyl)), wherein each alkyl is optionally substituted with one or more halogen (e.g., fluoro).

In some embodiments of Formula III, $R^3$, $R^4$, $R^5$, $R^6$, $R^7$, $R^8$, $R^9$, and $R^{10}$ are each —H. In some embodiments, one of $R^3$, $R^4$, $R^5$, $R^6$, $R^7$, $R^8$, $R^9$, and $R^{10}$ is —$C_1$-$C_6$alkyl (e.g., methyl) and the others are —H.

In some embodiments of Formula III and III-a, each R is independently selected from the group consisting of —H, —$C_1$-$C_6$alkyl, —$C_3$-$C_{12}$cycloalkyl, 3- to 14-membered heterocyclyl containing 1-4 heteroatoms independently selected from the group consisting of O, N, and S, $C_6$-$C_{14}$aryl (e.g., phenyl, naphthyl, or anthracenyl), and 5- to 14-membered heteroaryl containing 1-4 heteroatoms independently selected from the group consisting of O, N, and S, wherein each alkyl, cycloalkyl, heterocyclyl or aryl is optionally substituted with one or more halogen. In some embodiments, each R is independently selected from the group consisting of —H, —$C_1$-$C_6$alkyl, and 5- to 14-membered heteroaryl containing 1-4 heteroatoms independently selected from the group consisting of O, N, and S, wherein each alkyl is optionally substituted with one or more halogen. In some embodiments, each R is —H.

In some embodiments of Formula III and III-a, each R' is independently selected from the group consisting of —$C_1$-$C_6$alkyl, —$C_3$-$C_{12}$cycloalkyl, 3- to 14-membered heterocyclyl containing 1-4 heteroatoms independently selected from the group consisting of O, N, and S, and $C_6$-$C_{14}$aryl (e.g., phenyl, naphthyl, or anthracenyl), wherein each alkyl, cycloalkyl, heterocyclyl or aryl is optionally substituted with one or more halogen. In some embodiments, each R' is —$C_1$-$C_6$alkyl.

Another aspect of this invention relates to compounds of Formula IV:

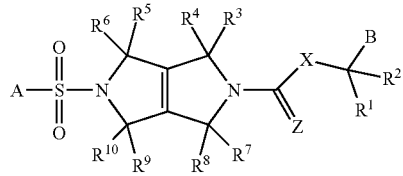

(IV)

or a pharmaceutically acceptable salt thereof,
wherein A, B, X, Z, $R^1$, $R^2$, $R^3$, $R^4$, $R^5$, $R^6$, $R^7$, $R^8$, $R^9$, and $R^{10}$ are as defined above for Formula IV and described in classes and subclasses herein, both singly and in combination.

In some embodiments, compounds are provided that are compounds of Formula IV-a:

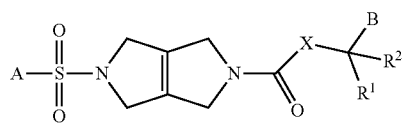

(IV-a)

or a pharmaceutically acceptable salt thereof,
wherein A, B, X, $R^1$, and $R^2$ are as defined above for Formula IV and described in classes and subclasses herein, both singly and in combination.

In some embodiments, compounds are provided that are compounds of Formula IV-b:

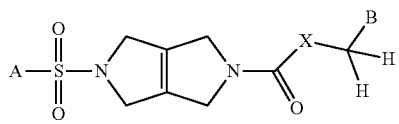

(IV-b)

or a pharmaceutically acceptable salt thereof,
wherein A, B, and X are as defined above for Formula IV and described in classes and subclasses herein, both singly and in combination.

In some embodiments, compounds are provided that are compounds of Formula IV-c:

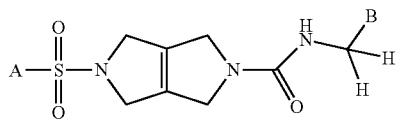

(IV-c)

or a pharmaceutically acceptable salt thereof,
wherein A and B are as defined above for Formula IV and described in classes and subclasses herein, both singly and in combination.

In some embodiments, compounds are provided that are compounds of Formula IV-d:

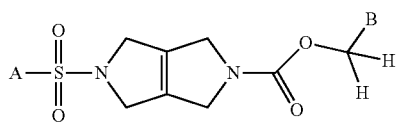

(IV-d)

or a pharmaceutically acceptable salt thereof,
wherein A and B are as defined above for Formula IV and described in classes and subclasses herein, both singly and in combination.

In some embodiments, compounds are provided that are compounds of Formula IV-e-1:

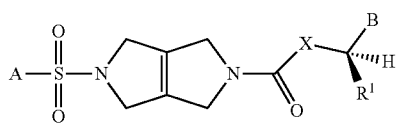

(IV-e-1)

or a pharmaceutically acceptable salt thereof,
wherein A, B, X, and $R^1$ are as defined above for Formula IV and described in classes and subclasses herein, both singly and in combination.

In some embodiments, compounds are provided that are compounds of Formula IV-e-2:

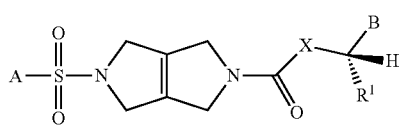

(IV-e-2)

or a pharmaceutically acceptable salt thereof, wherein A, B, X, and R¹ are as defined above for Formula IV and described in classes and subclasses herein, both singly and in combination.

In some embodiments, a compound of Formula IV-a is provided wherein:
A is a monocyclic or bicyclic 3- to 14-membered ring,
  wherein the ring is partially unsaturated or aromatic, and
  wherein the ring contains 0-4 heteroatoms independently selected from the group consisting of O, N, and S; and
  wherein the ring is optionally substituted with one or more $R^a$;
each $R^a$ is independently selected from the group consisting of halogen, —$C_1$-$C_6$alkyl, and —OR,
  wherein each alkyl is optionally substituted with one or more halogen;
X is O or $NR^e$;
$R^e$ is —H;
B is —H or a monocyclic 3- to 14-membered ring,
  wherein the ring is saturated or aromatic, and
  wherein the ring contains 0-4 heteroatoms independently selected from the group consisting of O, N, and S; and
  wherein the ring is optionally substituted with one or more $R^d$;
each $R^d$ is independently selected from the group consisting of halogen, —$C_1$-$C_6$alkyl, and —OR;
$R^1$ and $R^2$ are each independently —H, —$C_1$-$C_6$alkyl, —$(CR^bR^c)_n C_6$-$C_{14}$aryl, and —$(CR^bR^c)_n$OR,
  wherein each aryl is optionally substituted with one or more substituents selected from the group consisting of halogen;
or $R^1$ and $R^2$ combine with the carbon to which they are attached to form a 3- to 14-membered heterocyclyl containing 1-4 heteroatoms independently selected from the group consisting of O, N, and S;
or $R^e$ and $R^1$ combine with the nitrogen to which they are attached to form a 3- to 14-membered heterocyclyl containing 1-4 heteroatoms independently selected from the group consisting of O, N, and S,
  wherein the heterocyclyl is optionally substituted with one or more —OR or —$(CR^bR^c)_n C_6$-$C_{14}$aryl;
or $R^2$ is absent, and $R^1$ and B combine with the carbon to which they are attached to form $C_6$-$C_{14}$aryl ring or 5- to 14-membered heteroaryl ring,
  wherein each aryl or heteroaryl is optionally substituted with one or more halogen or —$C_1$-$C_6$alkyl;
each $R^b$ and $R^c$ is independently selected from the group consisting of —H;
each n is independently 0, 1, or 2; and
each R is independently selected from the group consisting of —H and —$C_1$-$C_6$alkyl, wherein each alkyl is optionally substituted with one or more halogen.

In some embodiments, a compound of Formula IV-a is provided wherein:
A is a monocyclic or bicyclic 3- to 14-membered ring selected from:

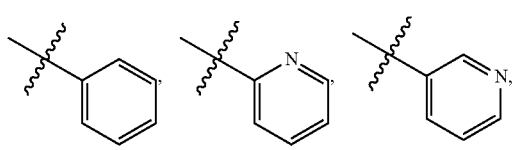

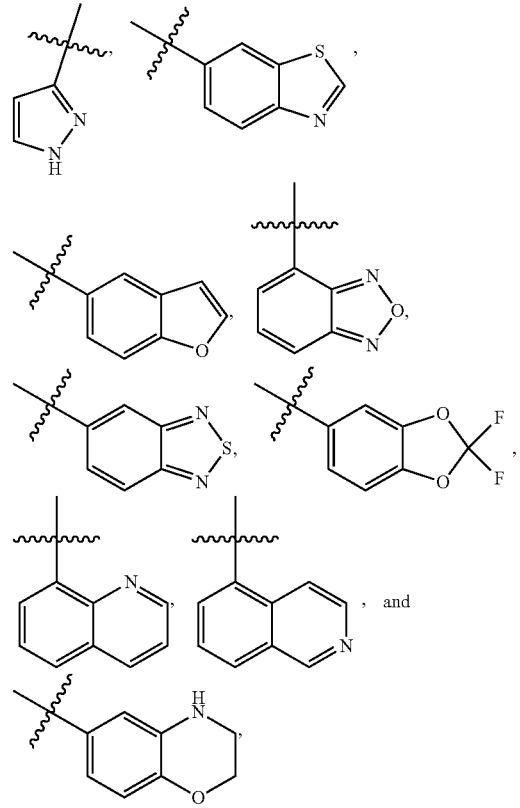

wherein the ring is optionally substituted with one or more $R^a$;
each $R^a$ is independently selected from the group consisting of fluoro, methyl, —$CF_3$, —$OCHF_2$, and —OMe;
X is O or $NR^e$;
$R^e$ is —H;
B is —H; or a monocyclic 3- to 6-membered ring selected from the group consisting of phenyl, pyridyl, pyrazinyl, furanyl, pyrazolyl, thiophenyl, isoxazolyl, thiazolyl, oxazolyl, triazolyl, oxadiazolyl, cyclopropyl, and tetrahydrofuranyl,
  wherein the ring is optionally substituted with one or more $R^d$;
each $R^d$ is independently selected from the group consisting of fluoro, methyl, —OMe, and —OiPr;
$R^1$ and $R^2$ are each independently —H, methyl, ethyl, isopropyl, —$CH_2$(phenyl), —$CH_2$OMe, and —$CH_2CH_2$OMe,
  wherein each phenyl is optionally substituted with one or more fluoro;
or $R^1$ and $R^2$ combine with the carbon to which they are attached to form a tetrahydrofuranyl;
or $R^e$ and $R^1$ combine with the nitrogen to which they are attached to form a morpholinyl or azetidinyl,
  wherein the azetidinyl is optionally substituted with one or more —OH or —$CH_2$(phenyl);
or $R^2$ is absent, and $R^1$ and B combine with the carbon to which they are attached to form a phenyl or isoxazolyl,
  wherein each phenyl or isoxazolyl is optionally substituted with one or more fluoro or methyl;
each $R^b$ and $R^c$ is —H;
each n is independently 0, 1, or 2; and
each R is independently —H, methyl, isopropyl or —$CHF_2$.

In some embodiments of Formula IV, IV-a, IV-b, IV-c, IV-d, IV-e-1, and IV-e-2, A is:

(i) a monocyclic 3- to 8-membered ring, comprising a $C_3$-$C_8$cycloalkyl, 3- to 8-membered heterocyclyl, phenyl, or 5- to 8-membered heteroaryl ring, wherein the ring contains 0-4 heteroatoms independently selected from the group consisting of O, N, and S, and wherein the ring is optionally substituted with one or more $R^a$; or (ii) a bicyclic 6- to 14-membered ring, comprising a $C_3$-$C_8$cycloalkyl, 3- to 11-membered heterocyclyl, phenyl, or 5- to 11-membered heteroaryl ring, wherein the ring is fused to an aromatic, saturated, or partially unsaturated 3- to 8-membered carbocyclic or an aromatic, saturated or partially unsaturated 3- to 8-membered heterocyclic ring, wherein the ring contains 0-4 heteroatoms independently selected from the group consisting of O, N, and S, and wherein the ring is optionally substituted with one or more $R^a$.

In some embodiments of Formula IV, IV-a, IV-b, IV-c, IV-d, IV-e-1, and IV-e-2, A is an aromatic monocyclic ring or a bicyclic ring wherein at least one of the rings is aromatic, and wherein the monocyclic ring or bicyclic ring contains 0-4 heteroatoms independently selected from the group consisting of O, N, and S, and wherein the monocyclic ring or bicyclic ring is optionally substituted with one or more $R^a$. In some embodiments, A is a monocyclic or bicyclic 5- to 10-membered ring, wherein the ring is saturated, fully or partially unsaturated, or aromatic, and wherein the ring contains 0-4 heteroatoms independently selected from the group consisting of O, N, and S; and wherein the ring is optionally substituted with one or more $R^a$.

In some embodiments of Formula IV, IV-a, IV-b, IV-c, IV-d, IV-e-1, and IV-e-2, A is a ring selected from the group consisting of:

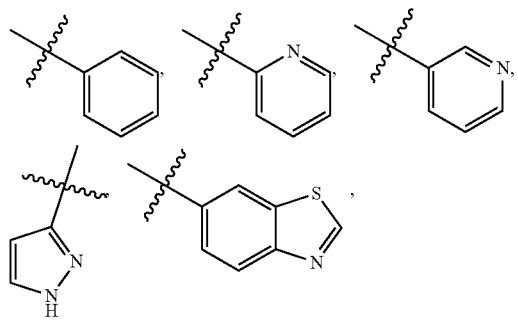

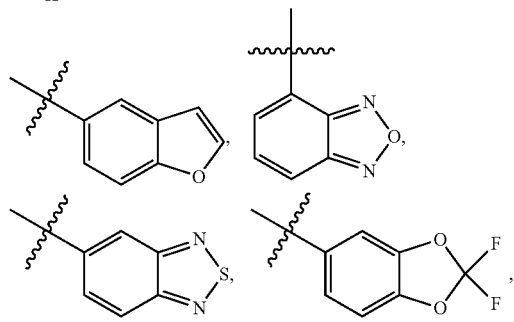

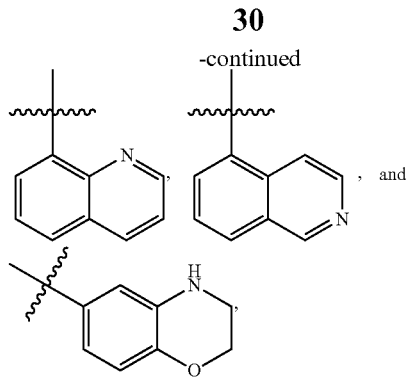

wherein the ring is optionally substituted with one or more $R^a$.

In some embodiments of Formula IV, IV-a, IV-b, IV-c, IV-d, IV-e-1, and IV-e-2, A is selected from the group consisting of:

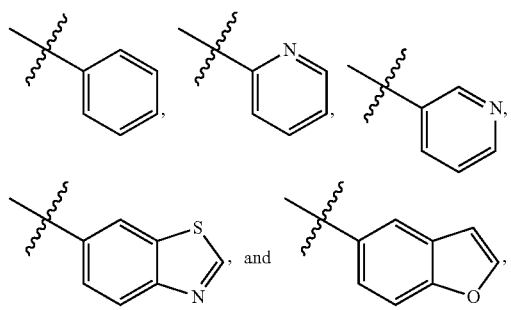

wherein the ring is optionally substituted with one or more $R^a$.

In some embodiments of Formula IV, IV-a, IV-b, IV-c, IV-d, IV-e-1, and IV-e-2, A is selected from the group consisting of:

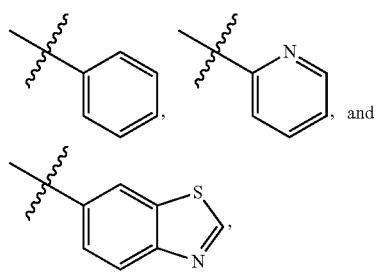

wherein the ring is optionally substituted with one or more $R^a$. In some embodiments, A is unsubstituted.

In some embodiments of Formula IV, IV-a, IV-b, IV-c, IV-d, IV-e-1, and IV-e-2, each $R^a$ is independently selected from the group consisting of halogen, —OR, and —NR$_2$, —$C_1$-$C_6$alkyl, —$C_3$-$C_{12}$cycloalkyl, and 3- to 14-membered heterocyclyl containing 1-4 heteroatoms independently selected from the group consisting of O, N, and S, wherein each alkyl, cycloalkyl, or heterocyclyl are optionally substituted with one or more halogen. In some embodiments, each $R^a$ is independently selected from the group consisting of halogen (e.g., fluoro), —$C_1$-$C_6$alkyl (e.g., methyl or —CF$_3$), and —OR (e.g., —OMe or —OCHF$_2$). In some embodiments, each $R^a$ is —OCHF$_2$.

In some embodiments of Formula IV, Z is O or S. In some embodiments, Z is O. In some embodiments, Z is S. In some embodiments, Z is NR (e.g., $NH_2$, NOH, or $NNH_2$).

In some embodiments of Formula IV, IV-a, IV-b, IV-e-1, and IV-e-2, X is O or NH. In some embodiments, X is O. In some embodiments, X is $NR^e$. In some embodiments, X is NH.

In some embodiments of Formula IV, IV-a, IV-b, IV-e-1, and IV-e-2, $R^e$ is —H. In some embodiments, $R^e$ is —$C_1$-$C_6$alkyl (e.g., methyl).

In some embodiments of Formula IV, IV-a, IV-b, IV-c, IV-d, IV-e-1, and IV-e-2, B is:
(i) —H; or
(ii) a monocyclic 3- to 8-membered ring, comprising a $C_3$-$C_8$cycloalkyl, 3- to 8-membered heterocyclyl, phenyl, or 5- to 8-membered heteroaryl ring,
   wherein the ring contains 0-4 heteroatoms independently selected from the group consisting of O, N, and S, and
   wherein the ring is optionally substituted with one or more $R^d$; or
(iii) a bicyclic 6- to 14-membered ring, comprising a $C_3$-$C_8$cycloalkyl, 3- to 11-membered heterocyclyl, phenyl, or 5- to 11-membered heteroaryl ring,
   wherein the ring is fused to an aromatic, saturated, or partially unsaturated 3- to 8-membered carbocyclic or an aromatic, saturated or partially unsaturated 3- to 8-membered heterocyclic ring,
   wherein the ring contains 0-4 heteroatoms independently selected from the group consisting of O, N, and S, and
   wherein the ring is optionally substituted with one or more $R^d$.

In some embodiments of Formula IV, IV-a, IV-b, IV-c, IV-d, IV-e-1, and IV-e-2, B is —H; or a monocyclic 3- to 8-membered ring, wherein the ring is saturated or aromatic, and wherein the ring contains 0-4 heteroatoms independently selected from the group consisting of O, N, and S; and wherein the ring is optionally substituted with one or more $R^d$. In some embodiments, B is —H; or a monocyclic 3- to 6-membered ring, wherein the ring is saturated or aromatic, and wherein the ring contains 0-4 heteroatoms independently selected from the group consisting of O, N, and S, and wherein the ring is optionally substituted with one or more $R^d$. In some embodiments, B is —H. In some embodiments, B is a monocyclic 3- to 6-membered ring, wherein the ring is saturated or aromatic, and wherein the ring contains 0-4 heteroatoms independently selected from the group consisting of O, N, and S, and wherein the ring is optionally substituted with one or more $R^d$. In some embodiments, B is unsubstituted.

In some embodiments of Formula IV, IV-a, IV-b, IV-c, IV-d, IV-e-1, and IV-e-2, B is —H, or a monocyclic 3- to 6-membered ring selected from the group consisting of phenyl, pyridyl, pyrazinyl, furanyl, pyrazolyl, thiophenyl, isoxazolyl, thiazolyl, oxazolyl, triazolyl, oxadiazolyl, cyclopropyl, and tetrahydrofuranyl, wherein the ring is optionally substituted with one or more $R^d$. In some embodiments, B is —H, or a monocyclic 3- to 6-membered ring selected from the group consisting of phenyl, pyridyl, pyrazinyl, furanyl, pyrazolyl, isoxazolyl, thiazolyl, oxazolyl, and tetrahydrofuranyl, wherein the ring is optionally substituted with one or more $R^d$. In some embodiments, B is a monocyclic 3- to 6-membered ring selected from the group consisting of phenyl and furanyl, wherein the ring is optionally substituted with one or more $R^d$.

In some embodiments of Formula IV, IV-a, IV-b, IV-c, IV-d, IV-e-1, and IV-e-2, each $R^d$ is independently selected from the group consisting of halogen, —OR, —$NR_2$, —$C_1$-$C_6$alkyl, —$C_3$-$C_{12}$cycloalkyl, and 3- to 14-membered heterocyclyl containing 1-4 heteroatoms independently selected from the group consisting of O, N, and S, wherein each alkyl, cycloalkyl, or heterocyclyl are optionally substituted with one or more halogen. In some embodiments, each $R^d$ is independently selected from the group consisting of halogen (e.g., fluoro), —$C_1$-$C_6$alkyl (e.g., methyl), and —OR (e.g., —OMe or —OiPr).

In some embodiments of Formula IV and IV-a, $R^1$ and $R^2$ are each independently:
—H, halogen, —$C_1$-$C_6$alkyl, —$(CR^bR^c)_nC_3$-$C_{12}$cycloalkyl, —$(CR^bR^c)_n$heterocyclyl, —$(CR^bR^c)_nC_6$-$C_{14}$aryl, —$(CR^bR^c)_n$heteroaryl, or —$(CR^bR^c)_n$OR,
   wherein each alkyl, cycloalkyl, heterocyclyl, aryl, or heteroaryl is optionally substituted with one or more substituents selected from the group consisting of halogen, —$C_1$-$C_6$alkyl, —OR, and oxo,
   wherein each heterocyclyl is 3- to 14-membered and contains 1-4 heteroatoms independently selected from the group consisting of O, N, and S, and
   wherein each heteroaryl is 5- to 14-membered and contains 1-4 heteroatoms independently selected from the group consisting of O, N, and S;
or $R^1$ and $R^2$ combine with the carbon to which they are attached to form a $C_3$-$C_{12}$cycloalkyl or 3- to 14-membered heterocyclyl containing 1-4 heteroatoms independently selected from the group consisting of O, N, and S,
   wherein each cycloalkyl or heterocyclyl is optionally substituted with one or more substituents selected from the group consisting of halogen, —$C_1$-$C_6$alkyl, —OR, and oxo;
or $R^e$ and $R^1$ combine with the nitrogen to which they are attached to form a 3- to 14-membered heterocyclyl containing 1-4 heteroatoms independently selected from the group consisting of O, N, and S,
   wherein the heterocyclyl is optionally substituted with one or more halogen, —$C_1$-$C_6$alkyl, oxo, —OR, and —$(CR^bR^c)_nC_6$-$C_{14}$aryl;
or $R^2$ is absent, and $R^1$ and B combine with the carbon to which they are attached to form a $C_6$-$C_{14}$ aryl ring or a 5- to 14-membered heteroaryl ring containing 1-4 heteroatoms independently selected from the group consisting of O, N, and S,
   wherein each aryl or heteroaryl is optionally substituted with one or more halogen, —$C_1$-$C_6$alkyl, or —OR.

In some embodiments of Formula IV and IV-a, $R^1$ and $R^2$ are each independently —H, halogen, —$C_1$-$C_6$alkyl, —$(CR^bR^c)_nC_3$-$C_{12}$cycloalkyl, —$(CR^bR^c)_n$heterocyclyl, —$(CR^bR^c)_n$aryl, —$(CR^bR^c)_n$heteroaryl, or —$(CR^bR^c)_n$OR, wherein each alkyl, cycloalkyl, heterocyclyl, aryl, or heteroaryl is optionally substituted with one or more substituents selected from the group consisting of halogen, —$C_1$-$C_6$alkyl, —OR, and oxo, wherein each heterocyclyl is 3- to 14-membered and contains 1-4 heteroatoms selected from the group consisting of O, N, and S, and wherein each heteroaryl is 5- to 14-membered and contains 1-4 heteroatoms selected from the group consisting of O, N, and S. In some embodiments, $R^1$ and $R^2$ combine with the carbon to which they are attached to form a $C_3$-$C_{12}$cycloalkyl or 3- to 14-membered heterocyclyl containing 1-4 heteroatoms independently selected from the group consisting of O, N, and S, wherein each cycloalkyl or heterocyclyl is optionally substituted with one or more substituents selected from the group consisting of halogen, —$C_1$-$C_6$alkyl, —OR, and oxo. In some embodiments, $R^e$ and $R^1$ combine with the nitrogen to which they are attached to form a 3- to 14-membered heterocyclyl containing 1-4 heteroatoms independently selected from the group consisting of O, N, and S, wherein the heterocyclyl is optionally substituted with one or more halogen, —$C_1$-$C_6$alkyl, oxo, —OR, and —$(CR^bR^c)_n$$C_6$-$C_{14}$aryl. In some embodiments, $R^2$ is absent, and $R^1$ and B combine with the carbon to which they are attached to form $C_6$-$C_{14}$ aryl ring or 5- to 14-membered heteroaryl ring containing 1-4 heteroatoms independently selected from the group consisting of O, N, and S, wherein each aryl or heteroaryl is optionally substituted with one or more halogen, —$C_1$-$C_6$alkyl, or —OR.

In some embodiments of Formula IV and IV-a, $R^1$ and $R^2$ are each independently:
—H, —$C_1$-$C_6$alkyl (e.g., methyl, ethyl, or isopropyl), —$(CR^bR^c)_n$$C_6$-$C_{14}$aryl (e.g., —$CH_2$(phenyl)), or —$(CR^bR^c)_n$OR (e.g., —$CH_2$OMe or —$CH_2CH_2$OMe), wherein each aryl is optionally substituted with one or more halogen (e.g., fluoro);

or $R^1$ and $R^2$ combine with the carbon to which they are attached to form a tetrahydrofuranyl;

or $R^e$ and $R^1$ combine with the nitrogen to which they are attached to form a morpholinyl or azetidinyl,
   wherein the azetidinyl is optionally substituted with one or more —OH or —$CH_2$(phenyl);

or $R^2$ is absent, and $R^1$ and B combine with the carbon to which they are attached to form a phenyl or isoxazolyl, wherein each phenyl or isoxazolyl is optionally substituted with one or more fluoro or methyl.

In some embodiments of Formula IV and IV-a, $R^1$ and $R^2$ are each independently —H, —$C_1$-$C_6$alkyl (e.g., methyl, ethyl, or isopropyl), —$(CR^bR^c)_n$$C_6$-$C_{14}$aryl (e.g., —$CH_2$(phenyl)), or —$(CR^bR^c)_n$OR (e.g., —$CH_2$OMe or —$CH_2CH_2$OMe), wherein each aryl is optionally substituted with one or more halogen (e.g., fluoro). In some embodiments, $R^1$ and $R^2$ are each —H.

In some embodiments of Formula IV, IV-a, IV-e-1, and IV-e-2, $R^b$ and $R^c$ are each —H. In some embodiments, $R^b$ and $R^c$ are each independently —H or halogen (e.g., fluoro). In some embodiments, $R^b$ and $R^c$ are each independently —H or —$C_1$-$C_6$alkyl (e.g., methyl).

In some embodiments of Formula IV, IV-a, IV-e-1, and IV-e-2, each n is independently 0, 1, or 2. In some embodiments, each n is independently 0 or 1. In some embodiments, each n is 0. In some embodiments, each n is 1. In some embodiments, each n is 2.

In some embodiments of Formula IV, $R^3$, $R^4$, $R^5$, $R^6$, $R^7$, $R^8$, $R^9$, and $R^{10}$ are each —H. In some embodiments, one of $R^3$, $R^4$, $R^5$, $R^6$, $R^7$, $R^8$, $R^9$, and $R^{10}$ is —$C_1$-$C_6$alkyl (e.g., methyl) and the others are —H.

In some embodiments of Formula IV, IV-a, IV-b, IV-c, IV-d, IV-e-1, and IV-e-2, each R is independently selected from the group consisting of —H, —$C_1$-$C_6$alkyl, —$C_3$-$C_{12}$cycloalkyl, 3- to 14-membered heterocyclyl containing 1-4 heteroatoms independently selected from the group consisting of O, N, and S, and $C_6$-$C_{14}$aryl (e.g., phenyl, naphthyl, or anthracenyl), wherein each alkyl, cycloalkyl, heterocyclyl or aryl is optionally substituted with one or more halogen. In some embodiments, each R is independently selected from the group consisting of —H or —$C_1$-$C_6$alkyl (e.g., methyl, isopropyl, or —$CHF_2$). In some embodiments R is —H.

In some embodiments of Formula IV, IV-a, IV-b, IV-c, IV-d, IV-e-1, and IV-e-2, each R' is independently selected from the group consisting of —$C_1$-$C_6$alkyl, —$C_3$-$C_{12}$cycloalkyl, 3- to 14-membered heterocyclyl containing 1-4 heteroatoms independently selected from the group consisting of O, N, and S, and $C_6$-$C_{14}$aryl (e.g., phenyl, naphthyl, or anthracenyl), wherein each alkyl, cycloalkyl, heterocyclyl or aryl is optionally substituted with one or more halogen. In some embodiments, each R' is —$C_1$-$C_6$alkyl.

In some embodiments, compounds are provided in Table 1:

TABLE 1

| Example | Structure | Name |
| --- | --- | --- |
| 1-1 | 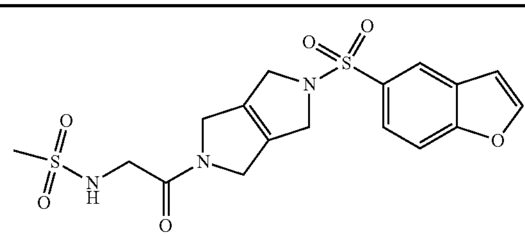 | N-(2-(5-(benzofuran-5-ylsulfonyl)-3,4,5,6-tetrahydropyrrolo[3,4-c]pyrrol-2(1H)-yl)-2-oxoethyl)methanesulfonamide |
| 1-2 | 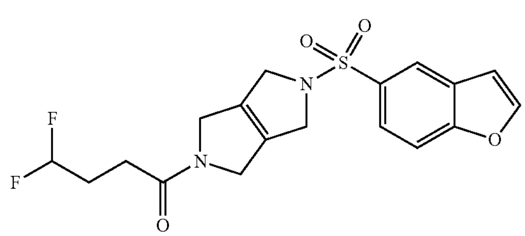 [SMILES: O=C(CCC(F)F)N1CC2=C(C1)CN(S(=O)(=O)c1ccc3occc3c1)C2] | 1-(5-(Benzofuran-5-ylsulfonyl)-3,4,5,6-tetrahydropyrrolo[3,4-c]pyrrol-2(1H)-yl)-4,4-difluorobutan-1-one |
| 1-3 | 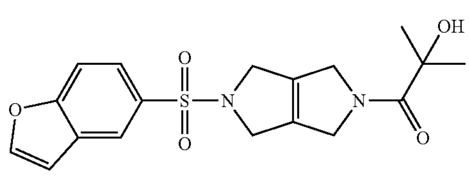 [SMILES: CC(C)(O)C(=O)N1CC2=C(C1)CN(S(=O)(=O)c1ccc3occc3c1)C2] | 1-(5-(Benzofuran-5-ylsulfonyl)-3,4,5,6-tetrahydropyrrolo[3,4-c]pyrrol-2(1H)-yl)-2-hydroxy-2-methylpropan-1-one |

TABLE 1-continued

| Example | Structure | Name |
|---|---|---|
| 1-4 | 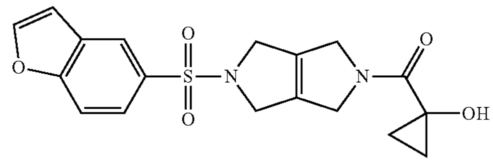 [SMILES: O=C(N1CC2=C(C1)CN(S(=O)(=O)c1ccc3occc3c1)C2)C1(O)CC1] | (5-(Benzofuran-5-ylsulfonyl)-3,4,5,6-tetrahydropyrrolo[3,4-c]pyrrol-2(1H)-yl)(1-hydroxycyclopropyl)methanone |
| 1-5 | 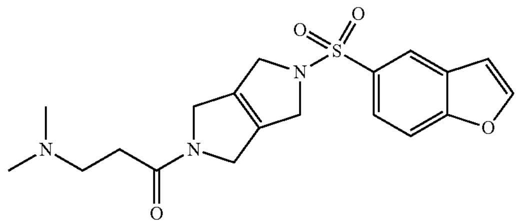 [SMILES: CN(C)CCC(=O)N1CC2=C(C1)CN(S(=O)(=O)c1ccc3occc3c1)C2] | 1-(5-(Benzofuran-5-ylsulfonyl)-3,4,5,6-tetrahydropyrrolo[3,4-c]pyrrol-2(1H)-yl)-3-(dimethylamino)propan-1-one |
| 1-6 | 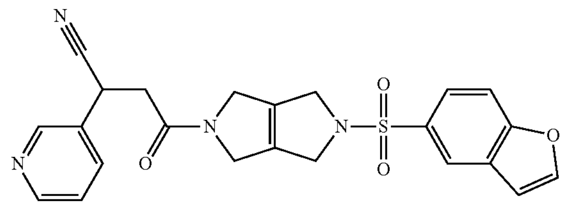 [SMILES: N#CC(CC(=O)N1CC2=C(C1)CN(S(=O)(=O)c1ccc3occc3c1)C2)c1cccnc1] | 4-[4-(1-Benzofuran-5-sulfonyl)-1H,2H,3H,4H,5H,6H-pyrrolo[3,4-c]pyrrol-2-yl]-4-oxo-2-(pyridin-3-yl)butanenitrile |
| 2-1 | 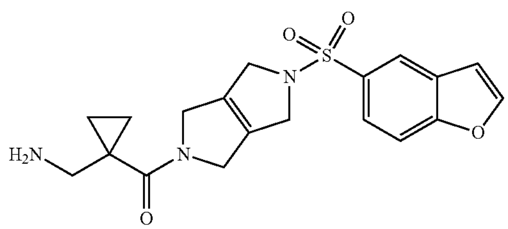 [SMILES: NCC1(C(=O)N2CC3=C(C2)CN(S(=O)(=O)c2ccc4occc4c2)C3)CC1] | (1-(Aminomethyl)cyclopropyl)(5-(benzofuran-5-ylsulfonyl)-3,4,5,6-tetrahydropyrrolo[3,4-c]pyrrol-2(1H)-yl)methanone |
| 3-1 | 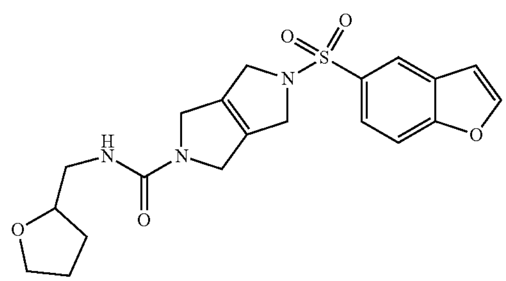 [SMILES: O=C(NCC1CCCO1)N1CC2=C(C1)CN(S(=O)(=O)c1ccc3occc3c1)C2] | 5-(Benzofuran-5-ylsulfonyl)-N-((tetrahydrofuran-2-yl)methyl)-3,4,5,6-tetrahydropyrrolo[3,4-c]pyrrole-2(1H)-carboxamide |
| 3-2 | 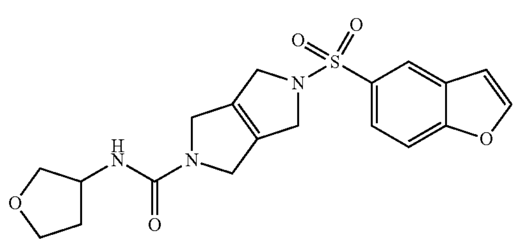 [SMILES: O=C(NC1CCOC1)N1CC2=C(C1)CN(S(=O)(=O)c1ccc3occc3c1)C2] | 5-(Benzofuran-5-ylsulfonyl)-N-(tetrahydrofuran-3-yl)-3,4,5,6-tetrahydropyrrolo[3,4-c]pyrrole-2(1H)-carboxamide |
| 3-3 | 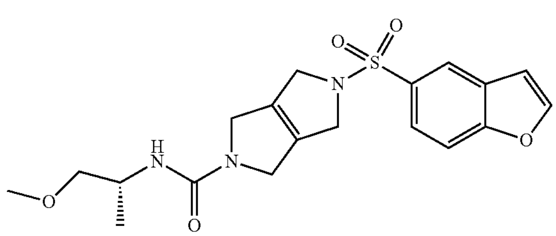 [SMILES: COC[C@@H](C)NC(=O)N1CC2=C(C1)CN(S(=O)(=O)c1ccc3occc3c1)C2] | (R)-5-(benzofuran-5-ylsulfonyl)-N-(1-methoxypropan-2-yl)-3,4,5,6-tetrahydropyrrolo[3,4-c]pyrrole-2(1H)-carboxamide |

TABLE 1-continued

| Example | Structure | Name |
|---|---|---|
| 3-4 | 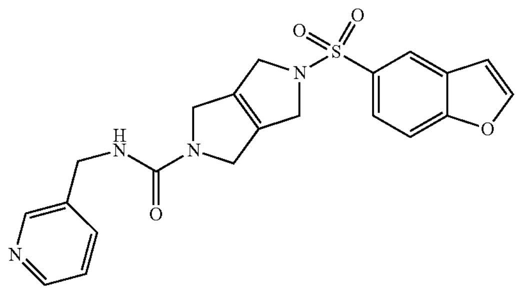 [SMILES: O=C(NCc1cccnc1)N1CC2=C(C1)CN(S(=O)(=O)c1ccc3occc3c1)C2] | 5-(Benzofuran-5-ylsulfonyl)-N-(pyridin-3-ylmethyl)-3,4,5,6-tetrahydropyrrolo[3,4-c]pyrrole-2(1H)-carboxamide |
| 3-5 | 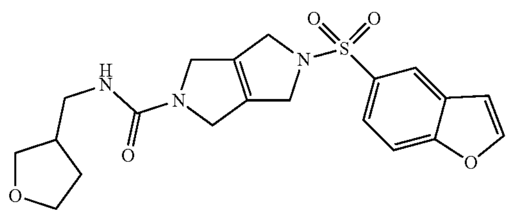 [SMILES: O=C(NCC1CCOC1)N1CC2=C(C1)CN(S(=O)(=O)c1ccc3occc3c1)C2] | 5-(Benzofuran-5-ylsulfonyl)-N-((tetrahydrofuran-3-yl)methyl)-3,4,5,6-tetrahydropyrrolo[3,4-c]pyrrole-2(1H)-carboxamide |
| 4-1 | 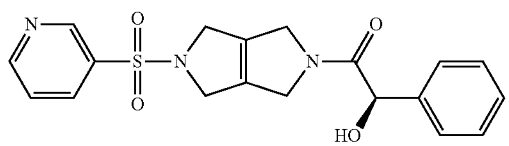 [SMILES: O=C([C@H](O)c1ccccc1)N1CC2=C(C1)CN(S(=O)(=O)c1cccnc1)C2] | (2R)-2-hydroxy-2-phenyl-1-[5-(pyridine-3-sulfonyl)-1H,2H,3H,4H,5H,6H-pyrrolo[3,4-c]pyrrol-2-yl]ethan-1-one |
| 4-2 | 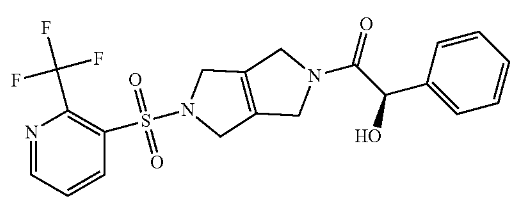 [SMILES: O=C([C@H](O)c1ccccc1)N1CC2=C(C1)CN(S(=O)(=O)c1cccnc1C(F)(F)F)C2] | (R)-2-hydroxy-2-phenyl-1-(5-(2-(trifluoromethyl)pyridin-3-ylsulfonyl)-4,5-dihydropyrrolo[3,4-c]pyrrol-2(1H,3H,4H)-yl)ethanone |
| 5-1 | 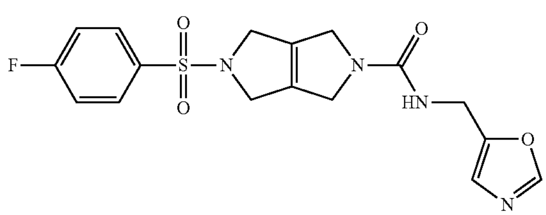 [SMILES: O=C(NCc1cnco1)N1CC2=C(C1)CN(S(=O)(=O)c1ccc(F)cc1)C2] | 5-(4-Fluorophenylsulfonyl)-N-(oxazol-5-ylmethyl)-3,4,5,6-tetrahydropyrrolo[3,4-c]pyrrole-2(1H)-carboxamide |
| 5-2 | 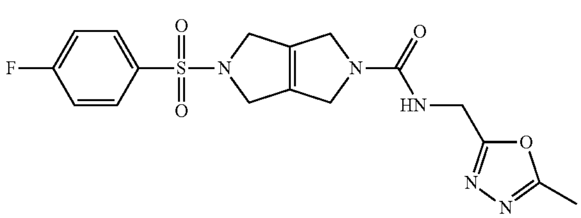 [SMILES: Cc1nnc(CNC(=O)N2CC3=C(C2)CN(S(=O)(=O)c2ccc(F)cc2)C3)o1] | 5-(4-Fluorophenylsulfonyl)-N-((5-methyl-1,3,4-oxadiazol-2-yl)methyl)-3,4,5,6-tetrahydropyrrolo[3,4-c]pyrrole-2(1H)-carboxamide |
| 6-1 | 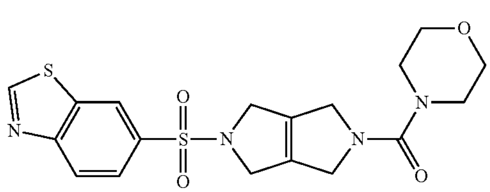 [SMILES: O=C(N1CCOCC1)N1CC2=C(C1)CN(S(=O)(=O)c1ccc3ncsc3c1)C2] | (5-(benzo[d]thiazol-6-ylsulfonyl)-3,4,5,6-tetrahydropyrrolo[3,4-c]pyrrol-2(1H)-yl)(morpholino)methanone |

TABLE 1-continued

| Example | Structure | Name |
|---|---|---|
| 7-1 | 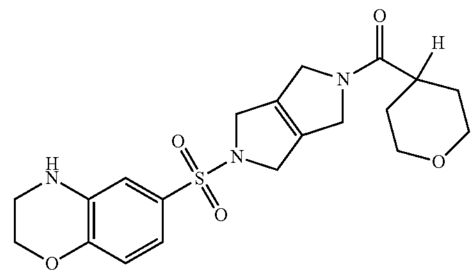 [SMILES: O=C(C1CCOCC1)N1CC2=C(C1)CN(S(=O)(=O)c1ccc3c(c1)NCCO3)C2] | (5-((3,4-dihydro-2H-benzo[b][1,4]oxazin-6-yl)sulfonyl)-3,4,5,6-tetrahydropyrrolo[3,4-c]pyrrol-2(1H)-yl)(tetrahydro-2H-pyran-4-yl)methanone |
| 8-1 | 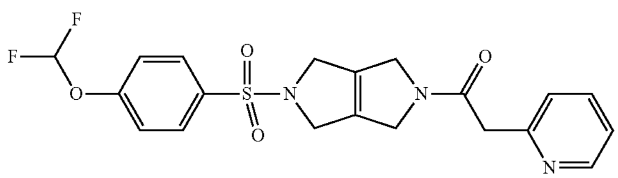 [SMILES: O=C(Cc1ccccn1)N1CC2=C(C1)CN(S(=O)(=O)c1ccc(OC(F)F)cc1)C2] | 1-(5-[[4-(difluoromethoxy)benzene]sulfonyl]-1H,2H,3H,4H,5H,6H-pyrrolo[3,4-c]pyrrol-2-yl)-2-(pyridin-2-yl)ethan-1-one |
| 8-2[a] | 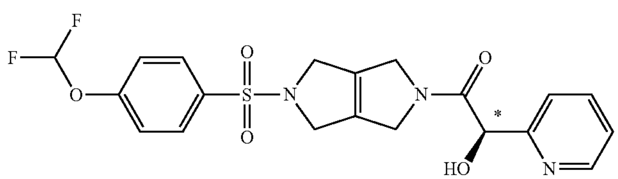 [SMILES: O=C([C@H](O)c1ccccn1)N1CC2=C(C1)CN(S(=O)(=O)c1ccc(OC(F)F)cc1)C2] | (R)-1-(5-((4-(difluoromethoxy)phenyl)sulfonyl)-3,4,5,6-tetrahydropyrrolo[3,4-c]pyrrol-2(1H)-yl)-2-hydroxy-2-(pyridin-2-yl)ethan-1-one |
| 8-3[a] | 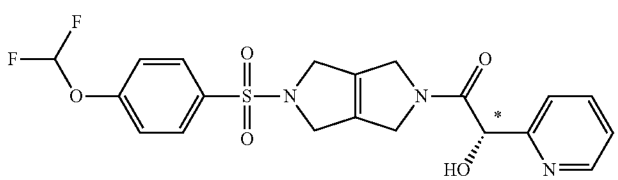 [SMILES: O=C([C@@H](O)c1ccccn1)N1CC2=C(C1)CN(S(=O)(=O)c1ccc(OC(F)F)cc1)C2] | (S)-1-(5-((4-(difluoromethoxy)phenyl)sulfonyl)-3,4,5,6-tetrahydropyrrolo[3,4-c]pyrrol-2(1H)-yl)-2-hydroxy-2-(pyridin-2-yl)ethan-1-one |
| 9-1 | 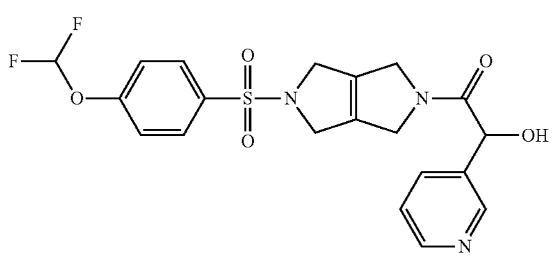 [SMILES: O=C(C(O)c1cccnc1)N1CC2=C(C1)CN(S(=O)(=O)c1ccc(OC(F)F)cc1)C2] | 1-(5-[[4-(Difluoromethoxy)benzene]sulfonyl]-1H,2H,3H,4H,5H,6H-pyrrolo[3,4-c]pyrrol-2-yl)-2-hydroxy-2-(pyridin-3-yl)ethan-1-one |
| 9-2 | 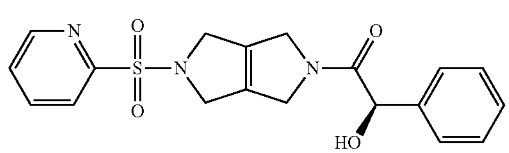 | (2R)-2-hydroxy-2-phenyl-1-[5-(pyridine-2-sulfonyl)-1H,2H,3H,4H,5H,6H-pyrrolo[3,4-c]pyrrol-2-yl]ethan-1-one |
| 9-3 | 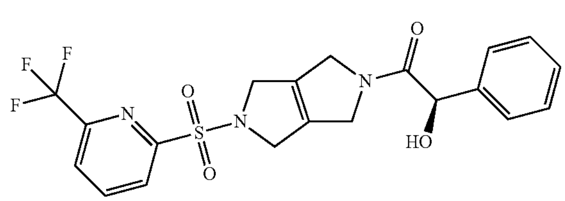 [SMILES: O=C([C@H](O)c1ccccc1)N1CC2=C(C1)CN(S(=O)(=O)c1cccc(C(F)(F)F)n1)C2] | (2R)-2-hydroxy-2-phenyl-1-[5-[6-(trifluoromethyl)pyridine-2-sulfonyl]-1H,2H,3H,4H,5H,6H-pyrrolo[3,4-c]pyrrol-2-yl]ethan-1-one |

TABLE 1-continued

| Example | Structure | Name |
|---|---|---|
| 9-4[b] | 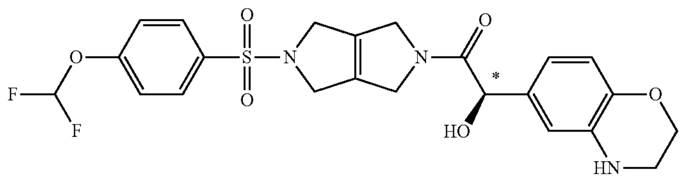 [SMILES: O=C([C@H](O)c1ccc2c(c1)NCCO2)N1CC2=C(C1)CN(S(=O)(=O)c1ccc(OC(F)F)cc1)C2] | (2R)-1-(5-[[4-(difluoromethoxy)benzene]sulfonyl]-1H,2H,3H,4H,5H,6H-pyrrolo[3,4-c]pyrrol-2-yl)-2-(3,4-dihydro-2H-1,4-benzoxazin-6-yl)-2-hydroxyethan-1-one |
| 9-5[b] | 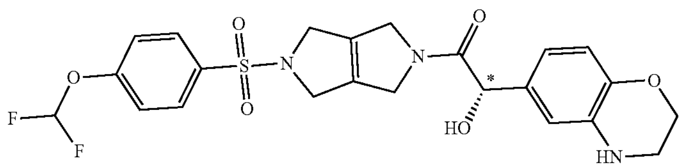 [SMILES: O=C([C@@H](O)c1ccc2c(c1)NCCO2)N1CC2=C(C1)CN(S(=O)(=O)c1ccc(OC(F)F)cc1)C2] | (2S)-1-(5-[[4-(difluoromethoxy)benzene]sulfonyl]-1H,2H,3H,4H,5H,6H-pyrrolo[3,4-c]pyrrol-2-yl)-2-(3,4-dihydro-2H-1,4-benzoxazin-6-yl)-2-hydroxyethan-1-one |
| 10-1[c] | 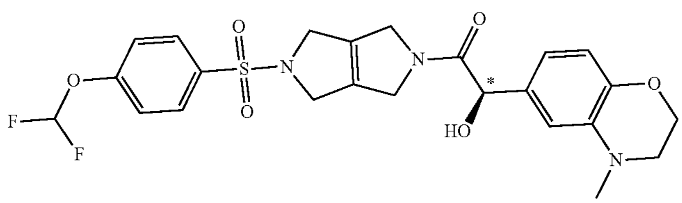 [SMILES: CN1CCOc2ccc([C@@H](O)C(=O)N3CC4=C(C3)CN(S(=O)(=O)c3ccc(OC(F)F)cc3)C4)cc21] | (2R)-1-(5-(4-(difluoromethoxy)phenylsulfonyl)-4,5-dihydropyrrolo[3,4-c]pyrrol-(1H,3H,4H)-yl)-2-hydroxy-2-(4-methyl-3,4-dihydro-2H-benzo[b][1,4]oxazin-6-yl)ethanone |
| 10-2[c] | 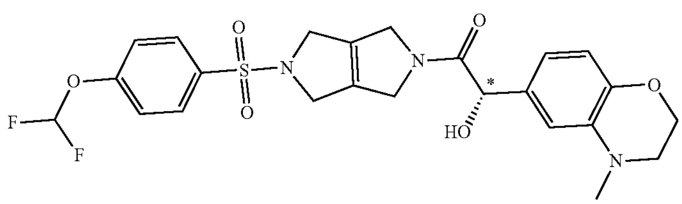 [SMILES: CN1CCOc2ccc([C@H](O)C(=O)N3CC4=C(C3)CN(S(=O)(=O)c3ccc(OC(F)F)cc3)C4)cc21] | (2S)-1-(5-(4-(difluoromethoxy)phenyl)sulfonyl)-4,5-dihydropyrrolo[3,4-c]pyrrol-2(1H,3H,4H)-yl)-2-hydroxy-2-(4-methyl-3,4-dihydro-2H-benzo[b][1,4]oxazin-6-yl)ethanone |
| 11-1[d] | 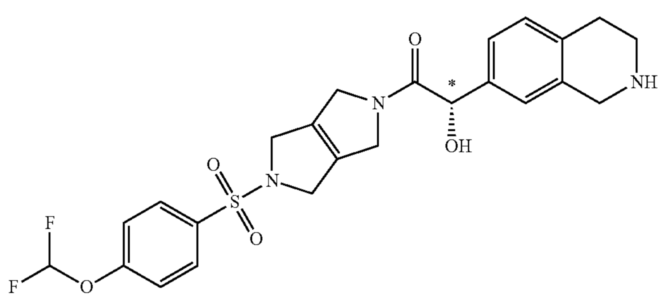 [SMILES: O=C([C@@H](O)c1ccc2c(c1)CNCC2)N1CC2=C(C1)CN(S(=O)(=O)c1ccc(OC(F)F)cc1)C2] | (2S)-1-(5-[[4-(Difluoromethoxy)benzene]sulfonyl]-1H,2H,3H,4H,5H,6H-pyrrolo[3,4-c]pyrrol-2-yl)-2-hydroxy-2-(1,2,3,4-tetrahydroisoquinolin-7-yl)ethan-1-one |
| 11-2[d] | 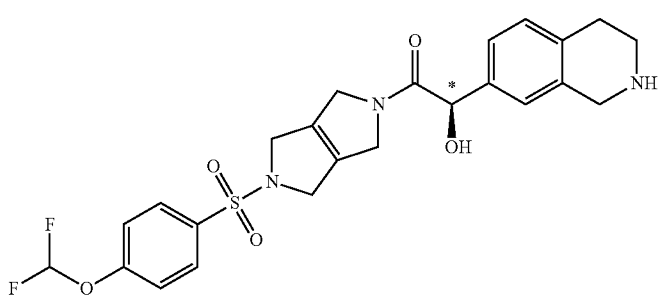 [SMILES: O=C([C@H](O)c1ccc2c(c1)CNCC2)N1CC2=C(C1)CN(S(=O)(=O)c1ccc(OC(F)F)cc1)C2] | (2R)-1-(5-[[4-(Difluoromethoxy)benzene]sulfonyl]-1H,2H,3H,4H,5H,6H-pyrrolo[3,4-c]pyrrol-2-yl)-2-hydroxy-2-(1,2,3,4-tetrahydroisoquinolin-7-yl)ethan-1-one |

TABLE 1-continued

| Example | Structure | Name |
|---|---|---|
| 12-1 | 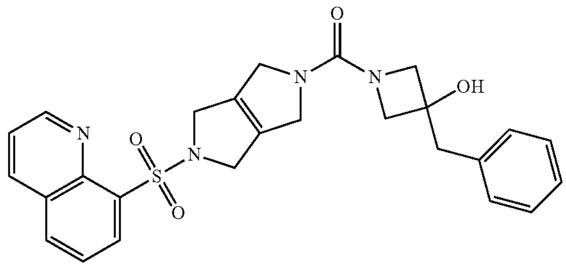 [SMILES: O=C(N1CC2=C(C1)CN(S(=O)(=O)c1cccc3cccnc13)C2)N1CC(O)(Cc2ccccc2)C1] | (3-Benzyl-3-hydroxyazetidin-1-yl)(5-(quinolin-8-ylsulfonyl)-4,5-dihydropyrrolo[3,4-c]pyrrol-2(1H,3H,4H)-yl)methanone |
| 13-1 | 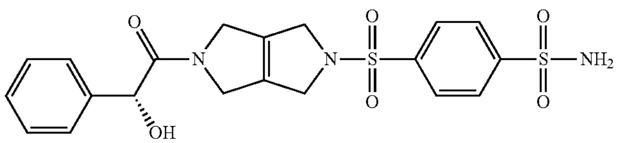 [SMILES: NS(=O)(=O)c1ccc(S(=O)(=O)N2CC3=C(CN(C(=O)[C@H](O)c4ccccc4)C3)C2)cc1] | (R)-4-((5-(2-hydroxy-2-phenylacetyl)-3,4,5,6-tetrahydropyrrolo[3,4-c]pyrrol-2(1H)-yl)sulfonyl)benzenesulfonamide |
| 14-1 | 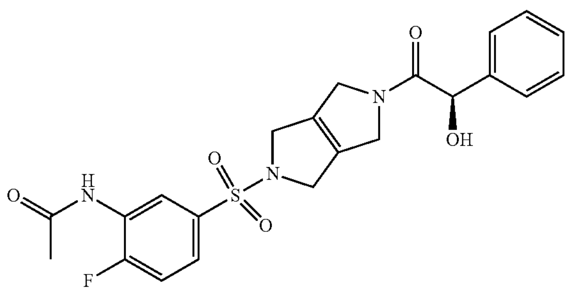 [SMILES: CC(=O)Nc1cc(S(=O)(=O)N2CC3=C(CN(C(=O)[C@H](O)c4ccccc4)C3)C2)ccc1F] | (R)-N-(2-fluoro-5-((5-(2-hydroxy-2-phenylacetyl)-3,4,5,6-tetrahydropyrrolo[3,4-c]pyrrol-2(1H)-yl)sulfonyl)phenyl)acetamide |
| 15-1 | 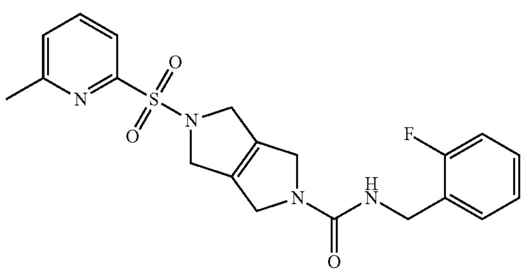 [SMILES: Cc1cccc(S(=O)(=O)N2CC3=C(CN(C(=O)NCc4ccccc4F)C3)C2)n1] | N-[(2-fluorophenyl)methyl]-5-(6-methylpyridine-2-sulfonyl)-1H,2H,3H,4H,5H,6H-pyrrolo[3,4-c]pyrrole-2-carboxamide |
| 16-1 | 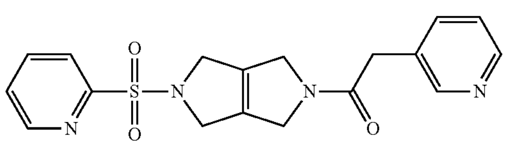 [SMILES: O=C(Cc1cccnc1)N1CC2=C(C1)CN(S(=O)(=O)c1ccccn1)C2] | 2-(Pyridin-3-yl)-1-[5-(pyridine-2-sulfonyl)-1H,2H,3H,4H,5H,6H-pyrrolo[3,4-c]pyrrol-2-yl]ethan-1-one |
| 17-1 | 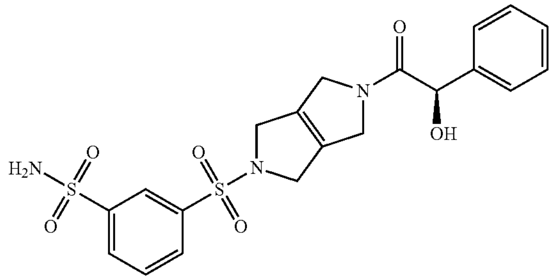 [SMILES: NS(=O)(=O)c1cccc(S(=O)(=O)N2CC3=C(CN(C(=O)[C@H](O)c4ccccc4)C3)C2)c1] | 3-[5-[(2R)-2-hydroxy-2-phenylacetyl]-1H,2H,3H,4H,5H,6H-pyrrolo[3,4-c]pyrrol-2-sulfonyl]benzene-1-sulfonamide |

TABLE 1-continued

| Example | Structure | Name |
|---|---|---|
| 18-1 | 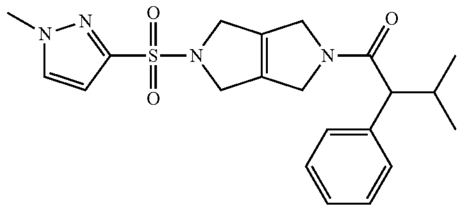 [SMILES: CC(C)C(C(=O)N1CC2=C(C1)CN(S(=O)(=O)c1ccn(C)n1)C2)c1ccccc1] | 3-Methyl-1-{5-[(1-methyl-1H-pyrazol-3-yl)sulfonyl]-1H,2H,3H,4H,5H,6H-pyrrolo[3,4-c]pyrrol-2-yl}-2-phenylbutan-1-one |
| 18-2 | 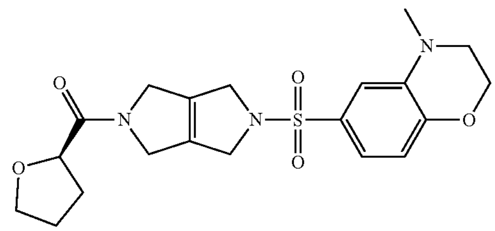 [SMILES: CN1CCOc2ccc(S(=O)(=O)N3CC4=C(CN(C(=O)[C@H]5CCCO5)C4)C3)cc21] | 4-Methyl-6-({5-[(2R)-oxolane-2-carbonyl]-1H,2H,3H,4H,5H,6H-pyrrolo[3,4-c]pyrrol-2-yl}sulfonyl)-3,4-dihydro-2H-1,4-benzoxazine |
| 18-3 | 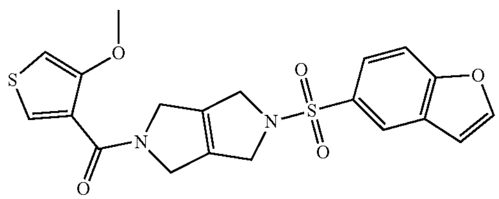 [SMILES: COc1cscc1C(=O)N1CC2=C(C1)CN(S(=O)(=O)c1ccc3occc3c1)C2] | 2-(1-Benzofuran-5-sulfonyl)-5-(4-methoxythiophene-3-carbonyl)-1H,2H,3H,4H,5H,6H-pyrrolo[3,4-c]pyrrole |
| 18-4 | 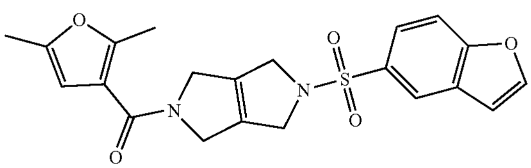 [SMILES: Cc1cc(C(=O)N2CC3=C(C2)CN(S(=O)(=O)c2ccc4occc4c2)C3)c(C)o1] | 2-(1-Benzofuran-5-sulfonyl)-5-(2,5-dimethylfuran-3-carbonyl)-1H,2H,3H,4H,5H,6H-pyrrolo[3,4-c]pyrrole |
| 18-5 | 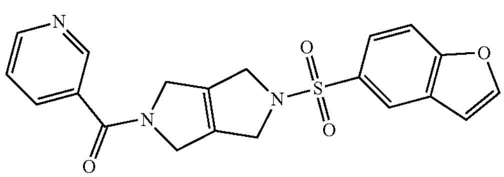 [SMILES: O=C(c1cccnc1)N1CC2=C(C1)CN(S(=O)(=O)c1ccc3occc3c1)C2] | 3-[5-(1-Benzofuran-5-sulfonyl)-1H,2H,3H,4H,5H,6H-pyrrolo[3,4-c]pyrrole-2-carbonyl]pyridine |
| 18-6 | 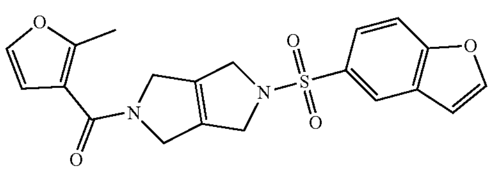 [SMILES: Cc1occc1C(=O)N1CC2=C(C1)CN(S(=O)(=O)c1ccc3occc3c1)C2] | 2-(1-Benzofuran-5-sulfonyl)-5-(2-methylfuran-3-carbonyl)-1H,2H,3H,4H,5H,6H-pyrrolo[3,4-c]pyrrole |
| 18-7 | 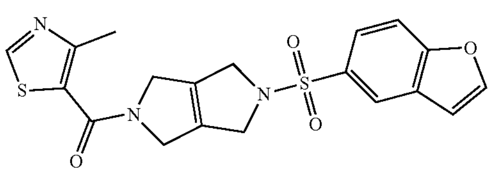 [SMILES: Cc1ncsc1C(=O)N1CC2=C(C1)CN(S(=O)(=O)c1ccc3occc3c1)C2] | 5-[5-(1-Benzofuran-5-sulfonyl)-1H,2H,3H,4H,5H,6H-pyrrolo[3,4-c]pyrrole-2-carbonyl]-4-methyl-1,3-thiazole |
| 18-8 | 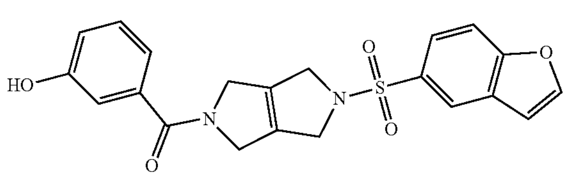 [SMILES: O=C(c1cccc(O)c1)N1CC2=C(C1)CN(S(=O)(=O)c1ccc3occc3c1)C2] | 3-[5-(1-Benzofuran-5-sulfonyl)-1H,2H,3H,4H,5H,6H-pyrrolo[3,4-c]pyrrole-2-carbonyl]phenol |

TABLE 1-continued

| Example | Structure | Name |
|---|---|---|
| 18-9 | 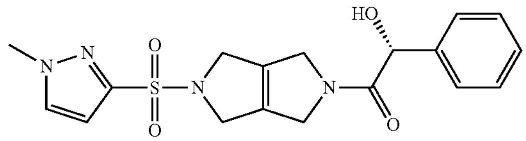 [SMILES: Cn1ccc(S(=O)(=O)N2CC3=C(CN(C(=O)[C@H](O)c4ccccc4)C3)C2)n1] | (2R)-2-hydroxy-1-{5-[(1-methyl-1H-pyrazol-3-yl)sulfonyl]-1H,2H,3H,4H,5H,6H-pyrrolo[3,4-c]pyrrol-2-yl}-2-phenylethan-1-one |
| 18-10 | 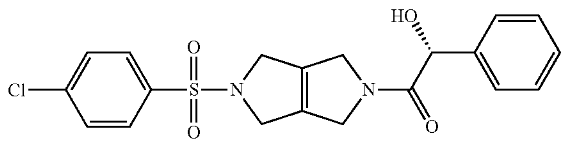 [SMILES: O=C([C@H](O)c1ccccc1)N1CC2=C(C1)CN(S(=O)(=O)c1ccc(Cl)cc1)C2] | (2R)-1-[5-(4-chlorobenzenesulfonyl)-1H,2H,3H,4H,5H,6H-pyrrolo[3,4-c]pyrrol-2-yl]-2-hydroxy-2-phenylethan-1-one |
| 18-11 | 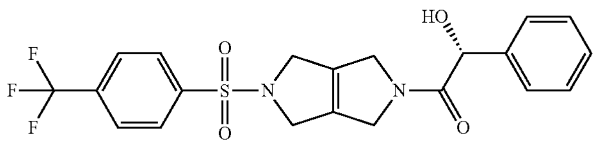 [SMILES: O=C([C@H](O)c1ccccc1)N1CC2=C(C1)CN(S(=O)(=O)c1ccc(C(F)(F)F)cc1)C2] | (2R)-2-hydroxy-2-phenyl-1-{5-[4-(trifluoromethyl)benzenesulfonyl]-1H,2H,3H,4H,5H,6H-pyrrolo[3,4-c]pyrrol-2-yl}ethan-1-one |
| 18-12 | 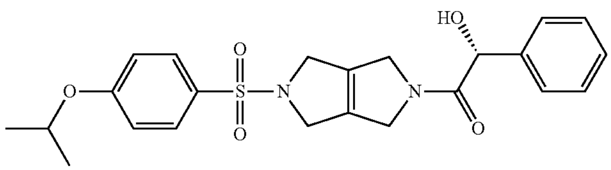 [SMILES: CC(C)Oc1ccc(S(=O)(=O)N2CC3=C(CN(C(=O)[C@H](O)c4ccccc4)C3)C2)cc1] | (2R)-2-hydroxy-2-phenyl-1-{5-[4-(propan-2-yloxy)benzenesulfonyl]-1H,2H,3H,4H,5H,6H-pyrrolo[3,4-c]pyrrol-2-yl}ethan-1-one |
| 18-13 | 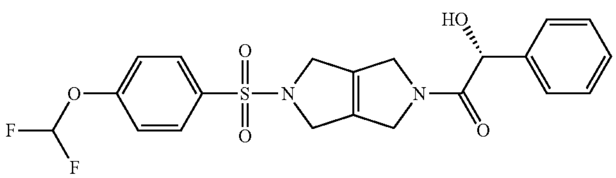 [SMILES: O=C([C@H](O)c1ccccc1)N1CC2=C(C1)CN(S(=O)(=O)c1ccc(OC(F)F)cc1)C2] | (2R)-1-{5-[4-(difluoromethoxy)benzenesulfonyl]-1H,2H,3H,4H,5H,6H-pyrrolo[3,4-c]pyrrol-2-yl}-2-hydroxy-2-phenylethan-1-one |
| 18-14 | 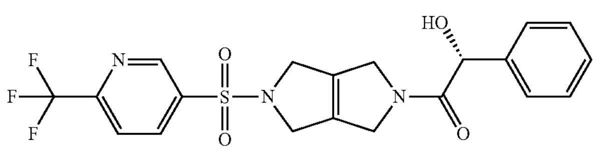 [SMILES: O=C([C@H](O)c1ccccc1)N1CC2=C(C1)CN(S(=O)(=O)c1ccc(C(F)(F)F)nc1)C2] | (2R)-2-hydroxy-2-phenyl-1-(5-{[6-(trifluoromethyl)pyridin-3-yl]sulfonyl}-1H,2H,3H,4H,5H,6H-pyrrolo[3,4-c]pyrrol-2-yl)ethan-1-one |
| 18-15 | 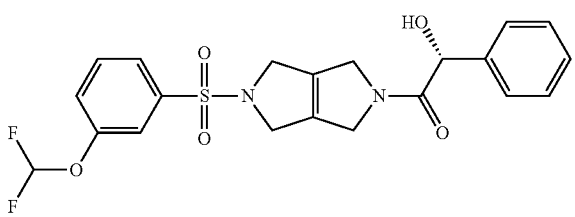 [SMILES: O=C([C@H](O)c1ccccc1)N1CC2=C(C1)CN(S(=O)(=O)c1cccc(OC(F)F)c1)C2] | (2R)-1-{5-[3-(difluoromethoxy)benzenesulfonyl]-1H,2H,3H,4H,5H,6H-pyrrolo[3,4-c]pyrrol-2-yl}-2-hydroxy-2-phenylethan-1-one |
| 18-16 | 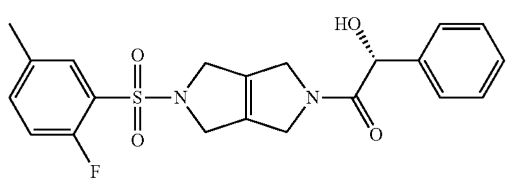 [SMILES: Cc1ccc(F)c(S(=O)(=O)N2CC3=C(CN(C(=O)[C@H](O)c4ccccc4)C3)C2)c1] | (2R)-1-[5-(2-fluoro-5-methylbenzenesulfonyl)-1H,2H,3H,4H,5H,6H-pyrrolo[3,4-c]pyrrol-2-yl]-2-hydroxy-2-phenylethan-1-one |
| 18-17 | 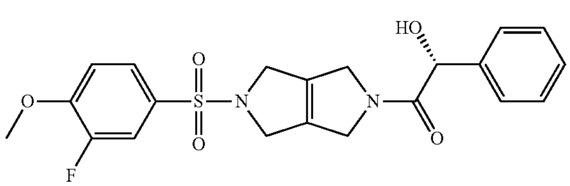 [SMILES: COc1ccc(S(=O)(=O)N2CC3=C(CN(C(=O)[C@H](O)c4ccccc4)C3)C2)cc1F] | (2R)-1-[5-(3-fluoro-4-methoxybenzenesulfonyl)-1H,2H,3H,4H,5H,6H-pyrrolo[3,4-c]pyrrol-2-yl]-2-hydroxy-2-phenylethan-1-one |

TABLE 1-continued

| Example | Structure | Name |
|---|---|---|
| 18-18 | 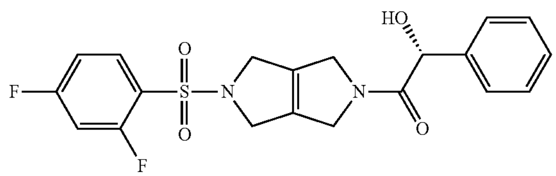 [SMILES: O=C([C@H](O)c1ccccc1)N1CC2=C(C1)CN(S(=O)(=O)c1ccc(F)cc1F)C2] | (2R)-1-[5-(2,4-difluorobenzenesulfonyl)-1H,2H,3H,4H,5H,6H-pyrrolo[3,4-c]pyrrol-2-yl]-2-hydroxy-2-phenylethan-1-one |
| 18-19 | 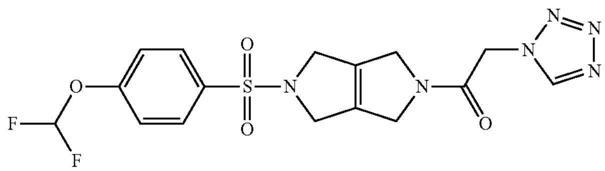 [SMILES: O=C(Cn1cnnn1)N1CC2=C(C1)CN(S(=O)(=O)c1ccc(OC(F)F)cc1)C2] | 1-{5-[4-(Difluoromethoxy)benzenesulfonyl]-1H,2H,3H,4H,5H,6H-pyrrolo[3,4-c]pyrrol-2-yl}-2-(1H-1,2,3,4-tetrazol-1-yl)ethan-1-one |
| 18-20 | 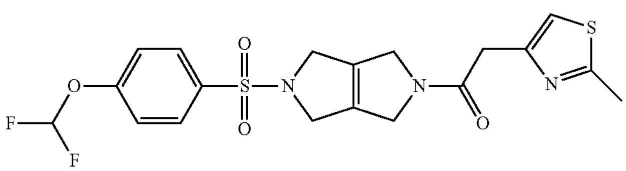 [SMILES: Cc1nc(CC(=O)N2CC3=C(C2)CN(S(=O)(=O)c2ccc(OC(F)F)cc2)C3)cs1] | 1-{5-[4-(Difluoromethoxy)benzenesulfonyl]-1H,2H,3H,4H,5H,6H-pyrrolo[3,4-c]pyrrol-2-yl}-2-(2-methyl-1,3-thiazol-4-yl)ethan-1-one |
| 18-21 | 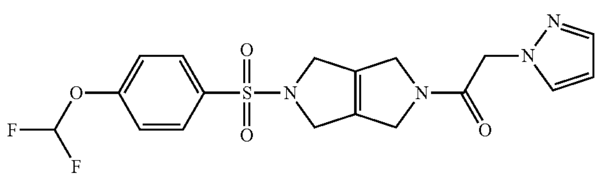 [SMILES: O=C(Cn1cccn1)N1CC2=C(C1)CN(S(=O)(=O)c1ccc(OC(F)F)cc1)C2] | 1-{5-[4-(Difluoromethoxy)benzenesulfonyl]-1H,2H,3H,4H,5H,6H-pyrrolo[3,4-c]pyrrol-2-yl}-2-(1H-pyrazol-1-yl)ethan-1-one |
| 18-22 | 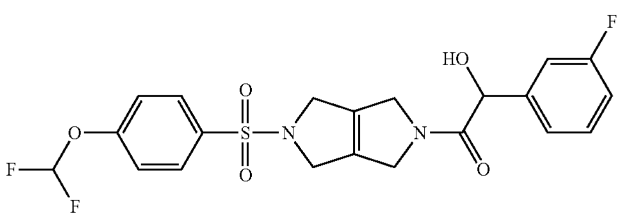 [SMILES: O=C(C(O)c1cccc(F)c1)N1CC2=C(C1)CN(S(=O)(=O)c1ccc(OC(F)F)cc1)C2] | 1-{5-[4-(Difluoromethoxy)benzenesulfonyl]-1H,2H,3H,4H,5H,6H-pyrrolo[3,4-c]pyrrol-2-yl}-2-(3-fluorophenyl)-2-hydroxyethan-1-one |
| 18-23 | 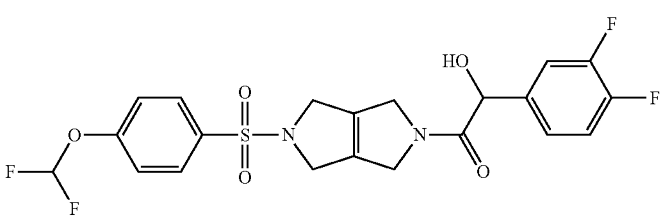 [SMILES: O=C(C(O)c1ccc(F)c(F)c1)N1CC2=C(C1)CN(S(=O)(=O)c1ccc(OC(F)F)cc1)C2] | 1-{5-[4-(Difluoromethoxy)benzenesulfonyl]-1H,2H,3H,4H,5H,6H-pyrrolo[3,4-c]pyrrol-2-yl}-2-(3,4-difluorophenyl)-2-hydroxyethan-1-one |
| 18-24 | 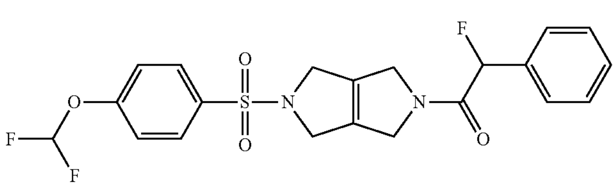 [SMILES: O=C(C(F)c1ccccc1)N1CC2=C(C1)CN(S(=O)(=O)c1ccc(OC(F)F)cc1)C2] | 1-{5-[4-(Difluoromethoxy)benzenesulfonyl]-1H,2H,3H,4H,5H,6H-pyrrolo[3,4-c]pyrrol-2-yl}-2-phenylethan-1-one |
| 18-25 | 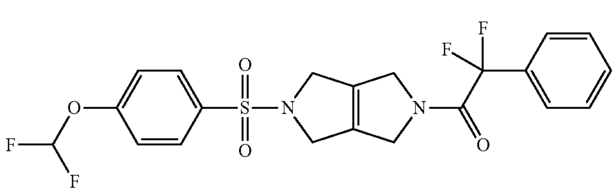 [SMILES: O=C(N1CC2=C(C1)CN(S(=O)(=O)c1ccc(OC(F)F)cc1)C2)C(F)(F)c1ccccc1] | 1-{5-[4-(Difluoromethoxy)benzenesulfonyl]-1H,2H,3H,4H,5H,6H-pyrrolo[3,4-c]pyrrol-2-yl}-2,2-difluoro-2-phenylethan-1-one |

TABLE 1-continued

| Example | Structure | Name |
|---|---|---|
| 18-26 | 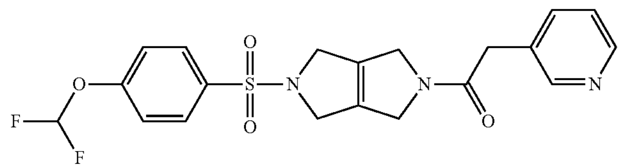 [SMILES: O=C(Cc1cccnc1)N1CC2=C(C1)CN(S(=O)(=O)c1ccc(OC(F)F)cc1)C2] | 1-{5-[4-(Difluoromethoxy)benzenesulfonyl]-1H,2H,3H,4H,5H,6H-pyrrolo[3,4-c]pyrrol-2-yl}-2-(pyridin-3-yl)ethan-1-one |
| 18-27 | 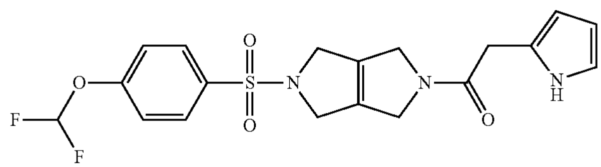 [SMILES: O=C(Cc1ccc[nH]1)N1CC2=C(C1)CN(S(=O)(=O)c1ccc(OC(F)F)cc1)C2] | 1-{5-[4-(Difluoromethoxy)benzenesulfonyl]-1H,2H,3H,4H,5H,6H-pyrrolo[3,4-c]pyrrol-2-yl}-2-(1H-pyrrol-2-yl)ethan-1-one |
| 18-28 | 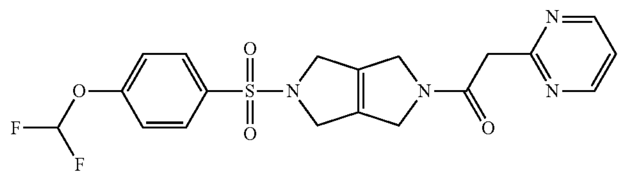 [SMILES: O=C(Cc1ncccn1)N1CC2=C(C1)CN(S(=O)(=O)c1ccc(OC(F)F)cc1)C2] | 1-{5-[4-(Difluoromethoxy)benzenesulfonyl]-1H,2H,3H,4H,5H,6H-pyrrolo[3,4-c]pyrrol-2-yl}-2-(pyrimidin-2-yl)ethan-1-one |
| 18-29 | 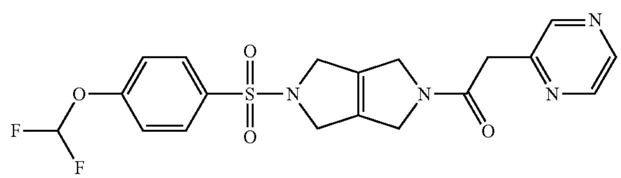 [SMILES: O=C(Cc1cnccn1)N1CC2=C(C1)CN(S(=O)(=O)c1ccc(OC(F)F)cc1)C2] | 1-{5-[4-(Difluoromethoxy)benzenesulfonyl]-1H,2H,3H,4H,5H,6H-pyrrolo[3,4-c]pyrrol-2-yl}-2-(pyrazin-2-yl)ethan-1-one |
| 18-30 | 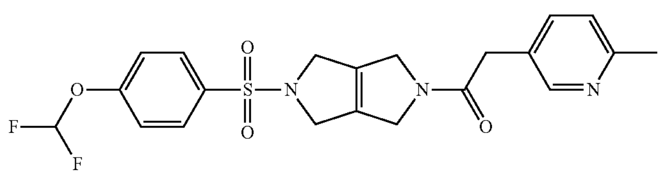 [SMILES: Cc1ccc(CC(=O)N2CC3=C(C2)CN(S(=O)(=O)c2ccc(OC(F)F)cc2)C3)cn1] | 1-{5-[4-(Difluoromethoxy)benzenesulfonyl]-1H,2H,3H,4H,5H,6H-pyrrolo[3,4-c]pyrrol-2-yl}-2-(6-methylpyridin-3-yl)ethan-1-one |
| 18-31 | 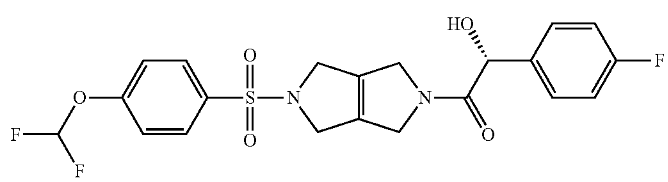 [SMILES: O=C([C@H](O)c1ccc(F)cc1)N1CC2=C(C1)CN(S(=O)(=O)c1ccc(OC(F)F)cc1)C2] | (2R)-1-{5-[4-(difluoromethoxy)benzenesulfonyl]-1H,2H,3H,4H,5H,6H-pyrrolo[3,4-c]pyrrol-2-yl}-2-(4-fluorophenyl)-2-hydroxyethan-1-one |
| 18-32 | 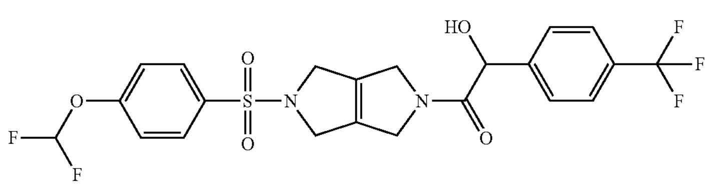 [SMILES: O=C(C(O)c1ccc(C(F)(F)F)cc1)N1CC2=C(C1)CN(S(=O)(=O)c1ccc(OC(F)F)cc1)C2] | 1-{5-[4-(Difluoromethoxy)benzenesulfonyl]-1H,2H,3H,4H,5H,6H-pyrrolo[3,4-c]pyrrol-2-yl}-2-hydroxy-2-[4-(trifluoromethyl)phenyl]ethan-1-one |
| 18-33 | 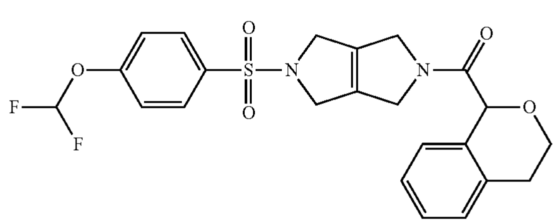 [SMILES: O=C(C1OCCc2ccccc21)N1CC2=C(C1)CN(S(=O)(=O)c1ccc(OC(F)F)cc1)C2] | 2-[4-(Difluoromethoxy)benzenesulfonyl]-5-(3,4-dihydro-1H-2-benzopyran-1-carbonyl)-1H,2H,3H,4H,5H,6H-pyrrolo[3,4-c]pyrrole |

TABLE 1-continued

| Example | Structure | Name |
|---|---|---|
| 18-34 | 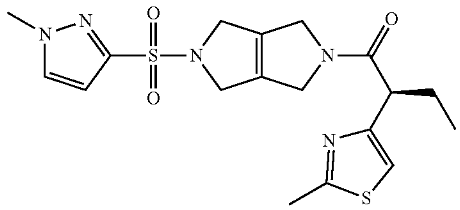 [SMILES: CC[C@H](C(=O)N1CC2=C(C1)CN(S(=O)(=O)c1ccn(C)n1)C2)c1csc(C)n1] | (2S)-2-(2-methyl-1,3-thiazol-4-yl)-1-{5-[(1-methyl-1H-pyrazol-3-yl)sulfonyl]-1H,2H,3H,4H,5H,6H-pyrrolo[3,4-c]pyrrol-2-yl}butan-1-one |
| 18-35 | 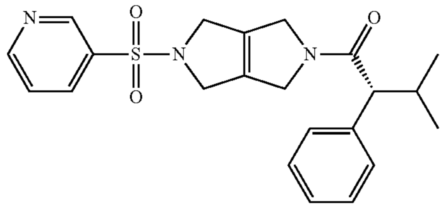 [SMILES: CC(C)[C@@H](C(=O)N1CC2=C(C1)CN(S(=O)(=O)c1cccnc1)C2)c1ccccc1] | (2R)-3-methyl-2-phenyl-1-[5-(pyridine-3-sulfonyl-1H,2H,3H,4H,5H,6H-pyrrolo[3,4-c]pyrrol-2-yl]butan-1-one |
| 18-36 | 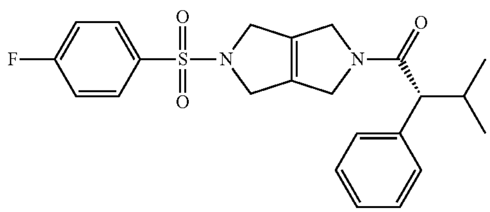 [SMILES: CC(C)[C@@H](C(=O)N1CC2=C(C1)CN(S(=O)(=O)c1ccc(F)cc1)C2)c1ccccc1] | (2R)-1-[5-(4-fluorobenzenesulfonyl)-1H,2H,3H,4H,5H,6H-pyrrolo[3,4-c]pyrrol-2-yl]-3-methyl-2-phenylbutan-1-one |
| 18-37 | 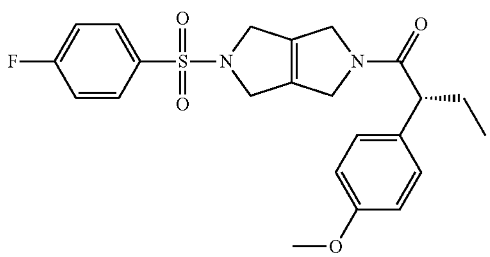 [SMILES: CC[C@@H](C(=O)N1CC2=C(C1)CN(S(=O)(=O)c1ccc(F)cc1)C2)c1ccc(OC)cc1] | (2R)-1-[5-(4-fluorobenzenesulfonyl)-1H,2H,3H,4H,5H,6H-pyrrolo[3,4-c]pyrrol-2-yl]-2-(4-methoxyphenyl)butan-1-one |
| 18-38 | 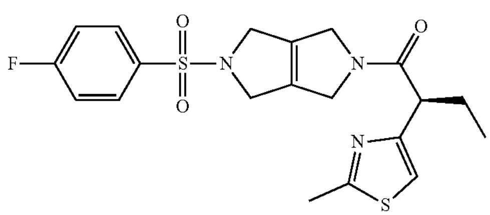 [SMILES: CC[C@H](C(=O)N1CC2=C(C1)CN(S(=O)(=O)c1ccc(F)cc1)C2)c1csc(C)n1] | (2S)-1-[5-(4-fluorobenzenesulfonyl)-1H,2H,3H,4H,5H,6H-pyrrolo[3,4-c]pyrrol-2-yl]-2-(2-methyl-1,3-thiazol-4-yl)butan-1-one |
| 18-39 | 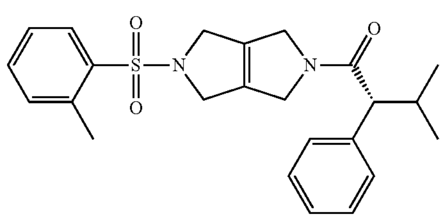 [SMILES: Cc1ccccc1S(=O)(=O)N1CC2=C(CN(C(=O)[C@@H](c3ccccc3)C(C)C)C2)C1] | (2R)-3-methyl-1-[5-(2-methylbenzenesulfonyl)-1H,2H,3H,4H,5H,6H-pyrrolo[3,4-c]pyrrol-2-yl]-2-phenylbutan-1-one |
| 18-40 | 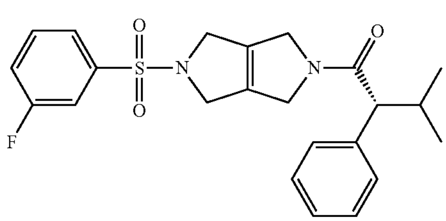 [SMILES: CC(C)[C@@H](C(=O)N1CC2=C(C1)CN(S(=O)(=O)c1cccc(F)c1)C2)c1ccccc1] | (2R)-1-[5-(3-fluorobenzenesulfonyl)-1H,2H,3H,4H,5H,6H-pyrrolo[3,4-c]pyrrol-2-yl]-3-methyl-2-phenylbutan-1-one |

TABLE 1-continued

| Example | Structure | Name |
|---|---|---|
| 18-41 | 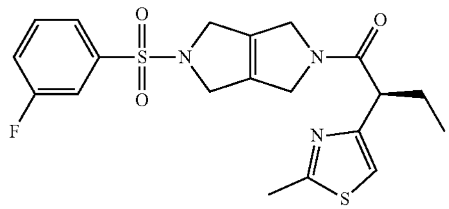 [SMILES: CC[C@H](C(=O)N1CC2=C(C1)CN(S(=O)(=O)c1cccc(F)c1)C2)c1csc(C)n1] | (2S)-1-[5-(3-fluorobenzenesulfonyl)-1H,2H,3H,4H,5H,6H-pyrrolo[3,4-c]pyrrol-2-yl]-2-(2-methyl-1,3-thiazol-4-yl)butan-1-one |
| 18-42 | 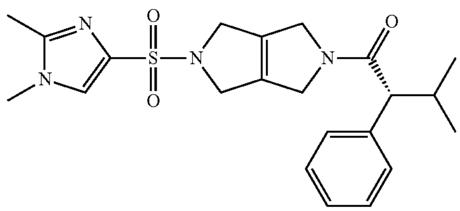 [SMILES: Cc1nc(S(=O)(=O)N2CC3=C(CN(C(=O)[C@@H](c4ccccc4)C(C)C)C3)C2)cn1C] | (2R)-1-{5-[(1,2-dimethyl-1H-imidazol-4-yl)sulfonyl]-1H,2H,3H,4H,5H,6H-pyrrolo[3,4-c]pyrrol-2-yl}-3-methyl-2-phenylbutan-1-one |
| 18-43 | 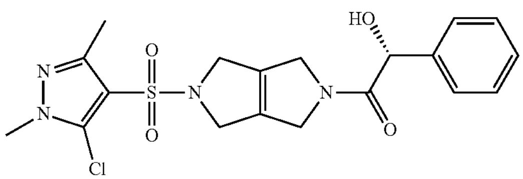 [SMILES: Cc1nn(C)c(Cl)c1S(=O)(=O)N1CC2=C(CN(C(=O)[C@H](O)c3ccccc3)C2)C1] | (2R)-1-{5-[(5-chloro-1,3-dimethyl-1H-pyrazol-4-yl)sulfonyl]-1H,2H,3H,4H,5H,6H-pyrrolo[3,4-c]pyrrol-2-yl}-2-hydroxy-2-phenylethan-1-one |
| 18-44 | 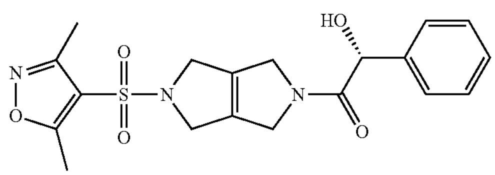 [SMILES: Cc1noc(C)c1S(=O)(=O)N1CC2=C(CN(C(=O)[C@H](O)c3ccccc3)C2)C1] | (2R)-1-{5-[(dimethyl-1,2-oxazol-4-yl)sulfonyl]-1H,2H,3H,4H,5H,6H-pyrrolo[3,4-c]pyrrol-2-yl}-2-hydroxy-2-phenylethan-1-one |
| 18-45 | 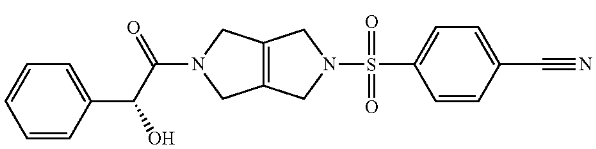 [SMILES: N#Cc1ccc(S(=O)(=O)N2CC3=C(CN(C(=O)[C@H](O)c4ccccc4)C3)C2)cc1] | 4-({5-[(2R)-2-hydroxy-2-phenylacetyl]-1H,2H,3H,4H,5H,6H-pyrrolo[3,4-c]pyrrol-2-yl}sulfonyl)benzonitrile |
| 18-46 | 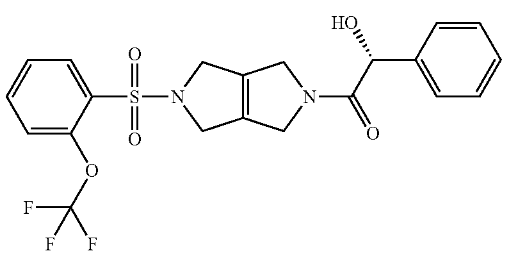 [SMILES: O=C([C@H](O)c1ccccc1)N1CC2=C(C1)CN(S(=O)(=O)c1ccccc1OC(F)(F)F)C2] | (2R)-2-hydroxy-2-phenyl-1-{5-[2-(trifluoromethoxy)benzenesulfonyl]-1H,2H,3H,4H,5H,6H-pyrrolo[3,4-c]pyrrol-2-yl}ethan-1-one |
| 18-47 | 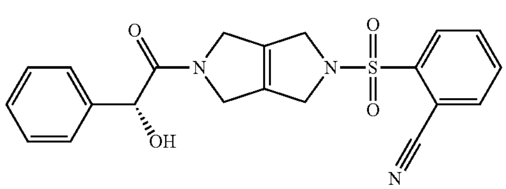 [SMILES: N#Cc1ccccc1S(=O)(=O)N1CC2=C(CN(C(=O)[C@H](O)c3ccccc3)C2)C1] | 2-({5-[(2R)-2-hydroxy-2-phenylacetyl]-1H,2H,3H,4H,5H,6H-pyrrolo[3,4-c]pyrrol-2-yl}sulfonyl)benzonitrile |
| 18-48 | 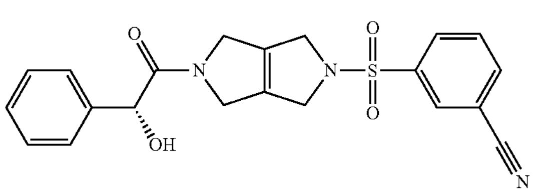 [SMILES: N#Cc1cccc(S(=O)(=O)N2CC3=C(CN(C(=O)[C@H](O)c4ccccc4)C3)C2)c1] | 3-({5-[(2R)-2-hydroxy-2-phenylacetyl]-1H,2H,3H,4H,5H,6H-pyrrolo[3,4-c]pyrrol-2-yl}sulfonyl)benzonitrile |

TABLE 1-continued

| Example | Structure | Name |
|---|---|---|
| 18-49 | 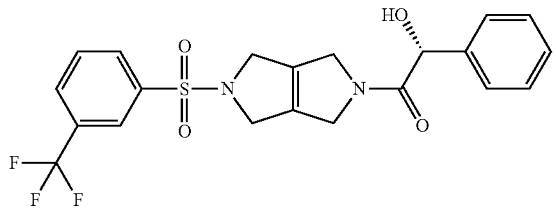 [SMILES: O=C([C@H](O)c1ccccc1)N1CC2=C(C1)CN(S(=O)(=O)c1cccc(C(F)(F)F)c1)C2] | (2R)-2-hydroxy-2-phenyl-1-{5-[3-(trifluoromethyl)benzenesulfonyl]-1H,2H,3H,4H,5H,6H-pyrrolo[3,4-c]pyrrol-2-yl}ethan-1-one |
| 18-50 | 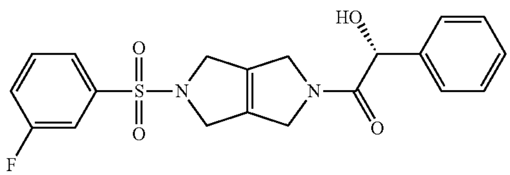 [SMILES: O=C([C@H](O)c1ccccc1)N1CC2=C(C1)CN(S(=O)(=O)c1cccc(F)c1)C2] | (2R)-1-[5-(3-fluorobenzenesulfonyl)-1H,2H,3H,4H,5H,6H-pyrrolo[3,4-c]pyrrol-2-yl]-2-hydroxy-2-phenylethan-1-one |
| 18-51 | 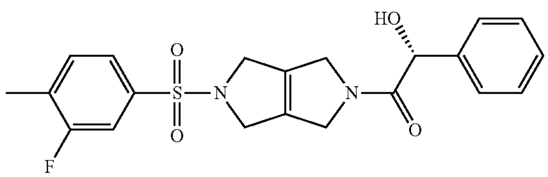 | (2R)-1-[5-(3-fluoro-4-methylbenzenesulfonyl)-1H,2H,3H,4H,5H,6H-pyrrolo[3,4-c]pyrrol-2-yl]-2-hydroxy-2-phenylethan-1-one |
| 18-52 | 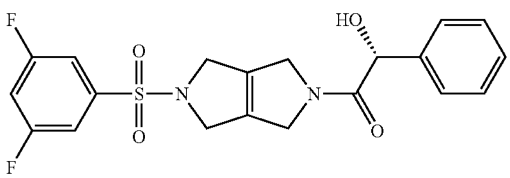 | (2R)-1-[5-(3,5-difluorobenzenesulfonyl)-1H,2H,3H,4H,5H,6H-pyrrolo[3,4-c]pyrrol-2-yl]-2-hydroxy-2-phenylethan-1-one |
| 18-53 | 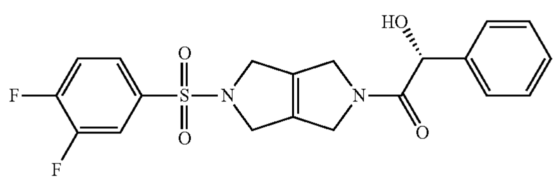 [SMILES: O=C([C@H](O)c1ccccc1)N1CC2=C(C1)CN(S(=O)(=O)c1ccc(F)c(F)c1)C2] | (2R)-1-[5-(3,4-difluorobenzenesulfonyl)-1H,2H,3H,4H,5H,6H-pyrrolo[3,4-c]pyrrol-2-yl]-2-hydroxy-2-phenylethan-1-one |
| 18-54 | 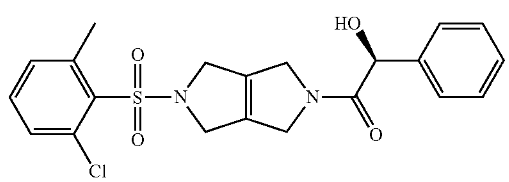 | (2S)-1-[5-(2-chloro-6-methylbenzenesulfonyl)-1H,2H,3H,4H,5H,6H-pyrrolo[3,4-c]pyrrol-2-yl]-2-hydroxy-2-phenylethan-1-one |
| 18-55 | 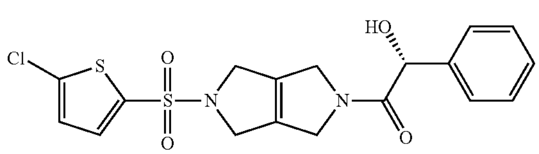 [SMILES: O=C([C@H](O)c1ccccc1)N1CC2=C(C1)CN(S(=O)(=O)c1ccc(Cl)s1)C2] | (2R)-1-{5-[(5-chlorothiophen-2-yl)sulfonyl]-1H,2H,3H,4H,5H,6H-pyrrolo[3,4-c]pyrrol-2-yl}-2-hydroxy-2-phenylethan-1-one |
| 18-56 | 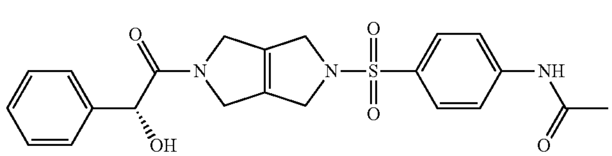 [SMILES: CC(=O)Nc1ccc(S(=O)(=O)N2CC3=C(CN(C(=O)[C@H](O)c4ccccc4)C3)C2)cc1] | N-[4-({5-[(2R)-2-hydroxy-2-phenylacetyl]-1H,2H,3H,4H,5H,6H-pyrrolo[3,4-c]pyrrol-2-yl}sulfonyl)phenyl]acetamide |

TABLE 1-continued

| Example | Structure | Name |
|---|---|---|
| 18-57 | 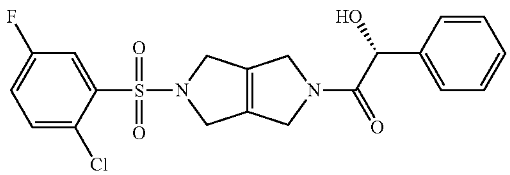 [SMILES: O=C([C@H](O)c1ccccc1)N1CC2=C(C1)CN(S(=O)(=O)c1cc(F)ccc1Cl)C2] | (2R)-1-[5-(2-chloro-5-fluorobenzenesulfonyl)-1H,2H,3H,4H,5H,6H-pyrrolo[3,4-c]pyrrol-2-yl]-2-hydroxy-2-phenylethan-1-one |
| 18-58 | 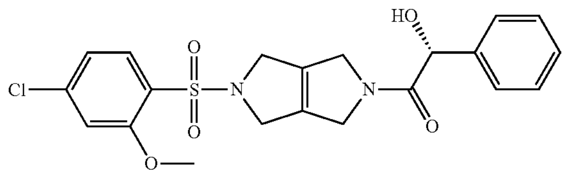 [SMILES: COc1cc(Cl)ccc1S(=O)(=O)N1CC2=C(CN(C(=O)[C@H](O)c3ccccc3)C2)C1] | (2R)-1-[5-(4-chloro-2-methoxybenzenesulfonyl)-1H,2H,3H,4H,5H,6H-pyrrolo[3,4-c]pyrrol-2-yl]-2-hydroxy-2-phenylethan-1-one |
| 18-59 | 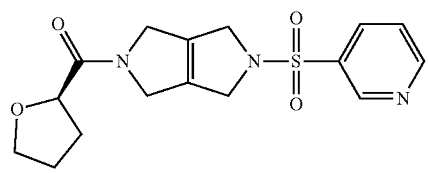 [SMILES: O=C([C@H]1CCCO1)N1CC2=C(C1)CN(S(=O)(=O)c1cccnc1)C2] | 3-({5-[(2R)-2-oxolane-2-carbonyl]-1H,2H,3H,4H,5H,6H-pyrrolo[3,4-c]pyrrol-2-yl}sulfonyl)pyridine |
| 18-60 | 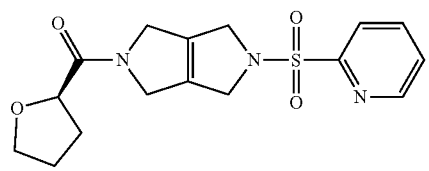 [SMILES: O=C([C@H]1CCCO1)N1CC2=C(C1)CN(S(=O)(=O)c1ccccn1)C2] | 2-({5-[(2R)-2-oxolane-2-carbonyl]-1H,2H,3H,4H,5H,6H-pyrrolo[3,4-c]pyrrol-2-yl}sulfonyl)pyridine |
| 18-61 | 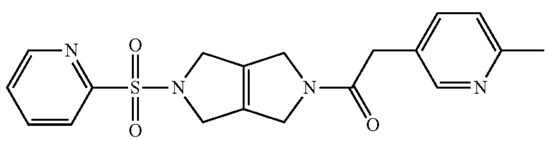 [SMILES: Cc1ccc(CC(=O)N2CC3=C(C2)CN(S(=O)(=O)c2ccccn2)C3)cn1] | 2-(6-Methylpyridin-3-yl)-1-[5-(pyridine-2-sulfonyl)-1H,2H,3H,4H,5H,6H-pyrrolo[3,4-c]pyrrol-2-yl]ethan-1-one |
| 18-62 | 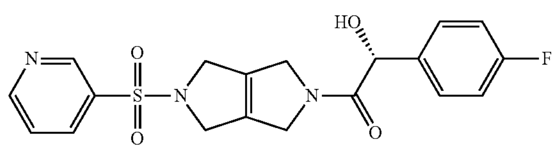 [SMILES: O=C([C@H](O)c1ccc(F)cc1)N1CC2=C(C1)CN(S(=O)(=O)c1cccnc1)C2] | (2R)-2-(4-fluorophenyl)-2-hydroxy-1-[5-(pyridine-3-sulfonyl)-1H,2H,3H,4H,5H,6H-pyrrolo[3,4-c]pyrrol-2-yl]ethan-1-one |
| 18-63 | 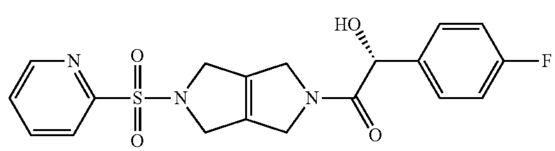 [SMILES: O=C([C@H](O)c1ccc(F)cc1)N1CC2=C(C1)CN(S(=O)(=O)c1ccccn1)C2] | (2R)-2-(4-fluorophenyl)-2-hydroxy-1-[5-(pyridine-2-sulfonyl)-1H,2H,3H,4H,5H,6H-pyrrolo[3,4-c]pyrrol-2-yl]ethan-1-one |
| 18-64 | 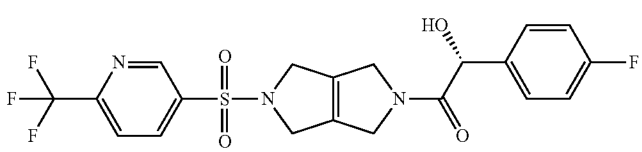 [SMILES: O=C([C@H](O)c1ccc(F)cc1)N1CC2=C(C1)CN(S(=O)(=O)c1ccc(C(F)(F)F)nc1)C2] | (2R)-2-(4-fluorophenyl)-2-hydroxy-1-(5-{[6-(trifluoromethyl)pyridin-3-yl]sulfonyl}-1H,2H,3H,4H,5H,6H-pyrrolo[3,4-c]pyrrol-2-yl)ethan-1-one |
| 18-65 | 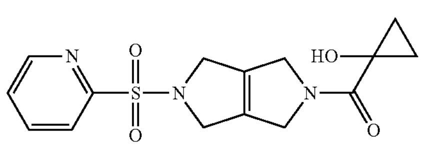 [SMILES: O=C(N1CC2=C(C1)CN(S(=O)(=O)c1ccccn1)C2)C1(O)CC1] | 1-[5-(Pyridine-2-sulfonyl)-1H,2H,3H,4H,5H,6H-pyrrolo[3,4-c]pyrrole-2-carbonyl]cyclopropan-1-ol |

TABLE 1-continued

| Example | Structure | Name |
|---|---|---|
| 18-66 | 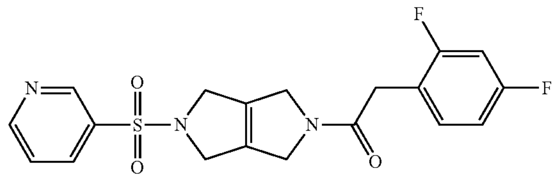 [SMILES: O=C(Cc1ccc(F)cc1F)N1CC2=C(C1)CN(S(=O)(=O)c1cccnc1)C2] | 2-(2,4-Difluorophenyl)-1-[5-(pyridine-3-sulfonyl)-1H,2H,3H,4H,5H,6H-pyrrolo[3,4-c]pyrrol-2-yl]ethan-1-one |
| 18-67 | 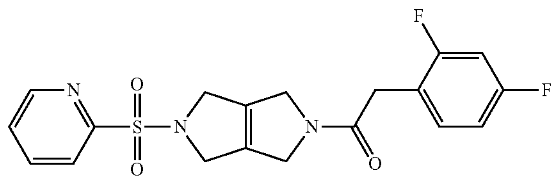 [SMILES: O=C(Cc1ccc(F)cc1F)N1CC2=C(C1)CN(S(=O)(=O)c1ccccn1)C2] | 2-(2,4-Difluorophenyl)-1-[5-(pyridine-2-sulfonyl)-1H,2H,3H,4H,5H,6H-pyrrolo[3,4-c]pyrrol-2-yl]ethan-1-one |
| 18-68 | 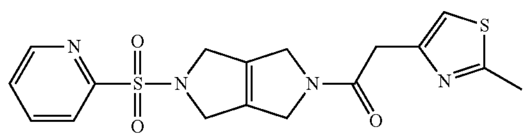 [SMILES: Cc1nc(CC(=O)N2CC3=C(C2)CN(S(=O)(=O)c2ccccn2)C3)cs1] | 2-(2-Methyl-1,3-thiazol-4-yl)-1-[5-(pyridine-2-sulfonyl)-1H,2H,3H,4H,5H,6H-pyrrolo[3,4-c]pyrrol-2-yl]ethan-1-one |
| 18-69 | 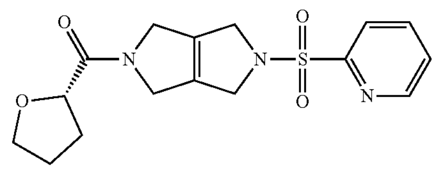 [SMILES: O=C([C@@H]1CCCO1)N1CC2=C(C1)CN(S(=O)(=O)c1ccccn1)C2] | 2-({5-[(2S)-oxolane-2-carbonyl]-1H,2H,3H,4H,5H,6H-pyrrolo[3,4-c]pyrrol-2-yl}sulfonyl)pyridine |
| 18-70 | 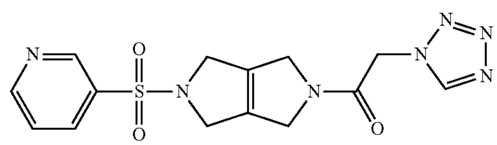 [SMILES: O=C(Cn1cnnn1)N1CC2=C(C1)CN(S(=O)(=O)c1cccnc1)C2] | 1-[5-(Pyridine-3-sulfonyl)-1H,2H,3H,4H,5H,6H-pyrrolo[3,4-c]pyrrol-2-yl]-2-(1H-1,2,3,4-tetrazol-1-yl)ethan-1-one |
| 18-71 | 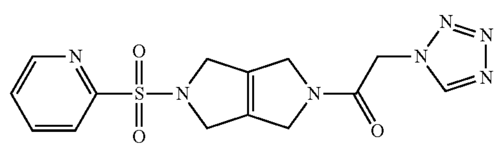 [SMILES: O=C(Cn1cnnn1)N1CC2=C(C1)CN(S(=O)(=O)c1ccccn1)C2] | 1-[5-(Pyridine-2-sulfonyl)-1H,2H,3H,4H,5H,6H-pyrrolo[3,4-c]pyrrol-2-yl]-2-(1H-1,2,3,4-tetrazol-1-yl)ethan-1-one |
| 18-72 | 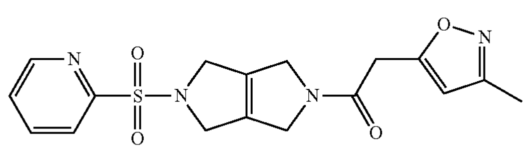 [SMILES: Cc1cc(CC(=O)N2CC3=C(C2)CN(S(=O)(=O)c2ccccn2)C3)on1] | 2-(3-Methyl-1,2-oxazol-5-yl)-1-[5-(pyridine-2-sulfonyl)-1H,2H,3H,4H,5H,6H-pyrrolo[3,4-c]pyrrol-2-yl]ethan-1-one |
| 18-73 | 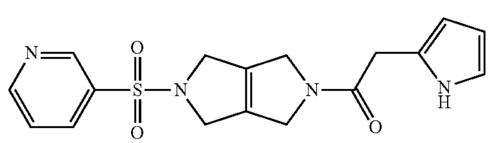 [SMILES: O=C(Cc1ccc[nH]1)N1CC2=C(C1)CN(S(=O)(=O)c1cccnc1)C2] | 1-[5-(Pyridine-3-sulfonyl)-1H,2H,3H,4H,5H,6H-pyrrolo[3,4-c]pyrrol-2-yl]-2-(1H-pyrrol-2-yl)ethan-1-one |
| 18-74 | 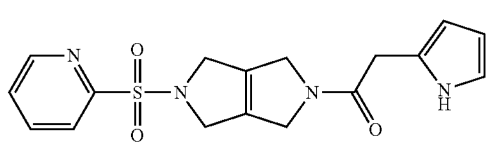 [SMILES: O=C(Cc1ccc[nH]1)N1CC2=C(C1)CN(S(=O)(=O)c1ccccn1)C2] | 1-[5-(Pyridine-2-sulfonyl)-1H,2H,3H,4H,5H,6H-pyrrolo[3,4-c]pyrrol-2-yl]-2-(1H-pyrrol-2-yl)ethan-1-one |

TABLE 1-continued

| Example | Structure | Name |
|---|---|---|
| 18-75 | 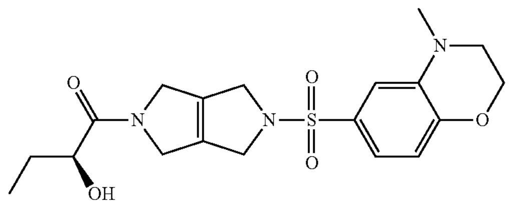 [SMILES: CC[C@H](O)C(=O)N1CC2=C(C1)CN(S(=O)(=O)c1ccc3c(c1)N(C)CCO3)C2] | (2S)-2-hydroxy-1-{5-[(4-methyl-3,4-dihydro-2H-1,4-benzoxazin-6-yl)sulfonyl]-1H,2H,3H,4H,5H,6H-pyrrolo[3,4-c]pyrrol-2-yl}butan-1-one |
| 18-76 | 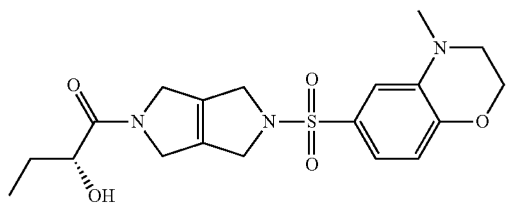 [SMILES: CC[C@@H](O)C(=O)N1CC2=C(C1)CN(S(=O)(=O)c1ccc3c(c1)N(C)CCO3)C2] | (2R)-2-hydroxy-1-{5-[(4-methyl-3,4-dihydro-2H-1,4-benzoxazin-6-yl)sulfonyl]-1H,2H,3H,4H,5H,6H-pyrrolo[3,4-c]pyrrol-2-yl}butan-1-one |
| 18-77 | 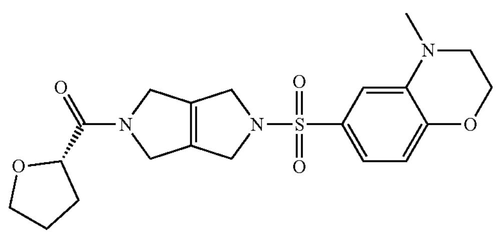 | 4-Methyl-6-({5-[(2S)-oxolane-2-carbonyl]-1H,2H,3H,4H,5H,6H-pyrrolo[3,4-c]pyrrol-2-yl}sulfonyl)-3,4-dihydro-1,4-benzoxazine |
| 18-78 | 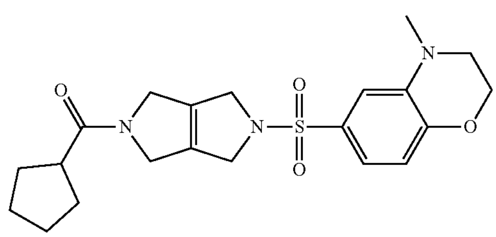 [SMILES: CN1CCOc2ccc(S(=O)(=O)N3CC4=C(CN(C(=O)C5CCCC5)C4)C3)cc21] | 6-({5-Cyclopentanecarbonyl-1H,2H,3H,4H,5H,6H-pyrrolo[3,4-c]pyrrol-2-yl}sulfonyl)-4-methyl-3,4-dihydro-2H-1,4-benzoxazine |
| 18-79 | 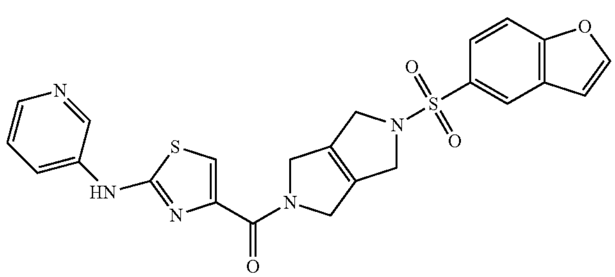 [SMILES: O=C(c1csc(Nc2cccnc2)n1)N1CC2=C(C1)CN(S(=O)(=O)c1ccc3occc3c1)C2] | N-{4-[5-(1-benzofuran-5-sulfonyl)-1H,2H,3H,4H,5H,6H-pyrrolo[3,4-c]pyrrole-2-carbonyl]-1,3-thiazol-2-yl}pyridin-3-amine |
| 18-80 | 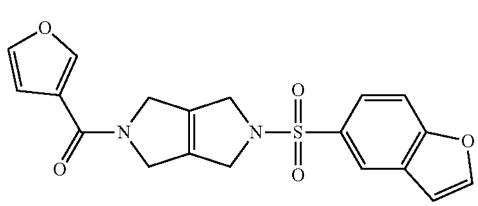 [SMILES: O=C(c1ccoc1)N1CC2=C(C1)CN(S(=O)(=O)c1ccc3occc3c1)C2] | 2-(1-Benzofuran-5-sulfonyl)-5-(furan-3-carbonyl)-1H,2H,3H,4H,5H,6H-pyrrolo[3,4-c]pyrrole |

TABLE 1-continued

| Example | Structure | Name |
|---|---|---|
| 18-81 | 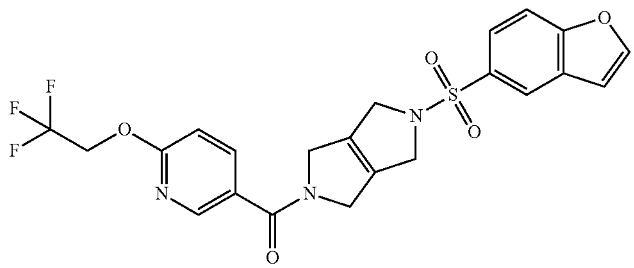 [SMILES: O=C(c1ccc(OCC(F)(F)F)nc1)N1CC2=C(C1)CN(S(=O)(=O)c1ccc3occc3c1)C2] | 5-[5-(1-Benzofuran-5-sulfonyl)-1H,2H,3H,4H,5H,6H-pyrrolo[3,4-c]pyrrole-2-carbonyl]-2-(2,2,2-trifluoroethoxy)pyridine |
| 18-82 | 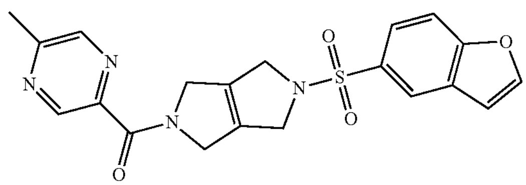 [SMILES: Cc1cnc(C(=O)N2CC3=C(C2)CN(S(=O)(=O)c2ccc4occc4c2)C3)cn1] | 2-[5-(1-Benzofuran-5-sulfonyl)-1H,2H,3H,4H,5H,6H-pyrrolo[3,4-c]pyrrole-2-carbonyl]-5-methylpyrazine |
| 18-83 | 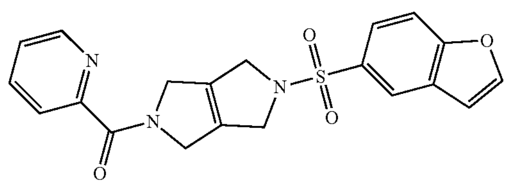 [SMILES: O=C(c1ccccn1)N1CC2=C(C1)CN(S(=O)(=O)c1ccc3occc3c1)C2] | 2-[5-(1-Benzofuran-5-sulfonyl)-1H,2H,3H,4H,5H,6H-pyrrolo[3,4-c]pyrrole-2-carbonyl]pyridine |
| 18-84 | 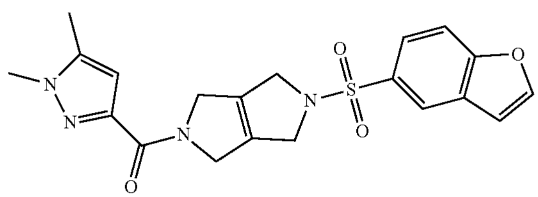 [SMILES: Cc1cc(C(=O)N2CC3=C(C2)CN(S(=O)(=O)c2ccc4occc4c2)C3)nn1C] | 3-[5-(1-Benzofuran-5-sulfonyl)-1H,2H,3H,4H,5H,6H-pyrrolo[3,4-c]pyrrole-2-carbonyl]-1,5-dimethyl-1H-pyrazole |
| 18-85 | 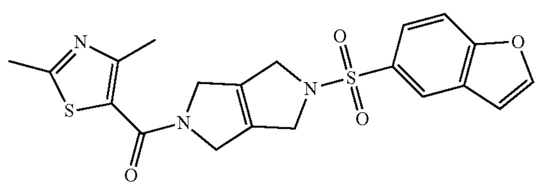 [SMILES: Cc1nc(C)c(C(=O)N2CC3=C(C2)CN(S(=O)(=O)c2ccc4occc4c2)C3)s1] | 5-[5-(1-Benzofuran-5-sulfonyl)-1H,2H,3H,4H,5H,6H-pyrrolo[3,4-c]pyrrole-2-carbonyl]-2,4-dimethyl-1,3-thiazole |
| 18-86 | 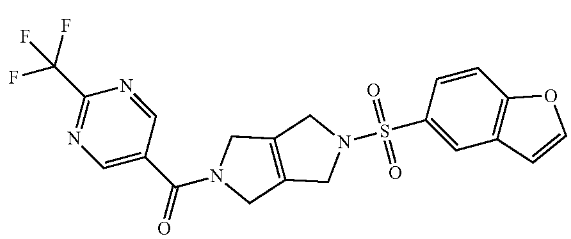 [SMILES: O=C(c1cnc(C(F)(F)F)nc1)N1CC2=C(C1)CN(S(=O)(=O)c1ccc3occc3c1)C2] | 5-[5-(1-Benzofuran-5-sulfonyl)-1H,2H,3H,4H,5H,6H-pyrrolo[3,4-c]pyrrole-2-carbonyl]-2-(trifluoromethyl)pyrimidine |
| 18-87 | 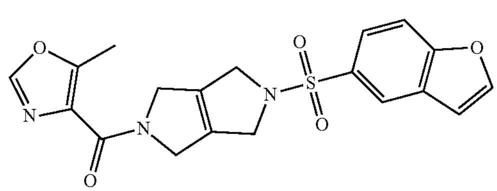 [SMILES: Cc1ocnc1C(=O)N1CC2=C(C1)CN(S(=O)(=O)c1ccc3occc3c1)C2] | 4-[5-(1-Benzofuran-5-sulfonyl)-1H,2H,3H,4H,5H,6H-pyrrolo[3,4-c]pyrrole-2-carbonyl]-5-methyl-1,3-oxazole |

TABLE 1-continued

| Example | Structure | Name |
|---|---|---|
| 18-88 | 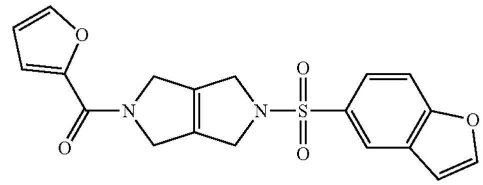 [SMILES: O=C(c1ccco1)N1CC2=C(C1)CN(S(=O)(=O)c1ccc3occc3c1)C2] | 2-(1-Benzofuran-5-sulfonyl)-5-(furan-2-carbonyl)-1H,2H,3H,4H,5H,6H-pyrrolo[3,4-c]pyrrole |
| 19-1 | 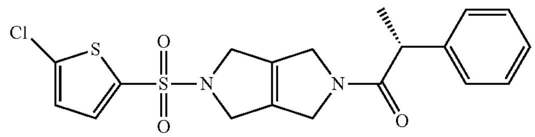 [SMILES: C[C@@H](C(=O)N1CC2=C(C1)CN(S(=O)(=O)c1ccc(Cl)s1)C2)c1ccccc1] | (2R)-1-{5-[(5-chlorothiophen-2-yl)sulfonyl]-1H,2H,3H,4H,5H,6H-pyrrolo[3,4-c]pyrrol-2-yl}-2-phenylpropan-1-one |
| 19-2 | 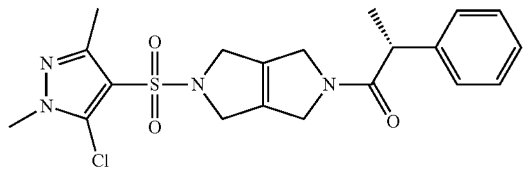 [SMILES: Cc1nn(C)c(Cl)c1S(=O)(=O)N1CC2=C(CN(C(=O)[C@H](C)c3ccccc3)C2)C1] | (2R)-1-{5-[(5-chloro-1,3-dimethyl-1H-pyrazol-4-yl)sulfonyl]-1H,2H,3H,4H,5H,6H-pyrrolo[3,4-c]pyrrol-2-yl}-2-phenylpropan-1-one |
| 19-3 | 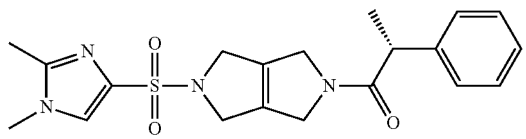 [SMILES: Cc1nc(S(=O)(=O)N2CC3=C(CN(C(=O)[C@H](C)c4ccccc4)C3)C2)cn1C] | (2R)-1-{5-[(1,2-dimethyl-1H-imidazol-4-yl)sulfonyl]-1H,2H,3H,4H,5H,6H-pyrrolo[3,4-c]pyrrol-2-yl}-2-phenylpropan-1-one |
| 19-4 | 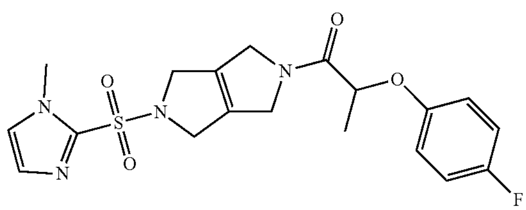 [SMILES: CC(Oc1ccc(F)cc1)C(=O)N1CC2=C(C1)CN(S(=O)(=O)c1nccn1C)C2] | 2-(4-Fluorophenoxy)-1-{5-[(1-methyl-1H-imidazol-2-yl)sulfonyl]-1H,2H,3H,4H,5H,6H-pyrrolo[3,4-c]pyrrol-2-yl}propan-1-one |
| 19-5 | 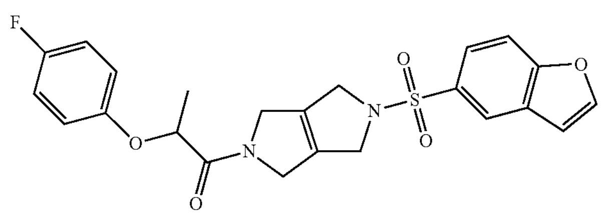 [SMILES: CC(Oc1ccc(F)cc1)C(=O)N1CC2=C(C1)CN(S(=O)(=O)c1ccc3occc3c1)C2] | 1-[5-(1-Benzofuran-5-sulfonyl)-1H,2H,3H,4H,5H,6H-pyrrolo[3,4-c]pyrrol-2-yl]-2-(4-fluorophenoxy)propan-1-one |
| 19-6 | 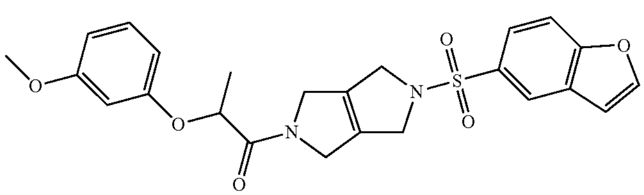 [SMILES: COc1cccc(OC(C)C(=O)N2CC3=C(C2)CN(S(=O)(=O)c2ccc4occc4c2)C3)c1] | 1-[5-(1-Benzofuran-5-sulfonyl)-1H,2H,3H,4H,5H,6H-pyrrolo[3,4-c]pyrrol-2-yl]-2-(3-methoxyphenoxy)propan-1-one |
| 19-7 | 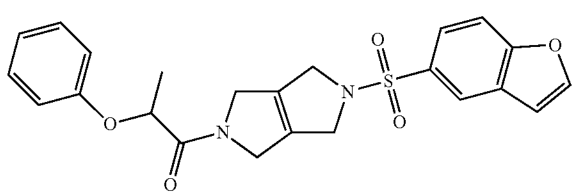 [SMILES: CC(Oc1ccccc1)C(=O)N1CC2=C(C1)CN(S(=O)(=O)c1ccc3occc3c1)C2] | 1-[5-(1-Benzofuran-5-sulfonyl)-1H,2H,3H,4H,5H,6H-pyrrolo[3,4-c]pyrrol-2-yl]-2-phenoxypropan-1-one |

TABLE 1-continued

| Example | Structure | Name |
|---|---|---|
| 19-8 | 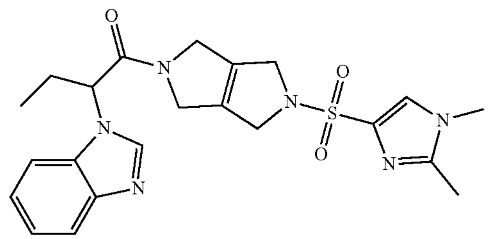 [SMILES: CCC(C(=O)N1CC2=C(C1)CN(S(=O)(=O)c1cn(C)c(C)n1)C2)n1cnc2ccccc21] | 2-(1H-1,3-benzodiazol-1-yl)-1-{5-[(1,2-dimethyl-1H-imidazol-4-yl)sulfonyl]-1H,2H,3H,4H,5H,6H-pyrrolo[3,4-c]pyrrol-2-yl}butan-1-one |
| 19-9 | 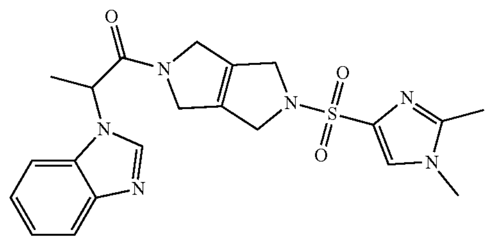 [SMILES: Cc1nc(S(=O)(=O)N2CC3=C(CN(C(=O)C(C)n4cnc5ccccc54)C3)C2)cn1C] | 2-(1H-1,3-benzodiazol-1-yl)-1-{5-[(1,2-dimethyl-1H-imidazol-4-yl)sulfonyl]-1H,2H,3H,4H,5H,6H-pyrrolo[3,4-c]pyrrol-2-yl}propan-1-one |
| 19-20 | (+/−) | (5-(Benzofuran-5-ylsulfonyl)-3,4,5,6-tetrahydropyrrolo[3,4-c]pyrrol-2(1H)-yl)((cis)-2-phenylcyclopropyl)methanone |
| 19-21 | 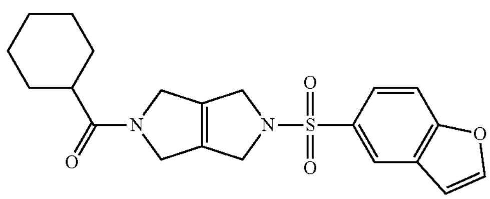 [SMILES: O=C(C1CCCCC1)N1CC2=C(C1)CN(S(=O)(=O)c1ccc3occc3c1)C2] | 2-(1-Benzofuran-5-sulfonyl)-5-cyclohexanecarbonyl-1H,2H,3H,4H,5H,6H-pyrrolo[3,4-c]pyrrole |
| 19-22 | 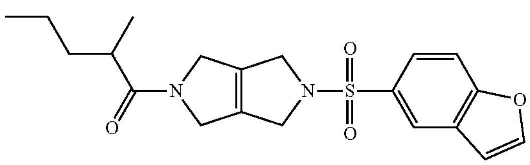 [SMILES: CCCC(C)C(=O)N1CC2=C(C1)CN(S(=O)(=O)c1ccc3occc3c1)C2] | 1-[5-(1-Benzofuran-5-sulfonyl)-1H,2H,3H,4H,5H,6H-pyrrolo[3,4-c]pyrrol-2-yl]-2-methylpentan-1-one |
| 19-23 | 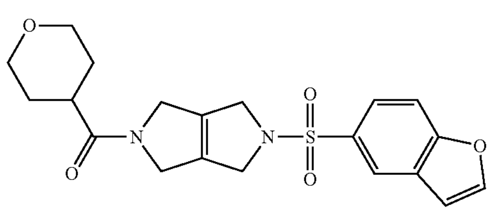 [SMILES: O=C(C1CCOCC1)N1CC2=C(C1)CN(S(=O)(=O)c1ccc3occc3c1)C2] | 2-(1-Benzofuran-5-sulfonyl)-5-(oxane-4-carbonyl)-1H,2H,3H,4H,5H,6H-pyrrolo[3,4-c]pyrrole |
| 19-24 | 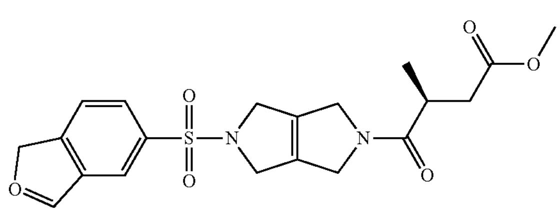 | Methyl (3S)-4-[5-(1-benzofuran-5-sulfonyl)-1H,2H,3H,4H,5H,6H-pyrrolo[3,4-c]pyrrol-2-yl]-3-methyl-4-oxobutanoate |

TABLE 1-continued

| Example | Structure | Name |
|---|---|---|
| 19-25 | 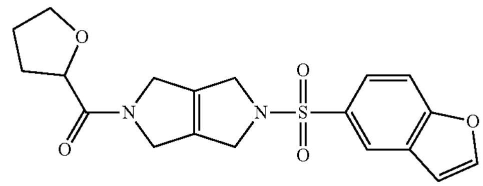 [SMILES: O=C(C1CCCO1)N1CC2=C(C1)CN(S(=O)(=O)c1ccc3occc3c1)C2] | 2-(1-Benzofuran-5-sulfonyl)-5-(oxolane-2-carbonyl)-1H,2H,3H,4H,5H,6H-pyrrolo[3,4-c]pyrrole |
| 19-26 | 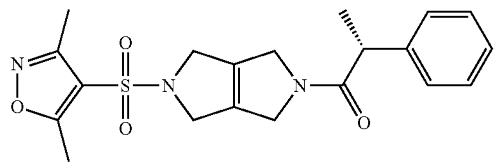 [SMILES: Cc1noc(C)c1S(=O)(=O)N1CC2=C(CN(C(=O)[C@H](C)c3ccccc3)C2)C1] | (2R)-1-{5-[(dimethyl-1,2-oxazol-4-yl)sulfonyl]-1H,2H,3H,4H,5H,6H-pyrrolo[3,4-c]pyrrol-2-yl}-2-phenylpropan-1-one |
| 19-27 | 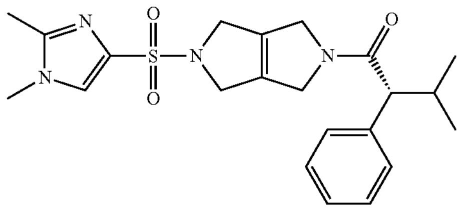 [SMILES: Cc1nc(S(=O)(=O)N2CC3=C(CN(C(=O)[C@@H](c4ccccc4)C(C)C)C3)C2)cn1C] | (2R)-1-{5-[(1,2-dimethyl-1H-imidazol-4-yl)sulfonyl]-1H,2H,3H,4H,5H,6H-pyrrolo[3,4-c]pyrrol-2-yl}-3-methyl-2-phenylbutan-1-one |
| 19-28 | 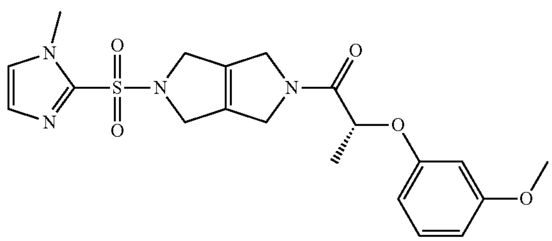 [SMILES: COc1cccc(O[C@H](C)C(=O)N2CC3=C(C2)CN(S(=O)(=O)c2nccn2C)C3)c1] | (2R)-2-(3-Methoxyphenoxy)-1-{5-[(1-methyl-1H-imidazol-2-yl)sulfonyl]-1H,2H,3H,4H,5H,6H-pyrrolo[3,4-c]pyrrol-2-yl}propan-1-one |
| 19-29 | 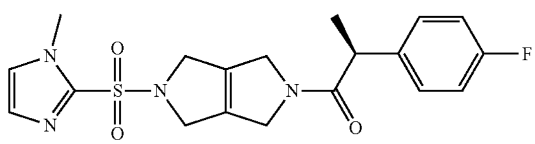 [SMILES: C[C@H](C(=O)N1CC2=C(C1)CN(S(=O)(=O)c1nccn1C)C2)c1ccc(F)cc1] | (2I)-2-(4-fluorophenyl)-1-{5-[(1-methyl-1H-imidazol-2-yl)sulfonyl]-1H,2H,3H,4H,5H,6H-pyrrolo[3,4-c]pyrrol-2-yl}propan-1-one |
| 19-30 | 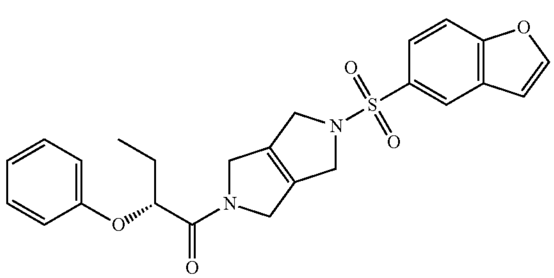 [SMILES: CC[C@@H](Oc1ccccc1)C(=O)N1CC2=C(C1)CN(S(=O)(=O)c1ccc3occc3c1)C2] | (2R)-1-[5-(1-benzofuran-5-sulfonyl)-1H,2H,3H,4H,5H,6H-pyrrolo[3,4-c]pyrrol-2-yl]-2-phenoxybutan-1-one |
| 19-31 | 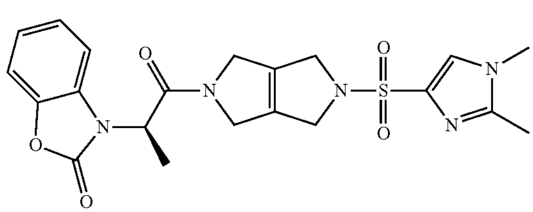 [SMILES: Cc1nc(S(=O)(=O)N2CC3=C(CN(C(=O)[C@@H](C)n4c(=O)oc5ccccc54)C3)C2)cn1C] | 3-[(2R)-1-{5-[(1,2-dimethyl-1H-imidazol-4-yl)sulfonyl]-1H,2H,3H,4H,5H,6H-pyrrolo[3,4-c]pyrrol-2-yl}-1-oxopropan-2-yl]-2,3-dihydro-1,3-benzoxazol-2-one |

TABLE 1-continued

| Example | Structure | Name |
|---|---|---|
| 19-32 | 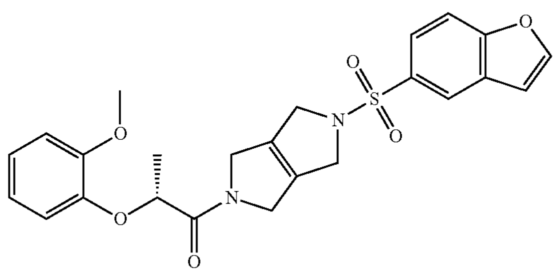 [SMILES: COc1ccccc1O[C@H](C)C(=O)N1CC2=C(C1)CN(S(=O)(=O)c1ccc3occc3c1)C2] | (2R)-1-[5-(1-benzofuran-5-sulfonyl)-1H,2H,3H,4H,5H,6H-pyrrolo[3,4-c]pyrrol-2-yl]-2-(2-methoxyphenoxy)propan-1-one |
| 19-33 | 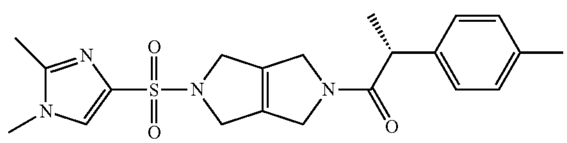 | (2R)-1-{5-[(1,2-dimethyl-1H-imidazol-4-yl)sulfonyl]-1H,2H,3H,4H,5H,6H-pyrrolo[3,4-c]pyrrol-2-yl}-2-(4-methylphenyl)propan-1-one |
| 20-1 | 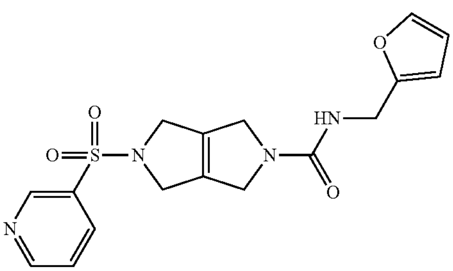 [SMILES: O=C(NCc1ccco1)N1CC2=C(C1)CN(S(=O)(=O)c1cccnc1)C2] | N-(furan-2-ylmethyl)-5-(pyridin-3-ylsulfonyl)-3,4,5,6-tetrahydropyrrolo[3,4-c]pyrrole-2(1H)-carboxamide |
| 20-2 | 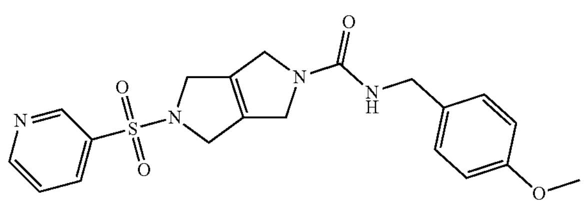 [SMILES: COc1ccc(CNC(=O)N2CC3=C(C2)CN(S(=O)(=O)c2cccnc2)C3)cc1] | N-[(4-methoxyphenyl)methyl]-5-(pyridine-3-sulfonyl)-1H,2H,3H,4H,5H,6H-pyrrolo[3,4-c]pyrrole-2-carboxamide |
| 20-3 | 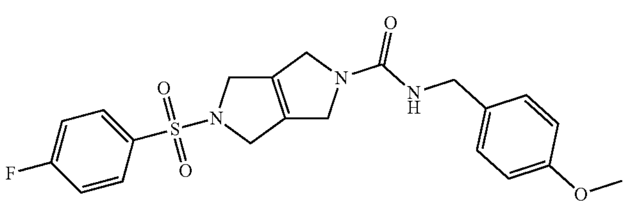 [SMILES: COc1ccc(CNC(=O)N2CC3=C(C2)CN(S(=O)(=O)c2ccc(F)cc2)C3)cc1] | 5-(4-Fluorobenzenesulfonyl)-N-[(4-methoxyphenyl)methyl]-1H,2H,3H,4H,5H,6H-pyrrolo[3,4-c]pyrrole-3-carboxamide |
| 20-4 | 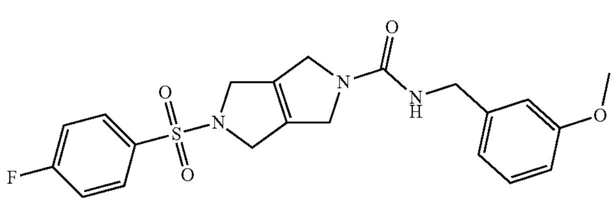 [SMILES: COc1cccc(CNC(=O)N2CC3=C(C2)CN(S(=O)(=O)c2ccc(F)cc2)C3)c1] | 5-(4-Fluorobenzenesulfonyl)-N-[(3-methoxyphenyl)methyl]-1H,2H,3H,4H,5H,6H-pyrrolo[3,4-c]pyrrole-2-carboxamide |
| 20-5 | 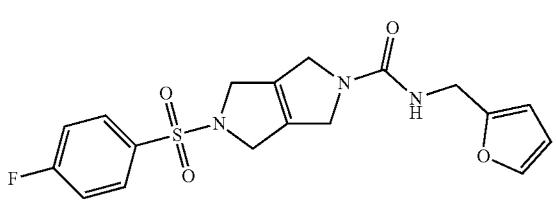 [SMILES: O=C(NCc1ccco1)N1CC2=C(C1)CN(S(=O)(=O)c1ccc(F)cc1)C2] | 5-(4-Fluorobenzenesulfonyl)-N-(furan-2-ylmethyl)-1H,2H,3H,4H,5H,6H-pyrrolo[3,4-c]pyrrole-2-carboxamide |

TABLE 1-continued

| Example | Structure | Name |
|---|---|---|
| 20-6 | 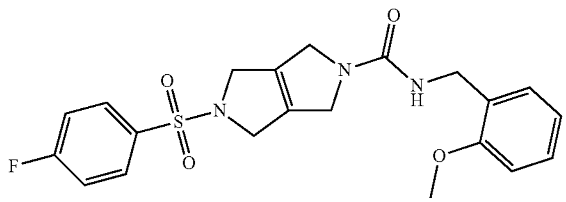 [SMILES: COc1ccccc1CNC(=O)N1CC2=C(C1)CN(S(=O)(=O)c1ccc(F)cc1)C2] | 5-(4-Fluorobenzenesulfonyl)-N-[(2-methoxyphenyl)methyl]-1H,2H,3H,4H,5H,6H-pyrrolo[3,4-c]pyrrole-2-carboxamide |
| 20-7 | 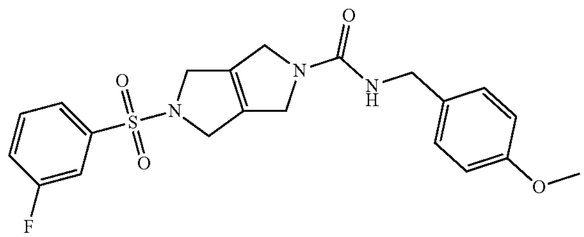 [SMILES: COc1ccc(CNC(=O)N2CC3=C(C2)CN(S(=O)(=O)c2cccc(F)c2)C3)cc1] | 5-(3-Fluorobenzenesulfonyl)-N-[(4-methoxyphenyl)methyl]-1H,2H,3H,4H,5H,6H-pyrrolo[3,4-c]pyrrole-2-carboxamide |
| 20-8 | 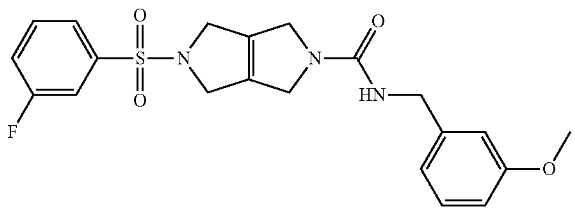 [SMILES: COc1cccc(CNC(=O)N2CC3=C(C2)CN(S(=O)(=O)c2cccc(F)c2)C3)c1] | 5-(3-Fluorobenzenesulfonyl)-N-[(3-methoxyphenyl)methyl]-1H,2H,3H,4H,5H,6H-pyrrolo[3,4-c]pyrrole-2-carboxamide |
| 20-9 | 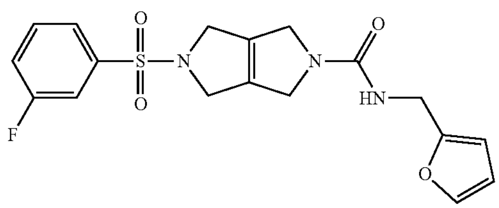 [SMILES: O=C(NCc1ccco1)N1CC2=C(C1)CN(S(=O)(=O)c1cccc(F)c1)C2] | 5-(3-Fluorobenzenesulfonyl)-N-(furan-2-ylmethyl)-1H,2H,3H,4H,5H,6H-pyrrolo[3,4-c]pyrrole-2-carboxamide |
| 20-10 | 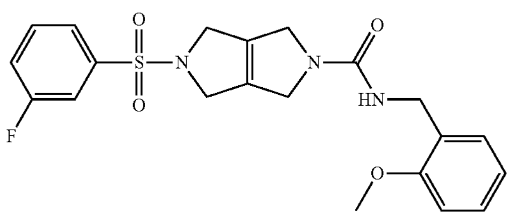 | 5-(3-Fluorobenzenesulfonyl)-N-[(2-methoxyphenyl)methyl]-1H,2H,3H,4H,5H,6H-pyrrolo[3,4-c]pyrrole-2-carboxamide |
| 20-11 | 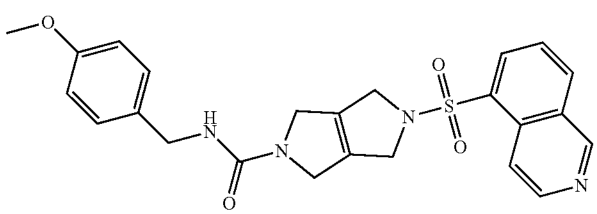 [SMILES: COc1ccc(CNC(=O)N2CC3=C(C2)CN(S(=O)(=O)c2cccc4cnccc24)C3)cc1] | 5-(Isoquinoline-5-sulfonyl)-N-[(4-methoxyphenyl)methyl]-1H,2H,3H,4H,5H,6H-pyrrolo[3,4-c]pyrrole-2-carboxamide |
| 20-12 | 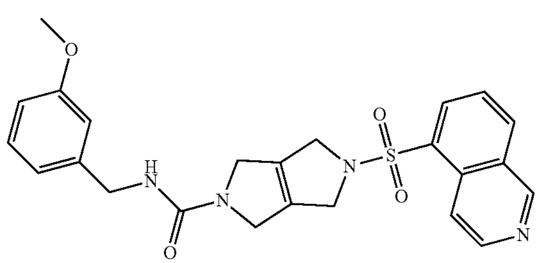 [SMILES: COc1cccc(CNC(=O)N2CC3=C(C2)CN(S(=O)(=O)c2cccc4cnccc24)C3)c1] | 5-(Isoquinoline-5-sulfonyl)-N-[(3-methoxyphenyl)methyl]-1H,2H,3H,4H,5H,6H-pyrrolo[3,4-c]pyrrole-2-carboxamide |

TABLE 1-continued

| Example | Structure | Name |
|---|---|---|
| 20-13 | 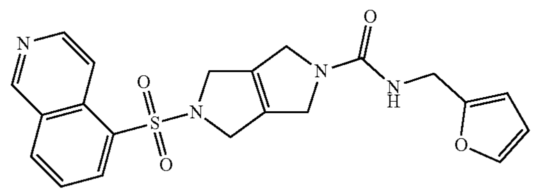 [SMILES: O=C(NCc1ccco1)N1CC2=C(C1)CN(S(=O)(=O)c1cccc3cnccc13)C2] | N-(furan-2-ylmethyl)-5-(isoquinoline-5-sulfonyl)-1H,2H,3H,4H,5H,6H-pyrrolo[3,4-c]pyrrole-2-carboxamide |
| 20-14 | 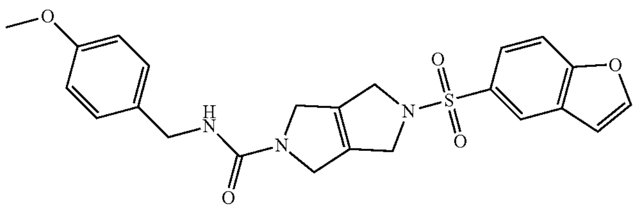 [SMILES: COc1ccc(CNC(=O)N2CC3=C(C2)CN(S(=O)(=O)c2ccc4occc4c2)C3)cc1] | 5-(1-Benzofuran-5-sulfonyl)-N-[(4-methoxyphenyl)methyl]-1H,2H,3H,4H,5H,6H-pyrrolo[3,4-c]pyrrole-2-carboxamide |
| 20-15 | 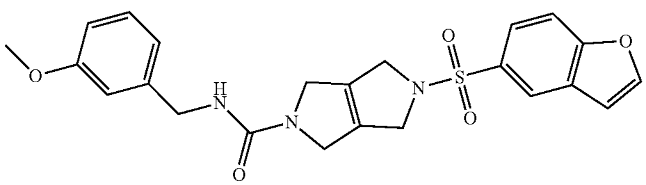 [SMILES: COc1cccc(CNC(=O)N2CC3=C(C2)CN(S(=O)(=O)c2ccc4occc4c2)C3)c1] | 5-(1-Benzofuran-5-sulfonyl)-N-[(3-methoxyphenyl)methyl]-1H,2H,3H,4H,5H,6H-pyrrolo[3,4-c]pyrrole-2-carboxamide |
| 20-16 | 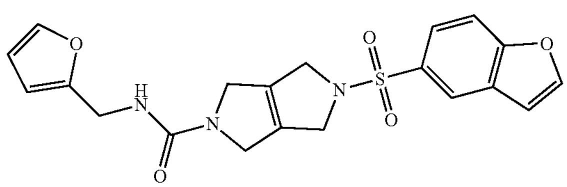 [SMILES: O=C(NCc1ccco1)N1CC2=C(C1)CN(S(=O)(=O)c1ccc3occc3c1)C2] | 5-(1-Benzofuran-5-sulfonyl)-N-(furan-2-ylmethyl)-1H,2H,3H,4H,5H,6H-pyrrolo[3,4-c]pyrrole-2-carboxamide |
| 20-17 | 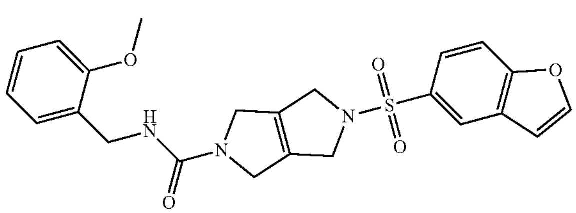 [SMILES: COc1ccccc1CNC(=O)N1CC2=C(C1)CN(S(=O)(=O)c1ccc3occc3c1)C2] | 5-(1-Benzofuran-5-sulfonyl)-N-[(2-methoxyphenyl)methyl]-1H,2H,3H,4H,5H,6H-pyrrolo[3,4-c]pyrrole-2-carboxamide |
| 20-18 | 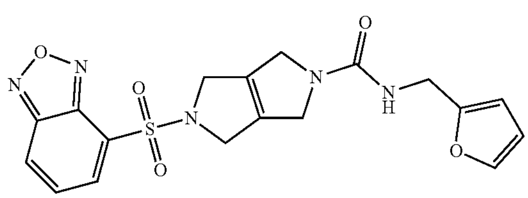 [SMILES: O=C(NCc1ccco1)N1CC2=C(C1)CN(S(=O)(=O)c1cccc3nonc13)C2] | 5-(2,1,3-Benzoxadiazole-4-sulfonyl)-N-(furan-2-ylmethyl)-1H,2H,3H,4H,5H,6H-pyrrolo[3,4-c]pyrrole-2-carboxamide |
| 20-19 | 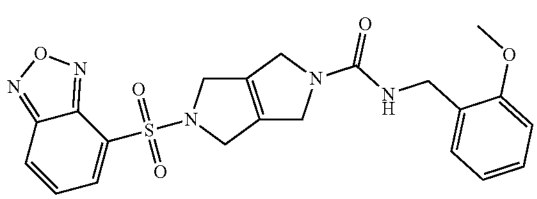 [SMILES: COc1ccccc1CNC(=O)N1CC2=C(C1)CN(S(=O)(=O)c1cccc3nonc13)C2] | 5-(2,1,3-Benzoxadiazole-4-sulfonyl)-N-[(2-methoxyphenyl)methyl]-1H,2H,3H,4H,5H,6H-pyrrolo[3,4-c]pyrrole-2-carboxamide |

TABLE 1-continued

| Example | Structure | Name |
|---|---|---|
| 20-20 | 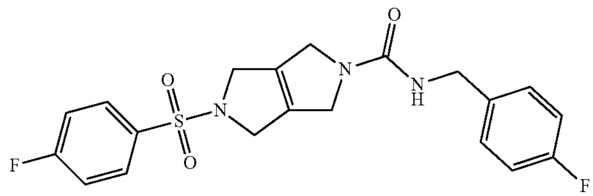 [SMILES: O=C(NCc1ccc(F)cc1)N1CC2=C(C1)CN(S(=O)(=O)c1ccc(F)cc1)C2] | 5-(4-Fluorobenzenesulfonyl)-N-[(4-fluorophenyl)methyl]-1H,2H,3H,4H,5H,6H-pyrrolo[3,4-c]pyrrole-2-carboxamide |
| 20-21 | 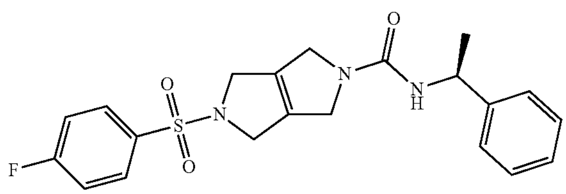 [SMILES: C[C@H](NC(=O)N1CC2=C(C1)CN(S(=O)(=O)c1ccc(F)cc1)C2)c1ccccc1] | 5-(4-Fluorobenzenesulfonyl)-N-[(1S)-1-phenylethyl]-1H,2H,3H,4H,5H,6H-pyrrolo[3,4-c]pyrrole-2-carboxamide |
| 20-22 | 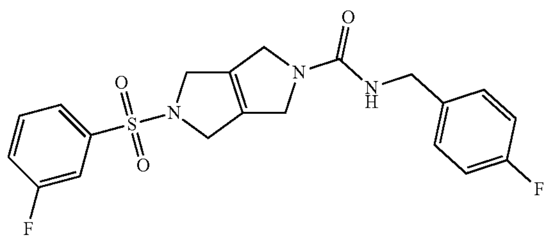 [SMILES: O=C(NCc1ccc(F)cc1)N1CC2=C(C1)CN(S(=O)(=O)c1cccc(F)c1)C2] | 5-(3-Fluorobenzenesulfonyl)-N-[(4-fluorophenyl)methyl]-1H,2H,3H,4H,5H,6H-pyrrolo[3,4-c]pyrrole-2-carboxamide |
| 20-23 | 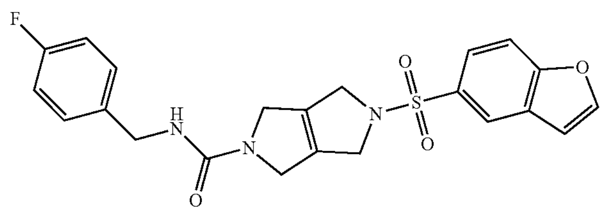 [SMILES: O=C(NCc1ccc(F)cc1)N1CC2=C(C1)CN(S(=O)(=O)c1ccc3occc3c1)C2] | 5-(1-Benzofuran-5-sulfonyl)-N-[(4-fluorophenyl)methyl]-1H,2H,3H,4H,5H,6H-pyrrolo[3,4-c]pyrrole-2-carboxamide |
| 20-24 | 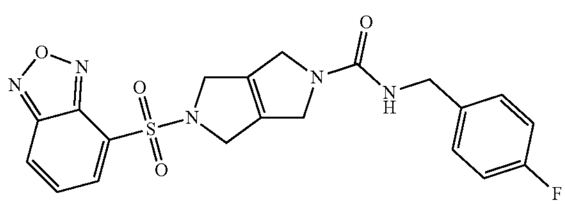 [SMILES: O=C(NCc1ccc(F)cc1)N1CC2=C(C1)CN(S(=O)(=O)c1cccc3nonc13)C2] | 5-(2,1,3-Benzoxadiazole-4-sulfonyl)-N-[(4-fluorophenyl)methyl]-1H,2H,3H,4H,5H,6H-pyrrolo[3,4-c]pyrrole-2-carboxamide |
| 20-25 | 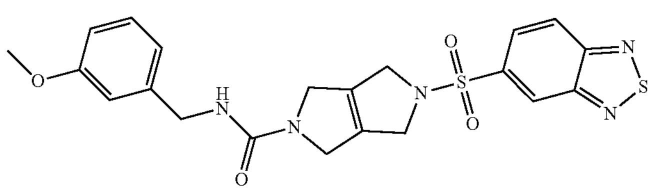 [SMILES: COc1cccc(CNC(=O)N2CC3=C(C2)CN(S(=O)(=O)c2ccc4nsnc4c2)C3)c1] | 5-(2,1,3-Benzothiadiazole-5-sulfonyl)-N-[(3-methoxyphenyl)methyl]-1H,2H,3H,4H,5H,6H-pyrrolo[3,4-c]pyrrole-2-carboxamide |
| 20-26 | 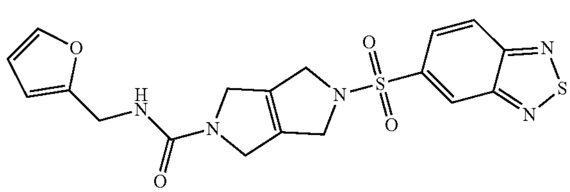 [SMILES: O=C(NCc1ccco1)N1CC2=C(C1)CN(S(=O)(=O)c1ccc3nsnc3c1)C2] | 5-(2,1,3-Benzothiadiazole-5-sulfonyl)-N-(furan-2-ylmethyl)-1H,2H,3H,4H,5H,6H-pyrrolo[3,4-c]pyrrole-2-carboxamide |

TABLE 1-continued

| Example | Structure | Name |
|---|---|---|
| 20-27 | 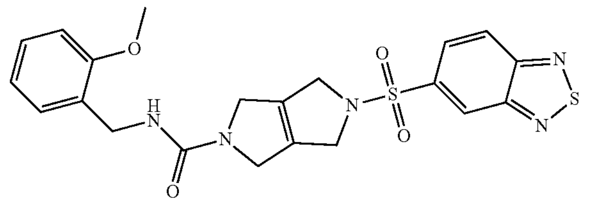 [SMILES: COc1ccccc1CNC(=O)N1CC2=C(C1)CN(S(=O)(=O)c1ccc3nsnc3c1)C2] | 5-(2,1,3-Benzothiadiazole-5-sulfonyl)-N-[(2-methoxyphenyl)methyl]-1H,2H,3H,4H,5H,6H-pyrrolo[3,4-c]pyrrole-2-carboxamide |
| 20-28 | 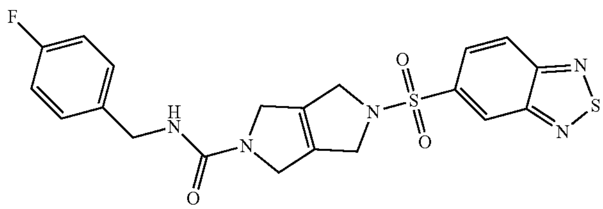 [SMILES: O=C(NCc1ccc(F)cc1)N1CC2=C(C1)CN(S(=O)(=O)c1ccc3nsnc3c1)C2] | 5-(2,1,3-Benzothiadiazole-5-sulfonyl)-N-[(4-fluorophenyl)methyl]-1H,2H,3H,4H,5H,6H-pyrrolo[3,4-c]pyrrole-2-carboxamide |
| 20-29 | 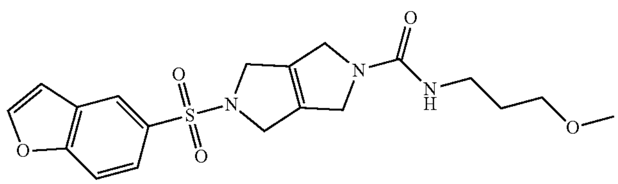 [SMILES: COCCCNC(=O)N1CC2=C(C1)CN(S(=O)(=O)c1ccc3occc3c1)C2] | 5-(1-Benzofuran-5-sulfonyl)-N-(3-methoxypropyl)-1H,2H,3H,4H,5H,6H-pyrrolo[3,4-c]pyrrole-2-carboxamide |
| 20-30 | 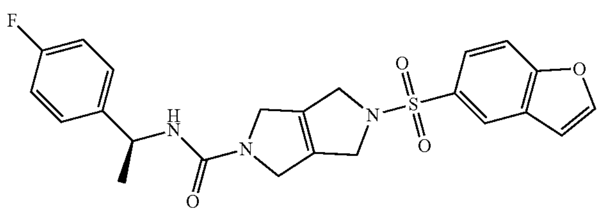 [SMILES: C[C@H](NC(=O)N1CC2=C(C1)CN(S(=O)(=O)c1ccc3occc3c1)C2)c1ccc(F)cc1] | 5-(1-Benzofuran-5-sulfonyl)-N-[(1S)-1-(4-fluorophenyl)ethyl]-1H,2H,3H,4H,5H,6H-pyrrolo[3,4-c]pyrrole-2-carboxamide |
| 20-31 | 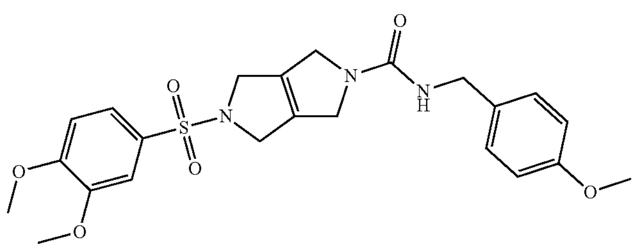 | 5-(3,4-Dimethoxybenzenesulfonyl)-N-[(4-methoxyphenyl)methyl]-1H,2H,3H,4H,5H,6H-pyrrolo[3,4-c]pyrrole-2-carboxamide |
| 20-32 | 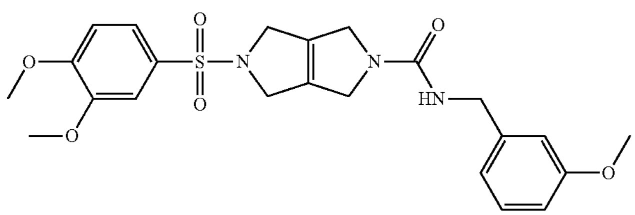 | 5-(3,4-Dimethoxybenzenesulfonyl)-N-[(3-methoxyphenyl)methyl]-1H,2H,3H,4H,5H,6H-pyrrolo[3,4-c]pyrrole-2-carboxamide |
| 20-33 | 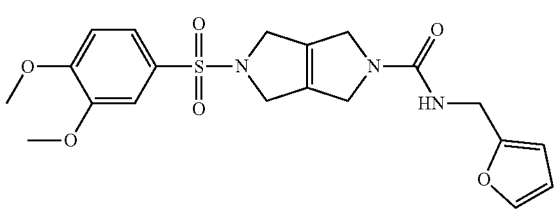 [SMILES: COc1ccc(S(=O)(=O)N2CC3=C(CN(C(=O)NCc4ccco4)C3)C2)cc1OC] | 5-(3,4-Dimethoxybenzenesulfonyl)-N-(furan-2-ylmethyl)-1H,2H,3H,4H,5H,6H-pyrrolo[3,4-c]pyrrole-2-carboxamide |

TABLE 1-continued

| Example | Structure | Name |
|---|---|---|
| 20-34 | 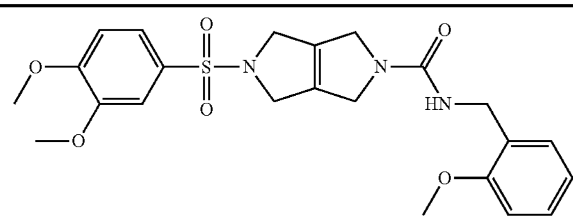 | 5-(3,4-Dimethoxybenzenesulfonyl)-N-[(2-methoxyphenyl)methyl]-1H,2H,3H,4H,5H,6H-pyrrolo[3,4-c]pyrrole-2-carboxamide |
| 20-35 | 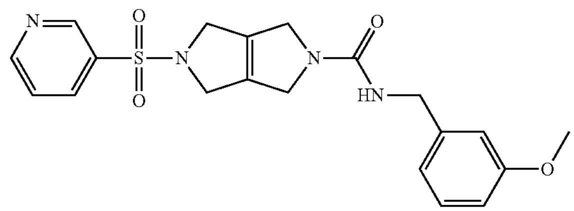 [SMILES: COc1cccc(CNC(=O)N2CC3=C(C2)CN(S(=O)(=O)c2cccnc2)C3)c1] | N-[(3-methoxyphenyl)methyl]-5-(pyridine-3-sulfonyl)-1H,2H,3H,4H,5H,6H-pyrrolo[3,4-c]pyrrole-2-carboxamide |
| 20-36 | 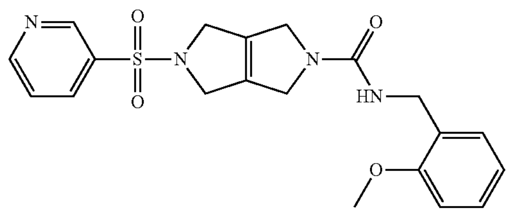 [SMILES: COc1ccccc1CNC(=O)N1CC2=C(C1)CN(S(=O)(=O)c1cccnc1)C2] | N-[(2-methoxyphenyl)methyl]-5-(pyridine-3-sulfonyl)-1H,2H,3H,4H,5H,6H-pyrrolo[3,4-c]pyrrole-2-carboxamide |
| 20-37 | 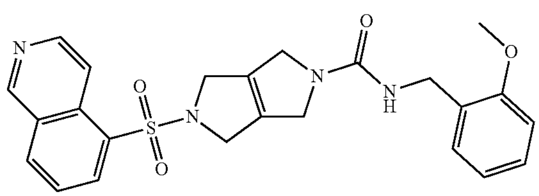 [SMILES: COc1ccccc1CNC(=O)N1CC2=C(C1)CN(S(=O)(=O)c1cccc3cnccc13)C2] | 5-(Isoquinoline-5-sulfonyl)-N-[(2-methoxyphenyl)methyl]-1H,2H,3H,4H,5H,6H-pyrrolo[3,4-c]pyrrole-2-carboxamide |
| 20-38 | 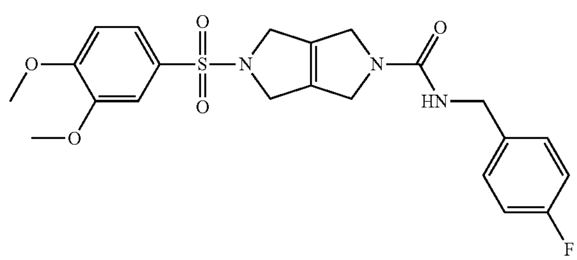 [SMILES: COc1ccc(S(=O)(=O)N2CC3=C(CN(C(=O)NCc4ccc(F)cc4)C3)C2)cc1OC] | 5-(3,4-Dimethoxybenzenesulfonyl)-N-[(4-fluorophenyl)methyl]-1H,2H,3H,4H,5H,6H-pyrrolo[3,4-c]pyrrole-2-carboxamide |
| 20-39 | 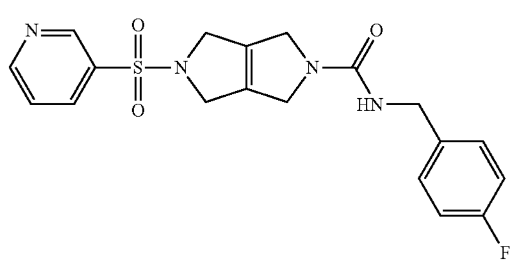 [SMILES: O=C(NCc1ccc(F)cc1)N1CC2=C(C1)CN(S(=O)(=O)c1cccnc1)C2] | N-[(4-fluorophenyl)methyl]-5-(pyridine-3-sulfonyl)-1H,2H,3H,4H,5H,6H-pyrrolo[3,4-c]pyrrole-2-carboxamide |
| 20-40 | 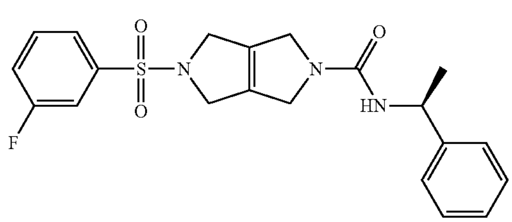 [SMILES: C[C@H](NC(=O)N1CC2=C(C1)CN(S(=O)(=O)c1cccc(F)c1)C2)c1ccccc1] | 5-(3-Fluorobenzenesulfonyl)-N-[(1S)-1-phenylethyl]-1H,2H,3H,4H,5H,6H-pyrrolo[3,4-c]pyrrole-2-carboxamide |

TABLE 1-continued

| Example | Structure | Name |
|---|---|---|
| 20-41 | 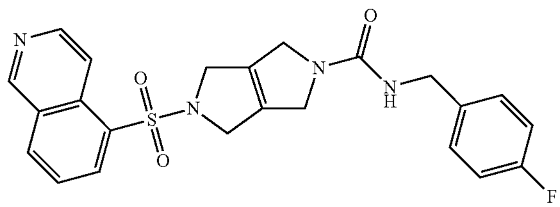 [SMILES: O=C(NCc1ccc(F)cc1)N1CC2=C(C1)CN(S(=O)(=O)c1cccc3cnccc13)C2] | N-[(4-fluorophenyl)methyl]-5-(isoquinoline-5-sulfonyl)-1H,2H,3H,4H,5H,6H-pyrrolo[3,4-c]pyrrole-2-carboxamide |
| 20-42 | 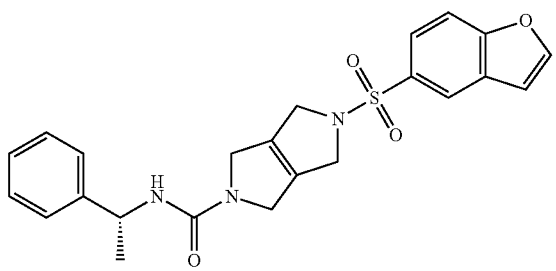 [SMILES: C[C@@H](NC(=O)N1CC2=C(C1)CN(S(=O)(=O)c1ccc3occc3c1)C2)c1ccccc1] | 5-(1-Benzofuran-5-sulfonyl)-N-[(1R)-1-phenylethyl]-1H,2H,3H,4H,5H,6H-pyrrolo[3,4-c]pyrrole-2-carboxamide |
| 20-43 | 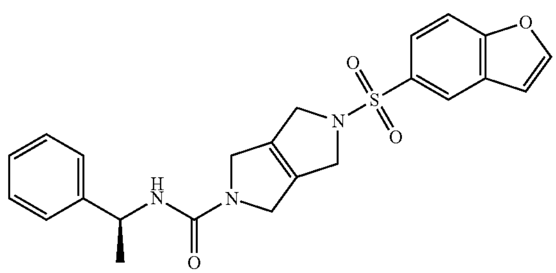 [SMILES: C[C@H](NC(=O)N1CC2=C(C1)CN(S(=O)(=O)c1ccc3occc3c1)C2)c1ccccc1] | 5-(1-Benzofuran-5-sulfonyl)-N-[(1S)-phenylethyl]-1H,2H,3H,4H,5H,6H-pyrrolo[3,4-c]pyrrole-2-carboxamide |
| 20-44 | 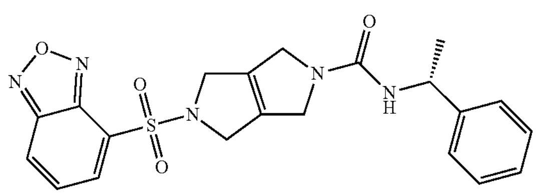 [SMILES: C[C@@H](NC(=O)N1CC2=C(C1)CN(S(=O)(=O)c1cccc3nonc13)C2)c1ccccc1] | 5-(2,1,3-Benzoxadiazole-4-sulfonyl)-N-[(1R)-1-phenylethyl]-1H,2H,3H,4H,5H,6H-pyrrolo[3,4-c]pyrrole-2-carboxamide |
| 20-45 | 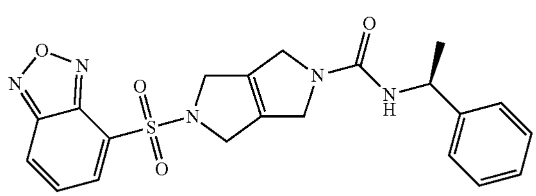 [SMILES: C[C@H](NC(=O)N1CC2=C(C1)CN(S(=O)(=O)c1cccc3nonc13)C2)c1ccccc1] | 5-(2,1,3-Benzoxadiazole-4-sulfonyl)-N-[(1S)-1-phenylethyl]-1H,2H,3H,4H,5H,6H-pyrrolo[3,4-c]pyrrole-2-carboxamide |
| 20-46 | 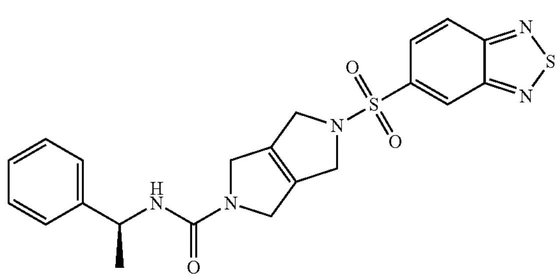 [SMILES: C[C@H](NC(=O)N1CC2=C(C1)CN(S(=O)(=O)c1ccc3nsnc3c1)C2)c1ccccc1] | 5-(2,1,3-Benzothiadiazole-5-sulfonyl)-N-[(1S)-1-phenylethyl]-1H,2H,3H,4H,5H,6H-pyrrolo[3,4-c]pyrrole-2-carboxamide |

TABLE 1-continued

| Example | Structure | Name |
|---|---|---|
| 20-47 | 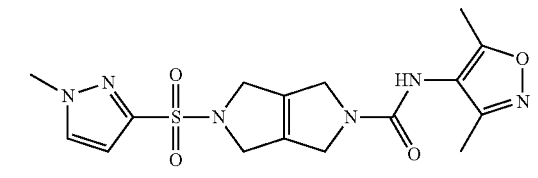 [SMILES: Cc1noc(C)c1NC(=O)N1CC2=C(C1)CN(S(=O)(=O)c1ccn(C)n1)C2] | N-(dimethyl-1,2-oxazol-4-yl)-5-[(1-methyl-1H-pyrazol-3-yl)sulfonyl]-1H,2H,3H,4H,5H,6H-pyrrolo[3,4-c]pyrrole-2-carboxamide |
| 20-48 | 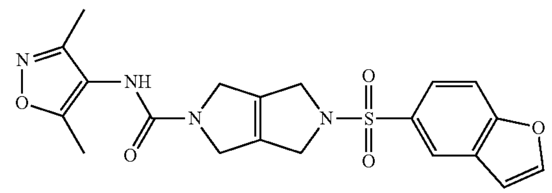 [SMILES: Cc1noc(C)c1NC(=O)N1CC2=C(C1)CN(S(=O)(=O)c1ccc3occc3c1)C2] | 5-(1-Benzofuran-5-sulfonyl)-N-(dimethyl-1,2-oxazol-4-yl)-1H,2H,3H,4H,5H,6H-pyrrolo[3,4-c]pyrrole-2-carboxamide |
| 20-49 | 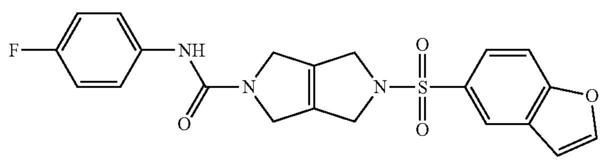 [SMILES: O=C(Nc1ccc(F)cc1)N1CC2=C(C1)CN(S(=O)(=O)c1ccc3occc3c1)C2] | 5-(1-Benzofuran-5-sulfonyl)-N-(4-fluorophenyl)-1H,2H,3H,4H,5H,6H-pyrrolo[3,4-c]pyrrole-2-carboxamide |
| 20-50 | 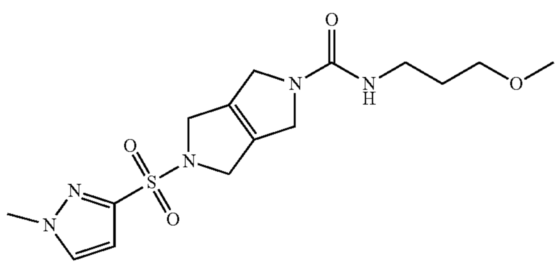 | N-(3-methoxypropyl)-5-[(1-methyl-1H-pyrazol-3-yl)sulfonyl]-1H,2H,3H,4H,5H,6H-pyrrolo[3,4-c]pyrrole-2-carboxamide |
| 20-51 | 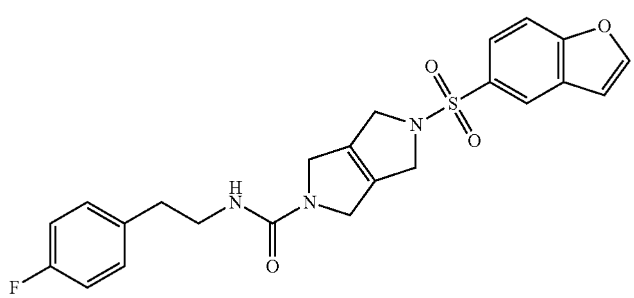 [SMILES: O=C(NCCc1ccc(F)cc1)N1CC2=C(C1)CN(S(=O)(=O)c1ccc3occc3c1)C2] | 5-(1-benzofuran-5-sulfonyl)-N-[2-(4-fluorophenyl)ethyl]-1H,2H,3H,4H,5H,6H-pyrrolo[3,4-c]pyrrole-2-carboxamide |
| 20-52 | 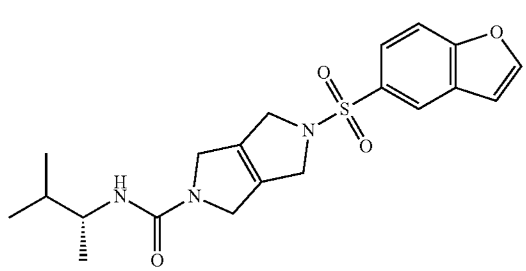 [SMILES: CC(C)[C@@H](C)NC(=O)N1CC2=C(C1)CN(S(=O)(=O)c1ccc3occc3c1)C2] | 5-(1-Benzofuran-5-sulfonyl)-N-[(2R)-3-methylbutan-2-yl]-1H,2H,3H,4H,5H,6H-pyrrolo[3,4-c]pyrrole-2-carboxamide |

TABLE 1-continued

| Example | Structure | Name |
|---|---|---|
| 20-53 | 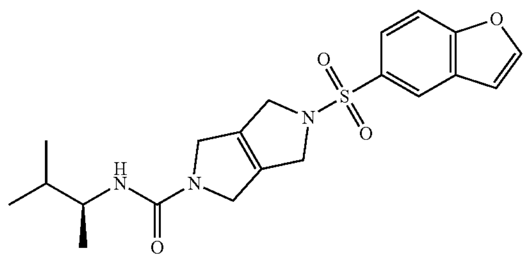 [SMILES: CC(C)[C@H](C)NC(=O)N1CC2=C(C1)CN(S(=O)(=O)c1ccc3occc3c1)C2] | 5-(1-Benzofuran-5-sulfonyl)-N-[(2S)-3-methylbutan-2-yl]-1H,2H,3H,4H,5H,6H-pyrrolo[3,4-c]pyrrole-2-carboxamide |
| 20-54 | 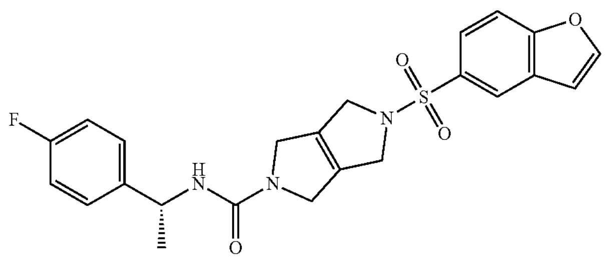 [SMILES: C[C@@H](NC(=O)N1CC2=C(C1)CN(S(=O)(=O)c1ccc3occc3c1)C2)c1ccc(F)cc1] | 5-(1-Benzofuran-5-sulfonyl)-N-[(1R)-1-(4-fluorophenyl)ethyl]-1H,2H,3H,4H,5H,6H-pyrrolo[3,4-c]pyrrole-2-carboxamide |
| 20-55 | 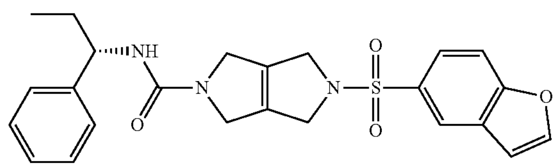 [SMILES: CC[C@H](NC(=O)N1CC2=C(C1)CN(S(=O)(=O)c1ccc3occc3c1)C2)c1ccccc1] | 5-(1-Benzofuran-5-sulfonyl)-N-[(1S)-1-phenylpropyl]-1H,2H,3H,4H,5H,6H-pyrrolo[3,4-c]pyrrole-2-carboxamide |
| 20-56 | 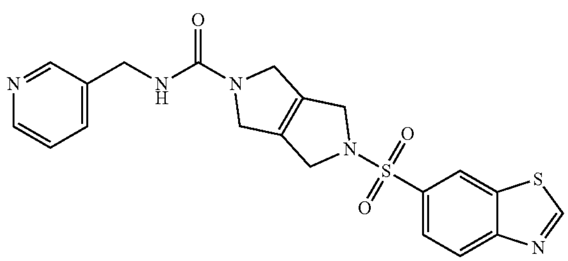 [SMILES: O=C(NCc1cccnc1)N1CC2=C(C1)CN(S(=O)(=O)c1ccc3ncsc3c1)C2] | 5-(1,3-Benzothiazole-6-sulfonyl)-N-(pyridin-3-ylmethyl)-1H,2H,3H,4H,5H,6H-pyrrolo[3,4-c]pyrrole-2-carboxamide |
| 21-1 | 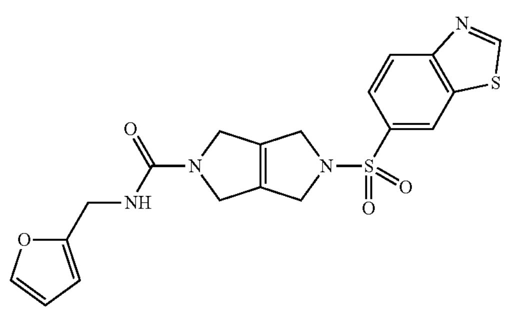 [SMILES: O=C(NCc1ccco1)N1CC2=C(C1)CN(S(=O)(=O)c1ccc3ncsc3c1)C2] | 5-(Benzo[d]thiazol-6-ylsulfonyl)-N-(furan-2-ylmethyl)-3,4,5,6-tetrahydropyrrolo[3,4-c]pyrrole-2(1H)-carboxamide |
| 21-2 | 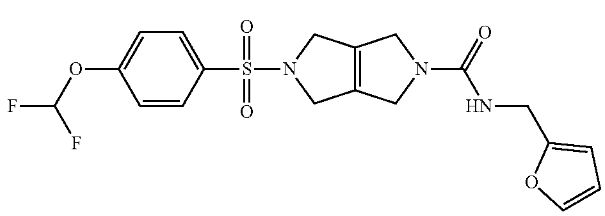 [SMILES: O=C(NCc1ccco1)N1CC2=C(C1)CN(S(=O)(=O)c1ccc(OC(F)F)cc1)C2] | 5-[4-(Difluoromethoxy)benzenesulfonyl]-N-(furan-2-ylmethyl)-1H,2H,3H,4H,5H,6H-pyrrolo[3,4-c]pyrrole-2-carboxamide |

TABLE 1-continued

| Example | Structure | Name |
|---|---|---|
| 21-3 | 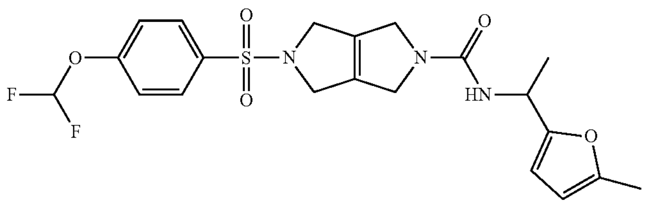 | 5-[4-(Difluoromethoxy)benzenesulfonyl]-N-[1-(5-methylfuran-2-yl)ethyl]-1H,2H,3H,4H,5H,6H-pyrrolo[3,4-c]pyrrole-2-carboxamide |
| 21-4 | 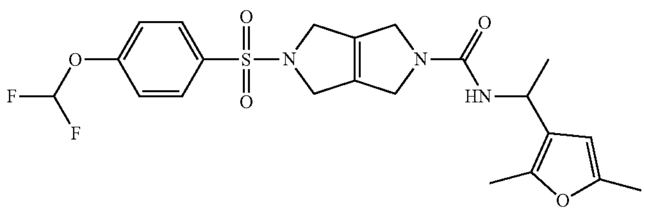 [SMILES: Cc1cc(C(C)NC(=O)N2CC3=C(C2)CN(S(=O)(=O)c2ccc(OC(F)F)cc2)C3)c(C)o1] | 5-[4-(Difluoromethoxy)benzenesulfonyl]-N-[1-(2,5-dimethylfuran-3-yl)ethyl]-1H,2H,3H,4H,5H,6H-pyrrolo[3,4-c]pyrrole-2-carboxamide |
| 21-5 | 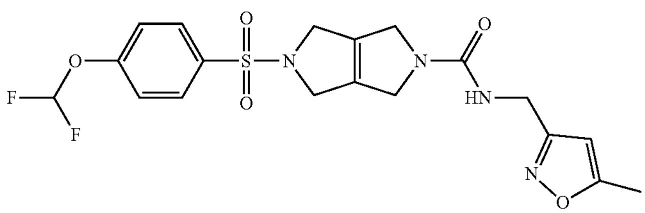 [SMILES: Cc1cc(CNC(=O)N2CC3=C(C2)CN(S(=O)(=O)c2ccc(OC(F)F)cc2)C3)no1] | 5-[4-(Difluoromethoxy)benzenesulfonyl]-N-[(5-methyl-1,2-oxazol-3-yl)methyl]-1H,2H,3H,4H,5H,6H-pyrrolo[3,4-c]pyrrole-2-carboxamide |
| 21-6 | 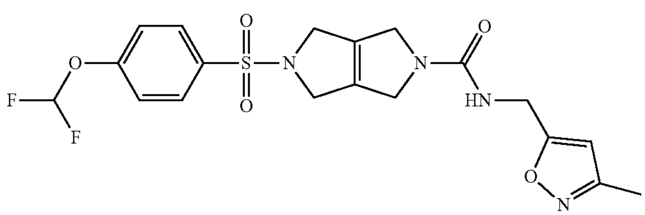 [SMILES: Cc1cc(CNC(=O)N2CC3=C(C2)CN(S(=O)(=O)c2ccc(OC(F)F)cc2)C3)on1] | 5-[4-(Difluoromethoxy)benzenesulfonyl]-N-[(3-methyl-1,2-oxazol-5-yl)methyl]-1H,2H,3H,4H,5H,6H-pyrrolo[3,4-c]pyrrole-2-carboxamide |
| 21-7 | 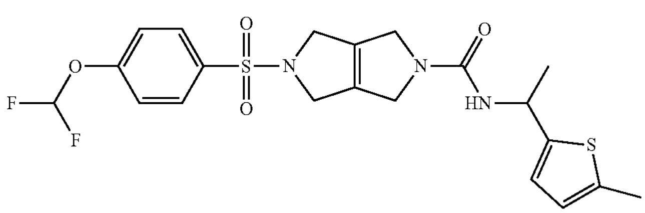 [SMILES: Cc1ccc(C(C)NC(=O)N2CC3=C(C2)CN(S(=O)(=O)c2ccc(OC(F)F)cc2)C3)s1] | 5-[4-(Difluoromethoxy)benzenesulfonyl]-N-[1-(5-methylthiophen-2-yl)ethyl]-1H,2H,3H,4H,5H,6H-pyrrolo[3,4-c]pyrrole-2-carboxamide |
| 21-8 | 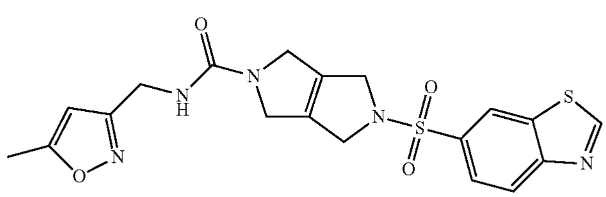 [SMILES: Cc1cc(CNC(=O)N2CC3=C(C2)CN(S(=O)(=O)c2ccc4ncsc4c2)C3)no1] | 5-(1,3-Benzothiazole-6-sulfonyl)-N-[(5-methyl-1,2-oxazol-3-yl)methyl]-1H,2H,3H,4H,5H,6H-pyrrolo[3,4-c]pyrrole-2-carboxamide |
| 21-9 | 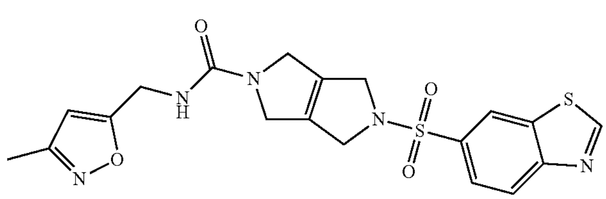 [SMILES: Cc1cc(CNC(=O)N2CC3=C(C2)CN(S(=O)(=O)c2ccc4ncsc4c2)C3)on1] | 5-(1,3-Benzothiazole-6-sulfonyl)-N-[(3-methyl-1,2-oxazol-5-yl)methyl]-1H,2H,3H,4H,5H,6H-pyrrolo[3,4-c]pyrrole-2-carboxamide |

TABLE 1-continued

| Example | Structure | Name |
|---|---|---|
| 21-10 | 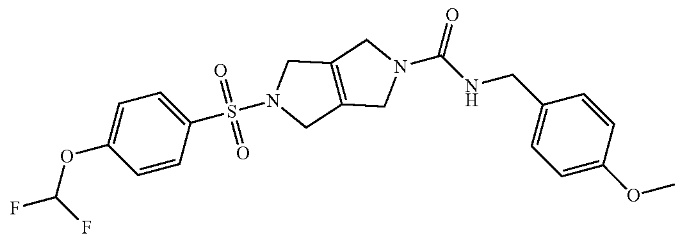 [SMILES: COc1ccc(CNC(=O)N2CC3=C(C2)CN(S(=O)(=O)c2ccc(OC(F)F)cc2)C3)cc1] | 5-[4-(Difluoromethoxy)benzenesulfonyl]-N-[(4-methoxyphenyl)methyl]-1H,2H,3H,4H,5H,6H-pyrrolo[3,4-c]pyrrole-2-carboxamide |
| 21-11 | 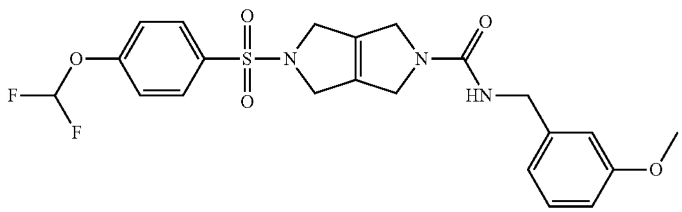 [SMILES: COc1cccc(CNC(=O)N2CC3=C(C2)CN(S(=O)(=O)c2ccc(OC(F)F)cc2)C3)c1] | 5-[4-(Difluoromethoxy)benzenesulfonyl]-N-[(3-methoxyphenyl)methyl]-1H,2H,3H,4H,5H,6H-pyrrolo[3,4-c]pyrrole-2-carboxamide |
| 21-12 | 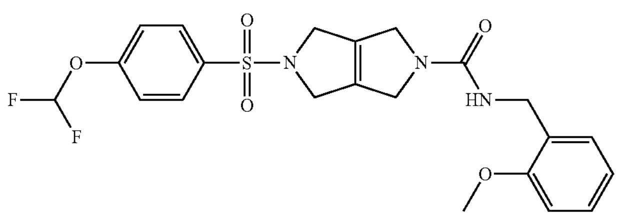 [SMILES: COc1ccccc1CNC(=O)N1CC2=C(C1)CN(S(=O)(=O)c1ccc(OC(F)F)cc1)C2] | 5-[4-(Difluoromethoxy)benzenesulfonyl]-N-[(2-methoxyphenyl)methyl]-1H,2H,3H,4H,5H,6H-pyrrolo[3,4-c]pyrrole-2-carboxamide |
| 21-13 | 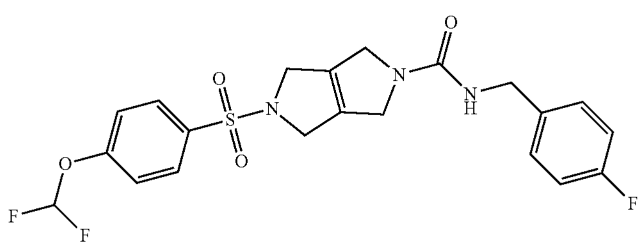 [SMILES: O=C(NCc1ccc(F)cc1)N1CC2=C(C1)CN(S(=O)(=O)c1ccc(OC(F)F)cc1)C2] | 5-[4-(Difluoromethoxy)benzenesulfonyl]-N-[(4-fluorophenyl)methyl]-1H,2H,3H,4H,5H,6H-pyrrolo[3,4-c]pyrrole-2-carboxamide |
| 21-14 | 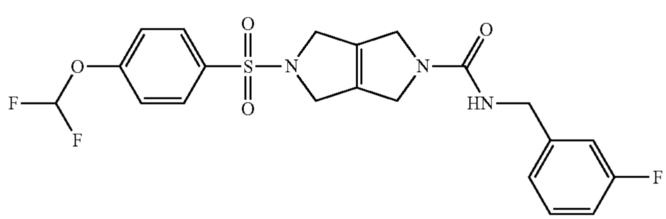 [SMILES: O=C(NCc1cccc(F)c1)N1CC2=C(C1)CN(S(=O)(=O)c1ccc(OC(F)F)cc1)C2] | 5-[4-(Difluoromethoxy)benzenesulfonyl]-N-[(3-fluorophenyl)methyl]-1H,2H,3H,4H,5H,6H-pyrrolo[3,4-c]pyrrole-2-carboxamide |
| 21-15 | 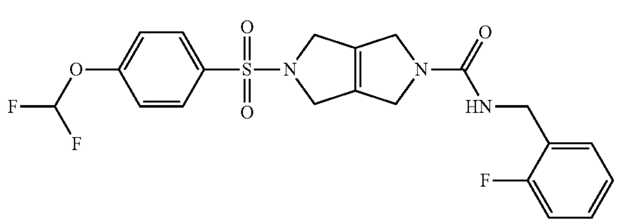 [SMILES: O=C(NCc1ccccc1F)N1CC2=C(C1)CN(S(=O)(=O)c1ccc(OC(F)F)cc1)C2] | 5-[4-(Difluoromethoxy)benzenesulfonyl]-N-[(2-fluorophenyl)methyl]-1H,2H,3H,4H,5H,6H-pyrrolo[3,4-c]pyrrole-2-carboxamide |

TABLE 1-continued

| Example | Structure | Name |
|---|---|---|
| 21-16 | 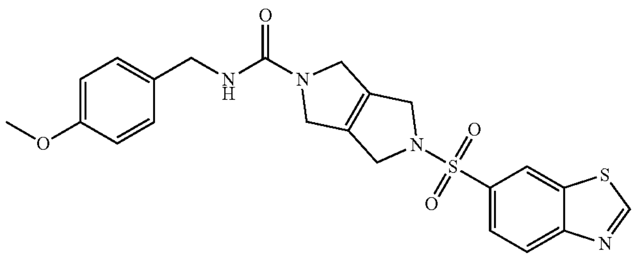 [SMILES: COc1ccc(CNC(=O)N2CC3=C(C2)CN(S(=O)(=O)c2ccc4ncsc4c2)C3)cc1] | 5-(1,3-Benzothiazole-6-sulfonyl)-N-[(4-methoxyphenyl)methyl]-1H,2H,3H,4H,5H,6H-pyrrolo[3,4-c]pyrrole-2-carboxamide |
| 21-17 | 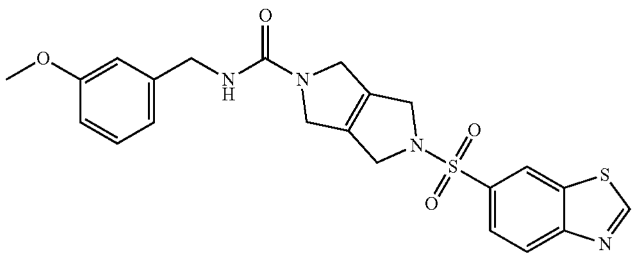 [SMILES: COc1cccc(CNC(=O)N2CC3=C(C2)CN(S(=O)(=O)c2ccc4ncsc4c2)C3)c1] | 5-(1,3-Benzothiazole-6-sulfonyl)-N-[(3-methoxyphenyl)methyl]-1H,2H,3H,4H,5H,6H-pyrrolo[3,4-c]pyrrole-2-carboxamide |
| 21-18 | 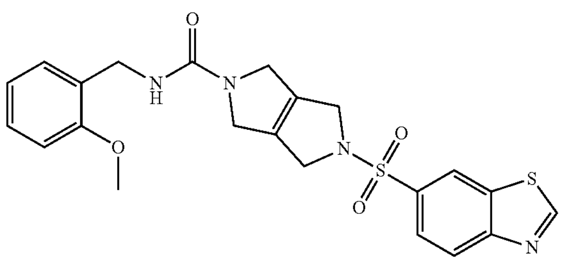 [SMILES: COc1ccccc1CNC(=O)N1CC2=C(C1)CN(S(=O)(=O)c1ccc3ncsc3c1)C2] | 5-(1,3-Benzothiazole-6-sulfonyl)-N-[(2-methoxyphenyl)methyl]-1H,2H,3H,4H,5H,6H-pyrrolo[3,4-c]pyrrole-2-carboxamide |
| 21-19 | 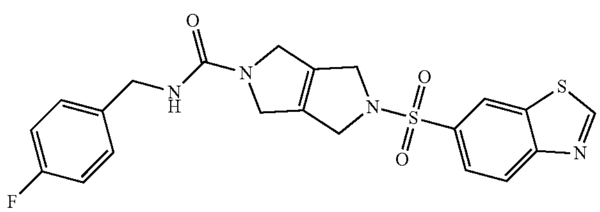 [SMILES: O=C(NCc1ccc(F)cc1)N1CC2=C(C1)CN(S(=O)(=O)c1ccc3ncsc3c1)C2] | 5-(1,3-Benzothiazole-6-sulfonyl)-N-[(4-fluorophenyl)methyl]-1H,2H,3H,4H,5H,6H-pyrrolo[3,4-c]pyrrole-2-carboxamide |
| 21-20 | 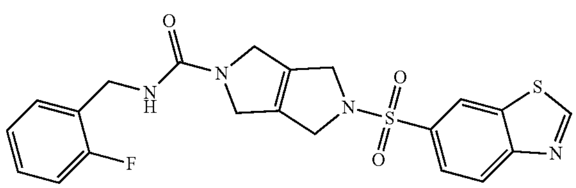 [SMILES: O=C(NCc1ccccc1F)N1CC2=C(C1)CN(S(=O)(=O)c1ccc3ncsc3c1)C2] | 5-(1,3-Benzothiazole-6-sulfonyl)-N-[(2-fluorophenyl)methyl]-1H,2H,3H,4H,5H,6H-pyrrolo[3,4-c]pyrrole-2-carboxamide |
| 21-21 | 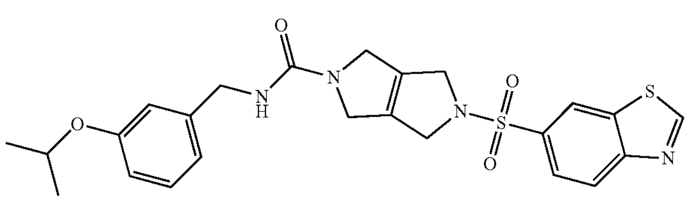 [SMILES: CC(C)Oc1cccc(CNC(=O)N2CC3=C(C2)CN(S(=O)(=O)c2ccc4ncsc4c2)C3)c1] | 5-(1,3-Benzothiazole-6-sulfonyl)-N-{[3-(propan-2-yloxy)phenyl]methyl}-1H,2H,3H,4H,5H,6H-pyrrolo[3,4-c]pyrrole-2-carboxamide |

TABLE 1-continued

| Example | Structure | Name |
|---|---|---|
| 21-22 | 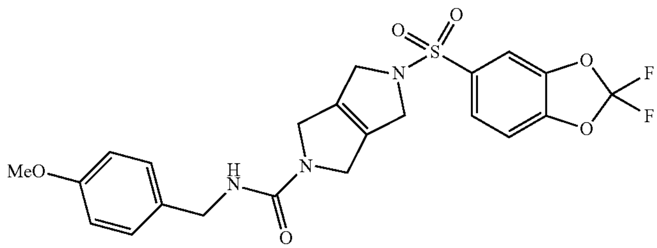 [SMILES: COc1ccc(CNC(=O)N2CC3=C(C2)CN(S(=O)(=O)c2ccc4c(c2)OC(F)(F)O4)C3)cc1] | 5-[(2,2-Difluoro-2H-1,3-benzodioxol-5-yl)sulfonyl]-N-[(4-methoxyphenyl)methyl]-1H,2H,3H,4H,5H,6H-pyrrolo[3,4-c]pyrrole-2-carboxamide |
| 21-23 | 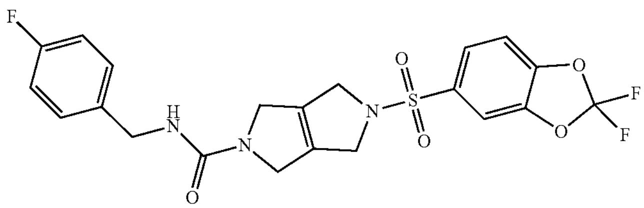 [SMILES: O=C(NCc1ccc(F)cc1)N1CC2=C(C1)CN(S(=O)(=O)c1ccc3c(c1)OC(F)(F)O3)C2] | 5-[(2,2-Difluoro-2H-1,3-benzodioxol-5-yl)sulfonyl]-N-[(4-fluorophenyl)methyl]-1H,2H,3H,4H,5H,6H-pyrrolo[3,4-c]pyrrole-2-carboxamide |
| 21-24 | 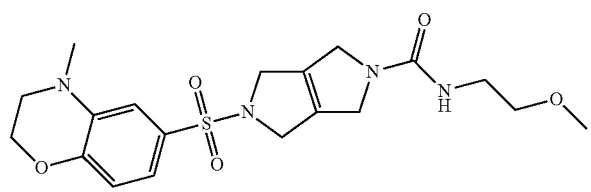 [SMILES: COCCNC(=O)N1CC2=C(C1)CN(S(=O)(=O)c1ccc3c(c1)N(C)CCO3)C2] | N-(2-methoxyethyl)-5-[(4-methyl-3,4-dihydro-2H-1,4-benzoxazin-6-yl)sulfonyl]-1H,2H,3H,4H,5H,6H-pyrrolo[3,4-c]pyrrole-2-carboxamide |
| 21-25 | 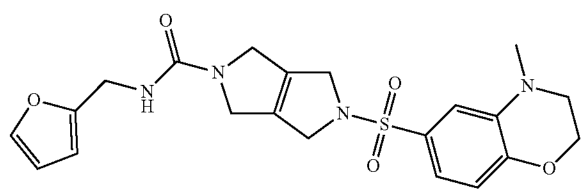 [SMILES: CN1CCOc2ccc(S(=O)(=O)N3CC4=C(CN(C(=O)NCc5ccco5)C4)C3)cc21] | N-(furan-2-ylmethyl)-5-[(4-methyl-3,4-dihydro-2H-1,4-benzoxazin-6-yl)sulfonyl]-1H,2H,3H,4H,5H,6H-pyrrolo[3,4-c]pyrrole-2-carboxamide |
| 21-26 | 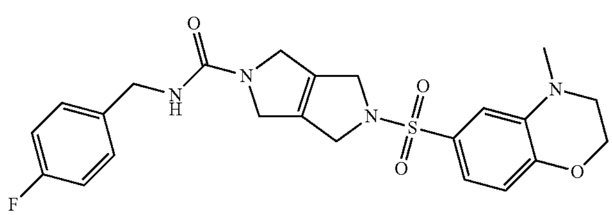 [SMILES: CN1CCOc2ccc(S(=O)(=O)N3CC4=C(CN(C(=O)NCc5ccc(F)cc5)C4)C3)cc21] | N-[(4-fluorophenyl)methyl]-5-[(4-methyl-3,4-dihydro-2H-1,4-benzoxazin-6-yl)sulfonyl]-1H,2H,3H,4H,5H,6H-pyrrolo[3,4-c]pyrrole-2-carboxamide |
| 21-27 | 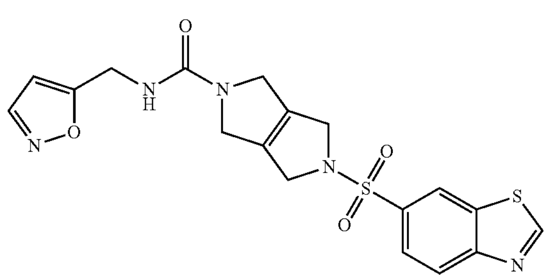 [SMILES: O=C(NCc1ccno1)N1CC2=C(C1)CN(S(=O)(=O)c1ccc3ncsc3c1)C2] | 5-(1,3-Benzothiazole-6-sulfonyl)-N-(1,2-oxazol-5-ylmethyl)-1H,2H,3H,4H,5H,6H-pyrrolo[3,4-c]pyrrole-2-carboxamide |

TABLE 1-continued

| Example | Structure | Name |
|---|---|---|
| 21-28 | 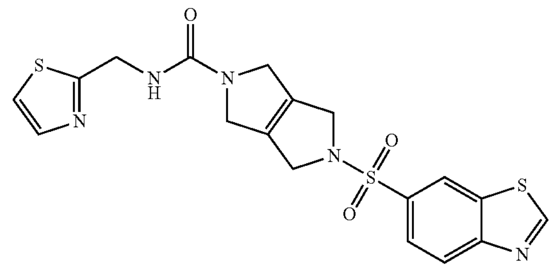 [SMILES: O=C(NCc1nccs1)N1CC2=C(C1)CN(S(=O)(=O)c1ccc3ncsc3c1)C2] | 5-(1,3-Benzothiazole-6-sulfony)-N-(1,3-thiazol-2-ylmethyl)-1H,2H,3H,4H,5H,6H-pyrrolo[3,4-c]pyrrole-2-carboxamide |
| 21-29 | 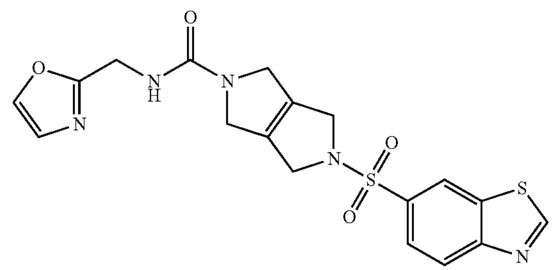 [SMILES: O=C(NCc1ncco1)N1CC2=C(C1)CN(S(=O)(=O)c1ccc3ncsc3c1)C2] | 5-(1,3-Benzothiazole-6-sulfonyl)-N-(1,3-oxazol-2-ylmethyl)-1H,2H,3H,4H,5H,6H-pyrrolo[3,4-c]pyrrole-2-carboxamide |
| 21-30 | 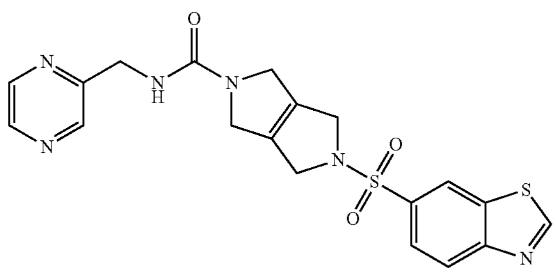 [SMILES: O=C(NCc1cnccn1)N1CC2=C(C1)CN(S(=O)(=O)c1ccc3ncsc3c1)C2] | 5-(1,3-Benzothiazole-6-sulfonyl)-N-(pyrazin-2-ylmethyl)-1H,2H,3H,4H,5H,6H-pyrrolo[3,4-c]pyrrole-2-carboxamide |
| 21-31 | 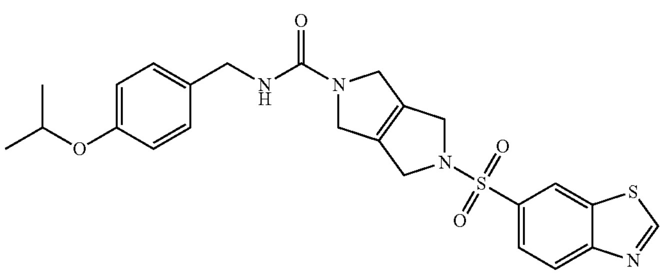 [SMILES: CC(C)Oc1ccc(CNC(=O)N2CC3=C(C2)CN(S(=O)(=O)c2ccc4ncsc4c2)C3)cc1] | 5-(1,3-Benzothiazole-6-sulfonyl)-N-{[4-(propan-2-yloxy)phenyl]methyl}-1H,2H,3H,4H,5H,6H-pyrrolo[3,4-c]pyrrole-2-carboxamide |
| 21-32 | 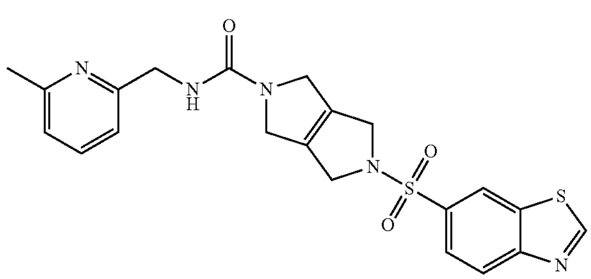 [SMILES: Cc1cccc(CNC(=O)N2CC3=C(C2)CN(S(=O)(=O)c2ccc4ncsc4c2)C3)n1] | 5-(1,3-Benzothiazole-6-sulfonyl)-N-[(6-methylpyridin-2-yl)methyl]-1H,2H,3H,4H,5H,6H-pyrrolo[3,4-c]pyrrole-2-carboxamide |

TABLE 1-continued

| Example | Structure | Name |
|---|---|---|
| 21-33 | 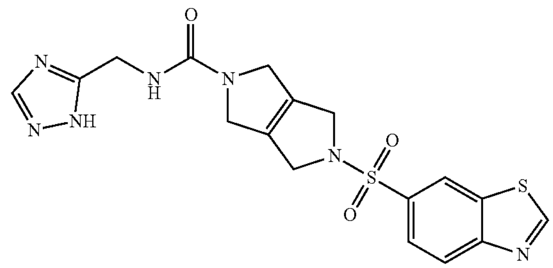 [SMILES: O=C(NCc1ncn[nH]1)N1CC2=C(C1)CN(S(=O)(=O)c1ccc3ncsc3c1)C2] | 5-(1,3-Benzothiazole-6-sulfonyl)-N-(1H-1,2,4-triazol-5-ylmethyl)-1H,2H,3H,4H,5H,6H-pyrrolo[3,4-c]pyrrole-2-carboxamide |
| 21-34 | 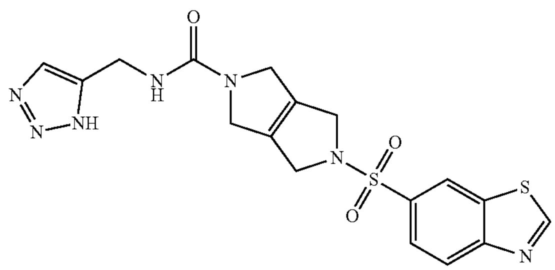 [SMILES: O=C(NCc1cnn[nH]1)N1CC2=C(C1)CN(S(=O)(=O)c1ccc3ncsc3c1)C2] | 5-(1,3-Benzothiazole-6-sulfonyl)-N-(1H-1,2,3-triazol-5-ylmethyl)-1H,2H,3H,4H,5H,6H-pyrrolo[3,4-c]pyrrole-2-carboxamide |
| 21-35 | 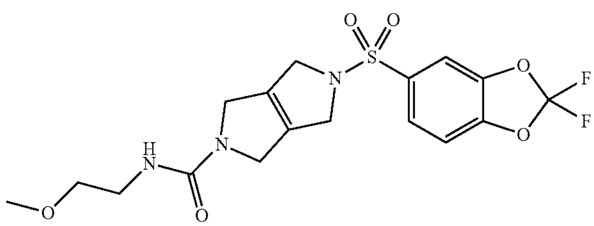 [SMILES: COCCNC(=O)N1CC2=C(C1)CN(S(=O)(=O)c1ccc3c(c1)OC(F)(F)O3)C2] | 5-((2,2-Difluorobenzo[d][1,3]dioxol-5-yl)sulfonyl)-N-(2-methoxyethyl)-3,4,5,6-tetrahydropyrrolo[3,4-c]pyrrole-2(1H)-carboxamide |
| 21-36 | 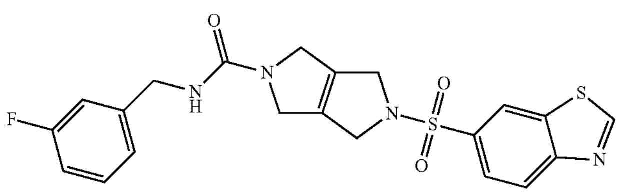 [SMILES: O=C(NCc1cccc(F)c1)N1CC2=C(C1)CN(S(=O)(=O)c1ccc3ncsc3c1)C2] | 5-(1,3-Benzothiazole-6-sulfonyl)-N-[(3-fluorophenyl)methyl]-1H,2H,3H,4H,5H,6H-pyrrolo[3,4-c]pyrrole-2-carboxamide |
| 21-37 | 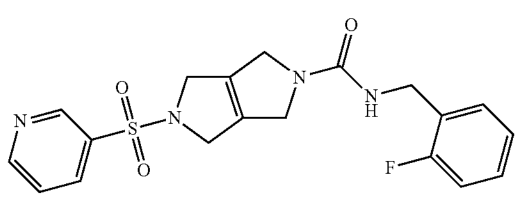 [SMILES: O=C(NCc1ccccc1F)N1CC2=C(C1)CN(S(=O)(=O)c1cccnc1)C2] | N-[(2-fluorophenyl)methyl]-5-(pyridine-3-sulfonyl)-1H,2H,3H,4H,5H,6H-pyrrolo[3,4-c]pyrrole-2-carboxamide |
| 21-38 | 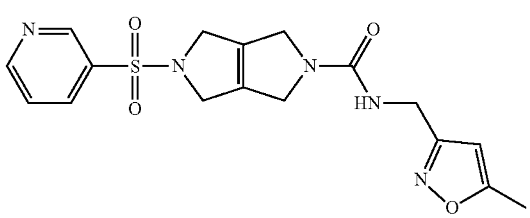 [SMILES: Cc1cc(CNC(=O)N2CC3=C(C2)CN(S(=O)(=O)c2cccnc2)C3)no1] | N-[(5-methyl-1,2-oxazol-3-yl)methyl]-5-(pyridine-3-sulfonyl)-1H,2H,3H,4H,5H,6H-pyrrolo[3,4-c]pyrrole-2-carboxamide |

TABLE 1-continued

| Example | Structure | Name |
|---|---|---|
| 21-39 | 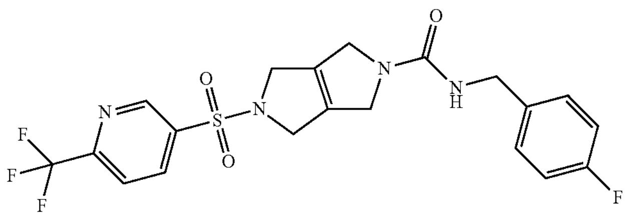 [SMILES: O=C(NCc1ccc(F)cc1)N1CC2=C(C1)CN(S(=O)(=O)c1ccc(C(F)(F)F)nc1)C2] | N-[(4-fluorophenyl)methyl]-5-{[6-(trifluoromethyl)pyridin-3-yl]sulfonyl}-1H,2H,3H,4H,5H,6H-pyrrolo[3,4-c]pyrrole-2-carboxamide |
| 21-40 | 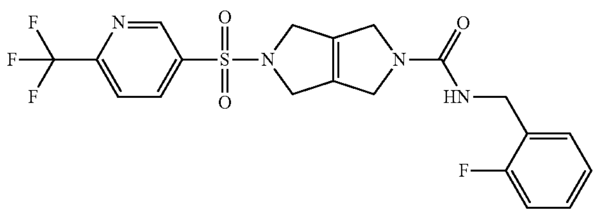 [SMILES: O=C(NCc1ccccc1F)N1CC2=C(C1)CN(S(=O)(=O)c1ccc(C(F)(F)F)nc1)C2] | N-[(2-fluorophenyl)methyl]-5-{[6-(trifluoromethyl)pyridin-3-yl]sulfonyl}-1H,2H,3H,4H,5H,6H-pyrrolo[3,4-c]pyrrole-2-carboxamide |
| 21-41 | 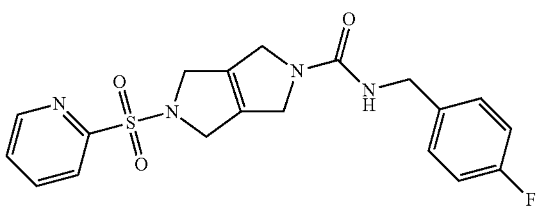 [SMILES: O=C(NCc1ccc(F)cc1)N1CC2=C(C1)CN(S(=O)(=O)c1ccccn1)C2] | N-[(4-fluorophenyl)methyl]-5-(pyridine-2-sulfonyl)-1H,2H,3H,4H,5H,6H-pyrrolo[3,4-c]pyrrole-2-carboxamide |
| 21-42 | 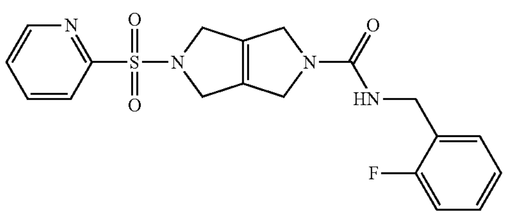 [SMILES: O=C(NCc1ccccc1F)N1CC2=C(C1)CN(S(=O)(=O)c1ccccn1)C2] | N-[(2-fluorophenyl)methyl]-5-(pyridine-2-sulfonyl)-1H,2H,3H,4H,5H,6H-pyrrolo[3,4-c]pyrrole-2-carboxamide |
| 21-43 | 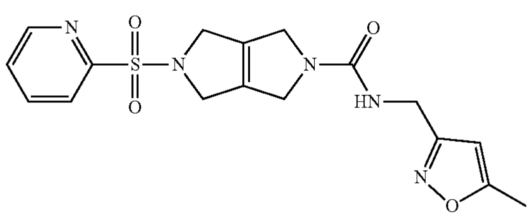 [SMILES: Cc1cc(CNC(=O)N2CC3=C(C2)CN(S(=O)(=O)c2ccccn2)C3)no1] | N-[(5-methyl-1,2-oxazol-3-yl)methyl]-5-(pyridine-2-sulfonyl)-1H,2H,3H,4H,5H,6H-pyrrolo[3,4-c]pyrrole-2-carboxamide |
| 22-1 | 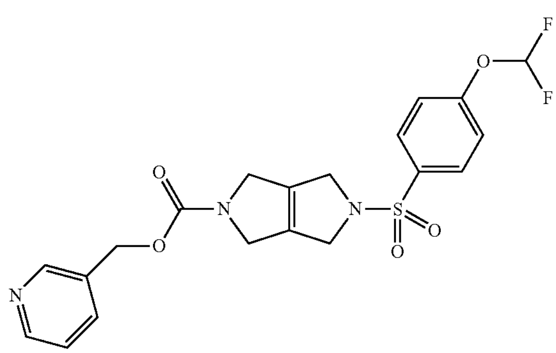 [SMILES: O=C(OCc1cccnc1)N1CC2=C(C1)CN(S(=O)(=O)c1ccc(OC(F)F)cc1)C2] | Pyridin-3-ylmethyl 5-((4-(difluoromethoxy)phenyl)sulfonyl)-3,4,5,6-tetrahydropyrrolo[3,4-c]pyrrole-2(1H)-carboxylate |

TABLE 1-continued

| Example | Structure | Name |
|---|---|---|
| 22-2 | 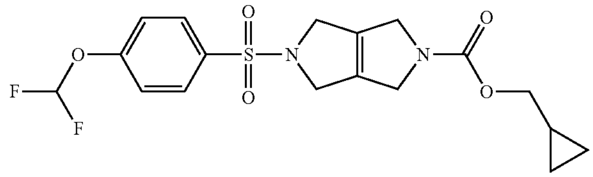 [SMILES: O=C(OCC1CC1)N1CC2=C(C1)CN(S(=O)(=O)c1ccc(OC(F)F)cc1)C2] | Cyclopropylmethyl 5-[4-(difluoromethoxy)benzenesulfonyl]-1H,2H,3H,4H,5H,6H-pyrrolo[3,4-c]pyrrole-2-carboxamide |
| 22-3 | 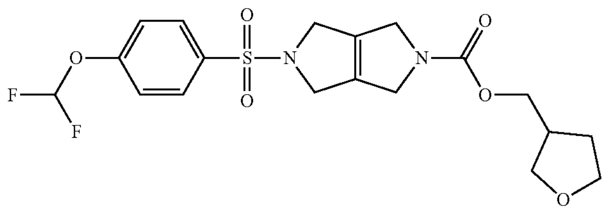 [SMILES: O=C(OCC1CCOC1)N1CC2=C(C1)CN(S(=O)(=O)c1ccc(OC(F)F)cc1)C2] | Oxolan-3-ylmethyl 5-[4-(difluoromethoxy)benzenesulfonyl]-1H,2H,3H,4H,5H,6H-pyrrolo[3,4-c]pyrrole-2-carboxamide |
| 22-4 | 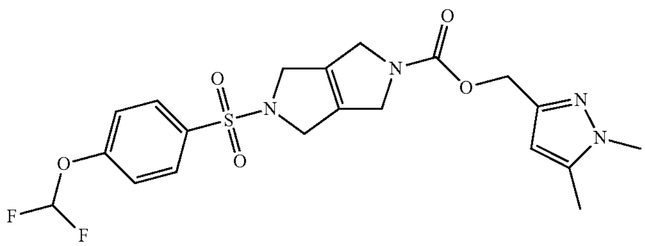 [SMILES: Cc1cc(COC(=O)N2CC3=C(C2)CN(S(=O)(=O)c2ccc(OC(F)F)cc2)C3)nn1C] | (1,5-Dimethyl-1H-pyrazol-3-yl)methyl 5-[4-(difluoromethoxy)benzenesulfonyl]-1H,2H,3H,4H,5H,6H-pyrrolo[3,4-c]pyrrole-2-carboxamide |
| 22-5 | 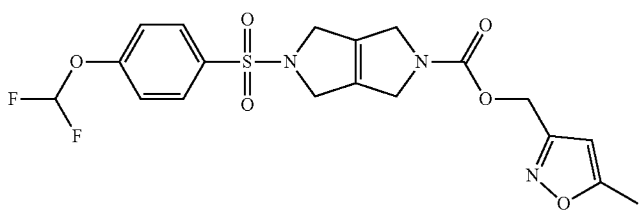 [SMILES: Cc1cc(COC(=O)N2CC3=C(C2)CN(S(=O)(=O)c2ccc(OC(F)F)cc2)C3)no1] | (5-Methyl-1,2-oxazol-3-yl)methyl 5-[4-(difluoromethoxy)benzenesulfonyl]-1H,2H,3H,4H,5H,6H-pyrrolo[3,4-c]pyrrole-2-carboxamide |
| 22-6 | 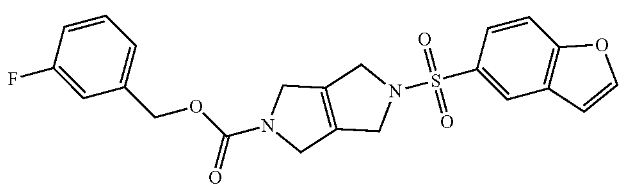 [SMILES: O=C(OCc1cccc(F)c1)N1CC2=C(C1)CN(S(=O)(=O)c1ccc3occc3c1)C2] | (3-Fluorophenyl)methyl 5-(1-benzofuran-5-sulfonyl)-1H,2H,3H,4H,5H,6H-pyrrolo[3,4-c]pyrrole-2-carboxamide |
| 22-7 | 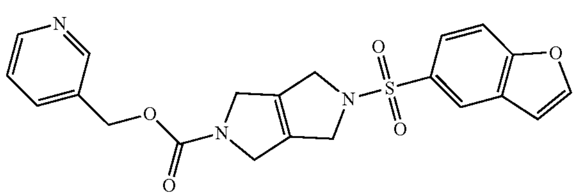 [SMILES: O=C(OCc1cccnc1)N1CC2=C(C1)CN(S(=O)(=O)c1ccc3occc3c1)C2] | Pyridin-3-ylmethyl 5-(1-benzofuran-5-sulfonyl)-1H,2H,3H,4H,5H,6H-pyrrolo[3,4-c]pyrrole-2-carboxamide |
| 23-1 | 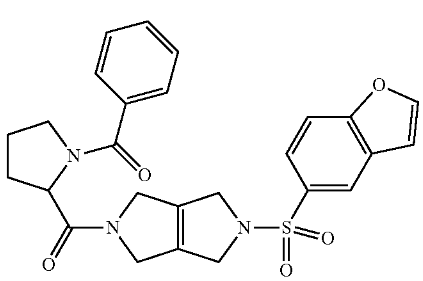 [SMILES: O=C(C1CCCN1C(=O)c1ccccc1)N1CC2=C(C1)CN(S(=O)(=O)c1ccc3occc3c1)C2] | 2-(Benzofuran-5-ylsulfonyl)-5-(benzoylprolyl)-1,2,3,4,5,6-hexahydropyrrolo[3,4-c]pyrrole |

TABLE 1-continued

| Example | Structure | Name |
|---|---|---|
| 23-2 | 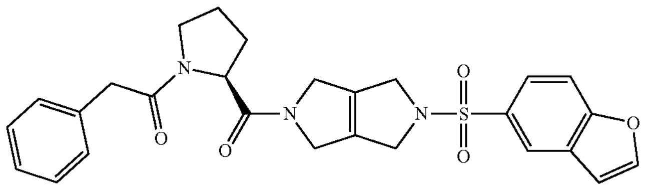 [SMILES: O=C([C@@H]1CCCN1C(=O)Cc1ccccc1)N1CC2=C(C1)CN(S(=O)(=O)c1ccc3occc3c1)C2] | 1-[(2S)-2-[5-(1-benzofuran-5-sulfonyl)-1H,2H,3H,4H,5H,6H-pyrrolo[3,4-c]pyrrole-2-carbonyl]pyrrolidin-1-yl]-2-phenylethan-1-one |
| 23-3 | 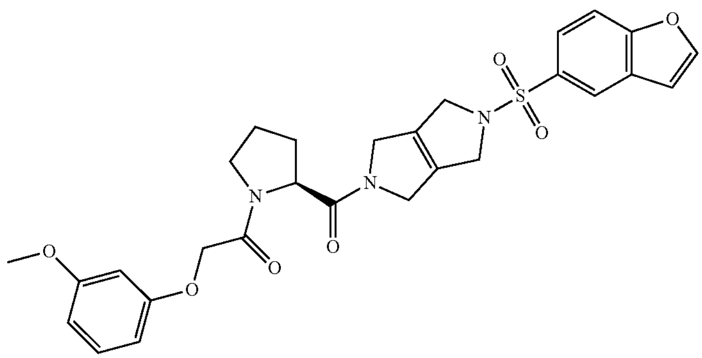 [SMILES: COc1cccc(OCC(=O)N2CCC[C@H]2C(=O)N2CC3=C(C2)CN(S(=O)(=O)c2ccc4occc4c2)C3)c1] | 1-[(2S)-2-[5-(1-benzofuran-5-sulfonyl)-1H,2H,3H,4H,5H,6H-pyrrolo[3,4-c]pyrrole-2-carbonyl]pyrrolidin-1-yl]-2-(3-methoxyphenoxy)ethan-1-one |
| 23-4 | 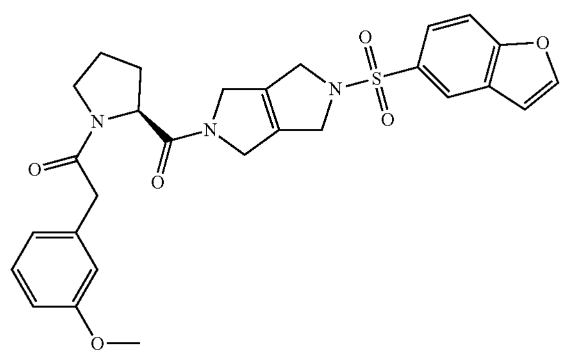 [SMILES: COc1cccc(CC(=O)N2CCC[C@H]2C(=O)N2CC3=C(C2)CN(S(=O)(=O)c2ccc4occc4c2)C3)c1] | 1-[(2S)-2-[5-(1-benzofuran-5-sulfonyl)-1H,2H,3H,4H,5H,6H-pyrrolo[3,4-c]pyrrole-2-carbonyl]pyrrolidin-1-yl]-2-(3-methoxyphenyl)ethan-1-one |
| 23-5 | 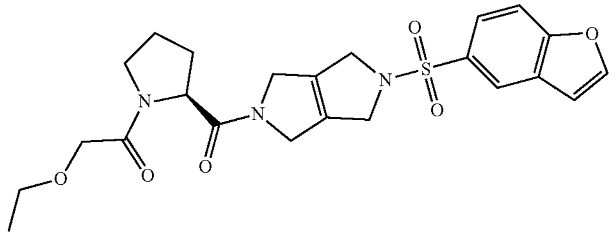 [SMILES: CCOCC(=O)N1CCC[C@H]1C(=O)N1CC2=C(C1)CN(S(=O)(=O)c1ccc3occc3c1)C2] | 1-[(2S)-2-[5-(1-benzofuran-5-sulfonyl)-1H,2H,3H,4H,5H,6H-pyrrolo[3,4-c]pyrrole-2-carbonyl]pyrrolidin-1-yl]-2-ethoxyethan-1-one |

TABLE 1-continued

| Example | Structure | Name |
|---|---|---|
| 23-6 | 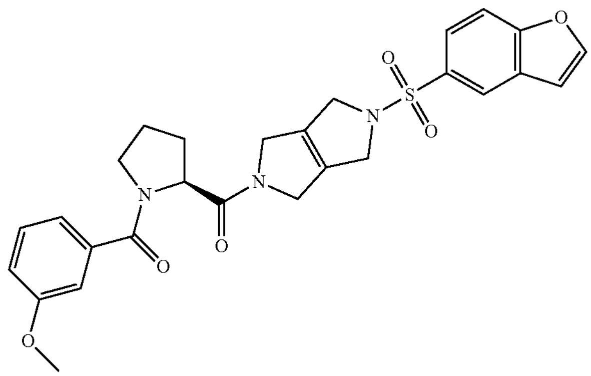 [SMILES: COc1cccc(C(=O)N2CCC[C@H]2C(=O)N2CC3=C(C2)CN(S(=O)(=O)c2ccc4occc4c2)C3)c1] | (2S)-2-[5-(1-benzofuran-5-sulfonyl)-1H,2H,3H,4H,5H,6H-pyrrolo[3,4-c]pyrrole-2-carbonyl]-1-(3-methoxybenzoyl)pyrrolidine |

$^a$Compounds 8-2 and 8-3 are enantiomers, but absolute stereochemistry is undetermined (*);
$^b$Compounds 9-4 and 9-5 are enantiomers, but absolute stereochemistry is undetermined (*);
$^c$Compounds 10-1 and 10-2 are enantiomers, but absolute stereochemistry is undetermined (*);
$^d$Compounds 11-1 and 11-2 are enantiomers, but absolute stereochemistry is undetermined (*).

Unless otherwise stated, it will be appreciated that when "one or more" substituents are recited for a particular variable, it includes one, two, three, four, or more substituents as valency permits.

In some embodiments of any Formula disclosed herein, a heterocyclyl at the $R^1$, $R^2$, or B position does not contain an O in the γ-position relative to $C(=Z^1)$ or $C(=O)$. In some embodiments of any Formula disclosed herein, a heterocyclyl at the $R^1$, $R^2$, or B position contains 1-4 heteroatoms independently selected from the group consisting of N and S.

Unless otherwise stated, structures depicted herein are also meant to include all stereoisomeric (e.g., enantiomeric or diastereomeric) forms of the structure, as well as all geometric or conformational isomeric forms of the structure; for example, the R and S configurations for each stereocenter. Therefore, single stereochemical isomers, as well as enantiomeric, diastereomeric, and geometric (or conformational) mixtures of the present compounds are within the scope of the disclosure. For example, in some cases Table 1 shows one or more stereoisomers of a compound, and unless otherwise indicated, represents each stereoisomer alone and/or as a mixture. Unless otherwise stated, all tautomeric forms of the compounds of the disclosure are within the scope of the disclosure.

In some embodiments, a compound of Formula I, II, III, or IV is obtained by a process comprising a purification method of Examples 8-2, 8-3, 9-4, 9-5, 10-1, 10-2, 11-1, or 11-2. In some embodiments, the compound is the obtained by a process comprising a purification method Examples 8-2, 8-3, 9-4, 9-5, 10-1, 10-2, 11-1, or 11-2 and is the $1^{st}$ eluting isomer of the purification method. In some embodiments, the compound is the obtained by a process comprising a purification method Examples 8-2, 8-3, 9-4, 9-5, 10-1, 10-2, 11-1, or 11-2 and is the $2^{nd}$ eluting isomer of the purification method. In some embodiments, the compound is the obtained by a process comprising a purification method Examples 8-2, 8-3, 9-4, 9-5, 10-1, 10-2, 11-1, or 11-2 and is the $3^{rd}$, $4^{th}$, $5^{th}$, $6^{th}$, $7^{th}$, or $8^{th}$ eluting isomer of the purification method.

In some embodiments, a PKR Activating Compound is obtained by a process comprising a purification method of Examples 8-2, 8-3, 9-4, 9-5, 10-1, 10-2, 11-1, or 11-2. In some embodiments, the PKR Activating Compound is the obtained by a process comprising a purification method Examples 8-2, 8-3, 9-4, 9-5, 10-1, 10-2, 11-1, or 11-2 and is the $1^{st}$ eluting isomer of the purification method. In some embodiments, the PKR Activating Compound is the obtained by a process comprising a purification method Examples 8-2, 8-3, 9-4, 9-5, 10-1, 10-2, 11-1, or 11-2 and is the $2^{nd}$ eluting isomer of the purification method. In some embodiments, the PKR Activating Compound is the obtained by a process comprising a purification method Examples 8-2, 8-3, 9-4, 9-5, 10-1, 10-2, 11-1, or 11-2 and is the $3^{rd}$, $4^{th}$, $5^{th}$, $6^{th}$, $7^{th}$ or $8^{th}$ eluting isomer of the purification method.

Additionally, unless otherwise stated, structures depicted herein are also meant to include compounds that differ only in the presence or absence of one or more isotopically enriched atoms. For example, compounds having the present structure including the replacement of hydrogen by deuterium or tritium, or the replacement of a carbon by a $^{13}$C- or $^{14}$C-enriched carbon are within the scope of this disclosure.

The disclosure also provides compound of Formulas I, II, III, and IV that are useful, for example, as analytical tools and/or control compounds in biological assays.

The compound of Formulas I, II, III, and IV may form salts which are also within the scope of this disclosure. Reference to a compound of Formula I, II, III, or IV herein is understood to include reference to salts thereof, unless otherwise indicated. Pharmaceutically acceptable salts are well known in the art. For example, S. M. Berge, et al. describes pharmaceutically acceptable salts in detail in J. Pharmaceutical Sciences, 66: 1-19 (1977).

The disclosure also includes pharmaceutical compositions comprising one or more compounds as described herein, or a pharmaceutically acceptable salt thereof, and a pharmaceutically acceptable excipient. In some embodiments, pharmaceutical compositions reported herein can be provided in a unit dosage form (e.g., capsule, tablet or the like). In some embodiments, pharmaceutical compositions reported herein can be provided in an oral dosage form. In some embodiments, the pharmaceutical composition is orally administered in any orally acceptable dosage form. In some embodiments, an oral dosage form of a compound of Formula I, II, III, or IV can be a capsule. In some embodiments, an oral dosage form of a compound of Formula I, II, III, or IV is a tablet. In some embodiments, an oral dosage form comprises one or more fillers, disintegrants, lubricants, glidants, antiadherents and/or anti-statics. In some embodiments, an oral dosage form is prepared via dry blending. In some embodiments, an oral dosage form is a tablet and is prepared via dry granulation. In some embodiments, a pharmaceutical composition is provided comprising a compound of Formula I, or a pharmaceutically acceptable salt thereof, and a pharmaceutically acceptable excipient. In some embodiments, a pharmaceutical composition is provided comprising a compound of Formula II, or a pharmaceutically acceptable salt thereof, and a pharmaceutically acceptable excipient. In some embodiments, a pharmaceutical composition is provided comprising a compound of Formula III, or a pharmaceutically acceptable salt thereof, and a pharmaceutically acceptable excipient. In some embodiments, a pharmaceutical composition is provided comprising a compound of Formula IV, or a pharmaceutically acceptable salt thereof, and a pharmaceutically acceptable excipient.

The pharmaceutical compositions provided herewith may be orally administered in any orally acceptable dosage form including, but not limited to, capsules, and tablets (e.g., in unit dosage forms). In some embodiments, a compound disclosed herein is formulated for oral administering to the subject at a dose of about 10 mg to about 1000 mg, e.g., as a capsule or tablet containing about 50 mg-about 100 mg of a compound disclosed herein and pharmaceutically acceptable carriers and/or excipients. Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician. Pharmaceutical compositions of a compound disclosed herein may comprise one or more additional excipients and/or carriers, with a compound disclosed herein (e.g., a compound of Formulae I, II, III and/or IV) present at dosage levels of between about 1 to 100%, and more preferably between about 5 to 95% by weight of the pharmaceutical composition.

The designations "α", "β", "γ", "δ", "ε", etc. are used herein to refer to a position in a molecule relative to a carbonyl group (e.g., C(=Z) or C(=O)), in accordance with standard nomenclature. For example, a carbon in the α-position (or an α-carbon) is a carbon atom in the position adjacent to a carbonyl group; and an oxygen in the β-position (or a β-oxygen) is an oxygen atom in the position two atoms away from a carbonyl group. The scheme below illustrates this nomenclature on an exemplary compound:

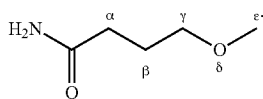

Methods of Using the Disclosed Compounds

Another aspect of the present disclosure is the use of compounds of Formula I, II, III, and IV. Compounds of Formula I, II, III, and IV are useful in medicine. For example, compounds and compositions described herein are activators of PKR. Methods of treatment (e.g., by activating PKR and/or PKM2) can comprise administering to a subject in need thereof a therapeutically effective amount of (i) a compound disclosed herein, or a pharmaceutically acceptable salt thereof or (ii) a pharmaceutical composition comprising a compound disclosed herein, or a pharmaceutically acceptable salt thereof, and a pharmaceutically acceptable carrier. In some embodiments, a method of treating a disease associated with modulation of PKR comprises administering a therapeutically effective amount of a compound disclosed herein. In some embodiments, a method of treating pyruvate kinase deficiency (PKD) comprises administering a therapeutically effective amount of a compound disclosed herein. In some embodiments, a method of treating PKD-associated hemolytic anemia comprises administering a therapeutically effective amount of a compound disclosed herein.

A method of treatment can comprise administering an amount of a compound disclosed herein (e.g., a compound of Formulae I, II, III and/or IV) sufficient to provide a blood concentration of 2,3-DPG that is reduced by at least 15% relative to the reference standard (e.g., from about 15% to about 60%). In some embodiments, the blood concentration of 2,3-DPG is reduced by at least about 15%, by at least about 20%, by at least about 25%, by at least about 30%, by at least about 35%, by at least about 40%, by at least about 45%, by at least about 50%, by at least about 55%, by at least about 60%. In some embodiments, the analysis is performed by sample analysis of bodily fluid, such as blood, by e.g., mass spectroscopy, e.g. LC-MS.

Compounds and compositions described herein are useful as activators of PKR mutants having lower activities compared to the wild type. Such mutations in PKR can affect enzyme activity (catalytic efficiency), regulatory properties (modulation by fructose bisphosphate (FBP)/ATP), and/or thermostability of the enzyme. Examples of such mutations include G332S, G364D, T384M, G37E, R479H, R479K, R486W, R532W, R510Q, and R490W. The activating activity of the present compounds against PKR mutants may be tested following a method described in Example 24. Compounds described herein are also activators of wild type PKR.

A method of treating a patient suffering from or susceptible to a disease or disorder associated with reduced PKM2 activity or reduced glycolysis can include administering a therapeutically effective amount of a compound disclosed herein to a patient in need thereof. The method can include the step of administering an effective amount of a compound described herein to the patient in need thereof, thereby treating, preventing or ameliorating the disease or disorder in the patient. In certain embodiment the compound described herein is provided in a pharmaceutical composition. In certain embodiments, the method includes the step of identifying or selecting a patient who would benefit from activation of PKM2 prior to treatment. Identifying or selecting such a patient can be on the basis of the level of PKM2 activity in a cell of the patient. The compound can be a compound described herein administered at a dosage and frequency sufficient to increase lactate production or oxidative phosphorylation. A method for treating diseases or conditions that are associated with increased 2,3-diphosphoglycerate levels can include administering to a subject in need thereof a therapeutically effective amount of (1) a compound disclosed herein or a pharmaceutically acceptable salt, solvate or hydrate thereof, (2) a pharmaceutical composition comprising a compound disclosed herein or a pharmaceutically acceptable salt, solvate or hydrate thereof, and a pharmaceutically acceptable carrier.

The compounds disclosed herein can be added directly to whole blood or packed cells extracorporeally or be provided to the subject (e.g., the patient). Without being bound by theory, a decrease in the level of 2, 3-DPG concentration induces a leftward shift of the oxygen-hemoglobin dissociation curve and shifts the allosteric equilibrium to the R, or oxygenated state, thus producing a therapeutic inhibition of the intracellular polymerization that underlies sickling by increasing oxygen affinity due to the 2,3-DPG depletion, thereby stabilizing the more soluble oxy-hemoglobin. In another embodiment, to regulate 2,3-diphosphoglycerate, a compound, composition or pharmaceutical composition described herein is added directly to whole blood or packed cells extracorporeally or be provided to the subject (e.g., the patient).

A method of increasing the level of PKM2 activity and/or glycolysis in a patient can include the administration of a therapeutically effective amount of a compound disclosed herein to a patient in need thereof. The method can comprise the step of administering an effective amount of a compound described herein to the patient in need thereof, thereby increasing the level of PKM2 activity and/or glycolysis in the patient. In some embodiments, a compound or a composition described herein is used to maintain PKM2 in its active conformation or activate pyruvate kinase activity in proliferating cells as a means to divert glucose metabolites into catabolic rather than anabolic processes in the patient.

A compound disclosed herein (e.g., a compound of Formulae I, II, III, and/or IV) can activate wild type PKR and/or mutant PKRs. Some examples of the mutant PKRs include G332S, G364D, T384M, G37E, R479H, R479K, R486W, R532W, R510Q, 190N, and R490W. Accordingly, a patient and/or subject can be selected for treatment using a compound of Formulae I, II, III, and/or IV by first evaluating the patient and/or subject to determine whether the subject carries a mutation in PKR (for examples, one of the mutations as described herein), and if the subject is determined to be carrying a mutation in PKR thus is in need of activation of the activity of the mutant PKR, then administering to the subject a therapeutically effective amount of a compound of Formulae I, II, III, and/or IV. A subject can be evaluated as carrying a mutation in PKR using methods known in the art. The subject can also be monitored, for example, subsequent to administration of a compound of Formulae I, II, III, and/or IV. A patient can be monitored for evaluation of certain PK/PD parameters of a compound of Formulae I, II, III, and/or IV such as levels of such compound, levels of 2,3-DPG, or levels of ATP.

In one aspect, the present invention provides a method of treating a subject, the method comprising: administering to the subject a compound of a compound of Formulae I, II, III, and/or IV; and acquiring a value for the level of a compound of Formulae I, II, III, and/or IV, the level of 2,3-diphosphoglycerate (2,3-DPG), the level of adenosine triphosphate (ATP), or the activity of PKR in the subject, to thereby evaluate the subject. The value for the level of a compound of Formulae I, II, III, and/or IV can be acquired by analyzing the plasma concentration of a compound of Formulae I, II, III, and/or IV. In some embodiments, the level of 2,3-DPG is acquired by analyzing the blood concentration of 2,3-DPG. The level of ATP can be acquired by analyzing the blood concentration of ATP. The activity of PKR can be acquired by analyzing the blood concentration of a $^{13}$C-label in the blood. For example, $^{13}$C-labeled glucose is administered to a subject, and incorporated into certain glycolytic intermediates in the blood.

A method of treatment can comprise administering an amount of a compound disclosed herein (e.g., a compound of Formulae I, II, III and/or IV) sufficient to provide a blood concentration of 2,3-DPG that is reduced by at least 15% relative to the reference standard (e.g; from about 15% to about 60%). In some embodiments, the blood concentration of 2,3-DPG is reduced by at least about 15%, by at least about 20%, by at least about 25%, by at least about 30%, by at least about 35%, by at least about 40%, by at least about 45%, by at least about 50%, by at least about 55%, by at least about 60%. In some embodiments, the analysis is performed by sample analysis of bodily fluid, such as blood, by e.g., mass spectroscopy, e.g. LC-MS.

The compounds described herein can activate mutant PKRs. Accordingly, a patient and/or subject can be selected for treatment using a compound described herein by first evaluating the patient and/or subject to determine whether the subject carries a mutation in PKR, and if the subject is determined to be carrying a mutation in PKR thus is in need of activation of the activity of the mutant PKR, then optionally administering to the subject a compound described herein. A subject can be evaluated as carrying a mutation in PKR using methods known in the art.

Methods of Synthesizing the Disclosed Compounds

The compounds of the present disclosure may be made by a variety of methods, including standard chemistry. Suitable synthetic routes are depicted in the schemes given below.

EXAMPLES

The following are illustrative, but non-limiting, examples of certain embodiments of the present disclosure. The synthetic schemes are presented for the synthesis of certain compounds herein disclosed. Definitions used in the following Schemes and elsewhere herein are:

ACN acetonitrile
AcOH acetic acid
AlCl$_3$ trichloroaluminum
Boc$_2$O di-tert-butyl dicarbonate
NaBH$_4$ sodium borohydride
Brine saturated aqueous sodium chloride solution
CDCl$_3$ deuterated chloroform
δ chemical shift
DCM dichloromethane or methylene chloride
DCE dichloroethane
DIEA N,N-diisopropylethylamine
DMAP N,N-dimethylaminopyridine
DMF N,N-dimethylformamide
DMSO dimethylsulfoxide
equiv equivalents
EtOAc ethyl acetate
H NMR proton nuclear magnetic resonance
HATU 2-(3H-[1,2,3]triazolo[4,5-b]pyridin-3-yl)-1,1,3,3-tetramethylisouronium hexafluorophosphate
HBTU O-(Benzotriazol-yl)N,N,N',N'-tetramethyluronium hexafluorophosphate
HPLC high pressure liquid chromatography
Hz hertz
LCMS liquid chromatography/mass spectrometry
(M+1) mass+1
MeOH methanol
NCS N-chlorosuccinimide
NaBH$_3$CN sodium cyanoborohydride
NaHCO$_3$ sodium bicarbonate
NaOH sodium hydroxide
Na$_2$SO$_4$ sodium sulfate
s-BuLi sec-butyllithium RT room temperature
Rt retention time
TEA triethylamine
TFA trifluoroacetic acid
TFAA trifluoroacetic anhydride
THF tetrahydrofuran
TLC thin layer chromatography
$ZnI_2$ zinc iodide Materials Unless otherwise noted, all materials were obtained from commercial suppliers and were used without further purification. Anhydrous solvents were obtained from Sigma-Aldrich (Milwaukee, WI) and used directly. All reactions involving air- or moisture-sensitive reagents were performed under a nitrogen atmosphere.

LCMS Method 1. Instruments: MS, Waters QDa Mass Detector; HPLC, Waters Acquity Binary Solvent Manager; UV, Waters Acquity PDA. Conditions: Mobile phase A, 95% water/5% acetonitrile with 0.1% formic acid; Mobile phase B, 95% acetonitrile/5% water with 0.09% formic acid. Column: Acquity UPLC BEH C18, 1.7 µm 2.1×50 mm. Column temperature, 35 QC. LC gradient: 5-100% B in 2.0 min, hold 100% to 2.2 min. LC Flow rate, 0.6 mL/min. UV wavelength, 220 nm and 254 nm, Ionization Mode: electrospray Ionization; pos/neg.

Intermediate 1: 2-(Benzofuran-5-ylsulfonyl)-1,2,3,4,5,6-hexahydropyrrolo[3,4-c]pyrrole hydrochloride

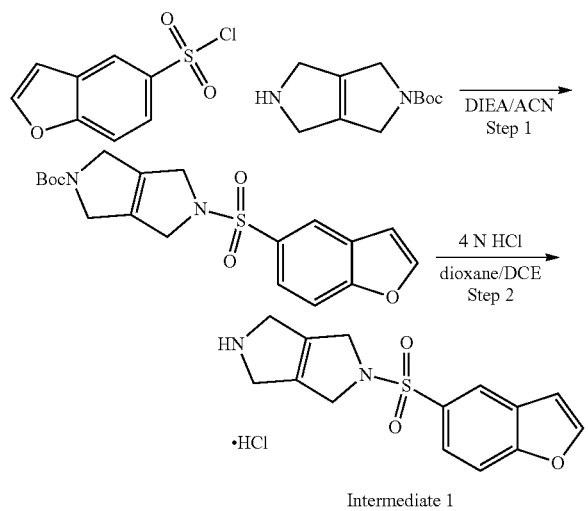

Intermediate 1

Step 1. tert-Butyl 5-(benzofuran-5-ylsulfonyl)-3,4,5,6-tetrahydropyrrolo[3,4-c]pyrrole-2(1H)-carboxylate To a solution of tert-butyl 3,4,5,6-tetrahydropyrrolo[3,4-c]pyrrole-2(1H)-carboxylate (0.7 g, 3.33 mmol) in acetonitrile (20 mL) and DIEA (1.70 mL, 9.76 mmol) was added benzofuran-5-sulfonyl chloride (17.48 ml, 3.50 mmol) in 1,4 dioxane (17 mL). The resulting mixture was stirred at RT overnight. The reaction mixture was worked up with saturated ammonium chloride solution and EtOAc. The combined organics were washed with brine, dried over $Na_2SO_4$, filtered off and concentrated under reduced pressure to give tert-butyl 5-(benzofuran-5-ylsulfonyl)-3,4,5,6-tetrahydropyrrolo[3,4-c]pyrrole-2(1H)-carboxylate (1.3 g, 3.33 mmol, 100%) as an oil. LCMS: m/z=413 [M+Na]$^+$.

Step 2. 2-(Benzofuran-5-ylsulfonyl)-1,2,3,4,5,6-hexahydropyrrolo[3,4-c]pyrrole hydrochloride Tert-butyl 5-(benzofuran-5-ylsulfonyl)-3,4,5,6-tetrahydropyrrolo[3,4-c]pyrrole-2(1H)-carboxylate (1.3 g, 3.33 mmol) was dissolved in a mixture of 1,4-dioxane (0.500 mL), DCE (0.25 mL) and 4 M HCl in 1,4-dioxane (0.125 mL) and the reaction was heated at 50° C. for 2 h. The solvents were evaporated under reduced pressure and the reaction mixture was azeotropically dried with toluene and dried further under vacuum overnight to give 2-(benzofuran-5-ylsulfonyl)-1,2,3,4,5,6-hexahydropyrrolo[3,4-c]pyrrole hydrochloride (0.95 mg, 3.33 mmol, 100%). LCMS: m/z=291 [M+H]$^+$.

Intermediate 2: 1-(6-((3,4,5,6-Tetrahydropyrrolo[3,4-c]pyrrol-2(1H)-yl)sulfonyl)-2,3-dihydro-4H-benzo[b][1,4]oxazin-4-yl)ethan-1-one

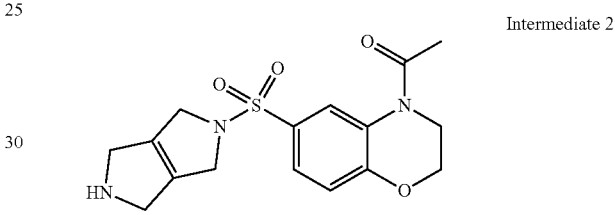

Intermediate 2

Prepared as described for Intermediate 1, using the appropriate synthetic precursors. 94% overall yield LCMS: m/z=350 [M+H]$^+$.

Intermediate 3: 2-(4-Fluorophenylsulfonyl)-1,2,3,4,5,6-hexahydropyrrolo[3,4-c]pyrrole, TFA Salt

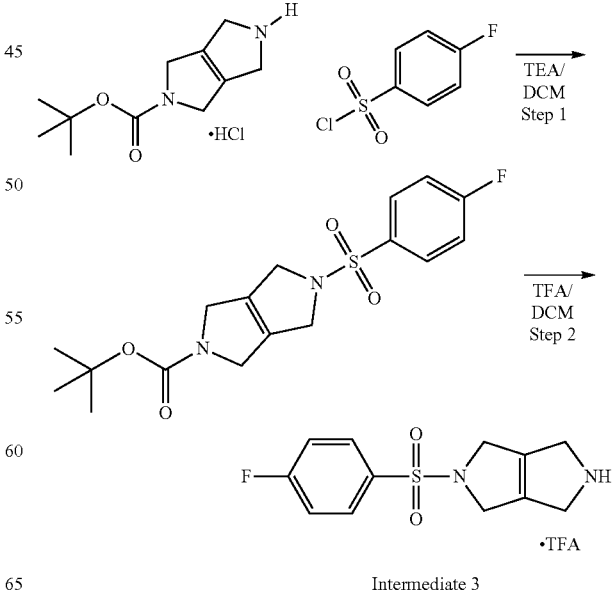

Intermediate 3

Step 1. tert-Butyl 5-(4-fluorophenylsulfonyl)-3,4,5,6-tetrahydropyrrolo[3,4-c]pyrrole-2(1H)-carboxylate A mixture of 4-fluorobenzene-1-sulfonyl chloride (2.366 g, 12.16 mmol), tert-butyl 3,4,5,6-tetrahydropyrrolo[3,4-c]pyrrole-2(1H)-carboxylate hydrochloride (2.5 g, 10.13 mmol) and triethylamine (4.24 mL, 30.4 mmol) in DCM (50 mL) was stirred at RT overnight. The solvent was removed under reduced pressure and the residue was taken up in EtOAc, washed with water twice, and dried over sodium sulfate. The crude material was purified on column chromatography on silica gel to afford tert-butyl 5-(4-fluorophenylsulfonyl)-3,4,5,6-tetrahydropyrrolo[3,4-c]pyrrole-2(1H)-carboxylate (2.5 g, 6.79 mmol, 67%). 1H NMR (300 MHz, CDCl3) δ ppm 7.73-7.92 (m, 2H), 7.14-7.32 (m, 2H), 3.93-4.19 (m, 8H), 1.40 (s, 9H).

Step 2. 2-(4-Fluorophenylsulfonyl)-1,2,3,4,5,6-hexahydropyrrolo[3,4-c]pyrrole, TFA Salt A solution of tert-butyl 5-(4-fluorophenylsulfonyl)-3,4,5,6-tetrahydropyrrolo[3,4-c]pyrrole-2(1H)-carboxylate (2.5 g, 6.79 mmol) in DCM/TFA (1:1, 80 mL) was stirred at RT for 3 days. The volatiles were removed under reduced pressure, the residue was treated with ether, filtered and dried under reduced pressure to give 2-(4-fluorophenylsulfonyl)-1,2,3,4,5,6-hexahydropyrrolo[3,4-c]pyrrole, TFA salt (2.48 g, 6.54 mmol, 96%). 1H NMR (300 MHz, DMSO-d6) δ ppm 9.57 (br s, 1H), 7.82-8.06 (m, 2H), 7.32-7.52 (m, 2H), 3.69-4.27 (m, 8H).

Intermediate 4: 2-(Pyridin-2-ylsulfonyl)-1,2,3,4,5,6-hexahydropyrrolo[3,4-c]pyrrole, TFA Salt

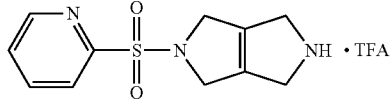

Intermediate 4

Prepared as described for Intermediate 3, using the appropriate synthetic precursors.

Step 1. tert-Butyl 5-(pyridine-2-sulfonyl)-1H,2H,3H,4H,5H,6H-pyrrolo[3,4-c]pyrrole-2-carboxylate Isolated as an orange solid (100 mg). The material was used without further purification. LCMS: m/z=352 [M+H]+.

Step 2. 2-(Pyridin-2-ylsulfonyl)-1,2,3,4,5,6-hexahydropyrrolo[3,4-c]pyrrole, TFA Salt Isolated as a white solid (90 mg, 87%). LCMS: m/z=252 [M+H]+.

Intermediate 5: 2-(6-(Trifluoromethyl)pyridin-2-ylsulfonyl)-1,2,3,4,5,6-hexahydropyrrolo[3,4-c]pyrrole, TFA Salt

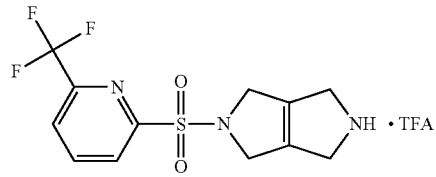

Intermediate 5

Prepared as described for Intermediate 3, using the appropriate synthetic precursors.

Step 1. tert-Butyl 5-[6-(trifluoromethyl)pyridine-2-sulfonyl]-1H,2H,3H,4H,5H,6H-pyrrolo[3,4-c]pyrrole-2-carboxylate Isolated as a light yellow solid (25 mg, 25%).

Step 2. 2-(6-(Trifluoromethyl)pyridin-2-ylsulfonyl)-1,2,3,4,5,6-hexahydropyrrolo[3,4-c]pyrrole, TFA Salt Isolated as a brown oil (21 mg, 81%).

Intermediate 6: 6-((3,4,5,6-Tetrahydropyrrolo[3,4-c]pyrrol-2(1H)-yl)sulfonyl)benzo[d]thiazole hydrochloride

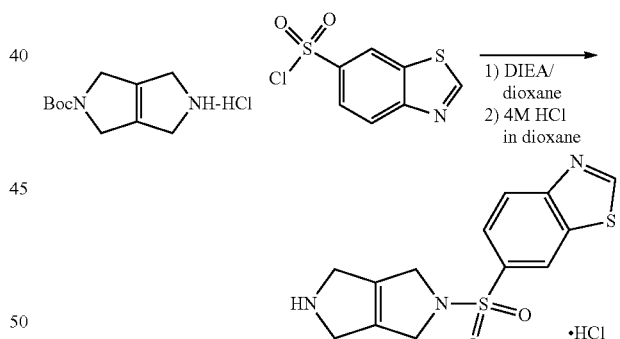

Intermediate 6

To a 50 mL round-bottomed flask was added tert-butyl 3,4,5,6-tetrahydropyrrolo[3,4-c]pyrrole-2(1H)-carboxylate hydrochloride (0.5 g, 2.026 mmol), DIEA (1.059 ml, 6.08 mmol), and dioxane (10 mL) to give a brown suspension. Benzo[d]thiazole-6-sulfonyl chloride (0.497 g, 2.128 mmol) was added. The reaction was heated at 50° C. with stirring for 2 hours. The volatiles were removed under reduced pressure. The residue was resuspended in dioxane (10 mL) and 4 M HCl in dioxane (5.07 ml, 20.26 mmol) was added. The reaction was heated at 50° C. with stirring for 2 hours. The volatiles were removed under reduced pressure to give 6-((3,4,5,6-tetrahydropyrrolo[3,4-c]pyrrol-2(1H)-yl)sulfonyl)benzo[d]thiazole hydrochloride (0.640 g, 1.865 mmol, 92%) as a brown oil that was used in the next step without further purification. LCMS: m/z=307.9 [M+H]+.

Intermediate 7: 2-((4-(Difluoromethoxy)phenyl) sulfonyl)-1,2,3,4,5,6-hexahydropyrrolo[3,4-c]pyrrole hydrochloride

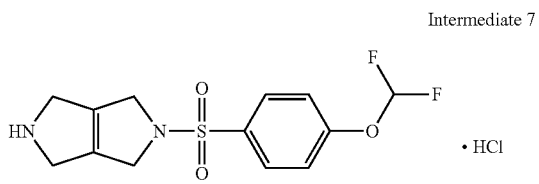 [SMILES: O=S(=O)(c1ccc(OC(F)F)cc1)N1CC2=C(CNC2)C1 ; "· HCl"]

Intermediate 7

Prepared according to the procedure for Intermediate 6, using the appropriate synthetic precursors. Obtained (0.652 g, 1.848 mmol, 91%). LCMS: m/z=317.1 [M+H]+.

Intermediate 8: 2-(3,4-Dihydro-2H-1,4-benzoxazin-6-yl)-2-hydroxyacetic Acid

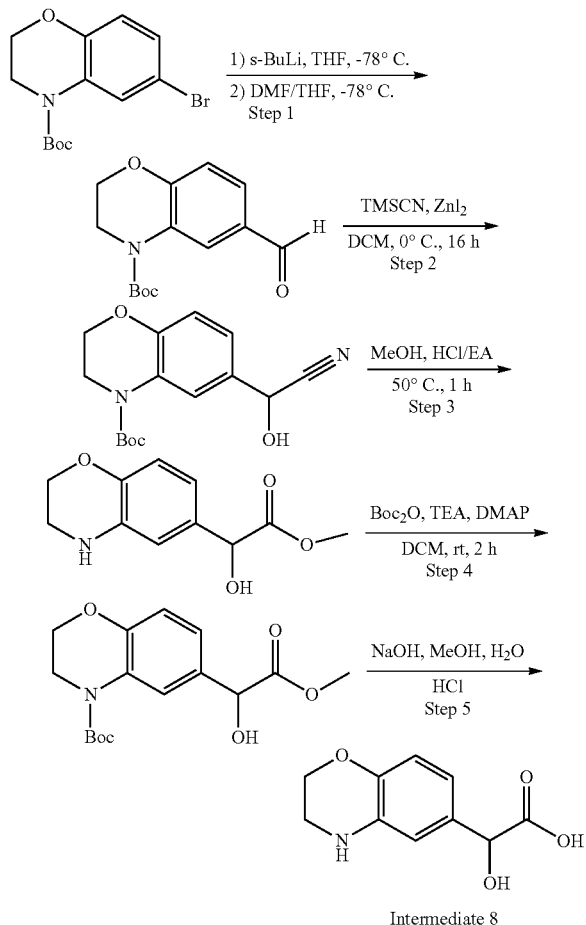

Intermediate 8

Step 1. tert-Butyl 6-formyl-3,4-dihydro-2H-1,4-benzoxazine-4-carboxylate

To a 50-mL 3-necked round-bottom flask purged and maintained with an inert atmosphere of nitrogen was added a solution of tert-butyl 6-bromo-3,4-dihydro-2H-1,4-benzoxazine-4-carboxylate (628 mg, 2.00 mmol, 1.00 equiv) in tetrahydrofuran (20 mL). The mixture was stirred at −78° C. and a solution of (2-methylpropyl)lithium (1.3 M in hexanes, 1.7 mL, 1.10 equiv) in tetrahydrofuran (10 mL) was added dropwise. The reaction mixture was stirred for 15 min at −78° C., then a solution of DMF (292 mg, 4.00 mmol, 2.00 equiv) in THF was added dropwise at −78° C. The reaction mixture was then stirred for 2 h at RT. Water (1 mL) was added, then the volatiles were removed under reduced pressure. The residue was dissolved in ethyl acetate (20 mL), washed with saturated aqueous sodium chloride solution (3×5 mL), dried over anhydrous sodium sulfate, filtered and concentrated under vacuum. The residue was purified on a silica gel TLC plate eluted with ethyl acetate/petroleum ether (1:3) to provide tert-butyl 6-formyl-3,4-dihydro-2H-1,4-benzoxazine-4-carboxylate (0.3 g, 57%) as a yellow solid. LCMS: m/z=305 [M+1+CH₃CN]+.

Step 2. tert-Butyl 6-[cyano(hydroxy)methyl]-3,4-dihydro-2H-1,4-benzoxazine-4-carboxylate A solution of tert-butyl 6-formyl-3,4-dihydro-2H-1,4-benzoxazine-4-carboxylate (1 g, 3.80 mmol) in dichloromethane (20 mL) was stirred at 0° C. in a 50-mL round-bottom flask. Trimethylsilanecarbonitrile (1.2 g, 12.10 mmol) was added dropwise at 0° C., followed by addition of ZnI₂ (120 mg, 0.38 mmol). The reaction solution was stirred for 16 h at RT and then concentrated under reduced pressure. The residue was diluted with ethyl acetate (50 mL), washed with brine (3×15 mL), dried over anhydrous sodium sulfate, filtered, and concentrated under reduced pressure to provide tert-butyl 6-[cyano(hydroxy)methyl]-3,4-dihydro-2H-1,4-benzoxazine-4-carboxylate (1.16 g) as a light brown oil. The material was used without further purification. LCMS: m/z=291 [M+1]+.

Step 3. Methyl 2-(3,4-dihydro-2H-1, 4-benzoxazin-6-yl)-2-hydroxyacetate

A solution of tert-butyl 6-[cyano(hydroxy)methyl]-3,4-dihydro-2H-1,4-benzoxazine-4-carboxylate (1 g, 3.44 mmol, 1.00 equiv) in methanol (10 mL) in a 25 mL round-bottom flask was treated dropwise with a saturated solution of HCl in ethyl acetate (15 mL). The reaction mixture was stirred for 1 h at 50° C. The volatiles were removed under reduced pressure and the residue was diluted with water (5 mL). The pH was adjusted to 8 with saturated aqueous sodium carbonate solution. The aqueous phase was extracted with ethyl acetate (50 mL), dried over anhydrous sodium sulfate, filtered and concentrated under reduced pressure. The residue was purified by column chromatography on silica gel, eluting with ethyl acetate/petroleum ether (1:1) to provide methyl 2-(3,4-dihydro-2H-1,4-benzoxazin-6-yl)-2-hydroxyacetate (320 mg, 42%) as a light brown oil. LCMS: m/z=265 [M+1+CH₃CN]+.

Step 4. tert-Butyl 6-(1-hydroxy-2-methoxy-2-oxoethyl)-3,4-dihydro-2H-1,4-benzoxazine-4-carboxylate A mixture of methyl 2-(3,4-dihydro-2H-1,4-benzoxazin-6-yl)-2-hydroxyacetate (240 mg, 1.08 mmol, 1.00 equiv), dichloromethane (3 mL), di-tert-butyl dicarbonate (281 mg, 1.29 mmol, 1.20 equiv), TEA (217 mg, 2.14 mmol, 2.00 equiv) and DMAP (13 mg, 0.11 mmol, 0.10 equiv) was stirred for 2 h at RT in a 25-mL round-bottom flask. The volatiles were removed under reduced pressure and the residue was diluted with ethyl acetate (30 mL), washed with brine (3×5 mL), dried over sodium sulfate, filtered and concentrated under reduced pressure. The residue was applied onto a silica gel column and eluted with $CH_3CN$:$H_2O$ (1:4) to provide tert-butyl 6-(1-hydroxy-2-methoxy-2-oxoethyl)-3,4-dihydro-2H-1,4-benzoxazine-4-carboxylate (210 mg, 60%) as a brown oil. LCMS: m/z=365 $[M+1+CH_3CN]^+$.

Step 5. 2-(3,4-Dihydro-2H-1,4-benzoxazin-6-yl)-2-hydroxyacetic acid

A mixture of tert-butyl 6-(1-hydroxy-2-methoxy-2-oxoethyl)-3,4-dihydro-2H-1,4-benzoxazine-4-carboxylate (110 mg, 0.34 mmol, 1.00 equiv), methanol (1.6 mL), water (0.4 mL) and sodium hydroxide (27 mg, 0.68 mmol, 2.00 equiv) in an 8-mL vial was stirred for 2 h at RT. The volatiles were removed under reduced pressure. The residue was diluted with water (5 mL) and the pH of the solution was adjusted to 4 with concentrated aqueous HCl solution, then the volatiles were removed under reduced pressure to provide 2-(3,4-dihydro-2H-1,4-benzoxazin-6-yl)-2-hydroxyacetic acid (120 mg) as a light brown solid. The material was used without further purification. LCMS: m/z=210 $[M+1]^+$.

Intermediate 9: 2-[2-[(tert-Butoxy)carbonyl]-1,2,3,4-tetrahydroisoquinolin-7-yl]-2-hydroxyacetic Acid

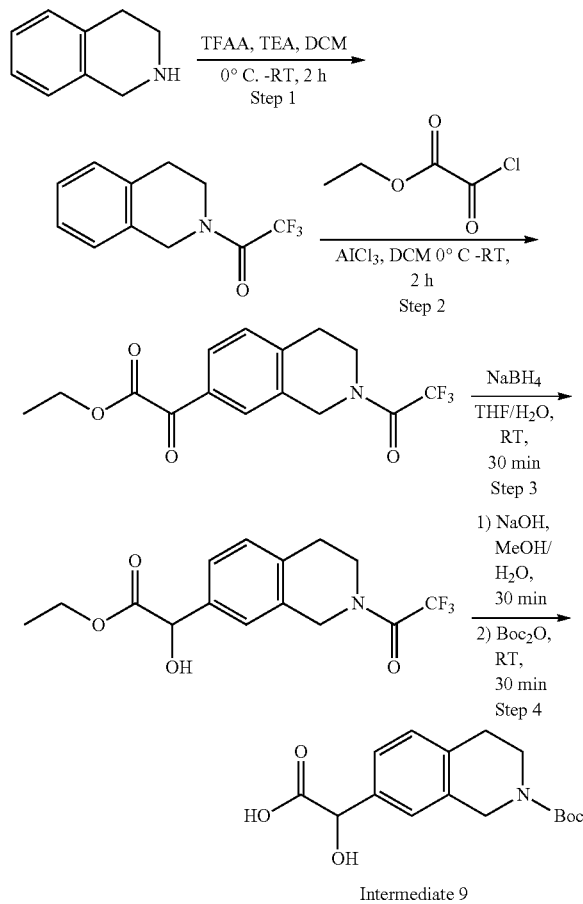

Intermediate 9

Step 1. 2,2,2-Trifluoro-1-(1,2,3,4-tetrahydroisoquinolin-2-yl)ethan-1-one

A mixture of 1,2,3,4-tetrahydroisoquinoline (1.0 g, 7.51 mmol), dichloromethane (15 mL) and TEA (1.1 g, 10.87 mmol) in a 50-mL 3-necked round-bottom flask was stirred for 10 min at 0° C. TFAA (1.9 g, 9.05 mmol) was added. The solution was stirred for 10 min at 0° C. then an additional 2 h at RT. The reaction mixture was concentrated under vacuum. The residue was purified by flash chromatography on silica gel and was eluted with ethyl acetate/petroleum ether (1:10) to provide 2,2,2-trifluoro-1-(1,2,3,4-tetrahydroisoquinolin-2-yl)ethan-1-one (1.49 g, 87%) as a yellow liquid. LCMS: m/z=271 $[M+CH_3CN+H]^+$.

Step 2. Ethyl 2-oxo-2-[2-(trifluoroacetyl)-1,2,3,4-tetrahydroisoquinolin-7-yl]acetate To a 50-mL 3-necked round-bottom flask purged and maintained with an inert atmosphere of nitrogen was added dichloromethane (30 mL) and $AlCl_3$ (7.0 g, 52.6 mmol). The reaction mixture was stirred for 10 min at 0° C. in a water/ice bath, then 2,2,2-trifluoro-1-(1,2,3,4-tetrahydroisoquinolin-2-yl)ethan-1-one (3.0 g, 13.09 mmol) and ethyl 2-chloro-2-oxoacetate (2.46 g, 18.02 mmol) were added. The reaction mixture was stirred for an additional 2 h at RT. The reaction mixture was cooled to 0° C. in a water/ice bath, then quenched by the addition of 2 N HCl solution (aqueous 5 mL). The solution was extracted with ethyl acetate and the extract was dried over anhydrous sodium sulfate, filtered and concentrated under vacuum. The residue was purified by flash column chromatography on silica gel and eluted with ethyl acetate/petroleum ether (1:10) to provide ethyl 2-oxo-2-[2-(trifluoroacetyl)-1,2,3,4-tetrahydroisoquinolin-7-yl]acetate (4.1 g, 95%) as a yellow oil. LCMS: m/z=330 $[M+H]^+$.

Step 3. Ethyl 2-hydroxy-2-[2-(trifluoroacetyl)-1,2,3,4-tetrahydroisoquinolin-7-yl]acetate A mixture of ethyl 2-oxo-2-[2-(trifluoroacetyl)-1,2,3,4-tetrahydroisoquinolin-7-yl]acetate (1.0 g, 3.04 mmol, 1.00 equiv), tetrahydrofuran (5 mL) and water (2.5 mL) in a 10-mL round-bottom flask was treated with $NaBH_4$ (56.2 g, 1.49 mol, 0.50 equiv). The reaction mixture was stirred for 30 min at RT, then cooled to 0° C. with a water/ice bath. The reaction was quenched by the addition of water (1 mL) and extracted with ethyl acetate (3×30 mL). The combined extracts were dried over anhydrous sodium sulfate, filtered, and concentrated under vacuum. The residue was purified by flash chromatography on silica gel eluted with ethyl acetate/petroleum ether (1:5) to provide ethyl 2-hydroxy-2-[2-(trifluoroacetyl)-1,2,3,4-tetrahydroisoquinolin-7-yl]acetate (0.93 g, 92%) as a light yellow oil. $^1$H NMR (300 MHz, $CDCl_3$): δ ppm 7.31-7.14 (m, 3H), 5.13 (d, J=6.0 Hz, 1H), 4.79-4.74 (m, 2H), 4.34-4.06 (m, 2H), 3.90-3.80 (m, 2H), 3.53 (d, J=6.0 Hz, 1H), 2.97-2.92 (m, 2H), 1.26 (t, J=3.0 Hz, 3H).

Step 4. 2-[2-[(tert-Butoxy)carbonyl]-1,2,3,4-tetrahydroisoquinolin-7-yl]-2-hydroxyacetic acid A solution of ethyl 2-hydroxy-2-[2-(trifluoroacetyl)-1,2,3,4-tetrahydroisoquinolin-7-yl]acetate (990 mg, 2.99 mmol, 1.00 equiv) in methanol (4 mL) and water (1 mL) in a 10-mL round-bottom flask was treated with sodium hydroxide (240 mg, 6.00 mmol, 2.00 equiv). The reaction mixture was stirred for 30 min at RT, then di-tert-butyl dicarbonate (1.3 g, 5.96 mmol, 2.00 equiv) was added and the reaction mixture was stirred for an additional 30 min at RT. The pH value of the solution was adjusted to 6 with 2 N aqueous HCl solution. The reaction mixture was extracted with ethyl acetate, and the extract was concentrated under vacuum. The residue was applied onto a silica gel column and eluted with dichloromethane/methanol (5:1) to provide 2-[2-[(tert-butoxy)carbonyl]-1,2,3,4-tetrahydroisoquinolin-7-yl]-2-hydroxyacetic acid (960 mg) as a white solid. The material was used without further purification.

Intermediate 10: (R)-2-hydroxy-2-phenyl-1-(3,4,5,6-tetrahydropyrrolo[3,4-c]pyrrol-2(1H)-yl)ethan-1-one, TFA Salt Step 2. (R)-2-hydroxy-2-phenyl-1-(3,4,5,6-tetrahydropyrrolo[3,4-c]pyrrol-2(1H)-yl)ethan-1-one, TFA Salt To an 8-mL vial was added tert-butyl 5-[(2R)-2-hydroxy-2-phenylacetyl]-1H,2H,3H,4H,5H,6H-pyrrolo[3,4-c]pyrrole-2-carboxylate (102 mg, 0.30 mmol, 1.00 equiv), DCM (2.00 mL) and TFA (2.00 mL). The solution was stirred for 2 h at RT, then concentrated under vacuum to provide (R)-2-hydroxy-2-phenyl-1-(3,4,5,6-tetrahydropyrrolo[3,4-c]pyrrol-2(1H)-yl)ethan-1-one, TFA salt (139 mg) as a brown oil. The material was used without further purification. LCMS: m/z=245 [M+1]$^+$.

Intermediate 11: (R)-2-hydroxy-2-phenyl-1-(3,4,5,6-tetrahydropyrrolo[3,4-c]pyrrol-2(1H)-yl)ethan-1-one hydrochloride

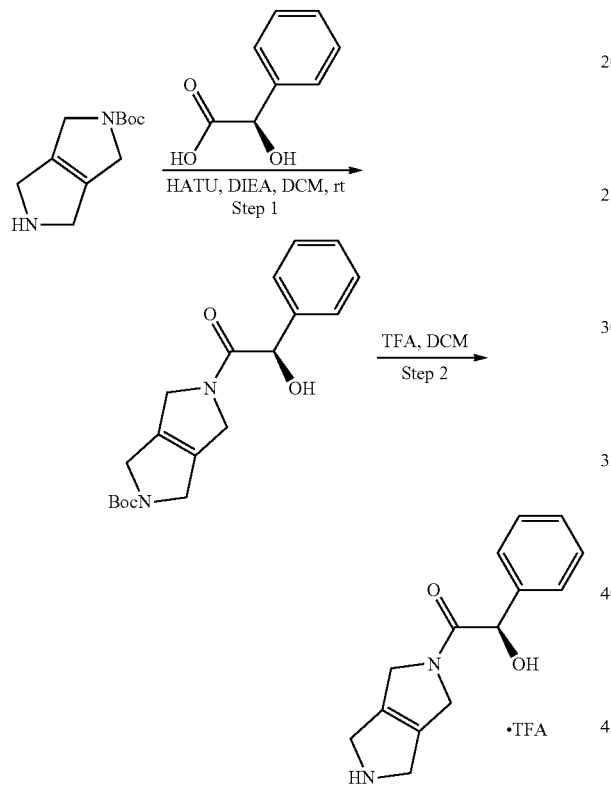

Intermediate 10

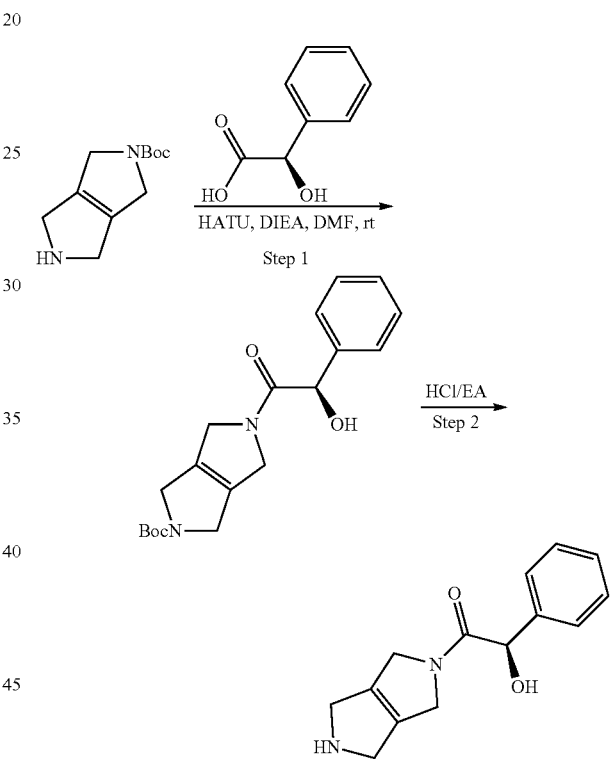

Intermediate 11

Step 1. tert-Butyl 5-[(2R)-2-hydroxy-2-phenylacetyl]-1H, 2H, 3H,4H,5H,6H-pyrrolo[3,4-c]pyrrole-2-carboxylate To an 8-mL vial was added tert-Butyl 1H,2H,3H,4H,5H,6H-pyrrolo[3,4-c]pyrrole-2-carboxylate (120 mg, 0.57 mmol, 1.00 equiv), DCM (2.00 mL), (2R)-2-hydroxy-2-phenylacetic acid (104 mg, 0.68 mmol, 1.20 equiv), DIEA (221 mg, 1.71 mmol, 3.00 equiv) and HATU (238 mg, 0.63 mmol, 1.10 equiv). The solution was stirred for 3 h at RT, then concentrated under vacuum. The residue was purified by silica gel column chromatography, eluting with ethyl acetate/petroleum ether (1:1) to provide tert-butyl 5-[(2R)-2-hydroxy-2-phenylacetyl]-1H,2H,3H,4H,5H,6H-pyrrolo[3,4-c]pyrrole-2-carboxylate (102 mg, 52%) as a light yellow oil. LCMS: m/z=345 [M+1]$^+$.

Step 1. tert-Butyl 5-[(2R)-2-hydroxy-2-phenylacetyl]-1H,2H,3H,4H,5H,6H-pyrrolo[3,4-c]pyrrole-2-carboxylate tert-Butyl 1H,2H,3H,4H,5H,6H-pyrrolo[3,4-c]pyrrole-2-carboxylate (200 mg, 0.95 mmol, 1.00 equiv), (2R)-2-hydroxy-2-phenylacetic acid (144 mg, 0.95 mmol, 1.00 equiv), HATU (532 mg, 1.40 mmol, 1.50 equiv), DIEA (181 mg, 1.40 mmol, 1.50 equiv) and DMF (5.00 mL) were combined in a 25-mL round-bottom flask. The solution was stirred for 2 h at RT. The reaction was then quenched by the addition of 20 mL of water. The solution was extracted with 3×15 mL of ethyl acetate and washed with 15 mL of brine. The organic phase was dried over anhydrous sodium sulfate and concentrated under vacuum. The residue was purified by silica gel column chromatography, eluting with ethyl acetate/petroleum ether (1:2) to provide tert-butyl 5-[(2R)-2-hydroxy-2-phenylacetyl]-1H,2H,3H,4H,5H,6H-pyrrolo[3,4-c]pyrrole-2-carboxylate (120 mg, 37%) as a light yellow solid.

Step 2. (R)-2-hydroxy-2-phenyl-1-(3,4,5,6-tetrahydropyrrolo[3,4-c]pyrrol-2(1H)-yl)ethan-1-one hydrochloride To a 25-mL round-bottom flask was added tert-butyl 5-[(2R)-2-hydroxy-2-phenylacetyl]-1H,2H,3H,4H,5H,6H-pyrrolo[3,4-c]pyrrole-2-carboxylate (120 mg, 0.35 mmol, 1.00 equiv) and ethyl acetate freshly saturated with hydrogen chloride (15.0 mL). The solution was stirred overnight at RT. The solids were filtered out and dried under vacuum to provide (R)-2-hydroxy-2-phenyl-1-(3,4,5,6-tetrahydropyrrolo[3,4-c]pyrrol-2(1H)-yl)ethan-1-one hydrochloride (85 mg, 87%) as a gray solid.

Example 1-1: N-(2-(5-(benzofuran-5-ylsulfonyl)-3,4,5,6-tetrahydropyrrolo[3,4-c]pyrrol-2(1H)-yl)-2-oxoethyl)methanesulfonamide

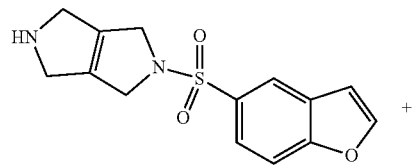

+

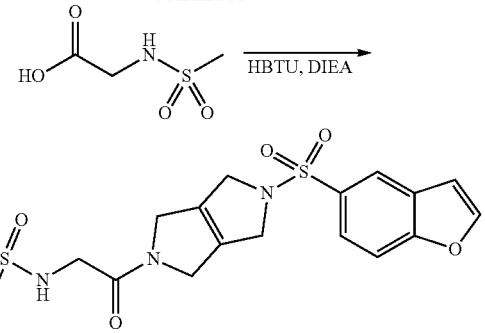

Example 1-1

To a solution of 2-(benzofuran-5-ylsulfonyl)-1,2,3,4,5,6-hexahydropyrrolo[3,4-c]pyrrole hydrochloride (1.07 g, 3.27 mmol) in acetonitrile with 10% DIEA (22 mL) was added (methylsulfonyl)glycine (561 mg, 3.66 mmol) in 1,4-dioxane with 5% DIEA (20 mL), followed by HBTU (1.263 g, 3.33 mmol) in acetonitrile (20 mL). The resulting mixture was stirred at RT overnight. Volatiles were evaporated under reduced pressure and the residue was partitioned between EtOAc and 1 N aqueous NaOH solution. The combined organic phases were washed with brine, dried over $Na_2SO_4$, filtered, and the volatiles were evaporated under reduced pressure. The residue was purified by prep HPLC to give N-(2-(5-(benzofuran-5-ylsulfonyl)-3,4,5,6-tetrahydropyrrolo[3,4-c]pyrrol-2(1H)-yl)-2-oxoethyl)methanesulfonamide.

The Examples in Table 2 below were prepared according to the procedure outlined above for Example 1-1, using the appropriate synthetic precursors.

TABLE 2

| Example | Structure Name | LCMS (m/z) |
|---|---|---|
| 1-2 | ![structure] 1-(5-(Benzofuran-5-ylsulfonyl)-3,4,5,6-tetrahydropyrrolo[3,4-c]pyrrol-2(1H)-yl)-4,4-difluorobutan-1-one | 397 |
| 1-3 | ![structure] 1-(5-(Benzofuran-5-ylsulfonyl)-3,4,5,6-tetrahydropyrrolo[3,4-c]pyrrol-2(1H)-yl)-2-hydroxy-2-methylpropan-1-one | 377.16 |

TABLE 2-continued

| Example | Structure Name | LCMS (m/z) |
|---|---|---|
| 1-4 | (5-(Benzofuran-5-ylsulfonyl)-3,4,5,6-tetrahydropyrrolo[3,4-c]pyrrol-2(1H)-yl)(1-hydroxycyclopropyl)methanone | 375.19 |
| 1-5 | 1-(5-(Benzofuran-5-ylsulfonyl)-3,4,5,6-tetrahydropyrrolo[3,4-c]pyrrol-2(1H)-yl)-3-(dimethylamino)propan-1-one | 390 |
| 1-6 | 4-[5-(1-Benzofuran-5-sulfonyl)-1H,2H,3H,4H,5H,6H-pyrrolo[3,4-c]pyrrol-2-yl]-4-oxo-2-(pyridin-3-yl)butanenitrile | 449.1 |

Example 2-1: (1-(Aminomethyl)cyclopropyl)(5-(benzofuran-5-ylsulfonyl)-3,4,5,6-tetrahydropyrrolo[3,4-c]pyrrol-2(1H)-yl)methanone

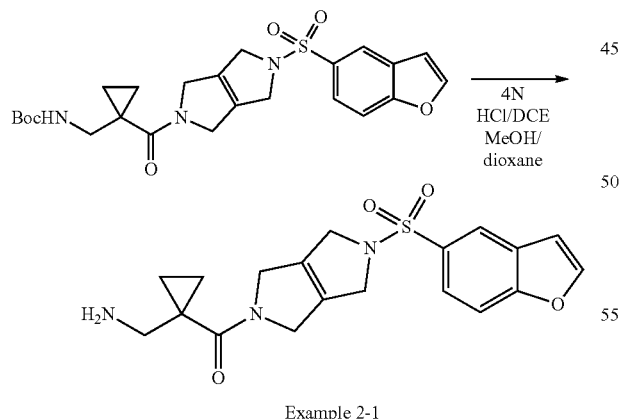

Example 2-1

To a solution of tert-butyl ((1-(5-(benzofuran-5-ylsulfonyl)-1,2,3,4,5,6-hexahydropyrrolo[3,4-c]pyrrole-2-carbonyl)cyclopropyl)methyl)carbamate (14.6 mg, 0.03 mmol) in a 3:1 mixture of DCE/MeOH (0.150 mL) was added 4 M HCl (75 µl, 0.300 mmol) in 1,4-dioxane and the reaction was agitated at RT for 2 hours. The reaction was concentrated and the residue partitioned between EtOAc and saturated aqueous $NaHCO_3$. The combined organics were washed with brine and dried over $Na_2SO_4$. The crude material was purified by prep HPLC to yield (1-(aminomethyl)cyclopropyl)(5-(benzofuran-5-ylsulfonyl)-3,4,5,6-tetrahydropyrrolo[3,4-c]pyrrol-2(1H)-yl)methanone. LCMS: m/z=388 [M+H]+.

Example 3-1: 5-(Benzofuran-5-ylsulfonyl)-N-((tetrahydrofuran-2-yl)methyl)-3,4,5,6-tetrahydropyrrolo[3,4-c]pyrrole-2(1H)-carboxamide

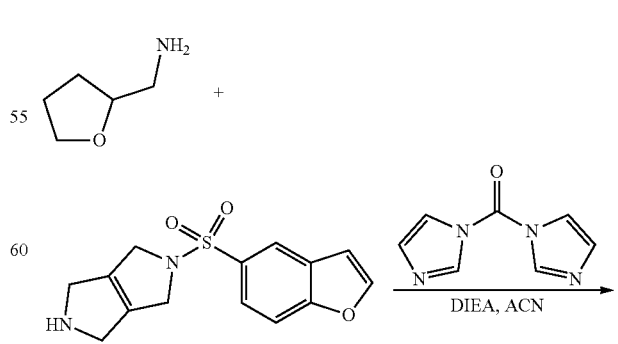

-continued

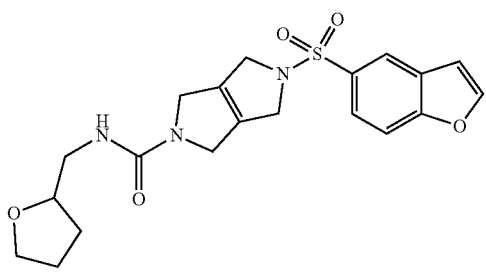

Example 3-1

To a 0.2 M solution of (tetrahydrofuran-2-yl)methanamine (320 μl, 0.064 mmol) in acetonitrile was added di(1H-imidazol-1-yl)methanone (15.57 mg, 0.096 mmol). The mixture was agitated at RT for 2 hours, then a 0.2 M solution of 2-(benzofuran-5-ylsulfonyl)-1,2,3,4,5,6-hexahydropyrrolo[3,4-c]pyrrole (330 μl, 0.066 mmol) in $CH_3CN$ with 10% DIEA was added and the mixture was agitated at 50° C. overnight. The solvent was evaporated and the residue was dissolved in 500 μL DMSO and purified by prep HPLC to yield 5-(benzofuran-5-ylsulfonyl)-N-((tetrahydrofuran-2-yl)methyl)-3,4,5,6-tetrahydropyrrolo[3,4-c]pyrrole-2(1H)-carboxamide (12 mg, 0.029 mmol, 44.9% yield). LCMS: m/z=418 [M+H]$^+$.

The Examples in Table 3 below were prepared according to the procedure outlined above for Example 3-1, using the appropriate synthetic precursors.

TABLE 3

| Example | Structure Name | LCMS (m/z) |
|---|---|---|
| 3-2 | 5-(Benzofuran-5-ylsulfonyl)-N-(tetrahydrofuran-3-yl)-3,4,5,6-tetrahydropyrrolo[3,4-c]pyrrole-2(1H)-carboxamide | 404 |
| 3-3 | (R)-5-(benzofuran-5-ylsulfonyl)-N-(1-methoxypropan-2-yl)-3,4,5,6-tetrahydropyrrolo[3,4-c]pyrrole-2(1H)-carboxamide | 406 |
| 3-4 | 5-(Benzofuran-5-ylsulfonyl)-N-(pyridin-3-ylmethyl)-3,4,5,6-tetrahydropyrrolo[3,4-c]pyrrole-2(1H)-carboxamide | 425 |

TABLE 3-continued

| Example | Structure Name | LCMS (m/z) |
|---|---|---|
| 3-5 | 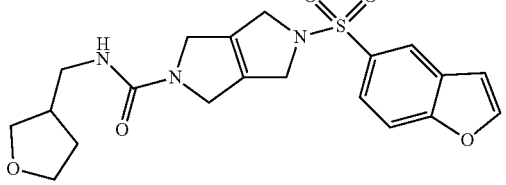<br>5-(Benzofuran-5-ylsulfonyl)-N-((tetrahydrofuran-3-yl)methyl)-3,4,5,6-tetrahydropyrrolo[3,4-c]pyrrole-2(1H)-carboxamide | 418 |

Example 4-1: (2R)-2-hydroxy-2-phenyl-1-[5-(pyridine-3-sulfonyl)-1H,2H,3H,4H,5H,6H-pyrrolo[3,4-c]pyrrol-2-yl]ethan-1-one

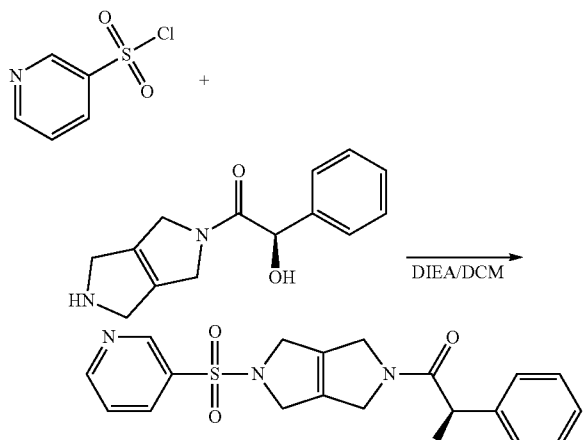

Example 4-1

To a solution of (R)-2-hydroxy-2-phenyl-1-(3,4,5,6-tetrahydropyrrolo[3,4-c]pyrrol-2(1H)-yl)ethan-1-one (113 mg, 0.462 mmol) and DIEA (0.242 mL, 1.385 mmol) in dichloromethane (6 mL) was added pyridine-3-sulfonyl chloride (54.3 mg, 0.462 mmol). The reaction mixture was stirred at room temperature for 4 hours. Dichloromethane was added to the reaction mixture and the organic phase was washed with water, saturated sodium bicarbonate and brine. The organic phase was concentrated and purified silica by flash column chromatography. (2R)-2-hydroxy-2-phenyl-1-[5-(pyridine-3-sulfonyl)-1H,2H,3H,4H,5H,6H-pyrrolo[3,4-c]pyrrol-2-yl]ethan-1-one was isolated. $^1$H NMR (300 MHz, CDCl$_3$): δ ppm 8.96 (d, J=1.5 Hz, 1H), 8.85 (dd, J1=1.8 Hz, J2=4.8 Hz, 1H), 8.19-8.23 (m, 1H), 7.63-7.67 (m, 1H), 7.29-7.34 (m, 5H), 5.63 (d, J=6.3 Hz 1H), 5.16 (d, J=6.3 Hz, 1H), 3.93-4.09 (m, 8H). LCMS: m/z=386 [M+H]$^+$.

The Example in Table 4 below were prepared according to the procedure outlined above for Example 4-1, using the appropriate synthetic precursors.

TABLE 4

| Example | Structure Name | LCMS (m/z) | $^1$H-NMR |
|---|---|---|---|
| 4-2 | 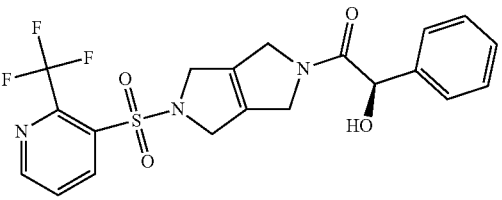<br>(R)-2-hydroxy-2-phenyl-1-(5-(2-(trifluoromethyl)pyridin-3-ylsulfonyl)-4,5-dihydropyrrolo[3,4-c]pyrrol-2(1H,3H,4H)-yl)ethanone | 454 | (300 MHz, CDCl$_3$, ppm): δ 8.87-8.86 (d, J = 2.7 Hz, 1H), 8.39 (d, J = 7.2 Hz, 1H), 7.68 (br s, 1H), 7.36 (s, 5H), 5.09 (br s, 1H), 4.38-4.11 (m, 8H), 3.69 (br s, 1H). |

Example 5-1: 5-(4-Fluorophenylsulfonyl)-N-(oxazol-5-ylmethyl)-3,4,5,6-tetrahydropyrrolo[3,4-c]pyrrole-2(1H)-carboxamide

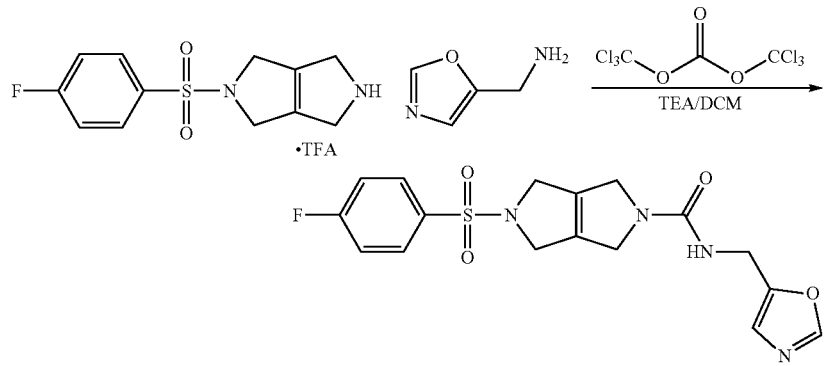

Example 5-1

In a 25 mL pear flask was added triphosgene (40.7 mg, 0.137 mmol) in DCM (5 ml) to give a colorless solution. The solution was cooled to −10° C. and a solution of oxazol-5-ylmethanamine (68.5 mg, 0.698 mmoL) and triethylamine (2.57 mmol) in DCM (10 mL) was added dropwise. The mixture was stirred at RT for 1 hour, then a solution of 2-(4-fluorophenylsulfonyl)-1,2,3,4,5,6-hexahydropyrrolo[3,4-c]pyrrole (TFA salt; 267 mg, 0.698 mmol) and triethylamine (2.54 mg, 2.52 mmol) in DCM (5 ml) was added. The mixture was stirred at RT for 5 hours. The reaction was diluted with methylene chloride and washed with aqueous NaOH (1 M), water, and brine. The organic phase was separated, dried with anhydrous magnesium sulfate, filtered and concentrated under reduced pressure. The crude material was purified by prep-HPLC to provide 5-(4-fluorophenylsulfonyl)-N-(oxazol-5-ylmethyl)-3,4,5,6-tetrahydropyrrolo[3,4-c]pyrrole-2(1H)-carboxamide (8 mg, 0.0204 mmol, 2.92%). $^1$H NMR (300 MHz, DMSO-d$_6$): δ ppm 8.39 (br d, J=1.76 Hz, 1H), 7.81-8.01 (m, 2H), 7.36-7.53 (m, 2H), 6.93 (brt, J=5.86 Hz, 1H), 6.18-6.26 (m, 1H), 4.32 (br d, J=5.57 Hz, 2H), 3.90-4.12 (m, 8H). LCMS: m/z=393.06 [M+H]$^+$.

Example 5-2: 5-(4-Fluorophenylsulfonyl)-N-((5-methyl-1,3,4-oxadiazol-2-yl)methyl)-3,4,5,6-tetrahydropyrrolo[3,4-c]pyrrole-2(1H)-carboxamide

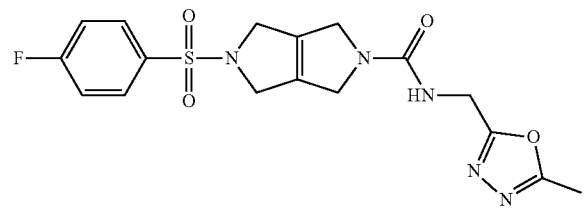

Example 5-2

Prepared as described for Example 5-1, using the appropriate synthetic precursors. (20 mg, 0.050 mmol, 7%). $^1$H NMR (300 MHz, DMSO-d$_6$): δ ppm 7.88 (dd, J=8.79, 5.28 Hz, 2H), 7.43 (t, J=8.79 Hz, 2H), 6.87-7.05 (m, 1H), 4.34 (br d, J=5.57 Hz, 2H), 4.04 (m, 4H), 3.85-3.96 (m, 4H), 2.40 (s, 3H). LCMS: m/z=408.10 [M+H]$^+$.

Example 6-1: (5-(benzo[d]thiazol-6-ylsulfonyl)-3,4,5,6-tetrahydropyrrolo[3,4-c]pyrrol-2(1H)-yl)(morpholino)methanone

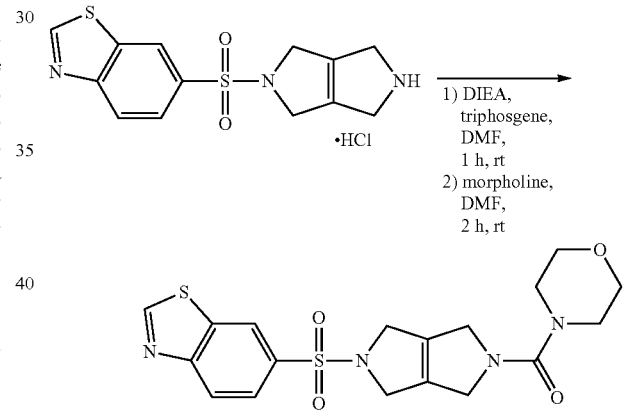

Example 6-1

To a 8-mL vial purged and maintained with an inert atmosphere of nitrogen was added a mixture of 6-[1H,2H,3H,4H,5H,6H-pyrrolo[3,4-c]pyrrole-2-sulfonyl]-1,3-benzothiazole hydrochloride (69 mg, 0.20 mmol, 1.00 equiv), N,N-dimethylformamide (2 mL) and DIEA (77 mg, 0.60 mmol, 3.00 equiv), followed by the addition of ditrichloromethyl carbonate (30 mg, 0.10 mmol, 0.50 equiv). The solution was stirred for 1.0 h at RT under nitrogen atmosphere. Morpholine was added (52 mg, 0.60 mmol, 3.00 equiv) and the reaction mixture was stirred for 2 h at RT. The crude product (200 mg) was purified by prep-HPLC with the following conditions: Column: SunFire Prep C18 5 um 19*150 mm; mobile phase: water (buffer of 10 mM NH$_4$HCO$_3$ and 0.05% NH$_3$·H$_2$O) and CH$_3$CN with a gradient of 16% to 34% CH$_3$CN in 10 min; detector UV wavelength: 220 nm. This provided (5-(benzo[d]thiazol-6-ylsulfonyl)-3,4,5,6-tetrahydropyrrolo[3,4-c]pyrrol-2(1H)-yl)(morpholino)methanone (21.6 mg, 26%) as a white solid. $^1$H NMR (300 MHz, CDCl$_3$, ppm): δ 9.22 (s, 1H), 8.53 (d, J=1.5 Hz, 1H), 8.29 (d, J=7.8 Hz, 1H), 7.98 (dd, J=8.4 Hz, J=1.8 Hz, 1H), 4.17-4.13 (m, 8H), 3.68-3.65 (m, 4H), 3.27-3.23 (m, 4H). LCMS: m/z=421 [M+H]⁺.

Example 7-1: (5-((3,4-dihydro-2H-benzo[b][1,4] oxazin-6-yl)sulfonyl)-3,4,5,6-tetrahydropyrrolo[3,4-c]pyrrol-2(1H)-yl)(tetrahydro-2H-pyran-4-yl)methanone

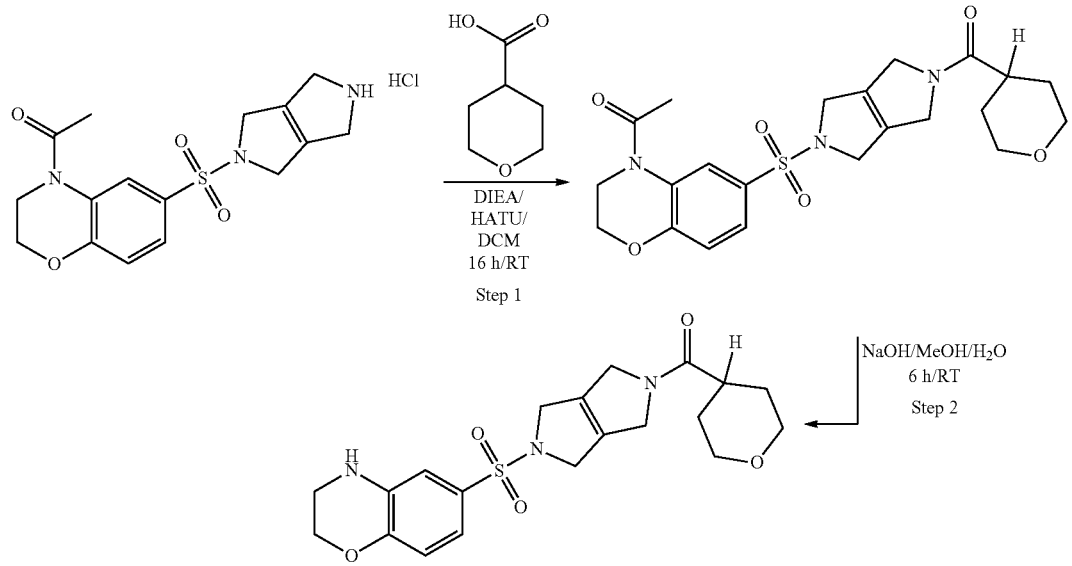

Example 7-1

Step 1. 1-(6-[5-[(Oxan-4-yl)carbonyl]-1H,2H,3H,4H,5H,6H-pyrrolo[3,4-c]pyrrole-2-sulfonyl]-3,4-dihydro-2H-1,4-benzoxazin-4-yl)ethan-1-one To an 8-mL vial purged and maintained with an inert atmosphere of nitrogen was added oxane-4-carboxylic acid (31 mg, 0.24 mmol, 1.20 equiv), dichloromethane (3 mL), DIEA (77 mg, 0.60 mmol, 3.00 equiv), 1-(6-[1H,2H,3H,4H,5H,6H-pyrrolo[3,4-c]pyrrole-2-sulfonyl]-3,4-dihydro-2H-1,4-benzoxazin-4-yl)ethan-1-one hydrochloride (77 mg, 0.20 mmol, 1.00 equiv) and HATU (91 mg, 0.24 mmol, 1.20 equiv). The reaction mixture was stirred for 16 h at RT, then concentrated under reduced pressure. The residue was purified by flash chromatography on silica gel eluted with dichloromethane/methanol (100/1) to provide 1-(6-[5-[(oxan-4-yl)carbonyl]-1H,2H,3H,4H,5H,6H-pyrrolo[3,4-c]pyrrole-2-sulfonyl]-3,4-dihydro-2H-1,4-benzoxazin-4-yl)ethan-1-one (90 mg, 98%) as a white solid. LCMS: m/z=462.2 [M+H]⁺.

Step 2. 6-[5-[(Oxan-4-yl)carbonyl]-1H,2H,3H,4H,5H,6H-pyrrolo[3,4-c]pyrrole-2-sulfonyl]-3,4-dihydro-2H-1,4-benzoxazine To an 8-mL vial was added 1-(6-[5-[(oxan-4-yl)carbonyl]-1H,2H,3H,4H,5H,6H-pyrrolo[3,4-c]pyrrole-2-sulfonyl]-3,4-dihydro-2H-1,4-benzoxazin-4-yl)ethan-1-one (90 mg, 0.20 mmol, 1.00 equiv), methanol (2 mL), water (0.5 mL) and sodium hydroxide (32 mg, 0.80 mmol, 4.00 equiv). The resulting solution was stirred for 6 h at RT. The crude product was purified by prep-HPLC with the following conditions: Column: Waters XBridge RP18 19*150 mm, 5 um; mobile phase: water (it contains 0.05% NH₃·H₂O) and CH₃CN with a gradient of 28% to 33% CH₃CN in 5 min; detector UV wavelength: 220 nm. This provided 6-[5-[(Oxan-4-yl)carbonyl]-1H,2H,3H,4H,5H,6H-pyrrolo[3,4-c]pyrrole-2-sulfonyl]-3,4-dihydro-2H-1,4-benzoxazine (32.3 mg, 39%) as a white solid. ¹H NMR (300 MHz, CDCl₃): δ ppm 7.14-7.11 (m, 2H), 6.87 (d, J=7.8 Hz, 1H), 4.32-4.00 (m, 12H), 3.48-3.42 (m, 4H), 2.56-2.48 (m, 1H), 2.01-1.81 (m, 2H), 1.62-1.58 (m, 2H). LCMS: m/z=420 [M+H]*.

Example 8-1: 1-(5-[[4-(difluoromethoxy)benzene]sulfonyl]-1H,2H,3H,4H,5H,6H-pyrrolo[3,4-c]pyrrol-2-yl)-2-(pyridin-2-yl)ethan-1-one

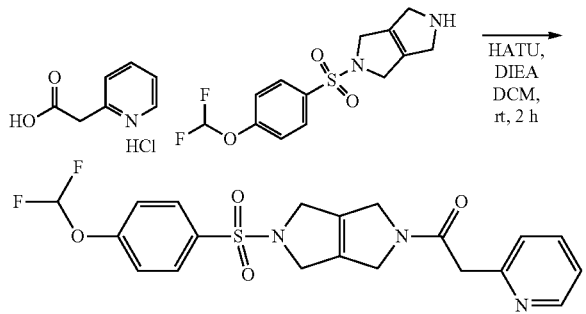

Example 8-1

Into a 50-mL round-bottom flask, was placed a mixture of 2-(pyridin-2-yl)acetic acid hydrochloride (48 mg, 0.28 mmol, 1.00 equiv), 2-[[4-(difluoromethoxy)benzene]sulfonyl]-1H,2H,3H,4H,5H,6H-pyrrolo[3,4-c]pyrrole hydrochloride (100 mg, 0.28 mmol, 1.00 equiv), DIEA (155 mg, 1.20 mmol, 4.00 equiv), dichloromethane (5 mL) and HATU (114 mg, 0.30 mmol, 1.00 equiv). The reaction mixture was stirred for 4 h at 25° C. The reaction was then quenched by the addition of 10 mL of water and the aqueous phase was extracted with 3×10 mL of dichloromethane and washed with water and brine. The crude product (80 mg) was purified by Prep-HPLC with the following conditions. Column: SunFire Prep C18 5 μm 19*150 mm; mobile phase: water (contains 0.1% TFA) and CH$_3$CN with a gradient of 43% to 73% CH$_3$CN in 7 min; detector UV wavelength: 220 nm. This resulted in 25.6 mg (21%) of 1-(5-[[4-(difluoromethoxy)benzene]sulfonyl]-1H,2H,3H,4H,5H,6H-pyrrolo[3,4-c]pyrrol-2-yl)-2-(pyridin-2-yl)ethan-1-one as a white solid. $^1$H NMR (300 MHz, DMSO-d6, ppm): δ 8.50-8.51 (d, J=4.2 Hz, 1H), 7.84-7.89 (m, 2H), 7.71-7.76 (t, J=7.5 Hz, 1H), 7.44-7.46 (d, J=8.1 Hz, 1H), 7.23-7.29 (m, 3H), 6.37-6.85 (t, J=72.6 Hz, 1H), 4.40 (br, 2H), 3.97-4.14 (br, 6H), 3.90-3.94 (br, 2H). LC-MS (ESI) m/z: Calculated for C$_{20}$H$_{19}$F$_2$N$_3$O$_4$S: 435.11; found: 436 [M+H]$^+$.

The Examples in Table 5 below were prepared according to the procedure outlined above for Example 8-1, using the appropriate synthetic precursors.

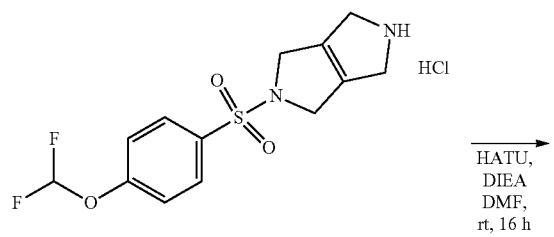

TABLE 5

| Example | Structure Name | LCMS (m/z) | $^1$H-NMR |
|---|---|---|---|
| 8-2 | (R)-1-(5-((4-(difluoromethoxy)phenyl)sulfonyl)-3,4,5,6-tetrahydropyrrolo[3,4-c]pyrrol-2(1H)-yl)-2-hydroxy-2-(pyridin-2-yl)ethan-1-one | 452 | (300 MHz, DMSO-d$_6$): δ ppm 8.44 (d, J = 3.9 Hz, 1H), 7.88-7.91 (m, 2H), 7.78-7.84 (m, 1H), 7.52 (d, J = 7.8 Hz, 1H), 7.41 (t, J = 63.6 Hz, 1H), 7.30-7.41 (m, 2H), 7.26-7.29 (m, 1H), 5.82 (d, J = 6.9 Hz, 1H), 5.28 (d, J = 6.9 Hz, 1H), 4.32 (br. s, 2H), 4.07 (br., 6H) |
| 8-3 | (S)-1-(5-((4-(difluoromethoxy)phenyl)sulfonyl)-3,4,5,6-tetrahydropyrrolo[3,4-c]pyrrol-2(1H)-yl)-2-hydroxy-2-(pyridin-2-yl)ethan-1-one | 452 (Rt: 1.11 min) | (300 MHz, DMSO-d$_6$): δ ppm 8.44 (d, J = 3.9 Hz, 1H), 7.88-7.91 (m, 2H), 7.78-7.84 (m, 1H), 7.52 (d, J = 7.8 Hz, 1H), 7.41 (t, J = 63.6 Hz, 1H), 7.30-7.41 (m, 2H), 7.26-7.29 (m, 1H), 5.82 (d, J = 6.9 Hz, 1H), 5.28 (d, J = 6.9 Hz, 1H), 4.32 (br. s, 2H), 4.07 (br., 6H) |

*Compounds 8-2 and 8-3 are enantiomers, but absolute stereochemistry is undetermined. These compounds were prepared as a racemate, then separated by Chiral-Prep-HPLC (SHIMADZU LC-20AT) with the following conditions: Column, REPAIRED IA; mobile phase: isocratic elution with DCM: IPA (10:90; with 0.1% DEA); flow rate: 20 mL/min; detector UV wavelength: 254 nm.

Example 9-1: 1-(5-[[4-(Difluoromethoxy)benzene]sulfonyl]-1H,2H,3H,4H,5H,6H-pyrrolo[3,4-c]pyrrol-2-yl)-2-hydroxy-2-(pyridin-3-yl)ethan-1-one

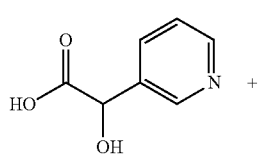 +

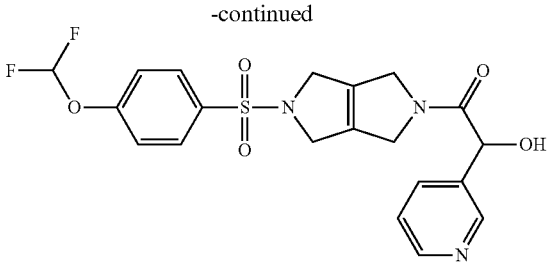

Example 9-1

Into a 8-mL vial (1 atm), was placed a mixture of 2-hydroxy-2-(pyridin-3-yl)acetic acid (39.8 mg, 0.26 mmol, 1.30 equiv), N,N-dimethylformamide (1.5 mL), 2-((4-(difluoromethoxy)phenyl)sulfonyl)-1,2,3,4,5,6-hexahydropyrrolo[3,4-c]pyrrolehydrochloride (70.6 mg, 0.20 mmol, 1.00 equiv), DIEA (65 mg, 0.50 mmol, 2.50 equiv) and HATU (91 mg, 0.24 mmol, 1.20 equiv). The resulting solution was stirred for 16 h at room temperature. The reaction solution was diluted with 50 mL of ethyl acetate, washed with 4×10 mL of brine, dried over anhydrous sodium sulfate and concentrated under vacuum. The crude product was purified by prep-TLC. This resulted in 1-(5-[[4-(Difluoromethoxy)benzene]sulfonyl]-1H,2H,3H,4H,5H,6H-pyrrolo[3,4-c]pyrrol-2-yl)-2-hydroxy-2-(pyridin-3-yl)ethan-1-one as an off-white solid. $^1$H NMR (300 MHz, CDCl$_3$): δ ppm 8.66 (d, J=4.8 Hz, 1H), 8.65-7.87 (m, 2H), 7.51-7.48 (m, 1H), 7.48-7.31 (m, 5H), 5.01 (s, 1H), 4.32-4.15 (m, 7H), 3.63 (d, J=12.3 Hz, 1H). LCMS m/z: 452 [M+H]$^+$.

The Examples in Table 6 below were prepared according to the procedure outlined above for Example 9-1, using the appropriate synthetic precursors.

TABLE 6

| Example | Structure Name | LCMS (m/z) | $^1$H-NMR |
|---|---|---|---|
| 9-2 | 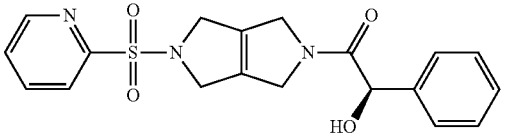<br>(2R)-2-hydroxy-2-phenyl-1-[5-(pyridine-2-sulfonyl)-1H,2H,3H,4H,5H,6H-pyrrolo[3,4-c]pyrrol-2-yl]ethan-1-one | 386 | (300 MHz, CDCl$_3$): δ ppm 8.66 (d, J = 4.8 Hz, 1H), 8.65-7.87 (m, 2H), 7.51-7.48 (m, 1H), 7.48-7.31 (m, 5H), 5.01 (s, 1H), 4.32-4.15 (m, 7H), 3.63 (d, J = 12.3 Hz, 1H) |
| 9-3 | 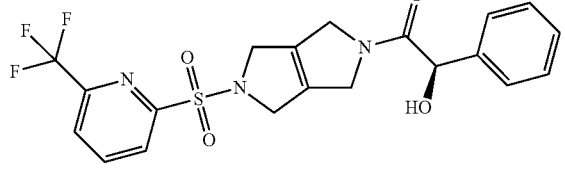<br>(2R)-2-hydroxy-2-phenyl-1-[5-[6-(trifluoromethyl)pyridine-2-sulfonyl]-1H,2H,3H,4H,5H,6H-pyrrolo[3,4-c]pyrrol-2-yl]ethan-1-one | 454 | (300 MHz, CDCl$_3$): δ ppm 8.12 (d, J = 3.9 Hz, 2H), 7.86-7.66 (m, 1H), 7.61-7.10 (m, 5H), 5.28-5.07 (br. s, 1H), 4.89-3.85 (m, 8H), 3.68-3.49 (br. s, 1H) |
| 9-4 | 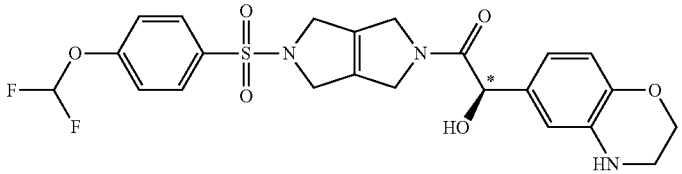<br>(2R)-1-(5-[[4-(difluoromethoxy)benzene]sulfonyl]-1H,2H,3H,4H,5H,6H-pyrrolo[3,4-c]pyrrol-2-yl)-2-(3,4-dihydro-2H-1,4-benzoxazin-6-yl)-2-hydroxyethan-1-one | 508 | (300 MHz, CDCl$_3$): δ ppm 7.84 (d, J = 8.4 Hz, 2H), 7.24-7.36 (m, 2H), 6.36-6.91 (m, 4H), 4.85 (br s, 1H), 4.11 (m, 9H), 3.67 (m, 1H), 3.41 (s, 2H) |
| 9-5 | 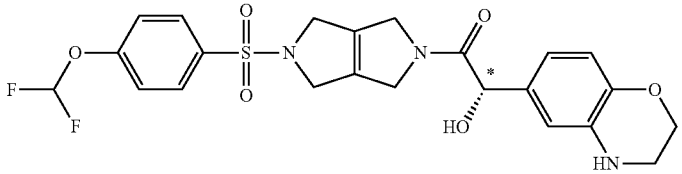<br>(2S)-1-(5-[[4-(difluoromethoxy)benzene]sulfonyl]-1H,2H,3H,4H,5H,6H-pyrrolo[3,4-c]pyrrol-2-yl)-2-(3,4-dihydro-2H-1,4-benzoxazin-6-yl)-2-hydroxyethan-1-one | 508 | (300 MHz, CDCl$_3$): δ ppm 7.83 (d, J = 8.7 Hz, 2H), 7.25 (d, 2H), 6.35-6.90 (m, 4H), 4.90 (s, 1H), 4.16 (m, 9H), 3.72 (m, 1H), 3.49 (s, 2H) |

*Example 9-4 and Example 9-5 are enantiomers, but absolute stereochemistry is undetermined. These compounds were prepared as a racemate, then separated by Chiral-Prep-HPLC (SHIMADZU LC-20AT) with the following conditions: Column: CHIRALPAK IC; mobile phase solvent A: ethanol, solvent B: methanol; detector UV wave length: 220 nm.

Example 9-2: Synthesis of (2R)-2-Hydroxy-2-phenyl-1-(5-(pyridin-2-ylsulfonyl)-3,4,5,6-tetrahydropyrrolo[3,4-c]pyrrol-2(1H)-yl)ethan-1-one

Intermediate A: tert-Butyl 5-(pyridin-2-ylsulfonyl)-3,4,5,6-tetrahydropyrrolo[3,4-c]pyrrole-2(1H)-carboxylate

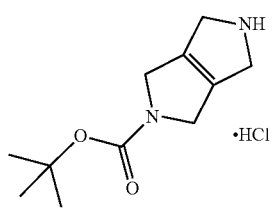

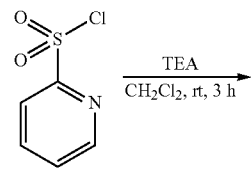

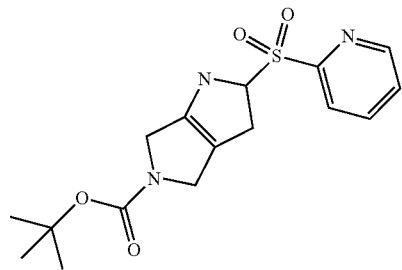

Intermediate A

To a suspension of tert-butyl 3,4,5,6-tetrahydropyrrolo[3,4-c]pyrrole-2(1H)-carboxylate, HCl (1.10 g, 4.46 mmol) in dichloromethane (25 mL) at room temperature was added TEA (1.49 mL, 10.7 mmol) followed by pyridine-2-sulfonyl chloride (0.950 g, 5.35 mmol). The reaction mixture was stirred at room temperature for 3 hours. The solvent was removed under reduced pressure and the residue was taken up in EtOAc (50 mL). The organic mixture was sequentially washed with water (50 mL) and saturated aqueous sodium chloride solution (50 mL). The organic layer was collected, dried over sodium sulfate, filtered and concentrated under reduced pressure. The crude material was purified by silica gel column chromatography (0% EtOAc/hexane for 5 min then 0-75% EtOAc/hexane for 30 min) to afford tert-butyl 5-(pyridin-2-ylsulfonyl)-3,4,5,6-tetrahydropyrrolo[3,4-c]pyrrole-2(1H)-carboxylate (0.57 g, 1.622 mmol, 36.4% yield). LCMS (m/z, M+H+) 351.9, 1H-NMR (300 MHz, CDCl3): δ ppm 8.69 (m, 1H), 8.00-7.88 (m, 2H), 7.49 (m, 1H), 4.33 (m, 4H), 4.05 (m, 4H), 1.45 (s, 9H).

Intermediate B: 2-(Pyridin-2-ylsulfonyl)-1,2,3,4,5,6-hexahydropyrrolo[3,4-c]pyrrole, HCl

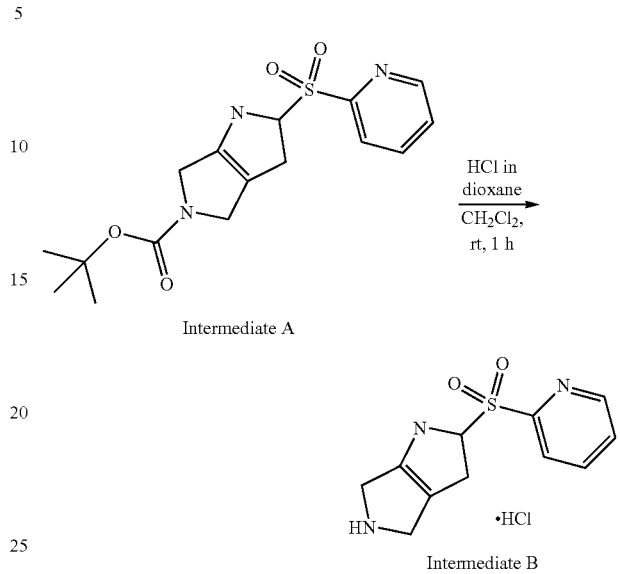

To a solution of tert-butyl 5-(pyridin-2-ylsulfonyl)-3,4,5,6-tetrahydropyrrolo[3,4-c]pyrrole-2(1H)-carboxylate (0.570 g, 1.62 mmol) in dichloromethane (4.96 ml) was added 4 M HCl/dioxane (17.6 ml). The reaction mixture was stirred at room temperature for 1 hour. The reaction mixture was concentrated under reduced pressure then triturated with ether. The white solid was filtered off to give 2-(pyridin-2-ylsulfonyl)-1,2,3,4,5,6-hexahydropyrrolo[3,4-c]pyrrole, HCl (0.547 g, 1.90 mmol, quantitative yield) that was used in the next step without further purification. LCMS (m/z, M+H+) 252.0, 1H-NMR (300 MHz, DMSO-d6): δ ppm 9.99 (br m, 2H), 8.75 (m, 1H), 8.13 (m, 1H), 7.97 (m, 1H), 7.71 (m 1H), 4.24 (m, 4H), 3.89 (m, 4H).

(R)-2-Hydroxy-2-phenyl-1-(5-(pyridin-2-ylsulfonyl)-3,4,5,6-tetrahydropyrrolo[3,4-c]pyrrol-2(1H)-yl)ethan-1-one

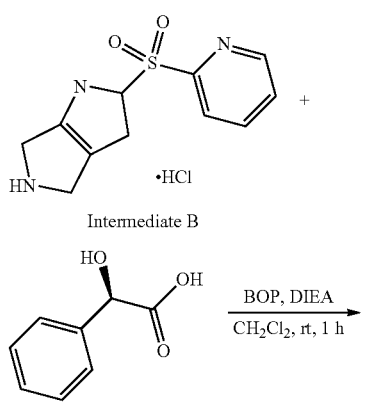

-continued

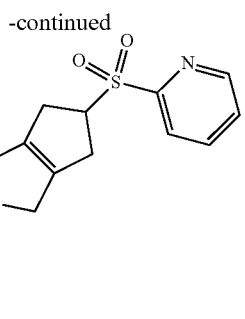

Example 9-2

To a suspension of 2-(pyridin-2-ylsulfonyl)-1,2,3,4,5,6-hexahydropyrrolo[3,4-c]pyrrole, HCl (0.547 g, 1.90 mmol) in dichloromethane (12.6 mL) was added (R)-2-hydroxy-2-phenylacetic acid (0.241 g, 1.58 mmol), BOP (0.771 g, 1.74 mmol) and DIEA (0.830 ml, 4.75 mmol). The reaction mixture was stirred at room temperature for 2 hours. Ethyl acetate (50 mL) was added and the organic phase was washed with saturated aqueous sodium hydrogen carbonate solution (50 mL) and saturated aqueous sodium chloride solution (50 mL). The organic phase was dried over magnesium sulfate, filtered, and concentrated under reduced pressure. The crude material was purified by silica gel column chromatography on (gradient of 0-10% MeOH/dichloromethane) to afford (R)-2-hydroxy-2-phenyl-1-(5-(pyridin-2-ylsulfonyl)-5,6-dihydropyrrolo[3,4-c]pyrrol-2(1H,3H,4H)-yl)ethanone (0.353 g, 0.916 mmol, 57.8% yield). LCMS (m/z, M+H+) 385.9, 1H-NMR (300 MHz, DMSO-d6): δ ppm 8.69 (m, 1H), 8.07 (m, 1H), 7.91 (m, 1H), 7.68-7.64 (m, 1H), 7.33-7.26 (m, 5H), 5.64 (d, J=6.0 Hz, 1H), 5.14 (d, J=6.3 Hz, 1H), 4.30-3.88 (m, 8H).

Examples 10-1 and 10-2: (2R)-1-(5-(4-(difluoromethoxy)phenylsulfonyl)-4,5-dihydropyrrolo[3,4-c]pyrrol-2(1H,3H,4H)-yl)-2-hydroxy-2-(4-methyl-3,4-dihydro-2H-benzo[b][1,4]oxazin-6-yl)ethanone and (2S)-1-(5-(4-(difluoromethoxy)phenylsulfonyl)-4,5-dihydropyrrolo[3,4-c]pyrrol-2(1H,3H,4H)-yl)-2-hydroxy-2-(4-methyl-3,4-dihydro-2H-benzo[b][1,4]oxazin-6-yl)ethanone 1-(5-[[4-(Difluoromethoxy)benzene]sulfonyl]-1H,2H,3H,4H,5H,6H-pyrrolo[3,4-c]pyrrol-2-yl)-2-(3,4-dihydro-2H-1,4-benzoxazin-6-yl)-2-hydroxyethan-1-one (174 mg, 0.34 mmol, 1.00 equiv), methanol (2 mL), formaldehyde (20.6 mg, 2.00 equiv), NaBH₃CN (64.8 mg, 1.03 mmol, 3.00 equiv) and acetic acid (2 mg, 0.03 mmol, 0.10 equiv) were added to a 10-mL round-bottom flask. The solution was stirred for 1 h at RT, then concentrated under reduced pressure. The residue was purified by flash column chromatography on silica gel eluted with dichloromethane/methanol (15:1) to provide racemic 1-(5-[[4-(difluoromethoxy)benzene]sulfonyl]-1H,2H,3H,4H,5H,6H-pyrrolo[3,4-c]pyrrol-2-yl)-2-hydroxy-2-(4-methyl-3,4-dihydro-2H-1,4-benzoxazin-6-yl)ethan-1-one (140 mg, 78%) as a white solid. The enantiomers were separated by Chiral-Prep-HPLC (SHIMADZU LC-20AT) with the following conditions: Column, Lux Cellulose-4; mobile phase solvent A: ethanol, solvent B: methanol; detector UV wavelength: 220 nm. This provided:

Example 10-1 (first eluting enantiomer): (2R)-1-(5-(4-(difluoromethoxy)phenylsulfonyl)-4,5-dihydropyrrolo[3,4-c]pyrrol-2(1H,3H,4H)-yl)-2-hydroxy-2-(4-methyl-3,4-dihydro-2H-benzo[b][1,4]oxazin-6-yl)ethanone Isolated as a white solid (26.5 mg, 19%). ¹H NMR (300 MHz, CDCl₃): δ ppm 7.89 (m, 2H), 7.39 (t, 3H), 6.49-6.65 (m, 3H), 5.32 (d, J=6.6 Hz, 1H), 4.98 (d, J=6.3 Hz, 1H), 3.81-4.25 (m, 10H), 3.21 (m, 2H), 2.75 (d, 3H). LCMS: m/z=522 [M+H]⁺. * Absolute stereochemistry undetermined.

Example 10-2 (second eluting enantiomer): (2S)-1-(5-(4-(difluoromethoxy)phenylsulfonyl)-4,5-dihydropyrrolo[3,4-c]pyrrol-2(1H,3H,4H)-yl)-2-hydroxy-2-(4-methyl-3,4-dihydro-2H-benzo[b][1,4]oxazin-6-yl)ethanone Isolated as a white solid (22.7 mg, 16%). ¹H NMR (300 MHz, CDCl₃): δ ppm 7.86 (m, 2H), 7.20 (m, 2H), 6.37-6.85 (m, 4H), 4.89 (s, 1H), 4.02-4.40 (m, 10H), 3.72 (m, 1H), 3.29 (m, 2H), 2.91 (s, 3H). LCMS: m/z=522 [M+H]⁺. * Absolute stereochemistry undetermined.

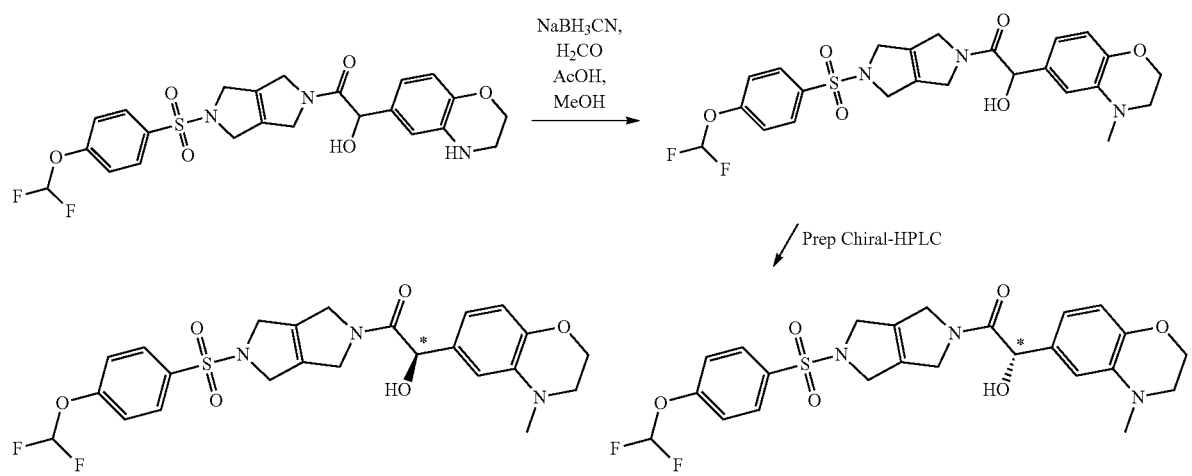 [SMILES: O=C(C(O)c1ccc2c(c1)NCCO2)N1CC2=C(C1)CN(S(=O)(=O)c1ccc(OC(F)F)cc1)C2 ; CN1CCOc2ccc(C(O)C(=O)N3CC4=C(C3)CN(S(=O)(=O)c3ccc(OC(F)F)cc3)C4)cc21 ; CN1CCOc2ccc([C@@H](O)C(=O)N3CC4=C(C3)CN(S(=O)(=O)c3ccc(OC(F)F)cc3)C4)cc21 ; CN1CCOc2ccc([C@H](O)C(=O)N3CC4=C(C3)CN(S(=O)(=O)c3ccc(OC(F)F)cc3)C4)cc21]

Examples 11-1 and 11-2: (2S)-1-(5-[[4-(Difluoromethoxy)benzene]sulfonyl]-1H,2H,3H,4H,5H,6H-pyrrolo[3,4-c]pyrrol-2-yl)-2-hydroxy-2-(1,2,3,4-tetrahydroisoquinolin-7-yl)ethan-1-one and (2R)-1-(5-[[4-(Difluoromethoxy)benzene]sulfonyl]-1H,2H, 3H,4H,5H,6H-pyrrolo[3,4-c]pyrrol-2-yl)-2-hydroxy-2-(1,2,3,4-tetrahydroisoquinolin-7-yl)ethan-1-one

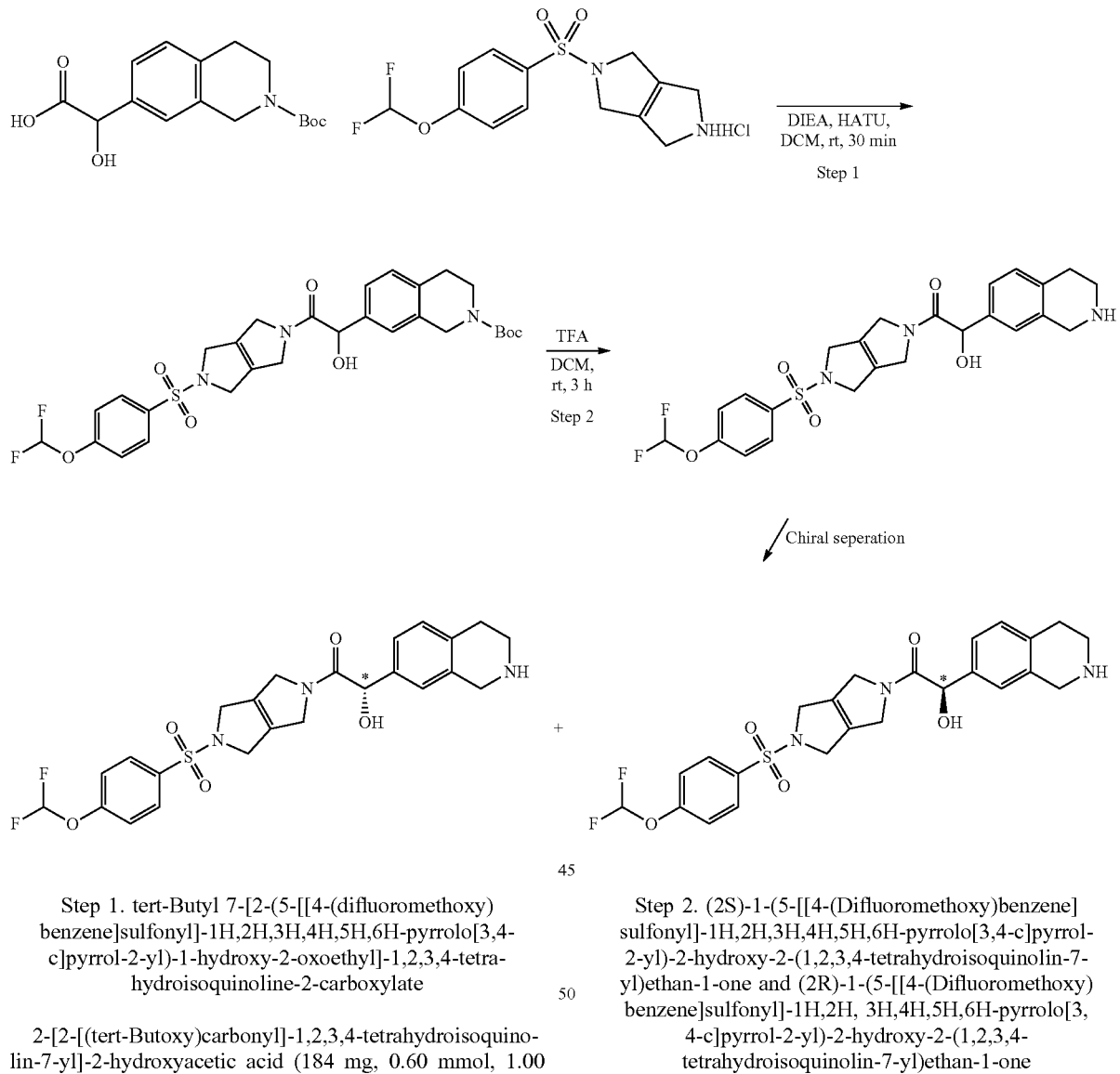

Step 1. tert-Butyl 7-[2-(5-[[4-(difluoromethoxy)benzene]sulfonyl]-1H,2H,3H,4H,5H,6H-pyrrolo[3,4-c]pyrrol-2-yl)-1-hydroxy-2-oxoethyl]-1,2,3,4-tetrahydroisoquinoline-2-carboxylate 2-[2-[(tert-Butoxy)carbonyl]-1,2,3,4-tetrahydroisoquinolin-7-yl]-2-hydroxyacetic acid (184 mg, 0.60 mmol, 1.00 equiv), 2-[[4-(difluoromethoxy)benzene]sulfonyl]-1H,2H,3H,4H,5H,6H-pyrrolo[3,4-c]pyrrole hydrochloride (187 mg, 0.53 mmol, 1.00 equiv), dichloromethane (5 mL), DIEA (205 mg, 1.59 mmol, 3.00 equiv) and HATU (242 mg, 0.64 mmol, 1.20 equiv) were added to a 50-mL round-bottom flask. The mixture was stirred for 30 min at RT, then the volatiles were removed under reduced pressure. The residue was purified by flash column chromatography on silica gel eluted with dichloromethane/methanol (15:1) to provide tert-butyl 7-[2-(5-[[4-(difluoromethoxy)benzene]sulfonyl]-1H,2H,3H,4H,5H,6H-pyrrolo[3,4-c]pyrrol-2-yl)-1-hydroxy-2-oxoethyl]-1,2,3,4-tetrahydroisoquinoline-2-carboxylate (318 mg, 88%) as a yellow solid. LCMS: m/z=606 [M+H]$^+$.

Step 2. (2S)-1-(5-[[4-(Difluoromethoxy)benzene]sulfonyl]-1H,2H,3H,4H,5H,6H-pyrrolo[3,4-c]pyrrol-2-yl)-2-hydroxy-2-(1,2,3,4-tetrahydroisoquinolin-7-yl)ethan-1-one and (2R)-1-(5-[[4-(Difluoromethoxy)benzene]sulfonyl]-1H,2H, 3H,4H,5H,6H-pyrrolo[3,4-c]pyrrol-2-yl)-2-hydroxy-2-(1,2,3,4-tetrahydroisoquinolin-7-yl)ethan-1-one tert-Butyl 7-[2-(5-[[4-(difluoromethoxy)benzene]sulfonyl]-1H,2H,3H,4H,5H,6H-pyrrolo[3,4-c]pyrrol-2-yl)-1-hydroxy-2-oxoethyl]-1,2,3,4-tetrahydroisoquinoline-2-carboxylate (60.5 mg, 0.10 mmol, 1.00 equiv), dichloromethane (3 mL), and trifluoroacetic acid (1 mL) were added to a 10-mL round-bottom flask. The solution was stirred for 3 h at RT. The pH of the solution was adjusted to 8.0 with 2 N aqueous sodium bicarbonate solution. The mixture was extracted with dichloromethane (3×15 mL), and the combined extracts were dried over anhydrous sodium sulfate, filtered, and concentrated under reduced pressure. The residue was purified by flash column chromatography on silica gel eluted with dichloromethane/methanol (10:1) to provide racemic 1-(5-[[4-(difluoromethoxy)benzene]sulfonyl]-1H,2H,3H,4H,5H,6H-pyrrolo[3,4-c]pyrrol-2-yl)-2-hydroxy-2-(1,2,3,4-tetrahydroisoquinolin-7-yl)ethan-1-one (40 mg, 79%) as a white solid. The enantiomers were separated by Chiral-Prep-HPLC (SHIMADZU LC-20AT) with the following conditions: Column, DAICEL CHIRALPAK IC 20*250 mm 5 um; mobile phase: solvent A: CH3CN (it contains 0.1% DEA), solvent B: IPA with gradient of 20 to 50% solvent B in 30 min; detector UV wavelength: 230 nm. This provided:

Example 11-1: (2S)-1-(5-[[4-(difluoromethoxy)benzene]sulfonyl]-1H,2H,3H,4H,5H,6H-pyrrolo[3,4-c]pyrrol-2-yl)-2-hydroxy-2-(1,2,3,4-tetrahydroisoquinolin-7-yl)ethan-1-one Isolated as a white solid (13.7 mg, 27%). $^1$H NMR (300 MHz, CD$_3$OD): δ ppm 7.89 (m, 2H), 7.35 (d, J=9.0 Hz, 2H), 7.24-6.75 (m, 4H), 5.33 (s, 1H), 4.25-4.09 (m, 7H), 3.98 (d, J=7.5 Hz, 2H), 3.83-3.79 (m, 1H), 3.09 (t, J=6.3 Hz, 2H), 2.86-2.81 (m, 2H). LCMS: m/z=506 [M+H]$^+$. * Absolute stereochemistry undetermined.

Example 11-2: (2R)-1-(5-[[4-(difluoromethoxy)benzene]sulfonyl]-1H,2H,3H,4H,5H,6H-pyrrolo[3,4-c]pyrrol-2-yl)-2-hydroxy-2-(1,2,3,4-tetrahydroisoquinolin-7-yl)ethan-1-one Isolated as a white solid (11.3 mg, 22%). $^1$H NMR (300 MHz, CD$_3$OD): δ ppm 7.89 (m, 2H), 7.35 (d, J=9.0 Hz, 2H), 7.24-6.75 (m, 4H), 5.15 (s, 1H), 4.25-4.09 (m, 7H), 3.98 (d, J=7.5 Hz, 2H), 3.83-3.78 (m, 1H), 3.09 (t, J=6.3 Hz, 2H), 2.86-2.81 (m, 2H). LCMS: m/z=506 [M+H]$^+$. * Absolute stereochemistry undetermined.

Example 19-1: (3-Benzyl-3-hydroxyazetidin-1-yl)(5-(quinolin-8-ylsulfonyl)-4,5-dihydropyrrolo[3,4-c]pyrrol-2(1H,3H,4)-yl)methanone

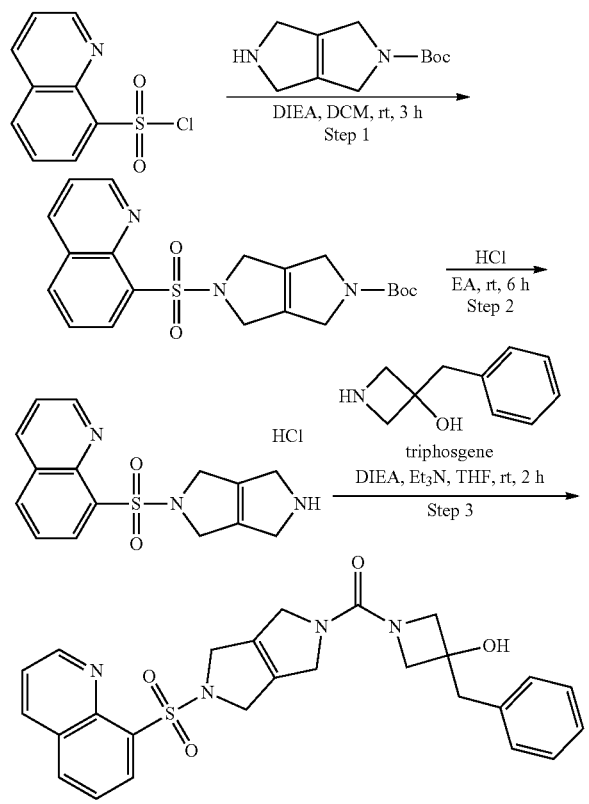

Example 12-1

Step 1. tert-Butyl 5-(quinolin-8-ylsulfonyl)-4,5-dihydropyrrolo[3,4-c]pyrrole-2(1H,3H,4H)-carboxylate tert-Butyl 4,5-dihydropyrrolo[3,4-c]pyrrole-2(1H,3H,4H)-carboxylate (84 mg, 0.40 mmol, 1.00 equiv), DCM (8.00 mL), DIEA (77.3 mg, 0.60 mmol, 1.50 equiv) and quinoline-8-sulfonyl chloride (100 mg, 0.44 mmol, 1.10 equiv) were combined in a 50-mL round-bottom flask. The solution was stirred for 16 h at 20° C., then concentrated under vacuum. The residue was diluted with ethyl acetate (10 mL), washed with water (3×3 mL), dried over anhydrous sodium sulfate, filtered then concentrated to provide tert-butyl 5-(quinolin-8-ylsulfonyl)-4,5-dihydropyrrolo[3,4-c]pyrrole-2(1H,3H,4H)-carboxylate as a pink solid (140 mg, 87%). LCMS: m/z=402 [M+H]$^+$.

Step 2. 8-(4,5-Dihydropyrrolo[3,4-c]pyrrol-2(1H,3H,4H)-ylsulfonyl)quinoline hydrochloride Ethyl acetate (5.60 mL), concentrated aqueous hydrogen chloride (38 mg, 3.00 equiv), and tert-butyl 5-(quinolin-8-ylsulfonyl)-4,5-dihydropyrrolo[3,4-c]pyrrole-2(1H,3H,4H)-carboxylate (140 mg, 0.35 mmol, 1.00 equiv) were combined in a 50-mL round-bottom flask. The solution was stirred for 6 h at 25° C., then the solids were collected by filtration to provide 8-(4,5-dihydropyrrolo[3,4-c]pyrrol-2(1H,3H,4H)-ylsulfonyl) quinoline hydrochloride as a pink solid (110 mg, 93%). LCMS: m/z=302 [M+H]$^+$.

Step 3. (3-Benzyl-3-hydroxyazetidin-1-yl)(5-(quinolin-8-ylsulfonyl)-4,5-dihydropyrrolo[3,4-c]pyrrol-2(1H,3H,4H)-yl)methanone 8-(4,5-Dihydropyrrolo[3,4-c]pyrrol-2(1H,3H,4H)-ylsulfonyl) quinoline hydrochloride (100 mg, 0.30 mmol, 1.00 equiv), THF (25.0 mL), TEA (179 mg, 1.77 mmol, 6.00 equiv) and ditrichloromethyl carbonate (44 mg, 0.15 mmol, 0.50 equiv) were combined in a 50-mL round-bottom flask. The solution was stirred for 2 h at 25° C. then 3-benzylazetidin-3-ol (97 mg, 0.59 mmol, 2.00 equiv) was added. The solution was stirred for an additional 2 h at 25° C., then diluted with ethyl acetate (50 mL), washed with water (3×25 mL), and dried over anhydrous sodium sulfate. The solids were filtered off. The filtrate was concentrated under vacuum. The crude material was purified by Prep-HPLC with the following conditions: Column, SunFire Prep C18 19*150 mm; mobile phase, water (containing 0.1% TFA) and ACN with a gradient of 39% to 44% of ACN in 6 min; detector UV wavelength, 220 nm. This provided (3-benzyl-3-hydroxyazetidin-1-yl)(5-(quinolin-8-ylsulfonyl)-4,5-dihydropyrrolo[3,4-c]pyrrol-2(1H,3H,4H)-yl)methanone as a white solid (44 mg, 30%). $^1$H NMR (300 MHz, CDCl$_3$, ppm): δ 9.05 (d, J=9.6 Hz, 1H), 8.56 (d, J=6.6 Hz, 1H), 8.32 (d, J=8.1 Hz, 1H), 8.07 (d, J=8.1 Hz, 1H), 7.64 (m, 1H), 7.56 (m, 1H), 7.35 (m, 3H), 7.22 (m, 2H), 4.51 (m, 4H), 4.10 (m, 6H), 3.85 (m, 2H), 3.06 (m, 2H). LCMS: m/z=491 [M+H]$^+$.

Example 13-1: (R)-4-((5-(2-hydroxy-2-phenylacetyl)-3,4,5,6-tetrahydropyrrolo[3,4-c]pyrrol-2(1H)-yl)sulfonyl)benzenesulfonamide

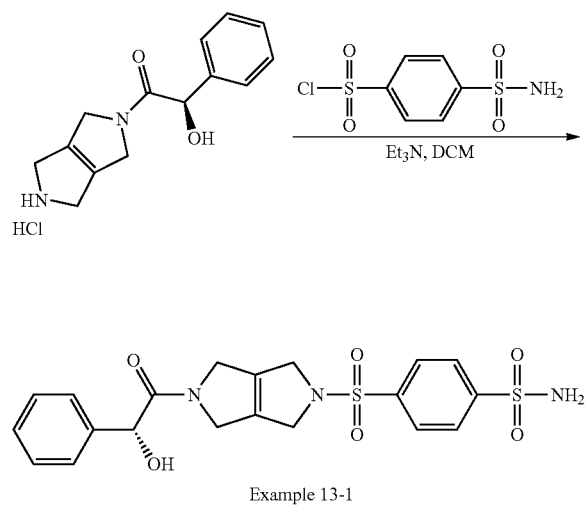

Example 13-1

(R)-2-hydroxy-2-phenyl-1-(3,4,5,6-tetrahydropyrrolo[3,4-c]pyrrol-2(1H)-yl)ethan-1-one hydrochloride (40 mg, 0.14 mmol, 1.00 equiv), TEA (36 mg, 0.36 mmol, 2.50 equiv) and DCM (4.00 mL) were combined and stirred in a 25-mL round-bottom flask. 4-Sulfamoylbenzene-1-sulfonyl chloride (36.4 mg, 0.14 mmol, 1.00 equiv) was added and the solution was stirred for 2 h at RT. The reaction was then quenched by addition of 4 mL of water, extracted with 3×10 mL of DCM, and washed with 10 mL of brine. The organic phase was dried over anhydrous sodium sulfate and concentrated under vacuum. The crude product was re-crystallized from methanol to provide (R)-4-((5-(2-hydroxy-2-phenylacetyl)-3,4,5,6-tetrahydropyrrolo[3,4-c]pyrrol-2(1H)-yl)sulfonyl)benzenesulfonamide (24 mg, 36%) as a white solid. $^1$H NMR (300 MHz, DMSO-$d_6$, ppm): δ 8.01 (s, 4H), 7.62 (br. s, 2H), 7.25-7.34 (m, 5H), 5.61-5.64 (d, 1H), 5.14-5.18 (d, 1H), 3.83-4.30 (m, 8H). LCMS: m/z=464 [M+H]$^+$.

Example 14-1: (R)—N-(2-fluoro-5-((5-(2-hydroxy-2-phenylacetyl)-3,4,5,6-tetrahydropyrrolo[3,4-c]pyrrol-2(1H)-yl)sulfonyl)phenyl)acetamide

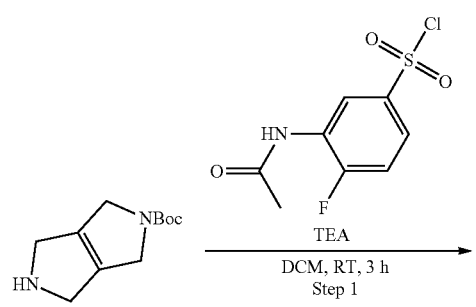

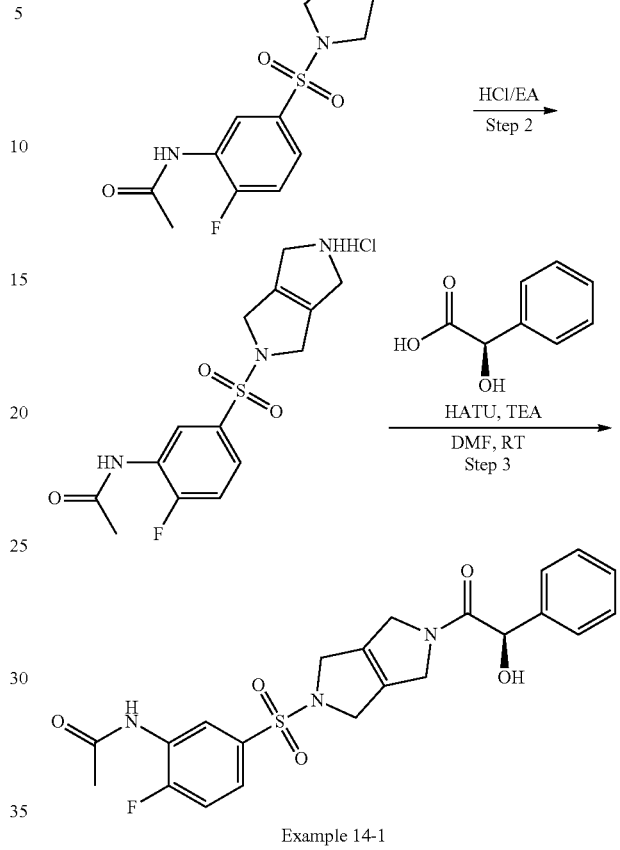

Example 14-1

Step 1. tert-Butyl 5-((3-acetamido-4-fluorophenyl)sulfonyl)-3,4,5,6-tetrahydropyrrolo[3,4-c]pyrrole-2(1H)-carboxylate To a 8-mL vial was added tert-butyl 3,4,5,6-tetrahydropyrrolo[3,4-c]pyrrole-2(1H)-carboxylate (75 mg, 0.36 mmol, 1.00 equiv), triethylamine (54 mg, 0.53 mmol, 1.50 equiv), 3-acetamido-4-fluorobenzene-1-sulfonyl chloride (90 mg, 0.36 mmol, 1.00 equiv), and DCM (1.00 mL). The solution was stirred for 3 h at RT. The reaction was then quenched by addition of 10 mL of water. The solution was extracted with 3×10 mL of DCM and washed with 10 mL of brine. The organic phase was dried over anhydrous sodium sulfate, filtered and concentrated under vacuum to provide tert-butyl 5-((3-acetamido-4-fluorophenyl)sulfonyl)-3,4,5,6-tetrahydropyrrolo[3,4-c]pyrrole-2(1H)-carboxylate (100 mg, 66%) as a white solid. LCMS: m/z=426 [M+H]$^+$.

Step 2. N-(2-fluoro-5-((3,4,5,6-tetrahydropyrrolo[3,4-c]pyrrol-2(1H)-yl)sulfonyl)phenyl)acetamide hydrochloride To a 50-mL round-bottom flask was added tert-butyl 5-((3-acetamido-4-fluorophenyl)sulfonyl)-3,4,5,6-tetrahydropyrrolo[3,4-c]pyrrole-2(1H)-carboxylate (100 mg, 0.24 mmol, 1.00 equiv) and ethyl acetate freshly saturated with hydrogen chloride gas (20 mL). The solution was stirred overnight at RT. The solids were collected by filtration to provide N-(2-fluoro-5-((3,4,5,6-tetrahydropyrrolo[3,4-c]pyrrol-2(1H)-yl)sulfonyl)phenyl)acetamide hydrochloride (65 mg, 76%) as a gray solid. LCMS: m/z=326 [M+H]+.

Step 3. (R)—N-(2-fluoro-5-((5-(2-hydroxy-2-phenylacetyl)-3,4,5,6-tetrahydropyrrolo[3,4-c]pyrrol-2(1H)-yl)sulfonyl)phenyl)acetamide To an 8-mL vial was added N-(2-fluoro-5-((3,4,5,6-tetrahydropyrrolo[3,4-c]pyrrol-2(1H)-yl)sulfonyl)phenyl)acetamide hydrochloride (60 mg, 0.17 mmol, 1.00 equiv), (2R)-2-hydroxy-2-phenylacetic acid (25 mg, 0.16 mmol, 1.00 equiv), HATU (94 mg, 0.25 mmol, 1.50 equiv) and DIEA (53 mg, 0.41 mmol, 2.50 equiv), and DMF (5.00 mL). The solution was stirred for 2 h at RT. The reaction was then quenched by the addition of 10 mL of water. The solution was extracted with 3×15 mL of ethyl acetate and washed with 15 mL of brine. The organic phase was dried over anhydrous sodium sulfate and concentrated under vacuum. The residue (50 mg) was purified by Prep-HPLC (waters I) with the following conditions: Column, Xbridge Prep RP18 5 μm 19*150 mm; mobile phase, water (containing 10 mM NH4HCO3+0.05% ammonia) and CH3CN with a gradient of 87% to 92% CH3CN in 7 min; detector UV wavelength, 254 nm. This provided (R)—N-(2-fluoro-5-((5-(2-hydroxy-2-phenylacetyl)-3,4,5,6-tetrahydropyrrolo[3,4-c]pyrrol-2(1H)-yl)sulfonyl)phenyl)acetamide (7 mg, 9%) as a white solid. 1H NMR (300 MHz, DMSO-d6, ppm): δ 10.04 (s, 1H), 8.49-8.52 (d, J=7.5 Hz, 1H), 7.27-7.53 (m, 7H), 5.61-5.63 (d, J=7.5 Hz, 1H), 5.14-5.16 (d, J=7.5 Hz, 1H), 3.89-4.11 (m, 8H), 2.11 (s, 3H). LCMS: m/z=460 [M+H]+.

Example 15-1: N-[(2-fluorophenyl)methyl]-5-(6-methylpyridine-2-sulfonyl)-1H,2H,3H,4H,5H,6H-pyrrolo[3,4-c]pyrrole-2-carboxamide

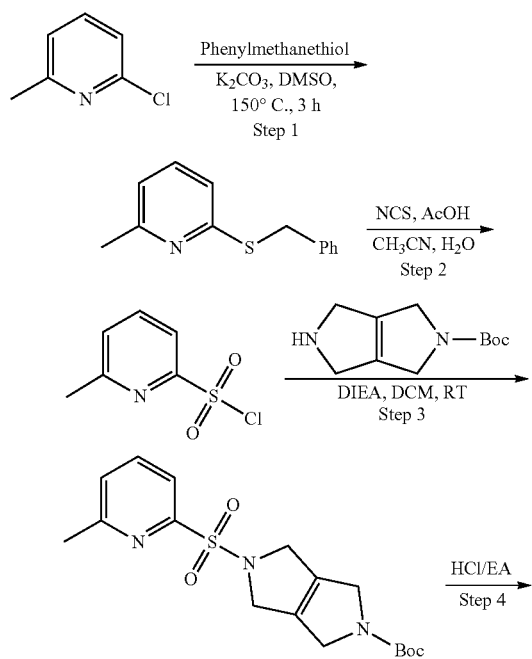

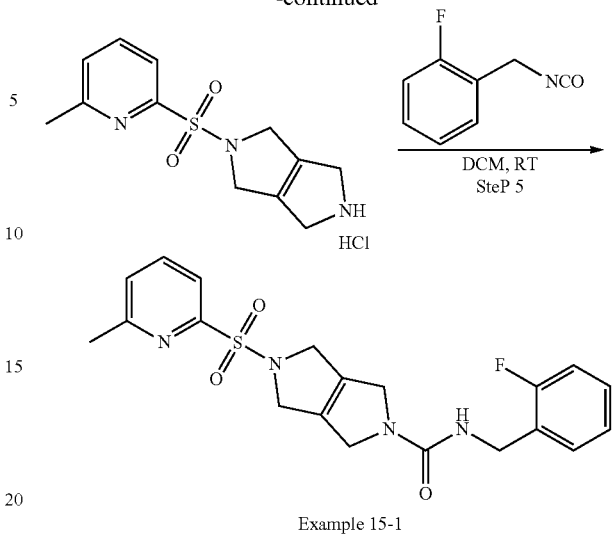

Example 15-1

Step 1. 2-(benzylsulfanyl)-6-methylpyridine

To a 250-mL round-bottom flask was added 2-chloro-6-methylpyridine (5.00 g, 39.19 mmol, 1.00 equiv), DMSO (80 mL), phenylmethanethiol (5.37 g, 43.24 mmol, 1.10 equiv) and potassium carbonate (10.9 g, 78.87 mmol, 2.00 equiv). The solution was stirred for 3 h at 150° C., then cooled to RT. The solution was diluted with 300 mL of ethyl acetate, washed with 4×50 mL of brine, dried over anhydrous sodium sulfate, filtered and concentrated under vacuum to provide 2-(benzylsulfanyl)-6-methylpyridine (7.60 g) as a light brown oil. The material was used without further purification. LCMS: m/z=216 [M+H]+.

Step 2. 6-Methylpyridine-2-sulfonyl chloride

To a 50-mL round-bottom flask was added 2-(benzylsulfanyl)-6-methylpyridine (580 mg, 2.69 mmol, 1.00 equiv), ACN (20.0 mL), water (0.60 mL) and AcOH (1.30 mL). NCS (1.80 g, 13.48 mmol, 5.00 equiv) was added in portions. The solution was stirred for 2 h at RT, then concentrated under vacuum. The residue was diluted with 5 mL of H2O. The pH value of the solution was adjusted to 8 with saturated aqueous sodium bicarbonate solution. The solution was extracted with 80 mL of ethyl acetate. The organic phase was washed with 3×10 mL of brine, dried over anhydrous sodium sulfate, filtered and concentrated under vacuum. The residue was purified by silica gel column chromatography, eluting with ethyl acetate/petroleum ether (1:5) to provide 6-methylpyridine-2-sulfonyl chloride (80 mg, 15%) as a viscous yellow oil. LCMS: m/z=192 [M+H]+.

Step 3. tert-Butyl 5-(6-methylpyridine-2-sulfonyl)-1H,2H,3H,4H,5H,6H-pyrrolo[3,4-c]pyrrole-2-carboxylate To an 8-mL vial was added 6-methylpyridine-2-sulfonyl chloride (70 mg, 0.37 mmol, 1.00 equiv), DCM (1.50 mL), DIEA (118 mg, 0.91 mmol, 2.50 equiv), and tert-butyl 1H,2H,3H,4H,5H,6H-pyrrolo[3,4-c]pyrrole-2-carboxylate (77 mg, 0.37 mmol, 1.00 equiv). The solution was stirred for 0.5 h at RT, then concentrated. The residue was purified by silica gel column chromatography with DCM/EA (2:1) to provide tert-butyl 5-(6-methylpyridine-2-sulfonyl)-1H,2H, 3H,4H,5H,6H-pyrrolo[3,4-c]pyrrole-2-carboxylate (100 mg, 75%) as a white solid. LCMS: m/z=366 [M+H]+.

Step 4. 2-Methyl-6-[1H,2H, 3H,4H,5H,6H-pyrrolo[3,4-c]pyrrole-2-sulfonyl]pyridine hydrochloride To an 8-mL vial was added tert-butyl 5-(6-methylpyridine-2-sulfonyl)-1H,2H,3H,4H,5H,6H-pyrrolo[3,4-c]pyrrole-2-carboxylate (90 mg, 0.25 mmol, 1.00 equiv) and DCM (1.50 mL). The stirred solution was treated dropwise with EA freshly saturated with hydrogen chloride (3.0 mL). The solution was stirred for 1 h at RT. The mixture was concentrated under vacuum to provide 2-methyl-6-[1H,2H, 3H,4H,5H,6H-pyrrolo[3,4-c]pyrrole-2-sulfonyl]pyridine hydrochloride (110 mg) as a brown oil. The material was used without further purification. LCMS: m/z=266 [M+H]+.

Step 5. N-[(2-fluorophenyl)methyl]-5-(6-methylpyridine-2-sulfonyl)-1H, 2H, 3H,4H, 5H,6H-pyrrolo[3,4-c]pyrrole-2-carboxamide To an 8-mL vial was added 1-fluoro-2-(isocyanatomethyl)benzene (100 mg, 0.66 mmol, 1.00 equiv), DMF (3.00 mL), DIEA (115 mg, 0.89 mmol, 3.00 equiv) and 2-methyl-6-[1H,2H,3H,4H,5H,6H-pyrrolo[3,4-c]pyrrole-2-sulfonyl]pyridine hydrochloride (49 mg, 0.14 mmol, 0.90 equiv). The solution was stirred for 1 h at RT, then concentrated. The residue was purified by Prep-HPLC (Waters I) with the following conditions: Column, Waters XBridge RP18 19*150 mm, 5 μm; mobile phase, water (containing 10 mM NH4HCO3+0.05% ammonia) and ACN with a gradient of 42% to 65% ACN in 7 min; flow rate, 20 mL/min; detector UV wavelength, 254 nm. This provided N-[(2-fluorophenyl)methyl]-5-(6-methylpyridine-2-sulfonyl)-1H,2H,3H,4H, 5H,6H-pyrrolo[3,4-c]pyrrole-2-carboxamide (54 mg, 20%) as a white solid. 1H NMR (300 MHz, CDCl3, ppm): δ 7.83-7.76 (m, 2H), 7.44-7.34 (m, 2H), 7.32-7.23 (m, 1H), 7.14-7.02 (m, 1H), 4.60 (d, J=6.0 Hz, 1H), 4.51 (d, J=5.7 Hz, 2H), 4.37 (s, 4H), 4.12 (s, 4H), 2.61 (s, 3H). LCMS: m/z=417 [M+H]+.

Example 16-1: 2-(Pyridin-3-yl)-1-[5-(pyridine-2-sulfonyl)-1H,2H,3H,4H,5H,6H-pyrrolo[3,4-c]pyrrol-2-yl]ethan-1-one

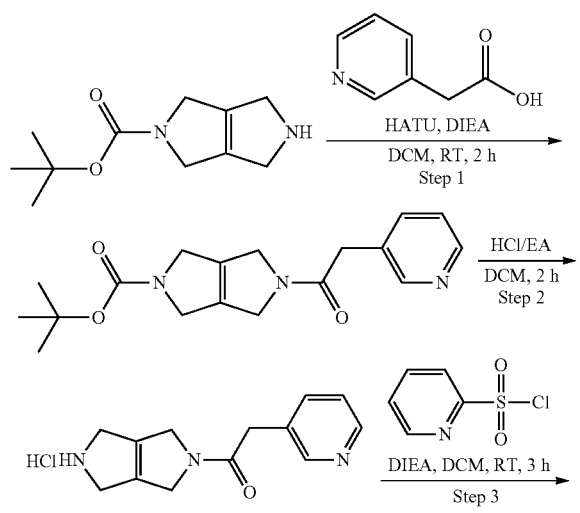

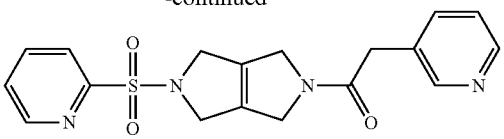

Example 16-1

Step 1. tert-Butyl 5-[2-(pyridin-4yl)acetyl]-1H,2H, 3H,4H, 5H,6H-pyrrolo[3,4-c]pyrrole-2-carboxylate To an 8-mL vial was added 2-(pyridin-3-yl)acetic acid (78.3 mg, 0.57 mmol, 1.20 equiv), DCM (2.00 mL), DIEA (184 mg, 1.42 mmol, 1.00 equiv), tert-butyl 1H,2H,3H,4H, 5H,6H-pyrrolo[3,4-c]pyrrole-2-carboxylate (100 mg, 0.48 mmol, 1.00 equiv) and HATU (200 mg, 0.53 mmol, 1.10 equiv). The solution was stirred for 2 h at RT, then concentrated under vacuum. The residue was purified by silica gel column chromatography, eluting with DCM/methanol (50:1) to provide tert-butyl 5-[2-(pyridin-4yl)acetyl]-1H,2H,3H, 4H,5H,6H-pyrrolo[3,4-c]pyrrole-2-carboxylate (135 mg) as a brown oil. The material was used without further purification. LCMS: m/z=330 [M+H]+.

Step 2. 2-(Pyridin-3-yl)-1-[1H,2H, 3H,4H,5H,6H-pyrrolo[3,4-c]pyrrol-2-yl]ethan-1-one hydrochloride To an 8-mL vial was added tert-butyl 5-[2-(pyridin-4yl)acetyl]-1H,2H,3H,4H,5H,6H-pyrrolo[3,4-c]pyrrole-2-carboxylate (135 mg, 0.41 mmol, 1.00 equiv) and DCM (2.00 mL). The stirred solution was treated with ethyl acetate freshly saturated with hydrogen chloride (2.00 mL). The solution was stirred for 2 h at RT, then the solids were collected by filtration to provide 2-(pyridin-3-yl)-1-[1H,2H, 3H,4H,5H,6H-pyrrolo[3,4-c]pyrrol-2-yl]ethan-1-one hydrochloride (125 mg) as a light brown solid. The material was used without further purification. LCMS: m/z=230 [M+H]+.

Step 3. 2-(Pyridin-3-yl)-1-[5-(pyridine-2-sulfonyl)-1H,2H,3H,4H,5H,6H-pyrrolo[3,4-c]pyrrol-2-yl]ethan-1-one To an 8-mL vial was added 2-(pyridin-3-yl)-1-[1H,2H, 3H,4H,5H,6H-pyrrolo[3,4-c]pyrrol-2-yl]ethan-1-one hydrochloride (115 mg, 0.43 mmol, 1.00 equiv), DMF (4 mL), pyridine-2-sulfonyl chloride (84.1 mg, 0.47 mmol, 1.10 equiv) and DIEA (139 mg, 1.08 mmol, 2.50 equiv). The solution was stirred for 2 h at RT. The mixture was purified by Prep-HPLC (Waters 2767) with the following conditions: Column, X-Bridge RP18, 19*150 mm, 5 μm; mobile phase, water (containing 10 mM NH4HCO3+0.05% ammonia) and CH3CN with a gradient of 16% to 36% CH3CN in 8 min; detector UV wavelength, 220 nm. This provided 2-(pyridin-3-yl)-1-[5-(pyridine-2-sulfonyl)-1H,2H,3H,4H,5H,6H-pyrrolo[3,4-c]pyrrol-2-yl]ethan-1-one (25.5 mg, 16%) as a light yellow solid. 1H NMR (300 MHz, DMSO-d6, ppm): δ 8.75 (d, J=3.9 Hz, 1H), 8.44-8.41 (m, 2H), 8.16-8.10 (m, 1H), 7.97 (d, J=7.8 Hz, 1H), 7.72 (dd, J=4.8 Hz, J=1.5 Hz, 1H), 7.71-7.69 (m, 1H), 7.32 (dd, J=7.2 Hz, J=4.8 Hz, 1H), 4.31-4.26 (m, 6H), 4.03 (s, 2H), 3.68 (s, 2H). LCMS: m/z=371 [M+H]+.

Example 17-1: 3-[5-[(2R)-2-hydroxy-2-phenylacetyl]-1H,2H,3H,4H,5H,6H-pyrrolo[3,4-c]pyrrole-2-sulfonyl]benzene-1-sulfonamide

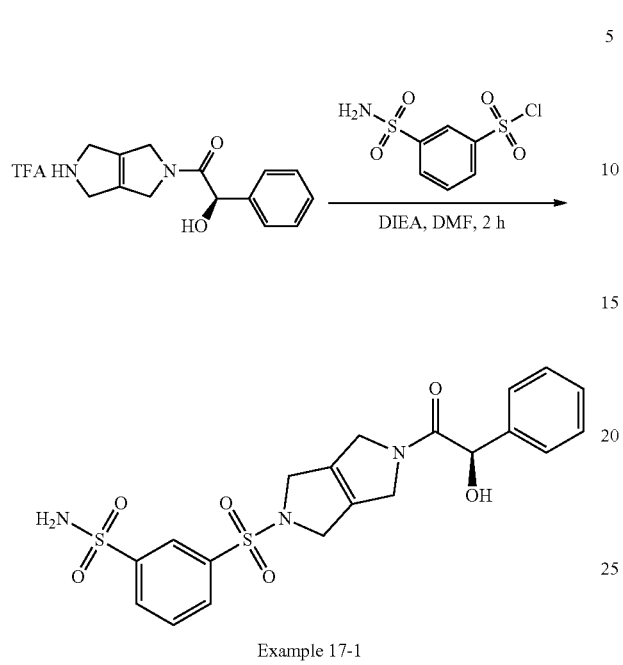

Example 17-1

Prepared as described for Step 3 of the preparation of Example 16-1 using the appropriate synthetic precursors, but with a two hour reaction time, and using a Prep-HPLC gradient of 20% to 40% ACN in 8 minutes. Isolated as a white solid (48.3 mg, 29%). $^1$H NMR (300 MHz, DMSO-$d_6$, ppm): δ 8.19 (d, J=1.5 Hz, 1H), 8.12-8.01 (m, 2H), 7.86-7.83 (m, 1H), 7.59 (s, 2H), 7.34-7.30 (m, 5H), 5.64 (d, J=6.3 Hz, 1H), 5.16 (d, J=6.0 Hz, 1H), 4.25-3.87 (m, 8H). LCMS: m/z=464 [M+H]$^+$.

Example 18-1: 3-Methyl-1-{5-[(1-methyl-1H-pyrazol-3-yl)sulfonyl]-1H,2H,3H,4H,5H,6H-pyrrolo[3,4-c]pyrrol-2-yl}-2-phenylbutan-1-one

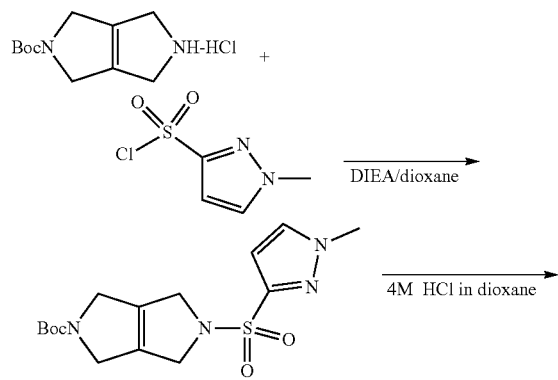

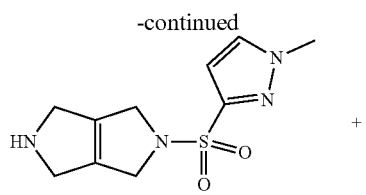

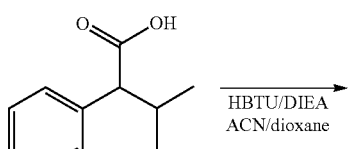

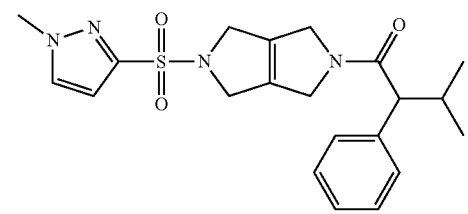

Example 18-1

To a 1.5 mL vial was added a 0.2 M solution of tert-butyl 3,4,5,6-tetrahydropyrrolo[3,4-c]pyrrole-2(1H)-carboxylate hydrochloride (100 μL, 20 μmol) in dioxane and neat DIEA (10 μL, 57 μmol) to give a brown suspension. A 0.2 M solution of 1-methyl-1H-pyrazole-3-sulfonyl chloride (105 μL, 20 μmol) in dioxane was added. The reaction was heated at 50° C. with shaking for 2 hours. 4 M HCl in dioxane (50.0 μL, 0.200 mmol) was then added. The reaction was heated at 50° C. with shaking for an additional 2 hours. The volatiles were removed under reduced pressure. ACN (200 uL) was added to the vial. The vial was shaken for 15 minutes to resuspend the residue. Neat DIEA (25 μL, 0.143 mmol) and a 0.2 M solution of 3-methyl-2-phenylbutanoic acid (110 μL, 22 μmol) in dioxane was added to the vial, followed by a 0.2 M solution of HBTU (110 μL, 22 μmol) in ACN. The reaction was heated at 50° C. with shaking for an additional 2 hours. The volatiles were removed under reduced pressure. The residue was mixed with 1 N NaOH (0.5 mL) and extracted with 3:1 EtOAc/ACN (2×0.5 mL). The volatiles were removed under reduced pressure. The compound was purified using mass-triggered HPLC to give 3-Methyl-1-{5-[(1-methyl-1H-pyrazol-3-yl)sulfonyl]-1H,2H,3H,4H,5H,6H-pyrrolo[3,4-c]pyrrol-2-yl}-2-phenylbutan-1-one. LCMS: m/z=415.1 [M+H]+.

The Examples in Table 7 below were prepared according to the procedure outlined above for Example 18-1, using the appropriate synthetic precursors.

TABLE 7

| Example | Name | Structure | LCMS (m/z) |
|---|---|---|---|
| 18-2 | 4-Methyl-6-({5-[(2R)-oxolane-2-carbonyl]-1H,2H,3H,4H,5H,6H-pyrrolo[3,4-c]pyrrol-2-yl}sulfonyl)-3,4-dihydro-2H-1,4-benzoxazine | 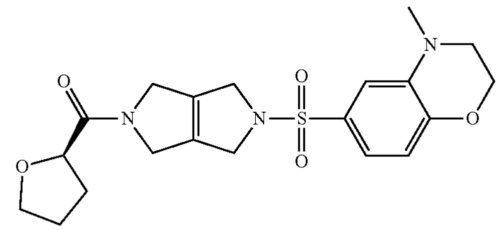 [SMILES: CN1CCOc2ccc(S(=O)(=O)N3CC4=C(CN(C(=O)[C@H]5CCCO5)C4)C3)cc21] | 420.2 |
| 18-3 | 2-(1-Benzofuran-5-sulfonyl)-5-(4-methoxythiophene-3-carbonyl)-1H,2H,3H,4H,5H,6H-pyrrolo[3,4-c]pyrrole | 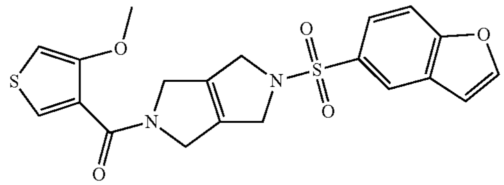 [SMILES: COc1cscc1C(=O)N1CC2=C(C1)CN(S(=O)(=O)c1ccc3occc3c1)C2] | 431.0 |
| 18-4 | 2-(1-Benzofuran-5-sulfonyl)-5-(2,5-dimethylfuran-3-carbonyl)-1H,2H,3H,4H,5H,6H-pyrrolo[3,4-c]pyrrole | 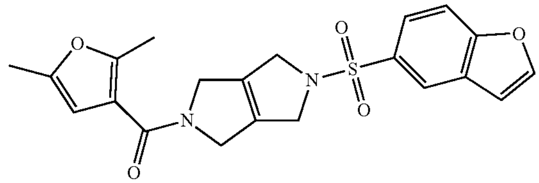 [SMILES: Cc1cc(C(=O)N2CC3=C(C2)CN(S(=O)(=O)c2ccc4occc4c2)C3)c(C)o1] | 413.1 |
| 18-5 | 3-[5-(1-Benzofuran-5-sulfonyl)-1H,2H,3H,4H,5H,6H-pyrrolo[3,4-c]pyrrole-2-carbonyl]pyridine | 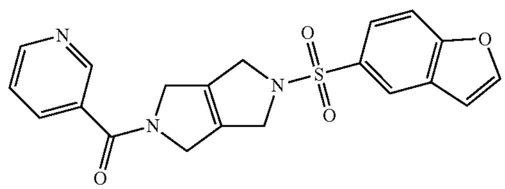 [SMILES: O=C(c1cccnc1)N1CC2=C(C1)CN(S(=O)(=O)c1ccc3occc3c1)C2] | 396.1 |
| 18-6 | 2-(1-Benzofuran-5-sulfonyl)-5-(2-methylfuran-3-carbonyl)-1H,2H,3H,4H,5H,6H-pyrrolo[3,4-c]pyrrole | 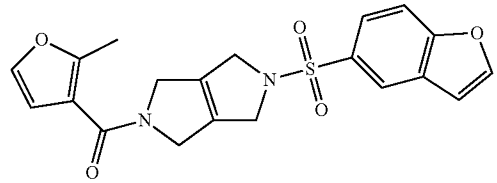 [SMILES: Cc1occc1C(=O)N1CC2=C(C1)CN(S(=O)(=O)c1ccc3occc3c1)C2] | 399.1 |
| 18-7 | 5-[5-(1-Benzofuran-5-sulfonyl)-1H,2H,3H,4H,5H,6H-pyrrolo[3,4-c]pyrrole-2-carbonyl]-4-methyl-1,3-thiazole | 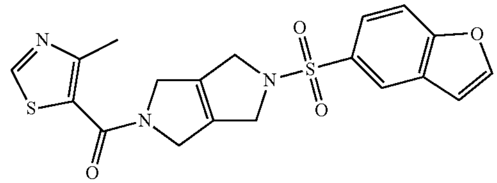 [SMILES: Cc1ncsc1C(=O)N1CC2=C(C1)CN(S(=O)(=O)c1ccc3occc3c1)C2] | 416.1 |
| 18-8 | 3-[5-(1-Benzofuran-5-sulfonyl)-1H,2H,3H,4H,5H,6H-pyrrolo[3,4-c]pyrrole-2-carbonyl]phenol | 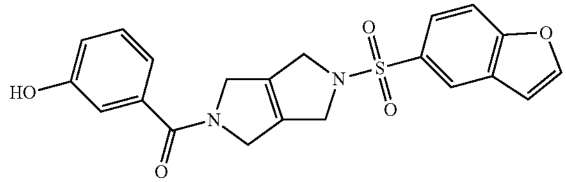 [SMILES: O=C(c1cccc(O)c1)N1CC2=C(C1)CN(S(=O)(=O)c1ccc3occc3c1)C2] | 411.1 |
| 18-9 | (2R)-2-hydroxy-1-{5-[(1-methyl-1H-pyrazol-3-yl)sulfonyl]-1H,2H,3H,4H,5H,6H-pyrrolo[3,4-c]pyrrol-2-yl}-2-phenylethan-1-one | 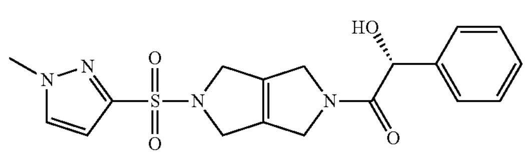 [SMILES: Cn1ccc(S(=O)(=O)N2CC3=C(CN(C(=O)[C@H](O)c4ccccc4)C3)C2)n1] | 389.1 |

TABLE 7-continued

| Example | Name | Structure | LCMS (m/z) |
|---|---|---|---|
| 18-10 | (2R)-1-[5-(4-chlorobenzenesulfonyl)-1H,2H,3H,4H,5H,6H-pyrrolo[3,4-c]pyrrol-2-yl]-2-hydroxy-2-phenylethan-1-one | 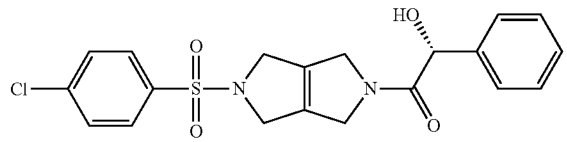 [SMILES: O=C([C@H](O)c1ccccc1)N1CC2=C(C1)CN(S(=O)(=O)c1ccc(Cl)cc1)C2] | 419.1 |
| 18-11 | (2R)-2-hydroxy-2-phenyl-1-{5-[4-(trifluoromethyl)benzenesulfonyl]-1H,2H,3H,4H,5H,6H-pyrrolo[3,4-c]pyrrol-2-yl}ethan-1-one | 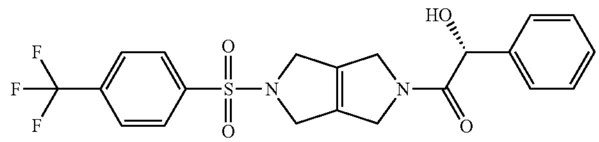 [SMILES: O=C([C@H](O)c1ccccc1)N1CC2=C(C1)CN(S(=O)(=O)c1ccc(C(F)(F)F)cc1)C2] | 453.1 |
| 18-12 | (2R)-2-hydroxy-2-phenyl-1-{5-[4-(propan-2-yloxy)benzenesulfonyl]-1H,2H,3H,4H,5H,6H-pyrrolo[3,4-c]pyrrol-2-yl}ethan-1-one | 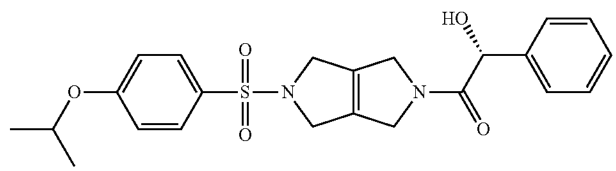 [SMILES: CC(C)Oc1ccc(S(=O)(=O)N2CC3=C(CN(C(=O)[C@H](O)c4ccccc4)C3)C2)cc1] | 443.1 |
| 18-13 | (2R)-1-{5-[4-(difluoromethoxy)benzenesulfonyl]-1H,2H,3H,4H,5H,6H-pyrrolo[3,4-c]pyrrol-2-yl}-2-hydroxy-2-phenylethan-1-one | 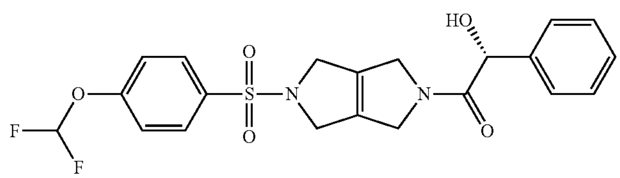 | 451.1 |
| 18-14 | (2R)-2-hydroxy-2-phenyl-1-(5-{[6-(trifluoromethyl)pyridin-3-yl]sulfonyl}-1H,2H,3H,4H,5H,6H-pyrrolo[3,4-c]pyrrol-2-yl)ethan-1-one | 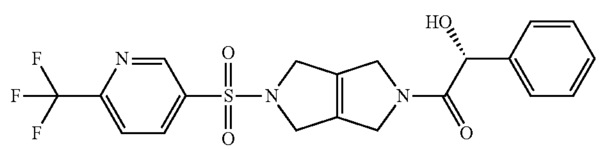 [SMILES: O=C([C@H](O)c1ccccc1)N1CC2=C(C1)CN(S(=O)(=O)c1ccc(C(F)(F)F)nc1)C2] | 454.1 |
| 18-15 | (2R)-1-{5-[3-(difluoromethoxy)benzenesulfonyl]-1H,2H,3H,4H,5H,6H-pyrrolo[3,4-c]pyrrol-2-yl}-2-hydroxy-2-phenylethan-1-one | 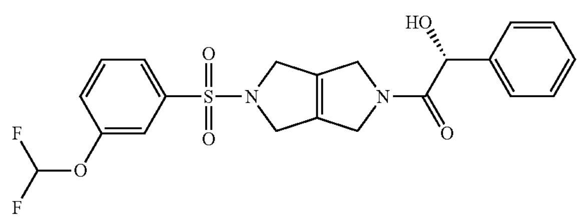 [SMILES: O=C([C@H](O)c1ccccc1)N1CC2=C(C1)CN(S(=O)(=O)c1cccc(OC(F)F)c1)C2] | 451.1 |
| 18-16 | (2R)-1-[5-(2-fluoro-5-methylbenzenesulfonyl)-1H,2H,3H,4H,5H,6H-pyrrolo[3,4-c]pyrrol-2-yl]-2-hydroxy-2-phenylethan-1-one | 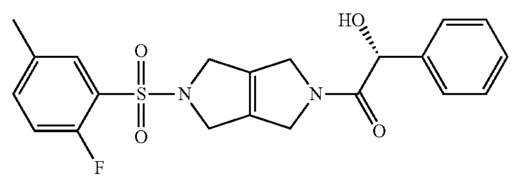 [SMILES: Cc1ccc(F)c(S(=O)(=O)N2CC3=C(CN(C(=O)[C@H](O)c4ccccc4)C3)C2)c1] | 417.1 |
| 18-17 | (2R)-1-[5-(3-fluoro-4-methoxybenzenesulfonyl)-1H,2H,3H,4H,5H,6H-pyrrolo[3,4-c]pyrrol-2-yl]-2-hydroxy-2-phenylethan-1-one | 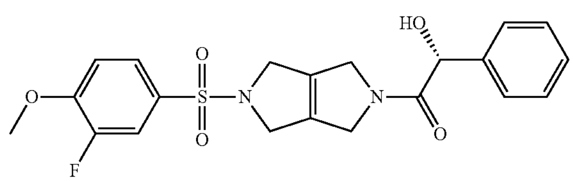 [SMILES: COc1ccc(S(=O)(=O)N2CC3=C(CN(C(=O)[C@H](O)c4ccccc4)C3)C2)cc1F] | 433.1 |
| 18-18 | (2R)-1-[5-(2,4-difluorobenzenesulfonyl)-1H,2H,3H,4H,5H,6H-pyrrolo[3,4-c]pyrrol-2-yl]-2-hydroxy-2-phenylethan-1-one | 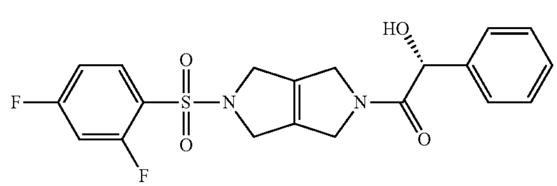 [SMILES: O=C([C@H](O)c1ccccc1)N1CC2=C(C1)CN(S(=O)(=O)c1ccc(F)cc1F)C2] | 421.1 |

TABLE 7-continued

| Example | Name | Structure | LCMS (m/z) |
|---|---|---|---|
| 18-19 | 1-{5-[4-(Difluoromethoxy)benzene-sulfonyl]-1H,2H,3H,4H,5H,6H-pyrrolo[3,4-c]pyrrol-2-yl}-2-(1H-1,2,3-tetrazol-1-yl)ethan-1-one | 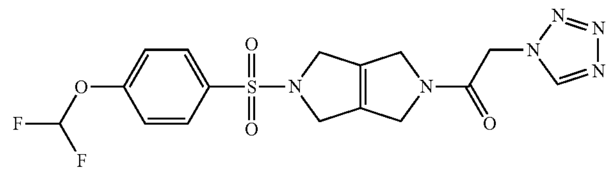 [SMILES: O=C(Cn1cnnn1)N1CC2=C(C1)CN(S(=O)(=O)c1ccc(OC(F)F)cc1)C2] | 427.1 |
| 18-20 | 1-{5-[4-(Difluoromethoxy)benzene-sulfonyl]-1H,2H,3H,4H,5H,6H-pyrrolo[3,4-c]pyrrol-2-yl}-2-(2-methyl-1,3-thiazol-4-yl)ethan-1-one | 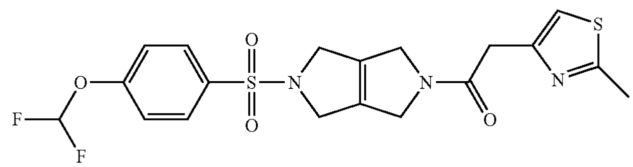 [SMILES: Cc1nc(CC(=O)N2CC3=C(C2)CN(S(=O)(=O)c2ccc(OC(F)F)cc2)C3)cs1] | 456.1 |
| 18-21 | 1-{5-[4-(Difluoromethoxy)benzenesulfonyl]-1H,2H,3H,4H,5H,6H-pyrrolo[3,4-c]pyrrol-2-yl}-2-(1H-pyrazol-1-yl)ethan-1-one | 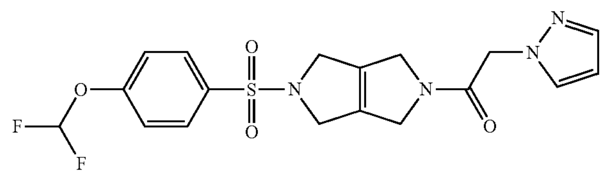 [SMILES: O=C(Cn1cccn1)N1CC2=C(C1)CN(S(=O)(=O)c1ccc(OC(F)F)cc1)C2] | 415.1 |
| 18-22 | 1-{5-[4-(Difluoromethoxy)benzenesulfonyl]-1H,2H,3H,4H,5H,6H-pyrrolo[3,4-c]pyrrol-2-yl}-2-(3-fluorophenyl)-2-hydroxyethan-1-one | 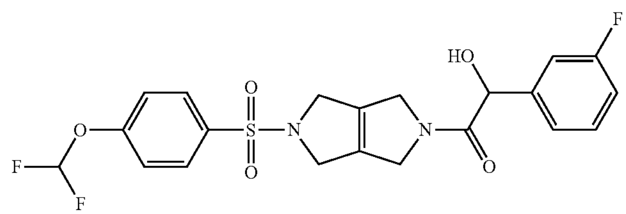 [SMILES: O=C(C(O)c1cccc(F)c1)N1CC2=C(C1)CN(S(=O)(=O)c1ccc(OC(F)F)cc1)C2] | 427.1 |
| 18-23 | 1-{5-[4-(Difluoromethoxy)benzenesulfonyl]-1H,2H,3H,4H,5H,6H-pyrrolo[3,4-c]pyrrol-2-yl}-2-(3,4-difluorophenyl)-2-hydroxyethan-1-one | 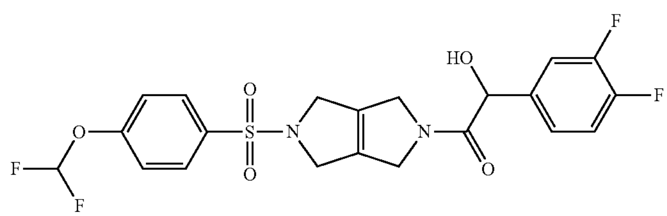 [SMILES: O=C(C(O)c1ccc(F)c(F)c1)N1CC2=C(C1)CN(S(=O)(=O)c1ccc(OC(F)F)cc1)C2] | 487.0 |
| 18-24 | 1-{5-[4-(Difluoromethoxy)benzenesulfonyl]-1H,2H,3H,4H,5H,6H-pyrrolo[3,4-c]pyrrol-2-yl}-2-fluoro-2-phenylethan-1-one | 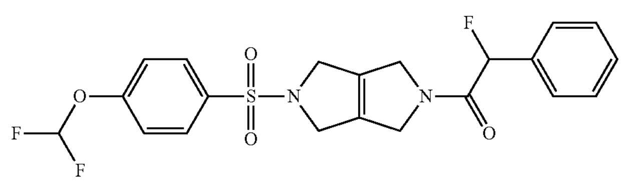 [SMILES: O=C(C(F)c1ccccc1)N1CC2=C(C1)CN(S(=O)(=O)c1ccc(OC(F)F)cc1)C2] | 453.0 |
| 18-25 | 1-{5-[4-(Difluoromethoxy)benzenesulfonyl]-1H,2H,3H,4H,5H,6H-pyrrolo[3,4-c]pyrrol-2-yl}-2,2-difluoro-2-phenylethan-1-one | 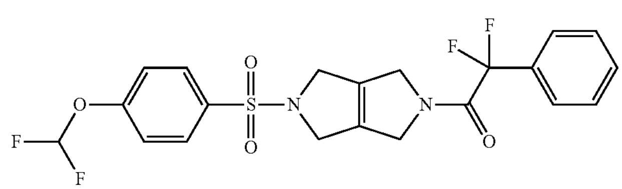 [SMILES: O=C(N1CC2=C(C1)CN(S(=O)(=O)c1ccc(OC(F)F)cc1)C2)C(F)(F)c1ccccc1] | 471.1 |
| 18-26 | 1-{5-[4-(Difluoromethoxy)benzenesulfonyl]-1H,2H,3H,4H,5H,6H-pyrrolo[3,4-c]pyrrol-2-yl}-2-(pyridin-3-yl)ethan-1-one | 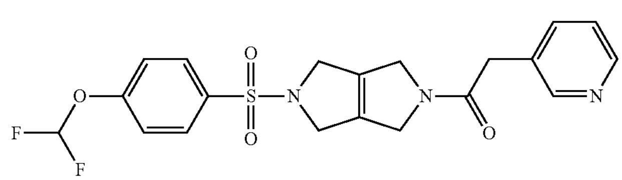 [SMILES: O=C(Cc1cccnc1)N1CC2=C(C1)CN(S(=O)(=O)c1ccc(OC(F)F)cc1)C2] | 436.1 |

TABLE 7-continued

| Example | Name | Structure | LCMS (m/z) |
|---|---|---|---|
| 18-27 | 1-{5-[4-(Difluoromethoxy)benzenesulfonyl]-1H,2H,3H,4H,5H,6H-pyrrolo[3,4-c]pyrrol-2-yl}-2-(1H-pyrrol-2-yl)ethan-1-one | 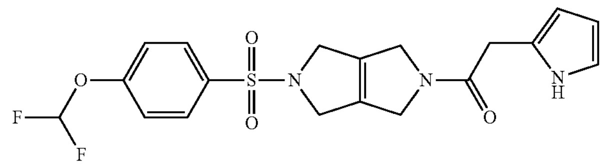 [SMILES: O=C(Cc1ccc[nH]1)N1CC2=C(C1)CN(S(=O)(=O)c1ccc(OC(F)F)cc1)C2] | 424.0 |
| 18-28 | 1-{5-[4-(Difluoromethoxy)benzenesulfonyl]-1H,2H,3H,4H,5H,6H-pyrrolo[3,4-c]pyrrol-2-yl}-2-(pyrimidin-2-yl)ethan-1-one | 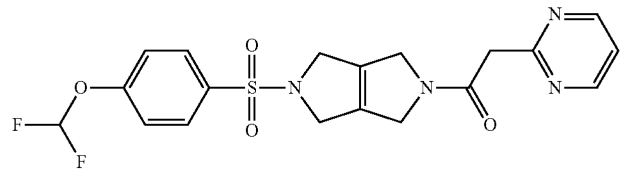 [SMILES: O=C(Cc1ncccn1)N1CC2=C(C1)CN(S(=O)(=O)c1ccc(OC(F)F)cc1)C2] | 437.0 |
| 18-29 | 1-{5-[4-(Difluoromethoxy)benzenesulfonyl]-1H,2H,3H,4H,5H,6H-pyrrolo[3,4-c]pyrrol-2-yl}-2-(pyrazin-2-yl)ethan-1-one | 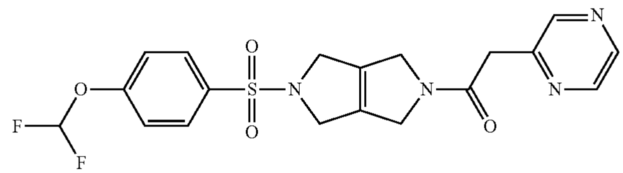 | 437.0 |
| 18-30 | 1-{5-[4-(Difluoromethoxy)benzenesulfonyl]-1H,2H,3H,4H,5H,6H-pyrrolo[3,4-c]pyrrol-2-yl}-2-(6-methylpyridin-3-yl)ethan-1-one | 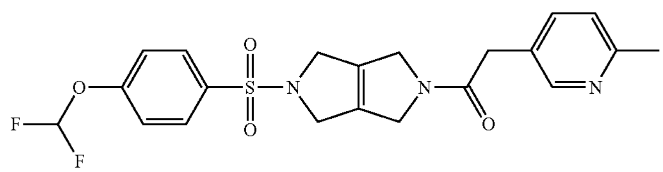 [SMILES: Cc1ccc(CC(=O)N2CC3=C(C2)CN(S(=O)(=O)c2ccc(OC(F)F)cc2)C3)cn1] | 450.1 |
| 18-31 | (2R)-1-{5-[4-(difluoromethoxy)benzenesulfonyl]-1H,2H,3H,4H,5H,6H-pyrrolo[3,4-c]pyrrol-2-yl}-2-(4-fluorophenyl)-2-hydroxyethan-1-one | 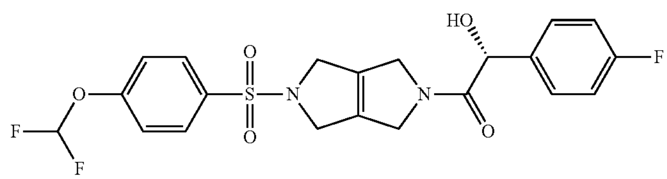 [SMILES: O=C([C@H](O)c1ccc(F)cc1)N1CC2=C(C1)CN(S(=O)(=O)c1ccc(OC(F)F)cc1)C2] | 469.1 |
| 18-32 | 1-{5-[4-(Difluoromethoxy)benzenesulfonyl]-1H,2H,3H,4H,5H,6H-pyrrolo[3,4-c]pyrrol-2-yl}-2-hydroxy-2-[4-(trifluoromethyl)phenyl]ethan-1-one | 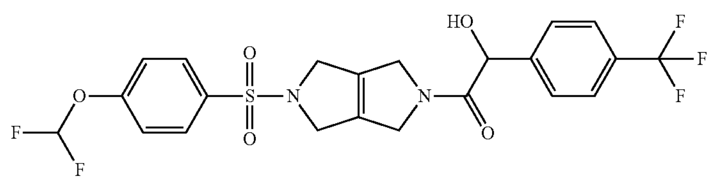 [SMILES: O=C(C(O)c1ccc(C(F)(F)F)cc1)N1CC2=C(C1)CN(S(=O)(=O)c1ccc(OC(F)F)cc1)C2] | 519.1 |
| 18-33 | 2-[4-(Difluoromethoxy)benzenesulfonyl]-5-(3,4-dihydro-1H-2-benzopyran-1-carbonyl)-1H,2H,3H,4H,5H,6H-pyrrolo[3,4-c]pyrrole | 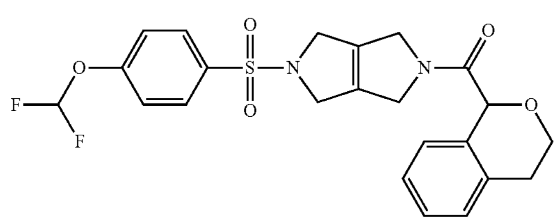 [SMILES: O=C(C1OCCc2ccccc21)N1CC2=C(C1)CN(S(=O)(=O)c1ccc(OC(F)F)cc1)C2] | 477.1 |
| 18-34 | (2S)-2-(2-methyl-1,3-thiazol-4-yl)-1-{5-[(1-methyl-1H-pyrazol-3-yl)sulfonyl]-1H,2H,3H,4H,5H,6H-pyrrolo[3,4-c]pyrrol-2-yl}butan-1-one | 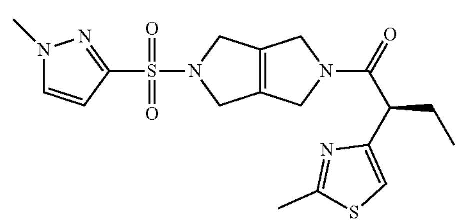 [SMILES: CC[C@H](C(=O)N1CC2=C(C1)CN(S(=O)(=O)c1ccn(C)n1)C2)c1csc(C)n1] | 422.1 |

TABLE 7-continued

| Example | Name | Structure | LCMS (m/z) |
|---|---|---|---|
| 18-35 | (2R)-3-methyl-2-phenyl-1-[5-(pyridine-2-sulfonyl)-1H,2H,3H,4H,5H,6H-pyrrolo[3,4-c]pyrrol-2-yl]butan-1-one | 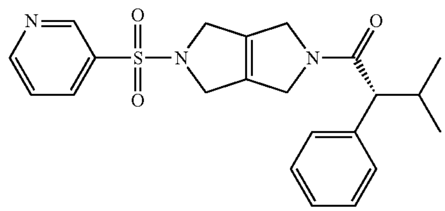 [SMILES: CC(C)[C@@H](C(=O)N1CC2=C(C1)CN(S(=O)(=O)c1cccnc1)C2)c1ccccc1] | 412.1 |
| 18-36 | (2R)-1-[5-(4-fluorobenzenesulfonyl)-1H,2H,3H,4H,5H,6H-pyrrolo[3,4-c]pyrrol-2-yl]-3-methyl-2-phenylbutan-1-one | 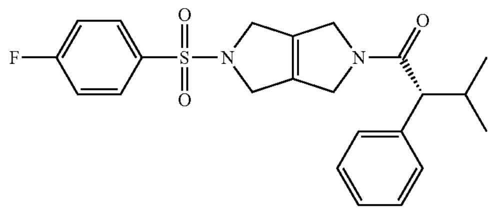 [SMILES: CC(C)[C@@H](C(=O)N1CC2=C(C1)CN(S(=O)(=O)c1ccc(F)cc1)C2)c1ccccc1] | 429.1 |
| 18-37 | (2R)-1-[5-(4-fluorobenzenesulfonyl)-1H,2H,3H,4H,5H,6H-pyrrolo[3,4-c]pyrrol-2-yl]-2-(4-methoxyphenyl)butan-1-one | 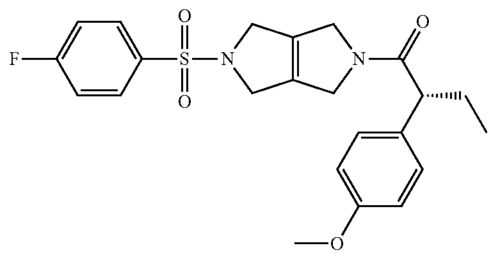 [SMILES: CC[C@@H](C(=O)N1CC2=C(C1)CN(S(=O)(=O)c1ccc(F)cc1)C2)c1ccc(OC)cc1] | 445.1 |
| 18-38 | (2S)-1-[5-(4-fluorobenzenesulfonyl)-1H,2H,3H,4H,5H,6H-pyrrolo[3,4-c]pyrrol-2-yl]-2-(2-methyl-1,3-thiazol-4-yl)butan-1-one | 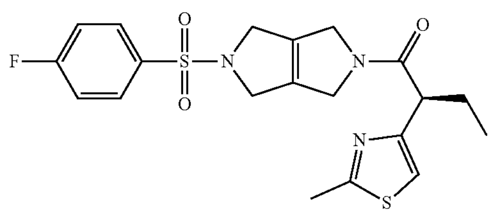 [SMILES: CC[C@H](C(=O)N1CC2=C(C1)CN(S(=O)(=O)c1ccc(F)cc1)C2)c1csc(C)n1] | 436.1 |
| 18-39 | (2R)-3-methyl-1-[5-(2-methylbenzenesulfonyl)-1H,2H,3H,4H,5H,6H-pyrrolo[3,4-c]pyrrol-2-yl]-2-phenylbutan-1-one | 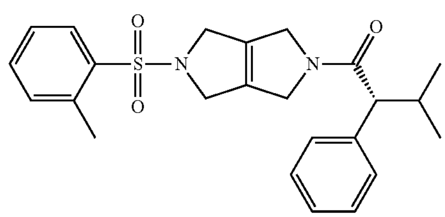 [SMILES: Cc1ccccc1S(=O)(=O)N1CC2=C(CN(C(=O)[C@@H](c3ccccc3)C(C)C)C2)C1] | 425.1 |
| 18-40 | (2R)-1-[5-(3-fluorobenzenesulfonyl)-1H,2H,3H,4H,5H,6H-pyrrolo[3,4-c]pyrrol-2-yl]-3-methyl-2-phenylbutan-1-one | 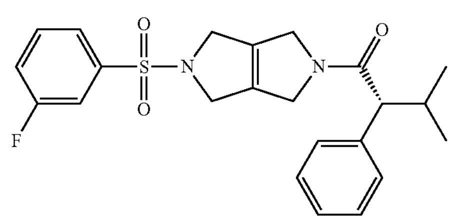 [SMILES: CC(C)[C@@H](C(=O)N1CC2=C(C1)CN(S(=O)(=O)c1cccc(F)c1)C2)c1ccccc1] | 429.1 |
| 18-41 | (2S)-1-[5-(3-fluorobenzenesulfonyl)-1H,2H,3H,4H,5H,6H-pyrrolo[3,4-c]pyrrol-2-yl]-2-(2-methyl-1,3-thiazol-4-yl)butan-1-one | 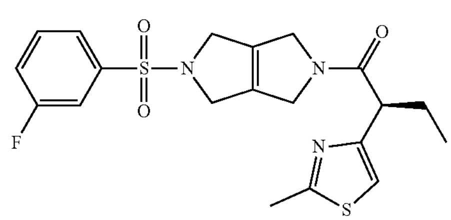 [SMILES: CC[C@H](C(=O)N1CC2=C(C1)CN(S(=O)(=O)c1cccc(F)c1)C2)c1csc(C)n1] | 436.1 |

TABLE 7-continued

| Example | Name | Structure | LCMS (m/z) |
|---|---|---|---|
| 18-42 | (2R)-1-{5-[(1,2-dimethyl-1H-imidazol-4-yl)sulfonyl]-1H,2H,3H,4H,5H,6H-pyrrolo[3,4-c]pyrrol-2-yl}-3-methyl-2-phenylbutan-1-one | 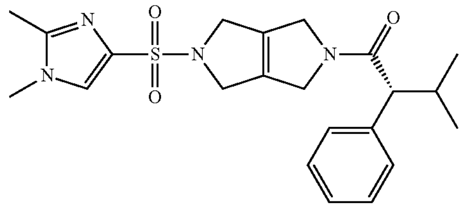 [SMILES: Cc1nc(S(=O)(=O)N2CC3=C(CN(C(=O)[C@@H](c4ccccc4)C(C)C)C3)C2)cn1C] | 429.1 |
| 18-43 | (2R)-1-{5-[(5-chloro-1,3-dimethyl-1H-pyrazol-4-yl)sulfonyl]-1H,2H,3H,4H,5H,6H-pyrrolo[3,4-c]pyrrol-2-yl}-2-hydroxy-2-phenylethan-1-one | 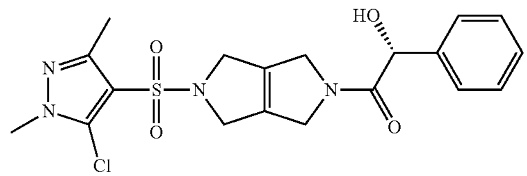 [SMILES: Cc1nn(C)c(Cl)c1S(=O)(=O)N1CC2=C(CN(C(=O)[C@H](O)c3ccccc3)C2)C1] | 437.1 |
| 18-44 | (2R)-1-{5-[(dimethyl-1,2-oxazol-4-yl)sulfonyl]-1H,2H,3H,4H,5H,6H-pyrrolo[3,4-c]pyrrol-2-yl}-2-hydroxy-2-phenylethan-1-one | 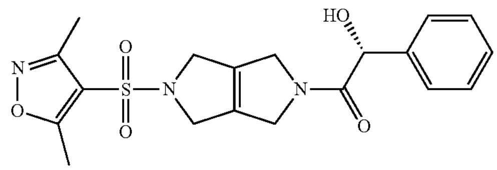 [SMILES: Cc1noc(C)c1S(=O)(=O)N1CC2=C(CN(C(=O)[C@H](O)c3ccccc3)C2)C1] | 404.1 |
| 18-45 | 4-({5-[(2R)-2-hydroxy-2-phenylacetyl]-1H,2H,3H,4H,5H,6H-pyrrolo[3,4-c]pyrrol-2-yl}sulfonyl)benzonitrile | 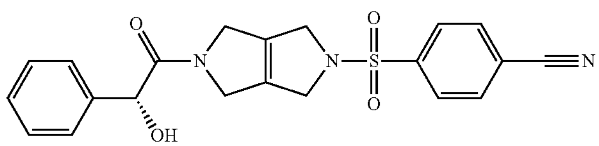 [SMILES: N#Cc1ccc(S(=O)(=O)N2CC3=C(CN(C(=O)[C@H](O)c4ccccc4)C3)C2)cc1] | 410.1 |
| 18-46 | (2R)-2-hydroxy-2-phenyl-1-{5-[2-(trifluoromethoxy)benzenesulfonyl]-1H,2H,3H,4H,5H,6H-pyrrolo[3,4-c]pyrrol-2-yl}ethan-1-one | 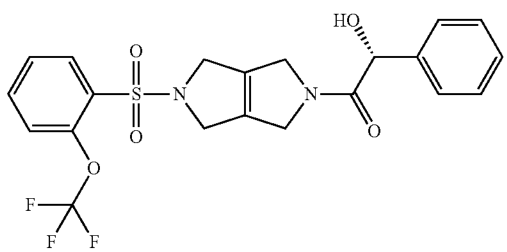 [SMILES: O=C([C@H](O)c1ccccc1)N1CC2=C(C1)CN(S(=O)(=O)c1ccccc1OC(F)(F)F)C2] | 469.1 |
| 18-47 | 2-({5-[(2R)-2-hydroxy-2-phenylacetyl]-1H,2H,3H,4H,5H,6H-pyrrolo[3,4-c]pyrrol-2-yl}sulfonyl)benzonitrile | 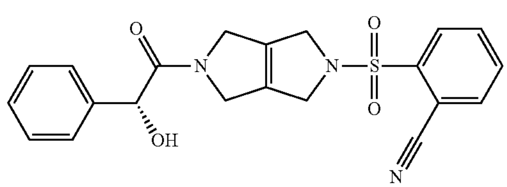 [SMILES: N#Cc1ccccc1S(=O)(=O)N1CC2=C(CN(C(=O)[C@H](O)c3ccccc3)C2)C1] | 410.1 |
| 18-48 | 3-({5-[(2R)-2-hydroxy-2-phenylacetyl]-1H,2H,3H,4H,5H,6H-pyrrolo[3,4-c]pyrrol-2-yl}sulfonyl)benzonitrile | 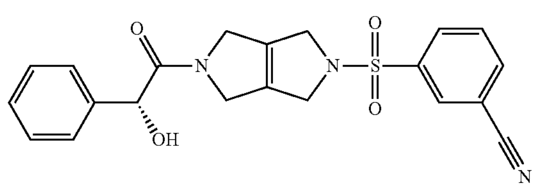 [SMILES: N#Cc1cccc(S(=O)(=O)N2CC3=C(CN(C(=O)[C@H](O)c4ccccc4)C3)C2)c1] | 410.2 |
| 18-49 | (2R)-2-hydroxy-2-phenyl-1-{5-[3-(trifluoromethyl)benzenesulfonyl]-1H,2H,3H,4H,5H,6H-pyrrolo[3,4-c]pyrrol-2-yl}ethan-1-one | 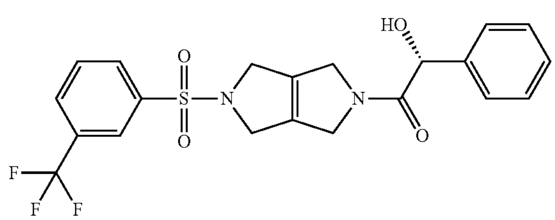 [SMILES: O=C([C@H](O)c1ccccc1)N1CC2=C(C1)CN(S(=O)(=O)c1cccc(C(F)(F)F)c1)C2] | 453.1 |

TABLE 7-continued

| Example | Name | Structure | LCMS (m/z) |
|---|---|---|---|
| 18-50 | (2R)-1-[5-(3-fluorobenzenesulfonyl)-1H,2H,3H,4H,5H,6H-pyrrolo[3,4-c]pyrrol-2-yl]-2-hydroxy-2-phenylethan-1-one | 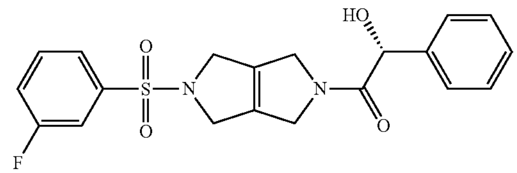 [SMILES: O=C([C@H](O)c1ccccc1)N1CC2=C(C1)CN(S(=O)(=O)c1cccc(F)c1)C2] | 403.1 |
| 18-51 | (2R)-1-[5-(3-fluoro-4-methylbenzenesulfonyl)-1H,2H,3H,4H,5H,6H-pyrrolo[3,4-c]pyrrol-2-yl]-2-hydroxy-2-phenylethan-1-one | 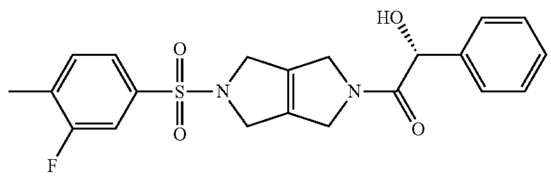 [SMILES: Cc1ccc(S(=O)(=O)N2CC3=C(CN(C(=O)[C@H](O)c4ccccc4)C3)C2)cc1F] | 417.1 |
| 18-52 | (2R)-1-[5-(3,5-difluorobenzenesulfonyl)-1H,2H,3H,4H,5H,6H-pyrrolo[3,4-c]pyrrol-2-yl]-2-hydroxy-2-phenylethan-1-one | 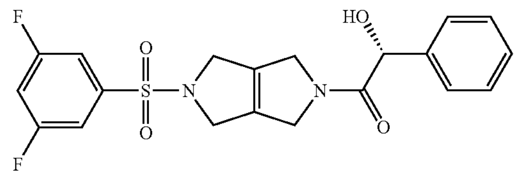 [SMILES: O=C([C@H](O)c1ccccc1)N1CC2=C(C1)CN(S(=O)(=O)c1cc(F)cc(F)c1)C2] | 421.1 |
| 18-53 | (2R)-1-[5-(3,4-difluorobenzenesulfonyl)-1H,2H,3H,4H,5H,6H-pyrrolo[3,4-c]pyrrol-2-yl]-2-hydroxy-2-phenylethan-1-one | 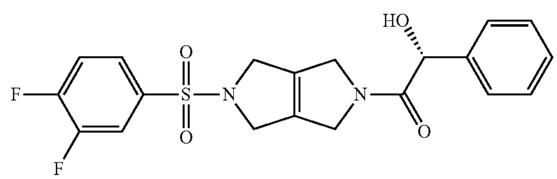 [SMILES: O=C([C@H](O)c1ccccc1)N1CC2=C(C1)CN(S(=O)(=O)c1ccc(F)c(F)c1)C2] | 421.1 |
| 18-54 | (2S)-1-[5-(2-chloro-6-methylbenzenesulfonyl)-1H,2H,3H,4H,5H,6H-pyrrolo[3,4-c]pyrrol-2-yl]-2-hydroxy-2-phenylethan-1-one | 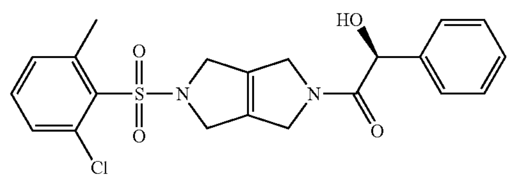 [SMILES: Cc1cccc(Cl)c1S(=O)(=O)N1CC2=C(CN(C(=O)[C@@H](O)c3ccccc3)C2)C1] | 433.1 |
| 18-55 | (2R)-1-{5-[(5-chlorothiophen-2-yl)sulfonyl]-1H,2H,3H,4H,5H,6H-pyrrolo[3,4-c]pyrrol-2-yl}-2-hydroxy-2-phenylethan-1-one | 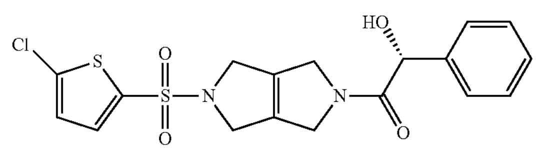 [SMILES: O=C([C@H](O)c1ccccc1)N1CC2=C(C1)CN(S(=O)(=O)c1ccc(Cl)s1)C2] | 425.0 |
| 18-56 | N-[4-({5-[(2R)-2-hydroxy-2-phenylacetyl]-1H,2H,3H,4H,5H,6H-pyrrolo[3,4-c]pyrrol-2-yl}sulfonyl)phenyl]acetamide | 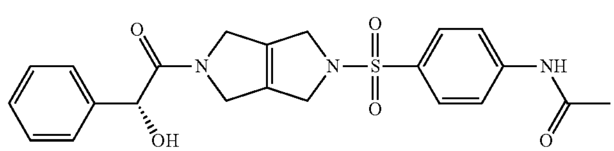 [SMILES: CC(=O)Nc1ccc(S(=O)(=O)N2CC3=C(CN(C(=O)[C@H](O)c4ccccc4)C3)C2)cc1] | 442.1 |
| 18-57 | (2R)-1-[5-(2-chloro-5-fluorobenzenesulfonyl)-1H,2H,3H,4H,5H,6H-pyrrolo[3,4-c]pyrrol-2-yl]-2-hydroxy-2-phenylethan-1-one | 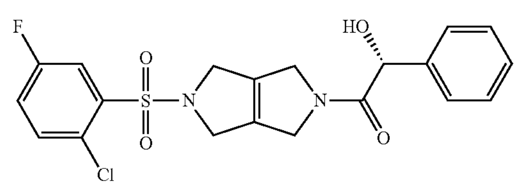 | 437.0 |
| 18-58 | (2R)-1-[5-(4-chloro-2-methoxybenzenesulfonyl)-1H,2H,3H,4H,5H,6H-pyrrolo[3,4-c]pyrrol-2-yl]-2-hydroxy-2-phenylethan-1-one | 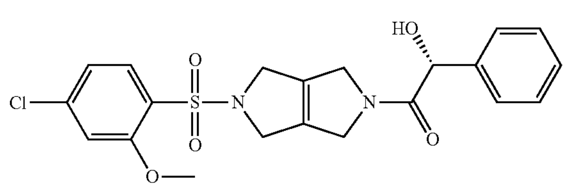 [SMILES: COc1cc(Cl)ccc1S(=O)(=O)N1CC2=C(CN(C(=O)[C@H](O)c3ccccc3)C2)C1] | 449.1 |

TABLE 7-continued

| Example | Name | Structure | LCMS (m/z) |
|---|---|---|---|
| 18-59 | 3-({5-[(2R)-oxolane-2-carbonyl]-1H,2H,3H,4H,5H,6H-pyrrolo[3,4-c]pyrrol-2-yl}sulfonyl)pyridine | 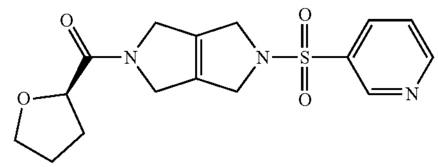 [SMILES: O=C([C@H]1CCCO1)N1CC2=C(C1)CN(S(=O)(=O)c1cccnc1)C2] | 350.2 |
| 18-60 | 2-({5-[(2R)-oxolane-2-carbonyl]-1H,2H,3H,4H,5H,6H-pyrrolo[3,4-c]pyrrol-2-yl}sulfonyl)pyridine | 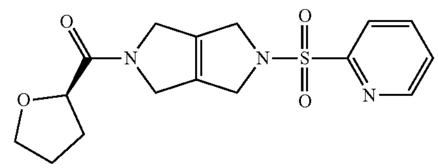 [SMILES: O=C([C@H]1CCCO1)N1CC2=C(C1)CN(S(=O)(=O)c1ccccn1)C2] | 350.2 |
| 18-61 | 2-(6-Methylpyridin-3-yl)-1-[5-(pyridine-2-sulfonyl)-1H,2H,3H,4H,5H,6H-pyrrolo[3,4-c]pyrrol-2-yl]ethan-1-one | 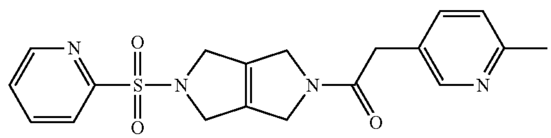 [SMILES: Cc1ccc(CC(=O)N2CC3=C(C2)CN(S(=O)(=O)c2ccccn2)C3)cn1] | 385.2 |
| 18-62 | (2R)-2-(4-fluorophenyl)-2-hydroxy-1-[5-(pyridine-3-sulfonyl)-1H,2H,3H,4H,5H,6H-pyrrolo[3,4-c]pyrrol-2-yl]ethan-1-one | 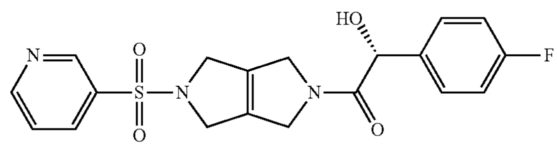 [SMILES: O=C([C@H](O)c1ccc(F)cc1)N1CC2=C(C1)CN(S(=O)(=O)c1cccnc1)C2] | 404.2 |
| 18-63 | (2R)-2-(4-fluorophenyl)-2-hydroxy-1-[5-(pyridine-2-sulfonyl)-1H,2H,3H,4H,5H,6H-pyrrolo[3,4-c]pyrrol-2-yl]ethan-1-one | 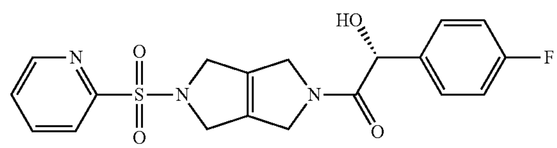 [SMILES: O=C([C@H](O)c1ccc(F)cc1)N1CC2=C(C1)CN(S(=O)(=O)c1ccccn1)C2] | 404.2 |
| 18-64 | (2R)-2-(4-fluorophenyl)-2-hydroxy-1-(5-{[6-(trifluoromethyl)pyridin-3-yl]sulfonyl}-1H,2H,3H,4H,5H,6H-pyrrolo[3,4-c]pyrrol-2-yl)ethan-1-one | 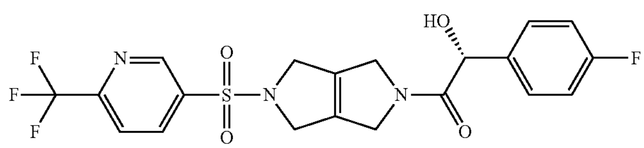 [SMILES: O=C([C@H](O)c1ccc(F)cc1)N1CC2=C(C1)CN(S(=O)(=O)c1ccc(C(F)(F)F)nc1)C2] | 474.2 |
| 18-65 | 1-[5-(Pyridine-2-sulfonyl)-1H,2H,3H,4H,5H,6H-pyrrolo[3,4-c]pyrrole-2-carbonyl]cyclopropan-1-ol | 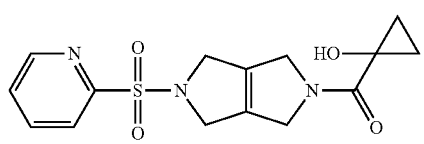 [SMILES: O=C(N1CC2=C(C1)CN(S(=O)(=O)c1ccccn1)C2)C1(O)CC1] | 336.2 |
| 18-66 | 2-(2,4-Difluorophenyl)-1-[5-(pyridine-3-sulfonyl)-1H,2H,3H,4H,5H,6H-pyrrolo[3,4-c]pyrrol-2-yl]ethan-1-one | 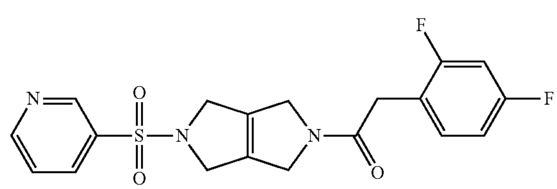 [SMILES: O=C(Cc1ccc(F)cc1F)N1CC2=C(C1)CN(S(=O)(=O)c1cccnc1)C2] | 406.2 |
| 18-67 | 2-(2,4-Difluorophenyl)-1-[5-(pyridine-2-sulfonyl)-1H,2H,3H,4H,5H,6H-pyrrolo[3,4-c]pyrrol-2-yl]ethan-1-one | 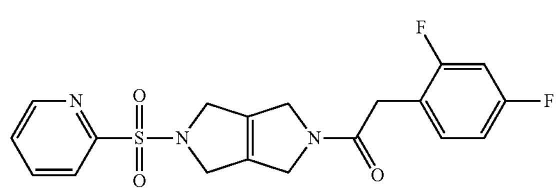 [SMILES: O=C(Cc1ccc(F)cc1F)N1CC2=C(C1)CN(S(=O)(=O)c1ccccn1)C2] | 406.2 |

TABLE 7-continued

| Example | Name | Structure | LCMS (m/z) |
|---|---|---|---|
| 18-68 | 2-(2-Methyl-1,3-thiazol-4-yl)-1-[5-(pyridine-2-sulfonyl)-1H,2H,3H,4H,5H,6H-pyrrolo[3,4-c]pyrrol-2-yl]ethan-1-one | 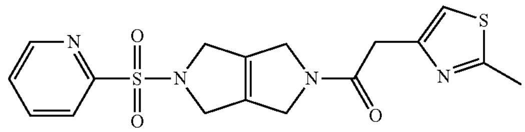 [SMILES: Cc1nc(CC(=O)N2CC3=C(C2)CN(S(=O)(=O)c2ccccn2)C3)cs1] | 391.2 |
| 18-69 | 2-({5-[(2S)-oxolane-2-carbonyl]-1H,2H,3H,4H,5H,6H-pyrrolo[3,4-c]pyrrol-2-yl}sulfonyl)pyridine | 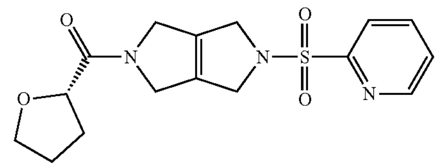 [SMILES: O=C([C@@H]1CCCO1)N1CC2=C(C1)CN(S(=O)(=O)c1ccccn1)C2] | 350.2 |
| 18-70 | 1-[5-(Pyridine-3-sulfonyl)-1H,2H,3H,4H,5H,6H-pyrrolo[3,4-c]pyrrol-2-yl]-2-(1H-1,2,3,4-tetrazol-1-yl)ethan-1-one | 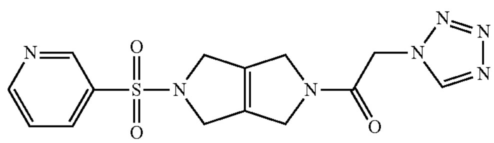 [SMILES: O=C(Cn1cnnn1)N1CC2=C(C1)CN(S(=O)(=O)c1cccnc1)C2] | 362.2 |
| 18-71 | 1-[5-(Pyridine-2-sulfonyl)-1H,2H,3H,4H,5H,6H-pyrrolo[3,4-c]pyrrol-2-yl]-2-(1H-1,2,3,4-tetrazol-1-yl)ethan-1-one | 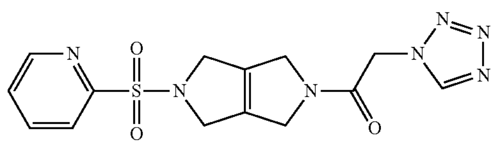 [SMILES: O=C(Cn1cnnn1)N1CC2=C(C1)CN(S(=O)(=O)c1ccccn1)C2] | 362.2 |
| 18-72 | 2-(3-Methyl-1,2-oxazol-5-yl)-1-[5-(pyridine-2-sulfonyl)-1H,2H,3H,4H,5H,6H-pyrrolo[3,4-c]pyrrol-2-yl]ethan-1-one | 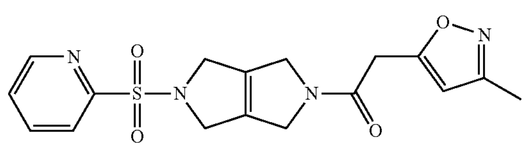 [SMILES: Cc1cc(CC(=O)N2CC3=C(C2)CN(S(=O)(=O)c2ccccn2)C3)on1] | 375.2 |
| 18-73 | 1-[5-(Pyridine-3-sulfonyl)-1H,2H,3H,4H,5H,6H-pyrrolo[3,4-c]pyrrol-2-yl]-2-(1H-pyrrol-2-yl)ethan-1-one | 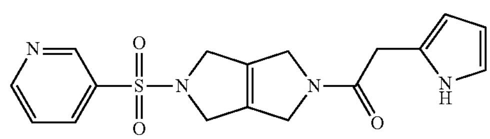 [SMILES: O=C(Cc1ccc[nH]1)N1CC2=C(C1)CN(S(=O)(=O)c1cccnc1)C2] | 359.2 |
| 18-74 | 1-[5-(Pyridine-2-sulfonyl)-1H,2H,3H,4H,5H,6H-pyrrolo[3,4-c]pyrrol-2-yl]-2-(1H-pyrrol-2-yl)ethan-1-one | 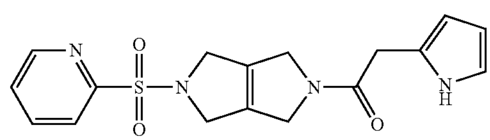 [SMILES: O=C(Cc1ccc[nH]1)N1CC2=C(C1)CN(S(=O)(=O)c1ccccn1)C2] | 359.2 |
| 18-75 | (2S)-2-hydroxy-1-{5-[(4-methyl-3,4-dihydro-2H-1,4-benzoxazin-6-yl)sulfonyl]-1H,2H,3H,4H,5H,6H-pyrrolo[3,4-c]pyrrol-2-yl}butan-1-one | 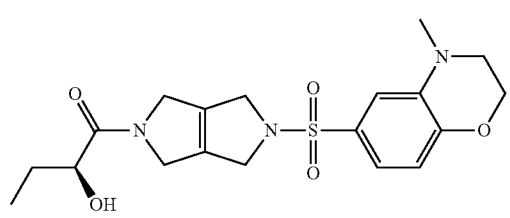 [SMILES: CC[C@H](O)C(=O)N1CC2=C(C1)CN(S(=O)(=O)c1ccc3c(c1)N(C)CCO3)C2] | 408.2 |
| 18-76 | (2R)-2-hydroxy-1-{5-[(4-methyl-3,4-dihydro-2H-1,4-benzoxazin-6-yl)sulfonyl]-1H,2H,3H,4H,5H,6H-pyrrolo[3,4-c]pyrrol-2-yl}butan-1-one | 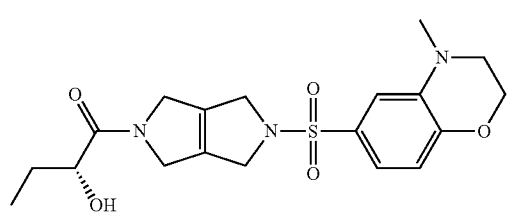 [SMILES: CC[C@@H](O)C(=O)N1CC2=C(C1)CN(S(=O)(=O)c1ccc3c(c1)N(C)CCO3)C2] | 408.2 |

TABLE 7-continued

| Example | Name | Structure | LCMS (m/z) |
|---|---|---|---|
| 18-77 | 4-Methyl-6-({5-[(2S)-oxolane-2-carbonyl]-1H,2H,3H,4H,5H,6H-pyrrolo[3,4-c]pyrrol-2-yl}sulfonyl)-3,4-dihydro-2H-1,4-benzoxazine | 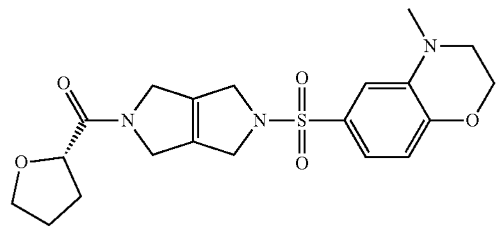 [SMILES: CN1CCOc2ccc(S(=O)(=O)N3CC4=C(CN(C(=O)[C@@H]5CCCO5)C4)C3)cc21] | 420.2 |
| 18-78 | 6-({5-Cyclopentanecarbonyl-1H,2H,3H,4H,5H,6H-pyrrolo[3,4-c]pyrrol-2-yl}sulfonyl)-4-methyl-3,4-dihydro-2H-1,4-benzoxazine | 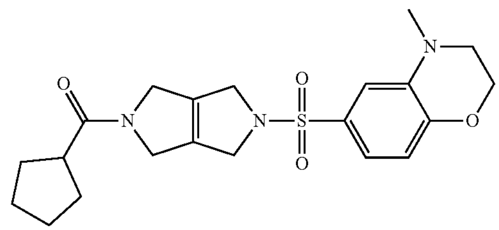 | 418.2 |
| 18-79 | N-{4-[5-(1-benzofuran-5-sulfonyl)-1H,2H,3H,4H,5H,6H-pyrrolo[3,4-c]pyrrole-2-carbonyl]-1,3-thiazol-2-yl}pyridin-3-amine | 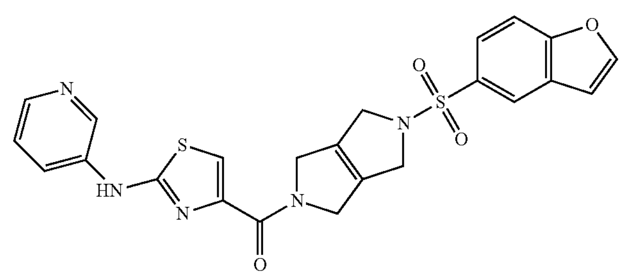 [SMILES: O=C(c1csc(Nc2cccnc2)n1)N1CC2=C(C1)CN(S(=O)(=O)c1ccc3occc3c1)C2] | 494.1 |
| 18-80 | 2-(1-Benzofuran-5-sulfonyl)-5-(furan-3-carbonyl)-1H,2H,3H,4H,5H,6H-pyrrolo[3,4-c]pyrrole | 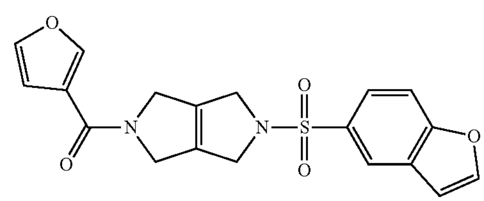 [SMILES: O=C(c1ccoc1)N1CC2=C(C1)CN(S(=O)(=O)c1ccc3occc3c1)C2] | 385.1 |
| 18-81 | 5-[5-(1-Benzofuran-5-sulfonyl)-1H,2H,3H,4H,5H,6H-pyrrolo[3,4-c]pyrrole-2-carbonyl]-2-(2,2,2-trifluoroethoxy)pyridine | 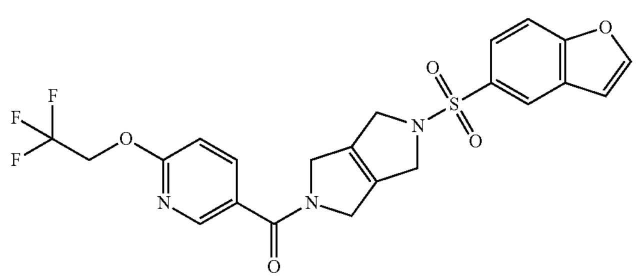 [SMILES: O=C(c1ccc(OCC(F)(F)F)nc1)N1CC2=C(C1)CN(S(=O)(=O)c1ccc3occc3c1)C2] | 494.1 |
| 18-82 | 2-[5-(1-Benzofuran-5-sulfonyl)-1H,2H,3H,4H,5H,6H-pyrrolo[3,4-c]pyrrole-2-carbonyl]-5-methylpyrazine | 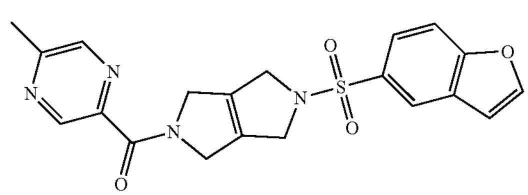 [SMILES: Cc1cnc(C(=O)N2CC3=C(C2)CN(S(=O)(=O)c2ccc4occc4c2)C3)cn1] | 411.1 |
| 18-83 | 2-[5-(1-Benzofuran-5-sulfonyl)-1H,2H,3H,4H,5H,6H-pyrrolo[3,4-c]pyrrole-2-carbonyl]pyridine | 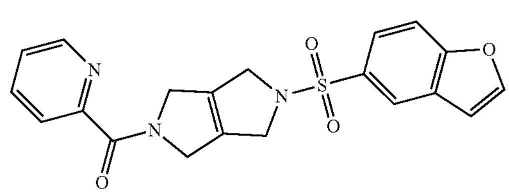 [SMILES: O=C(c1ccccn1)N1CC2=C(C1)CN(S(=O)(=O)c1ccc3occc3c1)C2] | 396.1 |

TABLE 7-continued

| Example | Name | Structure | LCMS (m/z) |
|---|---|---|---|
| 18-84 | 3-[5-(1-Benzofuran-5-sulfonyl)-1H,2H,3H,4H,5H,6H-pyrrolo[3,4-c]pyrrole-2-carbonyl]-1,5-dimethyl-1H-pyrazole | 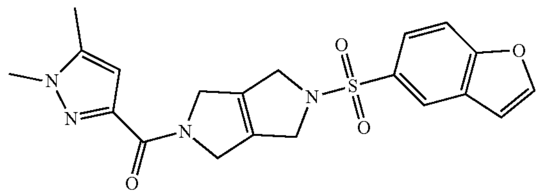 [SMILES: Cc1cc(C(=O)N2CC3=C(C2)CN(S(=O)(=O)c2ccc4occc4c2)C3)nn1C] | 413.1 |
| 18-85 | 5-[5-(1-Benzofuran-5-sulfonyl)-1H,2H,3H,4H,5H,6H-pyrrolo[3,4-c]pyrrole-2-carbonyl]-2,4-dimethyl-1,3-thiazole | 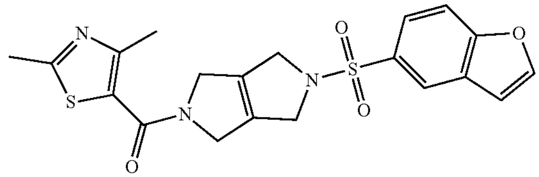 [SMILES: Cc1nc(C)c(C(=O)N2CC3=C(C2)CN(S(=O)(=O)c2ccc4occc4c2)C3)s1] | 430.1 |
| 18-86 | 5-[5-(1-Benzofuran-5-sulfonyl)-1H,2H,3H,4H,5H,6H-pyrrolo[3,4-c]pyrrole-2-carbonyl]-2-(trifluoromethyl)pyrimidine | 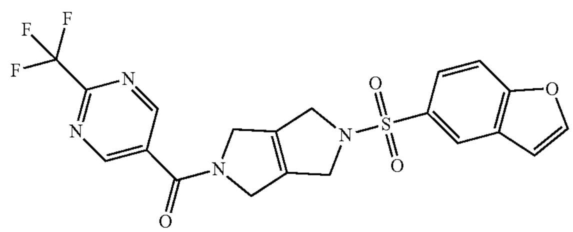 [SMILES: O=C(c1cnc(C(F)(F)F)nc1)N1CC2=C(C1)CN(S(=O)(=O)c1ccc3occc3c1)C2] | 506.1 |
| 18-87 | 4-[5-(1-Benzofuran-5-sulfonyl)-1H,2H,3H,4H,5H,6H-pyrrolo[3,4-c]pyrrole-2-carbonyl]-5-methyl-1,3-oxazole | 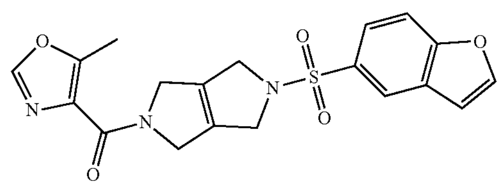 [SMILES: Cc1ocnc1C(=O)N1CC2=C(C1)CN(S(=O)(=O)c1ccc3occc3c1)C2] | 400.1 |
| 18-88 | 2-(1-Benzofuran-5-sulfonyl)-5-(furan-2-carbonyl)-1H,2H,3H,4H,5H,6H-pyrrolo[3,4-c]pyrrole | 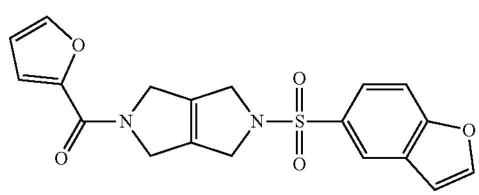 [SMILES: O=C(c1ccco1)N1CC2=C(C1)CN(S(=O)(=O)c1ccc3occc3c1)C2] | 385.1 |

Example 18-19: 1-(5-((4-(difluoromethoxy)phenyl)sulfonyl)-3,4,5,6-tetrahydropyrrolo[3,4-c]pyrrol-2(1H)-yl)-2-(1H-tetrazol-1-yl)ethan-1-one

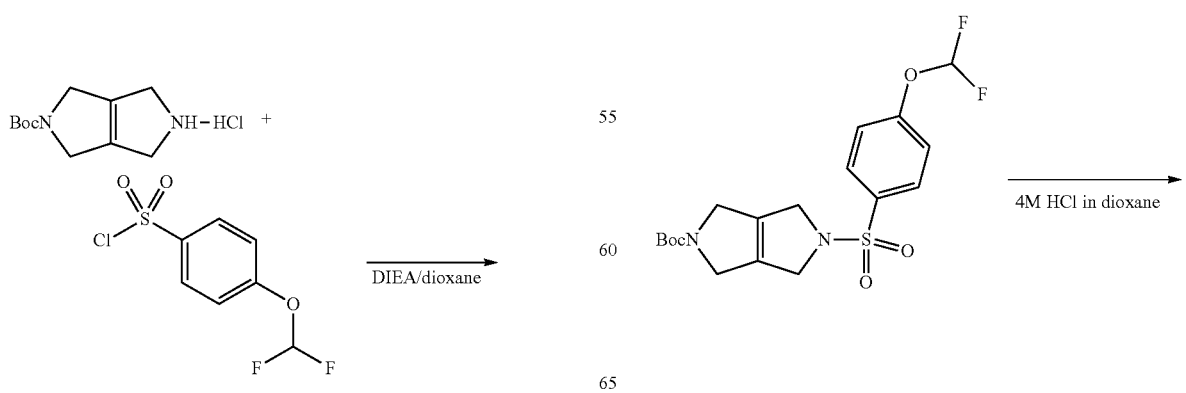

-continued

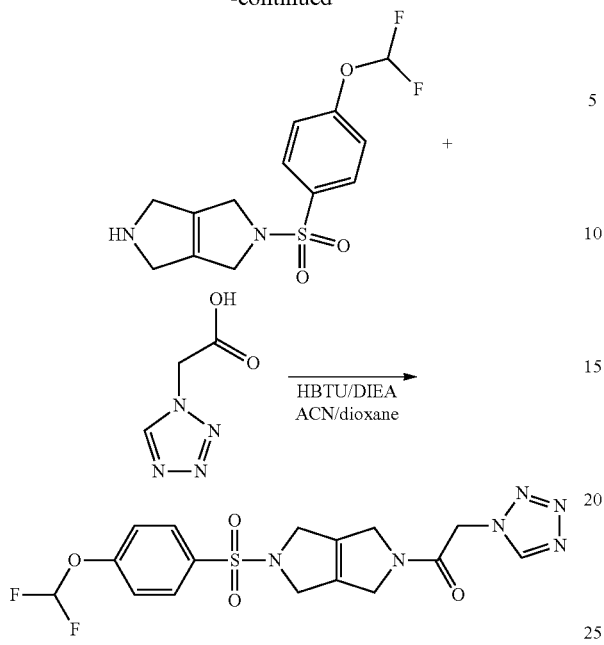

Example 18-19

A 0.2 M solution of 4-(difluoromethoxy)benzenesulfonyl chloride (158 µL, 31.5 µmol) in dioxane was added to a 1.5 mL vial charged with a 0.2 M solution of tert-butyl 3,4,5,6-tetrahydropyrrolo[3,4-c]pyrrole-2(1H)-carboxylate hydrochloride (150 µL, 30 µmol) in a solvent mixture of acetonitrile/DIEA (90:10). The reaction mixture was heated at 50° C. with shaking for 2 hours. Dioxane (200 µL), methanol (200 µL), and a solution of 4 N HCl in dioxane (100 µL, 0.200 mmol) was added. The reaction was heated at 50° C. with shaking for an additional 2 hours. The volatiles were removed under reduced pressure. ACN (200 uL) was added to the vial. The vial was shaken for 15 minutes to resuspend the residue. Neat DIEA (25 µL, 0.143 mmol) and a 0.2 M solution of 2-(1H-tetrazol-1-yl)acetic acid (165 µL, 33 µmol) in dioxane was added to the vial, followed by a 0.2 M solution of HBTU (165 µL, 33 µmol) in ACN. The reaction was heated at 50° C. with shaking for an additional 2 hours. The volatiles were removed under reduced pressure. The residue was mixed with 1 N NaOH (0.5 mL) and extracted with 3:1 EtOAc/ACN (2×0.5 mL). The organic layer was concentrated under reduced pressure. The compound was purified using mass-triggered HPLC to give 1-(5-((4-(difluoromethoxy)phenyl)sulfonyl)-3,4,5,6-tetrahydropyrrolo[3,4-c]pyrrol-2(1H)-yl)-2-(1H-tetrazol-1-yl)ethan-1-one (4.9 mg, 38% yield). LCMS: m/z=427.1 [M+H]+, Rt: 1.10 min (LCMS method 1).

Example 18-25: 1-(5-((4-(Difluoromethoxy)phenyl)sulfonyl)-3,4,5,6-tetrahydropyrrolo[3,4-c]pyrrol-2(1H)-yl)-2,2-difluoro-2-phenylethan-1-one

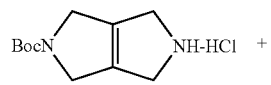   +

-continued

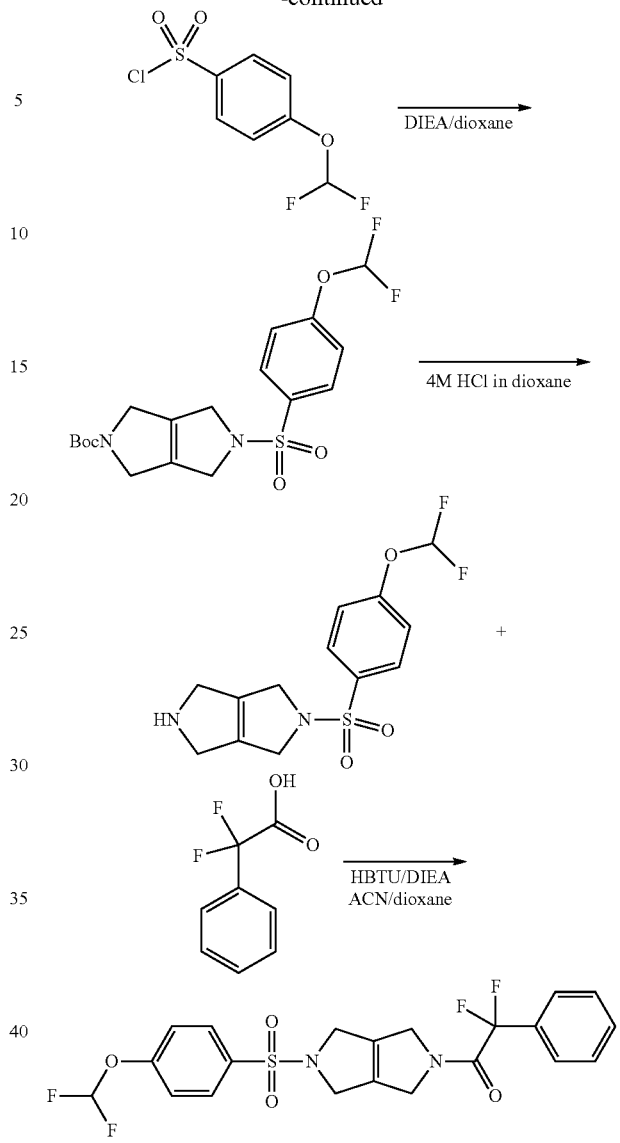

Example 18-25

A 0.2 M solution of 4-(difluoromethoxy)benzenesulfonyl chloride (158 µL, 31.5 µmol) in dioxane was added to a 1.5 mL vial charged with a 0.2 M solution of tert-butyl 3,4,5,6-tetrahydropyrrolo[3,4-c]pyrrole-2(1H)-carboxylate hydrochloride (150 µL, 30 µmol) in a solvent mixture of acetonitrile/DIEA (90:10). The reaction mixture was heated at 50° C. with shaking for 2 hours. Dioxane (200 µL), methanol (200 µL), and a solution of 4 N HCl in dioxane (100 µL, 0.200 mmol) was added. The reaction was heated at 50° C. with shaking for an additional 2 hours. The volatiles were removed under reduced pressure. ACN (200 uL) was added to the vial. The vial was shaken for 15 minutes to resuspend the residue. Neat DIEA (25 µL, 0.143 mmol) and a 0.2 M solution of 2,2-difluoro-2-phenylacetic acid (165 µL, 33 µmol) in dioxane was added to the vial, followed by a 0.2 M solution of HBTU (165 µL, 33 µmol) in ACN. The reaction was heated at 50° C. with shaking for an additional 2 hours. The volatiles were removed under reduced pressure. The residue was mixed with 1 N NaOH (0.5 mL) and extracted with 3:1 EtOAc/ACN (2×0.5 mL).

The organic layer was concentrated under reduced pressure. The compound was purified using mass-triggered HPLC to give 1-(5-((4-(difluoromethoxy)phenyl)sulfonyl)-3,4,5,6-tetrahydropyrrolo[3,4-c]pyrrol-2(1H)-yl)-2,2-difluoro-2-phenylethan-1-one (1.7 mg, 12% yield). LCMS: m/z=471.1 [M+H]+, Rt: 1.58 min (LCMS method 1).

Example 19-1: (2R)-1-{5-[(5-chlorothiophen-2-yl)sulfonyl]-1H,2H,3H,4H,5H,6H-pyrrolo[3,4-c]pyrrol-2-yl}-2-phenylpropan-1-one

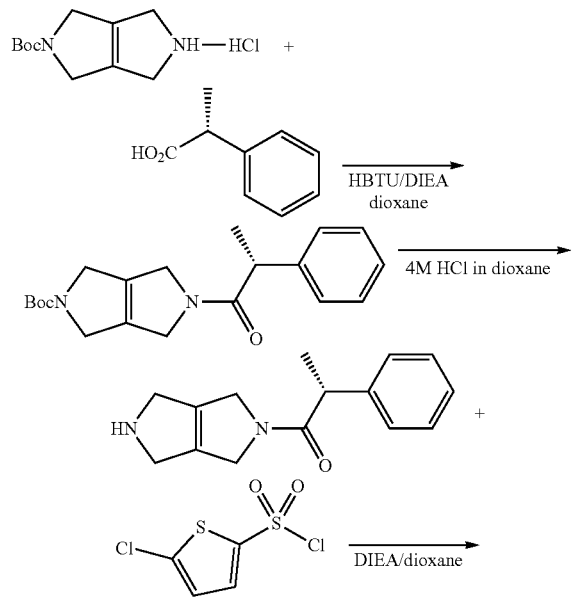

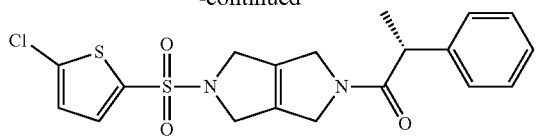

Example 19-1

To a 1.5 mL vial was added a 0.2 M solution of tert-butyl 3,4,5,6-tetrahydropyrrolo[3,4-c]pyrrole-2(1H)-carboxylate hydrochloride (100 µL, 20 µmol), a 0.2 M solution of (R)-2-phenylpropanoic acid (110 µL, 22 µmol), and neat DIEA (10 µL, 0.057 mmol) to give a brown suspension. A 0.2 M solution of HBTU (110 µL, 22 µmol) in ACN was added. The reaction was shaken for 2 hours at RT. 4 M HCl in dioxane (50.0 µL, 0.200 mmol) was added. The reaction was heated at 50° C. with shaking for an additional 2 hours. The volatiles were evaporated under reduced pressure. The residue was mixed with 1 N NaOH (0.5 mL) and extracted with 3:1 EtOAc/ACN (2×0.5 mL). The volatiles were evaporated under reduced pressure and ACN (200 µM) was added to the vial. The vial was shaken for 15 minutes to resuspend the residue, then neat DIEA (10 µL, 57 µmol) was added to the vial followed by a 0.2 M solution of 5-chlorothiophene-2-sulfonyl chloride (110 µL, 22 µmol) in dioxane. The reaction was heated at 50° C. with shaking for an additional 2 hours. The volatiles were removed under reduced pressure. The residue was mixed with 1 N NaOH (0.5 mL) and extracted with 3:1 EtOAc/ACN (2×0.5 mL). The volatiles were removed under reduced pressure. The compound was purified using mass-triggered HPLC to provide (2R)-1-{5-[(5-chlorothiophen-2-yl)sulfonyl]-1H,2H,3H,4H,5H,6H-pyrrolo[3,4-c]pyrrol-2-yl}-2-phenylpropan-1-one. LCMS: m/z=423.1 [M+H]+.

The Examples in Table 8 below were prepared according to the procedure outlined above for Example 19-1, using the appropriate synthetic precursors.

TABLE 8

| Example | Name | Structure | LCMS (m/z) |
|---|---|---|---|
| 19-2 | (2R)-1-{5-[(5-chloro-1,3-dimethyl-1H-pyrazol-4-yl)sulfonyl]-1H,2H,3H,4H,5H,6H-pyrrolo[3,4-c]pyrrol-2-yl}-2-phenylpropan-1-one | 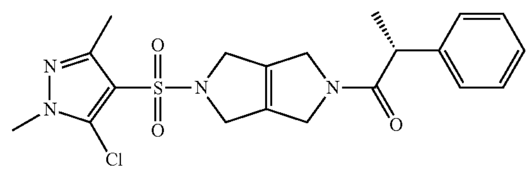 [SMILES: Cc1nn(C)c(Cl)c1S(=O)(=O)N1CC2=C(CN(C(=O)[C@H](C)c3ccccc3)C2)C1] | 435.2 |
| 19-3 | (2R)-1-{5-[(1,2-dimethyl-1H-imidazol-4-yl)sulfonyl]-1H,2H,3H,4H,5H,6H-pyrrolo[3,4-c]pyrrol-2-yl}-2-phenylpropan-1-one | 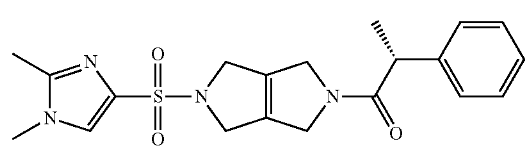 [SMILES: Cc1nc(S(=O)(=O)N2CC3=C(CN(C(=O)[C@H](C)c4ccccc4)C3)C2)cn1C] | 401.2 |
| 19-4 | 2-(4-Fluorophenoxy)-1-{5-[(1-methyl-1H-imidazol-2-yl)sulfonyl]-1H,2H,3H,4H,5H,6H-pyrrolo[3,4-c]pyrrol-2-yl}propan-1-one | 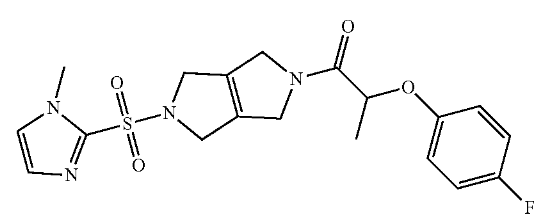 [SMILES: CC(Oc1ccc(F)cc1)C(=O)N1CC2=C(C1)CN(S(=O)(=O)c1nccn1C)C2] | 421.2 |

TABLE 8-continued

| Example | Name | Structure | LCMS (m/z) |
|---|---|---|---|
| 19-5 | 1-[5-(1-Benzofuran-5-sulfonyl)-1H,2H,3H,4H,5H,6H-pyrrolo[3,4-c]pyrrol-2-yl]-2-(4-fluorophenoxy)propan-1-one | 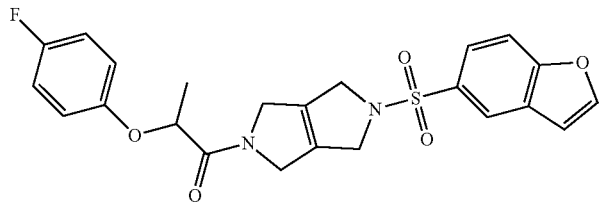 [SMILES: CC(Oc1ccc(F)cc1)C(=O)N1CC2=C(C1)CN(S(=O)(=O)c1ccc3occc3c1)C2] | 457.2 |
| 19-6 | 1-[5-(1-Benzofuran-5-sulfonyl)-1H,2H,3H,4H,5H,6H-pyrrolo[3,4-c]pyrrol-2-yl]-2-(3-methoxyphenoxy)propan-1-one | 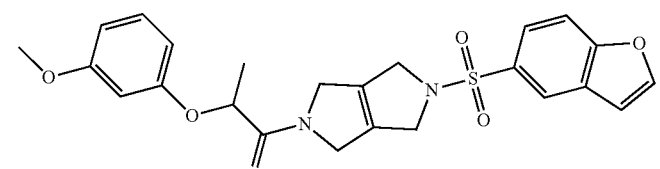 | 469.2 |
| 19-7 | 1-[5-(1-Benzofuran-5-sulfonyl)-1H,2H,3H,4H,5H,6H-pyrrolo[3,4-c]pyrrol-2-yl]-2-phenoxypropan-1-one | 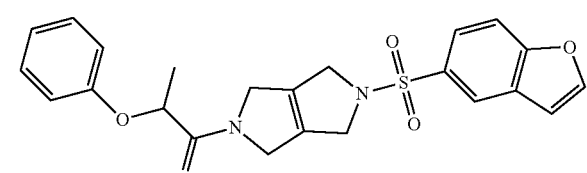 | 439.2 |
| 19-8 | 2-(1H-1,3-benzodiazol-1-yl)-1-{5-[(1,2-dimethyl-1H-imidazol-4-yl)sulfonyl]-1H,2H,3H,4H,5H,6H-pyrrolo[3,4-c]pyrrol-2-yl}butan-1-one | 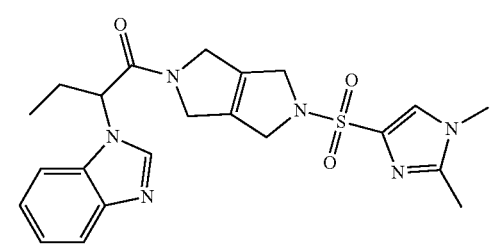 [SMILES: CCC(C(=O)N1CC2=C(C1)CN(S(=O)(=O)c1cn(C)c(C)n1)C2)n1cnc2ccccc21] | 455.2 |
| 19-9 | 2-(1H-1,3-benzodiazol-1-yl)-1-{5-[(1,2-dimethyl-1H-imidazol-4-yl)sulfonyl]-1H,2H,3H,4H,5H,6H-pyrrolo[3,4-c]pyrrol-2-yl}propan-1-one | 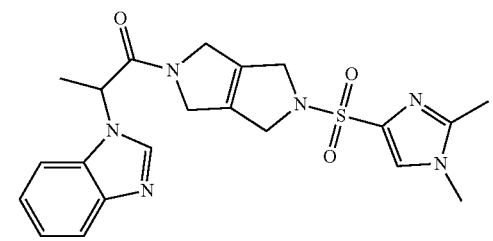 [SMILES: Cc1nc(S(=O)(=O)N2CC3=C(CN(C(=O)C(C)n4cnc5ccccc54)C3)C2)cn1C] | 441.2 |
| 19-20 | (5-(Benzofuran-5-ylsulfonyl)-3,4,5,6-tetrahydropyrrolo[3,4-c]pyrrol-2(1H)-yl)((cis)-2-phenylcyclopropyl)methanone | 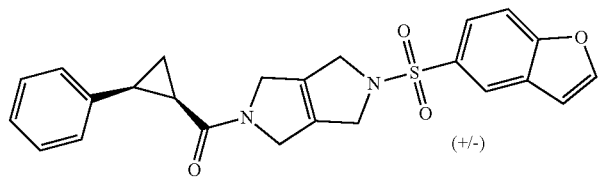 [SMILES: O=C([C@@H]1C[C@@H]1c1ccccc1)N1CC2=C(C1)CN(S(=O)(=O)c1ccc3occc3c1)C2] | 435.1 |
| 19-21 | 2-(1-Benzofuran-5-sulfonyl)-5-cyclohexanecarbonyl-1H,2H,3H,4H,5H,6H-pyrrolo[3,4-c]pyrrole | 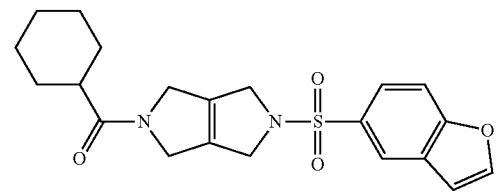 [SMILES: O=C(C1CCCCC1)N1CC2=C(C1)CN(S(=O)(=O)c1ccc3occc3c1)C2] | 401.2 |

TABLE 8-continued

| Example | Name | Structure | LCMS (m/z) |
|---|---|---|---|
| 19-22 | 1-[5-(1-Benzofuran-5-sulfonyl)-1H,2H,3H,4H,5H,6H-pyrrolo[3,4-c]pyrrol-2-yl]-2-methylpentan-1-one | 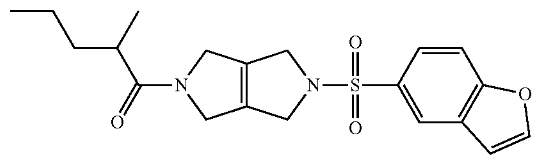 [SMILES: CCCC(C)C(=O)N1CC2=C(C1)CN(S(=O)(=O)c1ccc3occc3c1)C2] | 389.2 |
| 19-23 | 2-(1-Benzofuran-5-sulfonyl)-5-(oxane-4-carbonyl)-1H,2H,3H,4H,5H,6H-pyrrolo[3,4-c]pyrrole | 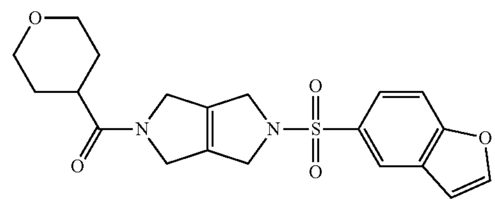 [SMILES: O=C(C1CCOCC1)N1CC2=C(C1)CN(S(=O)(=O)c1ccc3occc3c1)C2] | 403.2 |
| 19-24 | Methyl (3S)-4-[5-(1-benzofuran-5-sulfonyl)-1H,2H,3H,4H,5H,6H-pyrrolo[3,4-c]pyrrol-2-yl]-3-methyl-4-oxobutanoate | 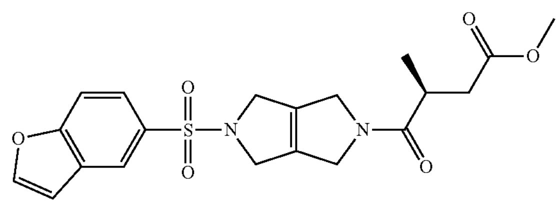 [SMILES: COC(=O)C[C@H](C)C(=O)N1CC2=C(C1)CN(S(=O)(=O)c1ccc3occc3c1)C2] | 419.2 |
| 19-25 | 2-(1-Benzofuran-5-sulfonyl)-5-(oxolane-2-carbonyl)-1H,2H,3H,4H,5H,6H-pyrrolo[3,4-c]pyrrole | 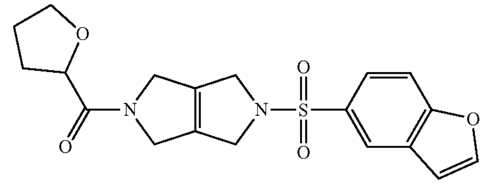 [SMILES: O=C(C1CCCO1)N1CC2=C(C1)CN(S(=O)(=O)c1ccc3occc3c1)C2] | |
| 19-26 | (2R)-1-{5-[(dimethyl-1,2-oxazol-4-yl)sulfonyl]-1H,2H,3H,4H,5H,6H-pyrrolo[3,4-c]pyrrol-2-yl}-2-phenylpropan-1-one | 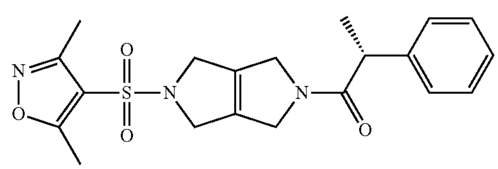 [SMILES: Cc1noc(C)c1S(=O)(=O)N1CC2=C(CN(C(=O)[C@H](C)c3ccccc3)C2)C1] | 402.2 |
| 19-27 | (2R)-1-{5-[(1,2-dimethyl-1H-imidazol-4-yl)sulfonyl]-1H,2H,3H,4H,5H,6H-pyrrolo[3,4-c]pyrrol-2-yl}-3-methyl-2-phenylbutan-1-one | 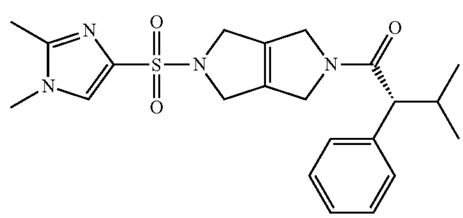 [SMILES: Cc1nc(S(=O)(=O)N2CC3=C(CN(C(=O)[C@@H](c4ccccc4)C(C)C)C3)C2)cn1C] | 429.3 |
| 19-28 | (2R)-2-(3-Methoxyphenoxy)-1-{5-[(1-methyl-1H-imidazol-2-yl)sulfonyl]-1H,2H,3H,4H,5H,6H-pyrrolo[3,4-c]pyrrol-2-yl}propan-1-one | 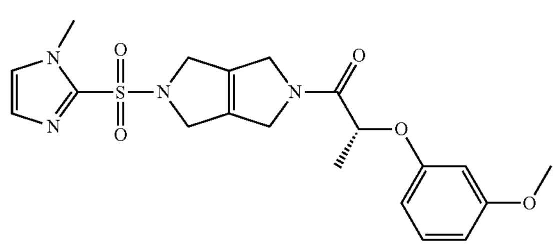 [SMILES: COc1cccc(O[C@H](C)C(=O)N2CC3=C(C2)CN(S(=O)(=O)c2nccn2C)C3)c1] | 433.2 |
| 19-29 | (2I)-2-(4-fluorophenyl)-1-{5-[(1-methyl-1H-imidazol-2-yl)sulfonyl]-1H,2H,3H,4H,5H,6H-pyrrolo[3,4-c]pyrrol-2-yl}propan-1-one | 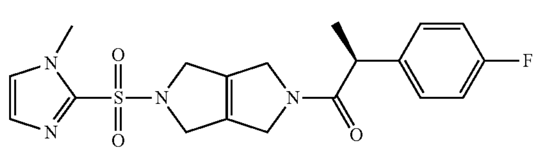 [SMILES: C[C@H](C(=O)N1CC2=C(C1)CN(S(=O)(=O)c1nccn1C)C2)c1ccc(F)cc1] | 405.2 |

TABLE 8-continued

| Example | Name | Structure | LCMS (m/z) |
|---|---|---|---|
| 19-30 | (2R)-1-[5-(benzofuran-5-sulfonyl)-1H,2H,3H,4H,5H,6H-pyrrolo[3,4-c]pyrrol-2-yl]-2-phenoxybutan-1-one | 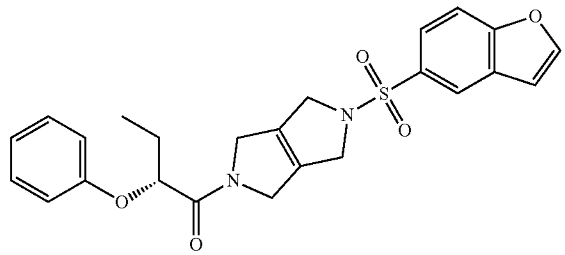 [SMILES: CC[C@@H](Oc1ccccc1)C(=O)N1CC2=C(C1)CN(S(=O)(=O)c1ccc3occc3c1)C2] | 453.2 |
| 19-31 | 3-[(2R)-1-{5-[(1,2-dimethyl-1H-imidazol-4-yl)sulfonyl]-1H,2H,3H,4H,5H,6H-pyrrolo[3,4-c]pyrrol-2-yl}-1-oxopropan-2-yl]-2,3-dihydro-1,3-benzoxazol-2-one | 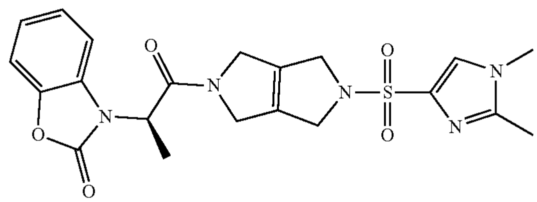 [SMILES: Cc1nc(S(=O)(=O)N2CC3=C(CN(C(=O)[C@@H](C)n4c(=O)oc5ccccc54)C3)C2)cn1C] | 458.2 |
| 19-32 | (2R)-1-[5-(1-benzofuran-5-sulfonyl)-1H,2H,3H,4H,5H,6H-pyrrolo[3,4-c]pyrrol-2-yl]-2-(2-methoxyphenoxy)propan-1-one | 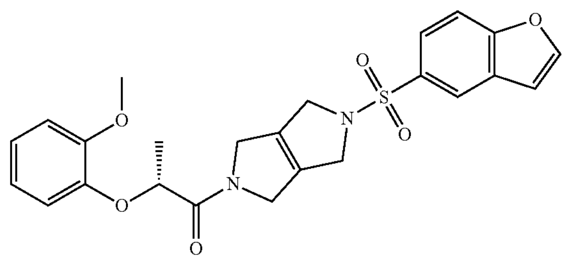 [SMILES: COc1ccccc1O[C@H](C)C(=O)N1CC2=C(C1)CN(S(=O)(=O)c1ccc3occc3c1)C2] | 469.2 |
| 19-33 | (2R)-1-{5-[(1,2-dimethyl-1H-imidazol-4-yl)sulfonyl]-1H,2H,3H,4H,5H,6H-pyrrolo[3,4-c]pyrrol-2-yl}-2-(4-methylphenyl)propan-1-one | 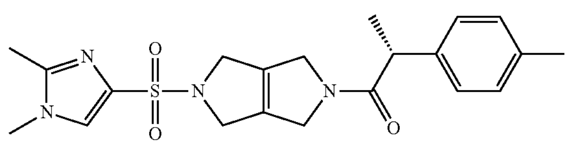 | 415.2 |

Example 19-9: 2-(1H-Benzo[d]imidazol-1-yl)-1-(5-((1,2-dimethyl-1H-imidazol-4-yl)sulfonyl)-3,4,5,6-tetrahydropyrrolo[3,4-c]pyrrol-2(1H)-yl)propan-1-one

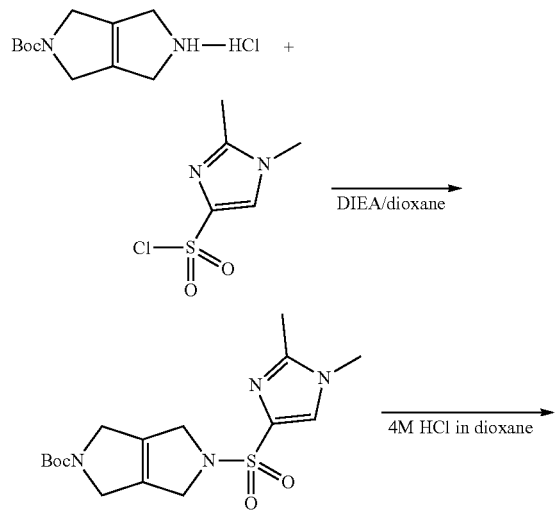

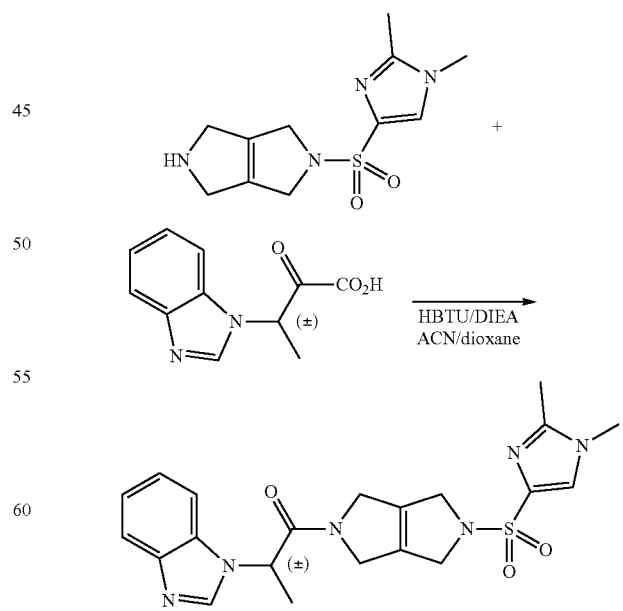

Example 19-9

A 0.2 M solution of 1,2-dimethyl-1H-imidazole-4-sulfonyl chloride (158 μL, 31.5 μmol) in dioxane was added to a 1.5 mL vial charged with a 0.2 M solution of tert-butyl 3,4,5,6-tetrahydropyrrolo[3,4-c]pyrrole-2(1H)-carboxylate hydrochloride (150 μL, 30 μmol) in a solvent mixture of acetonitrile/DIEA (90:10). The reaction mixture was heated at 50° C. with shaking for 2 hours. Dioxane (200 μL), methanol (200 μL), and a solution of 4 N HCl in dioxane (100 μL, 0.200 mmol) was added. The reaction was heated at 50° C. with shaking for an additional 2 hours. The volatiles were removed under reduced pressure. ACN (200 uL) was added to the vial. The vial was shaken for 15 minutes to resuspend the residue. Neat DIEA (25 μL, 0.143 mmol) and a 0.2 M solution of 3-(1H-benzo[d]imidazol-1-yl)-2-oxobutanoic acid (165 μL, 33 μmol) in dioxane was added to the vial, followed by a 0.2 M solution of HBTU (165 μL, 33 μmol) in ACN. The reaction was heated at 50° C. with shaking for an additional 2 hours. The volatiles were removed under reduced pressure. The residue was mixed with 1 N NaOH (0.5 mL) and extracted with 3:1 EtOAc/ACN (2×0.5 mL). The organic layer was concentrated under reduced pressure. The compound was purified using mass-triggered HPLC to give 2-(1H-benzo[d]imidazol-1-yl)-1-(5-((1,2-dimethyl-1H-imidazol-4-yl)sulfonyl)-3,4,5,6-tetrahydropyrrolo[3,4-c]pyrrol-2(1H)-yl)propan-1-one (7.5 mg, 55% yield). LCMS: m/z=455.2 [M+H]+, Rt: 0.78 min (LCMS method 1).

Example 20-1: N-(furan-2-ylmethyl)-5-(pyridin-3-ylsulfonyl)-3,4,5,6-tetrahydropyrrolo[3,4-c]pyrrole-2(1H)-carboxamide

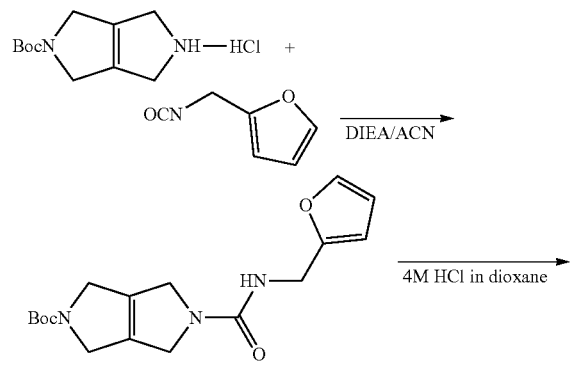

Example 20-1

To a 1.5 mL vial was added a 0.2 M solution of tert-butyl 3,4,5,6-tetrahydropyrrolo[3,4-c]pyrrole-2(1H)-carboxylate hydrochloride (100 μL, 20 μmol) in ACN, a 0.2 M solution of 2-(isocyanatomethyl)furan (110 μL, 22 μmol) in dioxane, and neat DIEA (10 μL, 57 μmol) to give a brown suspension. The reaction was shaken at RT for 2 hours. 4 M HCl in dioxane (50.0 μL, 0.200 mmol) was added. The reaction was heated at 50° C. with shaking for an additional 2 hours. The volatiles were removed under reduced pressure and ACN (0.2 μL) was added to the vial along with DIEA (25 μL, 0.143 mmol). The vial was shaken for 15 minutes to resuspend the residue, then a 0.2 M solution of pyridine-3-sulfonyl chloride (110 μL, 22 μmol) in dioxane was added. The reaction was heated at 50° C. with shaking for an additional 2 hours. The volatiles were removed under reduced pressure. The residue was mixed with 1 N NaOH (0.5 mL) and extracted with 3:1 EtOAc/ACN (2×0.5 mL). The volatiles were removed under reduced pressure. The compound was purified using mass-triggered HPLC to yield N-(furan-2-ylmethyl)-5-(pyridin-3-ylsulfonyl)-3,4,5,6-tetrahydropyrrolo[3,4-c]pyrrole-2(1H)-carboxamide (1.9 mg, 5.08 μmol, 25% yield). LCMS: m/z=375.2 [M+H]+.

The Examples in Table 9 below were prepared according to the procedure outlined above for Example 20-1, using the appropriate synthetic precursors.

TABLE 9

| Example | Name | Structure | LCMS (m/z) |
| --- | --- | --- | --- |
| 20-2 | N-[(4-methoxyphenyl)methyl]-5-(pyridine-3-sulfonyl)-1H,2H,3H,4H,5H,6H-pyrrolo[3,4-c]pyrrole-2-carboxamide | 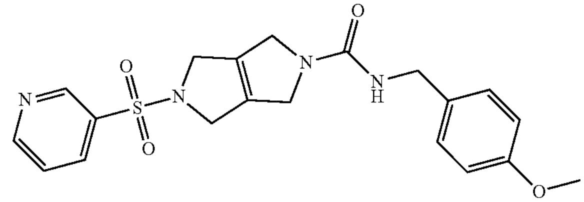 [SMILES: COc1ccc(CNC(=O)N2CC3=C(C2)CN(S(=O)(=O)c2cccnc2)C3)cc1] | 415.2 |

TABLE 9-continued

| Example | Name | Structure | LCMS (m/z) |
|---|---|---|---|
| 20-3 | 4-(4-Fluorobenzenesulfonyl)-N-[(4-methoxyphenyl)methyl]-1H,2H,3H,4H,5H,6H-pyrrolo[3,4-c]pyrrole-2-carboxamide | 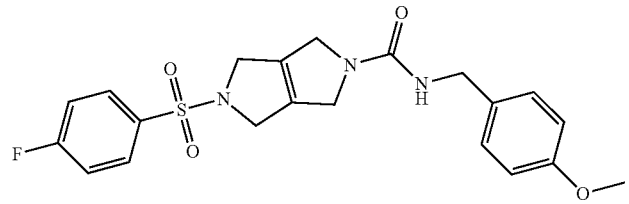 [SMILES: COc1ccc(CNC(=O)N2CC3=C(C2)CN(S(=O)(=O)c2ccc(F)cc2)C3)cc1] | 432.2 |
| 20-4 | 5-(4-Fluorobenzenesulfonyl)-N-[(3-methoxyphenyl)methyl]-1H,2H,3H,4H,5H,6H-pyrrolo[3,4-c]pyrrole-2-carboxamide | 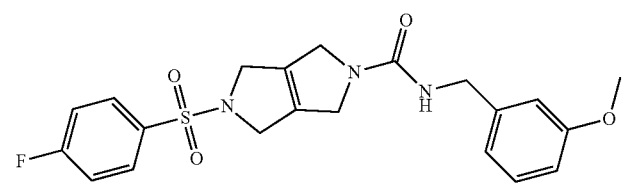 [SMILES: COc1cccc(CNC(=O)N2CC3=C(C2)CN(S(=O)(=O)c2ccc(F)cc2)C3)c1] | 432.2 |
| 20-5 | 5-(4-Fluorobenzenesulfonyl)-N-(furan-2-ylmethyl)-1H,2H,3H,4H,5H,6H-pyrrolo[3,4-c]pyrrole-2-carboxamide | 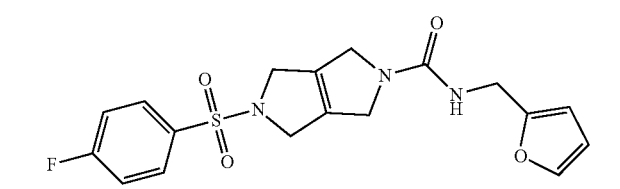 [SMILES: O=C(NCc1ccco1)N1CC2=C(C1)CN(S(=O)(=O)c1ccc(F)cc1)C2] | 392.2 |
| 20-6 | 5-(4-Fluorobenzenesulfonyl)-N-[(2-methoxyphenyl)methyl]-1H,2H,3H,4H,5H,6H-pyrrolo[3,4-c]pyrrole-2-carboxamide | 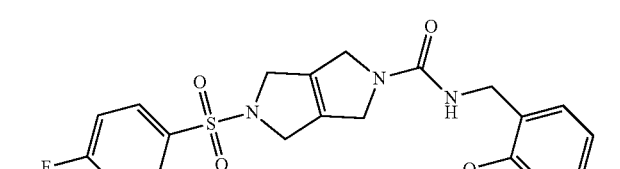 | 432.2 |
| 20-7 | 5-(3-Fluorobenzenesulfonyl)-N-[(4-methoxyphenyl)methyl]-1H,2H,3H,4H,5H,6H-pyrrolo[3,4-c]pyrrole-2-carboxamide | 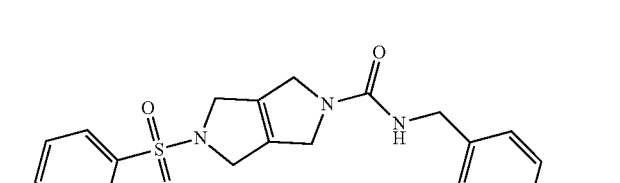 | 432.2 |
| 20-8 | 5-(3-Fluorobenzenesulfonyl)-N-[(3-methoxyphenyl)methyl]-1H,2H,3H,4H,5H,6H-pyrrolo[3,4-c]pyrrole-2-carboxamide | 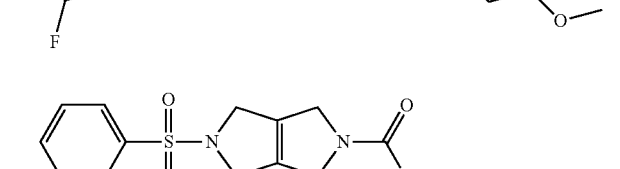 | 432.2 |
| 20-9 | 5-(3-Fluorobenzenesulfonyl)-N-(furan-2-ylmethyl)-1H,2H,3H,4H,5H,6H-pyrrolo[3,4-c]pyrrole-2-carboxamide | 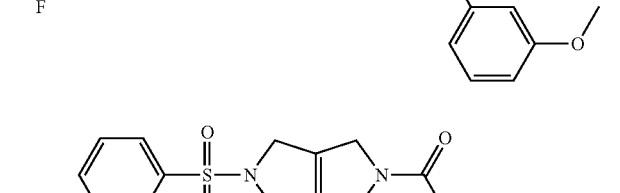 | 392.2 |

TABLE 9-continued

| Example | Name | Structure | LCMS (m/z) |
|---|---|---|---|
| 20-10 | 5-(3-Fluorobenzenesulfonyl)-N-[(2-methoxyphenyl)methyl]-1H,2H,3H,4H,5H,6H-pyrrolo[3,4-c]pyrrole-2-carboxamide | 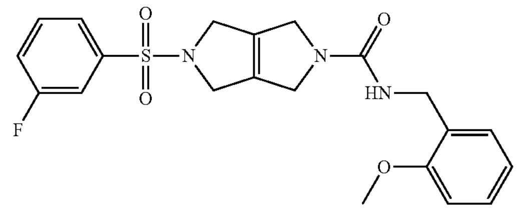 [SMILES: COc1ccccc1CNC(=O)N1CC2=C(C1)CN(S(=O)(=O)c1cccc(F)c1)C2] | 432.2 |
| 20-11 | 5-(Isoquinoline-5-sulfonyl)-N-[(4-methoxyphenyl)methyl]-1H,2H,3H,4H,5H,6H-pyrrolo[3,4-c]pyrrole-2-carboxamide | 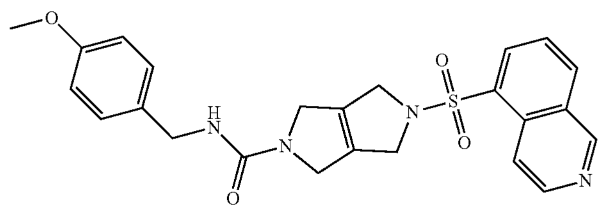 [SMILES: COc1ccc(CNC(=O)N2CC3=C(C2)CN(S(=O)(=O)c2cccc4cnccc24)C3)cc1] | 465.2 |
| 20-12 | 5-(Isoquinoline-5-sulfonyl)-N-[(3-methoxyphenyl)methyl]-1H,2H,3H,4H,5H,6H-pyrrolo[3,4-c]pyrrole-2-carboxamide | 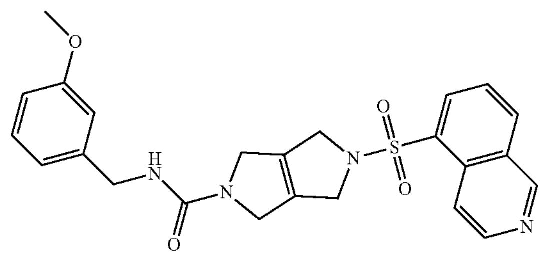 [SMILES: COc1cccc(CNC(=O)N2CC3=C(C2)CN(S(=O)(=O)c2cccc4cnccc24)C3)c1] | 465.2 |
| 20-13 | N-(furan-2-ylmethyl)-5-(isoquinoline-5-sulfonyl)-1H,2H,3H,4H,5H,6H-pyrrolo[3,4-c]pyrrole-2-carboxamide | 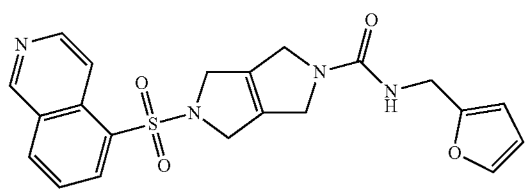 [SMILES: O=C(NCc1ccco1)N1CC2=C(C1)CN(S(=O)(=O)c1cccc3cnccc13)C2] | 425.2 |
| 20-14 | 5-(1-Benzofuran-5-sulfonyl)-N-[(4-methoxyphenyl)methyl]-1H,2H,3H,4H,5H,6H-pyrrolo[3,4-c]pyrrole-2-carboxamide | 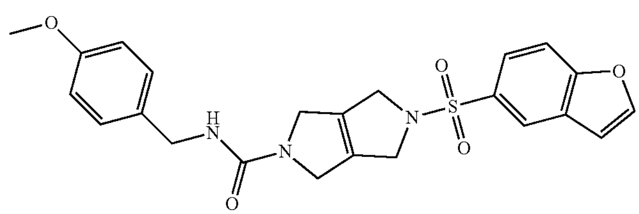 [SMILES: COc1ccc(CNC(=O)N2CC3=C(C2)CN(S(=O)(=O)c2ccc4occc4c2)C3)cc1] | 454.2 |
| 20-15 | 5-(1-Benzofuran-5-sulfonyl)-N-[(3-methoxyphenyl)methyl]-1H,2H,3H,4H,5H,6H-pyrrolo[3,4-c]pyrrole-2-carboxamide | 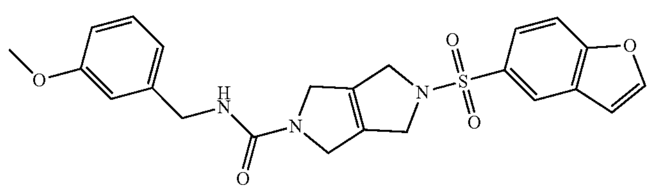 [SMILES: COc1cccc(CNC(=O)N2CC3=C(C2)CN(S(=O)(=O)c2ccc4occc4c2)C3)c1] | 454.2 |
| 20-16 | 5-(1-Benzofuran-5-sulfonyl)-N-(furan-2-ylmethyl)-1H,2H,3H,4H,5H,6H-pyrrolo[3,4-c]pyrrole-2-carboxamide | 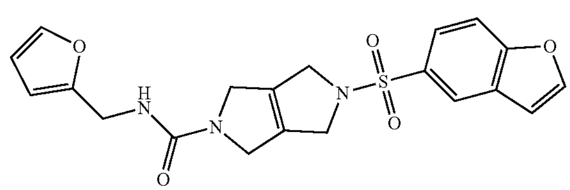 [SMILES: O=C(NCc1ccco1)N1CC2=C(C1)CN(S(=O)(=O)c1ccc3occc3c1)C2] | 414.2 |

TABLE 9-continued

| Example | Name | Structure | LCMS (m/z) |
|---|---|---|---|
| 20-17 | 5-(1-Benzofuran-5-sulfonyl)-N-[(2-methoxyphenyl)methyl]-1H,2H,3H,4H,5H,6H-pyrrolo[3,4-c]pyrrole-2-carboxamide | 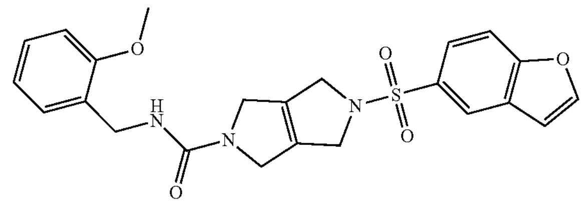 [SMILES: COc1ccccc1CNC(=O)N1CC2=C(C1)CN(S(=O)(=O)c1ccc3occc3c1)C2] | 454.2 |
| 20-18 | 5-(2,1,3-Benzoxadiazole-4-sulfonyl)-N-(furan-2-ylmethyl)-1H,2H,3H,4H,5H,6H-pyrrolo[3,4-c]pyrrole-2-carboxamide | 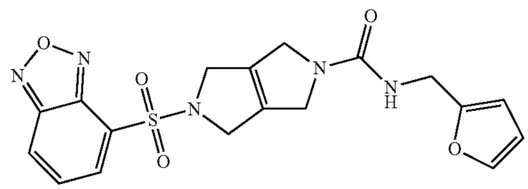 [SMILES: O=C(NCc1ccco1)N1CC2=C(C1)CN(S(=O)(=O)c1cccc3nonc13)C2] | 416.2 |
| 20-19 | 5-(2,1,3-Benzoxadiazole-4-sulfonyl)-N-[(2-methoxyphenyl)methyl]-1H,2H,3H,4H,5H,6H-pyrrolo[3,4-c]pyrrole-2-carboxamide | 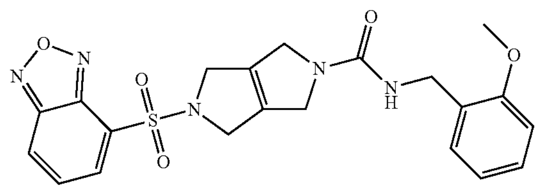 [SMILES: COc1ccccc1CNC(=O)N1CC2=C(C1)CN(S(=O)(=O)c1cccc3nonc13)C2] | 456.2 |
| 20-20 | 5-(4-Fluorobenzenesulfonyl)-N-[(4-fluorophenyl)methyl]-1H,2H,3H,4H,5H,6H-pyrrolo[3,4-c]pyrrole-2-carboxamide | 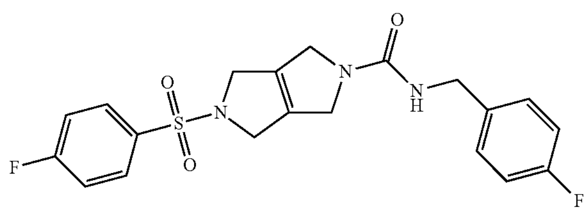 [SMILES: O=C(NCc1ccc(F)cc1)N1CC2=C(C1)CN(S(=O)(=O)c1ccc(F)cc1)C2] | 420.2 |
| 20-21 | 5-(4-Fluorobenzenesulfonyl)-N-[(1S)-1-phenylethyl]-1H,2H,3H,4H,5H,6H-pyrrolo[3,4-c]pyrrole-2-carboxamide | 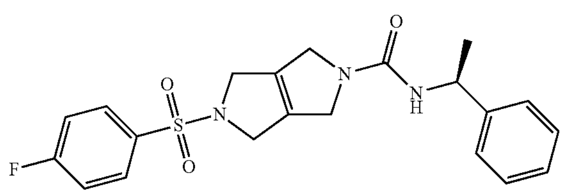 [SMILES: C[C@H](NC(=O)N1CC2=C(C1)CN(S(=O)(=O)c1ccc(F)cc1)C2)c1ccccc1] | 416.2 |
| 20-22 | 5-(3-Fluorobenzenesulfonyl)-N-[(4-fluorophenyl)methyl]-1H,2H,3H,4H,5H,6H-pyrrolo[3,4-c]pyrrole-2-carboxamide | 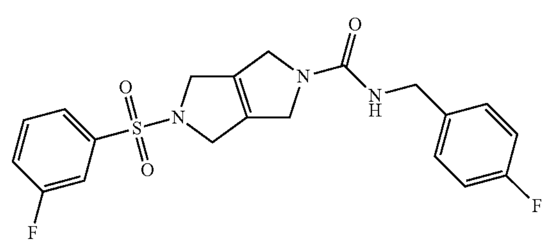 [SMILES: O=C(NCc1ccc(F)cc1)N1CC2=C(C1)CN(S(=O)(=O)c1cccc(F)c1)C2] | 420.2 |
| 20-23 | 5-(1-Benzofuran-5-sulfonyl)-N-[(4-fluorophenyl)methyl]-1H,2H,3H,4H,5H,6H-pyrrolo[3,4-c]pyrrole-2-carboxamide | 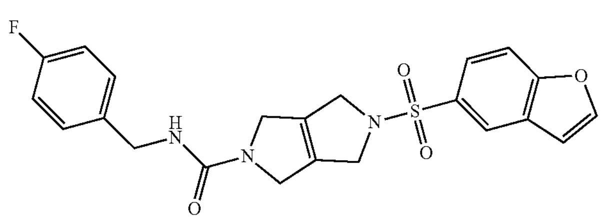 [SMILES: O=C(NCc1ccc(F)cc1)N1CC2=C(C1)CN(S(=O)(=O)c1ccc3occc3c1)C2] | 442.2 |

TABLE 9-continued

| Example | Name | Structure | LCMS (m/z) |
|---|---|---|---|
| 20-24 | 5-(2,1,3-Benzoxadiazole-4-sulfonyl)-N-[(4-fluorophenyl)methyl]-1H,2H,3H,4H,5H,6H-pyrrolo[3,4-c]pyrrole-2-carboxamide | 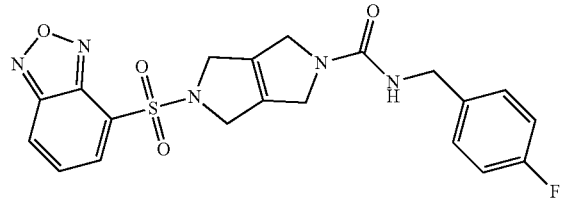 [SMILES: O=C(NCc1ccc(F)cc1)N1CC2=C(C1)CN(S(=O)(=O)c1cccc3nonc13)C2] | 444.2 |
| 20-25 | 5-(2,1,3-Benzothiadiazole-5-sulfonyl)-N-[(3-methoxyphenyl)methyl]-1H,2H,3H,4H,5H,6H-pyrrolo-[3,4-c]pyrrole-2-carboxamide | 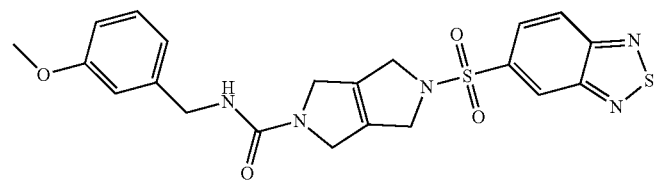 [SMILES: COc1cccc(CNC(=O)N2CC3=C(C2)CN(S(=O)(=O)c2ccc4nsnc4c2)C3)c1] | 472.2 |
| 20-26 | 5-(2,1,3-Benzothiadiazole-5-sulfonyl)-N-(furan-2-ylmethyl)-1H,2H,3H,4H,5H,6H-pyrrolo[3,4-c]pyrrole-2-carboxamide | 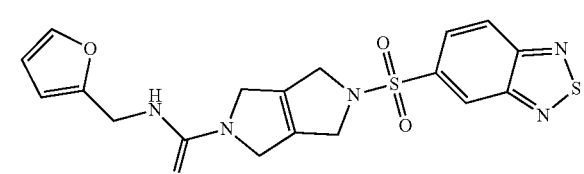 | 432.2 |
| 20-27 | 5-(2,1,3-Benzothiadiazole-5-sulfonyl)-N-[(2-methoxyphenyl)methyl]-1H,2H,3H,4H,5H,6H-pyrrolo[3,4-c]pyrrole-2-carboxamide | 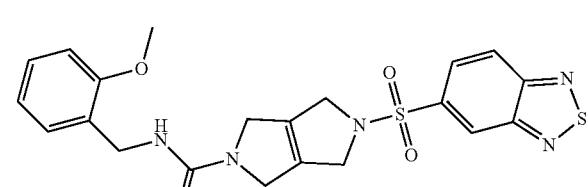 | 472.2 |
| 20-28 | 5-(2,1,3-Benzothiadiazole-5-sulfonyl)-N-[(4-fluorophenyl)methyl]-1H,2H,3H,4H,5H,6H-pyrrolo[3,4-c]pyrrole-2-carboxamide | 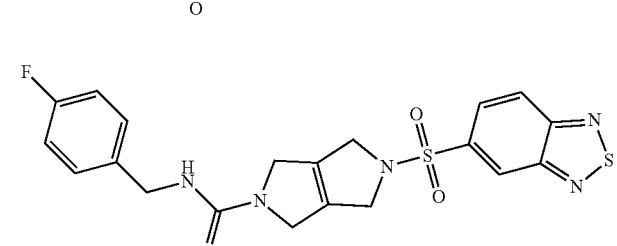 | 460.2 |
| 20-29 | 5-(1-Benzofuran-5-sulfonyl)-N-(3-methoxypropyl)-1H,2H,3H,4H,5H,6H-pyrrolo[3,4-c]pyrrole-2-carboxamide | 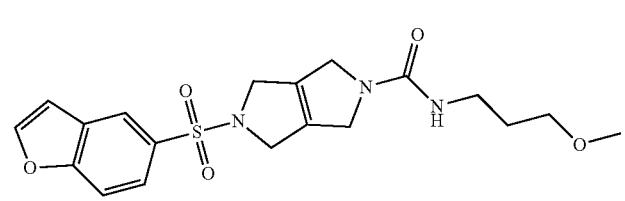 [SMILES: COCCCNC(=O)N1CC2=C(C1)CN(S(=O)(=O)c1ccc3occc3c1)C2] | 406.2 |
| 20-30 | 5-(1-Benzofuran-5-sulfonyl)-N-[(1S)-1-(4-fluorophenyl)ethyl]-1H,2H,3H,4H,5H,6H-pyrrolo[3,4-c]pyrrole-2-carboxamide | 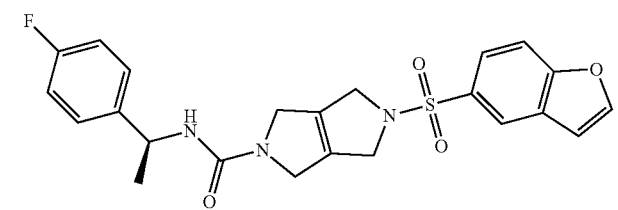 [SMILES: C[C@H](NC(=O)N1CC2=C(C1)CN(S(=O)(=O)c1ccc3occc3c1)C2)c1ccc(F)cc1] | 456.2 |

TABLE 9-continued

| Example | Name | Structure | LCMS (m/z) |
|---|---|---|---|
| 20-31 | 5-(3,4-Dimethoxybenzenesulfonyl)-N-[(4-methoxyphenyl)methyl]-1H,2H,3H,4H,5H,6H-pyrrolo[3,4-c]pyrrole-2-carboxamide | 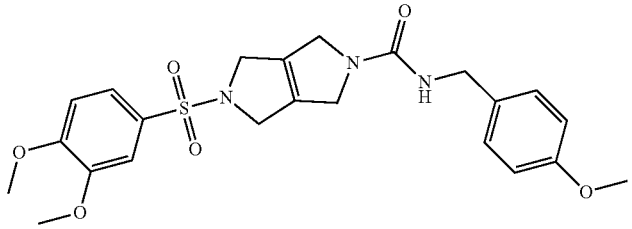 | 474.3 |
| 20-32 | 5-(3,4-Dimethoxybenzenesulfonyl)-N-[(3-methoxyphenyl)methyl]-1H,2H,3H,4H,5H,6H-pyrrolo[3,4-c]pyrrole-2-carboxamide | 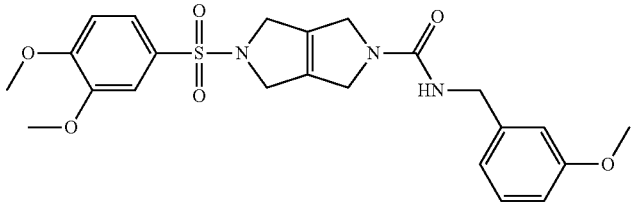 | 474.2 |
| 20-33 | 5-(3,4-Dimethoxybenzenesulfonyl)-N-(furan-2-ylmethyl)-1H,2H,3H,4H,5H,6H-pyrrolo[3,4-c]pyrrole-2-carboxamide | 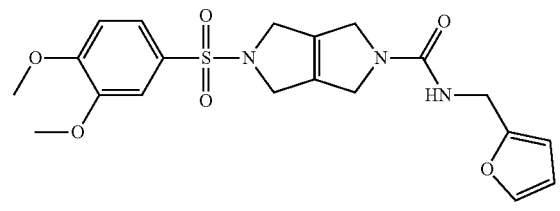 [SMILES: COc1ccc(S(=O)(=O)N2CC3=C(CN(C(=O)NCc4ccco4)C3)C2)cc1OC] | 434.2 |
| 20-34 | 5-(3,4-Dimethoxybenzenesulfonyl)-N-[(2-methoxyphenyl)methyl]-1H,2H,3H,4H,5H,6H-pyrrolo[3,4-c]pyrrole-2-carboxamide | 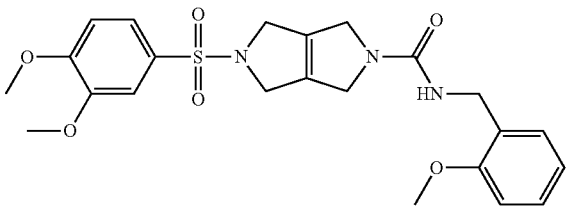 [SMILES: COc1ccccc1CNC(=O)N1CC2=C(C1)CN(S(=O)(=O)c1ccc(OC)c(OC)c1)C2] | 474.2 |
| 20-35 | N-[(3-methoxyphenyl)methyl]-5-(pyridine-3-sulfonyl)-1H,2H,3H,4H,5H,6H-pyrrolo[3,4-c]pyrrole-2-carboxamide | 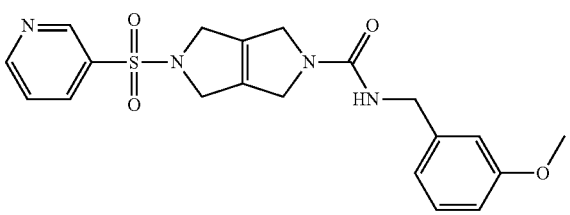 [SMILES: COc1cccc(CNC(=O)N2CC3=C(C2)CN(S(=O)(=O)c2cccnc2)C3)c1] | 415.2 |
| 20-36 | N-[(2-methoxyphenyl)methyl]-5-(pyridine-3-sulfonyl)-1H,2H,3H,4H,5H,6H-pyrrolo[3,4-c]pyrrole-2-carboxamide | 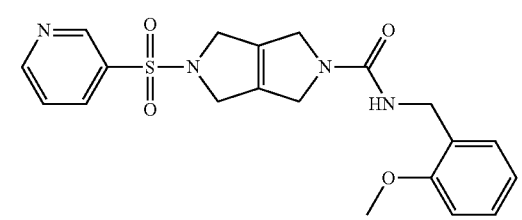 [SMILES: COc1ccccc1CNC(=O)N1CC2=C(C1)CN(S(=O)(=O)c1cccnc1)C2] | 415.2 |
| 20-37 | 5-(Isoquinoline-3-sulfonyl)-N-[(2-methoxyphenyl)methyl]-1H,2H,3H,4H,5H,6H-pyrrolo[3,4-c]pyrrole-2-carboxamide | 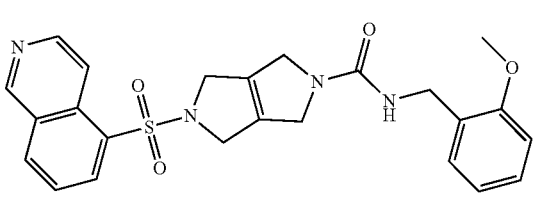 [SMILES: COc1ccccc1CNC(=O)N1CC2=C(C1)CN(S(=O)(=O)c1cccc3cnccc13)C2] | 465.3 |

TABLE 9-continued

| Example | Name | Structure | LCMS (m/z) |
|---|---|---|---|
| 20-38 | 5-(3,4-Dimethoxybenzenesulfonyl)-N-[(4-fluorophenyl)methyl]-1H,2H,3H,4H,5H,6H-pyrrolo[3,4-c]pyrrole-2-carboxamide | 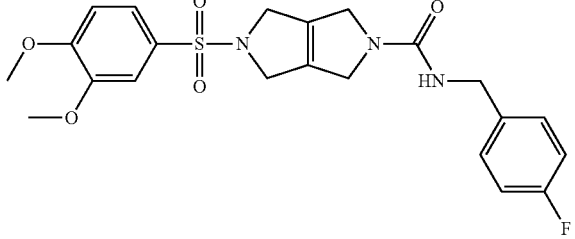 | 462.2 |
| 20-39 | N-[(4-fluorophenyl)methyl]-5-(pyridine-3-sulfonyl)-1H,2H,3H,4H,5H,6H-pyrrolo[3,4-c]pyrrole-2-carboxamide | 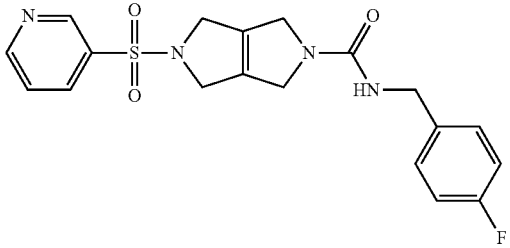 [SMILES: O=C(NCc1ccc(F)cc1)N1CC2=C(C1)CN(S(=O)(=O)c1cccnc1)C2] | 403.2 |
| 20-40 | 5-(3-Fluorobenzenesulfonyl)-N-[(1S)-1-phenylethyl]-1H,2H,3H,4H,5H,6H-pyrrolo[3,4-c]pyrrole-2-carboxamide | 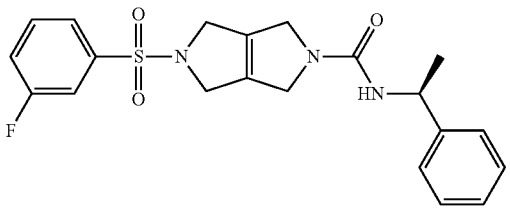 [SMILES: C[C@H](NC(=O)N1CC2=C(C1)CN(S(=O)(=O)c1cccc(F)c1)C2)c1ccccc1] | 416.2 |
| 20-41 | N-[(4-fluorophenyl)methyl]-5-(isoquinoline-5-sulfonyl)-1H,2H,3H,4H,5H,6H-pyrrolo[3,4-c]pyrrole-2-carboxamide | 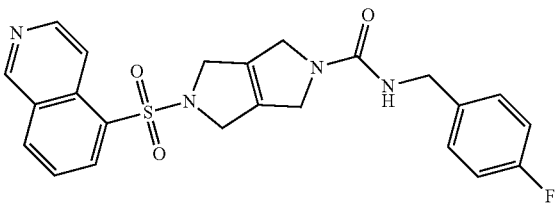 [SMILES: O=C(NCc1ccc(F)cc1)N1CC2=C(C1)CN(S(=O)(=O)c1cccc3cnccc13)C2] | 453.2 |
| 20-42 | 5-(1-Benzofuran-5-sulfonyl)-N-[(1R)-1-phenylethyl]-1H,2H,3H,4H,5H,6H-pyrrolo[3,4-c]pyrrole-2-carboxamide | 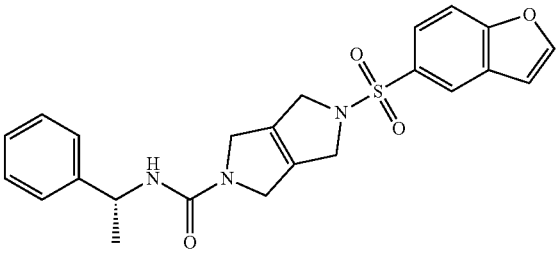 [SMILES: C[C@@H](NC(=O)N1CC2=C(C1)CN(S(=O)(=O)c1ccc3occc3c1)C2)c1ccccc1] | 438.2 |
| 20-43 | 5-(1-Benzofuran-5-sulfonyl)-N-[(1S)-1-phenylethyl]-1H,2H,3H,4H,5H,6H-pyrrolo[3,4-c]pyrrole-2-carboxamide | 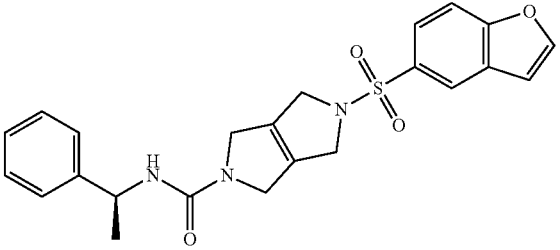 [SMILES: C[C@H](NC(=O)N1CC2=C(C1)CN(S(=O)(=O)c1ccc3occc3c1)C2)c1ccccc1] | 438.2 |

TABLE 9-continued

| Example | Name | Structure | LCMS (m/z) |
|---|---|---|---|
| 20-44 | 5-(2,1,3-Benzoxadiazole-4-sulfonyl)-N-[(1R)-1-phenylethyl]-1H,2H,3H,4H,5H,6H-pyrrolo[3,4-c]pyrrole-2-carboxamide | 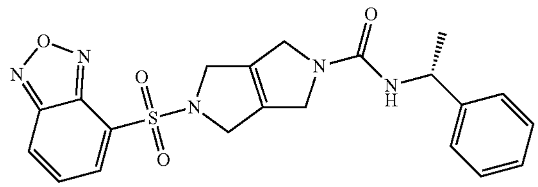 [SMILES: C[C@@H](NC(=O)N1CC2=C(C1)CN(S(=O)(=O)c1cccc3nonc13)C2)c1ccccc1] | 440.2 |
| 20-45 | 5-(2,1,3-Benzoxadiazole-4-sulfonyl)-N-[(1S)-1-phenylethyl]-1H,2H,3H,4H,5H,6H-pyrrolo[3,4-c]pyrrole-2-carboxamide | 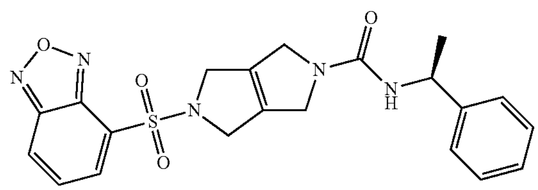 [SMILES: C[C@H](NC(=O)N1CC2=C(C1)CN(S(=O)(=O)c1cccc3nonc13)C2)c1ccccc1] | 440.2 |
| 20-46 | 5-(2,1,3-Benzothiadiazole-5-sulfonyl)-N-[(1S)-1-phenylethyl]-1H,2H,3H,4H,5H,6H-pyrrolo[3,4-c]pyrrole-2-carboxamide | 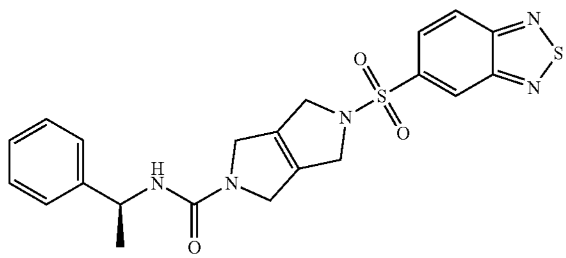 [SMILES: C[C@H](NC(=O)N1CC2=C(C1)CN(S(=O)(=O)c1ccc3nsnc3c1)C2)c1ccccc1] | 456.2 |
| 20-47 | N-(dimethyl-1,2-oxazol-4-yl)-5-[(1-methyl-1H-pyrazol-3-yl)sulfonyl]-1H,2H,3H,4H,5H,6H-pyrrolo[3,4-c]pyrrole-2-carboxamide | 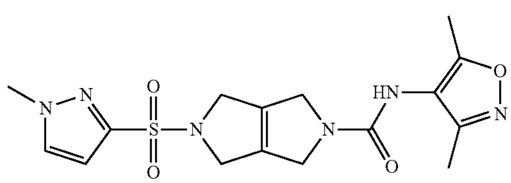 [SMILES: Cc1noc(C)c1NC(=O)N1CC2=C(C1)CN(S(=O)(=O)c1ccn(C)n1)C2] | 393.3 |
| 20-48 | 5-(1-Benzofuran-5-sulfonyl)-N-(dimethyl-1,2-oxazol-4-yl)-1H,2H,3H,4H,5H,6H-pyrrolo[3,4-c]pyrrole-2-carboxamide | 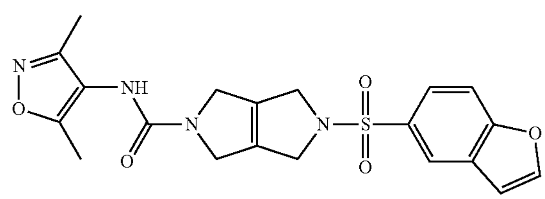 [SMILES: Cc1noc(C)c1NC(=O)N1CC2=C(C1)CN(S(=O)(=O)c1ccc3occc3c1)C2] | 429.2 |
| 20-49 | 5-(1-Benzofuran-5-sulfonyl)-N-(4-fluorophenyl)-1H,2H,3H,4H,5H,6H-pyrrolo[3,4-c]pyrrole-2-carboxamide | 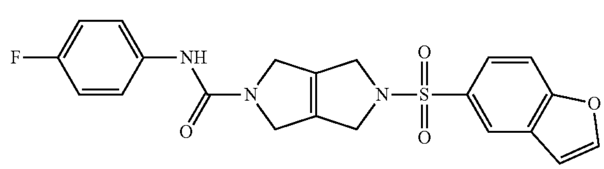 [SMILES: O=C(Nc1ccc(F)cc1)N1CC2=C(C1)CN(S(=O)(=O)c1ccc3occc3c1)C2] | m/z: 428.2 |
| 20-50 | N-(3-methoxypropyl)-5-[(1-methyl-1H-pyrazol-3-yl)sulfonyl]-1H,2H,3H,4H,5H,6H-pyrrolo[3,4-c]pyrrole-2-carboxamide | 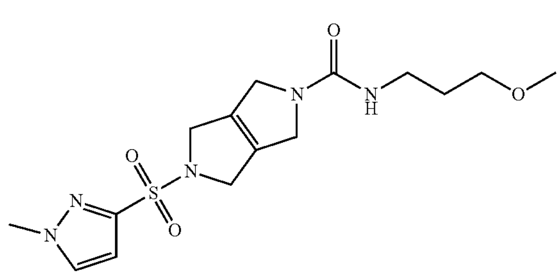 | 370.2 |

TABLE 9-continued

| Example | Name | Structure | LCMS (m/z) |
|---|---|---|---|
| 20-51 | 5-(1-benzofuran-5-sulfonyl)-N-[2-(4-fluorophenyl)ethyl]-1H,2H,3H,4H,5H,6H-pyrrolo[3,4-c]pyrrole-2-carboxamide | 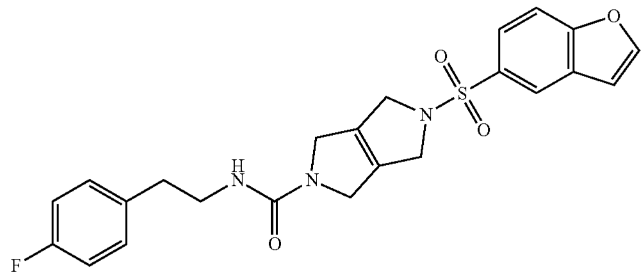 [SMILES: O=C(NCCc1ccc(F)cc1)N1CC2=C(C1)CN(S(=O)(=O)c1ccc3occc3c1)C2] | 456.2 |
| 20-52 | 5-(1-Benzofuran-5-sulfonyl)-N-[(2R)-3-methylbutan-2-yl]-1H,2H,3H,4H,5H,6H-pyrrolo[3,4-c]pyrrole-2-carboxamide | 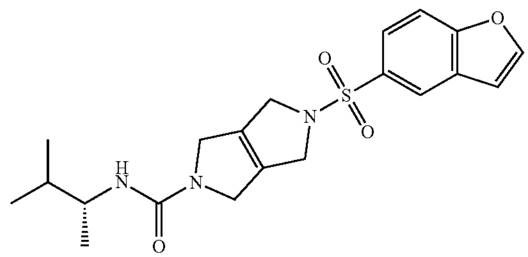 [SMILES: CC(C)[C@@H](C)NC(=O)N1CC2=C(C1)CN(S(=O)(=O)c1ccc3occc3c1)C2] | 404.3 |
| 20-53 | 5-(1-Benzofuran-5-sulfonyl)-N-[(2S)-3-methylbutan-2-yl]-1H,2H,3H,4H,5H,6H-pyrrolo[3,4-c]pyrrole-2-carboxamide | 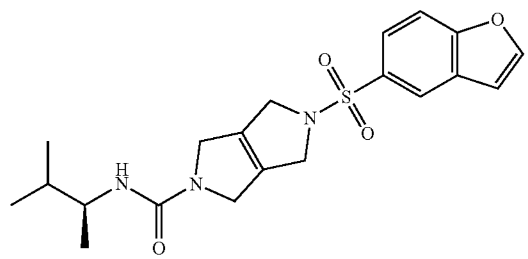 [SMILES: CC(C)[C@H](C)NC(=O)N1CC2=C(C1)CN(S(=O)(=O)c1ccc3occc3c1)C2] | 404.3 |
| 20-54 | 5-(1-Benzofuran-5-sulfonyl)-N-[(1R)-1-(4-fluorophenyl)ethyl]-1H,2H,3H,4H,5H,6H-pyrrolo[3,4-c]pyrrole-2-carboxamide | 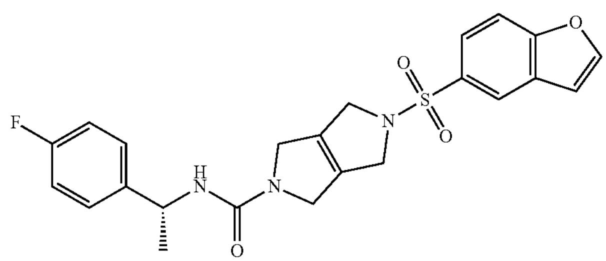 [SMILES: C[C@@H](NC(=O)N1CC2=C(C1)CN(S(=O)(=O)c1ccc3occc3c1)C2)c1ccc(F)cc1] | 456.2 |
| 20-55 | 5-(1-Benzofuran-5-sulfonyl)-N-[(1S)-1-phenylpropyl]-1H,2H,3H,4H,5H,6H-pyrrolo[3,4-c]pyrrole-2-carboxamide | 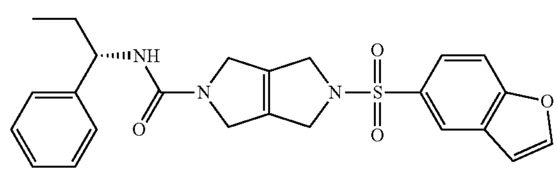 [SMILES: CC[C@H](NC(=O)N1CC2=C(C1)CN(S(=O)(=O)c1ccc3occc3c1)C2)c1ccccc1] | 452.2 |
| 20-56 | 5-(1,3-Benzothiazole-6-sulfonyl)-N-(pyridin-3-ylmethyl)-1H,2H,3H,4H,5H,6H-pyrrolo[3,4-c]pyrrole-2-carboxamide | 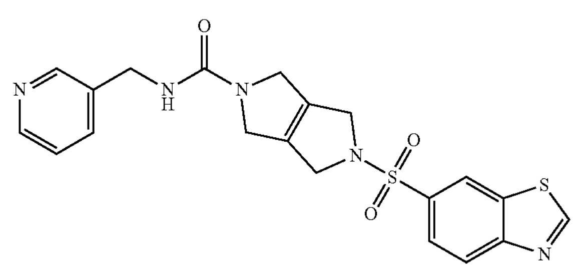 [SMILES: O=C(NCc1cccnc1)N1CC2=C(C1)CN(S(=O)(=O)c1ccc3ncsc3c1)C2] | 442.2 |

Example 21-1: 5-(Benzo[d]thiazol-6-ylsulfonyl)-N-(furan-2-ylmethyl)-3,4,5,6-tetrahydropyrrolo[3,4-c]pyrrole-2(1H)-carboxamide

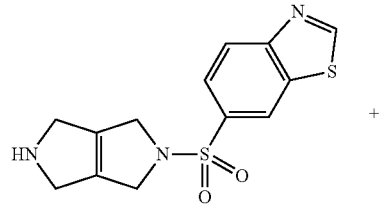

+

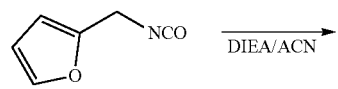

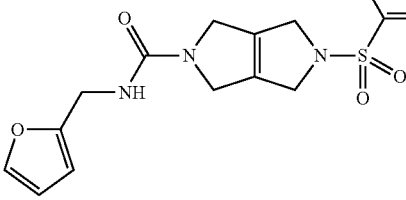

Example 21-1

To a 1.5 mL vial was added a 0.2 M solution of 6-((5,6-dihydropyrrolo[3,4-c]pyrrol-2(1H,3H,4H)-yl)sulfonyl)benzo[d]thiazole (150 μL, 0.030 mmol) in ACN, a 0.2 M solution of 2-(isocyanatomethyl)furan (150 μL, 0.030 mmol) in ACN, and DIEA (25 μL, 0.144 mmol) to give a brown suspension. The reaction was shaken at RT for 2 hours. The reaction was dried down under a stream of nitrogen. The residue was mixed with 1 N NaOH (0.5 mL) and extracted with EtOAc (2×0.5 mL). The extracts were dried under a stream of nitrogen. The compound was purified using mass-triggered HPLC to yield 5-(benzo[d]thiazol-6-ylsulfonyl)-N-(furan-2-ylmethyl)-3,4,5,6-tetrahydropyrrolo[3,4-c]pyrrole-2(1H)-carboxamide (2.1 mg, 4.88 mol, 16 yield). LCMS: m/z=431.0 [M+H]+.

The Examples in Table 10 below were prepared according to the procedure outlined above for Example 21-1, using the appropriate synthetic precursors.

TABLE 10

| Example | Name | Structure | LCMS (m/z) |
|---|---|---|---|
| 21-2 | 5-[4-(Difluoromethoxy)benzenesulfonyl]-N-(furan-2-ylmethyl)-1H,2H,3H,4H,5H,6H-pyrrolo[3,4-c]pyrrole-2-carboxamide | 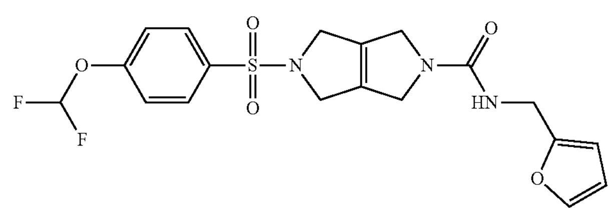 [SMILES: O=C(NCc1ccco1)N1CC2=C(C1)CN(S(=O)(=O)c1ccc(OC(F)F)cc1)C2] | 440.0 |
| 21-3 | 5-[4-(Difluoromethoxy)benzenesulfonyl]-N-[1-(5-methylfuran-2-yl)ethyl]-1H,2H,3H,4H,5H,6H-pyrrolo[3,4-c]pyrrole-2-carboxamide | 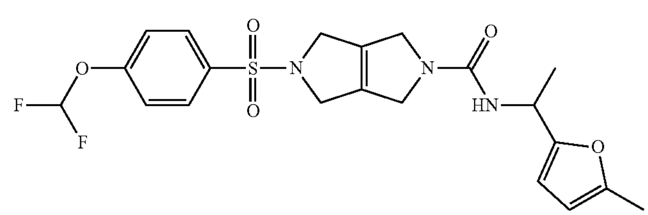 [SMILES: Cc1ccc(C(C)NC(=O)N2CC3=C(C2)CN(S(=O)(=O)c2ccc(OC(F)F)cc2)C3)o1] | 468.1 |
| 21-4 | 5-[4-(Difluoromethoxy)benzenesulfonyl]-N-[1-(2,5-dimethylfuran-3-yl)ethyl]-1H,2H,3H,4H,5H,6H-pyrrolo[3,4-c]pyrrole-2-carboxamide | 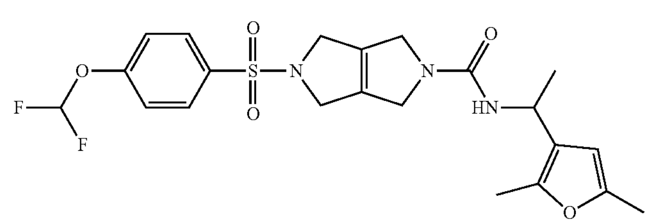 [SMILES: Cc1cc(C(C)NC(=O)N2CC3=C(C2)CN(S(=O)(=O)c2ccc(OC(F)F)cc2)C3)c(C)o1] | 482.1 |

TABLE 10-continued

| Example | Name | Structure | LCMS (m/z) |
|---|---|---|---|
| 21-5 | 5-[4-(Difluoromethoxy)benzenesulfonyl]-N-[(5-methyl-1,2-oxazol-3-yl)methyl]-1H,2H,3H,4H,5H,6H-pyrrolo[3,4-c]pyrrole-2-carboxamide | 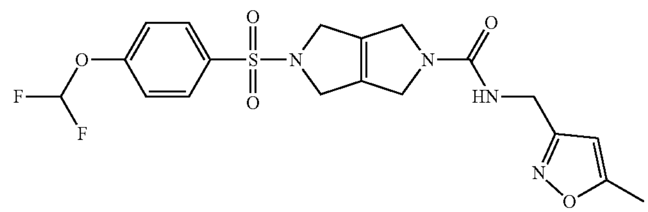 [SMILES: Cc1cc(CNC(=O)N2CC3=C(C2)CN(S(=O)(=O)c2ccc(OC(F)F)cc2)C3)no1] | 455.1 |
| 21-6 | 5-[4-(Difluoromethoxy)benzenesulfonyl]-N-[(3-methyl-1,2-oxazol-5-yl)methyl]-1H,2H,3H,4H,5H,6H-pyrrolo[3,4-c]pyrrole-2-carboxamide | 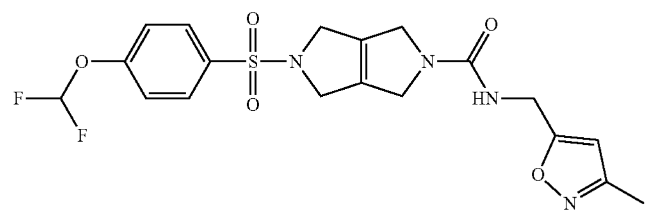 [SMILES: Cc1cc(CNC(=O)N2CC3=C(C2)CN(S(=O)(=O)c2ccc(OC(F)F)cc2)C3)on1] | 455.1 |
| 21-7 | 5-[4-(Difluoromethoxy)benzenesulfonyl]-N-[1-(5-methylthiophen-2-yl)ethyl]-1H,2H,3H,4H,5H,6H-pyrrolo[3,4-c]pyrrole-2-carboxamide | 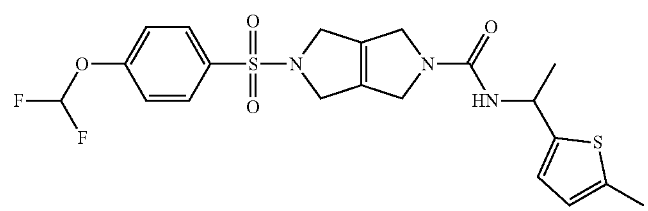 [SMILES: Cc1ccc(C(C)NC(=O)N2CC3=C(C2)CN(S(=O)(=O)c2ccc(OC(F)F)cc2)C3)s1] | 484.1 |
| 21-8 | 5-(1,3-Benzothiazole-6-sulfonyl)-N-[(5-methyl-1,2-oxazol-3-yl)methyl]-1H,2H,3H,4H,5H,6H-pyrrolo[3,4-c]pyrrole-2-carboxamide | 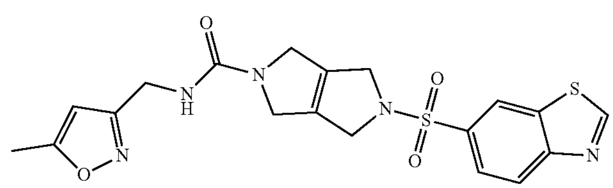 [SMILES: Cc1cc(CNC(=O)N2CC3=C(C2)CN(S(=O)(=O)c2ccc4ncsc4c2)C3)no1] | 446.1 |
| 21-9 | 5-(1,3-Benzothiazole-6-sulfonyl)-N-[(3-methyl-1,2-oxazol-5-yl)methyl]-1H,2H,3H,4H,5H,6H-pyrrolo[3,4-c]pyrrole-2-carboxamide | 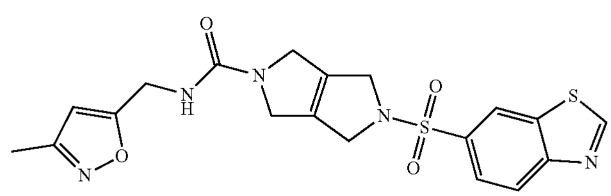 [SMILES: Cc1cc(CNC(=O)N2CC3=C(C2)CN(S(=O)(=O)c2ccc4ncsc4c2)C3)on1] | 446.2 |
| 21-10 | 5-[4-(Difluoromethoxy)benzenesulfonyl]-N-[(4-methoxyphenyl)methyl]-1H,2H,3H,4H,5H,6H-pyrrolo[3,4-c]pyrrole-2-carboxamide | 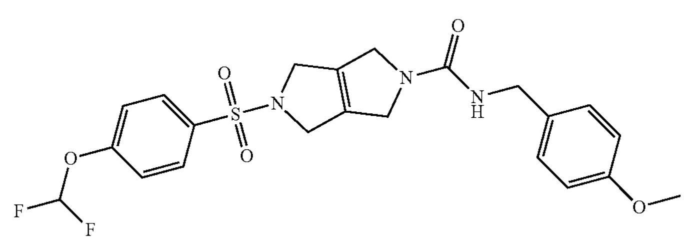 [SMILES: COc1ccc(CNC(=O)N2CC3=C(C2)CN(S(=O)(=O)c2ccc(OC(F)F)cc2)C3)cc1] | 480.2 |
| 21-11 | 5-[4-(Difluoromethoxy)benzenesulfonyl]-N-[(3-methoxyphenyl)methyl]-1H,2H,3H,4H,5H,6H-pyrrolo[3,4-c]pyrrole-2-carboxamide | 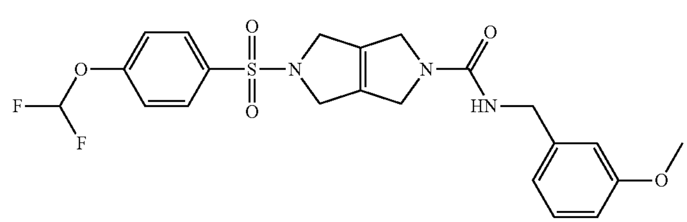 [SMILES: COc1cccc(CNC(=O)N2CC3=C(C2)CN(S(=O)(=O)c2ccc(OC(F)F)cc2)C3)c1] | 480.2 |

TABLE 10-continued

| Example | Name | Structure | LCMS (m/z) |
|---|---|---|---|
| 21-12 | 5-[4-(Difluoromethoxy)benzenesulfonyl]-N-[(2-methoxyphenyl)methyl]-1H,2H,3H,4H,5H,6H-pyrrolo[3,4-c]pyrrole-2-carboxamide | 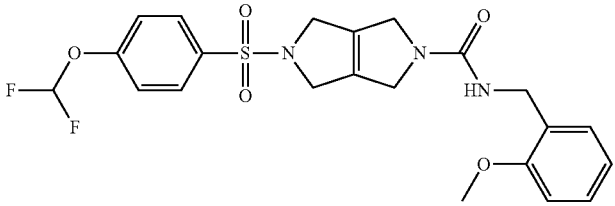 | 480.2 |
| 21-13 | 5-[4-(Difluoromethoxy)benzenesulfonyl]-N-[(4-fluorophenyl)methyl]-1H,2H,3H,4H,5H,6H-pyrrolo[3,4-c]pyrrole-2-carboxamide | 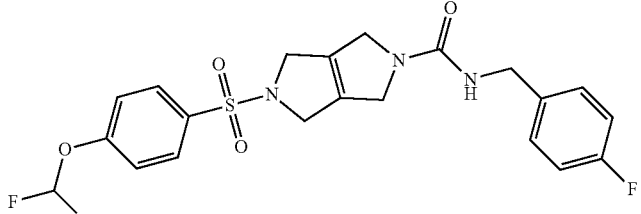 | 468.2 |
| 21-14 | 5-[4-(Difluoromethoxy)benzenesulfonyl]-N-[(3-fluorophenyl)methyl]-1H,2H,3H,4H,5H,6H-pyrrolo[3,4-c]pyrrole-2-carboxamide | 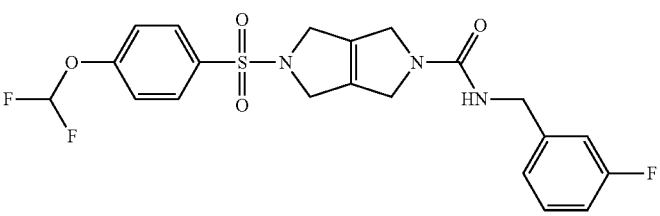 [SMILES: O=C(NCc1cccc(F)c1)N1CC2=C(C1)CN(S(=O)(=O)c1ccc(OC(F)F)cc1)C2] | 468.1 |
| 21-15 | 5-[4-(Difluoromethoxy)benzenesulfonyl]-N-[(2-fluorophenyl)methyl]-1H,2H,3H,4H,5H,6H-pyrrolo[3,4-c]pyrrole-2-carboxamide | 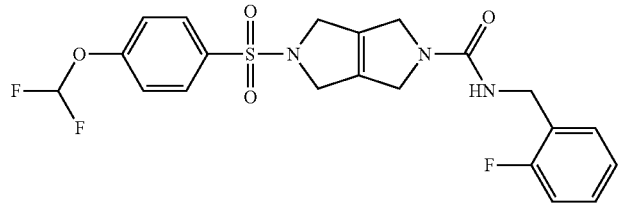 | 468.2 |
| 21-16 | 5-(1,3-Benzothiazole-6-sulfonyl)-N-[(4-methoxyphenyl)methyl]-1H,2H,3H,4H,5H,6H-pyrrolo[3,4-c]pyrrole-2-carboxamide | 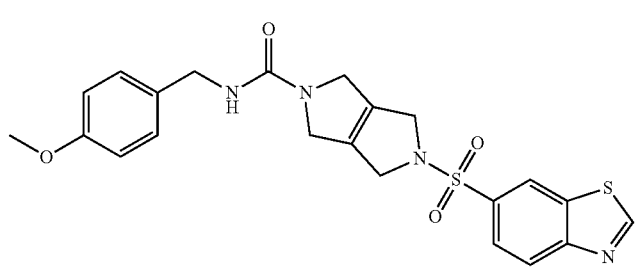 [SMILES: COc1ccc(CNC(=O)N2CC3=C(C2)CN(S(=O)(=O)c2ccc4ncsc4c2)C3)cc1] | 471.1 |
| 21-17 | 5-(1,3-Benzothiazole-6-sulfonyl)-N-[(3-methoxyphenyl)methyl]-1H,2H,3H,4H,5H,6H-pyrrolo[3,4-c]pyrrole-2-carboxamide | 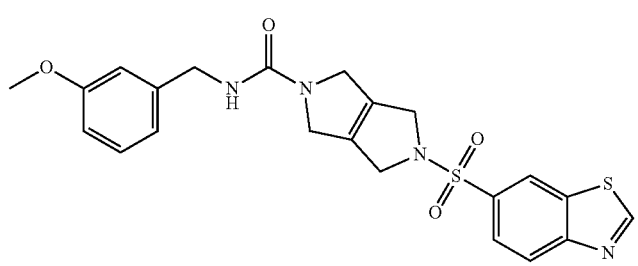 [SMILES: COc1cccc(CNC(=O)N2CC3=C(C2)CN(S(=O)(=O)c2ccc4ncsc4c2)C3)c1] | 471.1 |

TABLE 10-continued

| Example | Name | Structure | LCMS (m/z) |
|---|---|---|---|
| 21-18 | 5-(1,3-Benzothiazole-6-sulfonyl)-N-[(2-methoxyphenyl)methyl]-1H,2H,3H,4H,5H,6H-pyrrolo[3,4-c]pyrrole-2-carboxamide | 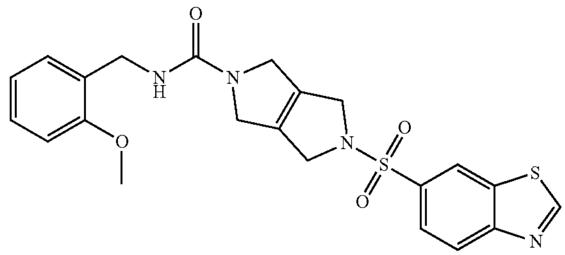 [SMILES: COc1ccccc1CNC(=O)N1CC2=C(C1)CN(S(=O)(=O)c1ccc3ncsc3c1)C2] | 471.1 |
| 21-19 | 5-(1,3-Benzothiazole-6-sulfonyl)-N-[(4-fluorophenyl)methyl]-1H,2H,3H,4H,5H,6H-pyrrolo[3,4-c]pyrrole-2-carboxamide | 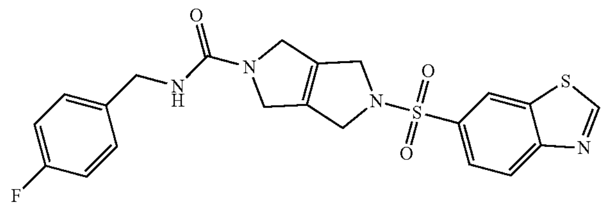 [SMILES: O=C(NCc1ccc(F)cc1)N1CC2=C(C1)CN(S(=O)(=O)c1ccc3ncsc3c1)C2] | 459.1 |
| 21-20 | 5-(1,3-Benzothiazole-6-sulfonyl)-N-[(2-fluorophenyl)methyl]-1H,2H,3H,4H,5H,6H-pyrrolo[3,4-c]pyrrole-2-carboxamide | 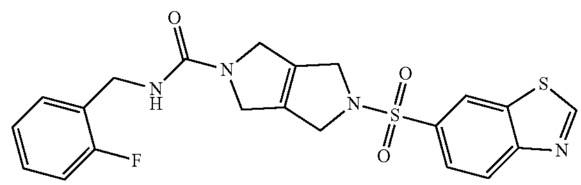 [SMILES: O=C(NCc1ccccc1F)N1CC2=C(C1)CN(S(=O)(=O)c1ccc3ncsc3c1)C2] | 459.1 |
| 21-21 | 5-(1,3-Benzothiazole-6-sulfonyl)-N-{[3-(propan-2-yloxy)phenyl]methyl}-1H,2H,3H,4H,5H,6H-pyrrolo[3,4-c]pyrrole-2-carboxamide | 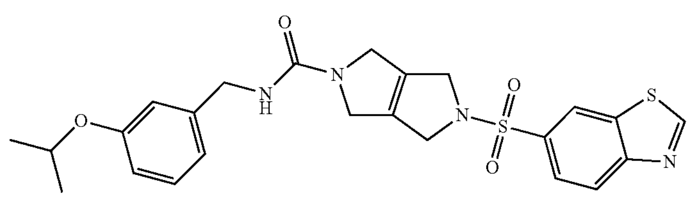 [SMILES: CC(C)Oc1cccc(CNC(=O)N2CC3=C(C2)CN(S(=O)(=O)c2ccc4ncsc4c2)C3)c1] | 499.2 |
| 21-22 | 5-[(2,2-Difluoro-2H-1,3-benzodioxol-5-yl)sulfonyl]-N-[(4-methoxyphenyl)methyl]-1H,2H,3H,4H,5H,6H-pyrrolo[3,4-c]pyrrole-2-carboxamide | 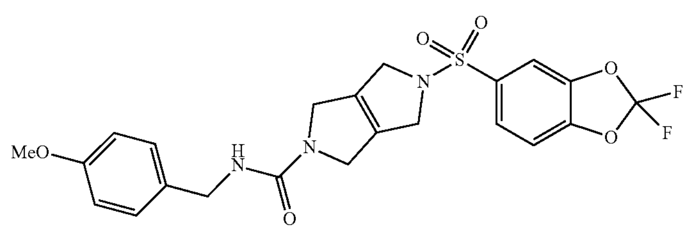 [SMILES: COc1ccc(CNC(=O)N2CC3=C(C2)CN(S(=O)(=O)c2ccc4c(c2)OC(F)(F)O4)C3)cc1] | 494 |
| 21-23 | 5-[(2,2-Difluoro-2H-1,3-benzodioxol-5-yl)sulfonyl]-N-[(4-fluorophenyl)methyl]-1H,2H,3H,4H,5H,6H-pyrrolo[3,4-c]pyrrole-2-carboxamide | 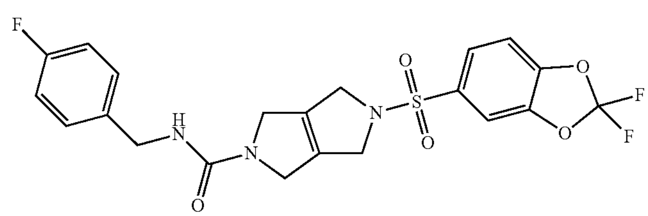 [SMILES: O=C(NCc1ccc(F)cc1)N1CC2=C(C1)CN(S(=O)(=O)c1ccc3c(c1)OC(F)(F)O3)C2] | 482 |
| 21-24 | N-(2-methoxyethyl)-5-[(4-methyl-3,4-dihydro-2H-benzoxazin-6-yl)sulfonyl]-1H,2H,3H,4H,5H,6H-pyrrolo[3,4-c]pyrrole-2-carboxamide | 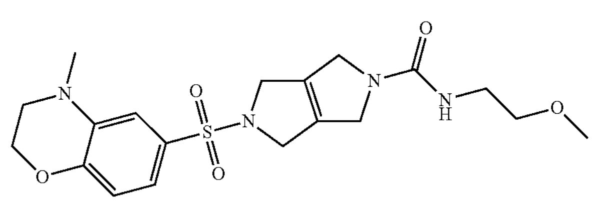 [SMILES: COCCNC(=O)N1CC2=C(C1)CN(S(=O)(=O)c1ccc3c(c1)N(C)CCO3)C2] | 423 |

TABLE 10-continued

| Example | Name | Structure | LCMS (m/z) |
|---|---|---|---|
| 21-25 | N-(furan-2-ylmethyl)-5-[(4-methyl-3,4-dihydro-2H-1,4-benzoxazin-6-yl)sulfonyl]-1H,2H,3H,4H,5H,6H-pyrrolo[3,4-c]pyrrole-2-carboxamide | 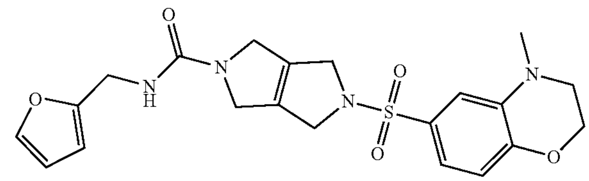 [SMILES: CN1CCOc2ccc(S(=O)(=O)N3CC4=C(CN(C(=O)NCc5ccco5)C4)C3)cc21] | 445 |
| 21-26 | N-[(4-fluorophenyl)methyl]-5-[(4-methyl-3,4-dihydro-2H-1,4-benzoxazin-6-yl)sulfonyl]-1H,2H,3H,4H,5H,6H-pyrrolo[3,4-c]pyrrole-2-carboxamide | 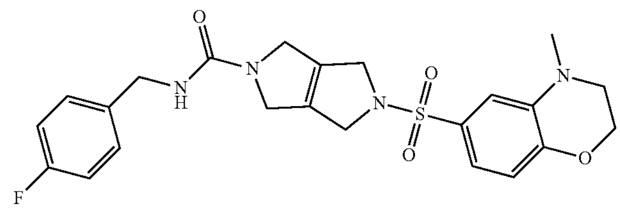 [SMILES: CN1CCOc2ccc(S(=O)(=O)N3CC4=C(CN(C(=O)NCc5ccc(F)cc5)C4)C3)cc21] | 473 |
| 21-27 | 5-(1,3-Benzothiazole-6-sulfonyl)-N-(1,2-oxazol-5-ylmethyl)-1H,2H,3H,4H,5H,6H-pyrrolo[3,4-c]pyrrole-2-carboxamide | 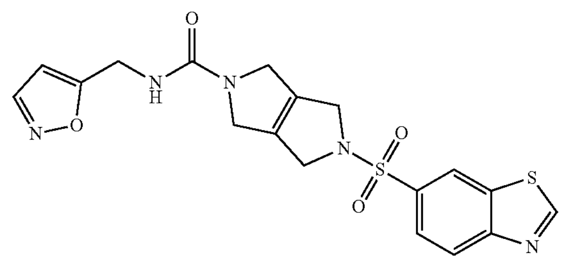 [SMILES: O=C(NCc1ccno1)N1CC2=C(C1)CN(S(=O)(=O)c1ccc3ncsc3c1)C2] | 432.2 |
| 21-28 | 5-(1,3-Benzothiazole-6-sulfonyl)-N-(1,3-thiazol-2-ylmethyl)-1H,2H,3H,4H,5H,6H-pyrrolo[3,4-c]pyrrole-2-carboxamide | 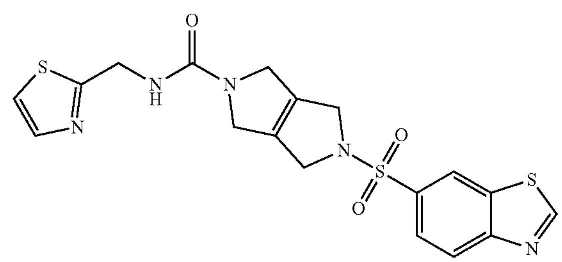 [SMILES: O=C(NCc1nccs1)N1CC2=C(C1)CN(S(=O)(=O)c1ccc3ncsc3c1)C2] | 448.1 |
| 21-29 | 5-(1,3-Benzothiazole-6-sulfonyl)-N-(1,3-oxazol-2-ylmethyl)-1H,2H,3H,4H,5H,6H-pyrrolo[3,4-c]pyrrole-2-carboxamide | 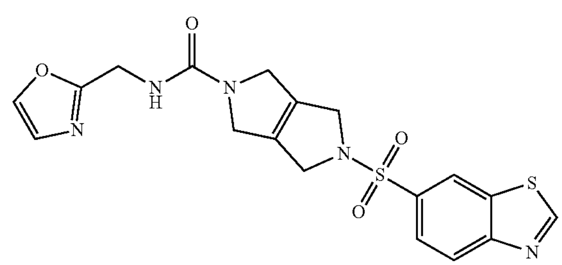 [SMILES: O=C(NCc1ncco1)N1CC2=C(C1)CN(S(=O)(=O)c1ccc3ncsc3c1)C2] | 432.2 |
| 21-30 | 5-(1,3-Benzothiazole-6-sulfonyl)-N-(pyrazin-2-ylmethyl)-1H,2H,3H,4H,5H,6H-pyrrolo[3,4-c]pyrrole-2-carboxamide | 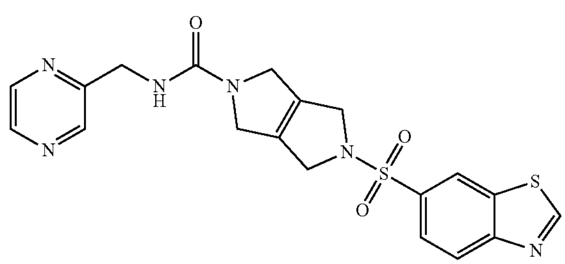 [SMILES: O=C(NCc1cnccn1)N1CC2=C(C1)CN(S(=O)(=O)c1ccc3ncsc3c1)C2] | 443.2 |

TABLE 10-continued

| Example | Name | Structure | LCMS (m/z) |
|---|---|---|---|
| 21-31 | 5-(1,3-Benzothiazole-6-sulfonyl)-N-{[4-(propan-2-yloxy)phenyl]methyl}-1H,2H,3H,4H,5H,6H-pyrrolo[3,4-c]pyrrole-2-carboxamide | 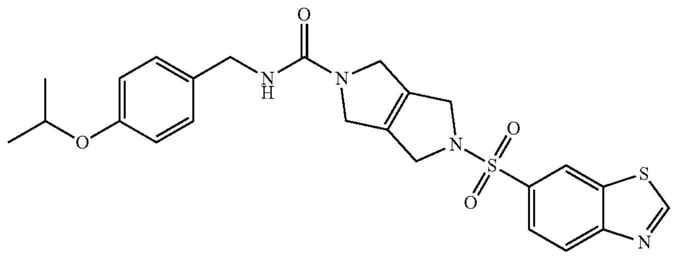 [SMILES: CC(C)Oc1ccc(CNC(=O)N2CC3=C(C2)CN(S(=O)(=O)c2ccc4ncsc4c2)C3)cc1] | 499.4 |
| 21-32 | 5-(1,3-Benzothiazole-6-sulfonyl)-N-[(6-methylpyridin-2-yl)methyl]-1H,2H,3H,4H,5H,6H-pyrrolo[3,4-c]pyrrole-2-carboxamide | 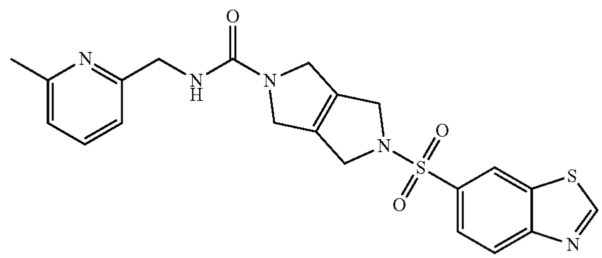 [SMILES: Cc1cccc(CNC(=O)N2CC3=C(C2)CN(S(=O)(=O)c2ccc4ncsc4c2)C3)n1] | 456.2 |
| 21-33 | 5-(1,3-Benzothiazole-6-sulfonyl)-N-(1H-1,2,4-triazol-5-ylmethyl)-1H,2H,3H,4H,5H,6H-pyrrolo[3,4-c]pyrrole-2-carboxamide | 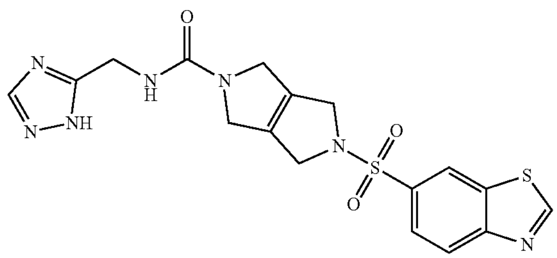 [SMILES: O=C(NCc1ncn[nH]1)N1CC2=C(C1)CN(S(=O)(=O)c1ccc3ncsc3c1)C2] | 432.2 |
| 21-34 | 5-(1,3-Benzothiazole-6-sulfonyl)-N-(1H-1,2,3-triazol-5-ylmethyl)-1H,2H,3H,4H,5H,6H-pyrrolo[3,4-c]pyrrole-2-carboxamide | 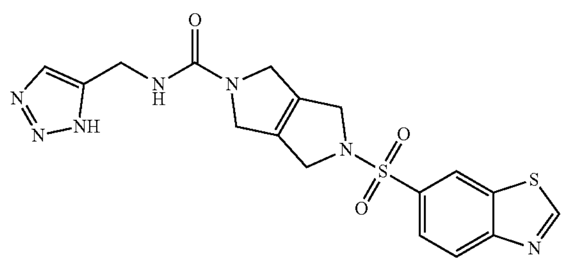 [SMILES: O=C(NCc1cnn[nH]1)N1CC2=C(C1)CN(S(=O)(=O)c1ccc3ncsc3c1)C2] | 432.2 |
| 21-35 | 5-((2,2-Difluorobenzo[d][1,3]dioxol-5-yl)sulfonyl)-N-(2-methoxyethyl)-3,4,5,6-tetrahydropyrrolo[3,4-c]pyrrole-2(1H)-carboxamide | 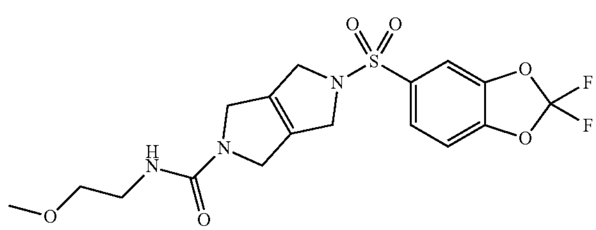 [SMILES: COCCNC(=O)N1CC2=C(C1)CN(S(=O)(=O)c1ccc3c(c1)OC(F)(F)O3)C2] | 432 |
| 21-36 | 5-(1,3-Benzothiazole-6-sulfonyl)-N-[(3-fluorophenyl)methyl]-1H,2H,3H,4H,5H,6H-pyrrolo[3,4-c]pyrrole-2-carboxamide | 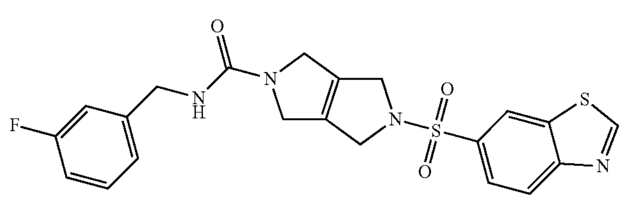 [SMILES: O=C(NCc1cccc(F)c1)N1CC2=C(C1)CN(S(=O)(=O)c1ccc3ncsc3c1)C2] | 459.1 |

TABLE 10-continued

| Example | Name | Structure | LCMS (m/z) |
|---|---|---|---|
| 21-37 | N-[(2-fluorophenyl)methyl]-5-(pyridine-3-sulfonyl)-1H,2H,3H,4H,5H,6H-pyrrolo[3,4-c]pyrrole-2-carboxamide | 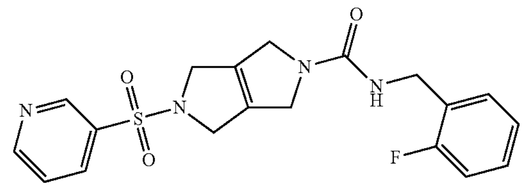 [SMILES: O=C(NCc1ccccc1F)N1CC2=C(C1)CN(S(=O)(=O)c1cccnc1)C2] | 403.2 |
| 21-38 | N-[(5-methyl-1,2-oxazol-3-yl)methyl]-5-(pyridine-3-sulfonyl)-1H,2H,3H,4H,5H,6H-pyrrolo[3,4-c]pyrrole-2-carboxamide | 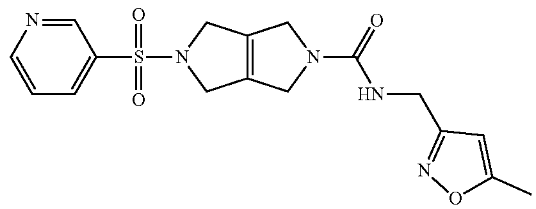 [SMILES: Cc1cc(CNC(=O)N2CC3=C(C2)CN(S(=O)(=O)c2cccnc2)C3)no1] | 390.3 |
| 21-39 | N-[(4-fluorophenyl)methyl]-5-{[6-(trifluoromethyl)pyridin-3-yl]sulfonyl}-1H,2H,3H,4H,5H,6H-pyrrolo[3,4-c]pyrrole-2-carboxamide | 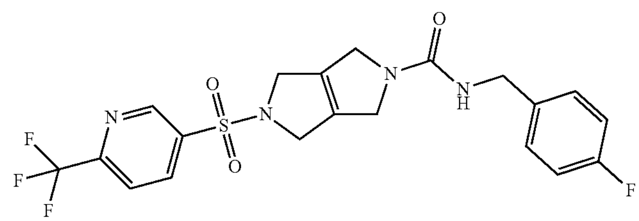 [SMILES: O=C(NCc1ccc(F)cc1)N1CC2=C(C1)CN(S(=O)(=O)c1ccc(C(F)(F)F)nc1)C2] | 471.3 |
| 21-40 | N-[(2-fluorophenyl)methyl]-5-{[6-(trifluoromethyl)pyridin-3-yl]sulfonyl}-1H,2H,3H,4H,5H,6H-pyrrolo[3,4-c]pyrrole-2-carboxamide | 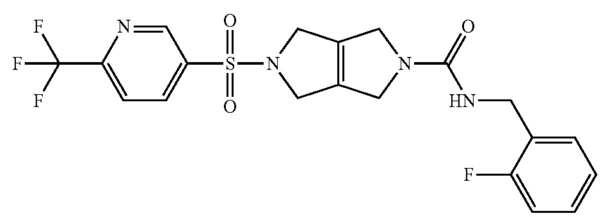 [SMILES: O=C(NCc1ccccc1F)N1CC2=C(C1)CN(S(=O)(=O)c1ccc(C(F)(F)F)nc1)C2] | 471.3 |
| 21-41 | N-[(4-fluorophenyl)methyl]-5-(pyridine-2-sulfonyl)-1H,2H,3H,4H,5H,6H-pyrrolo[3,4-c]pyrrole-2-carboxamide | 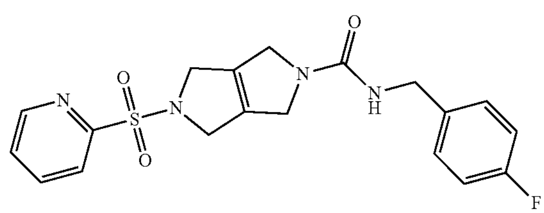 [SMILES: O=C(NCc1ccc(F)cc1)N1CC2=C(C1)CN(S(=O)(=O)c1ccccn1)C2] | 403.2 |
| 21-42 | N-[2-fluorophenyl)methyl]-5-(pyridine-2-sulfonyl)-1H,2H,3H,4H,5H,6H-pyrrolo[3,4-c]pyrrole-2-carboxamide | 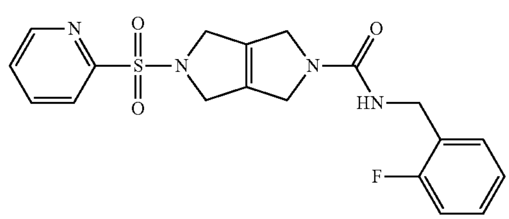 [SMILES: O=C(NCc1ccccc1F)N1CC2=C(C1)CN(S(=O)(=O)c1ccccn1)C2] | 403.2 |
| 21-43 | N-[(5-methyl-1,2-oxazol-3-yl)methyl]-5-(pyridine-2-sulfonyl)-1H,2H,3H,4H,5H,6H-pyrrolo[3,4-c]pyrrole-2-carboxamide | 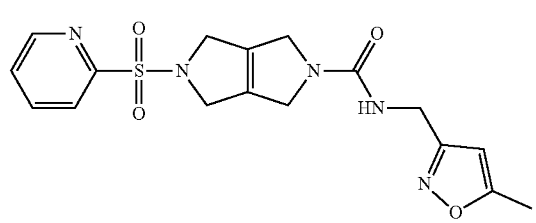 [SMILES: Cc1cc(CNC(=O)N2CC3=C(C2)CN(S(=O)(=O)c2ccccn2)C3)no1] | 390.3 |

Example 22-1: Pyridin-3-ylmethyl 5-((4-(difluoromethoxy)phenyl)sulfonyl)-3,4,5,6-tetrahydropyrrolo[3,4-c]pyrrole-2(1H)-carboxylate

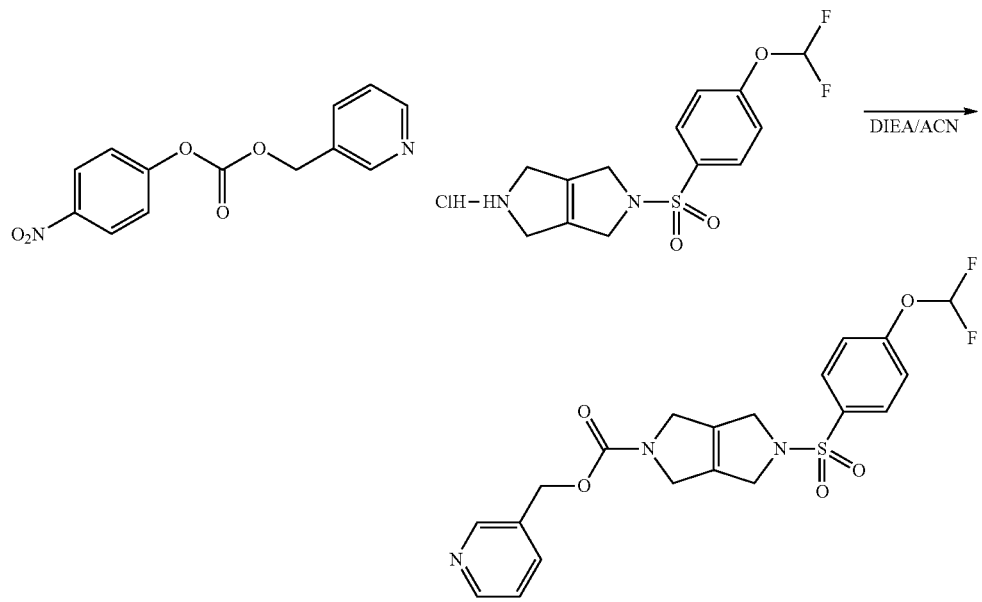

Example 22-1

In a 1.5 mL reaction vial was added a 0.2M solution of 4-nitrophenyl(pyridin-3-ylmethyl)carbonate (180 µL, 0.036 mmol) in ACN, neat DIEA (15 µL, 0.086 mmol) and a 0.2M solution of 2-((4-(difluoromethoxy)phenyl)sulfonyl)-1,2,3,4,5,6-hexahydropyrrolo[3,4-c]pyrrole hydrochloride (150 µL, 0.030 mmol) in ACN containing 5% DIEA to give a brown solution. The reaction was shaken at RT for 2 hours. The volatiles were removed under a stream of nitrogen. The residue was partitioned between 0.5 mL of 1N NaOH and 0.5 mL of EtOAc. The organic layer was removed. The aqueous layer was extracted with 0.5 mL of EtOAc. The organic layers were combined and the volatiles removed under a stream of nitrogen. The residue was purified using mass-triggered HPLC to provide pyridin-3-ylmethyl 5-((4-(difluoromethoxy)phenyl)sulfonyl)-3,4,5,6-tetrahydropyrrolo[3,4-c]pyrrole-2(1H)-carboxylate (5.6 mg, 12.4 µmol, 41% yield). LCMS: m/z=452.2 [M+H]+.

The Examples in Table 11 below were prepared according to the procedure outlined above for Example 22-1, using the appropriate synthetic precursors.

TABLE 11

| Example | Name | Structure | LCMS (m/z) |
|---|---|---|---|
| 22-2 | Cyclopropylmethyl 5-[4-(difluoromethoxy)benzenesulfonyl]-1H,2H,3H,4H,5H,6H-pyrrolo[3,4-c]pyrrole-2-carboxylate | 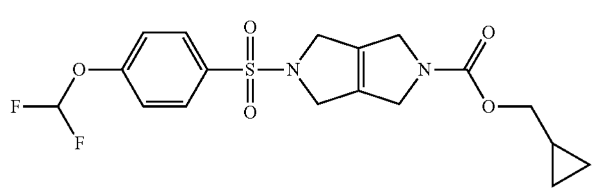 [SMILES: O=C(OCC1CC1)N1CC2=C(C1)CN(S(=O)(=O)c1ccc(OC(F)F)cc1)C2] | 415.2 |
| 22-3 | Oxolan-3-ylmethyl 5-[4-(difluoromethoxy)benzenesulfonyl]-1H,2H,3H,4H,5H,6H-pyrrolo[3,4-c]pyrrole-2-carboxylate | 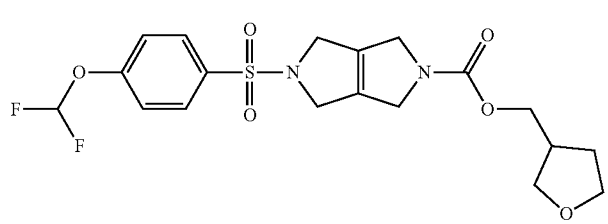 [SMILES: O=C(OCC1CCOC1)N1CC2=C(C1)CN(S(=O)(=O)c1ccc(OC(F)F)cc1)C2] | 445.2 |

TABLE 11-continued

| Example | Name | Structure | LCMS (m/z) |
|---|---|---|---|
| 22-4 | (1,5-Dimethyl-1H-pyrazol-3-yl)methyl 5-[4-(difluoromethoxy)benzenesulfonyl]-1H,2H,3H,4H,5H,6H-pyrrolo[3,4-c]pyrrole-2-carboxylate | 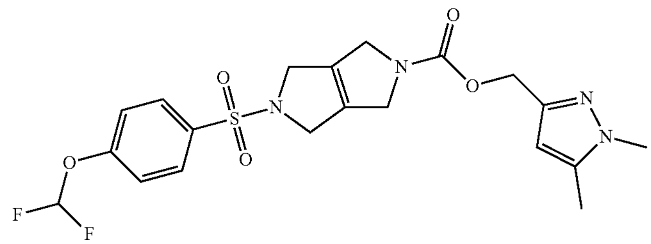 [SMILES: Cc1cc(COC(=O)N2CC3=C(C2)CN(S(=O)(=O)c2ccc(OC(F)F)cc2)C3)nn1C] | 469.2 |
| 22-5 | (5-Methyl-1,2-oxazol-3-yl)methyl-5-[4-(difluoromethoxy)benzenesulfonyl]-1H,2H,3H,4H,5H,6H-pyrrolo[3,4-c]pyrrole-2-carboxylate | 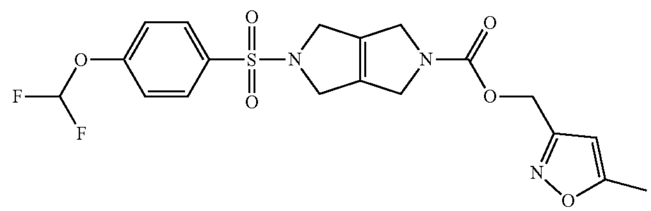 [SMILES: Cc1cc(COC(=O)N2CC3=C(C2)CN(S(=O)(=O)c2ccc(OC(F)F)cc2)C3)no1] | 456.2 |
| 22-6 | (3-Fluorophenyl)methyl 5-(1-benzofuran-5-sulfonyl)-1H,2H,3H,4H,5H,6H-pyrrolo[3,4-c]pyrrole-2-carboxylate | 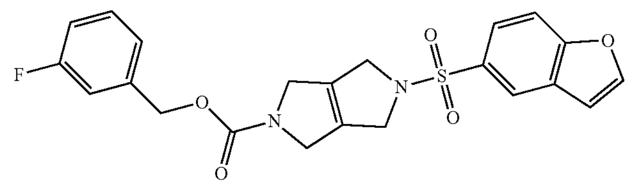 [SMILES: O=C(OCc1cccc(F)c1)N1CC2=C(C1)CN(S(=O)(=O)c1ccc3occc3c1)C2] | 443.2 |
| 22-7 | Pyridin-3-ylmethyl 5-(1-benzofuran-5-sulfonyl)-1H,2H,3H,4H,5H,6H-pyrrolo[3,4-c]pyrrole-2-carboxylate | 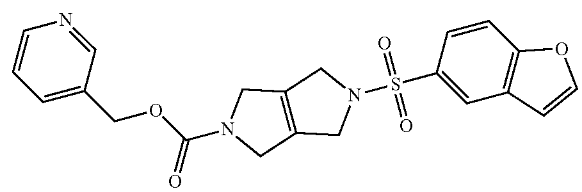 [SMILES: O=C(OCc1cccnc1)N1CC2=C(C1)CN(S(=O)(=O)c1ccc3occc3c1)C2] | 426.2 |

Example 23-1: 2-(Benzofuran-5-ylsulfonyl)-5-(benzoylprolyl)-1,2,3,4,5,6-hexahydropyrrolo[3,4-c]pyrrole

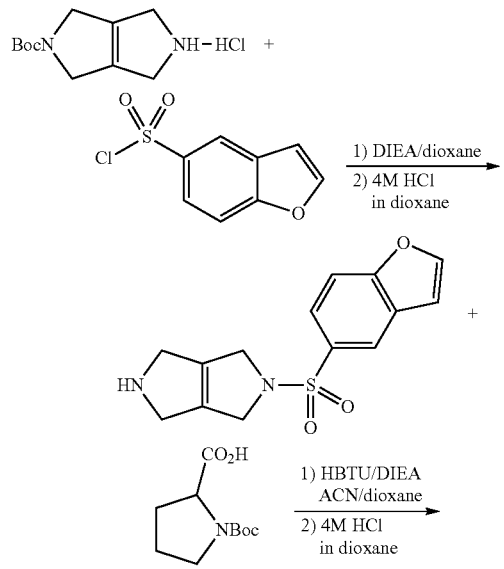

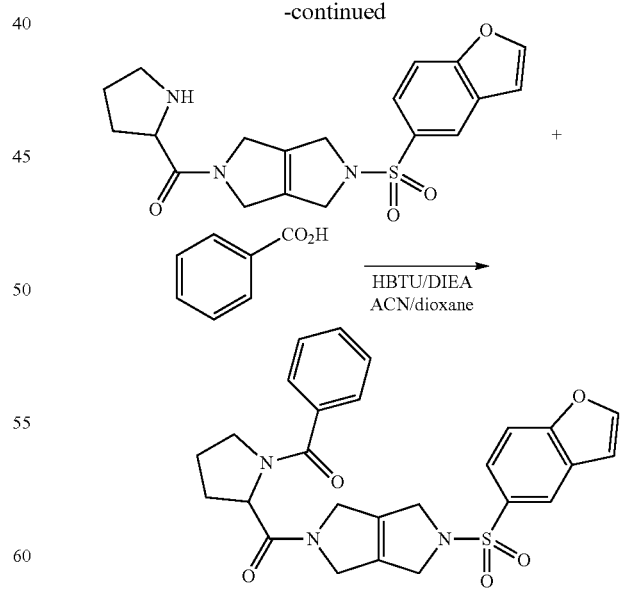

Example 23-1

To a 1.5 mL vial was added a 0.2 M solution of tert-butyl 3,4,5,6-tetrahydropyrrolo[3,4-c]pyrrole-2(1H)-carboxylate hydrochloride (150 µL, 30 µmol) in dioxane and neat DIEA (10 µL, 57 µmol) to give a brown suspension. A 0.2 M solution of benzofuran-5-sulfonyl chloride (158 µL, 31.5 µmol) in dioxane was added. The reaction was heated at 50° C. with shaking for 2 hours. 4 M HCl in dioxane (75.0 µL, 0.300 mmol) was then added. The reaction was heated at 50° C. with shaking for an additional 2 hours. The volatiles were removed under reduced pressure. ACN (200 µL) was added to the vial. The vial was shaken for 15 minutes to resuspend the residue. Neat DIEA (50 µL, 0.285 mmol) and a 0.2 M solution of (tert-butoxycarbonyl)proline (165 µL, 33 µmol) in dioxane was added to the vial, followed by a 0.2 M solution of HBTU (165 µL, 33 µmol) in ACN. The reaction was shaken at room temperature for an additional 2 hours. The volatiles were removed under reduced pressure. The residue was mixed with 1 N NaOH (0.5 mL) and extracted with 3:1 EtOAc/ACN (2×0.5 mL). The organic layers were combined and the volatiles were removed under reduced pressure. Dioxane (200 µL) was added to the vial. The vial was shaken for 15 minutes to resuspend the residue. 4 M HCl in dioxane (75.0 µL, 0.300 mmol) was then added. The reaction was heated at 50° C. with shaking for an additional 2 hours. The volatiles were removed under reduced pressure. ACN (200 µL) was added to the vial. The vial was shaken for 15 minutes to resuspend the residue. Neat DIEA (50 µL, 0.285 mmol) and a 0.2 M solution of benzoic acid (165 µL, 33 µmol) in dioxane was added to the vial, followed by a 0.2 M solution of HBTU (165 µL, 33 µmol) in ACN. The reaction was shaken at room temperature for an additional 2 hours. The volatiles were removed under reduced pressure. The residue was mixed with 1 N NaOH (0.5 mL) and extracted with 3:1 EtOAc/ACN (2×0.5 mL). The organic layers were combined and the volatiles were removed under reduced pressure. The compound was purified using mass-triggered HPLC to give 2-(benzofuran-5-ylsulfonyl)-5-(benzoylprolyl)-1,2,3,4,5,6-hexahydropyrrolo[3,4-c]pyrrole (2.0 mg, 6.52 µmol, 22% yield). LCMS: m/z=492.3.1 [M+H]+.

The Examples in Table 12 below were prepared according to the procedure outlined above for Example 23-1, using the appropriate synthetic precursors.

TABLE 12

| Example | Name | Structure | LCMS (m/z) |
| --- | --- | --- | --- |
| 23-2 | 1-[(2S)-2-[5-(1-benzofuran-5-sulfonyl)-1H,2H,3H,4H,5H,6H-pyrrolo[3,4-c]pyrrole-2-carbonyl]pyrrolidin-1-yl]-2-phenylethan-1-one | 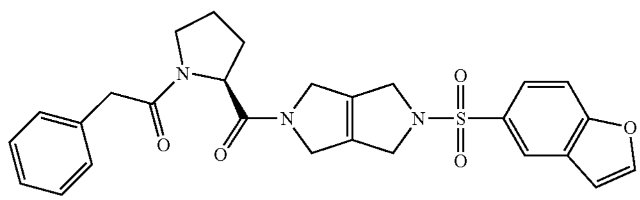 [SMILES: O=C([C@@H]1CCCN1C(=O)Cc1ccccc1)N1CC2=C(C1)CN(S(=O)(=O)c1ccc3occc3c1)C2] | 506.3 |
| 23-3 | 1-[(2S)-2-[5-(1-benzofuran-5-sulfonyl)-1H,2H,3H,4H,5H,6H-pyrrolo[3,4-c]pyrrole-2-carbonyl]pyrrolidin-1-yl]-2-(3-methoxyphenoxy)ethan-1-one | 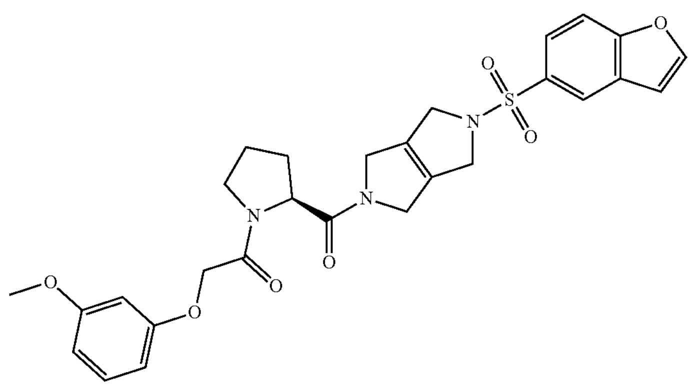 [SMILES: COc1cccc(OCC(=O)N2CCC[C@H]2C(=O)N2CC3=C(C2)CN(S(=O)(=O)c2ccc4occc4c2)C3)c1] | 552.3 |
| 23-4 | 1-[(2S)-2-[5-(1-benzofuran-5-sulfonyl)-1H,2H,3H,4H,5H,6H-pyrrolo[3,4-c]pyrrole-2-carbonyl]pyrrolidin-1-yl]-2-(3-methoxyphenyl)ethan-1-one | 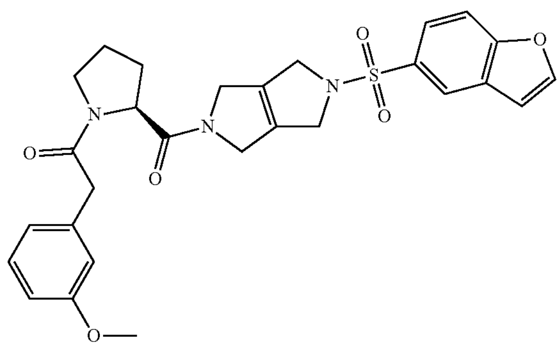 [SMILES: COc1cccc(CC(=O)N2CCC[C@H]2C(=O)N2CC3=C(C2)CN(S(=O)(=O)c2ccc4occc4c2)C3)c1] | 536.3 |

TABLE 12-continued

| Example | Name | Structure | LCMS (m/z) |
|---|---|---|---|
| 23-5 | 1-[(2S)-2-[5-(1-benzofuran-5-sulfonyl)-1H,2H,3H,4H,5H,6H-pyrrolo[3,4-c]pyrrole-2-carbonyl]pyrrolidin-1-yl]-2-ethoxyethan-1-one | 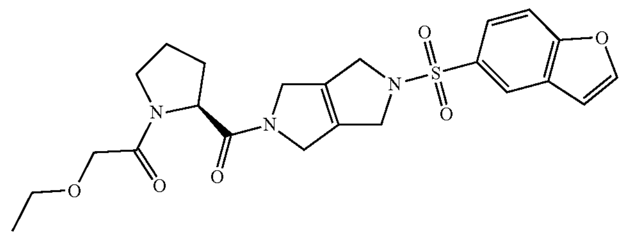 [SMILES: CCOCC(=O)N1CCC[C@H]1C(=O)N1CC2=C(C1)CN(S(=O)(=O)c1ccc3occc3c1)C2] | 474.3 |
| 23-6 | (2S)-2-[5-(1-benzofuran-5-sulfonyl)-1H,2H,3H,4H,5H,6H-pyrrolo[3,4-c]pyrrole-2-carbonyl]-1-(3-methoxybenzoyl)pyrrolidine | 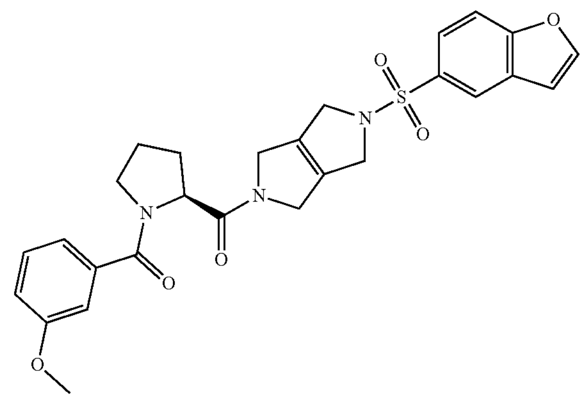 [SMILES: COc1cccc(C(=O)N2CCC[C@H]2C(=O)N2CC3=C(C2)CN(S(=O)(=O)c2ccc4occc4c2)C3)c1] | 522.3 |

Example 24. Luminescence Biochemical Assay

In some embodiments, a PKR Activating Compound refers to a compound having one or more characteristics when tested according to the following Luminescence Assay Protocol of Example 24 performed with wild type (wt) PKR and/or any one or more of G332S mutant form of PKR or R510Q mutant form of PKR: (1) an $AC_{50}$ value of less than 40 µM (e.g., compounds with $AC_{50}$ values of "+", or "+++" in Table 13); (2) a maximum % Fold (MAX % Fold) value of greater than 75%; and/or (3) a % Fold value at 1.54 µM compound concentration (% Fold@1.54 µM) of at least 75%. In some embodiments, a PKR Activating Compound can have: (1) an $AC_{50}$ value of less than 0.1 µM (e.g., compounds with $AC_{50}$ values of "+++" in Table 13), 0.1-1.0 µM (e.g., compounds with $AC_{50}$ values of "++" in Table 13), or 1.01-40 µM (e.g., compounds with $AC_{50}$ values of "+" in Table 13); (2) a MAX % Fold of 75%-250%, 250-500%, or 75%-500%; and/or (3) a % Fold@1.54 µM of 75%-250%, 250-500%, or 75%-500%. In some embodiments, a PKR Activating Compound has (1) an $AC_{50}$ value of less than 1.0 µM; (2) a MAX % Fold of 75%-500%; and/or (3) a % Fold@1.54 µM of 75%-500%.

The phosphorylation of Adenosine-5'-diphosphate (ADP) by various mutants of PKR was determined by the Kinase Glo Plus Assay (Promega) in the presence or absence of FBP [D-Fructose-1,6-diphosphate; BOC Sciences, CAS: 81028-91-3] as follows. Unless otherwise indicated, all reagents were purchased from Sigma-Aldrich. All reagents were prepared in buffer containing 50 mM Tris-HCl, 100 mM KCl, 5 mM $MgCl_2$, and 0.01% Triton X100, 0.03% BSA, and 1 mM DTT. Enzyme and PEP [Phospho(enol) pyruvic acid] were added at 2× to all wells of an assay-ready plate containing serial dilutions of test compounds or DMSO vehicle. Final enzyme concentrations for PKR(wt), PKR (R510Q), and PKR(G332S) were 0.8 nM, 0.8 nM, and 10 nM respectively. Final PEP concentration was 100 µM. The Enzyme/PEP mixture was incubated with compounds for 30 minutes at RT before the assay was initiated with the addition of 2×ADP [Adenosine-5'-diphosphate] and Kinase-GloPlus. Final concentration of ADP was 100 µM. Final concentration of KinaseGloPlus was 12.5%. For assays containing FBP, that reagent is added at 30 µM upon reaction initiation. Reactions were allowed to progress for 45 minutes at RT until luminescence was recorded by the BMG PHERAstar FS Multilabel Reader. All compounds were tested in triplicate at concentrations ranging from 42.5 µM to 2.2 nM in 0.83% DMSO.

Luminescence values were converted to % Fold increase by normalizing to the average of the DMSO control and multiplying by 100. Max, min, slope and $AC_{50}$ were determined by the standard four parameter fit algorithm of ActivityBase XE Runner. Compounds were evaluated with three parameters—$AC_{50}$, MAX % Fold, and % Fold@1.54 µM (FIG. 1). The $AC_{50}$ value for a compound is the concentration (µM) corresponding to the midway between the maximum and minimum values of the four parameter logistic curve fit (i.e., at which the % fold increase along the four parameter logistic curve fit is halfway between MAX % Fold and MIN % Fold (% Fold Midpoint)), MAX % Fold is the highest fold increase observed at any concentration of compound, and % Fold@1.54 µM is the fold increase at a compound concentration of 1.54 µM. The parameter % Fold@1.54 µM was selected to capture elements of both the $AC_{50}$ and MAX % Fold and to provide a ranking based on both potency and effect. The compound concentration of 1.54 µM was chosen as one that can optimally differentiate the set of compounds based on the range of activities observed.

As set forth in Table 13 below, $AC_{50}$ values (columns A, D, G) are defined as follows: ≤0.1 µM (+++); >0.1 µM and ≤1.0 µM (++); >1.0 µM and ≤40 µM (+); >40 µM (0). Max % FOLD values (columns B, E, H) are defined as follows: ≤75% (+); >75% and ≤250% (++); >250% and ≤500%

(+++). % Fold@1.54 μM values (columns C, F, J) are defined as follows: ≤75% (+); >75% and ≤250% (++); >250% and ≤50000 (+++).

TABLE 13

| Example | PKRG332S Conditions[1] | | | PKRR510Q Conditions[1] | | | WT Conditions[1] | | |
|---|---|---|---|---|---|---|---|---|---|
| | A | B | C | D | E | F | G | H | J |
| 1-1 | | | | | | | ++ | ++ | ++ |
| 1-2 | | | | | | | ++ | +++ | ++ |
| 1-3 | | | | | | | ++ | +++ | ++ |
| 1-4 | | | | | | | ++ | +++ | ++ |
| 1-5 | | | | | | | + | ++ | ++ |
| 2-1 | | | | | | | + | ++ | ++ |
| 3-1 | | | | | | | ++ | ++ | ++ |
| 3-2 | | | | | | | ++ | +++ | ++ |
| 3-3 | | | | | | | + | ++ | ++ |
| 3-4 | | | | | | | ++ | ++ | ++ |
| 3-5 | | | | | | | + | ++ | ++ |
| 4-1 | ++ | ++ | ++ | + | +++ | ++ | ++ | ++ | ++ |
| 4-2 | + | ++ | ++ | + | ++ | ++ | + | ++ | ++ |
| 5-1 | ++ | ++ | ++ | + | ++ | ++ | | | |
| 6-1 | + | ++ | ++ | + | +++ | ++ | + | ++ | ++ |
| 7-1 | ++ | ++ | ++ | + | +++ | ++ | ++ | +++ | ++ |
| 8-1 | +++ | ++ | ++ | ++ | +++ | +++ | ++ | +++ | +++ |
| 8-3 | ++ | ++ | ++ | ++ | +++ | +++ | ++ | +++ | +++ |
| 9-1 | +++ | ++ | ++ | +++ | +++ | +++ | +++ | +++ | +++ |
| 9-2 | ++ | ++ | ++ | ++ | +++ | ++ | +++ | ++ | ++ |
| 9-3 | + | ++ | ++ | + | +++ | ++ | ++ | ++ | ++ |
| 9-4 | ++ | ++ | ++ | + | +++ | ++ | + | +++ | ++ |
| 9-5 | +++ | ++ | ++ | +++ | +++ | +++ | +++ | +++ | +++ |
| 10-1 | ++ | ++ | ++ | + | ++ | ++ | + | +++ | ++ |
| 10-2 | +++ | ++ | ++ | ++ | +++ | +++ | +++ | +++ | +++ |
| 11-1 | + | ++ | ++ | ++ | +++ | +++ | + | ++ | ++ |
| 11-2 | ++ | ++ | ++ | +++ | +++ | +++ | +++ | +++ | ++ |
| 12-1 | + | ++ | ++ | + | ++ | ++ | + | ++ | ++ |
| 13-1 | | | | | | | + | ++ | ++ |
| 14-1 | + | ++ | ++ | + | ++ | ++ | + | ++ | ++ |
| 15-1 | ++ | ++ | ++ | +++ | +++ | +++ | +++ | +++ | +++ |
| 16-1 | + | ++ | ++ | + | ++ | ++ | + | +++ | ++ |
| 17-1 | + | ++ | ++ | + | ++ | ++ | + | ++ | ++ |
| 18-2 | + | ++ | ++ | + | ++ | ++ | ++ | ++ | ++ |
| 18-10 | | | | + | +++ | ++ | ++ | ++ | ++ |
| 18-11 | | | | + | +++ | ++ | ++ | ++ | ++ |
| 18-12 | ++ | ++ | ++ | + | +++ | ++ | ++ | ++ | ++ |
| 18-13 | +++ | ++ | ++ | +++ | +++ | +++ | +++ | +++ | +++ |
| 18-14 | | | | + | ++ | ++ | + | ++ | ++ |
| 18-15 | +++ | ++ | ++ | +++ | +++ | +++ | +++ | +++ | +++ |
| 18-16 | | | | +++ | +++ | +++ | +++ | ++ | ++ |
| 18-17 | | | | +++ | +++ | ++ | +++ | ++ | ++ |
| 18-18 | | | | ++ | +++ | +++ | +++ | ++ | ++ |
| 18-19 | +++ | ++ | ++ | ++ | +++ | +++ | +++ | +++ | +++ |
| 18-20 | + | ++ | ++ | + | +++ | ++ | ++ | +++ | +++ |
| 18-21 | ++ | ++ | ++ | + | +++ | ++ | + | +++ | ++ |
| 18-22 | +++ | ++ | ++ | ++ | +++ | ++ | ++ | +++ | ++ |
| 18-23 | ++ | ++ | ++ | + | +++ | ++ | ++ | +++ | ++ |
| 18-24 | +++ | ++ | ++ | +++ | +++ | +++ | ++ | +++ | +++ |
| 18-25 | +++ | ++ | ++ | +++ | +++ | +++ | +++ | +++ | +++ |
| 18-26 | +++ | ++ | ++ | ++ | +++ | +++ | ++ | +++ | +++ |
| 18-27 | + | ++ | ++ | + | ++ | ++ | + | ++ | ++ |
| 18-28 | ++ | ++ | ++ | + | +++ | +++ | + | +++ | +++ |
| 18-29 | +++ | ++ | ++ | + | +++ | ++ | + | +++ | ++ |
| 18-30 | +++ | ++ | ++ | ++ | +++ | +++ | ++ | +++ | +++ |
| 18-31 | +++ | ++ | ++ | +++ | +++ | +++ | +++ | +++ | +++ |
| 18-32 | ++ | ++ | ++ | + | ++ | ++ | + | ++ | ++ |
| 18-33 | | | | + | +++ | ++ | + | +++ | ++ |
| 18-43 | + | ++ | ++ | + | ++ | ++ | + | ++ | ++ |
| 18-44 | + | ++ | ++ | + | ++ | ++ | | | |
| 18-45 | | | | ++ | +++ | ++ | | | |
| 18-46 | | | | | | | + | ++ | ++ |
| 18-47 | + | ++ | ++ | ++ | ++ | ++ | ++ | ++ | ++ |
| 18-49 | | | | ++ | ++ | ++ | ++ | ++ | ++ |
| 18-50 | | | | ++ | ++ | ++ | ++ | ++ | ++ |
| 18-51 | + | ++ | ++ | + | ++ | ++ | + | ++ | ++ |
| 18-52 | + | ++ | ++ | + | ++ | ++ | + | ++ | ++ |
| 18-53 | + | ++ | ++ | + | ++ | ++ | + | ++ | ++ |
| 18-54 | + | ++ | ++ | + | ++ | ++ | + | ++ | ++ |
| 18-55 | | | | ++ | +++ | ++ | ++ | ++ | ++ |
| 18-56 | + | ++ | ++ | + | +++ | ++ | + | ++ | ++ |
| 18-57 | | | | | | | ++ | ++ | ++ |
| 18-58 | + | ++ | ++ | + | ++ | ++ | + | ++ | ++ |
| 18-59 | + | ++ | ++ | + | ++ | ++ | + | ++ | ++ |
| 18-60 | + | ++ | ++ | + | +++ | ++ | + | +++ | ++ |
| 18-61 | + | ++ | ++ | + | +++ | ++ | + | +++ | ++ |
| 18-62 | + | ++ | ++ | + | +++ | ++ | ++ | ++ | ++ |
| 18-63 | + | ++ | ++ | ++ | +++ | +++ | ++ | +++ | +++ |
| 18-64 | + | ++ | ++ | + | ++ | ++ | + | ++ | ++ |
| 18-65 | + | ++ | ++ | + | ++ | ++ | + | +++ | ++ |
| 18-66 | + | ++ | ++ | + | +++ | ++ | + | +++ | ++ |
| 18-67 | ++ | ++ | ++ | + | +++ | ++ | + | +++ | ++ |
| 18-68 | ++ | ++ | ++ | + | ++ | ++ | + | +++ | ++ |
| 18-69 | + | ++ | ++ | + | ++ | ++ | + | ++ | ++ |
| 18-70 | + | ++ | ++ | + | ++ | ++ | + | ++ | ++ |
| 18-73 | + | ++ | ++ | + | ++ | ++ | + | ++ | ++ |
| 18-75 | | | | | | | + | ++ | ++ |
| 18-76 | + | ++ | ++ | + | ++ | ++ | ++ | ++ | ++ |
| 18-77 | | | | | | | + | ++ | ++ |
| 18-78 | | | | | | | + | ++ | ++ |
| 18-79 | | | | | | | ++ | +++ | +++ |
| 18-81 | | | | | | | ++ | +++ | +++ |
| 18-82 | | | | | | | + | ++ | ++ |
| 18-83 | | | | | | | + | ++ | ++ |
| 18-84 | | | | | | | + | ++ | ++ |
| 18-85 | | | | | | | + | ++ | ++ |
| 18-86 | | | | | | | + | ++ | ++ |
| 19-1 | | | | + | ++ | ++ | | | |
| 19-2 | | | | + | ++ | ++ | | | |
| 19-3 | ++ | ++ | ++ | + | ++ | ++ | | | |
| 19-9 | ++ | ++ | ++ | + | ++ | ++ | | | |
| 20-2 | | | | | | | ++ | +++ | ++ |
| 20-3 | +++ | ++ | ++ | ++ | +++ | +++ | | | |
| 20-4 | ++ | ++ | ++ | ++ | ++ | ++ | | | |
| 20-6 | +++ | ++ | ++ | ++ | +++ | ++ | | | |
| 20-7 | | | | ++ | +++ | +++ | | | |
| 20-8 | + | ++ | ++ | + | ++ | ++ | | | |
| 20-11 | + | ++ | ++ | +++ | ++ | ++ | | | |
| 20-12 | + | ++ | ++ | + | ++ | ++ | | | |
| 20-19 | + | ++ | ++ | ++ | +++ | ++ | | | |
| 20-20 | +++ | ++ | ++ | ++ | +++ | ++ | | | |
| 20-23 | + | ++ | ++ | ++ | +++ | ++ | | | |
| 20-24 | + | ++ | ++ | ++ | +++ | ++ | | | |
| 20-25 | ++ | ++ | ++ | + | ++ | ++ | | | |
| 20-27 | + | ++ | ++ | + | +++ | ++ | | | |
| 20-28 | + | ++ | ++ | + | ++ | ++ | | | |
| 20-31 | | | | + | ++ | ++ | | | |
| 20-41 | + | ++ | ++ | + | ++ | ++ | | | |
| 20-56 | ++ | ++ | ++ | + | +++ | ++ | + | +++ | ++ |
| 21-1 | | | | | | | +++ | +++ | +++ |
| 21-2 | | | | | | | +++ | +++ | +++ |
| 21-3 | | | | | | | + | +++ | ++ |
| 21-4 | | | | | | | + | +++ | ++ |
| 21-5 | | | | ++ | +++ | +++ | ++ | +++ | +++ |
| 21-6 | | | | ++ | +++ | +++ | ++ | +++ | +++ |
| 21-7 | | | | | | | + | +++ | ++ |
| 21-8 | +++ | ++ | ++ | +++ | +++ | +++ | | | |
| 21-9 | | | | ++ | ++ | ++ | ++ | +++ | ++ |
| 21-10 | +++ | ++ | ++ | +++ | +++ | +++ | +++ | +++ | +++ |
| 21-11 | +++ | ++ | ++ | +++ | +++ | +++ | +++ | +++ | +++ |
| 21-12 | +++ | ++ | ++ | +++ | +++ | +++ | ++ | +++ | ++ |
| 21-13 | +++ | ++ | ++ | ++ | +++ | +++ | +++ | +++ | +++ |
| 21-14 | ++ | ++ | ++ | + | +++ | +++ | ++ | +++ | ++ |
| 21-15 | +++ | ++ | ++ | +++ | +++ | +++ | +++ | +++ | +++ |
| 21-16 | +++ | ++ | ++ | ++ | +++ | +++ | +++ | +++ | +++ |
| 21-17 | +++ | ++ | ++ | + | ++ | ++ | +++ | ++ | ++ |
| 21-18 | +++ | ++ | ++ | ++ | +++ | +++ | ++ | +++ | +++ |
| 21-19 | ++ | ++ | ++ | ++ | +++ | ++ | ++ | +++ | ++ |
| 21-20 | +++ | ++ | ++ | +++ | +++ | +++ | +++ | +++ | +++ |
| 21-21 | | | | + | +++ | ++ | ++ | ++ | ++ |
| 21-24 | ++ | ++ | ++ | ++ | +++ | ++ | | | |
| 21-26 | + | ++ | ++ | ++ | ++ | ++ | | | |
| 21-27 | | | | + | ++ | ++ | ++ | ++ | ++ |
| 21-28 | | | | ++ | +++ | ++ | ++ | +++ | ++ |
| 21-29 | | | | ++ | ++ | ++ | ++ | +++ | +++ |

TABLE 13-continued

| | PKRG332S Conditions[1] | | | PKRR510Q Conditions[1] | | | WT Conditions[1] | | |
|---|---|---|---|---|---|---|---|---|---|
| Example | A | B | C | D | E | F | G | H | J |
| 21-30 | | | | + | +++ | ++ | ++ | +++ | +++ |
| 21-31 | | | | + | ++ | ++ | + | ++ | ++ |
| 21-32 | | | | ++ | +++ | +++ | ++ | +++ | +++ |
| 21-36 | ++ | ++ | ++ | + | +++ | ++ | + | +++ | ++ |
| 21-37 | ++ | ++ | ++ | ++ | +++ | +++ | ++ | +++ | ++ |
| 21-38 | + | ++ | ++ | + | +++ | ++ | | | |
| 21-39 | + | ++ | ++ | + | ++ | ++ | + | ++ | ++ |
| 21-40 | + | ++ | ++ | ++ | ++ | ++ | ++ | ++ | ++ |
| 21-41 | + | ++ | ++ | ++ | ++ | ++ | ++ | +++ | ++ |
| 21-42 | ++ | ++ | ++ | ++ | +++ | +++ | ++ | +++ | +++ |
| 21-43 | ++ | ++ | ++ | + | +++ | ++ | + | +++ | ++ |
| 22-2 | + | ++ | ++ | + | +++ | ++ | + | +++ | ++ |
| 22-3 | + | ++ | ++ | + | ++ | ++ | + | ++ | ++ |
| 22-4 | ++ | ++ | ++ | + | +++ | +++ | ++ | +++ | +++ |
| 22-5 | ++ | ++ | ++ | ++ | +++ | +++ | ++ | +++ | +++ |
| 22-6 | | | | | | | ++ | +++ | +++ |
| 22-7 | | | | | | | ++ | +++ | +++ |

[1] A - AC50 LUM KGP FBP $AC_{50}$ μM gmean;
B - AC50 LUM KGP FBP MAX % FOLD mean;
C - AC50 LUM KGP FBP % Fold@1.54 μM mean
D - AC50 LUM KGP woFBP $AC_{50}$ μM gmean;
E - AC50 LUM KGP woFBP MAX % FOLD mean;
F - AC50 LUM KGP woFBP % Fold@1.54 μM mean
G - AC50 LUM KGP woFBP $AC_{50}$ μM gmean;
H - AC50 LUM KGP woFBP MAX % FOLD mean;
J - AC50 LUM KGP woFBP % Fold@1.54 μM mean

TABLE 14

Biological Data of Additional Compound

| | | PKR G332S | PKR R510Q | wt |
|---|---|---|---|---|
| | | Conditions[1] | | |
| Example | Structure | A | D | G |
| 23 | | 0 | 0 | |
| 24 | | | | + |
| 25 | | | + | + |

TABLE 14-continued

Biological Data of Additional Compound

| Example | Structure | PKR G332S Conditions¹ A | PKR R510Q D | wt G |
|---------|-----------|------|---|---|
| 26 | | | | + |
| 27 | | | | + |
| 28 | | | | + |
| 29 | | | | + |

TABLE 14-continued

Biological Data of Additional Compound

| Example | Structure | PKR G332S Conditions[1] A | PKR R510Q Conditions[1] D | wt Conditions[1] G |
|---|---|---|---|---|
| 30 | 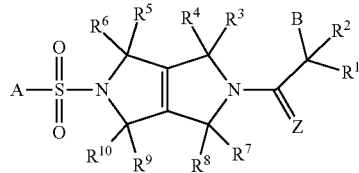 | + | + | + |

[1]A-AC50 LUM KGP FBP $AC_{50}$ μM gmean;
D-AC50 LUM KGP woFBP $AC_{50}$ μM gmean.
G-AC50 LUM KGP woFBP $AC_{50}$ μM gmean;

EQUIVALENTS

The present disclosure enables one of skill in the relevant art to make and use the inventions provided herein in accordance with multiple and varied embodiments. Various alterations, modifications, and improvements of the present disclosure that readily occur to those skilled in the art, including certain alterations, modifications, substitutions, and improvements are also part of this disclosure. Accordingly, the foregoing description and drawings are by way of example to illustrate the discoveries provided herein.

Embodiment 1. A compound of Formula I:

(I)

or a pharmaceutically acceptable salt thereof, wherein:

A is phenyl or monocyclic 5- to 6-membered heteroaryl ring containing 1-4 heteroatoms independently selected from the group consisting of O, N, and S,
  wherein each aryl or heteroaryl is optionally substituted with one or more $R^a$;

each $R^a$ is independently selected from the group consisting of halogen, —OR', —OC(O)R', —$NR_2$, —NRC(O)R', —$NRS(O)_2R'$, —CN, —$NO_2$, —SR, —C(O)R', —C(O)OR, —$C(O)NR_2$, —$S(O)_2R'$, —$S(O)_2NR_2$, —$C_1$-$C_6$alkyl, —$C_2$-$C_6$alkenyl, —$C_2$-$C_6$alkynyl, —$C_3$-$C_{12}$cycloalkyl, —$C_1$-$C_{12}$cycloalkenyl, 3- to 14-membered heterocyclyl containing 1-4 heteroatoms independently selected from the group consisting of O, N, and S, $C_6$-$C_{14}$aryl, and 5- to 14-membered heteroaryl containing 1-4 heteroatoms independently selected from the group consisting of O, N, and S,
  wherein each alkyl is optionally substituted with one or more halogen;

Z is O, S, or NR;

$R^1$ and $R^2$ are each independently selected from the group consisting of —H, halogen, —$C_1$-$C_6$alkyl, —$C_2$-$C_6$alkenyl, —$C_2$-$C_6$alkynyl, —$(CR^bR^c)_nC_3$-$C_{12}$cycloalkyl, —$(CR^bR^c)_nC_4$-$C_{12}$cycloalkenyl, —$(CR^bR^c)_n$heterocyclyl, —$(CR^bR^c)_nC_6$-$C_{14}$aryl, —$(CR^bR^c)_n$heteroaryl, —OR, —OC(O)R', —$OS(O)_2R'$, —$OS(O)_2NR_2$, —$OC(O)NR_2$, —OC(O)OR, —$(CR^bR^c)_nNR_2$, —$(CR^bR^c)_nNRC(O)R'$, —$(CR^bR^c)_nNRS(O)_2R'$, —$(CR^bR^c)_nNRC(O)NR_2$, —$(CR^bR^c)_nNRC(O)OR$, —$(CR^bR^c)_nCN$, —$(CR^bR^c)_nNO_2$, —$(CR^bR^c)_nSR$, —$(CR^bR^c)_nC(O)R'$, —$(CR^bR^c)_nC(O)OR$, —$(CR^bR^c)_nC(O)NR_2$, —$(CR^bR^c)_nSO_2R'$, —$(CR^bR^c)_nSO_2NR_2$, and —$(CR^bR^c)_nSO_2OR$,
  wherein each cycloalkyl, cycloalkenyl, heterocyclyl, aryl, or heteroaryl is optionally substituted with one or more substituents selected from the group consisting of halogen, —$C_1$-$C_6$ alkyl, —$C_2$-$C_6$alkenyl, —$C_2$-$C_6$alkynyl, oxo, and —OR, wherein —OR does not result in an O in the γ-position relative to C(=Z),
  wherein each alkyl, alkenyl, or alkynyl is optionally substituted with one or more halogen,
  wherein each heterocyclyl is 3- to 14-membered and contains 1-4 heteroatoms independently selected from the group consisting of O, N, and S and wherein the heterocyclyl does not contain an O in the γ-position relative to C(=Z), and
  wherein each heteroaryl is 5- to 14-membered and contains 1-4 heteroatoms independently selected from the group consisting of O, N, and S;

or $R^1$ and $R^2$ combine with the carbon to which they are attached to form oxo, a $C_3$-$C_{12}$cycloalkyl, or a 3- to 8-membered heterocyclyl containing 1-4 heteroatoms independently selected from the group consisting of O, N and S, and
  wherein the heterocyclyl does not contain an O in the γ-position relative to C(=Z), and
  wherein each cycloalkyl or heterocyclyl is optionally substituted with one or more substituents selected from the group consisting of halogen, —$C_1$-$C_6$alkyl, —$C_2$-$C_6$alkenyl, —$C_2$-$C_6$alkynyl, oxo, and —OR, wherein —OR does not result in an O in the γ-position relative to C(=Z);

R$^b$ and R are each independently selected from the group consisting of —H, halogen, and —C$_1$-C$_6$alkyl;

each n is independently 0, 1, 2, 3, or 4;

B is a monocyclic or bicyclic 3- to 14-membered ring,
wherein the ring is saturated, fully or partially unsaturated, or aromatic, and
wherein the ring contains 0-4 heteroatoms independently selected from the group consisting of O, N, and S,
wherein the ring is optionally substituted with (R$^d$)$_m$, and when the ring is saturated or partially unsaturated, then the ring does not contain an O in the γ-position relative to C(=Z);

each R$^d$ is independently selected from the group consisting of halogen, oxo, —OR, —OC(O)R', —NR$_2$, —NRC(O)R', —NRS(O)$_2$R', —CN, —NO$_2$, —SR, —C(O)R', —C(O)OR, —C(O)NR$_2$, —S(O)$_2$R', —S(O)$_2$NR$_2$, —C$_1$-C$_6$alkyl, —C$_2$-C$_6$alkenyl, —C$_2$-C$_6$alkynyl, —C$_3$-C$_{12}$cycloalkyl, —C$_4$-C$_{12}$cycloalkenyl, 3- to 14-membered heterocyclyl containing 1-4 heteroatoms independently selected from the group consisting of O, N, and S, C$_6$-C$_{14}$aryl, and 5- to 14-membered heteroaryl containing 1-4 heteroatoms independently selected from the group consisting of O, N, and S,
wherein each alkyl, alkenyl, alkynyl, cycloalkyl, cycloalkenyl, heterocyclyl, aryl, or heteroaryl is optionally substituted with one or more halogen, —C$_1$-C$_6$ alkyl, —C$_2$-C$_6$alkenyl, —C$_2$-C$_6$alkynyl, or —OR;

m is 0, 1, 2, 3, 4, 5, 6, 7, 8, 9, or 10;

R$^3$, R$^4$, R$^5$, R$^6$, R$^7$, R, R$^9$, and R$^{10}$ are each independently —H or —C$_1$-C$_6$ alkyl,
wherein each alkyl is optionally substituted with one or more halogen;

or R$^3$ and R$^4$, R$^5$ and R$^6$, R$^7$ and R$^8$, R$^9$ and R$^{10}$, or combinations thereof, combine with the carbon to which they are attached to form oxo, a C$_3$-C$_8$cycloalkyl, or a 3- to 8-membered heterocyclyl containing 1-4 heteroatoms independently selected from the group consisting of O, N, and S;

each R is independently selected from the group consisting of —H, —OH, —O(C$_1$-C$_6$alkyl), —NH$_2$, —NH(C$_1$-C$_6$alkyl), and —N(C$_1$-C$_6$alkyl)$_2$, —C$_1$-C$_6$alkyl, —C$_2$-C$_6$alkenyl, —C$_2$-C$_6$alkynyl, —C$_3$-C$_{12}$cycloalkyl, —C$_4$-C$_{12}$cycloalkenyl, 3- to 14-membered heterocyclyl containing 1-4 heteroatoms independently selected from the group consisting of O, N, and S, C$_6$-C$_{14}$aryl, and 5- to 14-membered heteroaryl containing 1-4 heteroatoms independently selected from the group consisting of O, N, and S,
wherein each alkyl, alkenyl, alkynyl, cycloalkyl, cycloalkenyl, heterocyclyl, aryl, or heteroaryl is optionally substituted with one or more halogen, —C$_1$-C$_6$ alkyl, —C$_2$-C$_6$alkenyl, —C$_2$-C$_6$alkynyl, —O(C$_1$-C$_6$alkyl), —NH(C$_1$-C$_6$alkyl), or —N(C$_1$-C$_6$alkyl)$_2$; and each R' is independently selected from the group consisting of —C$_1$-C$_6$alkyl, —C$_2$-C$_6$alkenyl, —C$_2$-C$_6$alkynyl, —C$_3$-C$_{12}$cycloalkyl, —C$_4$-C$_{12}$cycloalkenyl, 3- to 14-membered heterocyclyl containing 1-4 heteroatoms independently selected from the group consisting of O, N, and S, C$_6$-C$_{14}$aryl, and 5- to 14-membered heteroaryl containing 1-4 heteroatoms independently selected from the group consisting of O, N, and S,
wherein each alkyl, alkenyl, alkynyl, cycloalkyl, cycloalkenyl, heterocyclyl, aryl, or heteroaryl is optionally substituted with one or more halogen, —C$_1$-C$_6$alkyl, —C$_2$-C$_6$alkenyl, —C$_2$-C$_6$alkynyl, —O—C$_1$-C$_6$alkyl, —NH(C$_1$-C$_6$alkyl), or —N(C$_1$-C$_6$alkyl)$_2$.

Embodiment 2. The compound of embodiment 1, wherein the compound is of Formula I-a:

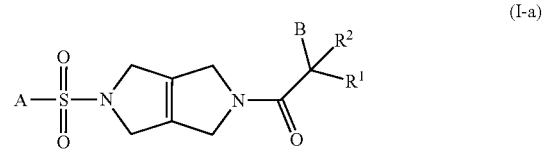

(I-a)

or a pharmaceutically acceptable salt thereof.

Embodiment 3. The compound of embodiment 2, wherein the compound is of Formula I-b:

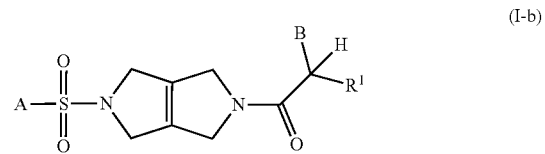

(I-b)

or a pharmaceutically acceptable salt thereof.

Embodiment 4. The compound of any one of embodiments 1-3, wherein B is an aromatic monocyclic ring or a bicyclic ring,
wherein at least one of the rings in the bicyclic ring is aromatic,
wherein the monocyclic ring or bicyclic ring contains 0-4 heteroatoms independently selected from the group consisting of O, N, and S, and
wherein the monocyclic ring or bicyclic ring is optionally substituted with (R$^d$)$_m$.

Embodiment 5. The compound of any one of embodiments 1-4, wherein R$^1$ and R$^2$ are each independently selected from the group consisting of —H, halogen, —C$_1$-C$_6$alkyl, and —OR, wherein —OR does not result in an O in the γ-position relative to C(=Z).

Embodiment 6. The compound of any one of embodiments 1-3, wherein the compound is of Formula I-c:

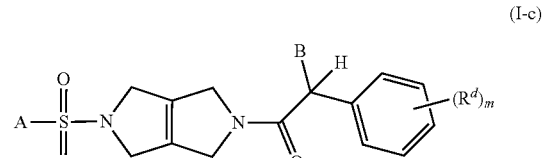

(I-c)

or a pharmaceutically acceptable salt thereof.

Embodiment 7. The compound of any one of embodiments 1-5, wherein the compound is of Formula I-d-1:

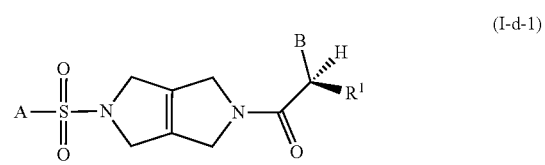

(I-d-1)

or a pharmaceutically acceptable salt thereof.

Embodiment 8. The compound of any one of embodiments 1-5, wherein the compound is of Formula I-d-2:

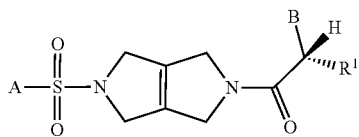

(I-d-2)

or a pharmaceutically acceptable salt thereof,

Embodiment 9. The compound of any one of embodiments 1-8, wherein A is phenyl or pyridyl, optionally substituted with one or more $R^a$.

Embodiment 10. The compound of any one of embodiments 1-9, wherein each $R^a$ is selected from the group consisting of halogen, —$C_1$-$C_6$alkyl, and —OR.

Embodiment 11. The compound of any one of embodiments 1-10, wherein A is pyridyl.

Embodiment 12. The compound of any one of embodiments 1-11, wherein each $R^d$ is selected from the group consisting of halogen, —$C_1$-$C_6$alkyl, and —OR.

Embodiment 13. The compound of any one of embodiments 1-12, wherein A is unsubstituted.

Embodiment 14. The compound of any one of embodiments 1-13, wherein each R is independently selected from the group consisting of —H and —$C_1$-$C_6$alkyl.

Embodiment 15. A compound of Formula II:

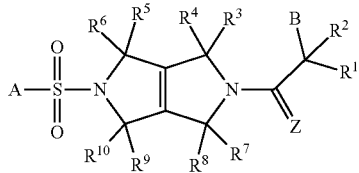

(II)

or a pharmaceutically acceptable salt thereof, wherein:
A is a monocyclic or bicyclic 3- to 14-membered ring,
  wherein the ring is saturated, fully or partially unsaturated, or aromatic, and
  wherein the ring contains 0-4 heteroatoms independently selected from the group consisting of O, N, and S; and
  wherein the ring is optionally substituted with one or more $R^a$;
each R is independently selected from the group consisting of halogen, —OR, —OC(O)R', —$NR_2$, —NRC(O)R', —NRS(O)$_2$R', —CN, —$NO_2$, —SR, —C(O)R', —C(O)OR, —C(O)$NR_2$, —S(O)$_2$R', —S(O)$_2NR_2$, —$C_1$-$C_6$alkyl, —$C_2$-$C_6$alkenyl, —$C_2$-$C_6$alkynyl, —$C_3$-$C_{12}$cycloalkyl, —$C_4$-$C_{12}$cycloalkenyl, 3- to 14-membered heterocyclyl containing 1-4 heteroatoms independently selected from the group consisting of O, N, and S, $C_6$-$C_{14}$aryl, and 5- to 14-membered heteroaryl containing 1-4 heteroatoms independently selected from the group consisting of O, N, and S,
  wherein each alkyl is optionally substituted with one or more halogen;
Z is O, S, or NR;
$R^1$, $R^2$, and B are each independently —H, halogen, —$C_1$-$C_6$alkyl, —$C_2$-$C_6$alkenyl, —$C_2$-$C_6$alkynyl, —OR, —OC(O)R', —OS(O)$_2$R', —OS(O)$_2NR_2$, —OC(O)$NR_2$, —OC(O)OR, —(CR$^b$R$^c$)$_n$NR$_2$, —(CR$^b$R$^c$)$_n$NRC(O)R', —(CR$^b$R$^c$)$_n$NRS(O)$_2$R', —(CR$^b$R$^c$)$_n$NRC(O)$NR_2$, —(CR$^b$R$^c$)$_n$NRC(O)OR, —(CR$^b$R$^c$)$_n$CN, —(CR$^b$R$^c$)$_n$NO$_2$, —(CR$^b$R$^c$)$_n$SR, —(CR$^b$R$^c$)$_n$C(O)R', —(CR$^b$R$^c$)$_n$C(O)OR, —(CR$^b$R$^c$)$_n$C(O)NR$_2$, —(CR$^b$R$^c$)$_n$SO$_2$R', —(CR$^b$R$^c$)$_n$SO$_2$NR$_2$, or —(CR$^b$R$^c$)$_n$SO$_2$OR,
  wherein each alkyl, alkenyl, or alkynyl is optionally substituted with one or more halogen;
or $R^1$ and $R^2$ combine with the carbon to which they are attached to form oxo, a $C_3$-$C_{12}$cycloalkyl, or a 3- to 14-membered heterocyclyl containing 1-4 heteroatoms independently selected from the group consisting of O, N and S,
  wherein the heterocyclyl does not contain an O in the γ-position relative to C(=Z),
  wherein each cycloalkyl or heterocyclyl is optionally substituted with one or more substituents selected from the group consisting of halogen, —$C_1$-$C_6$alkyl, —$C_2$-$C_6$alkenyl, —$C_2$-$C_6$alkynyl, —OR, oxo, —$C_6$aryl, and —C(O)R', and
  wherein each cycloalkyl or heterocyclyl is optionally fused with a $C_6$aryl or 5- to 6-membered heteroaryl containing 1-4 heteroatoms independently selected from the group consisting of O, N, and S;
each $R^b$ and $R^c$ is independently selected from the group consisting of —H, —$C_1$-$C_6$alkyl, and halogen;
each n is independently 0, 1, 2, 3, or 4;
$R^3$, $R^4$, $R^5$, $R^6$, $R^7$, R, $R^9$, and $R^{10}$ are each independently —H or —$C_1$-$C_6$ alkyl,
  wherein each alkyl is optionally substituted with one or more halogen;
or $R^3$ and $R^4$, $R^5$ and $R^6$, $R^7$ and $R^8$, $R^9$ and $R^{10}$, or combinations thereof, combine with the carbon to which they are attached to form oxo, a $C_3$-$C_8$cycloalkyl, or a 3- to 8-membered heterocyclyl containing 1-4 heteroatoms independently selected from the group consisting of O, N, and S;
each R is independently selected from the group consisting of —H, —OH, —O($C_1$-$C_6$alkyl), —$NH_2$, —NH($C_1$-$C_6$alkyl), —N($C_1$-$C_6$alkyl)$_2$, —$C_1$-$C_6$alkyl, —$C_2$-$C_6$alkenyl, —$C_2$-$C_6$alkynyl, —$C_3$-$C_{12}$cycloalkyl, —$C_4$-$C_{12}$cycloalkenyl, 3- to 14-membered heterocyclyl containing 1-4 heteroatoms independently selected from the group consisting of O, N, and S, —$C_6$-$C_{14}$aryl, and 5- to 14-membered heteroaryl containing 1-4 heteroatoms independently selected from the group consisting of O, N, and S,
  wherein each alkyl, alkenyl, alkynyl, cycloalkyl, cycloalkenyl, heterocyclyl, aryl, or heteroaryl is optionally substituted with one or more halogen, —$C_1$-$C_6$alkyl, —$C_2$-$C_6$alkenyl, —$C_2$-$C_6$alkynyl, —O($C_1$-$C_6$alkyl), —NH($C_1$-$C_6$alkyl), or —N($C_1$-$C_6$alkyl)$_2$; and
each R' is independently selected from the group consisting of —$C_1$-$C_6$alkyl, —$C_2$-$C_6$alkenyl, —$C_2$-$C_6$alkynyl, —$C_3$-$C_{12}$cycloalkyl, —$C_4$-$C_{12}$cycloalkenyl, 3- to 14-membered heterocyclyl containing 1-4 heteroatoms independently selected from the group consisting of O, N, and S, —(CR$^b$R$^c$)$_n$$C_6$-$C_{14}$aryl, —(CR$^b$R$^c$)$_n$O($C_6$-$C_{14}$aryl), and 5- to 14-membered heteroaryl containing 1-4 heteroatoms independently selected from the group consisting of O, N, and S,
  wherein each alkyl, alkenyl, alkynyl, cycloalkyl, cycloalkenyl, heterocyclyl, aryl, or heteroaryl is optionally substituted with one or more halogen, —$C_1$-$C_6$alkyl, —$C_2$-$C_6$alkenyl, —$C_2$-$C_6$alkynyl, —O($C_1$-$C_6$alkyl), —NH($C_1$-$C_6$alkyl), or —N($C_1$-$C_6$alkyl)$_2$;

provided that the compound is other than:

[Chemical structure showing a bicyclic compound with NH, sulfonyl linkage, pyrrolidine, and hydroxyl-tert-butyl ketone groups]

Embodiment 16. The compound of embodiment 15, wherein the compound is of Formula II-a:

(II-a)

[Chemical structure of Formula II-a showing A-S(O)₂-N-bicyclic pyrrolopyrrole-N-C(O)-C(R¹)(R²)-B]

or a pharmaceutically acceptable salt thereof.

Embodiment 17. The compound of embodiment 15 or 16, wherein the compound is of Formula II-b-1:

(II-b-1)

[Chemical structure of Formula II-b-1]

or a pharmaceutically acceptable salt thereof,
wherein $R^1$ is —H, halogen, —$C_1$-$C_6$alkyl, —$C_2$-$C_6$alkenyl, or —$C_2$-$C_6$alkynyl,
  wherein each alkyl, alkenyl, or alkynyl is optionally substituted with one or more halogen, and
wherein B is —OR, —OC(O)R', —OS(O)$_2$R', —OS(O)$_2$NR$_2$, —OC(O)NR$_2$, —OC(O)OR, —(CR$^b$R$^c$)$_n$NR$_2$, —(CR$^b$R$^c$)$_n$NRC(O)R', —(CR$^b$R$^c$)$_n$NRS(O)$_2$R', —(CR$^b$R$^c$)$_n$NRC(O)NR$_2$, —(CR$^b$R$^c$)$_n$NRC(O)OR, —(CR$^b$R$^c$)$_n$CN, —(CR$^b$R$^c$)$_n$NO$_2$, —(CR$^b$R$^c$)$_n$SR, —(CR$^b$R$^c$)$_n$C(O)R', —(CR$^b$R$^c$)$_n$C(O)OR, —(CR$^b$R$^c$)$_n$C(O)NR$_2$, —(CR$^b$R$^c$)$_n$SO$_2$R', —(CR$^b$R$^c$)$_n$SO$_2$NR$_2$, or —(CR$^b$R$^c$)$_n$SO$_2$OR.

Embodiment 18. The compound of embodiment 15 or 16, wherein the compound is of Formula II-b-2:

(II-b-2)

[Chemical structure of Formula II-b-2]

or a pharmaceutically acceptable salt thereof,
wherein $R^1$ is —H, halogen, —$C_1$-$C_6$alkyl, —$C_2$-$C_6$alkenyl, or —$C_2$-$C_6$alkynyl,
  wherein each alkyl, alkenyl, or alkynyl is optionally substituted with one or more halogen, and
wherein B is —OR, —OC(O)R', —OS(O)$_2$R', —OS(O)$_2$NR$_2$, —OC(O)NR$_2$, —OC(O)OR, —(CR$^b$R$^c$)$_n$NR$_2$, —(CR$^b$R$^c$)$_n$NRC(O)R', —(CR$^b$R$^c$)$_n$NRS(O)$_2$R', —(CR$^b$R$^c$)$_n$NRC(O)NR$_2$, —(CR$^b$R$^c$)$_n$NRC(O)OR, —(CR$^b$R$^c$)$_n$CN, —(CR$^b$R$^c$)$_n$NO$_2$, —(CR$^b$R$^c$)$_n$SR, —(CR$^b$R$^c$)$_n$C(O)R', —(CR$^b$R$^c$)$_n$C(O)OR, —(CR$^b$R$^c$)$_n$C(O)NR$_2$, —(CR$^b$R$^c$)$_n$SO$_2$R', —(CR$^b$R$^c$)$_n$SO$_2$NR$_2$, or —(CR$^b$R$^c$)$_n$SO$_2$OR.

Embodiment 19. The compound of any one of embodiments 15-18, wherein A is a monocyclic or bicyclic 3- to 10-membered ring,
  wherein the ring is partially unsaturated or aromatic, and
  wherein the ring contains 0-4 heteroatoms independently selected from the group consisting of O, N, and S; and
  wherein the ring is optionally substituted with one or more R.

Embodiment 20. The compound of any one of embodiments 15-19, wherein $R^a$ is selected from the group consisting of halogen, —OR, —NR$_2$, —$C_1$-$C_6$alkyl, —$C_3$-$C_{12}$cycloalkyl, and 3- to 14-membered heterocyclyl containing 1-4 heteroatoms independently selected from the group consisting of O, N, and S,
  wherein each alkyl, cycloalkyl, or heterocyclyl is optionally substituted with one or more halogen.

Embodiment 21. The compound of any one of embodiments 15-20, wherein:
$R^1$, $R^2$, and B are each independently —H, —$C_1$-$C_6$alkyl, —OR, —(CR$^b$R$^c$)$_n$NR$_2$, —(CR$^b$R$^c$)$_n$NRS(O)$_2$R', or —(CR$^b$R$^c$)$_n$C(O)OR,
  wherein each alkyl is optionally substituted with one or more halogen;
or $R^1$ and $R^2$ combine with the carbon to which they are attached to form a $C_3$-$C_{12}$cycloalkyl or 3- to 14-membered heterocyclyl containing 1-4 heteroatoms independently selected from the group consisting of O, N and S,
  wherein the heterocyclyl does not contain an O in the γ-position relative to C(=O),
  wherein each cycloalkyl or heterocyclyl is optionally substituted with one or more substituents selected from the group consisting of phenyl, and —C(O)R', and
  wherein each heterocyclyl is optionally fused with a phenyl or 5- to 6-membered heteroaryl containing 1-4 heteroatoms independently selected from the group consisting of O, N, and S.

Embodiment 22. The compound of any one of embodiments 15-21, wherein $R^1$, $R^2$, and B are each independently —H, —$C_1$-$C_6$alkyl, —OR, —(CR$^b$R$^c$)$_n$NR$_2$, —(CR$^b$R$^c$)$_n$NRS(O)$_2$R', or —(CR$^b$R$^c$)$_n$C(O)OR, wherein each alkyl is optionally substituted with one or more halogen.

Embodiment 23. The compound of any one of embodiments 15-21, wherein:
$R^1$ and $R^2$ combine with the carbon to which they are attached to form a $C_3$-$C_{12}$cycloalkyl or 3- to 14-membered heterocyclyl containing 1-4 heteroatoms independently selected from the group consisting of O, N and S,
  wherein the heterocyclyl does not contain an O in the γ-position relative to C(=O),
  wherein each cycloalkyl or heterocyclyl is optionally substituted with one or more substituents selected from the group consisting of phenyl, and —C(O)R', and
  wherein each heterocyclyl is optionally fused with a phenyl or 5- to 6-membered heteroaryl containing 1-4 heteroatoms independently selected from the group consisting of O, N, and S.

Embodiment 24. The compound of any one of embodiments 15-23, wherein B is —H.

Embodiment 25. The compound of any one of embodiments 15-24, wherein each R is independently selected from the group consisting of —H, —$C_1$-$C_6$alkyl, and $C_6$-$C_{14}$aryl.

Embodiment 26. The compound of any one of embodiments 15-25, wherein each R' is —$C_1$-$C_6$alkyl.

Embodiment 27. A compound of Formula III:

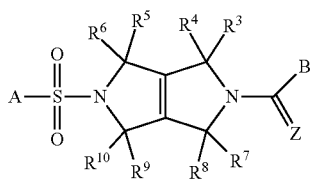

(III)

or a pharmaceutically acceptable salt thereof, wherein:
A is a monocyclic or bicyclic 3- to 14-membered ring,
  wherein the ring is saturated, fully or partially unsaturated, or aromatic, and
  wherein the ring contains 0-4 heteroatoms independently selected from the group consisting of O, N, and S; and
  wherein the ring is optionally substituted with one or more $R^a$;
each $R^a$ is independently selected from the group consisting of halogen, —OR', —OC(O)R', —NR$_2$, —NRC(O)R', —NRS(O)$_2$R', —CN, —NO$_2$, —SR, —C(O)R', —C(O)OR, —C(O)NR$_2$, —S(O)$_2$R', —S(O)$_2$NR$_2$, —C$_1$-C$_6$alkyl, —C$_2$-C$_6$alkenyl, —C$_2$-C$_6$alkynyl, —C$_3$-C$_{12}$cycloalkyl, —C$_4$-C$_{12}$cycloalkenyl, 3- to 14-membered heterocyclyl containing 1-4 heteroatoms independently selected from the group consisting of O, N, and S, C$_6$-C$_{14}$aryl, and 5- to 14-membered heteroaryl containing 1-4 heteroatoms independently selected from the group consisting of O, N, and S,
  wherein each alkyl is optionally substituted with one or more halogen;
Z is O, S, or NR;
B is a ring selected from the group consisting of —C$_6$-C$_{14}$aryl and 5- to 14-membered heteroaryl containing 1-4 heteroatoms independently selected from the group consisting of O, N, and S,
  wherein the ring is optionally substituted with one or more $R^d$;
each $R^d$ is independently selected from the group consisting of halogen, —OR', —OC(O)R', —NR$_2$, —NRC(O)R', —NRS(O)$_2$R', —CN, —NO$_2$, —SR, —C(O)R', —C(O)OR, —C(O)NR$_2$, —S(O)$_2$R', —S(O)$_2$NR$_2$, —C$_1$-C$_6$alkyl, —C$_2$-C$_6$alkenyl, —C$_2$-C$_6$alkynyl, —C$_3$-C$_{12}$cycloalkyl, —C$_4$-C$_{12}$cycloalkenyl, 3- to 14-membered heterocyclyl containing 1-4 heteroatoms independently selected from the group consisting of O, N, and S, C$_6$-C$_{14}$aryl, and 5- to 14-membered heteroaryl containing 1-4 heteroatoms independently selected from the group consisting of O, N, and S,
  wherein each alkyl, alkenyl, alkynyl, cycloalkyl, cycloalkenyl, heterocyclyl, aryl, or heteroaryl is optionally substituted with one or more halogen, —C$_1$-C$_6$ alkyl, —C$_2$-C$_6$alkenyl, —C$_2$-C$_6$alkynyl, or —OR;
$R^3$, $R^4$, $R^5$, $R^6$, $R^7$, R, $R^9$, and $R^{10}$ are each independently —H or —C$_1$-C$_6$ alkyl,
  wherein each alkyl is optionally substituted with one or more halogen;
or $R^3$ and $R^4$, $R^5$ and $R^6$, $R^7$ and $R^8$, $R^9$ and $R^{10}$, or combinations thereof, combine with the carbon to which they are attached to form oxo, a C$_3$-C$_8$cycloalkyl, or a 3- to 8-membered heterocyclyl containing 1-4 heteroatoms independently selected from the group consisting of O, N, and S;
each R is independently selected from the group consisting of —H, —OH, —O(C$_1$-C$_6$alkyl), —NH$_2$, —NH(C$_1$-C$_6$alkyl), —N(C$_1$-C$_6$alkyl)$_2$, —C$_1$-C$_6$alkyl, —C$_2$-C$_6$alkenyl, —C$_2$-C$_6$alkynyl, —C$_3$-C$_{12}$cycloalkyl, —C$_4$-C$_{12}$cycloalkenyl, 3- to 14-membered heterocyclyl containing 1-4 heteroatoms independently selected from the group consisting of O, N, and S, C$_6$-C$_{14}$aryl, and 5- to 14-membered heteroaryl containing 1-4 heteroatoms independently selected from the group consisting of O, N, and S,
  wherein each alkyl, alkenyl, alkynyl, cycloalkyl, cycloalkenyl, heterocyclyl, aryl, or heteroaryl is optionally substituted with one or more halogen, —C$_1$-C$_6$alkyl, —C$_2$-C$_6$alkenyl, —C$_2$-C$_6$alkynyl, —O—C$_1$-C$_6$alkyl, —NH(C$_1$-C$_6$alkyl), or —N(C$_1$-C$_6$alkyl)$_2$; and
each R' is independently selected from the group consisting of —C$_1$-C$_6$alkyl, —C$_2$-C$_6$alkenyl, —C$_2$-C$_6$alkynyl, —C$_3$-C$_{12}$cycloalkyl, —C$_4$-C$_{12}$cycloalkenyl, 3- to 14-membered heterocyclyl containing 1-4 heteroatoms independently selected from the group consisting of O, N, and S, C$_6$-C$_{14}$aryl, and 5- to 14-membered heteroaryl containing 1-4 heteroatoms independently selected from the group consisting of O, N, and S,
  wherein each alkyl, alkenyl, alkynyl, cycloalkyl, cycloalkenyl, heterocyclyl, aryl, or heteroaryl is optionally substituted with one or more halogen, —C$_1$-C$_6$alkyl, —C$_2$-C$_6$alkenyl, —C$_2$-C$_6$alkynyl, —O—C$_1$-C$_6$alkyl, —NH(C$_1$-C$_6$alkyl), or —N(C$_1$-C$_6$alkyl)$_2$.

Embodiment 28. The compound of embodiment 27, wherein the compound is of Formula III-a:

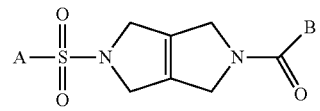

(III-a)

or a pharmaceutically acceptable salt thereof.

Embodiment 29. The compound of embodiment 27 or 28, wherein A is a 5- to 10-membered aromatic monocyclic ring or a bicyclic ring,
  wherein at least one of the rings of the bicyclic ring is aromatic,
  wherein the monocyclic ring or bicyclic ring contains 0-4 heteroatoms independently selected from the group consisting of O, N, and S, and
  wherein the monocyclic ring or bicyclic ring is optionally substituted with one or more R.

Embodiment 30. The compound of any one of embodiments 27-29, wherein A is a bicyclic aromatic ring containing 0-4 heteroatoms independently selected from the group consisting of O, N, and S.

Embodiment 31. The compound of any one of embodiments 27-30, wherein B is a ring selected from phenyl or 5- to 6-membered heteroaryl containing 1-4 heteroatoms independently selected from the group consisting of O, N, and S, wherein the ring is optionally substituted with one or more $R^d$.

Embodiment 32. The compound of any one of embodiments 27-31, wherein each $R^d$ is independently selected from the group consisting of —OR, —NR$_2$, and —C$_1$-C$_6$alkyl optionally substituted with one or more halogen.

Embodiment 33. The compound of any one of embodiments 27-32, wherein each R is independently selected from the group consisting of —H, —C$_1$-C$_6$alkyl optionally substituted with one or more halogen, and 5- to 14-membered heteroaryl containing 1-4 heteroatoms independently selected from the group consisting of O, N, and S.

Embodiment 34. A compound of Formula IV:

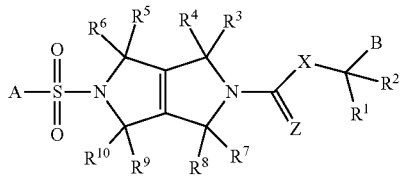

(IV)

or a pharmaceutically acceptable salt thereof, wherein: A is a monocyclic or bicyclic 3- to 14-membered ring, wherein the ring is saturated, fully or partially unsaturated, or aromatic, and wherein the ring contains 0-4 heteroatoms independently selected from the group consisting of O, N, and S; and wherein the ring is optionally substituted with one or more $R^a$;

each R is independently selected from the group consisting of halogen, —OR, —OC(O)R', —NR$_2$, —NRC(O)R', —NRS(O)$_2$R', —CN, —NO$_2$, —SR, —C(O)R', —C(O)OR, —C(O)NR$_2$, —S(O)$_2$R', —S(O)$_2$NR$_2$, —C$_1$-C$_6$alkyl, —C$_2$-C$_6$alkenyl, —C$_2$-C$_6$alkynyl, —C$_3$-C$_{12}$cycloalkyl, —C$_4$-C$_{12}$cycloalkenyl, 3- to 14-membered heterocyclyl containing 1-4 heteroatoms independently selected from the group consisting of O, N, and S, C$_6$-C$_{14}$aryl, and 5- to 14-membered heteroaryl containing 1-4 heteroatoms independently selected from the group consisting of O, N, and S,
  wherein each alkyl is optionally substituted with one or more halogen;

Z is O, S, or NR;

X is 0 or NR$^e$;

R$^e$ is —H or —C$_1$-C$_6$alkyl;

B is —H, or a monocyclic or bicyclic 3- to 14-membered ring, wherein the ring is saturated, fully or partially unsaturated, or aromatic, and wherein the ring contains 0-4 heteroatoms independently selected from the group consisting of O, N, and S; and wherein the ring is optionally substituted with one or more $R^d$;

each $R^d$ is independently selected from the group consisting of halogen, —OR, —OC(O)R', —NR$_2$, —NRC(O)R', —NRS(O)$_2$R', —CN, —NO$_2$, —SR, —C(O)R', —C(O)OR, —C(O)NR$_2$, —S(O)$_2$R', —S(O)$_2$NR$_2$, —C$_1$-C$_6$alkyl, —C$_2$-C$_6$alkenyl, —C$_2$-C$_6$alkynyl, —C$_3$-C$_{12}$cycloalkyl, —C$_4$-C$_{12}$cycloalkenyl, 3- to 14-membered heterocyclyl containing 1-4 heteroatoms independently selected from the group consisting of O, N, and S, C$_6$-C$_{14}$aryl, and 5- to 14-membered heteroaryl containing 1-4 heteroatoms independently selected from the group consisting of O, N, and S,
  wherein each alkyl, alkenyl, alkynyl, cycloalkyl, cycloalkenyl, heterocyclyl, aryl, or heteroaryl is optionally substituted with one or more halogen, —C$_1$-C$_6$alkyl, —C$_2$-C$_6$alkenyl, —C$_2$-C$_6$alkynyl, or —OR;

R$^1$ and R$^2$ are each independently —H, halogen, —C$_1$-C$_6$alkyl, —C$_2$-C$_6$alkenyl, —C$_2$-C$_6$alkynyl, —(CR$^b$R$^c$)$_n$C$_3$-C$_{12}$cycloalkyl, —(CR$^b$R$^c$)$_n$C$_4$-C$_{12}$cycloalkenyl, —(CR$^b$R$^c$)$_n$heterocyclyl, —(CR$^b$R$^c$), C$_6$-C$_{14}$aryl, —(CR$^b$R$^c$)$_n$heteroaryl, —(CR$^b$R$^c$)$_n$OR, —(CR$^b$R$^c$)$_n$OC(O)R', —(CR$^b$R$^c$)$_n$OS(O)$_2$R', —(CR$^b$R$^c$)$_n$OS(O)$_2$NR$_2$, —(CR$^b$R$^c$)$_n$OC(O)NR$_2$, —(CR$^b$R$^c$)$_n$OC(O)OR, —(CR$^b$R$^c$)$_n$NR$_2$, —(CR$^b$R$^c$)$_n$NRC(O)R', —(CR$^b$R$^c$)$_n$NRS(O)$_2$R', —(CR$^b$R$^c$)$_n$NRC(O)NR$_2$, —(CR$^b$R$^c$)$_n$NRC(O)OR, —(CR$^b$R$^c$)$_n$CN, —(CR$^b$R$^c$)$_n$NO$_2$, —(CR$^b$R$^c$)$_n$SR, —(CR$^b$R$^c$)$_n$C(O)R', —(CR$^b$R$^c$)$_n$C(O)OR, —(CR$^b$R$^c$)$_n$C(O)NR$_2$, —(CR$^b$R$^c$)$_n$SO$_2$R', —(CR$^b$R$^c$)$_n$SO$_2$NR$_2$, or —(CR$^b$R$^c$)$_n$SO$_2$OR,
  wherein each alkyl, alkenyl, alkynyl, cycloalkyl, cycloalkenyl, heterocyclyl, aryl, or heteroaryl is optionally substituted with one or more substituents selected from the group consisting of halogen, —C$_1$-C$_6$alkyl, —C$_2$-C$_6$alkenyl, —C$_2$-C$_6$alkynyl, —OR, and oxo,
  wherein each heterocyclyl is 3- to 14-membered and contains 1-4 heteroatoms independently selected from the group consisting of O, N, and S, and
  wherein each heteroaryl is 5- to 14-membered and contains 1-4 heteroatoms independently selected from the group consisting of O, N, and S;

or R$^1$ and R$^2$ combine with the carbon to which they are attached to form oxo, a C$_3$-C$_{12}$cycloalkyl, or a 3- to 14-membered heterocyclyl containing 1-4 heteroatoms independently selected from the group consisting of O, N, and S,
  wherein each cycloalkyl or heterocyclyl is optionally substituted with one or more substituents selected from the group consisting of halogen, —C$_1$-C$_6$alkyl, —C$_2$-C$_6$alkenyl, —C$_2$-C$_6$alkynyl, —OR, and oxo;

or R$^e$ and R$^1$ combine with the nitrogen to which they are attached to form a 3- to 14-membered heterocyclyl containing 1-4 heteroatoms independently selected from the group consisting of O, N, and S,
  wherein the heterocyclyl is optionally substituted with one or more halogen, —C$_1$-C$_6$alkyl, —C$_2$-C$_6$alkenyl, —C$_2$-C$_6$alkynyl, oxo, —OR, and —(CR$^b$R$^c$)$_n$C$_6$-C$_{14}$aryl;

or R$^2$ is absent, and R$^1$ and B combine with the carbon to which they are attached to form C$_6$-C$_{14}$aryl or 5- to 14-membered heteroaryl containing 1-4 heteroatoms independently selected from the group consisting of O, N, and S,
  wherein each aryl or heteroaryl is optionally substituted with one or more halogen, —C$_1$-C$_6$alkyl, —C$_2$-C$_6$alkenyl, —C$_2$-C$_6$alkynyl, or —OR;

each R and R is independently selected from the group consisting of —H, —C$_1$-C$_6$alkyl, and halogen;

each n is independently 0, 1, 2, 3, or 4;

R$^3$, R$^4$, R$^5$, R$^6$, R$^7$, R, R$^9$, and R$^{10}$ are each independently —H or —C$_1$-C$_6$alkyl,
  wherein each alkyl is optionally substituted with one or more halogen;

or R$^3$ and R$^4$, R$^5$ and R$^6$, R$^7$ and R$^8$, R$^9$ and R$^{10}$, or combinations thereof, combine with the carbon to which they are attached to form oxo, a C$_3$-C$_8$cycloalkyl, or a 3- to 8-membered heterocyclyl containing 1-4 heteroatoms independently selected from the group consisting of O, N, and S;

each R is independently selected from the group consisting of —H, —OH, —O(C$_1$-C$_6$alkyl), —NH$_2$, —NH(C$_1$-C$_6$alkyl), —N(C$_1$-C$_6$alkyl)$_2$, —C$_1$-C$_6$alkyl, —C$_2$-C$_6$alkenyl, —C$_2$-C$_6$alkynyl, —C$_3$-C$_{12}$cycloalkyl, —C$_4$-C$_{12}$cycloalkenyl, 3- to 14-membered heterocyclyl containing 1-4 heteroatoms independently selected from the group consisting of O, N, and S, C$_6$-C$_{14}$aryl, and 5- to 14-membered heteroaryl containing 1-4 heteroatoms independently selected from the group consisting of O, N, and S,
  wherein each alkyl, alkenyl, alkynyl, cycloalkyl, cycloalkenyl, heterocyclyl, aryl, or heteroaryl is optionally substituted with one or more halogen, —C$_1$-

$C_6$alkyl, —$C_2$-$C_6$alkenyl, —$C_2$-$C_6$alkynyl, —O—$C_1$-$C_6$alkyl, —NH($C_1$-$C_6$alkyl), or —N($C_1$-$C_6$alkyl)$_2$; and each R' is independently selected from the group consisting of —$C_1$-$C_6$alkyl, —$C_2$-$C_6$alkenyl, —$C_2$-$C_6$alkynyl, —$C_3$-$C_{12}$cycloalkyl, —$C_4$-$C_{12}$cycloalkenyl, 3- to 14-membered heterocyclyl containing 1-4 heteroatoms independently selected from the group consisting of O, N, and S, $C_6$-$C_{14}$aryl, and 5- to 14-membered heteroaryl containing 1-4 heteroatoms independently selected from the group consisting of O, N, and S, wherein each alkyl, alkenyl, alkynyl, cycloalkyl, cycloalkenyl, heterocyclyl, aryl, or heteroaryl is optionally substituted with one or more halogen, —$C_1$-$C_6$alkyl, —$C_2$-$C_6$alkenyl, —$C_2$-$C_6$alkynyl, —O—$C_1$-$C_6$alkyl, —NH($C_1$-$C_6$alkyl), or —N($C_1$-$C_6$alkyl)$_2$.

Embodiment 35. The compound of embodiment 34, wherein the compound is of Formula IV-a:

(IV-a)

[chemical structure]

or a pharmaceutically acceptable salt thereof.

Embodiment 36. The compound of embodiment 34 or 35, wherein the compound is of Formula IV-b:

(IV-b)

[chemical structure]

or a pharmaceutically acceptable salt thereof.

Embodiment 37. The compound of any one of embodiments 34-36, wherein the compound is of Formula IV-c:

(IV-c)

[chemical structure]

or a pharmaceutically acceptable salt thereof.

Embodiment 38. The compound of any one of embodiments 34-36, wherein the compound is of Formula IV-d:

(IV-d)

[chemical structure]

or a pharmaceutically acceptable salt thereof.

Embodiment 39. The compound of any one of embodiments 34-36, wherein the compound is of Formula IV-e-1:

(IV-e-1)

[chemical structure]

or a pharmaceutically acceptable salt thereof.

Embodiment 40. The compound of any one of embodiments 34-36, wherein the compound is of Formula IV-e-2:

(IV-e-2)

[chemical structure]

or a pharmaceutically acceptable salt thereof,

Embodiment 41. The compound of any one of embodiments 34-40, wherein A is a 5- to 10-membered aromatic monocyclic ring or a bicyclic ring,
  wherein at least one of the rings of the bicyclic ring is aromatic,
  wherein the monocyclic ring or bicyclic ring contains 0-4 heteroatoms independently selected from the group consisting of O, N, and S, and
  wherein the monocyclic ring or bicyclic ring is optionally substituted with one or more R.

Embodiment 42. The compound of any one of embodiments 34-41, wherein each $R^a$ is independently selected from the group consisting of halogen, —$C_1$-$C_6$alkyl, and —OR.

Embodiment 43. The compound of any one of embodiments 34-42, wherein:
B is a monocyclic 3- to 6-membered ring,
  wherein the ring is saturated or aromatic,
  wherein the ring contains 0-4 heteroatoms independently selected from the group consisting of O, N, and S, and
  wherein the ring is optionally substituted with one or more $R^d$.

Embodiment 44. The compound of any one of embodiments 34-43, wherein each $R^d$ is independently selected from the group consisting of halogen, —$C_1$-$C_6$alkyl, and —OR.

Embodiment 45. The compound of any one of embodiments 34-44, wherein:
  $R^1$ and $R^2$ are each independently selected from the group consisting of —H, —$C_1$-$C_6$alkyl, —$(CR^bR^c)_nC_6$-$C_{14}$aryl optionally substituted with one or more halogen, and —$(CR^bR^c)_n$OR;
  or $R^1$ and $R^2$ combine with the carbon to which they are attached to form a 3- to 14-membered heterocyclyl containing 1-4 heteroatoms independently selected from the group consisting of O, N, and S;
  or $R^e$ and $R^1$ combine with the nitrogen to which they are attached to form a 3- to 14-membered heterocyclyl containing 1-4 heteroatoms independently selected from the group consisting of O, N, and S and optionally substituted with one or more —OR or —$(CR^bR^c)_nC_6$-$C_{14}$aryl.

Embodiment 46. The compound of any one of embodiments 34-45, wherein $R^1$ and $R^2$ are each —H.

Embodiment 47. The compound of any one of embodiments 34-46, wherein $R^b$ and $R^e$ are each —H, and each n is 0, 1, or 2.

Embodiment 48. The compound of any one of embodiments 34-47, wherein each R is independently —H or —$C_1$-$C_6$alkyl optionally substituted with one or more halogen.

Embodiment 49. A compound selected from Table 1.

Embodiment 50. The compound of embodiment 49, wherein the compound is (2R)-2-hydroxy-2-phenyl-1-[5-(pyridine-2-sulfonyl)-1H,2H,3H,4H,5H,6H-pyrrolo[3,4-c]pyrrol-2-yl]ethan-1-one.

Embodiment 51. The compound of any one of embodiments 1-50, wherein the compound is a PKR Activating Compound having an $AC_{50}$ value≤40 μM in the assay of Example 24.

Embodiment 52. The compound of any one of embodiments 1-51, wherein the compound is a PKR Activating Compound having an $AC_{50}$ value≤1.0 μM in the assay of Example 24.

Embodiment 53. The compound of any one of embodiments 1-52, wherein the compound is a PKR Activating Compound having an $AC_{50}$ value≤0.1 μM in the assay of Example 24.

Embodiment 54. A pharmaceutically composition, comprising a compound of any one of embodiments 1-53, or a pharmaceutically acceptable salt thereof, and a pharmaceutically acceptable carrier.

We claim:
1. A compound of Formula I:

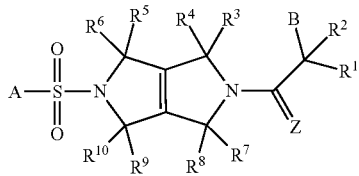

(I)

or a pharmaceutically acceptable salt thereof, wherein:
A is phenyl or monocyclic 5- to 6-membered heteroaryl ring containing 1-4 heteroatoms independently selected from the group consisting of O, N, and S,
  wherein each aryl or heteroaryl is optionally substituted with one or more $R^a$;
each $R^a$ is independently selected from the group consisting of halogen, —OR', —OC(O)R', —$NR_2$, —NRC(O)R', —NRS(O)$_2$R', —CN, —$NO_2$, —SR', —C(O)R', —C(O)OR', —C(O)$NR_2$, —S(O)$_2$R', —$C_1$-$C_6$alkyl, —$C_2$-$C_6$alkenyl, —$C_2$-$C_6$alkynyl, —$C_3$-$C_{12}$cycloalkyl, —$C_4$-$C_{12}$cycloalkenyl, 3- to 14-membered heterocyclyl containing 1-4 heteroatoms independently selected from the group consisting of O, N, and S, $C_6$-$C_{14}$aryl, and 5- to 14-membered heteroaryl containing 1-4 heteroatoms independently selected from the group consisting of O, N, and S,
  wherein each alkyl is optionally substituted with one or more halogen;
Z is O, S, or NR;
$R^1$ and $R^2$ are each independently selected from the group consisting of —H, halogen, —$C_1$-$C_6$alkyl, —$C_2$-$C_6$alkenyl, —$C_2$-$C_6$alkynyl, —$(CR^bR^c)_n$$C_3$-$C_{12}$cycloalkyl, —$(CR^bR^c)_n$$C_4$-$C_{12}$cycloalkenyl, —$(CR^bR^c)_n$heterocyclyl, —$(CR^bR^c)_n$$C_6$-$C_{14}$aryl, —$(CR^bR^c)_n$heteroaryl, —OR', —OC(O)R', —OS(O)$_2$R',
—OS(O)$_2$$NR_2$, —OC(O)$NR_2$, —OC(O)OR, —$(CR^bR^c)_n$$NR_2$, —$(CR^bR^c)_n$NRC(O)R', —$(CR^bR^c)_n$NRS(O)$_2$R', —$(CR^bR^c)_n$NRC(O)$NR_2$, —$(CR^bR^c)_n$NRC(O)OR, —$(CR^bR^c)_n$CN, —$(CR^bR^c)_n$$NO_2$, —$(CR^bR^c)_n$SR, $(CR^bR^c)_n$C(O)R', —$(CR^bR^c)_n$C(O)OR, —$(CR^bR^c)_n$C(O)$NR_2$, —$(CR^bR^c)_n$SO$_2$R', —$(CR^bR^c)_n$SO$_2$$NR_2$, and
—$(CR^bR^c)_n$SO$_2$OR,
  wherein each cycloalkyl, cycloalkenyl, heterocyclyl, aryl, or heteroaryl is optionally substituted with one or more substituents selected from the group consisting of halogen, —$C_1$-$C_6$ alkyl, —$C_2$-$C_6$alkenyl, —$C_2$-$C_6$alkynyl, oxo, and —OR, wherein —OR does not result in an O in the γ-position relative to C(=Z),
  wherein each alkyl, alkenyl, or alkynyl is optionally substituted with one or more halogen,
  wherein each heterocyclyl is 3- to 14-membered and contains 1-4 heteroatoms independently selected from the group consisting of O, N, and S and wherein the heterocyclyl does not contain an O in the γ-position relative to C(=Z), and
  wherein each heteroaryl is 5- to 14-membered and contains 1-4 heteroatoms independently selected from the group consisting of O, N, and S;
or $R^1$ and $R^2$ combine with the carbon to which they are attached to form oxo, a $C_3$-$C_{12}$cycloalkyl, or a 3- to 8-membered heterocyclyl containing 1-4 heteroatoms independently selected from the group consisting of O, N and S, and
  wherein the heterocyclyl does not contain an O in the γ-position relative to C(=Z), and
  wherein each cycloalkyl or heterocyclyl is optionally substituted with one or more substituents selected from the group consisting of halogen, —$C_1$-$C_6$alkyl, —$C_2$-$C_6$alkenyl, —$C_2$-$C_6$alkynyl, oxo, and —OR, wherein —OR does not result in an O in the γ-position relative to C(=Z);
$R^b$ and $R^c$ are each independently selected from the group consisting of —H, halogen, and —$C_1$-$C_6$alkyl;
each n is independently 0, 1, 2, 3, or 4;
B is a monocyclic or bicyclic 3- to 14-membered ring,
  wherein the ring is saturated, fully or partially unsaturated, or aromatic, and
  wherein the ring contains 0-4 heteroatoms independently selected from the group consisting of O, N, and S,
  wherein the ring is optionally substituted with $(R^d)_m$, and
  when the ring is saturated or partially unsaturated, then the ring does not contain an O in the γ-position relative to C(=Z);
each $R^d$ is independently selected from the group consisting of halogen, oxo, —OR', —OC(O)R', —$NR_2$, —NRC(O)R', —NRS(O)$_2$R', —CN, —$NO_2$, —SR, —C(O)R', —C(O)OR, —C(O)$NR_2$, —S(O)$_2$R', —S(O)$_2$$NR_2$,
—$C_1$-$C_6$alkyl, —$C_2$-$C_6$alkenyl, —$C_2$-$C_6$alkynyl, —$C_3$-$C_{12}$cycloalkyl, —$C_4$-$C_{12}$cycloalkenyl, 3- to 14-membered heterocyclyl containing 1-4 heteroatoms independently selected from the group consisting of O, N, and S, $C_6$-$C_{14}$aryl, and 5- to 14-membered heteroaryl containing 1-4 heteroatoms independently selected from the group consisting of O, N, and S, wherein each alkyl, alkenyl, alkynyl, cycloalkyl, cycloalkenyl, heterocyclyl, aryl, or heteroaryl is optionally substituted with one or more halogen, —$C_1$-$C_6$ alkyl, —$C_2$-$C_6$alkenyl, —$C_2$-$C_6$alkynyl, or —OR;

m is 0, 1, 2, 3, 4, 5, 6, 7, 8, 9, or 10;

$R^3$, $R^4$, $R^5$, $R^6$, $R^7$, $R^8$, $R^9$, and $R^{10}$ are each independently —H or —$C_1$-$C_6$ alkyl, wherein each alkyl is optionally substituted with one or more halogen;

or $R^3$ and $R^4$, $R^5$ and $R^6$, $R^7$ and $R^8$, $R^9$ and $R^{10}$, or combinations thereof, combine with the carbon to which they are attached to form oxo, a $C_3$-$C_8$cycloalkyl, or a 3-to 8-membered heterocyclyl containing 1-4 heteroatoms independently selected from the group consisting of O, N, and S;

each R is independently selected from the group consisting of —H, —OH, —O($C_1$-$C_6$alkyl), —$NH_2$, —NH($C_1$-$C_6$alkyl), and —N($C_1$-$C_6$alkyl)$_2$, —$C_1$-$C_6$alkyl, —$C_2$-$C_6$alkenyl, —$C_2$-$C_6$alkynyl, —$C_3$-$C_{12}$cycloalkyl, —$C_4$-$C_{12}$cycloalkenyl, 3-to 14-membered heterocyclyl containing 1-4 heteroatoms independently selected from the group consisting of O, N, and S, $C_6$-$C_{14}$aryl, and 5-to 14-membered heteroaryl containing 1-4 heteroatoms independently selected from the group consisting of O, N, and S, wherein each alkyl, alkenyl, alkynyl, cycloalkyl, cycloalkenyl, heterocyclyl, aryl, or heteroaryl is optionally substituted with one or more halogen, —$C_1$-$C_6$ alkyl, —$C_2$-$C_6$alkenyl, —$C_2$-$C_6$alkynyl, —O($C_1$-$C_6$alkyl), —NH($C_1$-$C_6$alkyl), or —N($C_1$-$C_6$alkyl)$_2$; and each R' is independently selected from the group consisting of —$C_1$-$C_6$alkyl, —$C_2$-$C_6$alkenyl, —$C_2$-$C_6$alkynyl, —$C_3$-$C_{12}$cycloalkyl, —$C_4$-$C_{12}$cycloalkenyl, 3-to 14-membered heterocyclyl containing 1-4 heteroatoms independently selected from the group consisting of O, N, and S, $C_6$-$C_{14}$aryl, and 5-to 14-membered heteroaryl containing 1-4 heteroatoms independently selected from the group consisting of O, N, and S, wherein each alkyl, alkenyl, alkynyl, cycloalkyl, cycloalkenyl, heterocyclyl, aryl, or heteroaryl is optionally substituted with one or more halogen, —$C_1$-$C_6$alkyl, —$C_2$-$C_6$alkenyl, —$C_2$-$C_6$alkynyl, —O—$C_1$-$C_6$alkyl, —NH($C_1$-$C_6$alkyl), or —N($C_1$-$C_6$alkyl)$_2$.

2. The compound of claim 1, wherein the compound is of Formula I-a:

(I-a)

or a pharmaceutically acceptable salt thereof.

3. The compound of claim 2, wherein the compound is of Formula I-b:

(I-b)

or a pharmaceutically acceptable salt thereof.

4. The compound of claim 1, or a pharmaceutically acceptable salt thereof, wherein B is an aromatic monocyclic ring or a bicyclic ring,
wherein at least one of the rings in the bicyclic ring is aromatic,
wherein the monocyclic ring or bicyclic ring contains 0-4 heteroatoms independently selected from the group consisting of O, N, and S, and
wherein the monocyclic ring or bicyclic ring is optionally substituted with $(R^d)_m$.

5. The compound of claim 1, or a pharmaceutically acceptable salt thereof, wherein $R^1$ and $R^2$ are each independently selected from the group consisting of —H, halogen, —$C_1$-$C_6$alkyl, and —OR, wherein —OR does not result in an O in the γ-position relative to C(=Z).

6. The compound of claim 3, wherein the compound is of Formula I-c:

(I-c)

or a pharmaceutically acceptable salt thereof.

7. The compound of claim 1, wherein the compound is of Formula I-d-1:

(I-d-1)

or a pharmaceutically acceptable salt thereof.

8. The compound of claim 1, or a pharmaceutically acceptable salt thereof, wherein A is phenyl or pyridyl, optionally substituted with one or more $R^a$.

9. The compound of claim 1, or a pharmaceutically acceptable salt thereof, wherein A is pyridyl.

10. The compound of claim 1, or a pharmaceutically acceptable salt thereof, wherein A is unsubstituted.

11. The compound of claim 1, wherein the compound is:

or a pharmaceutically acceptable salt thereof.

12. The compound of claim 1, wherein the compound is:

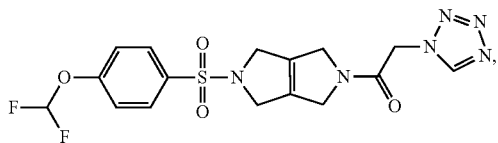 [SMILES: O=C(Cn1cnnn1)N1CC2=C(C1)CN(S(=O)(=O)c1ccc(OC(F)F)cc1)C2]

or a pharmaceutically acceptable salt thereof.

13. The compound of claim 1, wherein the compound is:

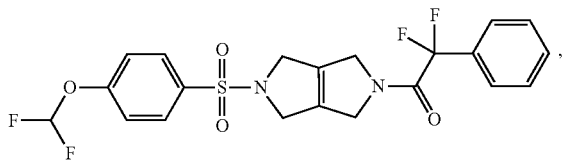 [SMILES: O=C(N1CC2=C(C1)CN(S(=O)(=O)c1ccc(OC(F)F)cc1)C2)C(F)(F)c1ccccc1]

or a pharmaceutically acceptable salt thereof.

14. The compound of claim 1, wherein the compound is:

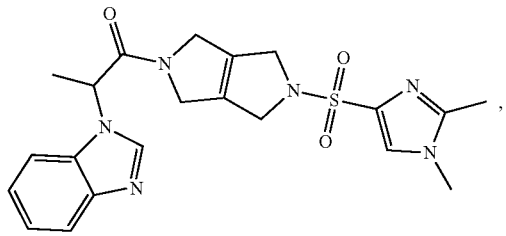 [SMILES: Cc1nc(S(=O)(=O)N2CC3=C(CN(C(=O)C(C)n4cnc5ccccc54)C3)C2)cn1C]

or a pharmaceutically acceptable salt thereof.

15. A method for treating pyruvate kinase deficiency (PKD) in a subject in need thereof, the method comprising administering to the subject a therapeutically effective amount of a compound of Formula (I), or a pharmaceutically acceptable salt thereof, to activate pyruvate kinase R, wherein Formula (I) is:

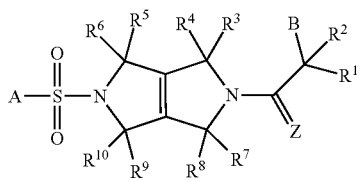

(I)

or a pharmaceutically acceptable salt thereof, wherein:

A is phenyl or monocyclic 5-to 6-membered heteroaryl ring containing 1-4 heteroatoms independently selected from the group consisting of O, N, and S, wherein each aryl or heteroaryl is optionally substituted with one or more $R^a$;

each $R^a$ is independently selected from the group consisting of halogen, —OR, —OC(O)R', —NR$_2$, —NRC(O)R', —NRS(O)$_2$R', —CN, —NO$_2$, —SR, —C(O)R', —C(O)OR, —C(O)NR$_2$, —S(O)$_2$R', —S(O)$_2$NR$_2$, —C$_1$-C$_6$alkyl, —C$_2$-C$_6$alkenyl, —C$_2$-C$_6$alkynyl, —C$_3$-C$_{12}$cycloalkyl, —C$_4$-C$_{12}$cycloalkenyl, 3-to 14-membered heterocyclyl containing 1-4 heteroa- toms independently selected from the group consist- ing of O, N, and S, C$_6$-C$_{14}$aryl, and 5-to 14-mem- bered heteroaryl containing 1-4 heteroatoms independently selected from the group consisting of O, N, and S, wherein each alkyl is optionally substituted with one or more halogen;

Z is O, S, or NR;

$R^1$ and $R^2$ are each independently selected from the group consisting of —H, halogen, —C$_1$-C$_6$alkyl, —C$_2$-C$_6$alkenyl, —C$_2$-C$_6$alkynyl, —(CR$^b$R$^c$)$_n$C$_3$-C$_{12}$cycloalkyl, —(CR$^b$R$^c$)$_n$C$_4$-C$_{12}$cycloalkenyl, —(CR$^b$R$^c$)$_n$heterocyclyl, —(CR$^b$R$^c$)$_n$C$_6$-C$_{14}$aryl, —(CR$^b$R$^c$)$_n$heteroaryl, —OR, —OC(O) R', —OS(O)$_2$R',
—OS(O)$_2$NR$_2$, —OC(O)NR$_2$, —OC(O)OR, —(CR$^b$R$^c$)$_n$NR$_2$, —(CR$^b$R$^c$)$_n$NRC(O)R', —(CR$^b$R$^c$) $_n$NRS(O)$_2$R',
—(CR$^b$R$^c$)$_n$NRC(O)NR$_2$, —(CR$^b$R$^c$)$_n$NRC(O)OR, —(CR$^b$R$^c$)$_n$CN, —(CR$^b$R$^c$)$_n$NO$_2$, —(CR$^b$R$^c$)$_n$SR, —(CR$^b$R$^c$)$_n$C(O)R', —(CR$^b$R$^c$)$_n$C(O)OR, —(CR$^b$R$^c$), C(O)NR$_2$, —(CR$^b$R$^c$)$_n$SO$_2$R',—
(CR$^b$R$^c$)$_n$SO$_2$NR$_2$, and
—(CR$^b$R$^c$)$_n$SO$_2$OR, wherein each cycloalkyl, cycloalkenyl, heterocyclyl, aryl, or heteroaryl is optionally substituted with one or more substituents selected from the group con- sisting of halogen, —C$_1$-C$_6$ alkyl, —C$_2$-C$_6$alkenyl, —C$_2$-C$_6$alkynyl, oxo, and —OR, wherein —OR does not result in an O in the γ-position relative to C(=Z), wherein each alkyl, alkenyl, or alkynyl is optionally substituted with one or more halogen, wherein each heterocyclyl is 3-to 14-membered and contains 1-4 heteroatoms independently selected from the group consisting of O, N, and S and wherein the heterocyclyl does not contain an O in the γ-po- sition relative to C(=Z), and wherein each heteroaryl is 5-to 14-membered and con- tains 1-4 heteroatoms independently selected from the group consisting of O, N, and S;

or $R^1$ and $R^2$ combine with the carbon to which they are attached to form oxo, a C$_3$-C$_{12}$cycloalkyl, or a 3-to 8-membered heterocyclyl containing 1-4 heteroatoms independently selected from the group consisting of O, N and S, and wherein the heterocyclyl does not contain an O in the γ-position relative to C(=Z), and wherein each cycloalkyl or heterocyclyl is optionally substituted with one or more substituents selected from the group consisting of halogen, —C$_1$-C$_6$alkyl, —C$_2$-C$_6$alkenyl, —C$_2$-C$_6$alkynyl, oxo, and —OR, wherein —OR does not result in an O in the γ-po- sition relative to C(=Z);

$R^b$ and $R^c$ are each independently selected from the group consisting of —H, halogen, and —C$_1$-C$_6$alkyl;

each n is independently 0, 1, 2, 3, or 4;

B is a monocyclic or bicyclic 3-to 14-membered ring,
wherein the ring is saturated, fully or partially unsatu- rated, or aromatic, and
wherein the ring contains 0-4 heteroatoms indepen- dently selected from the group consisting of O, N, and S,
wherein the ring is optionally substituted with (R$^d$)$_m$, and when the ring is saturated or partially unsatu- rated, then the ring does not contain an O in the γ-position relative to C(=Z);

each $R^d$ is independently selected from the group consisting of halogen, oxo, —OR', —OC(O)R', —NR$_2$, —NRC(O)R', —NRS(O)$_2$R', —CN, —NO$_2$, —SR, —C(O)R', —C(O)OR, —C(O)NR$_2$, —S(O)$_2$R', —S(O)$_2$NR$_2$,
—C$_1$-C$_6$alkyl, —C$_2$-C$_6$alkenyl, —C$_2$-C$_6$alkynyl, —C$_3$-C$_{12}$cycloalkyl, —C$_4$-C$_{12}$cycloalkenyl, 3-to 14-membered heterocyclyl containing 1-4 heteroatoms independently selected from the group consisting of O, N, and S, C$_6$-C$_{14}$aryl, and 5-to 14-membered heteroaryl containing 1-4 heteroatoms independently selected from the group consisting of O, N, and S,
wherein each alkyl, alkenyl, alkynyl, cycloalkyl, cycloalkenyl, heterocyclyl, aryl, or heteroaryl is optionally substituted with one or more halogen, —C$_1$-C$_6$ alkyl, —C$_2$-C$_6$alkenyl, —C$_2$-C$_6$alkynyl, or —OR;

m is 0, 1, 2, 3, 4, 5, 6, 7, 8, 9, or 10;

$R^3$, $R^4$, $R^5$, $R^6$, $R^7$, $R^8$, $R^9$, and $R^{10}$ are each independently —H or —C$_1$-C$_6$ alkyl,
wherein each alkyl is optionally substituted with one or more halogen;

or $R^3$ and $R^4$, $R^5$ and $R^6$, $R^7$ and $R^8$, $R^9$ and $R^{10}$, or combinations thereof, combine with the carbon to which they are attached to form oxo, a C$_3$-C$_8$cycloalkyl, or a 3-to 8-membered heterocyclyl containing 1-4 heteroatoms independently selected from the group consisting of O, N, and S;

each R is independently selected from the group consisting of —H, —OH, —O(C$_1$-C$_6$alkyl), —NH$_2$, —NH(C$_1$-C$_6$alkyl), and —N(C$_1$-C$_6$alkyl)$_2$, —C$_1$-C$_6$alkyl, —C$_2$-C$_6$alkenyl, —C$_2$-C$_6$alkynyl, —C$_3$-C$_{12}$cycloalkyl, —C$_4$-C$_{12}$cycloalkenyl, 3-to 14-membered heterocyclyl containing 1-4 heteroatoms independently selected from the group consisting of O, N, and S, C$_6$-C$_{14}$aryl, and 5-to 14-membered heteroaryl containing 1-4 heteroatoms independently selected from the group consisting of O, N, and S,
wherein each alkyl, alkenyl, alkynyl, cycloalkyl, cycloalkenyl, heterocyclyl, aryl, or heteroaryl is optionally substituted with one or more halogen, —C$_1$-C$_6$ alkyl, —C$_2$-C$_6$alkenyl, —C$_2$-C$_6$alkynyl, —O(C$_1$-C$_6$alkyl), —NH(C$_1$-C$_6$alkyl), or —N(C$_1$-C$_6$alkyl)$_2$; and each R' is independently selected from the group consisting of —C$_1$-C$_6$alkyl, —C$_2$-C$_6$alkenyl, —C$_2$-C$_6$alkynyl, —C$_3$-C$_{12}$cycloalkyl, —C$_4$-C$_{12}$cycloalkenyl, 3-to 14-membered heterocyclyl containing 1-4 heteroatoms independently selected from the group consisting of O, N, and S, C$_6$-C$_{14}$aryl, and 5-to 14-membered heteroaryl containing 1-4 heteroatoms independently selected from the group consisting of O, N, and S,
wherein each alkyl, alkenyl, alkynyl, cycloalkyl, cycloalkenyl, heterocyclyl, aryl, or heteroaryl is optionally substituted with one or more halogen, —C$_1$-C$_6$alkyl, —C$_2$-C$_6$alkenyl, —C$_2$-C$_6$alkynyl, —O—C$_1$-C$_6$alkyl, —NH(C$_1$-C$_6$alkyl), or —N(C$_1$-C$_6$alkyl)$_2$.

16. The method of claim 15, wherein the compound is:

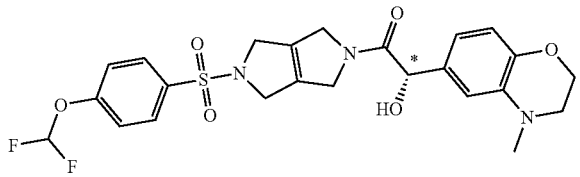 [SMILES: CN1CCOc2ccc([C@H](O)C(=O)N3CC4=C(C3)CN(S(=O)(=O)c3ccc(OC(F)F)cc3)C4)cc21]

or a pharmaceutically acceptable salt thereof.

17. The method of claim 15, wherein the compound is:

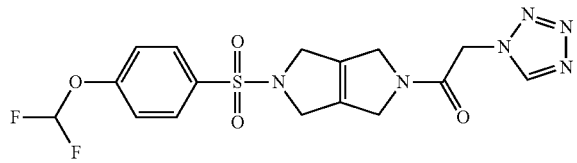

or a pharmaceutically acceptable salt thereof.

18. The method of claim 15, wherein the compound is:

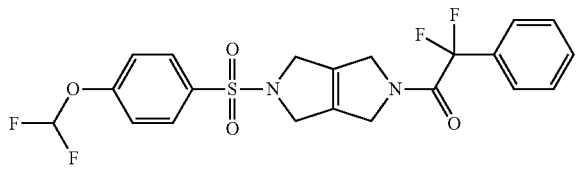

or a pharmaceutically acceptable salt thereof.

19. The method of claim 15, wherein the compound is:

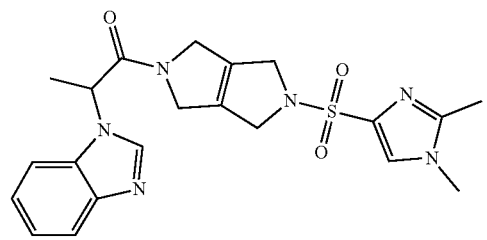 [SMILES: Cc1nc(S(=O)(=O)N2CC3=C(CN(C(=O)C(C)n4cnc5ccccc54)C3)C2)cn1C]

or a pharmaceutically acceptable salt thereof.

* * * * *